United States Patent
Grice et al.

(10) Patent No.: US 10,323,038 B2
(45) Date of Patent: Jun. 18, 2019

(54) PYRAZOLE COMPOUNDS AND METHODS OF MAKING AND USING SAME

(71) Applicant: ABIDE THERAPEUTICS, INC., San Diego, CA (US)

(72) Inventors: Cheryl A. Grice, Encinitas, CA (US); Todd K. Jones, Solana Beach, CA (US); Katharine K. Duncan, San Diego, CA (US); Justin S. Cisar, San Diego, CA (US); Jeffrey E. Merit, San Diego, CA (US); Olivia D. Weber, San Diego, CA (US)

(73) Assignee: ABIDE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/777,201

(22) PCT Filed: Nov. 18, 2016

(86) PCT No.: PCT/US2016/062873
§ 371 (c)(1),
(2) Date: May 17, 2018

(87) PCT Pub. No.: WO2017/087863
PCT Pub. Date: May 26, 2017

(65) Prior Publication Data
US 2018/0327416 A1    Nov. 15, 2018

Related U.S. Application Data

(60) Provisional application No. 62/258,375, filed on Nov. 20, 2015.

(51) Int. Cl.
| | | |
|---|---|---|
| *C07D 487/10* | (2006.01) | |
| *C07D 487/04* | (2006.01) | |
| *C07D 471/10* | (2006.01) | |
| *C07D 519/00* | (2006.01) | |
| *C07D 403/06* | (2006.01) | |
| *C07D 491/08* | (2006.01) | |
| *C07D 231/40* | (2006.01) | |
| *C07D 231/38* | (2006.01) | |
| *C07D 403/12* | (2006.01) | |
| *C07D 417/12* | (2006.01) | |
| *C07D 401/12* | (2006.01) | |
| *C07D 413/12* | (2006.01) | |
| *C07D 498/08* | (2006.01) | |

(52) U.S. Cl.
CPC ......... *C07D 487/10* (2013.01); *C07D 231/38* (2013.01); *C07D 231/40* (2013.01); *C07D 401/12* (2013.01); *C07D 403/06* (2013.01); *C07D 403/12* (2013.01); *C07D 413/12* (2013.01); *C07D 417/12* (2013.01); *C07D 471/10* (2013.01); *C07D 487/04* (2013.01); *C07D 491/08* (2013.01); *C07D 498/08* (2013.01); *C07D 519/00* (2013.01)

(58) Field of Classification Search
None
See application file for complete search history.

(56) References Cited

U.S. PATENT DOCUMENTS

| | | |
|---|---|---|
| 3,308,130 A | 3/1967 | Bousquet |
| 7,772,236 B2 | 8/2010 | Beavers et al. |
| 2003/0013712 A1 | 1/2003 | Tullis et al. |
| 2011/0172230 A1 | 7/2011 | Ishii et al. |
| 2012/0065191 A1 | 3/2012 | Kiss et al. |
| 2014/0018318 A1 | 1/2014 | Cravatt et al. |
| 2015/0051211 A1 | 2/2015 | Ji et al. |
| 2017/0029390 A1 | 2/2017 | Butler et al. |
| 2017/0190669 A1 | 7/2017 | Boger et al. |

FOREIGN PATENT DOCUMENTS

| | | |
|---|---|---|
| WO | WO-2010074588 A2 | 7/2010 |
| WO | WO-2013078771 A1 | 6/2013 |
| WO | WO-2015179559 A2 | 11/2015 |
| WO | WO-2016014975 A2 | 1/2016 |
| WO | WO-2017087854 A1 | 5/2017 |
| WO | WO-2017087858 A1 | 5/2017 |
| WO | WO-2017087863 A1 | 5/2017 |
| WO | WO-2017096315 A1 | 6/2017 |

OTHER PUBLICATIONS

Baggelaar et al. Development of an activity-based probe and in silico design reveal highly selective inhibitors for diacylglycerol lipase-α in brain. Angew Chem Int Ed Engl 52(46):12081-12085 (2013).
Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Bundgaard et al. Design of Prodrugs pp. 7-9, 21-24 (1985).
Fleisher et al. Improved oral drug delivery: solubility limitations overcome by the use of prodrugs. Advanced Drug Delivery Reviews 19:115-130 (1996).
Horig et al. From bench to clinic and back: Perspective on the 1st IQPC Translational Research conference. J Transl Med 2(1):44 (2004).
Janssen et al. Discovery of glycine sulfonamides as dual inhibitors of sn-1-diacylglycerol lipase α and α/β-hydrolase domain 6. J Med Chem 57(15):6610-6622 (2014).
Kohnz et al. Chemical approaches to therapeutically target the metabolism and signaling of the endocannabinoid 2-AG and eicosanoids. Chem Soc Rev 43(19):6859-6869 (2014).
Long et al. Selective blockade of 2-arachidonoylglycerol hydrolysis produces cannabinoid behavioral effects. Nat Chem Biol. 5(1):37-44 (2009).

(Continued)

*Primary Examiner* — Kamal A Saeed
(74) *Attorney, Agent, or Firm* — Wilson Sonsini Goodrich & Rosati

(57) ABSTRACT

Provided herein are pyrazole compounds and pharmaceutical compositions comprising said compounds. The subject compounds and compositions are useful as modulators of MAGL and/or FAAH. Furthermore, the subject compounds and compositions are useful for the treatment of, for example, pain.

20 Claims, No Drawings

(56) References Cited

OTHER PUBLICATIONS

Lysenko et al. Monoacylglycerol lipase inhibitor JZL184 improves behavior and neural properties in Ts65Dn mice, a model of down syndrome. PLoS One 9(12):e114521 (2013).
Morren et al. The filaricidal derivatives of 1-methylpiperazine. Bulletin des Societes Chimiques Belges 59(3-4):228-237 (1950).
Mulvihill et al. Therapeutic potential of monoacylglycerol lipase inhibitors. Life Sci 92(8-9):492-497 (2013).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Ogasawara et al. Rapid and profound rewiring of brain lipid signaling networks by acute diacylglycerol lipase inhibition. PNAS USA 113(1):26-33 (2016).
Otrubova et al. Discovery libraries targeting the major enzyme classes: the serine hydrolases. Bioorg Med Chem Lett 24(16):3807-3813 (2014).
PCT/US2015/031834 International Preliminary Report on Patentability dated Dec. 1, 2016.
PCT/US2015/031834 International Search Report and Written Opinion dated Apr. 20, 2016.
PCT/US2016/062862 International Preliminary Report on Patentability dated May 31, 2018.
PCT/US2016/062862 International Search Report and Written Opinion dated Jan. 27, 2017.
PCT/US2016/062868 International Preliminary Report on Patentability dated May 31, 2018.
PCT/US2016/062868 International Search Report and Written Opinion dated Jan. 30, 2017.
PCT/US2016/062873 International Preliminary Report on Patentability dated May 31, 2018.
PCT/US2016/062873 International Search Report and Written Opinion dated Jan. 27, 2017.
PCT/US2016/064844 International Preliminary Report on Patentability dated Jun. 14, 2018.
PCT/US2016/064844 International Search Report and Written Opinion dated Feb. 15, 2017.
PCT/US2018/033959 International Search Report and Written Opinion dated Jul. 23, 2018.
PCT/US2018/033964 International Search Report and Written Opinion dated Sep. 13, 2018.
PCT/US2018/033964 Invitation to Pay Additional Fees dated Jul. 20, 2018.
Schafer et al. Failure is an option: learning from unsuccessful proof-of-concept trials. Drug Discov Today 13(21-22):913-916 (2008).
U.S. Appl. No. 15/315,998 Office Action dated Nov. 2, 2017.
Van Den Nieuwendijk et al. Synthesis of Eight 1-Deoxynojirimycin Isomers from a Single Chiral Cyanohydrin. Eur JOC 18:3437-3446 (2012).
Van Den Nieuwendijk et al. Synthesis of L-altro-1-deoxynojirimycin, D-allo-1-deoxynojirimycin, and D-galacto-1-deoxynojirimycin from a single chiral cyanohydrin. Org lett 12(17):3957-3959 (2010).
Van Der Wel et al. A natural substrate-based fluorescence assay for inhibitor screening on diacylglycerol lipase α. J Lipid Res 56(4):927-935 (2015).

PYRAZOLE COMPOUNDS AND METHODS OF MAKING AND USING SAME

CROSS-REFERENCE

This application is filed pursuant to 35 U.S.C. § 371 as a United States National Phase Application of International Application No. PCT/US2016/062873, filed Nov. 18, 2016, which claims the benefit of U.S. Provisional Application No. 62/258,375, filed on Nov. 20, 2015, each of which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. Fatty acid amide hydrolase (FAAH) is another enzyme responsible for hydrolyzing endocannabinoids such as anandamide.

BRIEF SUMMARY OF THE INVENTION

This disclosure provides, for example, compounds and compositions which are modulators of MAGL and/or FAAH, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL, and/or FAAH activity in warm-blooded animals such as humans.

In one aspect is a compound of Formula (I):

Formula (I)

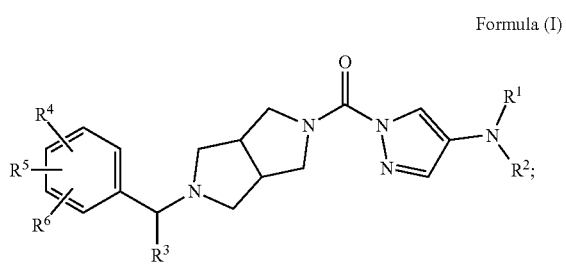

wherein:
- $R^1$ is —C(O)$R^{15}$ or —SO$_2$$R^{15}$;
- $R^2$ is H or $C_{1-6}$alkyl;
- $R^3$ is H or optionally substituted phenyl;
- $R^4$ is H, halogen, —OR$^7$, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
- $R^5$ is H, halogen, $C_{1-6}$alkyl, $C_{1-6}$haloalkyl, or phenyl; or $R^4$ and $R^5$ are combined to form a heterocycloalkyl ring;
- $R^6$ is H, halogen or $C_{1-6}$alkyl;
- $R^7$ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)NR$^{10}$R$^{11}$;
- $R^{10}$ and $R^{11}$ are each independently H, or $C_{1-6}$alkyl; or $R^{10}$ and $R^{11}$ together with the nitrogen to which they are attached are combined to form a heterocycloalkyl ring; and
- $R^{15}$ is $C_{1-6}$alkyl;

or a solvate, hydrate, tautomer, N-oxide, or pharmaceutically acceptable salt thereof.

In another aspect is a compound of Formula (II):

Formula (II)

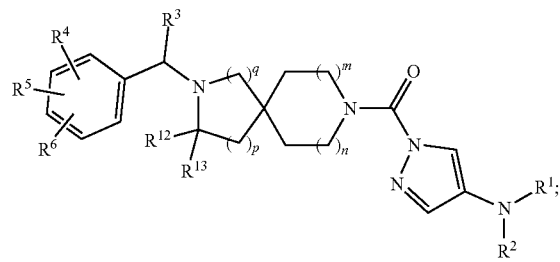

wherein:
- $R^1$ is —C(O)$R^{15}$ or —SO$_2$$R^{15}$;
- $R^2$ is H or $C_{1-6}$alkyl;
- $R^3$ is H or optionally substituted phenyl;
- $R^4$ is H, halogen, —OR$^7$, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
- $R^5$ is H, halogen, $C_{1-6}$alkyl, $C_{1-6}$haloalkyl, or phenyl; or $R^4$ and $R^5$ are combined to form a heterocycloalkyl ring;
- $R^6$ is H, halogen or $C_{1-6}$alkyl;
- $R^7$ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)NR$^{10}$R$^{11}$;
- $R^{10}$ and $R^{11}$ are each independently H, or $C_{1-6}$alkyl; or $R^{10}$ and $R^{11}$ together with the nitrogen to which they are attached are combined to form a heterocycloalkyl ring;
- $R^{12}$ is H or $C_{1-6}$alkyl;
- $R^{13}$ is H or $C_{1-6}$alkyl;
- $R^{15}$ is $C_{1-6}$alkyl;
- n is 0 or 1;
- m is 0 or 1;
- p is 0 or 1; and
- q is 1 or 2;

wherein when m and n are 0, then p is 1 and q is 2;
when m and n are 1, then q is 1; and
when m is 1 and n is 0, or m is 0 and n is 1, then p is 1 and q is 1;

or a solvate, hydrate, tautomer, N-oxide, or pharmaceutically acceptable salt thereof.

In another embodiment is a compound of Formula (IIa):

Formula (IIa)

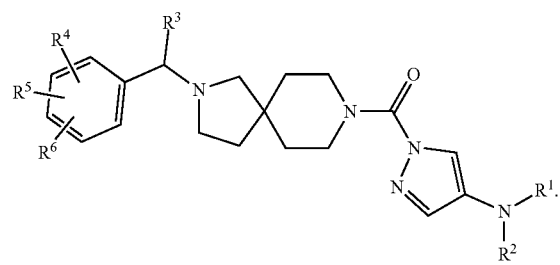

In another embodiment is a compound of Formula (IIb):

Formula (IIb)

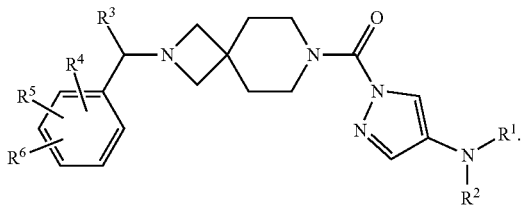

In another embodiment is a compound of Formula (IIc):

Formula (IIc)

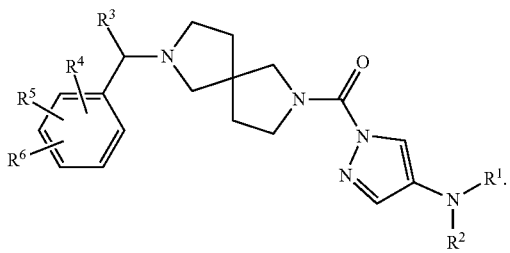

In another embodiment is a compound of Formula (IId):

Formula (IId)

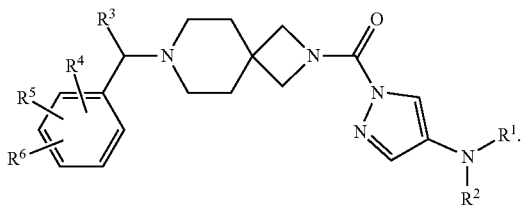

In another aspect is a compound of Formula (III):

Formula (III)

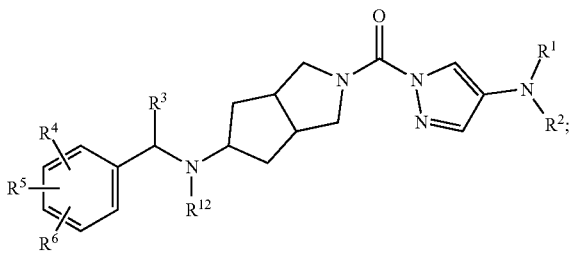

wherein:
R$^1$ is —C(O)R$^{15}$ or —SO$_2$R$^{15}$;
R$^2$ is H or C$_{1-6}$alkyl;
R$^3$ is H or optionally substituted phenyl;
R$^4$ is H, halogen, —OR$^7$, C$_{1-6}$alkyl, C$_{1-6}$haloalkyl, optionally substituted heterocycloalkyl, optionally substituted C$_{1-6}$alkyl-heterocycloalkyl, optionally substituted phenyl, or optionally substituted heteroaryl;
R$^5$ is H, halogen, C$_{1-6}$alkyl, C$_{1-6}$haloalkyl, or phenyl; or R$^4$ and R$^5$ are combined to form a heterocycloalkyl ring;
R$^6$ is H, halogen or C$_{1-6}$alkyl;
R$^7$ is H, C$_{1-6}$alkyl, optionally substituted phenyl, optionally substituted C$_{1-6}$alkyl-phenyl, optionally substituted heteroaryl, optionally substituted heterocycloalkyl, or —C$_{1-6}$alkylC(O)NR$^{10}$R$^{11}$;
R$^{10}$ and R$^{11}$ are each independently H, or C$_{1-6}$alkyl; or R$^{10}$ and R$^{11}$ together with the nitrogen to which they are attached are combined to form a heterocycloalkyl ring;
R$^{12}$ is H, C$_{1-6}$alkyl, or —C(O)C$_{1-6}$alkyl; and
R$^{15}$ is C$_{1-6}$alkyl;
or a solvate, hydrate, tautomer, N-oxide, or pharmaceutically acceptable salt thereof.

In another embodiment is a compound of Formula (III), or a solvate, hydrate, tautomer, N-oxide, or pharmaceutically acceptable salt thereof, wherein R$^{12}$ is H. In another embodiment is a compound of Formula (III), or a solvate, hydrate, tautomer, N-oxide, or pharmaceutically acceptable salt thereof, wherein R$^{12}$ is C$_{1-6}$alkyl. In another embodiment is a compound of Formula (III), or a solvate, hydrate, tautomer, N-oxide, or pharmaceutically acceptable salt thereof, wherein R$^{12}$ is —C(O)C$_{1-6}$alkyl.

In another aspect is a compound of Formula (IV):

Formula (IV)

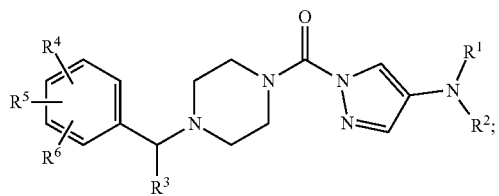

wherein:
R$^1$ is —C(O)R$^{15}$ or —SO$_2$R$^{15}$;
R$^2$ is H or C$_{1-6}$alkyl;
R$^3$ is H or optionally substituted phenyl;
R$^4$ is H, halogen, —OR$^7$, C$_{1-6}$alkyl, C$_{1-6}$haloalkyl, optionally substituted heterocycloalkyl, optionally substituted C$_{1-6}$alkyl-heterocycloalkyl, optionally substituted phenyl, or optionally substituted heteroaryl;
R$^5$ is H, halogen, C$_{1-6}$alkyl, C$_{1-6}$haloalkyl, or phenyl; or R$^4$ and R$^5$ are combined to form a heterocycloalkyl ring;
R$^6$ is H, halogen or C$_{1-6}$alkyl;
R$^7$ is H, C$_{1-6}$alkyl, optionally substituted phenyl, optionally substituted C$_{1-6}$alkyl-phenyl, optionally substituted heteroaryl, optionally substituted heterocycloalkyl, or —C$_{1-6}$alkylC(O)NR$^{10}$R$^{11}$;
R$^{10}$ and R$^{11}$ are each independently H, or C$_{1-6}$alkyl; or R$^{10}$ and R$^{11}$ together with the nitrogen to which they are attached are combined to form a heterocycloalkyl ring; and
R$^{15}$ is C$_{1-6}$alkyl;
or a solvate, hydrate, tautomer, N-oxide, or pharmaceutically acceptable salt thereof.

In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein R$^4$ is optionally substituted heterocycloalkyl. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein R$^4$ is optionally substituted heterocycloalkyl selected from

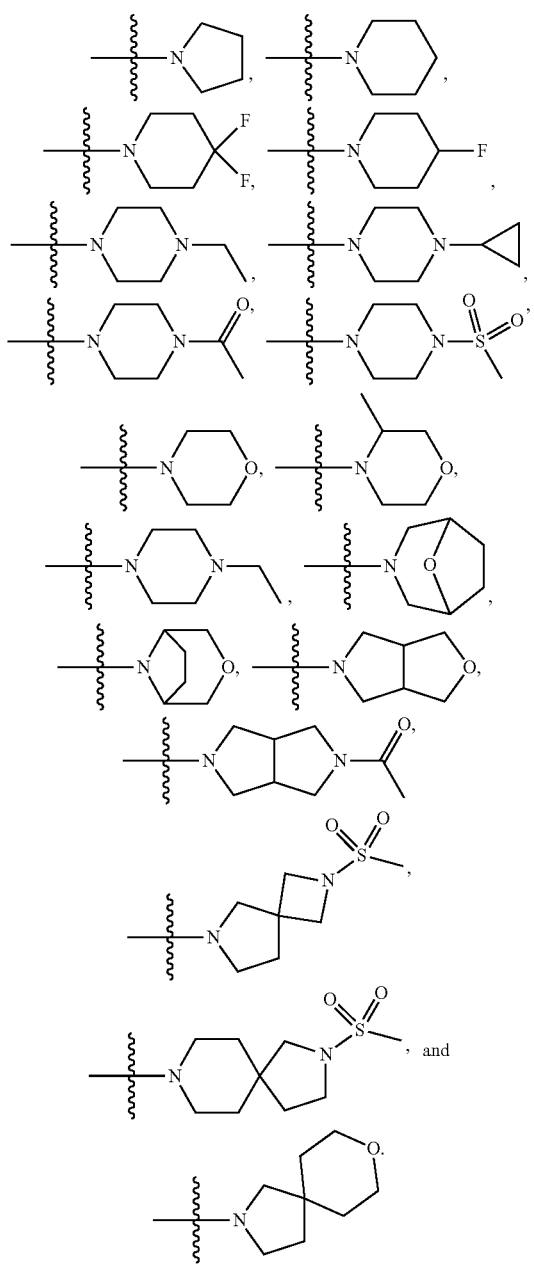

In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is

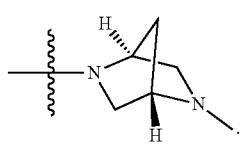 [SMILES: *N1C[C@@H]2C[C@H]1CN2C]

In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is —$OR^7$. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is —$OR^7$ and $R^7$ is $C_{1-6}$alkyl,

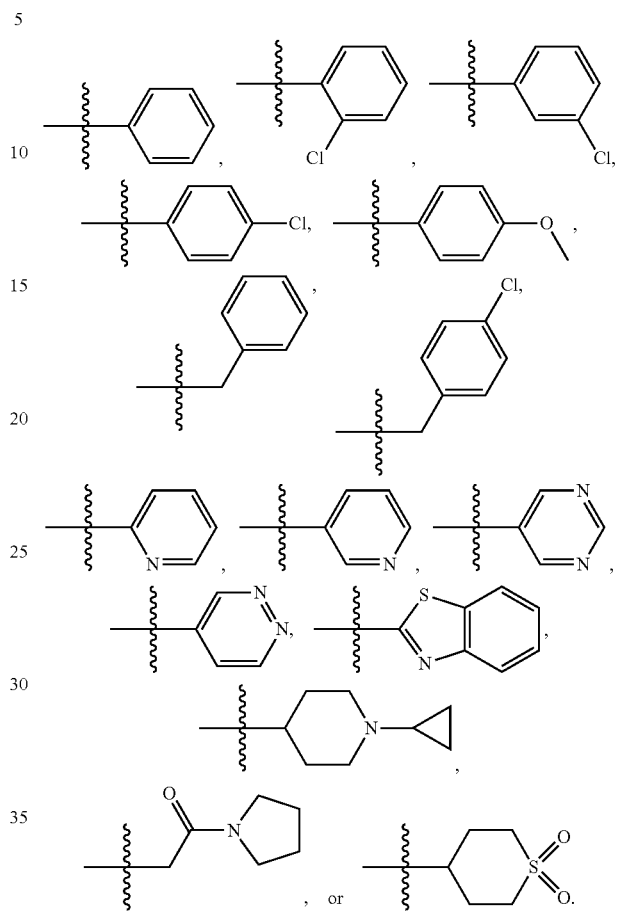

In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is optionally substituted heteroaryl. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is

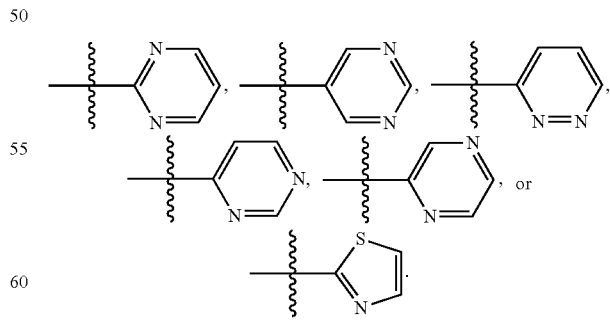

In another embodiment is a compound of Formula (I), (II), (IIa), (IIb), (IIc), (IId), (III), or (IV), or a solvate, hydrate, tautomer, N-oxide, or pharmaceutically acceptable salt thereof, $R^4$ is

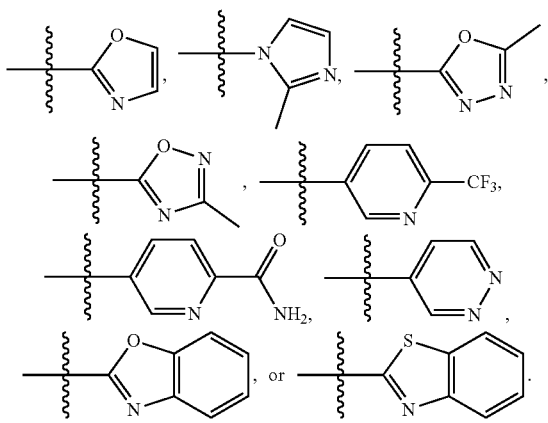

In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is halogen. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is —Cl. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is $C_{1-6}$haloalkyl. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^4$ is —CF$_3$. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^5$ is H. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^5$ is halogen. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^5$ is —Cl. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^5$ is $C_{1-6}$haloalkyl. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^5$ is —CF$_3$. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^5$ is phenyl. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^6$ is H. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^3$ is H. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^3$ is optionally substituted phenyl. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^2$ is H. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^2$ is optionally substituted $C_{1-6}$alkyl. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^2$ is —CH$_3$. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^1$ is —C(O)R$^{15}$. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^1$ is —C(O)R$^{15}$ and R$^{15}$ is —CH$_3$. In another embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^1$ is —SO$_2$R$^{15}$. In a further embodiment is a compound of Formula (I), (II), (IIa), (IIb), (IIc), (IId), (III), or (IV), or a solvate, hydrate, tautomer, N-oxide, or pharmaceutically acceptable salt thereof, wherein $R^1$ is —SO$_2$R$^{15}$ and R$^{15}$ is —CH$_3$.

In another embodiment is a pharmaceutical composition comprising a compound of Formula (I), (II), (IIa), (IIb), (IIc), (IId), (III), or (IV) described herein, or a solvate, hydrate, tautomer, N-oxide, or a pharmaceutically acceptable salt thereof, and at least one pharmaceutically acceptable excipient.

In another embodiment is a method of treating a disease or disorder selected from the group consisting of multiple sclerosis, Alzheimer's disease, and inflammatory bowel disease, comprising administering a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof, to a patient in need thereof. In some embodiments, the disease is multiple sclerosis. In some embodiments, the disease is Alzheimer's disease. In some embodiments, the disease is inflammatory bowel disease.

In another embodiment is a method of treating pain in a patient, comprising administering a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof, to a patient in need thereof to treat said pain. In another embodiment is a method of treating neuropathic pain in a patient, comprising administering a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof, to a patient in need thereof to treat said neuropathic pain. In another embodiment is a method of treating inflammatory pain in a patient, comprising administering a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof, to a patient in need thereof to treat said inflammatory pain.

In another embodiment is a method of treating a disease or disorder in a patient comprising administering to the patient in need thereof a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof, wherein the disease is selected from epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating epilepsy/seizure disorder in a patient in need thereof, comprising administering to the patient a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof. In another embodiment is a method of treating neuromyelitis optica (NMO) in a patient in need thereof, comprising administering to the patient a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof. In another embodiment is a method of treating Tourette syndrome in a patient in need thereof, comprising administering to the patient a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof. In another embodiment is a method of treating persistent motor tic disorder in a patient in need thereof, comprising administering to the patient a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof. In another embodiment is a method of treating persistent vocal tic disorder in a patient in need thereof, comprising administering to the patient a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof. In another embodiment is a method of treating abdominal pain associated with irritable bowel syndrome in a patient in need thereof, comprising administering to the patient a therapeutically effective amount of a compound of Formula (I), (II), (IIa), (IIb), (IIc), (IId), (III), or (IV) described herein, or a solvate, hydrate, tautomer, N-oxide, or a pharmaceutically acceptable salt thereof.

DETAILED DESCRIPTION OF THE INVENTION

This disclosure is directed, at least in part, to modulators or inhibitors of MAGL and/or FAAH. For example, provided herein are compounds capable of inhibiting MAGL and/or FAAH. In some embodiments, the compounds described herein are dual inhibitors capable of inhibiting MAGL and FAAH.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH2 radical.
"Cyano" refers to the —CN radical.
"Nitro" refers to the —NO2 radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^f$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^f$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^f$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^f$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula -Rc-aryl where Rc is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula -Rd-aryl where Rd is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula -Re-aryl, where Re is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyrimidinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tOR^a$ (where t is 1 or 2), —$R^b$—S(O)$_tR^a$ (where t is 1 or 2) and —$R^b$—S(O)$_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

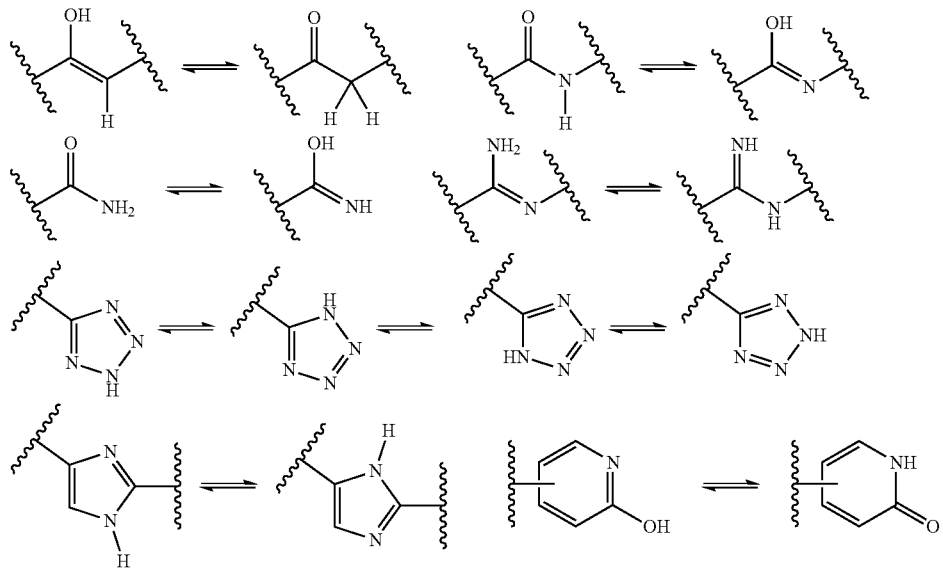

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, the prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds

The compounds of Formula (I), (Ia), (II), (IIa), (IIb), (IIc), (IId), (III), (IIIa), (IV), or (IVa) described herein are inhibitors of MAGL and/or FAAH. In some embodiments, the compounds are inhibitors of MAGL. In some embodiments, the compounds are inhibitors of FAAH. In some embodiments, the compounds are inhibitors of MAGL and FAAH. The compounds of Formula (I), (Ia), (II), (IIa), (IIb), (IIc), (IId), (III), (IIIa), (IV), or (IVa) described herein, and compositions comprising these compounds, are useful for the treatment of pain, multiple sclerosis, Alzheimer's disease, and/or inflammatory bowel disease.

In one embodiment is a compound of Formula (I):

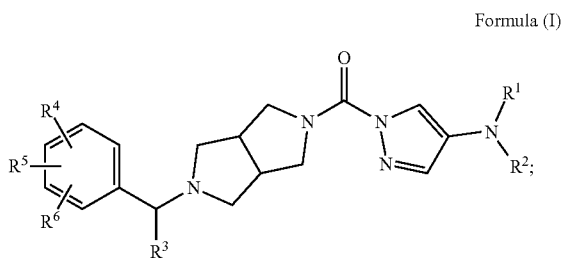

Formula (I)

wherein:
- $R^1$ is —C(O)$R^{15}$ or —S$_2R^{15}$;
- $R^2$ is H or C$_{1-6}$alkyl;
- $R^3$ is H or optionally substituted phenyl;
- $R^4$ is H, halogen, —OR$^7$, C$_{1-6}$alkyl, C$_{1-6}$haloalkyl, optionally substituted heterocycloalkyl, optionally substituted C$_{1-6}$alkyl-heterocycloalkyl, optionally substituted phenyl, or optionally substituted heteroaryl;
- $R^5$ is H, halogen, C$_{1-6}$alkyl, C$_{1-6}$haloalkyl, or phenyl; or $R^4$ and $R^5$ are combined to form a heterocycloalkyl ring;
- $R^6$ is H, halogen or C$_{1-6}$alkyl;
- $R^7$ is H, C$_{1-6}$alkyl, optionally substituted phenyl, optionally substituted C$_{1-6}$alkyl-phenyl, optionally substituted heteroaryl, optionally substituted heterocycloalkyl, or —C$_{1-6}$alkylC(O)NR$^{10}$R$^{11}$;
- $R^{10}$ and $R^{11}$ are each independently H, or C$_{1-6}$alkyl; or $R^{10}$ and $R^{11}$ together with the nitrogen to which they are attached are combined to form a heterocycloalkyl ring; and
- $R^{15}$ is C$_{1-6}$alkyl;
- or a solvate, hydrate, tautomer, N-oxide, or pharmaceutically acceptable salt thereof.

In another embodiment is a compound of Formula (I), wherein R2 is H. In another embodiment is a compound of Formula (I), wherein R2 is C1-6alkyl. In another embodiment is a compound of Formula (I), wherein $R^2$ is —CH$_3$.

In another embodiment is a compound of Formula (I), wherein $R^1$ is —C(O)R$^{15}$. In another embodiment is a compound of Formula (I), wherein $R^1$ is —C(O)R$^{15}$ and $R^{15}$ is —CH$_3$. In another embodiment is a compound of Formula (I), wherein $R^1$ is —SO$_2$R$^{15}$. In another embodiment is a compound of Formula (I), wherein $R^1$ is —SO$_2$R$^{15}$ and $R^{15}$ is —CH$_3$. In another embodiment is a compound of Formula (I), wherein $R^1$ is —C(O)R$^{15}$ and $R^2$ is H. In another embodiment is a compound of Formula (I), wherein $R^1$ is —C(O)R$^{15}$, $R^{15}$ is —CH$_3$, and $R^2$ is H. In another embodiment is a compound of Formula (I), wherein $R^1$ is —SO$_2$R$^{15}$ and $R^2$ is H. In another embodiment is a compound of Formula (I), wherein $R^1$ is —SO$_2$R$^{15}$, $R^{15}$ is —CH$_3$, and $R^2$ is H. In another embodiment is a compound of Formula (I), wherein $R^1$ is —C(O)R$^{15}$ and $R^2$ is C$_{1-6}$alkyl. In another embodiment is a compound of Formula (I), wherein $R^1$ is —C(O)R$^{15}$, $R^{15}$ is —CH$_3$, and $R^2$ is C$_{1-6}$alkyl. In another embodiment is a compound of Formula (I), wherein $R^1$ is —SO$_2$R$^{15}$ and $R^2$ is C$_{1-6}$alkyl. In another embodiment is a compound of Formula (I), wherein $R^1$ is —SO$_2$R$^{15}$, $R^{15}$ is —CH$_3$, and $R^2$ is C$_{1-6}$alkyl. In another embodiment is a compound of Formula (I), wherein $R^1$ is —C(O)R$^{15}$ and $R^2$ is —CH$_3$. In another embodiment is a compound of Formula (I), wherein R1 is —C(O)R15, R15 is —CH3, and R2 is —CH3. In another embodiment is a compound of Formula (I), wherein R1 is —SO2R15 and R2 is —CH3. In another embodiment is a compound of Formula (I), wherein R1 is —SO2R15, R15 is —CH3, and R2 is —CH3.

In another embodiment is a compound of Formula (I), wherein R3 is H. In another embodiment is a compound of Formula (I), wherein R3 is optionally substituted phenyl.

In another embodiment is a compound of Formula (I), wherein $R^4$ is H. In another embodiment is a compound of Formula (I), wherein $R^4$ is halogen. In another embodiment is a compound of Formula (I), wherein $R^4$ is —Cl. In another embodiment is a compound of Formula (I), wherein $R^4$ is —F. In another embodiment is a compound of Formula (I), wherein $R^4$ is C$_{1-6}$ alkyl. In another embodiment is a compound of Formula (I), wherein $R^4$ is C$_{1-6}$haloalkyl. In another embodiment is a compound of Formula (I), wherein $R^4$ is —CF$_3$. In another embodiment is a compound of Formula (I), wherein $R^4$ is optionally substituted phenyl. In another embodiment is a compound of Formula (I), wherein $R^4$ is optionally substituted heteroaryl. In another embodiment is a compound of Formula (I), wherein $R^4$ is

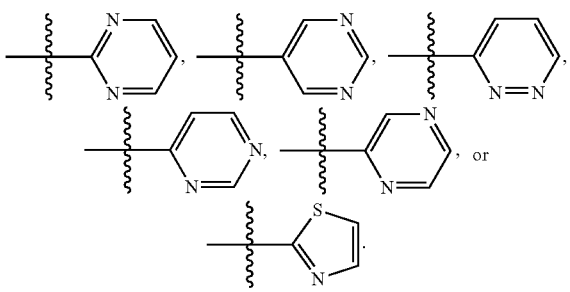

In another embodiment is a compound of Formula (I), wherein $R^4$ is

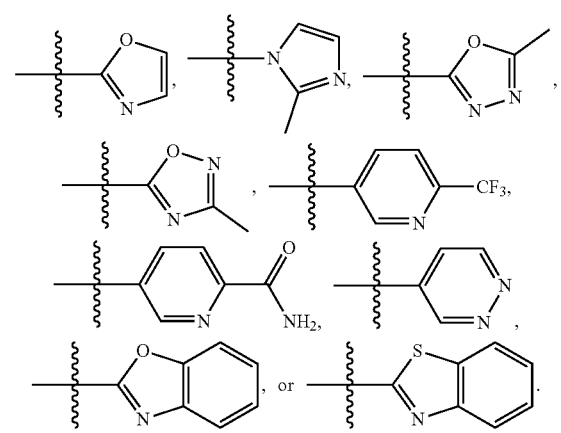

In another embodiment is a compound of Formula (I), wherein $R^4$ is optionally substituted C$_{1-6}$alkyl-heterocycloalkyl. In another embodiment is a compound of Formula (I), wherein $R^4$ is optionally substituted heterocycloalkyl. In another embodiment is a compound of Formula (I), wherein $R^4$ is optionally substituted heterocycloalkyl selected from

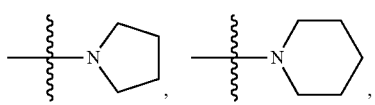

-continued

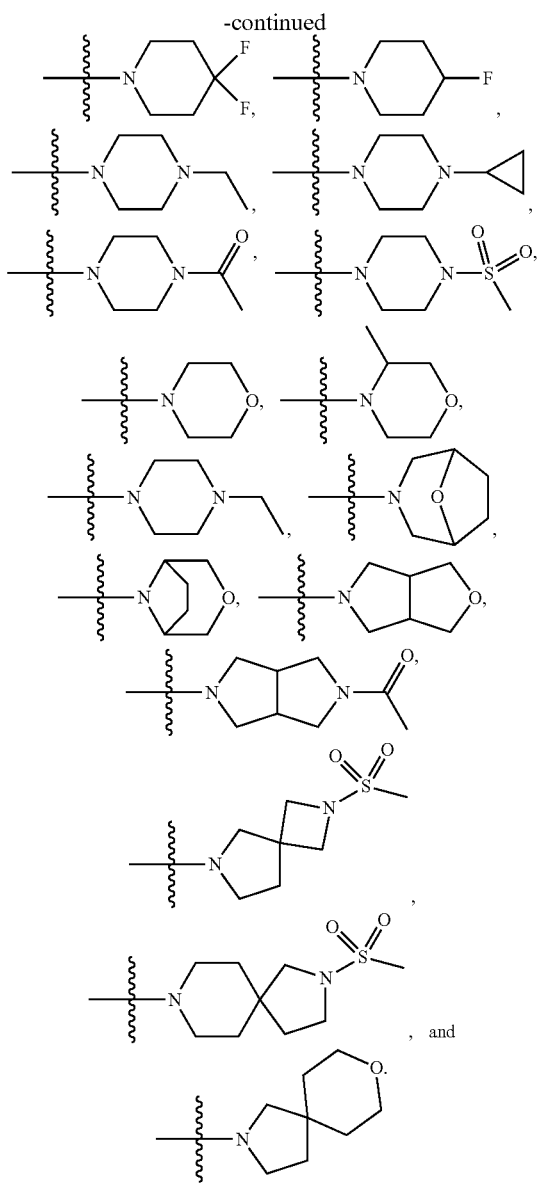

In a further embodiment is a compound of Formula (I), wherein R⁴ is

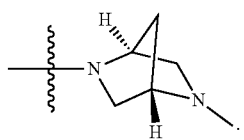 [SMILES: *N1C[C@@H]2C[C@H]1CN2C]

In another embodiment is a compound of Formula (I), wherein R⁴ is —OR⁷. In another embodiment is a compound of Formula (I), wherein R⁴ is —OR⁷, and R⁷ is $C_{1-6}$alkyl. In another embodiment is a compound of Formula (I), wherein R⁴ is —OR⁷, and R⁷ is optionally substituted phenyl. In another embodiment is a compound of Formula (I), wherein R⁴ is —OR⁷, and R⁷ is optionally substituted $C_{1-6}$alkyl-phenyl. In another embodiment is a compound of Formula (I), wherein R⁴ is —OR⁷, and R⁷ is optionally substituted heteroaryl. In another embodiment is a compound of Formula (I), wherein R⁴ is —OR⁷, and R⁷ is optionally substituted heterocycloalkyl. In another embodiment is a compound of Formula (I), wherein R⁴ is —OR⁷, and R⁷ is —$C_{1-6}$alkylC(O)NR⁹R¹⁰. In another embodiment is a compound of Formula (I), wherein R⁴ is —OR⁷, and R⁷ is —$C_{1-6}$alkylC(O)NR⁹R¹⁰, and R⁹ and R¹⁰ are each independently H, or $C_{1-6}$alkyl. In another embodiment is a compound of Formula (I), wherein R⁴ is —OR⁷, and R⁷ is —$C_{1-6}$alkylC(O)NR⁹R¹⁰, and R⁹ and R¹⁰ together with the nitrogen to which they are attached are combined to form a heterocycloalkyl ring. In another embodiment is a compound of Formula (I), wherein R⁴ is —OR⁷, and R⁷ is $C_{1-6}$alkyl,

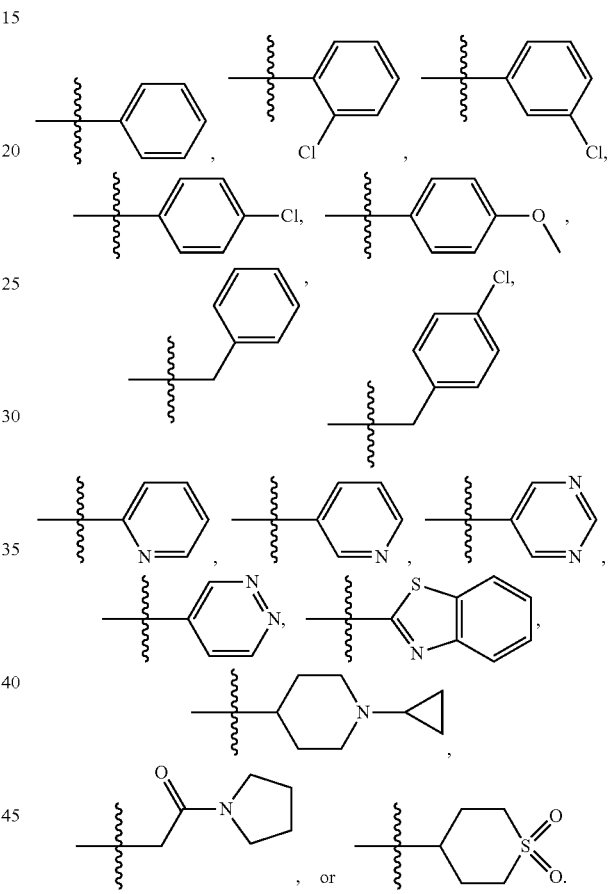

In another embodiment is a compound of Formula (I), wherein R⁵ is H. In another embodiment is a compound of Formula (I), wherein R⁵ is halogen. In another embodiment is a compound of Formula (I), wherein R⁵ is —Cl. In another embodiment is a compound of Formula (I), wherein R⁵ is —F. In another embodiment is a compound of Formula (I), wherein R⁵ is $C_{1-6}$ alkyl. In another embodiment is a compound of Formula (I), wherein R⁵ is $C_{1-6}$haloalkyl. In another embodiment is a compound of Formula (I), wherein R⁵ is —CF₃. In another embodiment is a compound of Formula (I), wherein R⁵ is phenyl.

In another embodiment is a compound of Formula (I), wherein R6 is H. In another embodiment is a compound of Formula (I), wherein R6 is halogen. In another embodiment is a compound of Formula (I), wherein R6 is —Cl. In another embodiment is a compound of Formula (I), wherein R6 is —F. In another embodiment is a compound of Formula (I), wherein R6 is C1-6alkyl.

In another embodiment is a compound of Formula (I) having the structure of Formula (Ia):

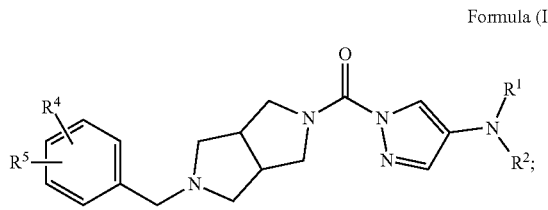

Formula (Ia)

wherein:
R¹ is —C(O)R¹⁵ or —SO₂R¹⁵;
R² is H or $C_{1-6}$alkyl;
R⁴ is H, halogen, —OR⁷, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
R⁵ is H, halogen, $C_{1-6}$alkyl, $C_{1-6}$haloalkyl, or phenyl; or
R⁴ and R⁵ are combined to form a heterocycloalkyl ring;
R⁷ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)NR¹⁰R¹¹;
R¹⁰ and R¹¹ are each independently H, or $C_{1-6}$alkyl; or R¹⁰ and R¹¹ together with the nitrogen to which they are attached are combined to form a heterocycloalkyl ring; and
R¹⁵ is $C_{1-6}$alkyl;
or a solvate, hydrate, tautomer, N-oxide, or pharmaceutically acceptable salt thereof.

In another embodiment is a compound of Formula (Ia), wherein R2 is H. In another embodiment is a compound of Formula (Ia), wherein R2 is C1-6alkyl. In another embodiment is a compound of Formula (Ia), wherein R2 is —CH3.

In another embodiment is a compound of Formula (Ia), wherein R1 is —C(O)R15. In another embodiment is a compound of Formula (Ia), wherein R¹ is —C(O)R¹⁵ and R¹⁵ is —CH₃. In another embodiment is a compound of Formula (Ia), wherein R¹ is —SO₂R¹⁵. In another embodiment is a compound of Formula (Ia), wherein R¹ is —SO₂R¹⁵ and R¹⁵ is —CH₃. In another embodiment is a compound of Formula (Ia), wherein R¹ is —C(O)R¹⁵ and R² is H. In another embodiment is a compound of Formula (Ia), wherein R¹ is —C(O)R¹⁵, R¹⁵ is —CH₃, and R² is H. In another embodiment is a compound of Formula (Ia), wherein R¹ is —SO₂R¹⁵ and R² is H. In another embodiment is a compound of Formula (Ia), wherein R¹ is —SO₂R¹⁵, R¹⁵ is —CH₃, and R² is H. In another embodiment is a compound of Formula (Ia), wherein R¹ is —C(O)R¹⁵ and R² is $C_{1-6}$alkyl. In another embodiment is a compound of Formula (Ia), wherein R¹ is —C(O)R¹⁵, R¹⁵ is —CH₃, and R² is $C_{1-6}$alkyl. In another embodiment is a compound of Formula (Ia), wherein R¹ is —SO₂R¹⁵ and R² is $C_{1-6}$alkyl. In another embodiment is a compound of Formula (Ia), wherein R¹ is —SO₂R¹⁵, R¹⁵ is —CH₃, and R² is $C_{1-6}$alkyl. In another embodiment is a compound of Formula (Ia), wherein R¹ is —C(O)R¹⁵ and R² is —CH₃. In another embodiment is a compound of Formula (Ia), wherein R¹ is —C(O)R¹⁵, R¹⁵ is —CH₃, and R² is —CH₃. In another embodiment is a compound of Formula (Ia), wherein R¹ is —SO₂R¹⁵ and R² is —CH₃. In another embodiment is a compound of Formula (Ia), wherein R¹ is —SO₂R¹⁵, R¹⁵ is —CH₃, and R² is —CH₃.

In another embodiment is a compound of Formula (Ia), wherein R⁴ is H. In another embodiment is a compound of Formula (Ia), wherein R⁴ is halogen. In another embodiment is a compound of Formula (Ia), wherein R⁴ is —Cl. In another embodiment is a compound of Formula (Ia), wherein R⁴ is —F. In another embodiment is a compound of Formula (Ia), wherein R⁴ is $C_{1-6}$alkyl. In another embodiment is a compound of Formula (Ia), wherein R⁴ is $C_{1-6}$haloalkyl. In another embodiment is a compound of Formula (Ia), wherein R⁴ is —CF₃. In another embodiment is a compound of Formula (Ia), wherein R⁴ is optionally substituted phenyl. In another embodiment is a compound of Formula (Ia), wherein R⁴ is optionally substituted heteroaryl. In another embodiment is a compound of Formula (Ia), wherein R⁴ is

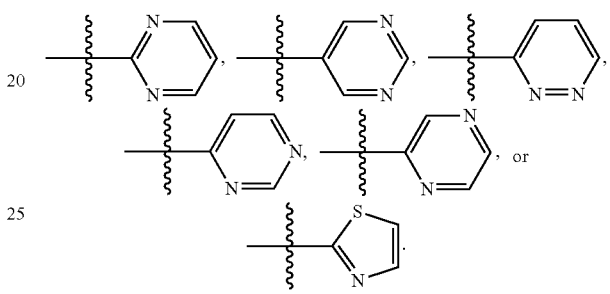

In another embodiment is a compound of Formula (Ia), wherein R⁴ is

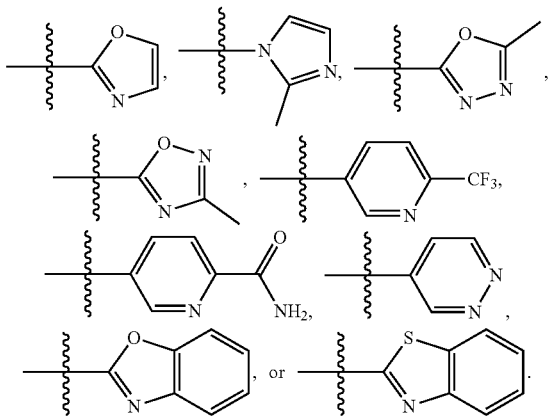

In another embodiment is a compound of Formula (Ia), wherein R⁴ is optionally substituted $C_{1-6}$alkyl-heterocycloalkyl. In another embodiment is a compound of Formula (Ia), wherein R⁴ is optionally substituted heterocycloalkyl. In another embodiment is a compound of Formula (Ia), wherein R⁴ is optionally substituted heterocycloalkyl selected from

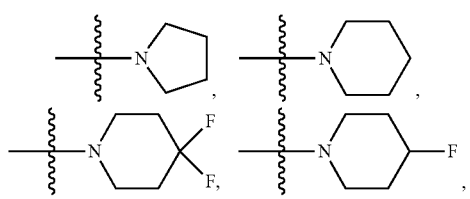

compound of Formula (Ia), wherein $R^4$ is —$OR^7$, and $R^7$ is —$C_{1-6}$alkylC(O)NR$^9$R$^{10}$, and $R^9$ and $R^{10}$ together with the nitrogen to which they are attached are combined to form a heterocycloalkyl ring. In another embodiment is a compound of Formula (Ia), wherein $R^4$ is —$OR^7$, and $R^7$ is $C_{1-6}$alkyl,

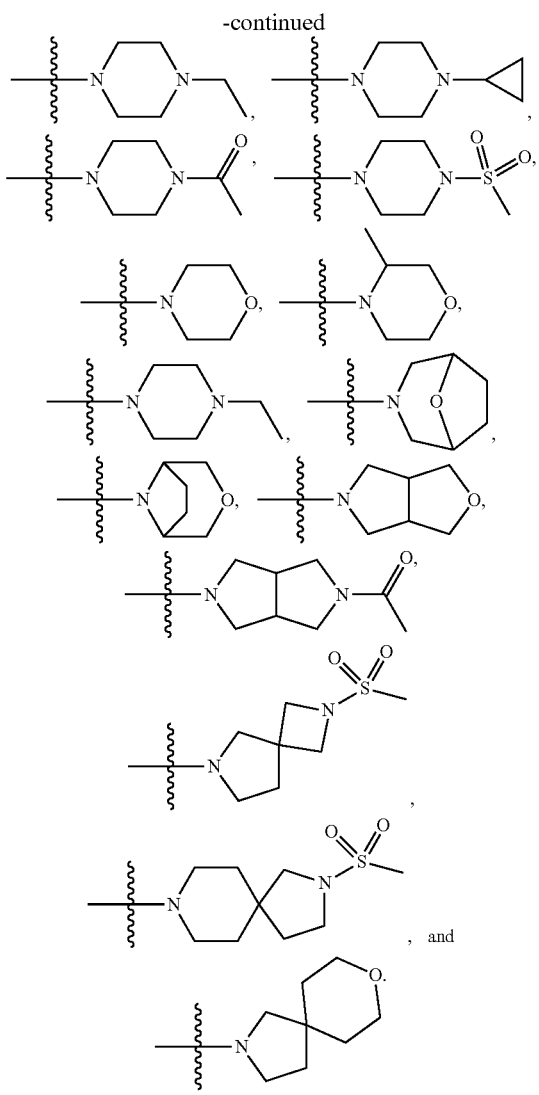
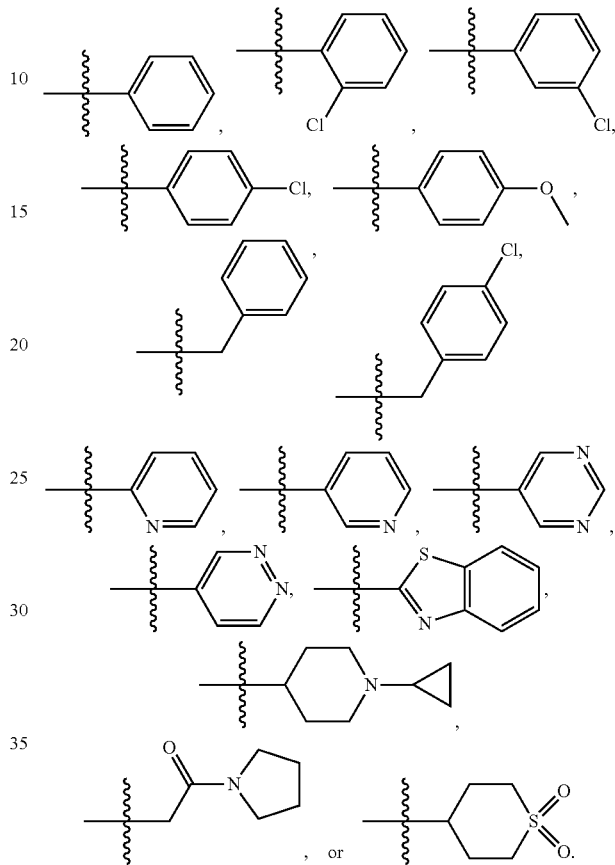

In a further embodiment is a compound of Formula (Ia), wherein $R^4$ is

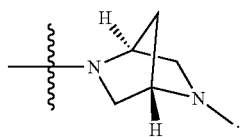 [SMILES: *N1C[C@@H]2C[C@H]1CN2C]

In another embodiment is a compound of Formula (Ia), wherein $R^4$ is —$OR^7$. In another embodiment is a compound of Formula (Ia), wherein $R^4$ is —$OR^7$, and $R^7$ is $C_{1-6}$alkyl. In another embodiment is a compound of Formula (Ia), wherein $R^4$ is —$OR^7$, and $R^7$ is optionally substituted phenyl. In another embodiment is a compound of Formula (Ia), wherein $R^4$ is —$OR^7$, and $R^7$ is optionally substituted $C_{1-6}$alkyl-phenyl. In another embodiment is a compound of Formula (Ia), wherein $R^4$ is —$OR^7$, and $R^7$ is optionally substituted heteroaryl. In another embodiment is a compound of Formula (Ia), wherein $R^4$ is —$OR^7$, and $R^7$ is optionally substituted heterocycloalkyl. In another embodiment is a compound of Formula (Ia), wherein $R^4$ is —$OR^7$, and $R^7$ is —$C_{1-6}$alkylC(O)NR$^9$R$^{10}$. In another embodiment is a compound of Formula (Ia), wherein $R^4$ is —$OR^7$, and $R^7$ is —$C_{1-6}$alkylC(O)NR$^9$R$^{10}$, and $R^9$ and $R^{10}$ are each independently H, or $C_{1-6}$alkyl. In another embodiment is a In another embodiment is a compound of Formula (Ia), wherein $R^5$ is H. In another embodiment is a compound of Formula (Ia), wherein $R^5$ is halogen. In another embodiment is a compound of Formula (Ia), wherein $R^5$ is —Cl. In another embodiment is a compound of Formula (Ia), wherein $R^5$ is —F. In another embodiment is a compound of Formula (Ia), wherein $R^5$ is $C_{1-6}$alkyl. In another embodiment is a compound of Formula (Ia), wherein $R^5$ is $C_{1-6}$haloalkyl. In another embodiment is a compound of Formula (Ia), wherein $R^5$ is —$CF_3$. In another embodiment is a compound of Formula (Ia), wherein $R^5$ is phenyl.

In another embodiment is a compound of Formula (II):

Formula (II)

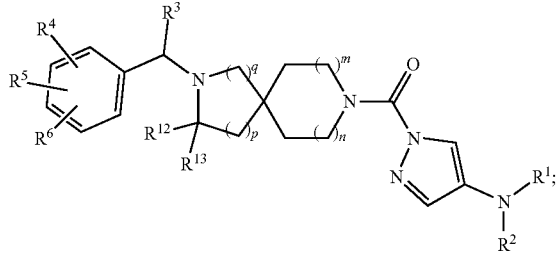

wherein:
$R^1$ is —C(O)R$^{15}$ or —SO$_2$R$^{15}$;
$R^2$ is H or $C_{1-6}$alkyl;

$R^3$ is H or optionally substituted phenyl;

$R^4$ is H, halogen, —$OR^7$, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;

$R^5$ is H, halogen, $C_{1-6}$alkyl, $C_{1-6}$haloalkyl, or phenyl; or $R^4$ and $R^5$ are combined to form a heterocycloalkyl ring;

$R^6$ is H, halogen or $C_{1-6}$alkyl;

$R^7$ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)$NR^{10}R^{11}$;

$R^{10}$ and $R^{11}$ are each independently H, or $C_{1-6}$alkyl; or $R^{10}$ and $R^{11}$ together with the nitrogen to which they are attached are combined to form a heterocycloalkyl ring;

$R^{12}$ is H or $C_{1-6}$alkyl;

$R^{13}$ is H or $C_{1-6}$alkyl;

$R^{15}$ is $C_{1-6}$alkyl;

n is 0 or 1;

m is 0 or 1;

p is 0 or 1; and q is 1 or 2;

wherein when m and n are 0, then p is 1 and q is 2;

when m and n are 1, then q is 1; and when m is 1 and n is 0, or m is 0 and n is 1, then p is 1 and q is 1;

or a solvate, hydrate, tautomer, N-oxide, or pharmaceutically acceptable salt thereof.

In another embodiment is a compound of Formula (II), wherein m is 0, n is 0, p is 1, and q is 2. In another embodiment is a compound of Formula (II), wherein m is 0, n is 1, p is 1, and q is 1. In another embodiment is a compound of Formula (II), wherein m is 1, n is 0, p is 1, and q is 1. In another embodiment is a compound of Formula (II), wherein m is 1, n is 1, p is 0, and q is 1. In another embodiment is a compound of Formula (II), wherein m is 1, n is 1, p is 1, and q is 1.

In another embodiment is a compound of Formula (II), wherein R12 and R13 are H. In another embodiment is a compound of Formula (II), wherein R12 and R13 are C1-6alkyl. In another embodiment is a compound of Formula (II), wherein R12 and R13 are —CH3. In another embodiment is a compound of Formula (II), wherein R12 is H and R13 are —CH3.

In another embodiment is a compound of Formula (II), wherein R2 is H. In another embodiment is a compound of Formula (II), wherein R2 is C1-6alkyl. In another embodiment is a compound of Formula (II), wherein R2 is —CH3.

In another embodiment is a compound of Formula (II), wherein $R^1$ is —C(O)$R^{15}$. In another embodiment is a compound of Formula (II), wherein $R^1$ is —C(O)$R^{15}$ and $R^{15}$ is —CH$_3$. In another embodiment is a compound of Formula (II), wherein $R^1$ is —SO$_2$$R^{15}$. In another embodiment is a compound of Formula (II), wherein $R^1$ is —SO$_2$$R^{15}$ and $R^{15}$ is —CH$_3$. In another embodiment is a compound of Formula (II), wherein $R^1$ is —C(O)$R^{15}$ and $R^2$ is H. In another embodiment is a compound of Formula (II), wherein $R^1$ is —C(O)$R^{15}$, $R^{15}$ is —CH$_3$, and $R^2$ is H. In another embodiment is a compound of Formula (II), wherein $R^1$ is —SO$_2$$R^{15}$ and $R^2$ is H. In another embodiment is a compound of Formula (II), wherein $R^1$ is —SO$_2$$R^{15}$, $R^{15}$ is —CH$_3$, and $R^2$ is H. In another embodiment is a compound of Formula (II), wherein $R^1$ is —C(O)$R^{15}$ and $R^2$ is $C_{1-6}$alkyl. In another embodiment is a compound of Formula (II), wherein $R^1$ is —C(O)$R^{15}$, $R^{15}$ is —CH$_3$, and $R^2$ is $C_{1-6}$alkyl. In another embodiment is a compound of Formula (II), wherein $R^1$ is —SO$_2$$R^{15}$ and $R^2$ is $C_{1-6}$alkyl. In another embodiment is a compound of Formula (II), wherein $R^1$ is —SO$_2$$R^{15}$, $R^{15}$ is —CH$_3$, and $R^2$ is $C_{1-6}$alkyl. In another embodiment is a compound of Formula (II), wherein $R^1$ is —C(O)$R^{15}$ and $R^2$ is —CH$_3$. In another embodiment is a compound of Formula (II), wherein $R^1$ is —C(O)$R^{15}$, $R^{15}$ is —CH$_3$, and $R^2$ is —CH$_3$. In another embodiment is a compound of Formula (II), wherein $R^1$ is —SO$_2$$R^{15}$ and $R^2$ is —CH$_3$. In another embodiment is a compound of Formula (II), wherein $R^1$ is —SO$_2$$R^{15}$, $R^{15}$ is —CH$_3$, and $R^2$ is —CH$_3$.

In another embodiment is a compound of Formula (II), wherein R3 is H. In another embodiment is a compound of Formula (II), wherein R3 is optionally substituted phenyl.

In another embodiment is a compound of Formula (II), wherein R4 is H. In another embodiment is a compound of Formula (II), wherein $R^4$ is halogen. In another embodiment is a compound of Formula (II), wherein $R^4$ is —Cl. In another embodiment is a compound of Formula (II), wherein $R^4$ is —F. In another embodiment is a compound of Formula (II), wherein $R^4$ is $C_{1-6}$alkyl. In another embodiment is a compound of Formula (II), wherein $R^4$ is $C_{1-6}$haloalkyl. In another embodiment is a compound of Formula (II), wherein $R^4$ is —CF$_3$. In another embodiment is a compound of Formula (II), wherein $R^4$ is optionally substituted phenyl. In another embodiment is a compound of Formula (II), wherein $R^4$ is optionally substituted heteroaryl. In another embodiment is a compound of Formula (II), wherein $R^4$ is

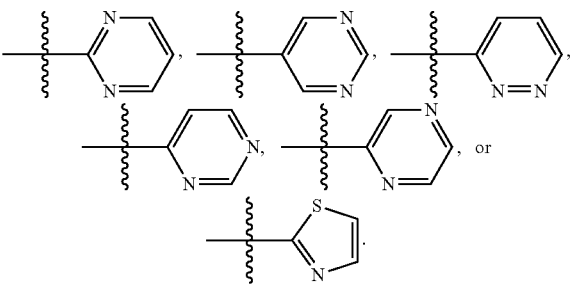

In another embodiment is a compound of Formula (II), wherein $R^4$ is

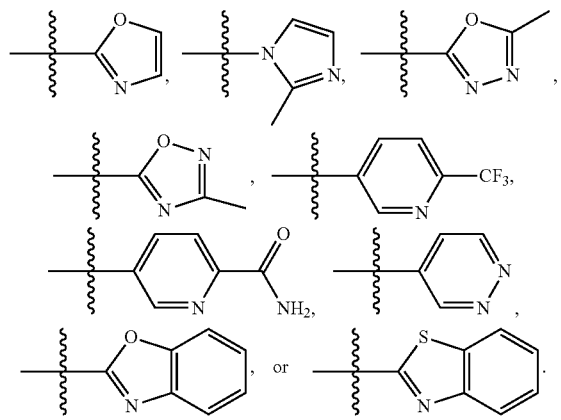

In another embodiment is a compound of Formula (II), wherein $R^4$ is optionally substituted $C_{1-6}$alkyl-heterocycloalkyl. In another embodiment is a compound of Formula (II), wherein $R^4$ is optionally substituted heterocycloalkyl. In another embodiment is a compound of Formula (II), wherein $R^4$ is optionally substituted heterocycloalkyl selected from

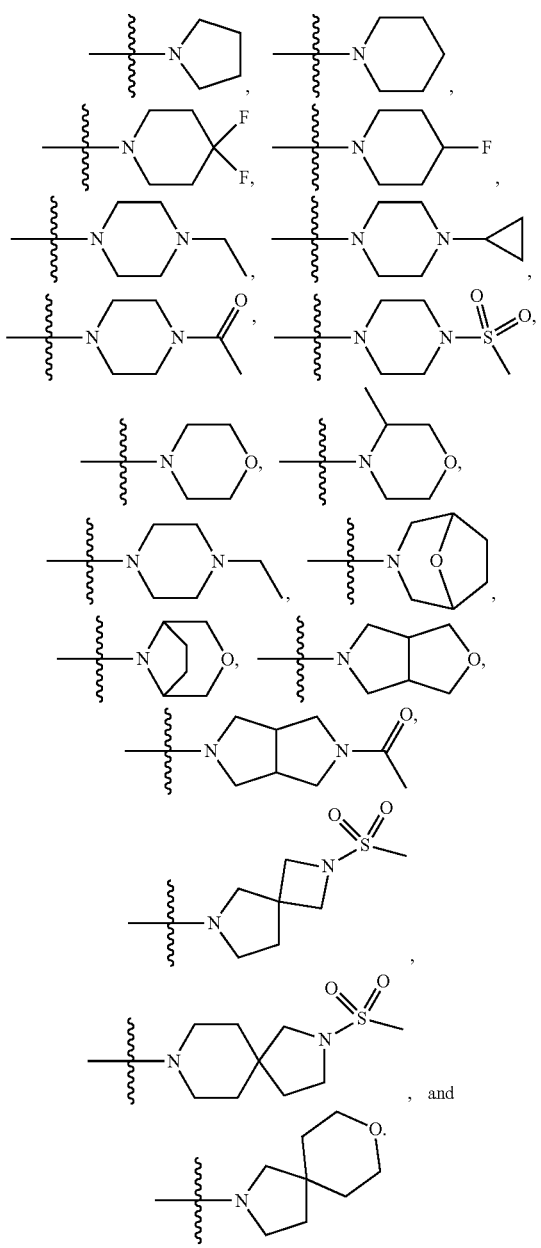

In a further embodiment is a compound of Formula (II), wherein $R^4$ is

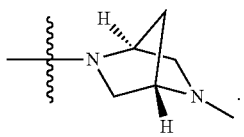 [SMILES: *N1C[C@@H]2C[C@H]1CN2C]

In another embodiment is a compound of Formula (II), wherein $R^4$ is —$OR^7$. In another embodiment is a compound of Formula (II), wherein $R^4$ is —$OR^7$, and $R^7$ is $C_{1-6}$alkyl. In another embodiment is a compound of Formula (II), wherein $R^4$ is —$OR^7$, and $R^7$ is optionally substituted phenyl. In another embodiment is a compound of Formula (II), wherein $R^4$ is —$OR^7$, and $R^7$ is optionally substituted $C_{1-6}$alkyl-phenyl. In another embodiment is a compound of Formula (II), wherein $R^4$ is —$OR^7$, and $R^7$ is optionally substituted heteroaryl. In another embodiment is a compound of Formula (II), wherein $R^4$ is —$OR^7$, and $R^7$ is optionally substituted heterocycloalkyl. In another embodiment is a compound of Formula (II), wherein $R^4$ is —$OR^7$, and $R^7$ is —$C_{1-6}$alkylC(O)$NR^9R^{10}$. In another embodiment is a compound of Formula (II), wherein $R^4$ is —$OR^7$, and $R^7$ is —$C_{1-6}$alkylC(O)$NR^9R^{10}$, and $R^9$ and $R^{10}$ are each independently H, or $C_{1-6}$alkyl. In another embodiment is a compound of Formula (II), wherein $R^4$ is —$OR^7$, and $R^7$ is —$C_{1-6}$alkylC(O)$NR^9R^{10}$, and $R^9$ and $R^{10}$ together with the nitrogen to which they are attached are combined to form a heterocycloalkyl ring. In another embodiment is a compound of Formula (II), wherein $R^4$ is —$OR^7$, and $R^7$ is $C_{1-6}$alkyl,

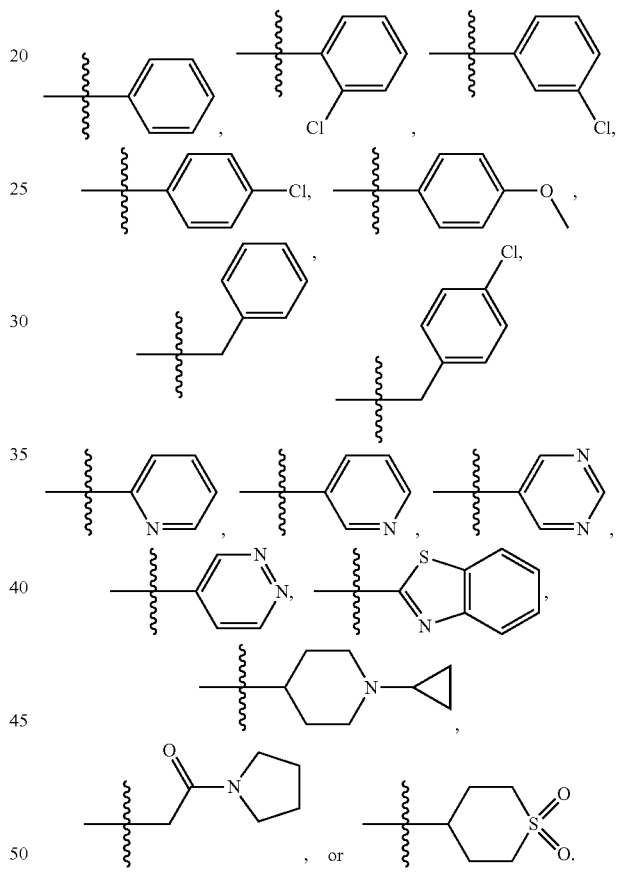

In another embodiment is a compound of Formula (II), wherein R5 is H. In another embodiment is a compound of Formula (II), wherein R5 is halogen. In another embodiment is a compound of Formula (II), wherein R5 is —Cl. In another embodiment is a compound of Formula (II), wherein R5 is —F. In another embodiment is a compound of Formula (II), wherein R5 is C1-6alkyl. In another embodiment is a compound of Formula (II), wherein R5 is C1-6haloalkyl. In another embodiment is a compound of Formula (II), wherein R5 is —CF3. In another embodiment is a compound of Formula (II), wherein R5 is phenyl.

In another embodiment is a compound of Formula (II), wherein $R^6$ is H. In another embodiment is a compound of Formula (II), wherein $R^6$ is halogen. In another embodiment is a compound of Formula (II), wherein $R^6$ is —Cl. In another embodiment is a compound of Formula (II), wherein R⁶ is —F. In another embodiment is a compound of Formula (II), wherein R⁶ is $C_{1-6}$alkyl.

In another embodiment is a compound of Formula (IIa):

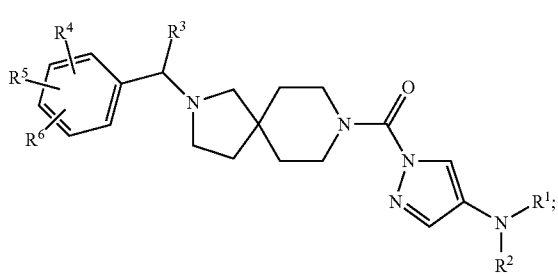

Formula (IIa)

wherein:
- R¹ is —C(O)R¹⁵ or —SO₂R¹⁵;
- R² is H or $C_{1-6}$alkyl;
- R³ is H or optionally substituted phenyl;
- R⁴ is H, halogen, —OR⁷, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
- R⁵ is H, halogen, $C_{1-6}$alkyl, $C_{1-6}$haloalkyl, or phenyl; or R⁴ and R⁵ are combined to form a heterocycloalkyl ring;
- R⁶ is H, halogen or $C_{1-6}$alkyl;
- R⁷ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)NR¹⁰R¹¹;
- R¹⁰ and R¹¹ are each independently H, or $C_{1-6}$alkyl; or R¹⁰ and R¹¹ together with the nitrogen to which they are attached are combined to form a heterocycloalkyl ring; and
- R¹⁵ is $C_{1-6}$alkyl;

or a solvate, hydrate, tautomer, N-oxide, or pharmaceutically acceptable salt thereof.

In another embodiment is a compound of Formula (IIa), wherein R2 is H. In another embodiment is a compound of Formula (IIa), wherein R2 is C1-6alkyl. In another embodiment is a compound of Formula (IIa), wherein R2 is —CH₃.

In another embodiment is a compound of Formula (IIa), wherein R¹ is —C(O)R¹⁵. In another embodiment is a compound of Formula (IIa), wherein R¹ is —C(O)R¹⁵ and R¹⁵ is —CH₃. In another embodiment is a compound of Formula (IIa), wherein R¹ is —SO₂R¹⁵. In another embodiment is a compound of Formula (IIa), wherein R¹ is —SO₂R¹⁵ and R¹⁵ is —CH₃. In another embodiment is a compound of Formula (IIa), wherein R¹ is —C(O)R¹⁵ and R² is H. In another embodiment is a compound of Formula (IIa), wherein R¹ is —C(O)R¹⁵, R¹⁵ is —CH₃, and R² is H. In another embodiment is a compound of Formula (IIa), wherein R¹ is —SO2R¹⁵ and R² is H. In another embodiment is a compound of Formula (IIa), wherein R¹ is —SO₂R¹⁵, R¹⁵ is —CH₃, and R² is H. In another embodiment is a compound of Formula (IIa), wherein R¹ is —C(O)R¹⁵ and R² is $C_{1-6}$alkyl. In another embodiment is a compound of Formula (IIa), wherein R¹ is —C(O)R¹⁵, R¹⁵ is —CH₃, and R² is $C_{1-6}$alkyl. In another embodiment is a compound of Formula (IIa), wherein R¹ is —SO₂R¹⁵ and R² is $C_{1-6}$alkyl. In another embodiment is a compound of Formula (IIa), wherein R¹ is —SO₂R¹⁵, R¹⁵ is —CH₃, and R² is $C_{1-6}$alkyl. In another embodiment is a compound of Formula (IIa), wherein R¹ is —C(O)R¹⁵ and R² is —CH₃. In another embodiment is a compound of Formula (IIa), wherein R¹ is —C(O)R¹⁵, R¹⁵ is —CH₃, and R² is —CH₃. In another embodiment is a compound of Formula (IIa), wherein R¹ is —SO₂R¹⁵ and R² is —CH₃. In another embodiment is a compound of Formula (IIa), wherein R¹ is —SO₂R¹⁵, R¹⁵ is —CH₃, and R² is —CH₃.

In another embodiment is a compound of Formula (IIa), wherein R3 is H. In another embodiment is a compound of Formula (IIa), wherein R3 is optionally substituted phenyl.

In another embodiment is a compound of Formula (IIa), wherein R⁴ is H. In another embodiment is a compound of Formula (IIa), wherein R⁴ is halogen. In another embodiment is a compound of Formula (IIa), wherein R⁴ is —Cl. In another embodiment is a compound of Formula (IIa), wherein R⁴ is —F. In another embodiment is a compound of Formula (IIa), wherein R⁴ is $C_{1-6}$alkyl. In another embodiment is a compound of Formula (IIa), wherein R⁴ is $C_{1-6}$haloalkyl. In another embodiment is a compound of Formula (IIa), wherein R⁴ is —CF₃. In another embodiment is a compound of Formula (IIa), wherein R⁴ is optionally substituted phenyl. In another embodiment is a compound of Formula (IIa), wherein R⁴ is optionally substituted heteroaryl. In another embodiment is a compound of Formula (IIa), wherein R⁴ is

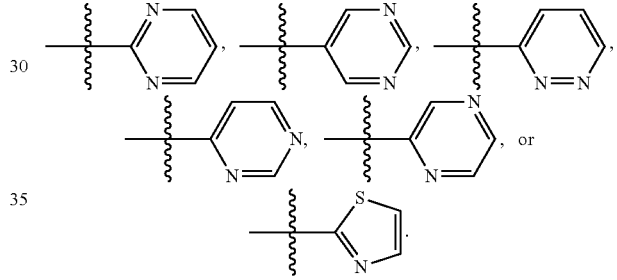

In another embodiment is a compound of Formula (IIa), wherein R⁴ is

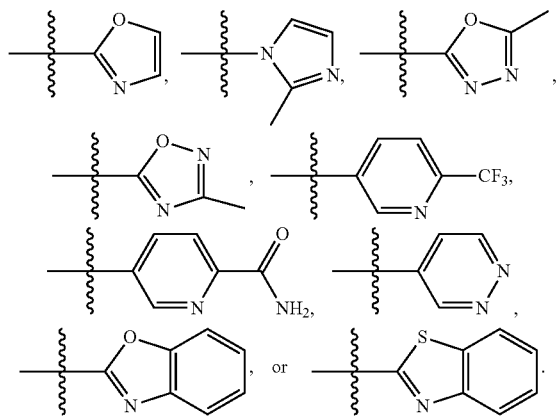

In another embodiment is a compound of Formula (IIa), wherein R⁴ is optionally substituted $C_{1-6}$alkyl-heterocycloalkyl. In another embodiment is a compound of Formula (IIa), wherein R⁴ is optionally substituted heterocycloalkyl. In another embodiment is a compound of Formula (IIa), wherein R⁴ is optionally substituted heterocycloalkyl selected from

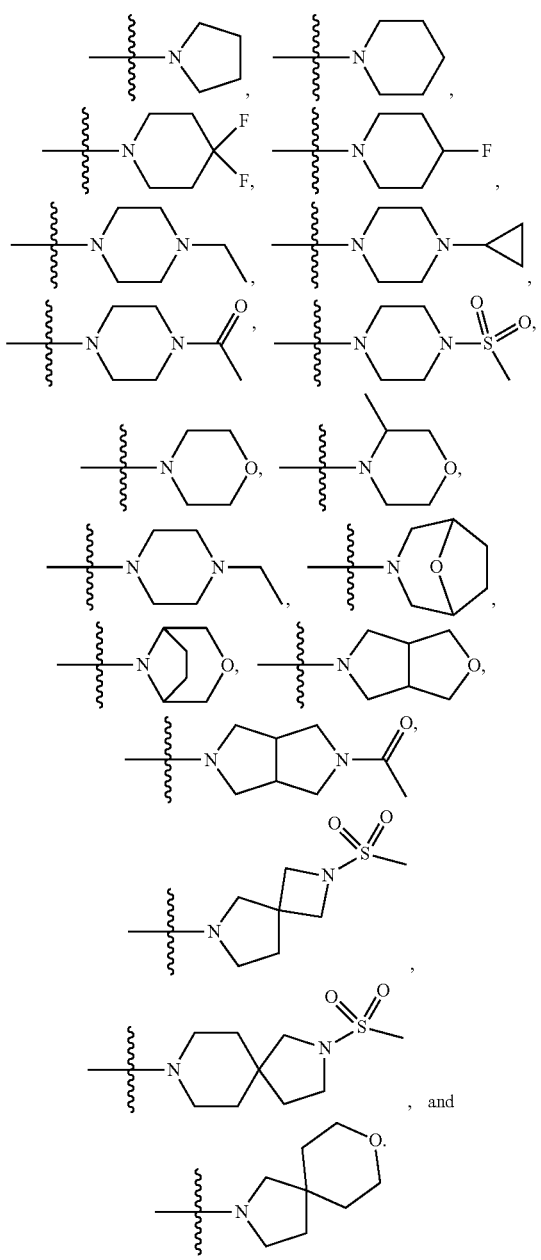

In another embodiment is a compound of Formula (IIa), wherein $R^4$ is

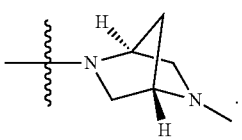 [SMILES: *N1C[C@@H]2C[C@H]1CN2C]

In another embodiment is a compound of Formula (IIa), wherein $R^4$ is —$OR^7$. In another embodiment is a compound of Formula (IIa), wherein $R^4$ is —$OR^7$, and $R^7$ is $C_{1-6}$alkyl. In another embodiment is a compound of Formula (IIa), wherein $R^4$ is —$OR^7$, and $R^7$ is optionally substituted phenyl. In another embodiment is a compound of Formula (IIa), wherein $R^4$ is —$OR^7$, and $R^7$ is optionally substituted $C_{1-6}$alkyl-phenyl. In another embodiment is a compound of Formula (IIa), wherein $R^4$ is —$OR^7$, and $R^7$ is optionally substituted heteroaryl. In another embodiment is a compound of Formula (IIa), wherein $R^4$ is —$OR^7$, and $R^7$ is optionally substituted heterocycloalkyl. In another embodiment is a compound of Formula (IIa), wherein $R^4$ is —$OR^7$, and $R^7$ is —$C_{1-6}$alkylC(O)$NR^9R^{10}$. In another embodiment is a compound of Formula (IIa), wherein $R^4$ is —$OR^7$, and $R^7$ is —$C_{1-6}$alkylC(O)$NR^9R^{10}$, and $R^9$ and $R^{10}$ are each independently H, or $C_{1-6}$alkyl. In another embodiment is a compound of Formula (IIa), wherein $R^4$ is —$OR^7$, and $R^7$ is —$C_{1-6}$alkylC(O)$NR^9R^{10}$, and $R^9$ and $R^{10}$ together with the nitrogen to which they are attached are combined to form a heterocycloalkyl ring. In another embodiment is a compound of Formula (IIa), wherein $R^4$ is —$OR^7$, and $R^7$ is $C_{1-6}$alkyl,

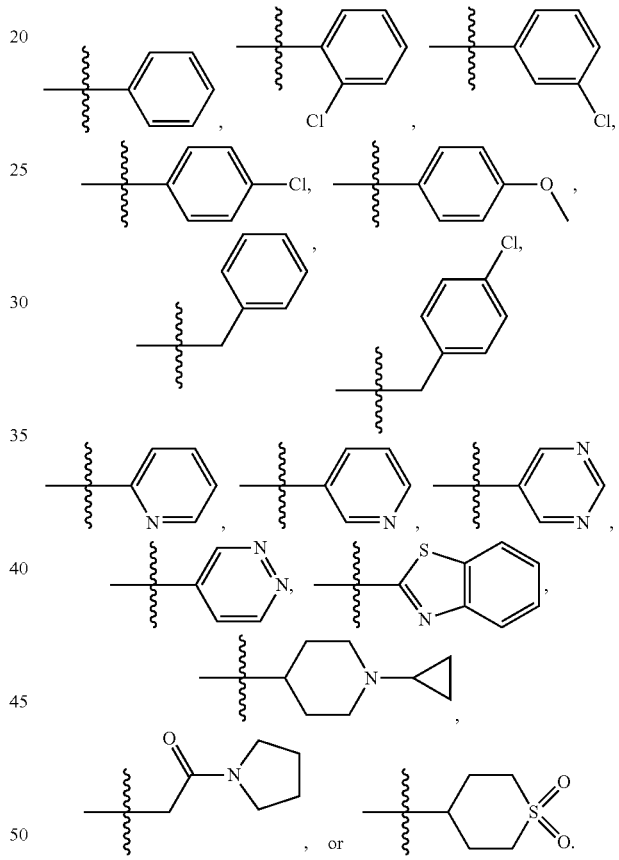

In another embodiment is a compound of Formula (IIa), wherein $R^5$ is H. In another embodiment is a compound of Formula (IIa), wherein $R^5$ is halogen. In another embodiment is a compound of Formula (IIa), wherein $R^5$ is —Cl. In another embodiment is a compound of Formula (IIa), wherein $R^5$ is —F. In another embodiment is a compound of Formula (IIa), wherein $R^5$ is $C_{1-6}$alkyl. In another embodiment is a compound of Formula (IIa), wherein $R^5$ is $C_{1-6}$haloalkyl. In another embodiment is a compound of Formula (IIa), wherein $R^5$ is —$CF_3$. In another embodiment is a compound of Formula (IIa), wherein $R^5$ is phenyl.

In another embodiment is a compound of Formula (IIa), wherein R6 is H. In another embodiment is a compound of Formula (IIa), wherein R6 is halogen. In another embodiment is a compound of Formula (IIa), wherein R6 is —Cl.

In another embodiment is a compound of Formula (IIa), wherein R6 is —F. In another embodiment is a compound of Formula (IIa), wherein R6 is C1-6alkyl.

In another embodiment is a compound of Formula (IIb):

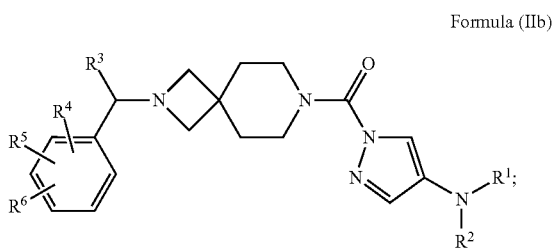

Formula (IIb)

wherein:
- R$^1$ is —C(O)R$^{15}$ or —SO$_2$R$^{15}$;
- R$^2$ is H or C$_{1-6}$alkyl;
- R$^3$ is H or optionally substituted phenyl;
- R$^4$ is H, halogen, —OR$^7$, C$_{1-6}$alkyl, C$_{1-6}$haloalkyl, optionally substituted heterocycloalkyl, optionally substituted C$_{1-6}$alkyl-heterocycloalkyl, optionally substituted phenyl, or optionally substituted heteroaryl;
- R$^5$ is H, halogen, C$_{1-6}$alkyl, C$_{1-6}$haloalkyl, or phenyl; or R$^4$ and R$^5$ are combined to form a heterocycloalkyl ring;
- R$^6$ is H, halogen or C$_{1-6}$alkyl;
- R$^7$ is H, C$_{1-6}$alkyl, optionally substituted phenyl, optionally substituted C$_{1-6}$alkyl-phenyl, optionally substituted heteroaryl, optionally substituted heterocycloalkyl, or —C$_{1-6}$alkylC(O)NR$^{10}$R$^{11}$;
- R$^{10}$ and R$^{11}$ are each independently H, or C$_{1-6}$alkyl; or R$^{10}$ and R$^{11}$ together with the nitrogen to which they are attached are combined to form a heterocycloalkyl ring; and
- R$^{15}$ is C$_{1-6}$alkyl;

or a solvate, hydrate, tautomer, N-oxide, or pharmaceutically acceptable salt thereof.

In another embodiment is a compound of Formula (IIb), wherein R2 is H. In another embodiment is a compound of Formula (IIb), wherein R2 is C1-6alkyl. In another embodiment is a compound of Formula (IIb), wherein R2 is —CH3.

In another embodiment is a compound of Formula (IIb), wherein R$^1$ is —C(O)R$^{15}$. In another embodiment is a compound of Formula (IIb), wherein R$^1$ is —C(O)R$^{15}$ and R$^{15}$ is —CH$_3$. In another embodiment is a compound of Formula (IIb), wherein R$^1$ is —SO$_2$R$^{15}$. In another embodiment is a compound of Formula (IIb), wherein R$^1$ is —SO$_2$R$^{15}$ and R$^{15}$ is —CH$_3$. In another embodiment is a compound of Formula (IIb), wherein R$^1$ is —C(O)R$^{15}$ and R$^2$ is H. In another embodiment is a compound of Formula (IIb), wherein R$^1$ is —C(O)R$^{15}$, R$^{15}$ is —CH$_3$, and R$^2$ is H. In another embodiment is a compound of Formula (IIb), wherein R$^1$ is —SO$_2$R$^{15}$ and R$^2$ is H. In another embodiment is a compound of Formula (IIb), wherein R$^1$ is —SO$_2$R$^{15}$, R$^{15}$ is —CH$_3$, and R$^2$ is H. In another embodiment is a compound of Formula (IIb), wherein R$^1$ is —C(O)R$^{15}$ and R$^2$ is C$_{1-6}$alkyl. In another embodiment is a compound of Formula (IIb), wherein R$^1$ is —C(O)R$^{15}$, R$^{15}$ is —CH$_3$, and R$^2$ is C$_{1-6}$alkyl. In another embodiment is a compound of Formula (IIb), wherein R$^1$ is —SO$_2$R$^{15}$ and R$^2$ is C$_{1-6}$alkyl. In another embodiment is a compound of Formula (IIb), wherein R$^1$ is —SO$_2$R$^{15}$, R$^{15}$ is —CH$_3$, and R$^2$ is C$_{1-6}$alkyl. In another embodiment is a compound of Formula (IIb), wherein R1 is —C(O)R15 and R2 is —CH3. In another embodiment is a compound of Formula (IIb), wherein R1 is —C(O)R15, R15 is —CH3, and R2 is —CH3. In another embodiment is a compound of Formula (IIb), wherein R1 is —SO2R15 and R2 is —CH3. In another embodiment is a compound of Formula (IIb), wherein R1 is —SO2R15, R15 is —CH3, and R2 is —CH3.

In another embodiment is a compound of Formula (IIb), wherein R3 is H. In another embodiment is a compound of Formula (IIb), wherein R3 is optionally substituted phenyl.

In another embodiment is a compound of Formula (IIb), wherein R$^4$ is H. In another embodiment is a compound of Formula (IIb), wherein R$^4$ is halogen. In another embodiment is a compound of Formula (IIb), wherein R$^4$ is —Cl. In another embodiment is a compound of Formula (IIb), wherein R$^4$ is —F. In another embodiment is a compound of Formula (IIb), wherein R$^4$ is C$_{1-6}$alkyl. In another embodiment is a compound of Formula (IIb), wherein R$^4$ is C$_{1-6}$haloalkyl. In another embodiment is a compound of Formula (IIb), wherein R$^4$ is —CF$_3$. In another embodiment is a compound of Formula (IIb), wherein R$^4$ is optionally substituted phenyl. In another embodiment is a compound of Formula (IIb), wherein R$^4$ is optionally substituted heteroaryl. In another embodiment is a compound of Formula (IIb), wherein R$^4$ is

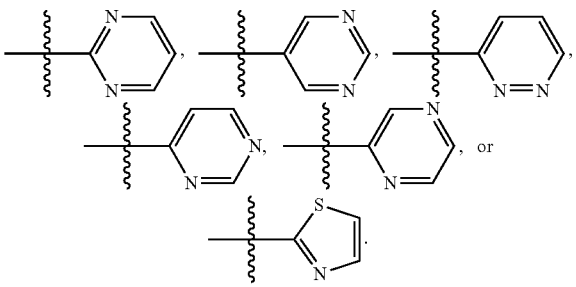

In another embodiment is a compound of Formula (IIb), wherein R$^4$ is

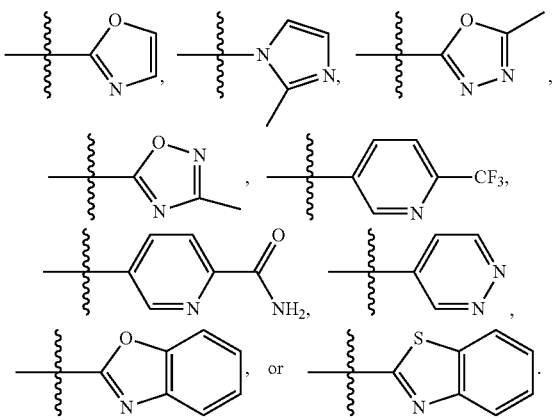

In another embodiment is a compound of Formula (IIb), wherein R$^4$ is optionally substituted C$_{1-6}$alkyl-heterocycloalkyl. In another embodiment is a compound of Formula (IIb), wherein R$^4$ is optionally substituted heterocycloalkyl. In another embodiment is a compound of Formula (IIb), wherein R$^4$ is optionally substituted heterocycloalkyl selected from

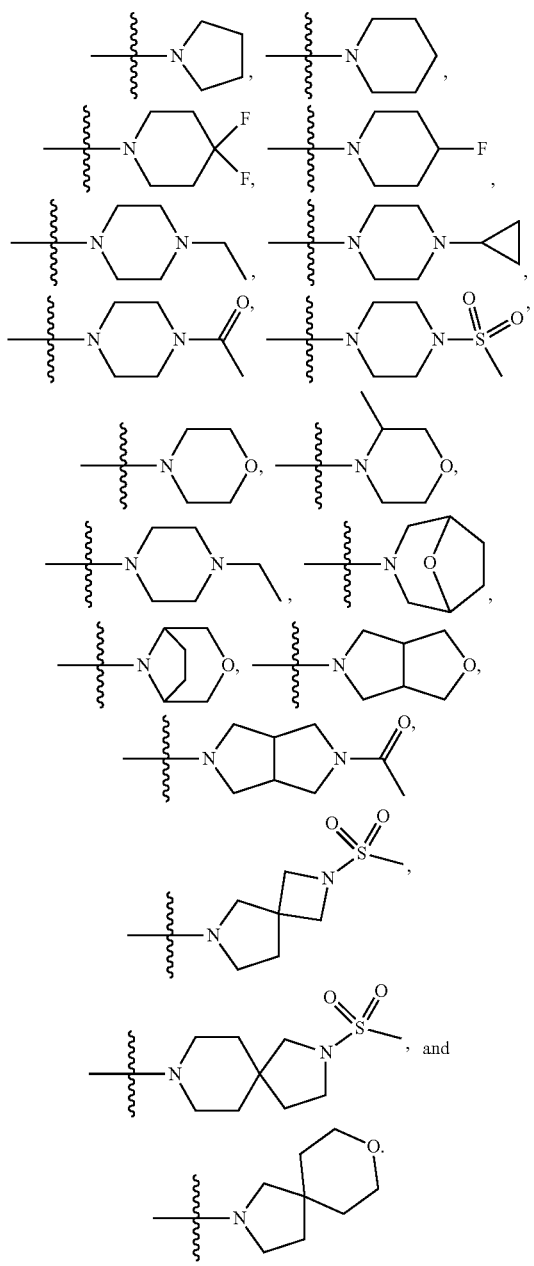

In another embodiment is a compound of Formula (IIb), wherein $R^4$ is

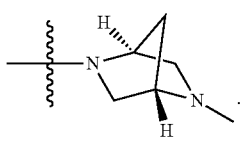 [SMILES: *N1C[C@@H]2C[C@H]1CN2C]

In another embodiment is a compound of Formula (IIb), wherein $R^4$ is —$OR^7$. In another embodiment is a compound of Formula (IIb), wherein $R^4$ is —$OR^7$, and $R^7$ is $C_{1-6}$alkyl. In another embodiment is a compound of Formula (IIb), wherein $R^4$ is —$OR^7$, and $R^7$ is optionally substituted phenyl. In another embodiment is a compound of Formula (IIb), wherein $R^4$ is —$OR^7$, and $R^7$ is optionally substituted $C_{1-6}$alkyl-phenyl. In another embodiment is a compound of Formula (IIb), wherein $R^4$ is —$OR^7$, and $R^7$ is optionally substituted heteroaryl. In another embodiment is a compound of Formula (IIb), wherein $R^4$ is —$OR^7$, and $R^7$ is optionally substituted heterocycloalkyl. In another embodiment is a compound of Formula (IIb), wherein $R^4$ is —$OR^7$, and $R^7$ is —$C_{1-6}$alkylC(O)$NR^9R^{10}$. In another embodiment is a compound of Formula (IIb), wherein $R^4$ is —$OR^7$, and $R^7$ is —$C_{1-6}$alkylC(O)$NR^9R^{10}$, and $R^9$ and $R^{10}$ are each independently H, or $C_{1-6}$alkyl. In another embodiment is a compound of Formula (IIb), wherein $R^4$ is —$OR^7$, and $R^7$ is —$C_{1-6}$alkylC(O)$NR^9R^{10}$, and $R^9$ and $R^{10}$ together with the nitrogen to which they are attached are combined to form a heterocycloalkyl ring. In another embodiment is a compound of Formula (IIb), wherein $R^4$ is —$OR^7$, and $R^7$ is $C_{1-6}$alkyl,

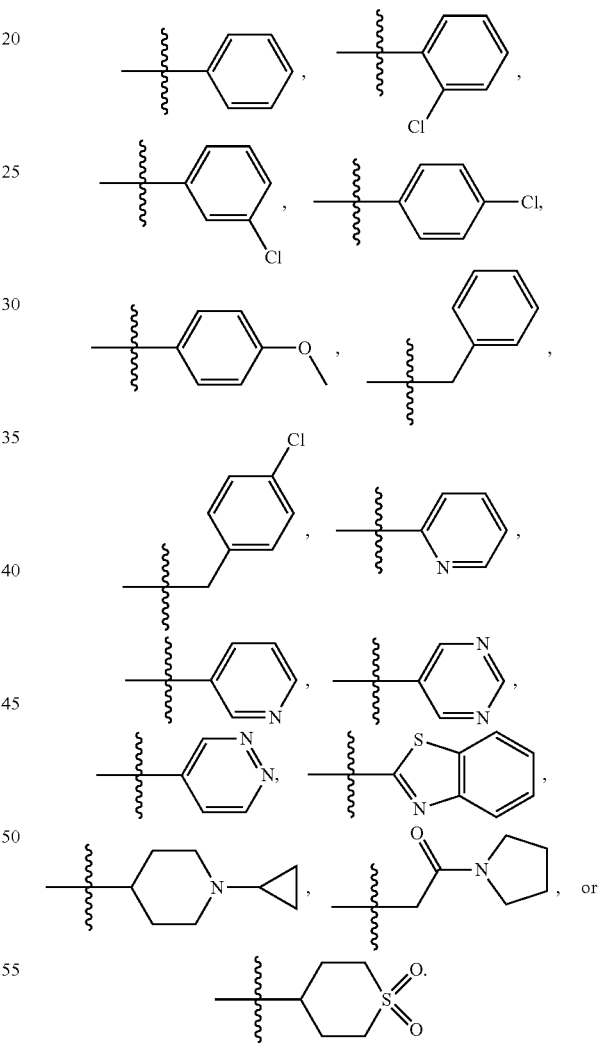

In another embodiment is a compound of Formula (IIb), wherein $R^5$ is H. In another embodiment is a compound of Formula (IIb), wherein $R^5$ is halogen. In another embodiment is a compound of Formula (IIb), wherein $R^5$ is —Cl. In another embodiment is a compound of Formula (IIb), wherein $R^5$ is —F. In another embodiment is a compound of Formula (IIb), wherein $R^5$ is $C_{1-6}$alkyl. In another embodiment is a compound of Formula (IIb), wherein $R^5$ is $C_{1-6}$haloalkyl. In another embodiment is a compound of Formula (IIb), wherein R⁵ is —CF₃. In another embodiment is a compound of Formula (IIb), wherein R5 is phenyl.

In another embodiment is a compound of Formula (IIb), wherein R6 is H. In another embodiment is a compound of Formula (IIb), wherein R6 is halogen. In another embodiment is a compound of Formula (IIb), wherein R6 is —Cl. In another embodiment is a compound of Formula (IIb), wherein R6 is —F. In another embodiment is a compound of Formula (IIb), wherein R6 is C1-6alkyl.

In another embodiment is a compound of Formula (IIc):

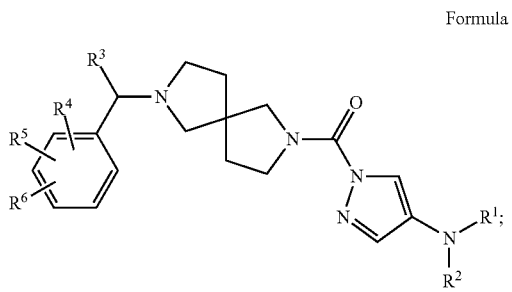

Formula (IIc)

wherein:
R¹ is —C(O)R¹⁵ or —SO₂R¹⁵;
R² is H or C₁₋₆alkyl;
R³ is H or optionally substituted phenyl;
R⁴ is H, halogen, —OR⁷, C₁₋₆alkyl, C₁₋₆haloalkyl, optionally substituted heterocycloalkyl, optionally substituted C₁₋₆alkyl-heterocycloalkyl, optionally substituted phenyl, or optionally substituted heteroaryl;
R⁵ is H, halogen, C₁₋₆alkyl, C₁₋₆haloalkyl, or phenyl; or R⁴ and R⁵ are combined to form a heterocycloalkyl ring;
R⁶ is H, halogen or C₁₋₆alkyl;
R⁷ is H, C₁₋₆alkyl, optionally substituted phenyl, optionally substituted C₁₋₆alkyl-phenyl, optionally substituted heteroaryl, optionally substituted heterocycloalkyl, or —C₁₋₆alkylC(O)NR¹⁰R¹¹;
R¹⁰ and R¹¹ are each independently H, or C₁₋₆alkyl; or R¹⁰ and R¹¹ together with the nitrogen to which they are attached are combined to form a heterocycloalkyl ring; and
R¹⁵ is C₁₋₆alkyl;
or a solvate, hydrate, tautomer, N-oxide, or pharmaceutically acceptable salt thereof.

In another embodiment is a compound of Formula (IIc), wherein R² is H. In another embodiment is a compound of Formula (IIc), wherein R² is C₁₋₆alkyl. In another embodiment is a compound of Formula (IIc), wherein R² is —CH₃.

In another embodiment is a compound of Formula (IIc), wherein R¹ is —C(O)R¹⁵. In another embodiment is a compound of Formula (IIc), wherein R¹ is —C(O)R¹⁵ and R¹⁵ is —CH₃. In another embodiment is a compound of Formula (IIc), wherein R¹ is —SO₂R¹⁵. In another embodiment is a compound of Formula (IIc), wherein R¹ is —SO₂R¹⁵ and R¹⁵ is —CH₃. In another embodiment is a compound of Formula (IIc), wherein R¹ is —C(O)R¹⁵ and R² is H. In another embodiment is a compound of Formula (IIc), wherein R¹ is —C(O)R¹⁵, R¹⁵ is —CH₃, and R² is H. In another embodiment is a compound of Formula (IIc), wherein R¹ is —SO₂R¹⁵ and R² is H. In another embodiment is a compound of Formula (IIc), wherein R¹ is —SO₂R¹⁵, R¹⁵ is —CH₃, and R² is H. In another embodiment is a compound of Formula (IIc), wherein R¹ is —C(O)R¹⁵ and R² is C₁₋₆alkyl. In another embodiment is a compound of Formula (IIc), wherein R¹ is —C(O)R¹⁵, R¹⁵ is —CH₃, and R² is C₁₋₆alkyl. In another embodiment is a compound of Formula (IIc), wherein R¹ is —SO₂R¹⁵ and R² is C₁₋₆alkyl. In another embodiment is a compound of Formula (IIc), wherein R¹ is —SO₂R¹⁵, R¹⁵ is —CH₃, and R² is C₁₋₆alkyl. In another embodiment is a compound of Formula (IIc), wherein R¹ is —C(O)R¹⁵ and R² is —CH₃. In another embodiment is a compound of Formula (IIc), wherein R1 is —C(O)R15, R15 is —CH3, and R2 is —CH3. In another embodiment is a compound of Formula (IIc), wherein R1 is —SO2R15 and R2 is —CH3. In another embodiment is a compound of Formula (IIc), wherein R1 is —SO2R15, R15 is —CH3, and R2 is —CH3.

In another embodiment is a compound of Formula (IIc), wherein R3 is H. In another embodiment is a compound of Formula (IIc), wherein R3 is optionally substituted phenyl.

In another embodiment is a compound of Formula (IIc), wherein R4 is H. In another embodiment is a compound of Formula (IIc), wherein R⁴ is halogen. In another embodiment is a compound of Formula (IIc), wherein R⁴ is —Cl. In another embodiment is a compound of Formula (IIc), wherein R⁴ is —F. In another embodiment is a compound of Formula (IIc), wherein R⁴ is C₁₋₆alkyl. In another embodiment is a compound of Formula (IIc), wherein R⁴ is C₁₋₆haloalkyl. In another embodiment is a compound of Formula (IIc), wherein R⁴ is —CF₃. In another embodiment is a compound of Formula (IIc), wherein R⁴ is optionally substituted phenyl. In another embodiment is a compound of Formula (IIc), wherein R⁴ is optionally substituted heteroaryl. In another embodiment is a compound of Formula (IIc), wherein R⁴ is

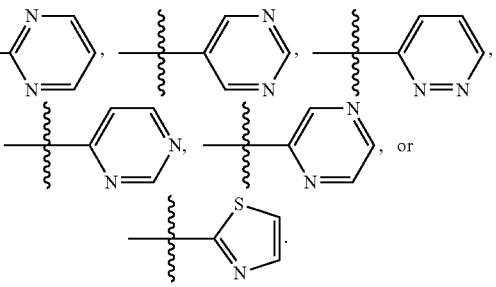

In another embodiment is a compound of Formula (IIc), wherein R⁴ is

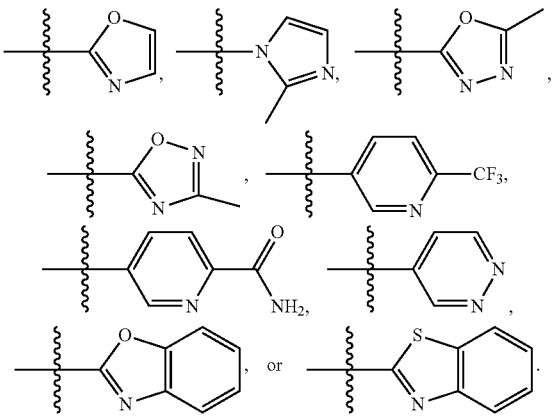

In another embodiment is a compound of Formula (IIc), wherein R⁴ is optionally substituted C₁₋₆alkyl-heterocycloalkyl. In another embodiment is a compound of Formula (IIc), wherein R⁴ is optionally substituted heterocycloalkyl.

In another embodiment is a compound of Formula (IIc), wherein R⁴ is optionally substituted heterocycloalkyl selected from

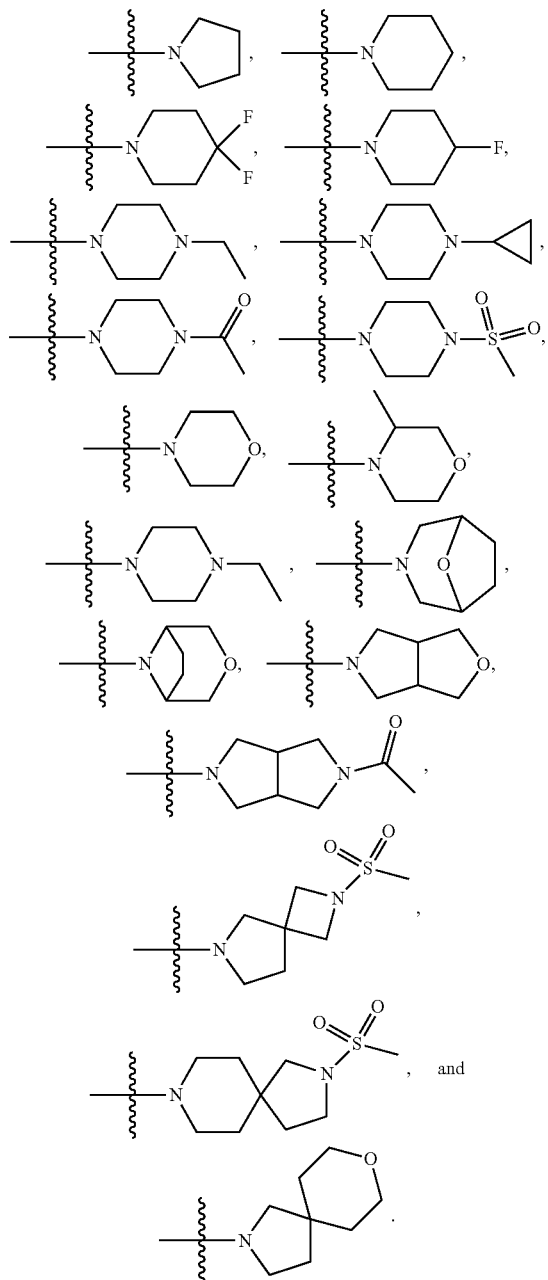

In another embodiment is a compound of Formula (IIc), wherein R⁴ is

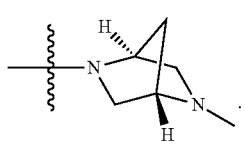 [SMILES: *N1C[C@@H]2C[C@H]1CN2C]

In another embodiment is a compound of Formula (IIc), wherein R⁴ is —OR⁷. In another embodiment is a compound of Formula (IIc), wherein R⁴ is —OR⁷, and R⁷ is $C_{1-6}$alkyl. In another embodiment is a compound of Formula (IIc), wherein R⁴ is —OR⁷, and R⁷ is optionally substituted phenyl. In another embodiment is a compound of Formula (IIc), wherein R⁴ is —OR⁷, and R⁷ is optionally substituted $C_{1-6}$alkyl-phenyl. In another embodiment is a compound of Formula (IIc), wherein R⁴ is —OR⁷, and R⁷ is optionally substituted heteroaryl. In another embodiment is a compound of Formula (IIc), wherein R⁴ is —OR⁷, and R⁷ is optionally substituted heterocycloalkyl. In another embodiment is a compound of Formula (IIc), wherein R⁴ is —OR⁷, and R⁷ is —$C_{1-6}$alkylC(O)NR⁹R¹⁰. In another embodiment is a compound of Formula (IIc), wherein R⁴ is —OR⁷, and R⁷ is —$C_{1-6}$alkylC(O)NR⁹R¹⁰, and R⁹ and R¹⁰ are each independently H, or $C_{1-6}$alkyl. In another embodiment is a compound of Formula (IIc), wherein R⁴ is —OR⁷, and R⁷ is —$C_{1-6}$alkylC(O)NR⁹R¹⁰, and R⁹ and R¹⁰ together with the nitrogen to which they are attached are combined to form a heterocycloalkyl ring. In another embodiment is a compound of Formula (IIc), wherein R⁴ is —OR⁷, and R⁷ is $C_{1-6}$alkyl,

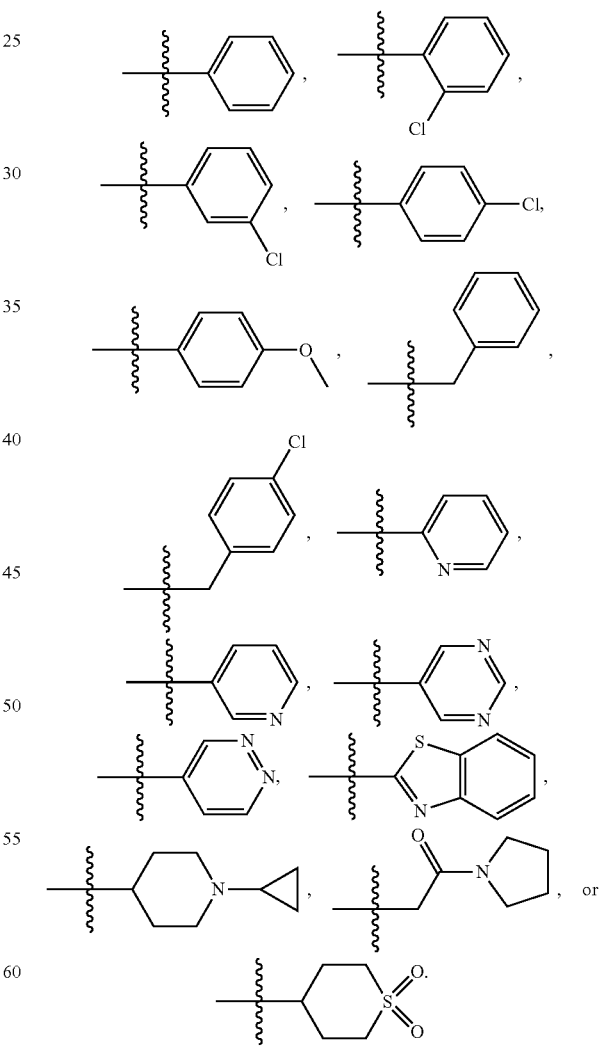

In another embodiment is a compound of Formula (IIc), wherein R5 is H. In another embodiment is a compound of Formula (IIc), wherein R5 is halogen. In another embodiment is a compound of Formula (IIc), wherein R5 is —Cl. In another embodiment is a compound of Formula (IIc), wherein R5 is —F. In another embodiment is a compound of Formula (IIc), wherein R5 is C1-6alkyl. In another embodiment is a compound of Formula (IIc), wherein R5 is C1-6haloalkyl. In another embodiment is a compound of Formula (IIc), wherein R5 is —CF3. In another embodiment is a compound of Formula (IIc), wherein R5 is phenyl.

In another embodiment is a compound of Formula (IIc), wherein R6 is H. In another embodiment is a compound of Formula (IIc), wherein R6 is halogen. In another embodiment is a compound of Formula (IIc), wherein R6 is —Cl. In another embodiment is a compound of Formula (IIc), wherein R6 is —F. In another embodiment is a compound of Formula (IIc), wherein R6 is C1-6alkyl.

In another embodiment is a compound of Formula (IId):

Formula (IId)

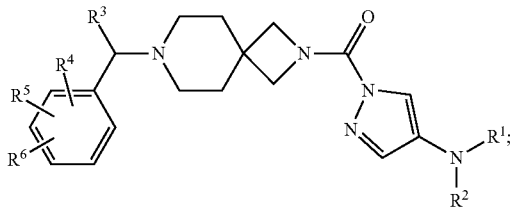

wherein:
R$^1$ is —C(O)R$^{15}$ or —SO$_2$R$^{15}$;
R$^2$ is H or C$_{1-6}$alkyl;
R$^3$ is H or optionally substituted phenyl;
R$^4$ is H, halogen, —OR$^7$, C$_{1-6}$alkyl, C$_{1-6}$haloalkyl, optionally substituted heterocycloalkyl, optionally substituted C$_{1-6}$alkyl-heterocycloalkyl, optionally substituted phenyl, or optionally substituted heteroaryl;
R$^5$ is H, halogen, C$_{1-6}$alkyl, C$_{1-6}$haloalkyl, or phenyl; or R$^4$ and R$^5$ are combined to form a heterocycloalkyl ring;
R$^6$ is H, halogen or C$_{1-6}$alkyl;
R$^7$ is H, C$_{1-6}$alkyl, optionally substituted phenyl, optionally substituted C$_{1-6}$alkyl-phenyl, optionally substituted heteroaryl, optionally substituted heterocycloalkyl, or —C$_{1-6}$alkylC(O)NR$^{10}$R$^{11}$;
R$^{10}$ and R$^{11}$ are each independently H, or C$_{1-6}$alkyl; or R$^{10}$ and R$^{11}$ together with the nitrogen to which they are attached are combined to form a heterocycloalkyl ring; and
R$^{15}$ is C$_{1-6}$alkyl;
or a solvate, hydrate, tautomer, N-oxide, or pharmaceutically acceptable salt thereof.

In another embodiment is a compound of Formula (IId), wherein R$^2$ is H. In another embodiment is a compound of Formula (IId), wherein R$^2$ is C$_{1-6}$alkyl. In another embodiment is a compound of Formula (IId), wherein R$^2$ is —CH$_3$.

In another embodiment is a compound of Formula (IId), wherein R$^1$ is —C(O)R$^{15}$. In another embodiment is a compound of Formula (IId), wherein R$^1$ is —C(O)R$^{15}$ and R$^{15}$ is —CH$_3$. In another embodiment is a compound of Formula (IId), wherein R$^1$ is —SO$_2$R$^{15}$. In another embodiment is a compound of Formula (IId), wherein R$^1$ is —SO$_2$R$^{15}$ and R$^{15}$ is —CH$_3$. In another embodiment is a compound of Formula (IId), wherein R$^1$ is —C(O)R$^{15}$ and R$^2$ is H. In another embodiment is a compound of Formula (IId), wherein R$^1$ is —C(O)R$^{15}$, R$^{15}$ is —CH$_3$, and R$^2$ is H. In another embodiment is a compound of Formula (IId), wherein R$^1$ is —SO$_2$R$^{15}$ and R$^2$ is H. In another embodiment is a compound of Formula (IId), wherein R$^1$ is —SO$_2$R$^{15}$, R$^{15}$ is —CH$_3$, and R$^2$ is H. In another embodiment is a compound of Formula (IId), wherein R$^1$ is —C(O)R$^{15}$ and R$^2$ is C$_{1-6}$alkyl. In another embodiment is a compound of Formula (IId), wherein R$^1$ is —C(O)R$^{15}$, R$^{15}$ is —CH$_3$, and R$^2$ is C$_{1-6}$alkyl. In another embodiment is a compound of Formula (IId), wherein R$^1$ is —SO$_2$R$^{15}$ and R$^2$ is C$_{1-6}$alkyl. In another embodiment is a compound of Formula (IId), wherein R$^1$ is —SO$_2$R$^{15}$, R$^{15}$ is —CH$_3$, and R$^2$ is C$_{1-6}$alkyl. In another embodiment is a compound of Formula (IId), wherein R$^1$ is —C(O)R$^{15}$ and R$^2$ is —CH$_3$. In another embodiment is a compound of Formula (IId), wherein R1 is —C(O)R15, R15 is —CH3, and R2 is —CH3. In another embodiment is a compound of Formula (IId), wherein R1 is —SO2R15 and R2 is —CH3. In another embodiment is a compound of Formula (IId), wherein R1 is —SO2R15, R15 is —CH3, and R2 is —CH3.

In another embodiment is a compound of Formula (IId), wherein R3 is H. In another embodiment is a compound of Formula (IId), wherein R3 is optionally substituted phenyl.

In another embodiment is a compound of Formula (IId), wherein R$^4$ is H. In another embodiment is a compound of Formula (IId), wherein R$^4$ is halogen. In another embodiment is a compound of Formula (IId), wherein R$^4$ is —Cl. In another embodiment is a compound of Formula (IId), wherein R$^4$ is —F. In another embodiment is a compound of Formula (IId), wherein R$^4$ is C$_{1-6}$alkyl. In another embodiment is a compound of Formula (IId), wherein R$^4$ is C$_{1-6}$haloalkyl. In another embodiment is a compound of Formula (IId), wherein R$^4$ is —CF$_3$. In another embodiment is a compound of Formula (IId), wherein R$^4$ is optionally substituted phenyl. In another embodiment is a compound of Formula (IId), wherein R$^4$ is optionally substituted heteroaryl. In another embodiment is a compound of Formula (IId), wherein R$^4$ is

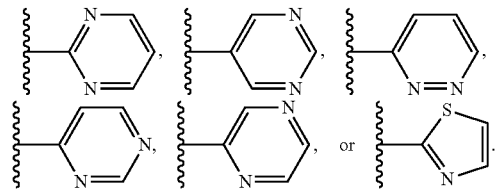

In another embodiment is a compound of Formula (IId), wherein R$^4$ is

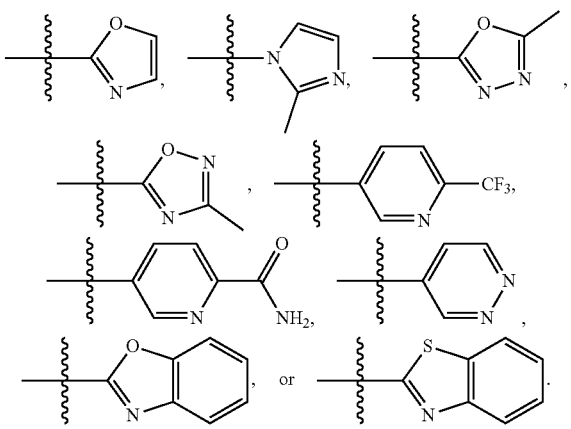

In another embodiment is a compound of Formula (IId), wherein R$^4$ is optionally substituted C$_{1-6}$alkyl-heterocycloalkyl. In another embodiment is a compound of Formula (IId), wherein R$^4$ is optionally substituted heterocycloalkyl. In another embodiment is a compound of Formula (IId), wherein R$^4$ is optionally substituted heterocycloalkyl selected from

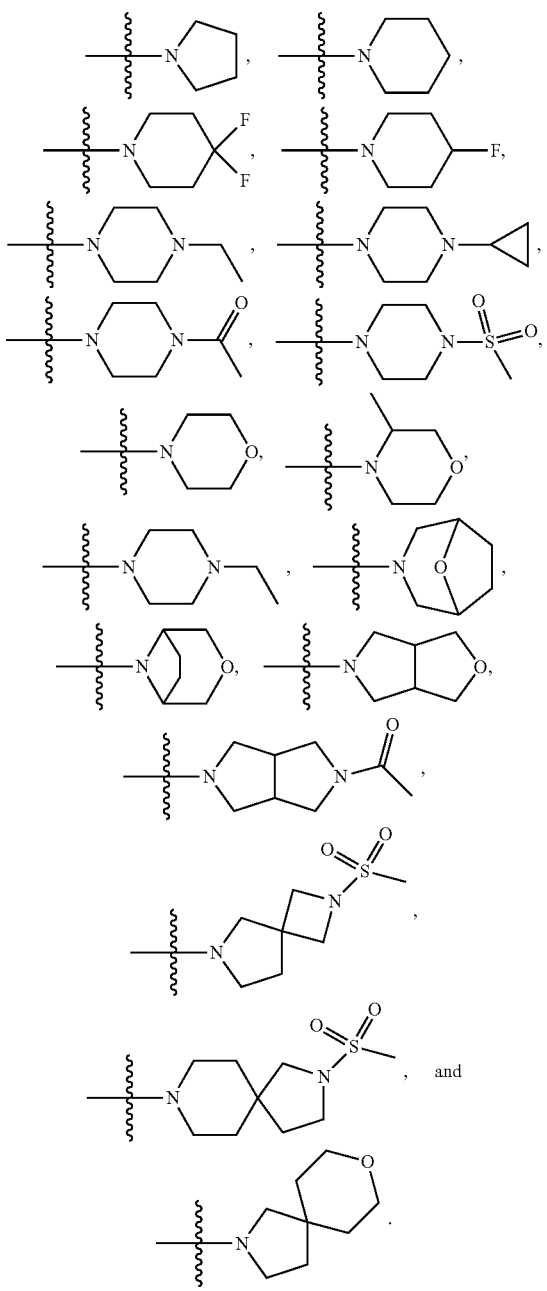

In another embodiment is a compound of Formula (IId), wherein $R^4$ is

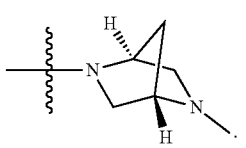 [SMILES: *N1C[C@@H]2C[C@H]1CN2C]

In another embodiment is a compound of Formula (IId), wherein $R^4$ is $-OR^7$. In another embodiment is a compound of Formula (IId), wherein $R^4$ is $-OR^7$, and $R^7$ is $C_{1-6}$alkyl. In another embodiment is a compound of Formula (IId), wherein $R^4$ is $-OR^7$, and $R^7$ is optionally substituted phenyl. In another embodiment is a compound of Formula (IId), wherein $R^4$ is $-OR^7$, and $R^7$ is optionally substituted $C_{1-6}$alkyl-phenyl. In another embodiment is a compound of Formula (IId), wherein $R^4$ is $-OR^7$, and $R^7$ is optionally substituted heteroaryl. In another embodiment is a compound of Formula (IId), wherein $R^4$ is $-OR^7$, and $R^7$ is optionally substituted heterocycloalkyl. In another embodiment is a compound of Formula (IId), wherein $R^4$ is $-OR^7$, and $R^7$ is $-C_{1-6}$alkylC(O)NR$^9$R$^{10}$. In another embodiment is a compound of Formula (IId), wherein $R^4$ is $-OR^7$, and $R^7$ is $-C_{1-6}$alkylC(O)NR$^9$R$^{10}$, and $R^9$ and $R^{10}$ are each independently H, or $C_{1-6}$alkyl. In another embodiment is a compound of Formula (IId), wherein $R^4$ is $-OR^7$, and $R^7$ is $-C_{1-6}$alkylC(O)NR$^9$R$^{10}$, and $R^9$ and $R^{10}$ together with the nitrogen to which they are attached are combined to form a heterocycloalkyl ring. In another embodiment is a compound of Formula (IId), wherein $R^4$ is $-OR^7$, and $R^7$ is $C_{1-6}$alkyl,

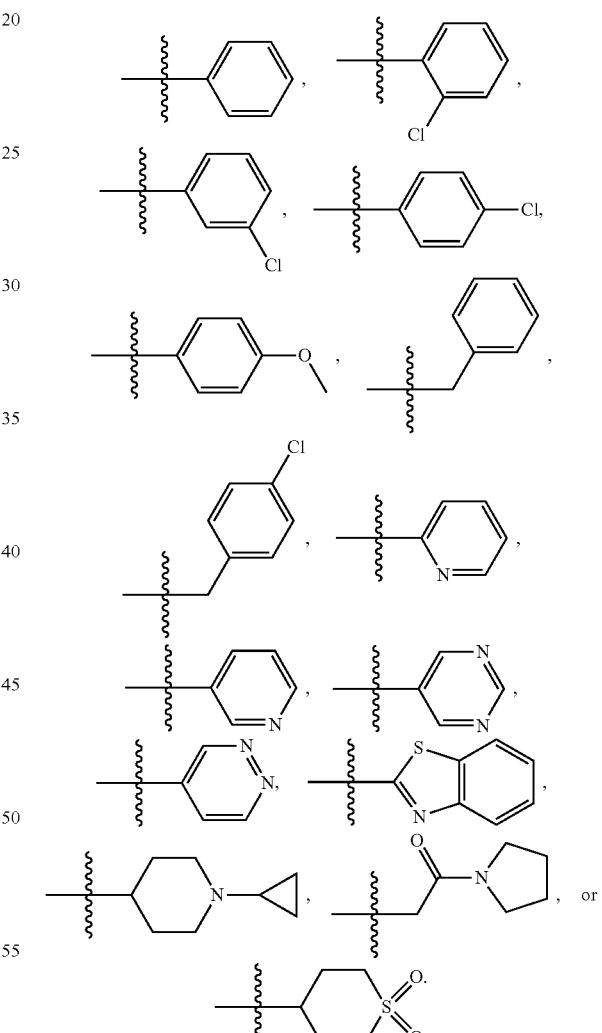

In another embodiment is a compound of Formula (IId), wherein R5 is H. In another embodiment is a compound of Formula (IId), wherein R5 is halogen. In another embodiment is a compound of Formula (IId), wherein R5 is —Cl. In another embodiment is a compound of Formula (IId), wherein R5 is —F. In another embodiment is a compound of Formula (IId), wherein R5 is C1-6alkyl. In another embodiment is a compound of Formula (IId), wherein R5 is C1-6haloalkyl. In another embodiment is a compound of Formula (IId), wherein R5 is —CF3. In another embodiment is a compound of Formula (IId), wherein R5 is phenyl.

In another embodiment is a compound of Formula (IId), wherein R6 is H. In another embodiment is a compound of Formula (IId), wherein $R^6$ is halogen. In another embodiment is a compound of Formula (IId), wherein $R^6$ is —Cl. In another embodiment is a compound of Formula (IId), wherein $R^6$ is —F. In another embodiment is a compound of Formula (IId), wherein $R^6$ is $C_{1-6}$alkyl.

In another embodiment is a compound of Formula (III):

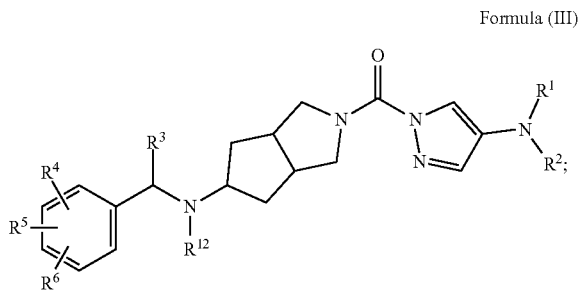

Formula (III)

wherein:
$R^1$ is —C(O)$R^{15}$ or —SO$_2R^{15}$;
$R^2$ is H or $C_{1-6}$alkyl;
$R^3$ is H or optionally substituted phenyl;
$R^4$ is H, halogen, —OR$^7$, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
$R^5$ is H, halogen, $C_{1-6}$alkyl, $C_{1-6}$haloalkyl, or phenyl; or $R^4$ and $R^5$ are combined to form a heterocycloalkyl ring;
$R^6$ is H, halogen or $C_{1-6}$alkyl;
$R^7$ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)NR$^{10}$R$^{11}$;
$R^{10}$ and $R^{11}$ are each independently H, or $C_{1-6}$alkyl; or $R^{10}$ and $R^{11}$ together with the nitrogen to which they are attached are combined to form a heterocycloalkyl ring;
$R^{12}$ is H, $C_{1-6}$alkyl, or —C(O)$C_{1-6}$alkyl; and
$R^{15}$ is $C_{1-6}$alkyl;
or a solvate, hydrate, tautomer, N-oxide, or pharmaceutically acceptable salt thereof.

In another embodiment is a compound of Formula (III), wherein $R^2$ is H. In another embodiment is a compound of Formula (III), wherein $R^2$ is $C_{1-6}$alkyl. In another embodiment is a compound of Formula (III), wherein $R^2$ is —CH$_3$.

In another embodiment is a compound of Formula (III), wherein $R^1$ is —C(O)$R^{15}$. In another embodiment is a compound of Formula (III), wherein $R^1$ is —C(O)$R^{15}$ and $R^{15}$ is —CH$_3$. In another embodiment is a compound of Formula (III), wherein $R^1$ is —SO$_2R^{15}$. In another embodiment is a compound of Formula (III), wherein $R^1$ is —SO$_2R^{15}$ and $R^{15}$ is —CH$_3$. In another embodiment is a compound of Formula (III), wherein $R^1$ is —C(O)$R^{15}$ and $R^2$ is H. In another embodiment is a compound of Formula (III), wherein $R^1$ is —C(O)$R^{15}$, $R^{15}$ is —CH$_3$, and $R^2$ is H. In another embodiment is a compound of Formula (III), wherein $R^1$ is —SO$_2R^{15}$ and $R^2$ is H. In another embodiment is a compound of Formula (III), wherein $R^1$ is —SO$_2R^{15}$, $R^{15}$ is —CH$_3$, and $R^2$ is H. In another embodiment is a compound of Formula (III), wherein $R^1$ is —C(O)$R^{15}$ and $R^2$ is $C_{1-6}$alkyl. In another embodiment is a compound of Formula (III), wherein $R^1$ is —C(O)$R^{15}$, $R^{15}$ is —CH$_3$, and $R^2$ is $C_{1-6}$alkyl. In another embodiment is a compound of Formula (III), wherein $R^1$ is —SO$_2R^{15}$ and $R^2$ is $C_{1-6}$alkyl. In another embodiment is a compound of Formula (III), wherein $R^1$ is —SO$_2R^{15}$, $R^{15}$ is —CH$_3$, and $R^2$ is $C_{1-6}$alkyl. In another embodiment is a compound of Formula (III), wherein $R^1$ is —C(O)$R^{15}$ and $R^2$ is —CH$_3$. In another embodiment is a compound of Formula (III), wherein $R^1$ is —C(O)$R^{15}$, $R^{15}$ is —CH$_3$, and $R^2$ is —CH$_3$. In another embodiment is a compound of Formula (III), wherein R1 is —SO2R15 and R2 is —CH3. In another embodiment is a compound of Formula (III), wherein R1 is —SO2R15, R15 is —CH3, and R2 is —CH3.

In another embodiment is a compound of Formula (III), wherein R3 is H. In another embodiment is a compound of Formula (III), wherein R3 is optionally substituted phenyl.

In another embodiment is a compound of Formula (III), wherein $R^4$ is H. In another embodiment is a compound of Formula (III), wherein $R^4$ is halogen. In another embodiment is a compound of Formula (III), wherein $R^4$ is —Cl. In another embodiment is a compound of Formula (III), wherein $R^4$ is —F. In another embodiment is a compound of Formula (III), wherein $R^4$ is $C_{1-6}$alkyl. In another embodiment is a compound of Formula (III), wherein $R^4$ is $C_{1-6}$haloalkyl. In another embodiment is a compound of Formula (III), wherein $R^4$ is —CF$_3$. In another embodiment is a compound of Formula (III), wherein $R^4$ is optionally substituted phenyl. In another embodiment is a compound of Formula (III), wherein $R^4$ is optionally substituted heteroaryl. In another embodiment is a compound of Formula (III), wherein $R^4$ is

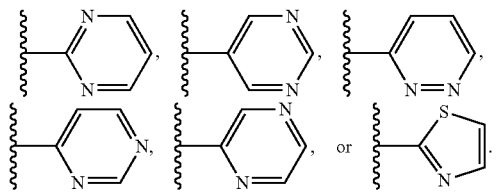

In another embodiment is a compound of Formula (III), wherein $R^4$ is

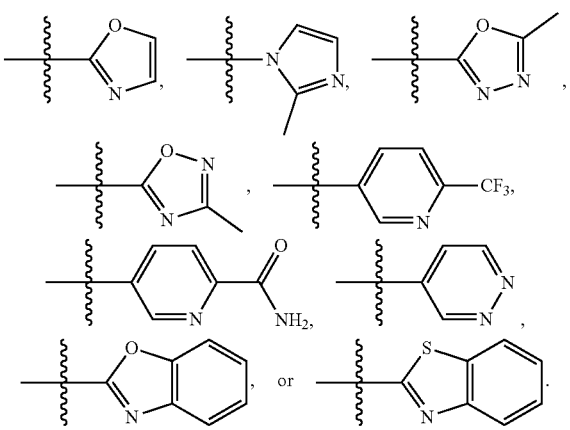

In another embodiment is a compound of Formula (III), wherein $R^4$ is optionally substituted $C_{1-6}$alkyl-heterocycloalkyl. In another embodiment is a compound of Formula (III), wherein R⁴ is optionally substituted heterocycloalkyl. In another embodiment is a compound of Formula (III), wherein R⁴ is optionally substituted heterocycloalkyl selected from

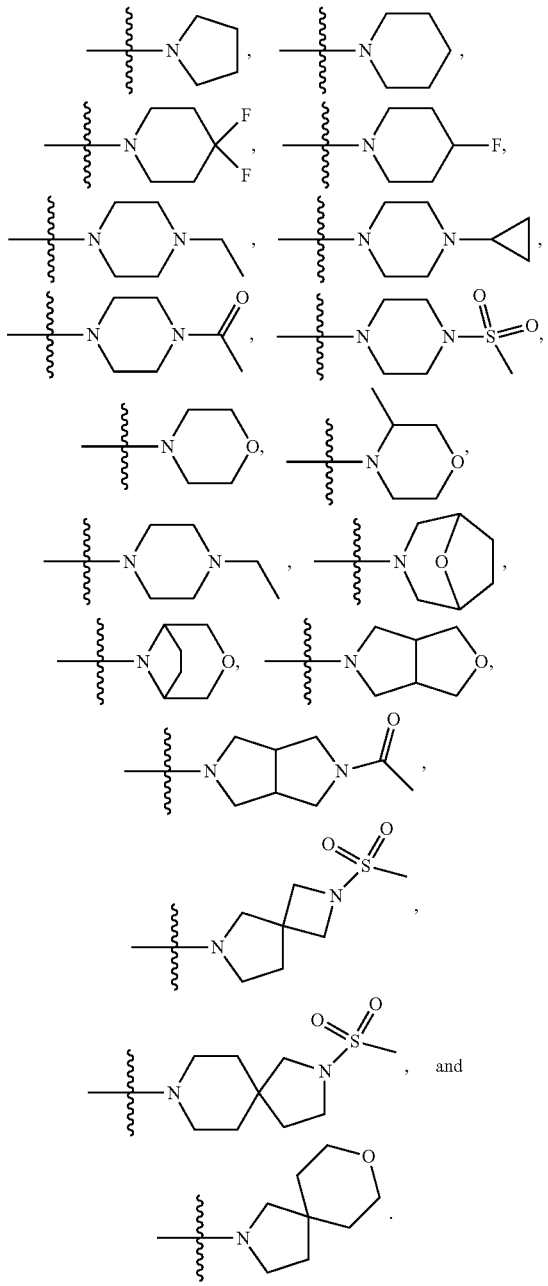

In another embodiment is a compound of Formula (III), wherein R⁴ is

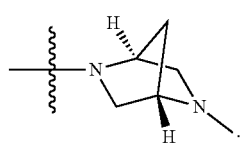 [SMILES: *N1C[C@@H]2C[C@H]1CN2C]

In another embodiment is a compound of Formula (III), wherein R⁴ is —OR⁷. In another embodiment is a compound of Formula (III), wherein R⁴ is —OR⁷, and R⁷ is $C_{1-6}$alkyl. In another embodiment is a compound of Formula (III), wherein R⁴ is —OR⁷, and R⁷ is optionally substituted phenyl. In another embodiment is a compound of Formula (III), wherein R⁴ is —OR⁷, and R⁷ is optionally substituted $C_{1-6}$alkyl-phenyl. In another embodiment is a compound of Formula (III), wherein R⁴ is —OR⁷, and R⁷ is optionally substituted heteroaryl. In another embodiment is a compound of Formula (III), wherein R⁴ is —OR⁷, and R⁷ is optionally substituted heterocycloalkyl. In another embodiment is a compound of Formula (III), wherein R⁴ is —OR⁷, and R⁷ is —$C_{1-6}$alkylC(O)NR⁹R¹⁰. In another embodiment is a compound of Formula (III), wherein R⁴ is —OR⁷, and R⁷ is —$C_{1-6}$alkylC(O)NR⁹R¹⁰, and R⁹ and R¹⁰ are each independently H, or $C_{1-6}$alkyl. In another embodiment is a compound of Formula (III), wherein R⁴ is —OR⁷, and R⁷ is —$C_{1-6}$alkylC(O)NR⁹R¹⁰, and R⁹ and R¹⁰ together with the nitrogen to which they are attached are combined to form a heterocycloalkyl ring. In another embodiment is a compound of Formula (III), wherein R⁴ is —OR⁷, and R⁷ is $C_{1-6}$alkyl,

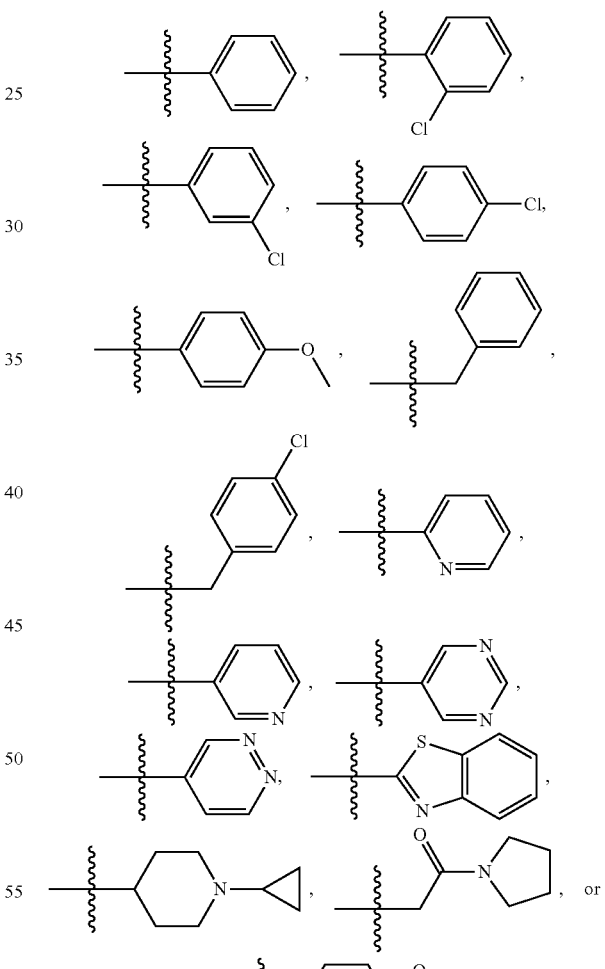

In another embodiment is a compound of Formula (III), wherein R5 is H. In another embodiment is a compound of Formula (III), wherein R5 is halogen. In another embodiment is a compound of Formula (III), wherein R5 is —Cl. In another embodiment is a compound of Formula (III), wherein R5 is —F. In another embodiment is a compound of Formula (III), wherein R5 is C1-6alkyl. In another embodiment is a compound of Formula (III), wherein R5 is C1-6haloalkyl. In another embodiment is a compound of Formula (III), wherein R5 is —CF3. In another embodiment is a compound of Formula (III), wherein R5 is phenyl.

In another embodiment is a compound of Formula (III), wherein $R^6$ is H. In another embodiment is a compound of Formula (III), wherein $R^6$ is halogen. In another embodiment is a compound of Formula (III), wherein $R^6$ is —Cl. In another embodiment is a compound of Formula (III), wherein $R^6$ is —F. In another embodiment is a compound of Formula (III), wherein $R^6$ is $C_{1-6}$alkyl.

In another embodiment is a compound of Formula (III), wherein R12 is H. In another embodiment is a compound of Formula (III), wherein R12 is C1-6alkyl. In another embodiment is a compound of Formula (III), wherein R12 is —C(O)C1-6alkyl.

In another embodiment is a compound of Formula (III) having the structure of Formula (IIIa):

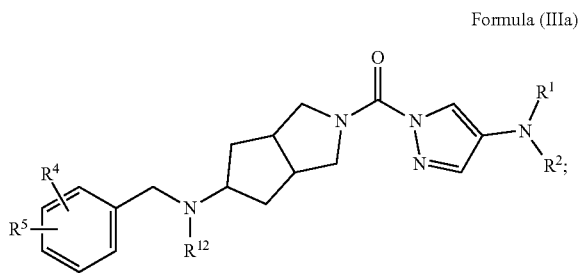

Formula (IIIa)

wherein:
$R^1$ is —C(O)$R^{15}$ or —SO$_2$$R^{15}$;
$R^2$ is H or $C_{1-6}$alkyl;
$R^4$ is H, halogen, —O$R^7$, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
$R^5$ is H, halogen, $C_{1-6}$alkyl, $C_{1-6}$haloalkyl, or phenyl; or $R^4$ and $R^5$ are combined to form a heterocycloalkyl ring;
$R^7$ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)N$R^{10}R^{11}$;
$R^{10}$ and $R^{11}$ are each independently H, or $C_{1-6}$alkyl; or $R^{10}$ and $R^{11}$ together with the nitrogen to which they are attached are combined to form a heterocycloalkyl ring;
$R^{12}$ is H, $C_{1-6}$alkyl, or —C(O)$C_{1-6}$alkyl; and
$R^{15}$ is $C_{1-6}$alkyl;
or a solvate, hydrate, tautomer, N-oxide, or pharmaceutically acceptable salt thereof.

In another embodiment is a compound of Formula (IIIa), wherein R2 is H. In another embodiment is a compound of Formula (IIIa), wherein R2 is C1-6alkyl. In another embodiment is a compound of Formula (IIIa), wherein R2 is —CH3.

In another embodiment is a compound of Formula (IIIa), wherein $R^1$ is —C(O)$R^{15}$. In another embodiment is a compound of Formula (IIIa), wherein $R^1$ is —C(O)$R^{15}$ and $R^{15}$ is —CH$_3$. In another embodiment is a compound of Formula (IIIa), wherein $R^1$ is —SO$_2$$R^{15}$. In another embodiment is a compound of Formula (IIIa), wherein $R^1$ is —SO$_2$$R^{15}$ and $R^{15}$ is —CH$_3$. In another embodiment is a compound of Formula (IIIa), wherein $R^1$ is —C(O)$R^{15}$ and $R^2$ is H. In another embodiment is a compound of Formula (IIIa), wherein $R^1$ is —C(O)$R^{15}$, $R^{15}$ is —CH$_3$, and $R^2$ is H. In another embodiment is a compound of Formula (IIIa), wherein $R^1$ is —SO$_2$$R^{15}$ and $R^2$ is H. In another embodiment is a compound of Formula (IIIa), wherein $R^1$ is —SO$_2$$R^{15}$, $R^{15}$ is —CH$_3$, and $R^2$ is H. In another embodiment is a compound of Formula (IIIa), wherein $R^1$ is —C(O)$R^{15}$ and $R^2$ is $C_{1-6}$alkyl. In another embodiment is a compound of Formula (IIIa), wherein $R^1$ is —C(O)$R^{15}$, $R^{15}$ is —CH$_3$, and $R^2$ is $C_{1-6}$alkyl. In another embodiment is a compound of Formula (IIIa), wherein $R^1$ is —SO$_2$$R^{15}$ and $R^2$ is $C_{1-6}$alkyl. In another embodiment is a compound of Formula (IIIa), wherein $R^1$ is —SO$_2$$R^{15}$, $R^{15}$ is —CH$_3$, and $R^2$ is $C_{1-6}$alkyl. In another embodiment is a compound of Formula (IIIa), wherein $R^1$ is —C(O)$R^{15}$ and $R^2$ is —CH$_3$. In another embodiment is a compound of Formula (IIIa), wherein $R^1$ is —C(O)$R^{15}$, $R^{15}$ is —CH$_3$, and $R^2$ is —CH$_3$. In another embodiment is a compound of Formula (IIIa), wherein $R^1$ is —SO$_2$$R^{15}$ and $R^2$ is —CH$_3$. In another embodiment is a compound of Formula (IIIa), wherein $R^1$ is —SO$_2$$R^{15}$, $R^{15}$ is —CH$_3$, and $R^2$ is —CH$_3$.

In another embodiment is a compound of Formula (IIIa), wherein $R^4$ is H. In another embodiment is a compound of Formula (IIIa), wherein $R^4$ is halogen. In another embodiment is a compound of Formula (IIIa), wherein $R^4$ is —Cl. In another embodiment is a compound of Formula (IIIa), wherein $R^4$ is —F. In another embodiment is a compound of Formula (IIIa), wherein $R^4$ is $C_{1-6}$alkyl. In another embodiment is a compound of Formula (IIIa), wherein $R^4$ is $C_{1-6}$haloalkyl. In another embodiment is a compound of Formula (IIIa), wherein $R^4$ is —CF$_3$. In another embodiment is a compound of Formula (IIIa), wherein $R^4$ is optionally substituted phenyl. In another embodiment is a compound of Formula (IIIa), wherein $R^4$ is optionally substituted heteroaryl. In another embodiment is a compound of Formula (IIIa), wherein $R^4$ is

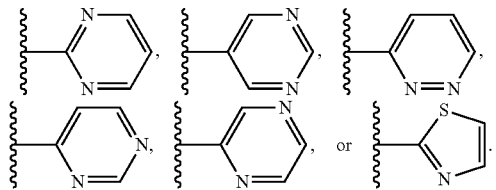

In another embodiment is a compound of Formula (IIIa), wherein $R^4$ is

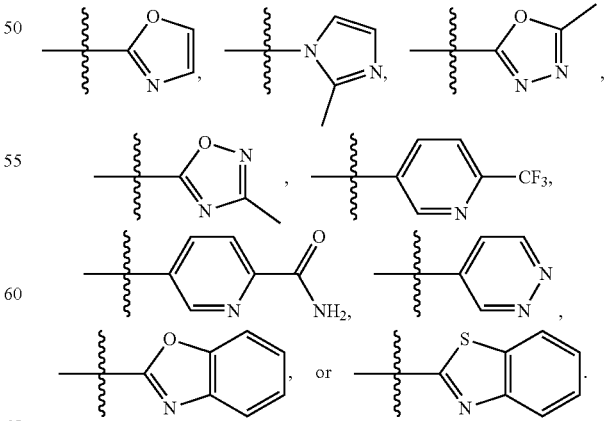

In another embodiment is a compound of Formula (IIIa), wherein $R^4$ is optionally substituted $C_{1-6}$alkyl-heterocycloalkyl. In another embodiment is a compound of Formula (IIIa), wherein $R^4$ is optionally substituted heterocycloalkyl. In another embodiment is a compound of Formula (IIIa), wherein $R^4$ is optionally substituted heterocycloalkyl selected from

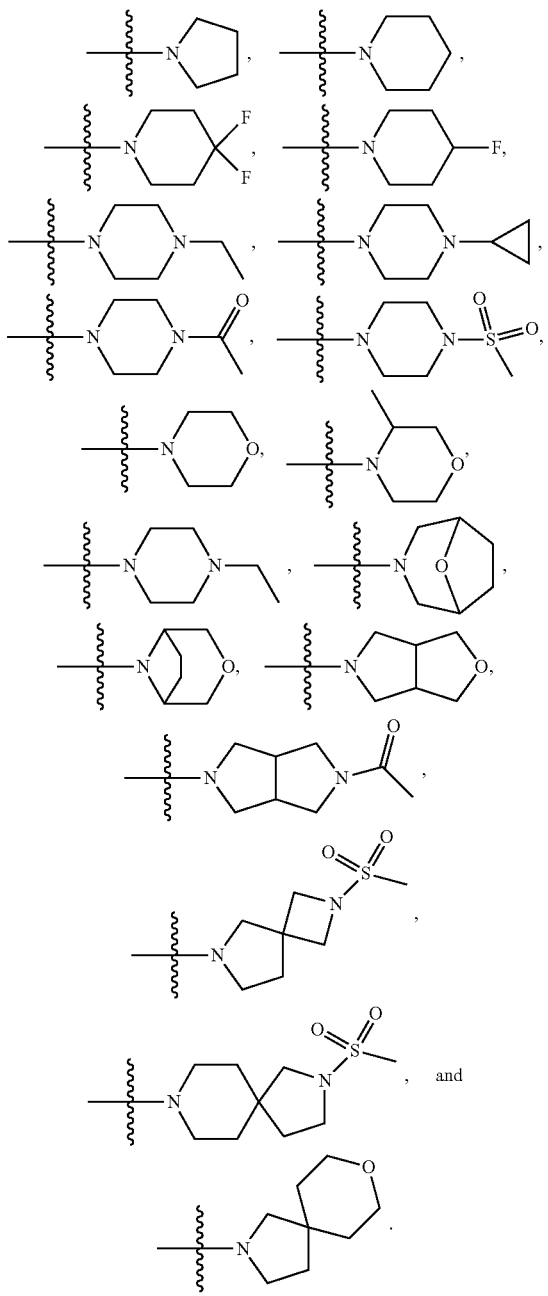

In another embodiment is a compound of Formula (IIIa), wherein $R^4$ is

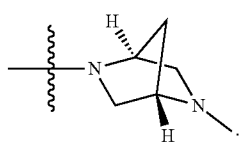

In another embodiment is a compound of Formula (IIIa), wherein $R^4$ is —$OR^7$. In another embodiment is a compound of Formula (IIIa), wherein $R^4$ is —$OR^7$, and $R^7$ is $C_{1-6}$alkyl. In another embodiment is a compound of Formula (IIIa), wherein $R^4$ is —$OR^7$, and $R^7$ is optionally substituted phenyl. In another embodiment is a compound of Formula (IIIa), wherein $R^4$ is —$OR^7$, and $R^7$ is optionally substituted $C_{1-6}$alkyl-phenyl. In another embodiment is a compound of Formula (IIIa), wherein $R^4$ is —$OR^7$, and $R^7$ is optionally substituted heteroaryl. In another embodiment is a compound of Formula (IIIa), wherein $R^4$ is —$OR^7$, and $R^7$ is optionally substituted heterocycloalkyl. In another embodiment is a compound of Formula (IIIa), wherein $R^4$ is —$OR^7$, and $R^7$ is —$C_{1-6}$alkylC(O)$NR^9R^{10}$. In another embodiment is a compound of Formula (IIIa), wherein $R^4$ is —$OR^7$, and $R^7$ is —$C_{1-6}$alkylC(O)$NR^9R^{10}$, and $R^9$ and $R^{10}$ are each independently H, or $C_{1-6}$alkyl. In another embodiment is a compound of Formula (IIIa), wherein $R^4$ is —$OR^7$, and $R^7$ is —$C_{1-6}$alkylC(O)$NR^9R^{10}$, and $R^9$ and $R^{10}$ together with the nitrogen to which they are attached are combined to form a heterocycloalkyl ring. In another embodiment is a compound of Formula (IIIa), wherein $R^4$ is —$OR^7$, and $R^7$ is $C_{1-6}$alkyl,

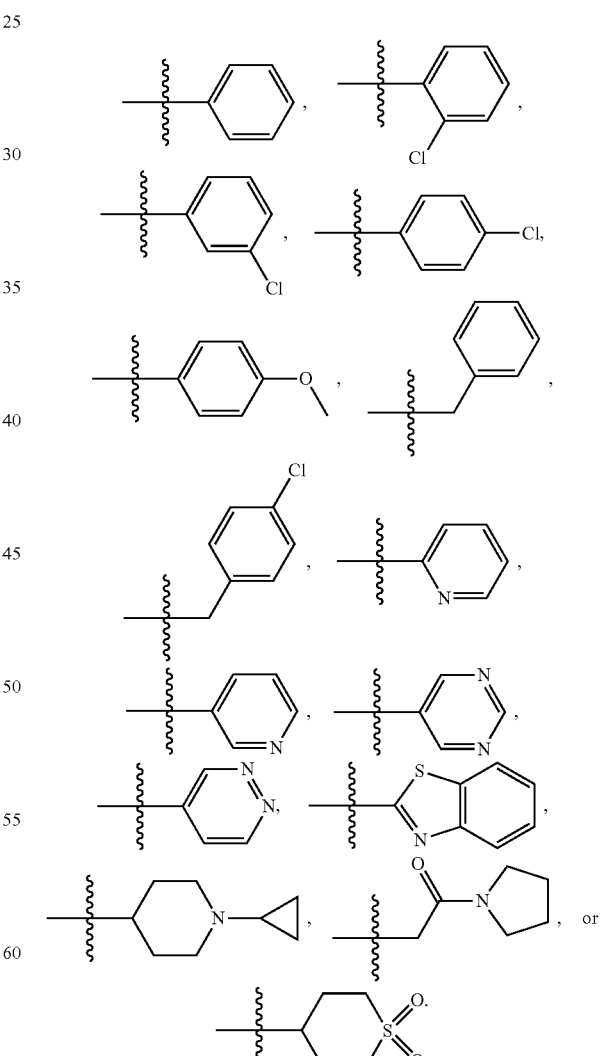

In another embodiment is a compound of Formula (IIIa), wherein $R^5$ is H. In another embodiment is a compound of Formula (IIIa), wherein $R^5$ is halogen. In another embodiment is a compound of Formula (IIIa), wherein $R^5$ is —Cl. In another embodiment is a compound of Formula (IIIa), wherein $R^5$ is —F. In another embodiment is a compound of Formula (IIIa), wherein $R^5$ is $C_{1-6}$alkyl. In another embodiment is a compound of Formula (IIIa), wherein $R^5$ is $C_{1-6}$haloalkyl. In another embodiment is a compound of Formula (IIIa), wherein $R^5$ is —$CF_3$. In another embodiment is a compound of Formula (IIIa), wherein $R^5$ is phenyl.

In another embodiment is a compound of Formula (IIIa), wherein $R^{12}$ is H. In another embodiment is a compound of Formula (IIIa), wherein $R^{12}$ is $C_{1-6}$alkyl. In another embodiment is a compound of Formula (IIIa), wherein $R^{12}$ is —C(O)$C_{1-6}$alkyl.

In another embodiment is a compound of Formula (IV):

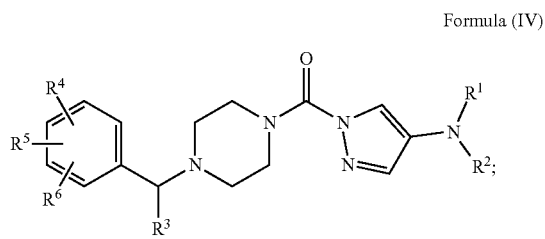

Formula (IV)

wherein:
$R^1$ is —C(O)$R^{15}$ or —SO$_2R^{15}$;
$R^2$ is H or $C_{1-6}$alkyl;
$R^3$ is H or optionally substituted phenyl;
$R^4$ is H, halogen, —$OR^7$, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
$R^5$ is H, halogen, $C_{1-6}$alkyl, $C_{1-6}$haloalkyl, or phenyl; or $R^4$ and $R^5$ are combined to form a heterocycloalkyl ring;
$R^6$ is H, halogen or $C_{1-6}$alkyl;
$R^7$ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)NR$^{10}$R$^{11}$;
$R^{10}$ and $R^{11}$ are each independently H, or $C_{1-6}$alkyl; or $R^{10}$ and $R^{11}$ together with the nitrogen to which they are attached are combined to form a heterocycloalkyl ring; and
$R^{15}$ is $C_{1-6}$alkyl;
or a solvate, hydrate, tautomer, N-oxide, or pharmaceutically acceptable salt thereof.

In another embodiment is a compound of Formula (IV), wherein $R^2$ is H. In another embodiment is a compound of Formula (IV), wherein $R^2$ is $C_{1-6}$alkyl. In another embodiment is a compound of Formula (IV), wherein $R^2$ is —$CH_3$.

In another embodiment is a compound of Formula (IV), wherein $R^1$ is —C(O)$R^{15}$. In another embodiment is a compound of Formula (IV), wherein $R^1$ is —C(O)$R^{15}$ and $R^{15}$ is —$CH_3$. In another embodiment is a compound of Formula (IV), wherein $R^1$ is —SO$_2R^{15}$. In another embodiment is a compound of Formula (IV), wherein $R^1$ is —SO$_2R^{15}$ and $R^{15}$ is —$CH_3$. In another embodiment is a compound of Formula (IV), wherein $R^1$ is —C(O)$R^{15}$ and $R^2$ is H. In another embodiment is a compound of Formula (IV), wherein $R^1$ is —C(O)$R^{15}$, $R^{15}$ is —$CH_3$, and $R^2$ is H. In another embodiment is a compound of Formula (IV), wherein $R^1$ is —SO$_2R^{15}$ and $R^2$ is H. In another embodiment is a compound of Formula (IV), wherein $R^1$ is —SO$_2R^{15}$, $R^{15}$ is —$CH_3$, and $R^2$ is H. In another embodiment is a compound of Formula (IV), wherein $R^1$ is —C(O)$R^{15}$ and $R^2$ is $C_{1-6}$alkyl. In another embodiment is a compound of Formula (IV), wherein $R^1$ is —C(O)$R^{15}$, $R^{15}$ is —$CH_3$, and $R^2$ is $C_{1-6}$alkyl. In another embodiment is a compound of Formula (IV), wherein $R^1$ is —SO$_2R^{15}$ and $R^2$ is $C_{1-6}$alkyl. In another embodiment is a compound of Formula (IV), wherein $R^1$ is —SO$_2R^{15}$, $R^{15}$ is —$CH_3$, and $R^2$ is $C_{1-6}$alkyl. In another embodiment is a compound of Formula (IV), wherein $R^1$ is —C(O)$R^{15}$ and $R^2$ is —$CH_3$. In another embodiment is a compound of Formula (IV), wherein $R^1$ is —C(O)$R^{15}$, $R^{15}$ is —$CH_3$, and $R^2$ is —$CH_3$. In another embodiment is a compound of Formula (IV), wherein $R^1$ is —SO$_2R^{15}$ and $R^2$ is —$CH_3$. In another embodiment is a compound of Formula (IV), wherein $R^1$ is —SO$_2R^{15}$, $R^{15}$ is —$CH_3$, and $R^2$ is —$CH_3$.

In another embodiment is a compound of Formula (IV), wherein $R^3$ is H. In another embodiment is a compound of Formula (IV), wherein $R^3$ is optionally substituted phenyl.

In another embodiment is a compound of Formula (IV), wherein $R^4$ is H. In another embodiment is a compound of Formula (IV), wherein $R^4$ is halogen. In another embodiment is a compound of Formula (IV), wherein $R^4$ is —Cl. In another embodiment is a compound of Formula (IV), wherein $R^4$ is —F. In another embodiment is a compound of Formula (IV), wherein $R^4$ is $C_{1-6}$alkyl. In another embodiment is a compound of Formula (IV), wherein $R^4$ is $C_{1-6}$haloalkyl. In another embodiment is a compound of Formula (IV), wherein $R^4$ is —$CF_3$. In another embodiment is a compound of Formula (IV), wherein $R^4$ is optionally substituted phenyl. In another embodiment is a compound of Formula (IV), wherein $R^4$ is optionally substituted heteroaryl. In another embodiment is a compound of Formula (IV), wherein $R^4$ is

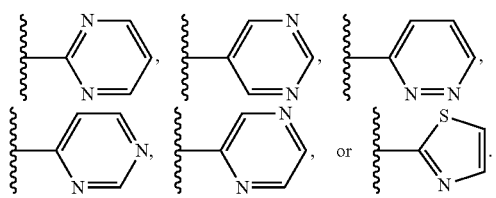

In another embodiment is a compound of Formula (IV), wherein $R^4$ is

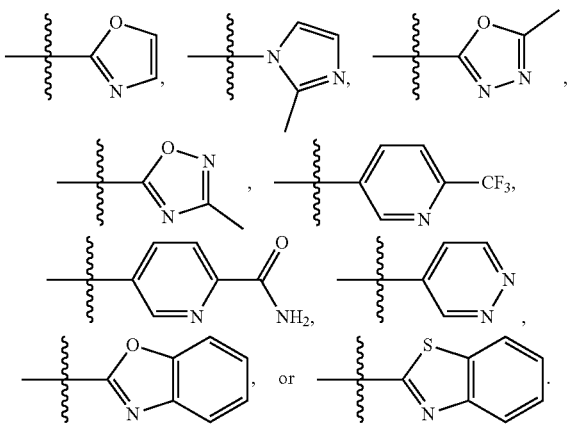

In another embodiment is a compound of Formula (IV), wherein $R^4$ is optionally substituted $C_{1-6}$alkyl-heterocycloalkyl. In another embodiment is a compound of Formula (IV), wherein $R^4$ is optionally substituted heterocycloalkyl.

In another embodiment is a compound of Formula (IV), wherein R⁴ is optionally substituted heterocycloalkyl selected from

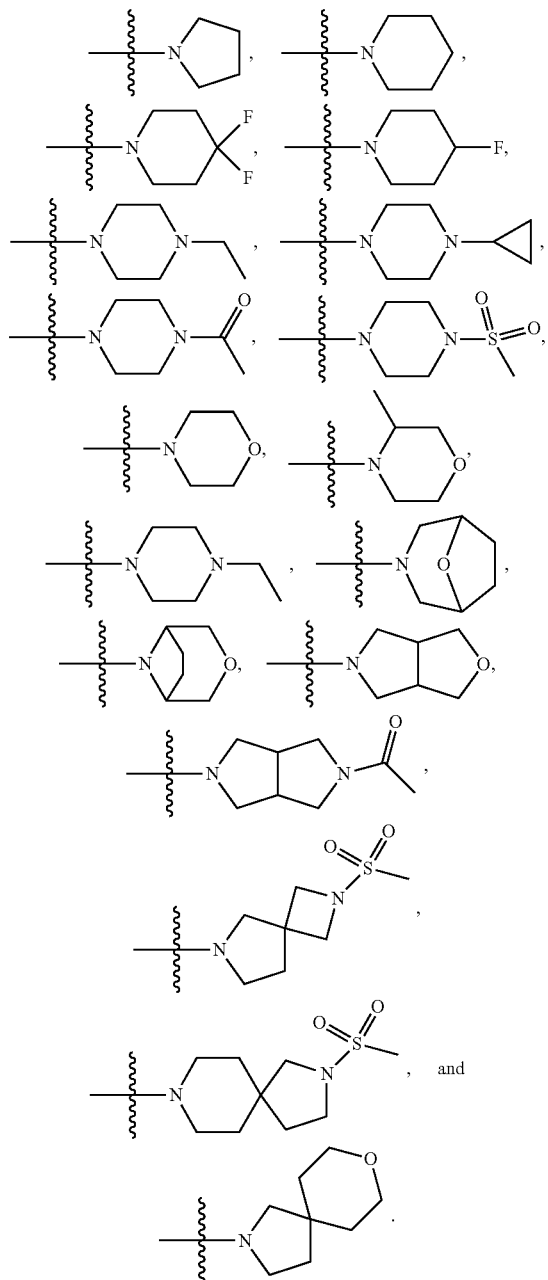

In another embodiment is a compound of Formula (IV), wherein R⁴ is

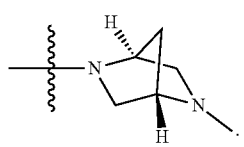 [SMILES: *N1C[C@@H]2C[C@H]1CN2C]

In another embodiment is a compound of Formula (IV), wherein R⁴ is —OR⁷. In another embodiment is a compound of Formula (IV), wherein R⁴ is —OR⁷, and R⁷ is $C_{1-6}$alkyl. In another embodiment is a compound of Formula (IV), wherein R⁴ is —OR⁷, and R⁷ is optionally substituted phenyl. In another embodiment is a compound of Formula (IV), wherein R⁴ is —OR⁷, and R⁷ is optionally substituted $C_{1-6}$alkyl-phenyl. In another embodiment is a compound of Formula (IV), wherein R⁴ is —OR⁷, and R⁷ is optionally substituted heteroaryl. In another embodiment is a compound of Formula (IV), wherein R⁴ is —OR⁷, and R⁷ is optionally substituted heterocycloalkyl. In another embodiment is a compound of Formula (IV), wherein R⁴ is —OR⁷, and R⁷ is —$C_{1-6}$alkylC(O)NR⁹R¹⁰. In another embodiment is a compound of Formula (IV), wherein R⁴ is —OR⁷, and R⁷ is —$C_{1-6}$alkylC(O)NR⁹R¹⁰, and R⁹ and R¹⁰ are each independently H, or $C_{1-6}$alkyl. In another embodiment is a compound of Formula (IV), wherein R⁴ is —OR⁷, and R⁷ is —$C_{1-6}$alkylC(O)NR⁹R¹⁰, and R⁹ and R¹⁰ together with the nitrogen to which they are attached are combined to form a heterocycloalkyl ring. In another embodiment is a compound of Formula (IV), wherein R⁴ is —OR⁷, and R⁷ is $C_{1-6}$alkyl,

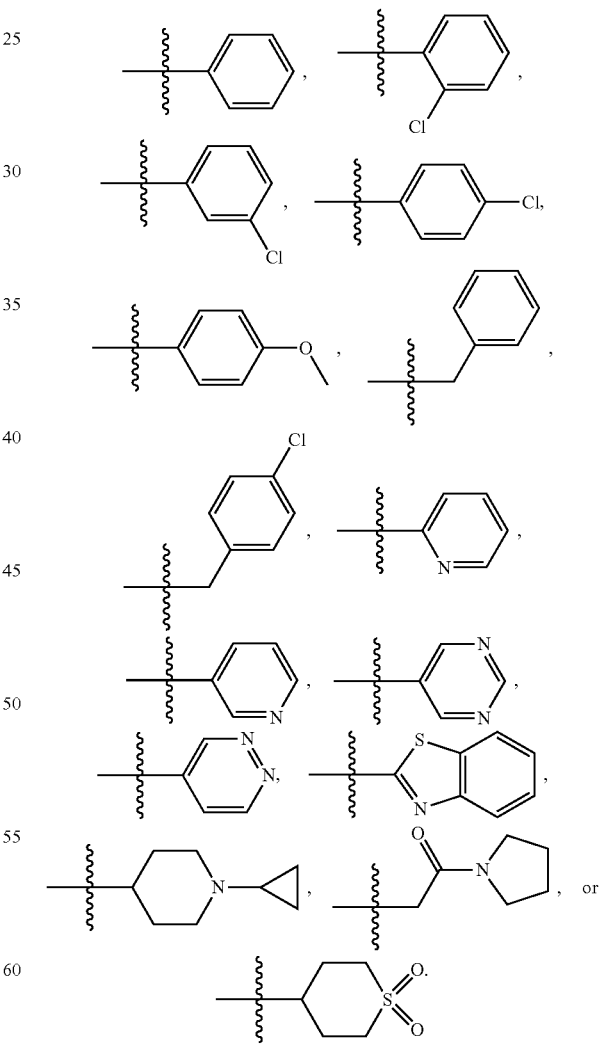

In another embodiment is a compound of Formula (IV), wherein R⁵ is H. In another embodiment is a compound of Formula (IV), wherein R⁵ is halogen. In another embodiment is a compound of Formula (IV), wherein $R^5$ is —Cl. In another embodiment is a compound of Formula (IV), wherein $R^5$ is —F. In another embodiment is a compound of Formula (IV), wherein $R^5$ is $C_{1-6}$alkyl. In another embodiment is a compound of Formula (IV), wherein $R^5$ is $C_{1-6}$haloalkyl. In another embodiment is a compound of Formula (IV), wherein $R^5$ is —$CF_3$. In another embodiment is a compound of Formula (IV), wherein $R^5$ is phenyl.

In another embodiment is a compound of Formula (IV), wherein $R^6$ is H. In another embodiment is a compound of Formula (IV), wherein $R^6$ is halogen. In another embodiment is a compound of Formula (IV), wherein $R^6$ is —Cl. In another embodiment is a compound of Formula (IV), wherein $R^6$ is —F. In another embodiment is a compound of Formula (IV), wherein $R^6$ is $C_{1-6}$alkyl.

In another embodiment is a compound of Formula (IV) having the structure of Formula (IVa):

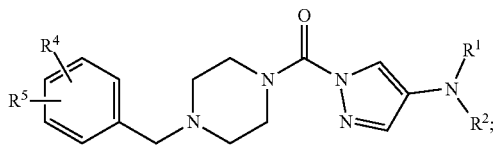

Formula (IVa)

wherein:
- $R^1$ is —$C(O)R^{15}$ or —$SO_2R^{15}$;
- $R^2$ is H or $C_{1-6}$alkyl;
- $R^4$ is H, halogen, —$OR^7$, $C_{1-6}$alkyl, $C_{1-6}$haloalkyl, optionally substituted heterocycloalkyl, optionally substituted $C_{1-6}$alkyl-heterocycloalkyl, optionally substituted phenyl, or optionally substituted heteroaryl;
- $R^5$ is H, halogen, $C_{1-6}$alkyl, $C_{1-6}$haloalkyl, or phenyl; or
- $R^4$ and $R^5$ are combined to form a heterocycloalkyl ring;
- $R^7$ is H, $C_{1-6}$alkyl, optionally substituted phenyl, optionally substituted $C_{1-6}$alkyl-phenyl, optionally substituted heteroaryl, optionally substituted heterocycloalkyl, or —$C_{1-6}$alkylC(O)NR$^{10}$R$^{11}$;
- $R^{10}$ and $R^{11}$ are each independently H, or $C_{1-6}$alkyl; or $R^{10}$ and $R^{11}$ together with the nitrogen to which they are attached are combined to form a heterocycloalkyl ring; and
- $R^{15}$ is $C_{1-6}$alkyl;

or a solvate, hydrate, tautomer, N-oxide, or pharmaceutically acceptable salt thereof.

In another embodiment is a compound of Formula (IVa), wherein R2 is H. In another embodiment is a compound of Formula (IVa), wherein R2 is C1-6alkyl. In another embodiment is a compound of Formula (IVa), wherein R2 is —CH3.

In another embodiment is a compound of Formula (IVa), wherein $R^1$ is —$C(O)R^{15}$. In another embodiment is a compound of Formula (IVa), wherein $R^1$ is —$C(O)R^{15}$ and $R^{15}$ is —$CH_3$. In another embodiment is a compound of Formula (IVa), wherein $R^1$ is —$SO_2R^{15}$. In another embodiment is a compound of Formula (IVa), wherein $R^1$ is —$SO_2R^{15}$ and $R^{15}$ is —$CH_3$. In another embodiment is a compound of Formula (IVa), wherein $R^1$ is —$C(O)R^{15}$ and $R^2$ is H. In another embodiment is a compound of Formula (IVa), wherein $R^1$ is —$C(O)R^{15}$, $R^{15}$ is —$CH_3$, and $R^2$ is H. In another embodiment is a compound of Formula (IVa), wherein $R^1$ is —$SO_2R^{15}$ and $R^2$ is H. In another embodiment is a compound of Formula (IVa), wherein $R^1$ is —$SO_2R^{15}$, $R^{15}$ is —$CH_3$, and $R^2$ is H. In another embodiment is a compound of Formula (IVa), wherein $R^1$ is —$C(O)R^{15}$ and $R^2$ is $C_{1-6}$alkyl. In another embodiment is a compound of Formula (IVa), wherein $R^1$ is —$C(O)R^{15}$, $R^{15}$ is —$CH_3$, and $R^2$ is $C_{1-6}$alkyl. In another embodiment is a compound of Formula (IVa), wherein $R^1$ is —$SO_2R^{15}$ and $R^2$ is $C_{1-6}$alkyl. In another embodiment is a compound of Formula (IVa), wherein $R^1$ is —$SO_2R^{15}$, $R^{15}$ is —$CH_3$, and $R^2$ is $C_{1-6}$alkyl. In another embodiment is a compound of Formula (IVa), wherein $R^1$ is —$C(O)R^{15}$ and $R^2$ is —$CH_3$. In another embodiment is a compound of Formula (IVa), wherein $R^1$ is —$C(O)R^{15}$, $R^{15}$ is —$CH_3$, and $R^2$ is —$CH_3$. In another embodiment is a compound of Formula (IVa), wherein $R^1$ is —$SO_2R^{15}$ and $R^2$ is —$CH_3$. In another embodiment is a compound of Formula (IVa), wherein $R^1$ is —$SO_2R^{15}$, $R^{15}$ is —$CH_3$, and $R^2$ is —$CH_3$.

In another embodiment is a compound of Formula (IVa), wherein $R^4$ is H. In another embodiment is a compound of Formula (IVa), wherein $R^4$ is halogen. In another embodiment is a compound of Formula (IVa), wherein $R^4$ is —Cl. In another embodiment is a compound of Formula (IVa), wherein $R^4$ is —F. In another embodiment is a compound of Formula (IVa), wherein $R^4$ is $C_{1-6}$alkyl. In another embodiment is a compound of Formula (IVa), wherein $R^4$ is $C_{1-6}$haloalkyl. In another embodiment is a compound of Formula (IVa), wherein $R^4$ is —$CF_3$. In another embodiment is a compound of Formula (IVa), wherein $R^4$ is optionally substituted phenyl. In another embodiment is a compound of Formula (IVa), wherein $R^4$ is optionally substituted heteroaryl. In another embodiment is a compound of Formula (IVa), wherein $R^4$ is

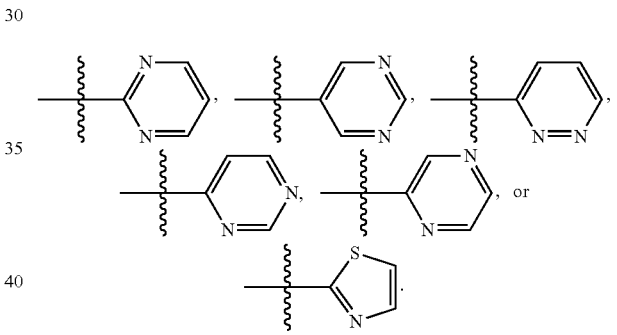

In another embodiment is a compound of Formula (IVa), wherein $R^4$ is

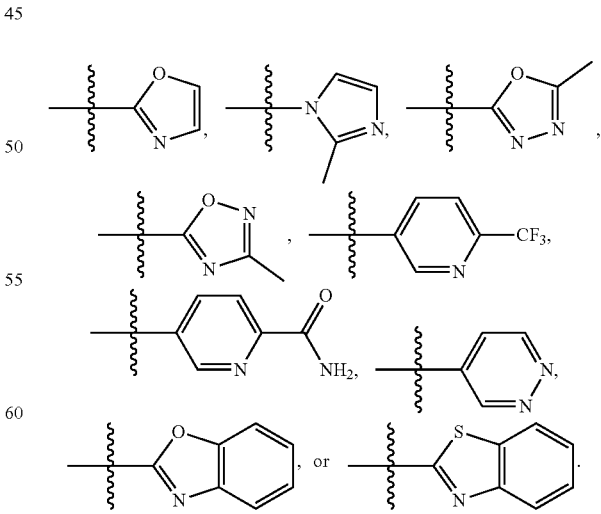

In another embodiment is a compound of Formula (IVa), wherein $R^4$ is optionally substituted $C_{1-6}$alkyl-heterocycloalkyl. In another embodiment is a compound of Formula (IVa), wherein $R^4$ is optionally substituted heterocycloalkyl. In another embodiment is a compound of Formula (IVa), wherein $R^4$ is optionally substituted heterocycloalkyl selected from

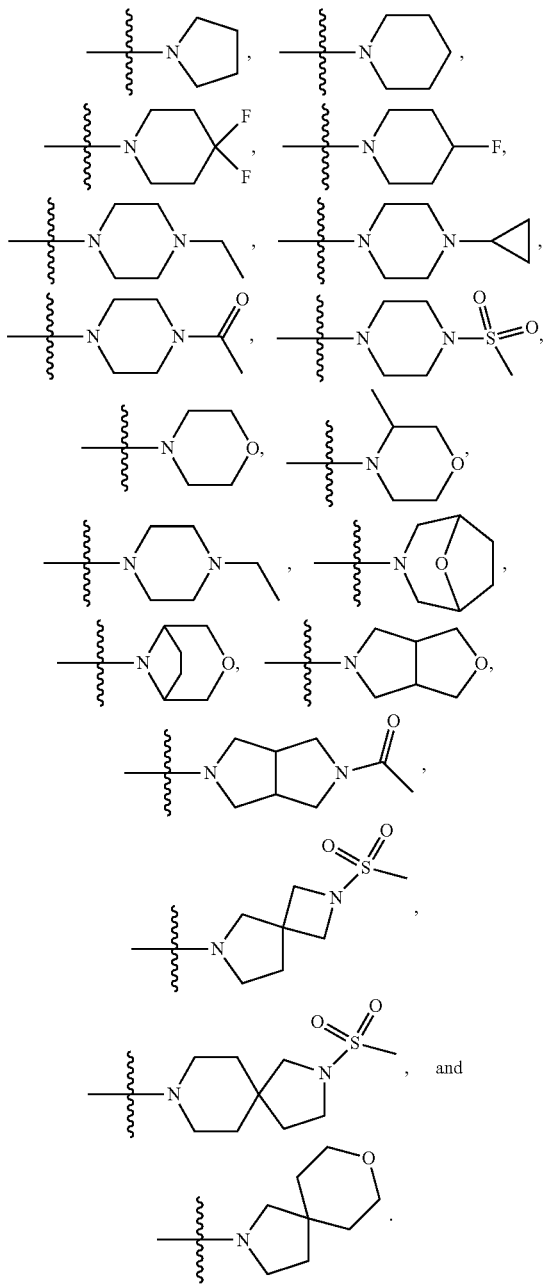

In another embodiment is a compound of Formula (IVa), wherein $R^4$ is

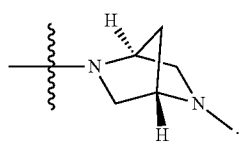

In another embodiment is a compound of Formula (IVa), wherein $R^4$ is —$OR^7$. In another embodiment is a compound of Formula (IVa), wherein $R^4$ is —$OR^7$. In another embodiment is a compound of Formula (IVa), wherein $R^4$ is —$OR^7$, and $R^7$ is $C_{1-6}$alkyl. In another embodiment is a compound of Formula (IVa), wherein $R^4$ is —$OR^7$, and $R^7$ is optionally substituted phenyl. In another embodiment is a compound of Formula (IVa), wherein $R^4$ is —$OR^7$, and $R^7$ is optionally substituted $C_{1-6}$alkyl-phenyl. In another embodiment is a compound of Formula (IVa), wherein $R^4$ is —$OR^7$, and $R^7$ is optionally substituted heteroaryl. In another embodiment is a compound of Formula (IVa), wherein $R^4$ is —$OR^7$, and $R^7$ is optionally substituted heterocycloalkyl. In another embodiment is a compound of Formula (IVa), wherein $R^4$ is —$OR^7$, and $R^7$ is —$C_{1-6}$alkylC(O)$NR^9R^{10}$. In another embodiment is a compound of Formula (IVa), wherein $R^4$ is —$OR^7$, and $R^7$ is —$C_{1-6}$alkylC(O)$NR^9R^{10}$, and $R^9$ and $R^{10}$ are each independently H, or $C_{1-6}$alkyl. In another embodiment is a compound of Formula (IVa), wherein $R^4$ is —$OR^7$, and $R^7$ is —$C_{1-6}$alkylC(O)$NR^9R^{10}$, and $R^9$ and $R^{10}$ together with the nitrogen to which they are attached are combined to form a heterocycloalkyl ring. In another embodiment is a compound of Formula (IVa), wherein $R^4$ is —$OR^7$, and $R^7$ is $C_{1-6}$alkyl,

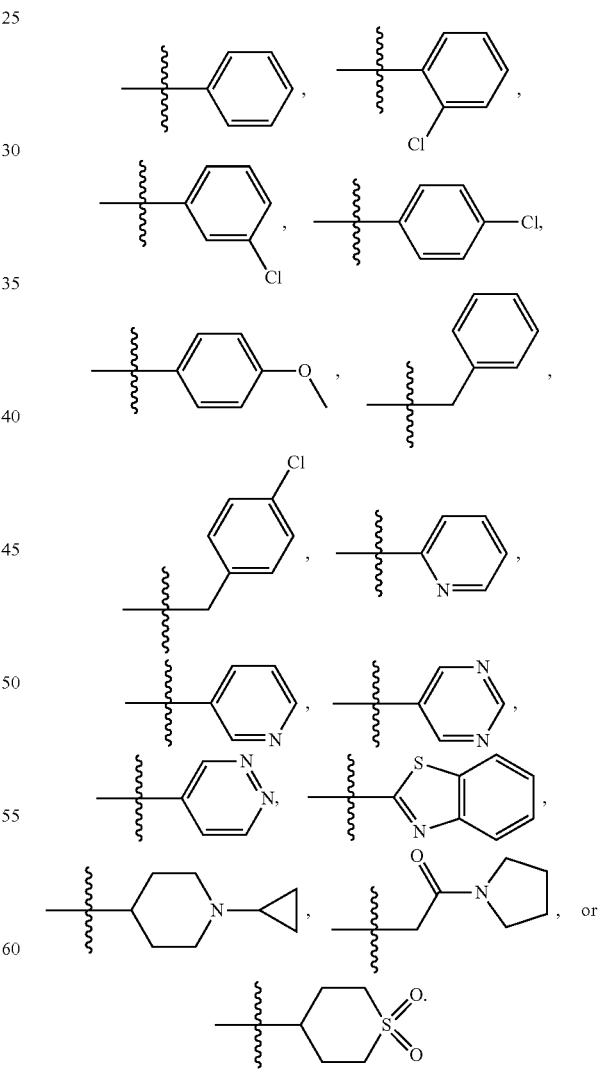

In another embodiment is a compound of Formula (IVa), wherein $R^5$ is H. In another embodiment is a compound of Formula (IVa), wherein R5 is halogen. In another embodiment is a compound of Formula (IVa), wherein R5 is —Cl. In another embodiment is a compound of Formula (IVa), wherein R5 is —F. In another embodiment is a compound of Formula (IVa), wherein R5 is C1-6alkyl. In another embodiment is a compound of Formula (IVa), wherein R5 is C1-6haloalkyl. In another embodiment is a compound of Formula (IVa), wherein R5 is —CF3. In another embodiment is a compound of Formula (IVa), wherein R5 is phenyl.

Further embodiments provided herein include combinations of one or more of the particular embodiments set forth above.

In some embodiments, the compound disclosed herein has the structure provided in Table 1.

TABLE 1

| Ex. | Names | Structures |
| --- | --- | --- |
| 1 | N-(1-(7-(3,4-dichlorobenzyl)-2,7-diazaspiro[4.4]nonane-2-carbonyl)-1H-pyrazol-4-yl)-N-methylacetamide | 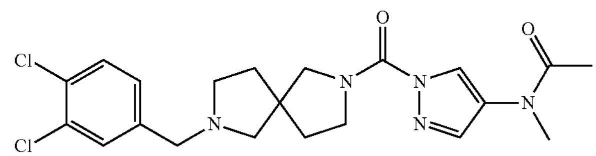 [SMILES: CC(=O)N(C)c1cnn(C(=O)N2CCC3(CCN(Cc4ccc(Cl)c(Cl)c4)C3)C2)c1] |
| 2 | N-methyl-N-(1-(7-(4-(trifluoromethyl)benzyl)-2,7-diazaspiro[4.4]nonane-2-carbonyl)-1H-pyrazol-4-yl)acetamide | 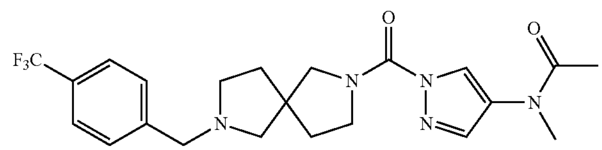 [SMILES: CC(=O)N(C)c1cnn(C(=O)N2CCC3(CCN(Cc4ccc(C(F)(F)F)cc4)C3)C2)c1] |
| 3 | N-methyl-N-(1-(7-(4-morpholinobenzyl)-2,7-diazaspiro[4.4]nonane-2-carbonyl)-1H-pyrazol-4-yl)acetamide | 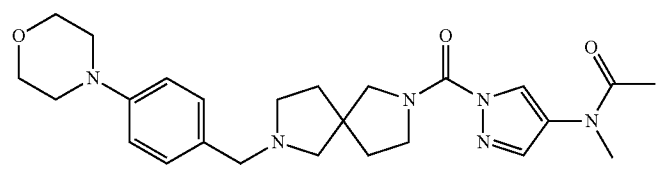 [SMILES: CC(=O)N(C)c1cnn(C(=O)N2CCC3(CCN(Cc4ccc(N5CCOCC5)cc4)C3)C2)c1] |
| 4 | N-(1-(7-(2-chloro-4-morpholinobenzyl)-2,7-diazaspiro[4.4]nonane-2-carbonyl)-1H-pyrazol-4-yl)-N-methylacetamide | 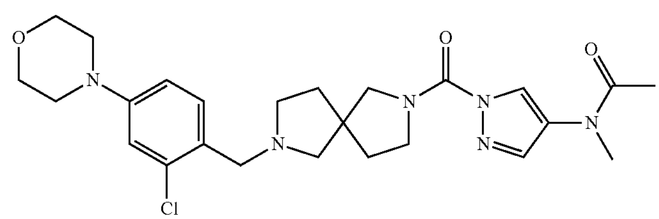 [SMILES: CC(=O)N(C)c1cnn(C(=O)N2CCC3(CCN(Cc4ccc(N5CCOCC5)cc4Cl)C3)C2)c1] |
| 5 | N-methyl-N-(1-(7-(2-methyl-4-morpholinobenzyl)-2,7-diazaspiro[4.4]nonane-2-carbonyl)-1H-pyrazol-4-yl)acetamide | 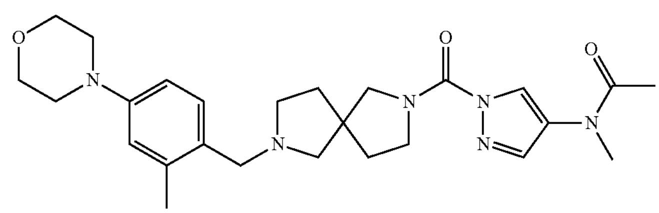 [SMILES: CC(=O)N(C)c1cnn(C(=O)N2CCC3(CCN(Cc4ccc(N5CCOCC5)cc4C)C3)C2)c1] |
| 6 | 1-(5-(2-chlorobenzyl)octahydropyrrolo[3,4-c]pyrrole-2-carbonyl)-N-(methylsulfonyl)-1H-pyrazole-4-carboxamide | 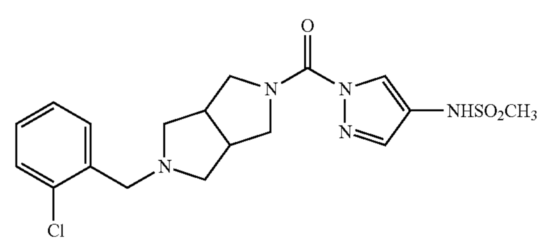 |
| 7 | 1-(5-(3-chlorobenzyl)octahydropyrrolo[3,4-c]pyrrole-2-carbonyl)-N-(methylsulfonyl)-1H-pyrazole-4-carboxamide | 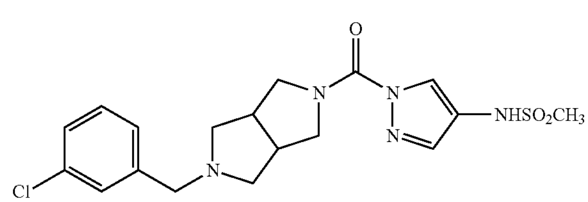 |

TABLE 1-continued

| Ex. | Names |
|-----|-------|
| 8 | 1-(5-(4-chlorobenzyl)octahydropyrrolo[3,4-c]pyrrole-2-carbonyl)-N-(methylsulfonyl)-1H-pyrazole-4-carboxamide |
| 9 | N-acetyl-1-(5-(2-chlorobenzyl)octahydropyrrolo[3,4-c]pyrrole-2-carbonyl)-N-methyl-1H-pyrazole-4-carboxamide |
| 10 | N-acetyl-1-(5-(3-chlorobenzyl)octahydropyrrolo[3,4-c]pyrrole-2-carbonyl)-N-methyl-1H-pyrazole-4-carboxamide |
| 11 | N-acetyl-1-(5-(4-chlorobenzyl)octahydropyrrolo[3,4-c]pyrrole-2-carbonyl)-N-methyl-1H-pyrazole-4-carboxamide |
| 12 | N-(1-(5-(3,4-dichlorobenzyl)octahydropyrrolo[3,4-c]pyrrole-2-carbonyl)-1H-pyrazol-4-yl)-N-methylacetamide |
| 13 | N-methyl-N-(1-(5-(4-(pyrrolidin-1-yl)benzyl)octahydropyrrolo[3,4-c]pyrrole-2-carbonyl)-1H-pyrazol-4-yl)acetamide |
| 14 | N-methyl-N-(1-(5-(4-(trifluoromethyl)benzyl)octahydropyrrolo[3,4-c]pyrrole-2-carbonyl)-1H-pyrazol-4-yl)acetamide |
| 15 | N-methyl-N-(1-(5-(4-morpholinobenzyl)octahydropyrrolo[3,4-c]pyrrole-2-carbonyl)-1H-pyrazol-4-yl)acetamide |

TABLE 1-continued

| Ex. | Names | Structures |
|---|---|---|
| 16 | N-(1-(5-(2-chloro-4-morpholinobenzyl)octahydropyrrolo[3,4-c]pyrrole-2-carbonyl)-1H-pyrazol-4-yl)-N-methylacetamide | 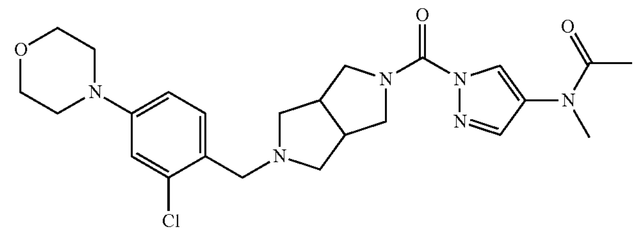 [SMILES: CC(=O)N(C)c1cnn(C(=O)N2CC3CN(Cc4ccc(N5CCOCC5)cc4Cl)CC3C2)c1] |
| 17 | N-methyl-N-(1-(5-(2-methyl-4-morpholinobenzyl)octahydropyrrolo[3,4-c]pyrrole-2-carbonyl)-1H-pyrazol-4-yl)acetamide | 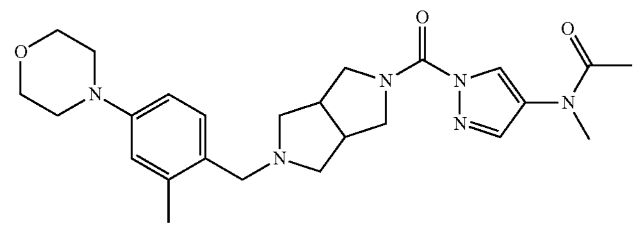 [SMILES: CC(=O)N(C)c1cnn(C(=O)N2CC3CN(Cc4ccc(N5CCOCC5)cc4C)CC3C2)c1] |
| 18 | N-(1-(7-(3,4-dichlorobenzyl)-2,7-diazaspiro[3.5]nonane-2-carbonyl)-1H-pyrazol-4-yl)-N-methylacetamide | 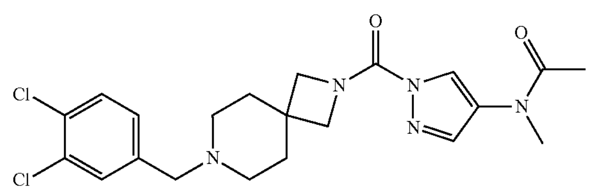 [SMILES: CC(=O)N(C)c1cnn(C(=O)N2CC3(CCN(Cc4ccc(Cl)c(Cl)c4)CC3)C2)c1] |
| 19 | N-methyl-N-(1-(7-(4-(pyrrolidin-1-yl)benzyl)-2,7-diazaspiro[3.5]nonane-2-carbonyl)-1H-pyrazol-4-yl)acetamide | 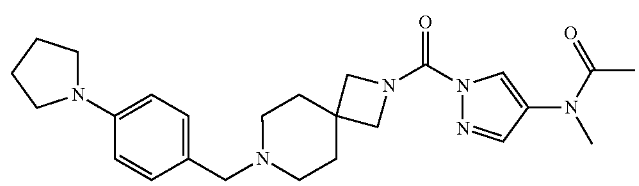 [SMILES: CC(=O)N(C)c1cnn(C(=O)N2CC3(CCN(Cc4ccc(N5CCCC5)cc4)CC3)C2)c1] |
| 20 | N-methyl-N-(1-(7-(4-(trifluoromethyl)benzyl)-2,7-diazaspiro[3.5]nonane-2-carbonyl)-1H-pyrazol-4-yl)acetamide | 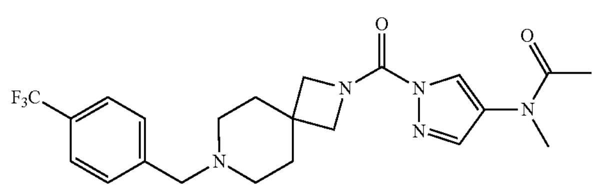 [SMILES: CC(=O)N(C)c1cnn(C(=O)N2CC3(CCN(Cc4ccc(C(F)(F)F)cc4)CC3)C2)c1] |
| 21 | N-methyl-N-(1-(7-(4-morpholinobenzyl)-2,7-diazaspiro[3.5]nonane-2-carbonyl)-1H-pyrazol-4-yl)acetamide | 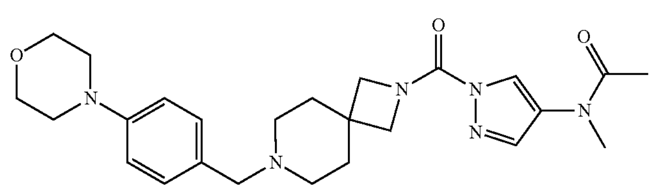 [SMILES: CC(=O)N(C)c1cnn(C(=O)N2CC3(CCN(Cc4ccc(N5CCOCC5)cc4)CC3)C2)c1] |
| 22 | N-(1-(7-(2-chloro-4-morpholinobenzyl)-2,7-diazaspiro[3.5]nonane-2-carbonyl)-1H-pyrazol-4-yl)-N-methylacetamide | 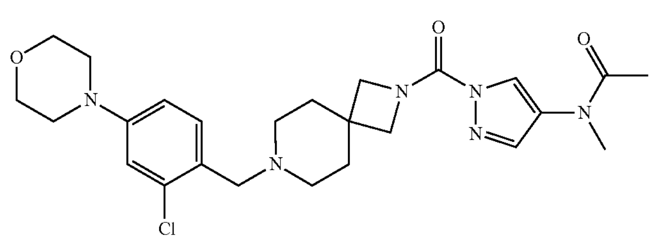 [SMILES: CC(=O)N(C)c1cnn(C(=O)N2CC3(CCN(Cc4ccc(N5CCOCC5)cc4Cl)CC3)C2)c1] |

TABLE 1-continued

| Ex. | Names |
|---|---|
| 23 | N-methyl-N-(1-(7-(2-methyl-4-morpholinobenzyl)-2,7-diazaspiro[3.5]nonane-2-carbonyl)-1H-pyrazol-4-yl)acetamide |
| 24 | N-(1-(2-(3,4-dichlorobenzyl)-2,7-diazaspiro[3.5]nonane-7-carbonyl)-1H-pyrazol-4-yl)-N-methylacetamide |
| 25 | N-methyl-N-(1-(2-(4-(pyrrolidin-1-yl)benzyl)-2,7-diazaspiro[3.5]nonane-7-carbonyl)-1H-pyrazol-4-yl)acetamide |
| 26 | N-methyl-N-(1-(2-(4-(trifluoromethyl)benzyl)-2,7-diazaspiro[3.5]nonane-7-carbonyl)-1H-pyrazol-4-yl)acetamide |
| 27 | N-methyl-N-(1-(2-(4-morpholinobenzyl)-2,7-diazaspiro[3.5]nonane-7-carbonyl)-1H-pyrazol-4-yl)acetamide |
| 28 | N-(1-(2-(2-chloro-4-morpholinobenzyl)-2,7-diazaspiro[3.5]nonane-7-carbonyl)-1H-pyrazol-4-yl)-N-methylacetamide |
| 29 | N-methyl-N-(1-(2-(2-methyl-4-morpholinobenzyl)-2,7-diazaspiro[3.5]nonane-7-carbonyl)-1H-pyrazol-4-yl)acetamide |

TABLE 1-continued

| Ex. | Names | Structures |
|---|---|---|
| 30 | N-methyl-N-(1-(2-(3-(pyrrolidin-1-yl)benzyl)-2,7-diazaspiro[3.5]nonane-7-carbonyl)-1H-pyrazol-4-yl)acetamide | 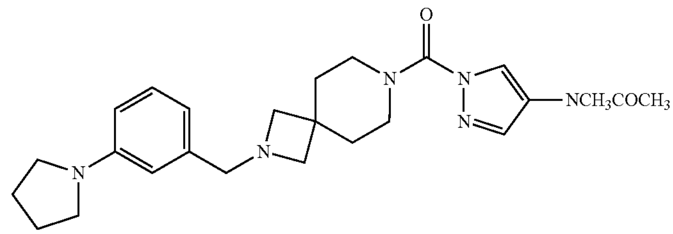 |
| 31 | N-(1-(2-(4-fluorobenzyl)-2,7-diazaspiro[3.5]nonane-7-carbonyl)-1H-pyrazol-4-yl)-N-methylacetamide | 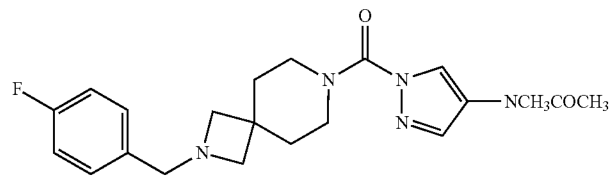 |
| 32 | N-methyl-N-(1-(2-(4-methylbenzyl)-2,7-diazaspiro[3.5]nonane-7-carbonyl)-1H-pyrazol-4-yl)acetamide | 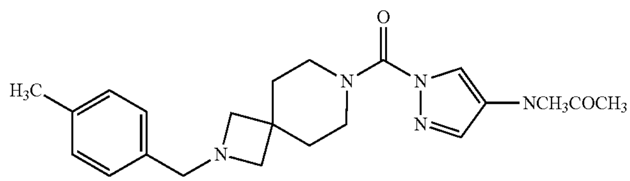 |
| 33 | N-(1-(2-(4-methoxybenzyl)-2,7-diazaspiro[3.5]nonane-7-carbonyl)-1H-pyrazol-4-yl)-N-methylacetamide | 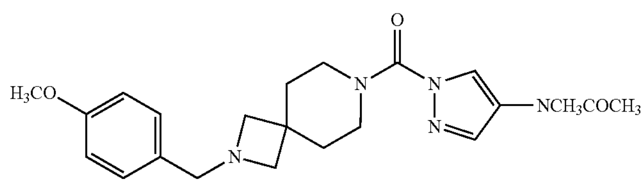 |
| 34 | N-(1-(2-(3-chlorobenzyl)-2,7-diazaspiro[3.5]nonane-7-carbonyl)-1H-pyrazol-4-yl)-N-methylacetamide | 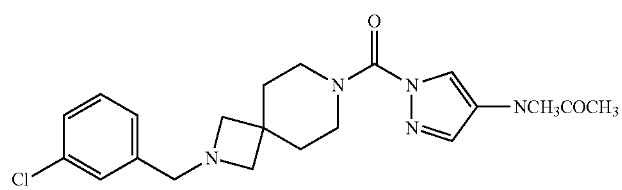 |
| 35 | N-(1-(2-(3-fluorobenzyl)-2,7-diazaspiro[3.5]nonane-7-carbonyl)-1H-pyrazol-4-yl)-N-methylacetamide | 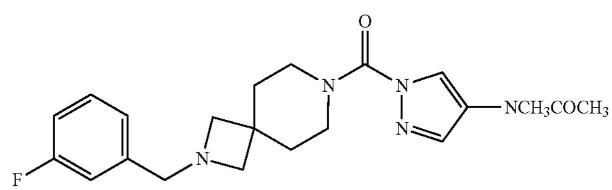 |
| 36 | N-methyl-N-(1-(2-(3-methylbenzyl)-2,7-diazaspiro[3.5]nonane-7-carbonyl)-1H-pyrazol-4-yl)acetamide | 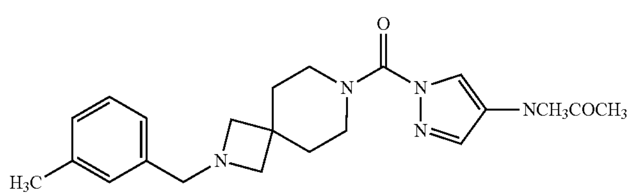 |
| 37 | N-(1-(2-(3-methoxybenzyl)-2,7-diazaspiro[3.5]nonane-7-carbonyl)-1H-pyrazol-4-yl)-N-methylacetamide | 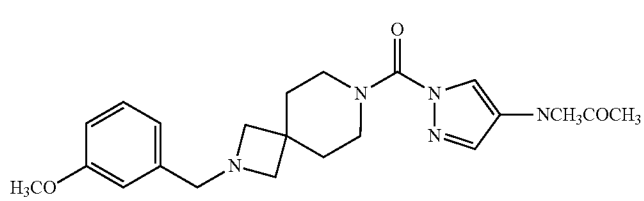 |

TABLE 1-continued

| Ex. | Names | Structures |
|---|---|---|
| 38 | N-methyl-N-(1-(2-(3-(trifluoromethyl)benzyl)-2,7-diazaspiro[3.5]nonane-7-carbonyl)-1H-pyrazol-4-yl)acetamide | 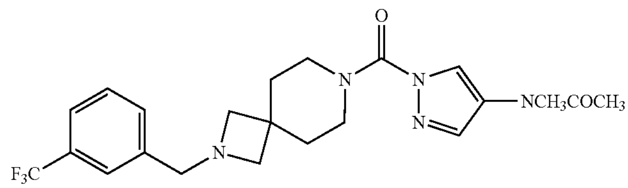 |
| 39 | N-methyl-N-(1-(2-(3-morpholinobenzyl)-2,7-diazaspiro[3.5]nonane-7-carbonyl)-1H-pyrazol-4-yl)acetamide | 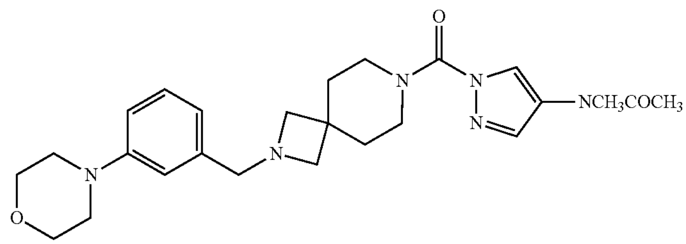 |
| 40 | N-(1-(2-(2-chlorobenzyl)-2,7-diazaspiro[3.5]nonane-7-carbonyl)-1H-pyrazol-4-yl)-N-methylacetamide | 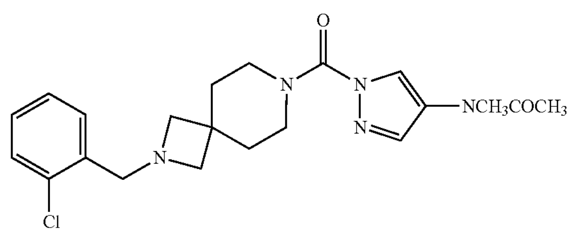 |
| 41 | N-(1-(2-(2-fluorobenzyl)-2,7-diazaspiro[3.5]nonane-7-carbonyl)-1H-pyrazol-4-yl)-N-methylacetamide | 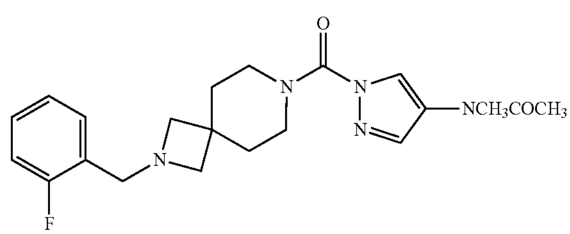 |
| 42 | N-methyl-N-(1-(2-(2-methylbenzyl)-2,7-diazaspiro[3.5]nonane-7-carbonyl)-1H-pyrazol-4-yl)acetamide | 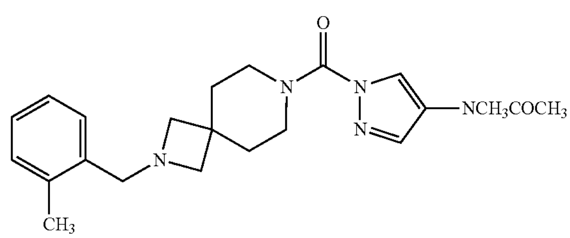 |
| 43 | N-(1-(2-(2-methoxybenzyl)-2,7-diazaspiro[3.5]nonane-7-carbonyl)-1H-pyrazol-4-yl)-N-methylacetamide | 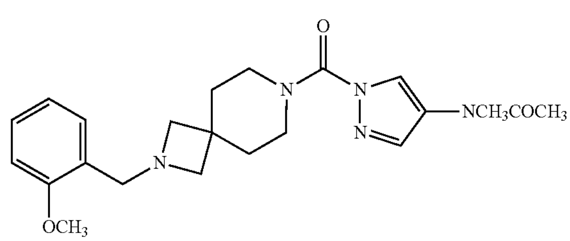 |
| 44 | N-methyl-N-(1-(2-(2-(trifluoromethyl)benzyl)-2,7-diazaspiro[3.5]nonane-7-carbonyl)-1H-pyrazol-4-yl)acetamide | 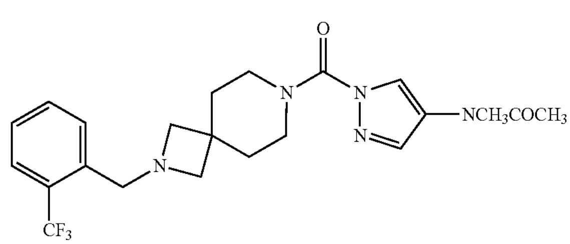 |

TABLE 1-continued

| Ex. | Names |
|-----|-------|
| 45 | N-methyl-N-(1-(2-(2-(pyrrolidin-1-yl)benzyl)-2,7-diazaspiro[3.5]nonane-7-carbonyl)-1H-pyrazol-4-yl)acetamide |
| 46 | N-methyl-N-(1-(2-(2-morpholinobenzyl)-2,7-diazaspiro[3.5]nonane-7-carbonyl)-1H-pyrazol-4-yl)acetamide |
| 47 | N-methyl-N-(1-(7-(4-(pyrrolidin-1-yl)benzyl)-2,7-diazaspiro[4.4]nonane-2-carbonyl)-1H-pyrazol-4-yl)acetamide |
| 48 | N-methyl-N-(1-(7-(3-morpholinobenzyl)-2,7-diazaspiro[4.4]nonane-2-carbonyl)-1H-pyrazol-4-yl)acetamide |
| 49 | N-(1-(7-(2,6-dichlorobenzyl)-2,7-diazaspiro[4.4]nonane-2-carbonyl)-1H-pyrazol-4-yl)-N-methylacetamide |
| 50 | N-(1-(7-(2-chlorobenzyl)-2,7-diazaspiro[4.4]nonane-2-carbonyl)-1H-pyrazol-4-yl)-N-methylacetamide |

TABLE 1-continued

| Ex. | Names |
|---|---|
| 51 | N-(1-(7-(2,4-dichlorobenzyl)-2,7-diazaspiro[4.4]nonane-2-carbonyl)-1H-pyrazol-4-yl)-N-methylacetamide |
| 52 | N-(1-(7-(2-fluorobenzyl)-2,7-diazaspiro[4.4]nonane-2-carbonyl)-1H-pyrazol-4-yl)-N-methylacetamide |
| 53 | N-(1-(7-(3,5-dichlorobenzyl)-2,7-diazaspiro[4.4]nonane-2-carbonyl)-1H-pyrazol-4-yl)-N-methylacetamide |
| 54 | N-methyl-N-(1-(7-(2-methylbenzyl)-2,7-diazaspiro[4.4]nonane-2-carbonyl)-1H-pyrazol-4-yl)acetamide |
| 55 | N-(1-(7-(2-chloro-4-methylbenzyl)-2,7-diazaspiro[4.4]nonane-2-carbonyl)-1H-pyrazol-4-yl)-N-methylacetamide |
| 56 | N-(1-(7-(2-methoxybenzyl)-2,7-diazaspiro[4.4]nonane-2-carbonyl)-1H-pyrazol-4-yl)-N-methylacetamide |
| 57 | N-(1-(7-(3-chloro-2-methylbenzyl)-2,7-diazaspiro[4.4]nonane-2-carbonyl)-1H-pyrazol-4-yl)-N-methylacetamide |

TABLE 1-continued

| Ex. | Names | Structures |
|---|---|---|
| 58 | N-methyl-N-(1-(7-(2-(trifluoromethyl)benzyl)-2,7-diazaspiro[4.4]nonane-2-carbonyl)-1H-pyrazol-4-yl)acetamide | 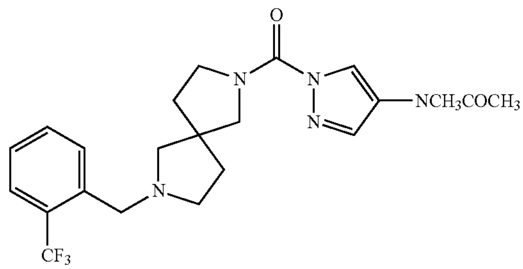 |
| 59 | N-(1-(7-(2,3-dichlorobenzyl)-2,7-diazaspiro[4.4]nonane-2-carbonyl)-1H-pyrazol-4-yl)-N-methylacetamide | 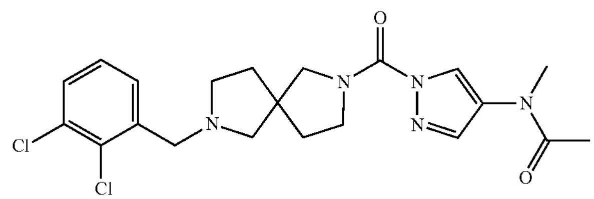 [SMILES: CC(=O)N(C)c1cnn(C(=O)N2CCC3(CCN(Cc4cccc(Cl)c4Cl)C3)C2)c1] |
| 60 | N-methyl-N-(1-(7-(2-(pyrrolidin-1-yl)benzyl)-2,7-diazaspiro[4.4]nonane-2-carbonyl)-1H-pyrazol-4-yl)acetamide | 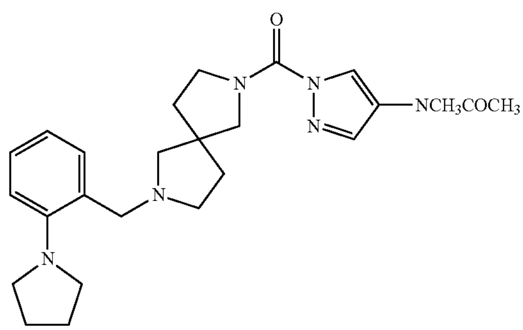 |
| 61 | N-methyl-N-(1-(7-(3-morpholino-4-(trifluoromethyl)benzyl)-2,7-diazaspiro[4.4]nonane-2-carbonyl)-1H-pyrazol-4-yl)acetamide | 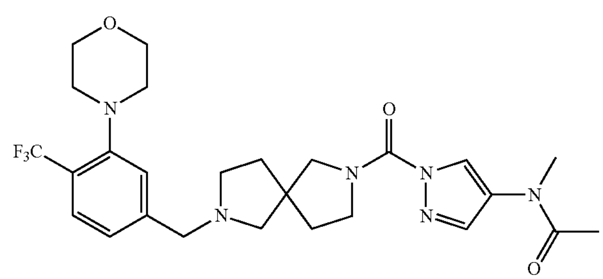 [SMILES: CC(=O)N(C)c1cnn(C(=O)N2CCC3(CCN(Cc4ccc(C(F)(F)F)c(N5CCOCC5)c4)C3)C2)c1] |
| 62 | N-methyl-N-(1-(7-(2-morpholinobenzyl)-2,7-diazaspiro[4.4]nonane-2-carbonyl)-1H-pyrazol-4-yl)acetamide | 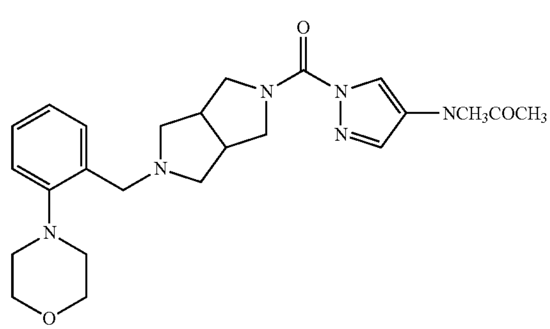 |

TABLE 1-continued

| Ex. | Names |
|---|---|
| 63 | N-(1-(7-(3-chloro-5-morpholinobenzyl)-2,7-diazaspiro[4.4]nonane-2-carbonyl)-1H-pyrazol-4-yl)-N-methylacetamide |
| 64 | N-methyl-N-(1-(7-(3-(trifluoromethyl)benzyl)-2,7-diazaspiro[4.4]nonane-2-carbonyl)-1H-pyrazol-4-yl)acetamide |
| 65 | N-methyl-N-(1-(7-(3-(trifluoromethyl)benzyl)-2,7-diazaspiro[4.4]nonane-2-carbonyl)-1H-pyrazol-4-yl)acetamide (single enantiomer) |
| 66 | N-methyl-N-(1-(7-(3-(trifluoromethyl)benzyl)-2,7-diazaspiro[4.4]nonane-2-carbonyl)-1H-pyrazol-4-yl)acetamide (single enantiomer) |
| 67 | N-(1-(7-(3-chloro-4-(pyrrolidin-1-yl)benzyl)-2,7-diazaspiro[4.4]nonane-2-carbonyl)-1H-pyrazol-4-yl)-N-methylacetamide |
| 68 | N-methyl-N-(1-(7-(3-morpholino-5-(trifluoromethyl)benzyl)-2,7-diazaspiro[4.4]nonane-2-carbonyl)-1H-pyrazol-4-yl)acetamide |
| 69 | N-methyl-N-(1-(7-(4-(pyrrolidin-1-yl)-3-(trifluoromethyl)benzyl)-2,7-diazaspiro[4.4]nonane-2-carbonyl)-1H-pyrazol-4-yl)acetamide |

TABLE 1-continued

| Ex. | Names | Structures |
|---|---|---|
| 70 | N-(1-(7-(5-chloro-2-(trifluoromethyl)benzyl)-2,7-diazaspiro[4.4]nonane-2-carbonyl)-1H-pyrazol-4-yl)-N-methylacetamide | 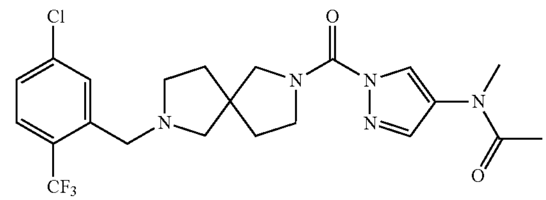 [SMILES: CC(=O)N(C)c1cnn(C(=O)N2CCC3(CCN(Cc4cc(Cl)ccc4C(F)(F)F)C3)C2)c1] |
| 71 | N-(1-(7-(2-chloro-5-(trifluoromethyl)benzyl)-2,7-diazaspiro[4.4]nonane-2-carbonyl)-1H-pyrazol-4-yl)-N-methylacetamide | 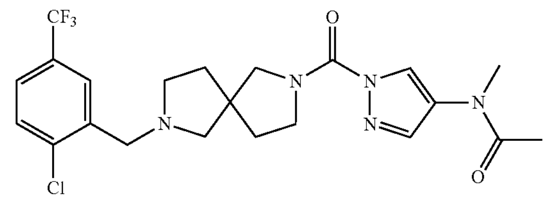 [SMILES: CC(=O)N(C)c1cnn(C(=O)N2CCC3(CCN(Cc4cc(C(F)(F)F)ccc4Cl)C3)C2)c1] |
| 72 | N-(1-(7-(2,5-bis(trifluoromethyl)benzyl)-2,7-diazaspiro[4.4]nonane-2-carbonyl)-1H-pyrazol-4-yl)-N-methylacetamide | 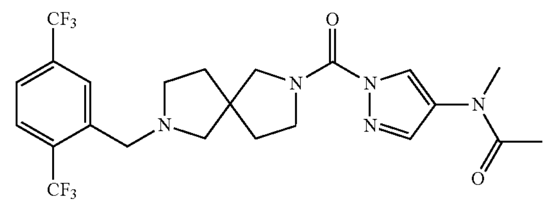 |
| 73 | N-methyl-N-(1-(7-(5-(pyrrolidin-1-yl)-2-(trifluoromethyl)benzyl)-2,7-diazaspiro[4.4]nonane-2-carbonyl)-1H-pyrazol-4-yl)acetamide | 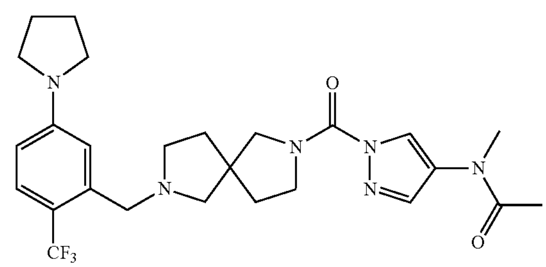 [SMILES: CC(=O)N(C)c1cnn(C(=O)N2CCC3(CCN(Cc4cc(N5CCCC5)ccc4C(F)(F)F)C3)C2)c1] |
| 74 | N-methyl-N-(1-(7-(2-(pyrrolidin-1-yl)-5-(trifluoromethyl)benzyl)-2,7-diazaspiro[4.4]nonane-2-carbonyl)-1H-pyrazol-4-yl)acetamide | 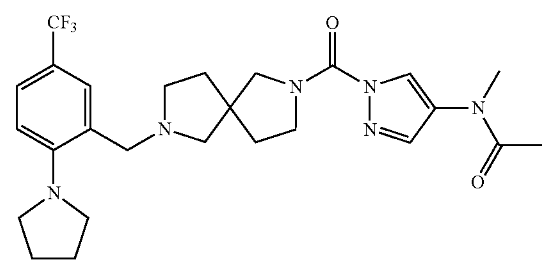 [SMILES: CC(=O)N(C)c1cnn(C(=O)N2CCC3(CCN(Cc4cc(C(F)(F)F)ccc4N4CCCC4)C3)C2)c1] |
| 75 | N-(1-(7-(4-fluorobenzyl)-2,7-diazaspiro[4.4]nonane-2-carbonyl)-1H-pyrazol-4-yl)-N-methylacetamide | 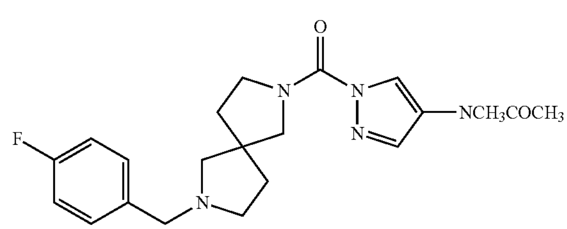 |
| 76 | N-methyl-N-(1-(7-(4-methylbenzyl)-2,7-diazaspiro[4.4]nonane-2-carbonyl)-1H-pyrazol-4-yl)acetamide | 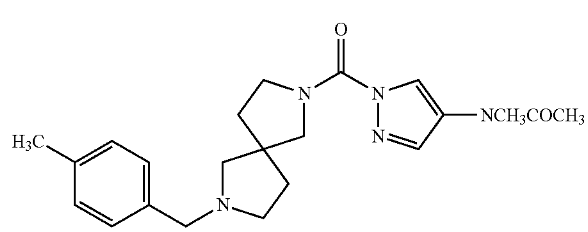 |

TABLE 1-continued

| Ex. | Names |
|---|---|
| 77 | N-(1-(7-(4-methoxybenzyl)-2,7-diazaspiro[4.4]nonane-2-carbonyl)-1H-pyrazol-4-yl)-N-methylacetamide |
| 78 | N-(1-(7-(3-chlorobenzyl)-2,7-diazaspiro[4.4]nonane-2-carbonyl)-1H-pyrazol-4-yl)-N-methylacetamide |
| 79 | N-(1-(7-(3-fluorobenzyl)-2,7-diazaspiro[4.4]nonane-2-carbonyl)-1H-pyrazol-4-yl)-N-methylacetamide |
| 80 | N-methyl-N-(1-(7-(3-methylbenzyl)-2,7-diazaspiro[4.4]nonane-2-carbonyl)-1H-pyrazol-4-yl)acetamide |
| 81 | N-(1-(7-(3-methoxybenzyl)-2,7-diazaspiro[4.4]nonane-2-carbonyl)-1H-pyrazol-4-yl)-N-methylacetamide |
| 82 | N-methyl-N-(1-(7-(3-(pyrrolidin-1-yl)benzyl)-2,7-diazaspiro[4.4]nonane-2-carbonyl)-1H-pyrazol-4-yl)acetamide |
| 83 | N-methyl-N-(1-(7-(3-methylbenzyl)-2,7-diazaspiro[3.5]nonane-2-carbonyl)-1H-pyrazol-4-yl)acetamide |

TABLE 1-continued

| Ex. | Names | Structures |
|---|---|---|
| 84 | N-(1-(7-(4-chlorobenzyl)-2,7-diazaspiro[3.5]nonane-2-carbonyl)-1H-pyrazol-4-yl)-N-methylacetamide | 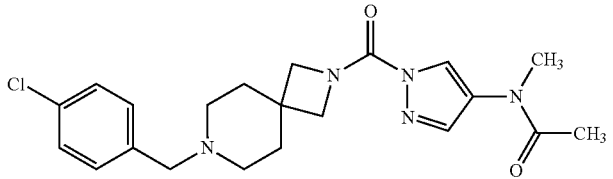 [SMILES: CC(=O)N(C)c1cnn(C(=O)N2CC3(CCN(Cc4ccc(Cl)cc4)CC3)C2)c1] |
| 85 | N-(1-(7-(3-chlorobenzyl)-2,7-diazaspiro[3.5]nonane-2-carbonyl)-1H-pyrazol-4-yl)-N-methylacetamide | 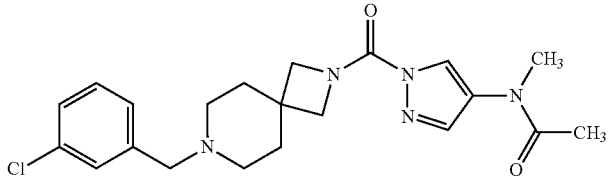 [SMILES: CC(=O)N(C)c1cnn(C(=O)N2CC3(CCN(Cc4cccc(Cl)c4)CC3)C2)c1] |
| 86 | N-(1-(7-(2-chlorobenzyl)-2,7-diazaspiro[3.5]nonane-2-carbonyl)-1H-pyrazol-4-yl)-N-methylacetamide | 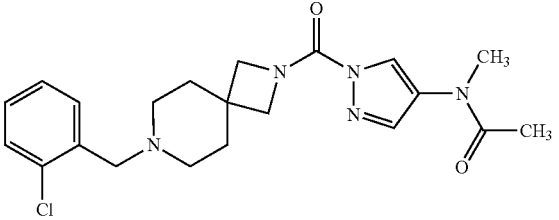 [SMILES: CC(=O)N(C)c1cnn(C(=O)N2CC3(CCN(Cc4ccccc4Cl)CC3)C2)c1] |
| 87 | N-methyl-N-(1-(7-(4-methylbenzyl)-2,7-diazaspiro[3.5]nonane-2-carbonyl)-1H-pyrazol-4-yl)acetamide | 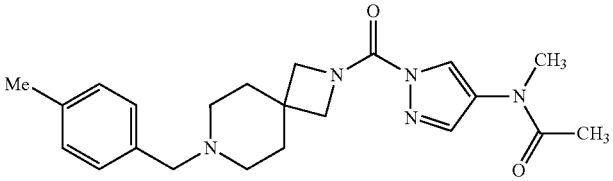 [SMILES: CC(=O)N(C)c1cnn(C(=O)N2CC3(CCN(Cc4ccc(C)cc4)CC3)C2)c1] |
| 88 | N-methyl-N-(1-(7-(3-(trifluoromethyl)benzyl)-2,7-diazaspiro[3.5]nonane-2-carbonyl)-1H-pyrazol-4-yl)acetamide | 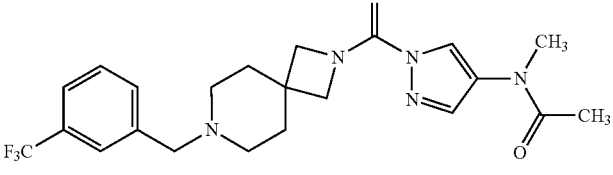 |
| 89 | N-methyl-N-(1-(7-(2-methylbenzyl)-2,7-diazaspiro[3.5]nonane-2-carbonyl)-1H-pyrazol-4-yl)acetamide | 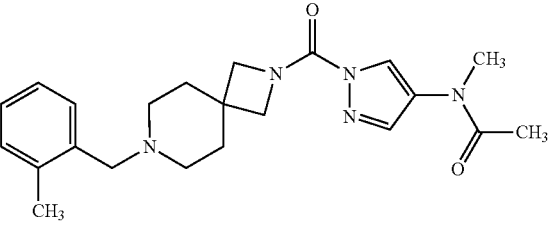 |
| 90 | N-methyl-N-(1-(7-(2-(trifluoromethyl)benzyl)-2,7-diazaspiro[3.5]nonane-2-carbonyl)-1H-pyrazol-4-yl)acetamide | 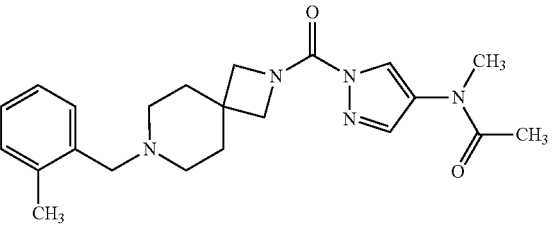 [SMILES: CC(=O)N(C)c1cnn(C(=O)N2CC3(CCN(Cc4ccccc4C)CC3)C2)c1] |

TABLE 1-continued

| Ex. | Names |
|---|---|
| 91 | N-methyl-N-(1-(5-(4-methylbenzyl)octahydropyrrolo[3,4-c]pyrrole-2-carbonyl)-1H-pyrazol-4-yl)acetamide |
| 92 | N-methyl-N-(1-(5-(3-methylbenzyl)octahydropyrrolo[3,4-c]pyrrole-2-carbonyl)-1H-pyrazol-4-yl)acetamide |
| 93 | N-methyl-N-(1-(5-(4-(pyrrolidin-1-yl)-2-(trifluoromethyl)benzyl)octahydropyrrolo[3,4-c]pyrrole-2-carbonyl)-1H-pyrazol-4-yl)acetamide |
| 94 | N-methyl-N-(1-(5-(2-methylbenzyl)octahydropyrrolo[3,4-c]pyrrole-2-carbonyl)-1H-pyrazol-4-yl)acetamide |
| 95 | N-(1-(5-(3-chloro-4-morpholinobenzyl)octahydropyrrolo[3,4-c]pyrrole-2-carbonyl)-1H-pyrazol-4-yl)-N-methylacetamide |
| 96 | N-methyl-N-(1-(5-(2-(trifluoromethyl)benzyl)octahydropyrrolo[3,4-c]pyrrole-2-carbonyl)-1H-pyrazol-4-yl)acetamide |
| 97 | N-methyl-N-(1-(5-(4-(pyrrolidin-1-yl)-3-(trifluoromethyl)benzyl)octahydropyrrolo[3,4-c]pyrrole-2-carbonyl)-1H-pyrazol-4-yl)acetamide |

TABLE 1-continued

| Ex. | Names |
|---|---|
| 98 | N-(1-(5-(4-chloro-3-(trifluoromethyl)benzyl)octahydropyrrolo[3,4-c]pyrrole-2-carbonyl)-1H-pyrazol-4-yl)-N-methylacetamide |
| 99 | N-methyl-N-(1-(5-(4-morpholino-3-(trifluoromethyl)benzyl)octahydropyrrolo[3,4-c]pyrrole-2-carbonyl)-1H-pyrazol-4-yl)acetamide |
| 100 | N-(1-(5-(4-fluoro-3-(pyrrolidin-1-yl)benzyl)octahydropyrrolo[3,4-c]pyrrole-2-carbonyl)-1H-pyrazol-4-yl)-N-methylacetamide |
| 101 | N-(1-(5-(4-(8-oxa-3-azabicyclo[3.2.1]octan-3-yl)-2-(trifluoromethyl)benzyl)octahydropyrrolo[3,4-c]pyrrole-2-carbonyl)-1H-pyrazol-4-yl)-N-methylacetamide |
| 102 | N-(1-(5-(4-(3-oxa-8-azabicyclo[3.2.1]octan-8-yl)-2-(trifluoromethyl)benzyl)octahydropyrrolo[3,4-c]pyrrole-2-carbonyl)-1H-pyrazol-4-yl)-N-methylacetamide |
| 103 | N-(1-(5-(3-chloro-2-methylbenzyl)octahydropyrrolo[3,4-c]pyrrole-2-carbonyl)-1H-pyrazol-4-yl)-N-methylacetamide |

TABLE 1-continued

| Ex. | Names |
|---|---|
| 104 | N-(1-(5-(5-chloro-2-(trifluoromethyl)benzyl)octahydropyrrolo[3,4-c]pyrrole-2-carbonyl)-1H-pyrazol-4-yl)-N-methylacetamide |
| 105 | N-(1-(5-(3,5-dichlorobenzyl)octahydropyrrolo[3,4-c]pyrrole-2-carbonyl)-1H-pyrazol-4-yl)-N-methylacetamide |
| 106 | N-(1-(5-(2-chloro-5-(trifluoromethyl)benzyl)octahydropyrrolo[3,4-c]pyrrole-2-carbonyl)-1H-pyrazol-4-yl)-N-methylacetamide |
| 107 | N-(1-(5-(2,3-dichlorobenzyl)octahydropyrrolo[3,4-c]pyrrole-2-carbonyl)-1H-pyrazol-4-yl)N-methylacetamide |
| 108 | N-(1-(5-(3,5-dimethylbenzyl)octahydropyrrolo[3,4-c]pyrrole-2-carbonyl)-1H-pyrazol-4-yl)N-methylacetamide |
| 109 | N-(1-(5-(2,5-dichlorobenzyl)octahydropyrrolo[3,4-c]pyrrole-2-carbonyl)-1H-pyrazol-4-yl)N-methylacetamide |
| 110 | N-(1-(5-(3-chloro-5-(pyrrolidin-1-yl)benzyl)octahydropyrrolo[3,4-c]pyrrole-2-carbonyl)-1H-pyrazol-4-yl)N-methylacetamide |

TABLE 1-continued

| Ex. | Names | Structures |
|---|---|---|
| 111 | N-(1-(5-(2,6-dichlorobenzyl)octahydropyrrolo[3,4-c]pyrrole-2-carbonyl)-1H-pyrazol-4-yl)N-methylacetamide | 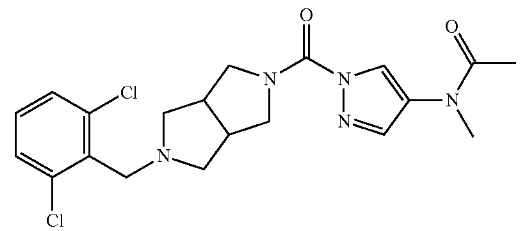 |
| 112 | N-methyl-N-(1-(5-(3-(pyrrolidin-1-yl)-5-(trifluoromethyl)benzyl)octahydropyrrolo[3,4-c]pyrrole-2-carbonyl)-1H-pyrazol-4-yl)acetamide | 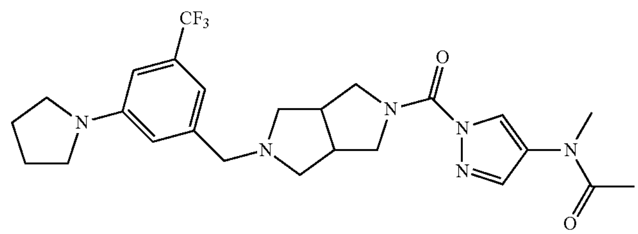 [SMILES: CC(=O)N(C)c1cnn(C(=O)N2CC3CN(Cc4cc(Cl)cc(N5CCCC5)c4)CC3C2)c1] |
| 113 | N-(1-(5-(2,4-dichlorobenzyl)octahydropyrrolo[3,4-c]pyrrole-2-carbonyl)-1H-pyrazol-4-yl)-N-methylacetamide | 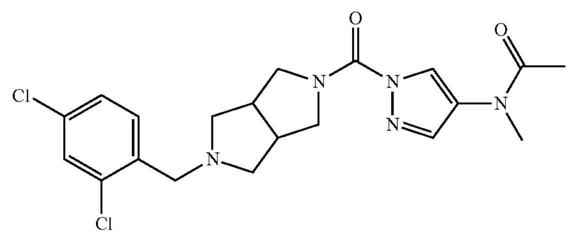 [SMILES: CC(=O)N(C)c1cnn(C(=O)N2CC3CN(Cc4ccc(Cl)cc4Cl)CC3C2)c1] |
| 114 | N-methyl-N-(1-(5-(3-morpholino-5-(trifluoromethyl)benzyl)octahydropyrrolo[3,4-c]pyrrole-2-carbonyl)-1H-pyrazol-4-yl)acetamide | 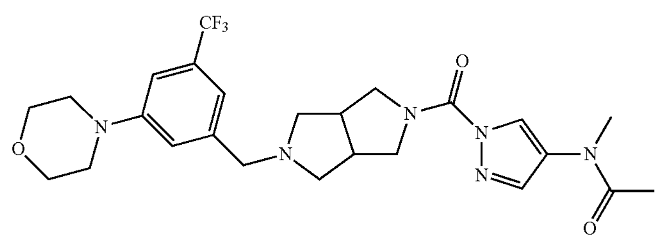 [SMILES: CC(=O)N(C)c1cnn(C(=O)N2CC3CN(Cc4cc(N5CCOCC5)cc(C(F)(F)F)c4)CC3C2)c1] |
| 115 | N-(1-(5-(2-chloro-4-methylbenzyl)octahydropyrrolo[3,4-c]pyrrole-2-carbonyl)-1H-pyrazol-4-yl)-N-methylacetamide | 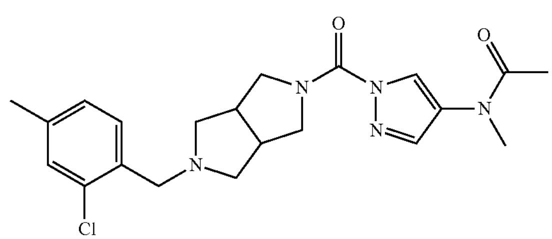 [SMILES: CC(=O)N(C)c1cnn(C(=O)N2CC3CN(Cc4ccc(C)cc4Cl)CC3C2)c1] |
| 116 | N-(1-(5-(3,5-bis(trifluoromethyl)benzyl)octahydropyrrolo[3,4-c]pyrrole-2-carbonyl)-1H-pyrazol-4-yl)-N-methylacetamide | 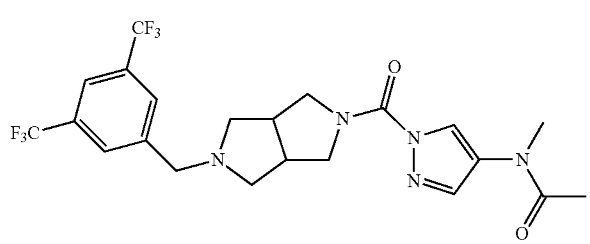 [SMILES: CC(=O)N(C)c1cnn(C(=O)N2CC3CN(Cc4cc(C(F)(F)F)cc(C(F)(F)F)c4)CC3C2)c1] |

TABLE 1-continued

| Ex. | Names | Structures |
|---|---|---|
| 117 | N-methyl-N-(1-(5-(3-(trifluoromethyl)benzyl)octahydropyrrolo[3,4-c]pyrrole-2-carbonyl)-1H-pyrazol-4-yl)acetamide | 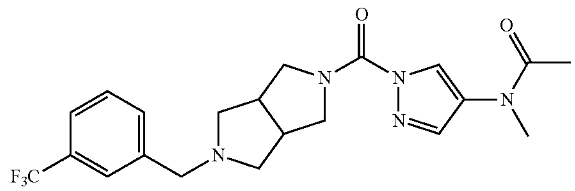 [SMILES: CC(=O)N(C)c1cnn(C(=O)N2CC3CN(Cc4cccc(C(F)(F)F)c4)CC3C2)c1] |
| 118 | N-(1-(5-(3-chloro-5-(tetrahydro-1H-furo[3,4-c]pyrrol-5(3H)-yl)benzyl)octahydropyrrolo[3,4-c]pyrrole-2-carbonyl)-1H-pyrazol-4-yl)-N-methylacetamide | 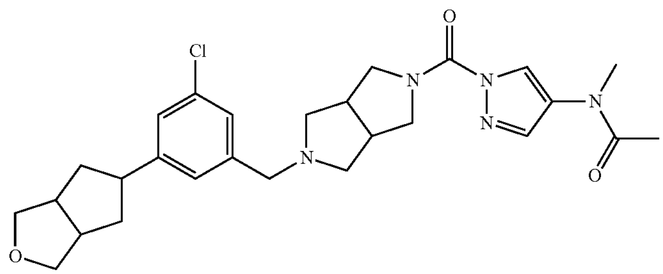 [SMILES: CC(=O)N(C)c1cnn(C(=O)N2CC3CN(Cc4cc(Cl)cc(C5CC6COCC6C5)c4)CC3C2)c1] |
| 119 | N-methyl-N-(1-(5-(3-(pyrrolidin-1-yl)benzyl)octahydropyrrolo[3,4-c]pyrrole-2-carbonyl)-1H-pyrazol-4-yl)acetamide | 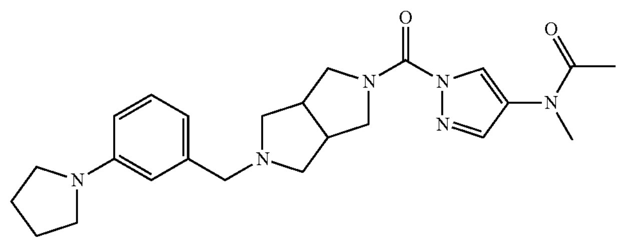 [SMILES: CC(=O)N(C)c1cnn(C(=O)N2CC3CN(Cc4cccc(N5CCCC5)c4)CC3C2)c1] |
| 120 | N-(1-(5-(3-chloro-5-(4-cyclopropylpiperazin-1-yl)benzyl)octahydropyrrolo[3,4-c]pyrrole-2-carbonyl)-1H-pyrazol-4-yl)-N-methylacetamide | 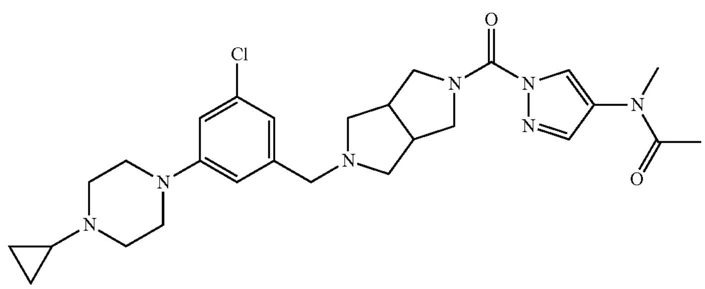 [SMILES: CC(=O)N(C)c1cnn(C(=O)N2CC3CN(Cc4cc(Cl)cc(N5CCN(C6CC6)CC5)c4)CC3C2)c1] |
| 121 | N-methyl-N-(1-(5-(3-morpholinobenzyl)octahydropyrrolo[3,4-c]pyrrole-2-carbonyl)-1H-pyrazol-4-yl)acetamide | 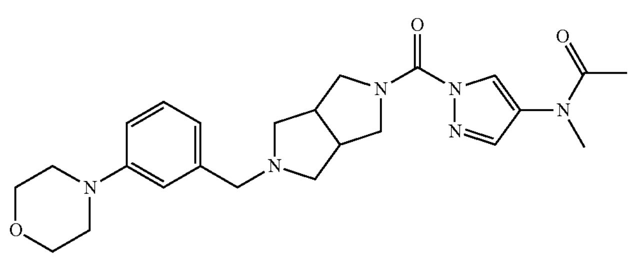 [SMILES: CC(=O)N(C)c1cnn(C(=O)N2CC3CN(Cc4cccc(N5CCOCC5)c4)CC3C2)c1] |
| 122 | N-(1-(5-(3-chloro-4-fluorobenzyl)octahydropyrrolo[3,4-c]pyrrole-2-carbonyl)-1H-pyrazol-4-yl)-N-methylacetamide | 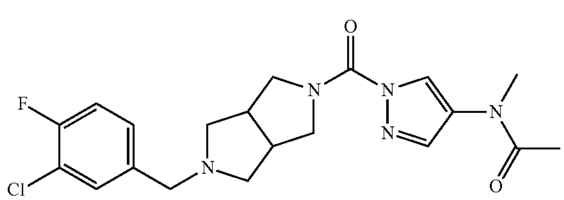 [SMILES: CC(=O)N(C)c1cnn(C(=O)N2CC3CN(Cc4ccc(F)c(Cl)c4)CC3C2)c1] |

TABLE 1-continued

| Ex. | Names | Structures |
|---|---|---|
| 123 | N-(1-(5-(3-chloro-4-(pyrrolidin-1-yl)benzyl)octahydropyrrolo[3,4-c]pyrrole-2-carbonyl)-1H-pyrazol-4-yl)-N-methylacetamide | 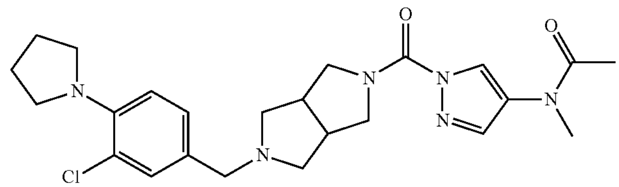 [SMILES: CC(=O)N(C)c1cnn(C(=O)N2CC3CN(Cc4ccc(N5CCCC5)c(Cl)c4)CC3C2)c1] |
| 124 | N-methyl-N-(1-(5-(3-morpholino-4-(trifluoromethyl)benzyl)octahydropyrrolo[3,4-c]pyrrole-2-carbonyl)-1H-pyrazol-4-yl)acetamide | 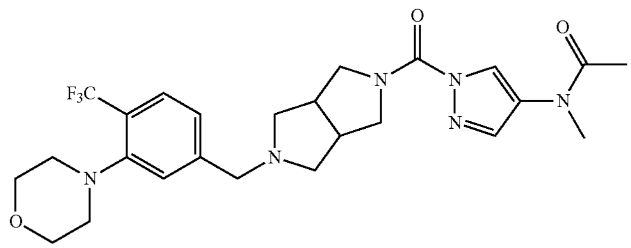 [SMILES: CC(=O)N(C)c1cnn(C(=O)N2CC3CN(Cc4ccc(C(F)(F)F)c(N5CCOCC5)c4)CC3C2)c1] |
| 125 | N-(1-(5-(3-chloro-5-morpholinobenzyl)octahydropyrrolo[3,4-c]pyrrole-2-carbonyl)-1H-pyrazol-4-yl)-N-methylacetamide | 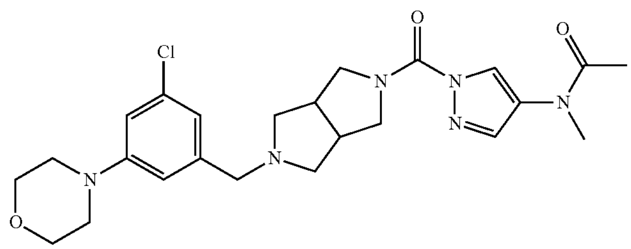 [SMILES: CC(=O)N(C)c1cnn(C(=O)N2CC3CN(Cc4cc(Cl)cc(N5CCOCC5)c4)CC3C2)c1] |
| 126 | N-(1-(5-(2,5-bis(trifluoromethyl)benzyl)octahydropyrrolo[3,4-c]pyrrole-2-carbonyl)-1H-pyrazol-4-yl)-N-methylacetamide | 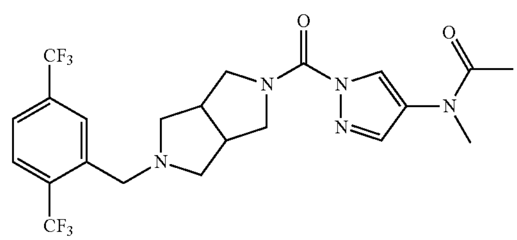 [SMILES: CC(=O)N(C)c1cnn(C(=O)N2CC3CN(Cc4cc(C(F)(F)F)ccc4C(F)(F)F)CC3C2)c1] |
| 127 | N-methyl-N-(1-(5-(5-(pyrrolidin-1-yl)-2-(trifluoromethyl)benzyl)octahydropyrrolo[3,4-c]pyrrole-2-carbonyl)-1H-pyrazol-4-yl)acetamide | 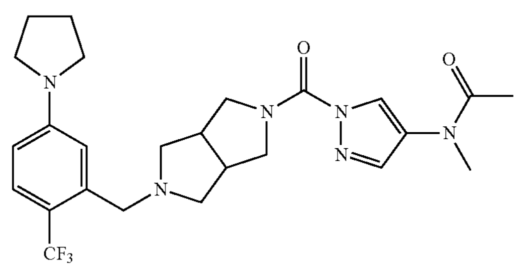 [SMILES: CC(=O)N(C)c1cnn(C(=O)N2CC3CN(Cc4cc(N5CCCC5)ccc4C(F)(F)F)CC3C2)c1] |
| 128 | N-methyl-N-(1-(5-(2-(pyrrolidin-1-yl)-5-(trifluoromethyl)benzyl)octahydropyrrolo[3,4-c]pyrrole-2-carbonyl)-1H-pyrazol-4-yl)acetamide | 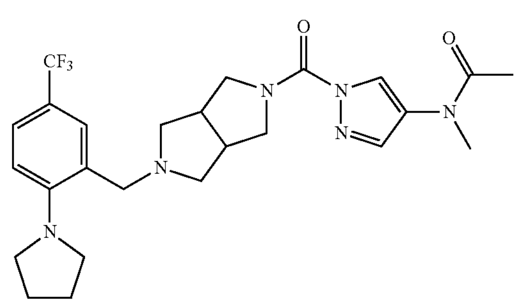 [SMILES: CC(=O)N(C)c1cnn(C(=O)N2CC3CN(Cc4cc(C(F)(F)F)ccc4N4CCCC4)CC3C2)c1] |

TABLE 1-continued

| Ex. | Names |
|---|---|
| 129 | N-(1-(5-(4-chloro-3-morpholinobenzyl)octahydropyrrolo[3,4-c]pyrrole-2-carbonyl)-1H-pyrazol-4-yl)-N-methylacetamide |
| 130 | N-methyl-N-(1-(5-(3-(pyrrolidin-1-yl)-4-(trifluoromethyl)benzyl)octahydropyrrolo[3,4-c]pyrrole-2-carbonyl)-1H-pyrazol-4-yl)acetamide |
| 131 | N-methyl-N-(1-(5-(4-morpholino-2-(trifluoromethyl)benzyl)octahydropyrrolo[3,4-c]pyrrole-2-carbonyl)-1H-pyrazol-4-yl)acetamide |
| 132 | N-(1-(5-(2-chloro-4-(pyrrolidin-1-yl)benzyl)octahydropyrrolo[3,4-c]pyrrole-2-carbonyl)-1H-pyrazol-4-yl)-N-methylacetamide |
| 133 | N-(1-(cis-5-((2-chlorobenzyl)amino)octahydrocyclopenta[c]pyrrole-2-carbonyl)-1H-pyrazol-4-yl)-N-methylacetamide |
| 134 | N-(1-(cis-5-((3-chlorobenzyl)amino)octahydrocyclopenta[c]pyrrole-2-carbonyl)-1H-pyrazol-4-yl)-N-methylacetamide |

TABLE 1-continued

| Ex. | Names | Structures |
|---|---|---|
| 135 | N-(1-(cis-5-((4-chlorobenzyl)amino)octahydrocyclopenta[c]pyrrole-2-carbonyl)-1H-pyrazol-4-yl)-N-methylacetamide | 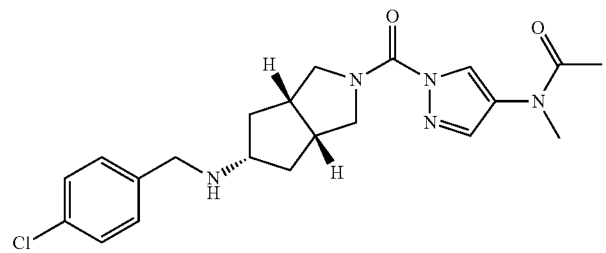 [SMILES: CC(=O)N(C)c1cnn(C(=O)N2C[C@H]3C[C@@H](NCc4ccc(Cl)cc4)C[C@H]3C2)c1] |
| 136 | N-(1-(trans-5-((2-chlorobenzyl)amino)octahydrocyclopenta[c]pyrrole-2-carbonyl)-1H-pyrazol-4-yl)-N-methylacetamide | 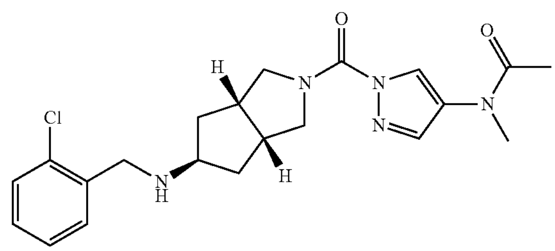 [SMILES: CC(=O)N(C)c1cnn(C(=O)N2C[C@H]3C[C@H](NCc4ccccc4Cl)C[C@H]3C2)c1] |
| 137 | N-(1-(trans-5-((3-chlorobenzyl)amino)octahydrocyclopenta[c]pyrrole-2-carbonyl)-1H-pyrazol-4-yl)-N-methylacetamide | 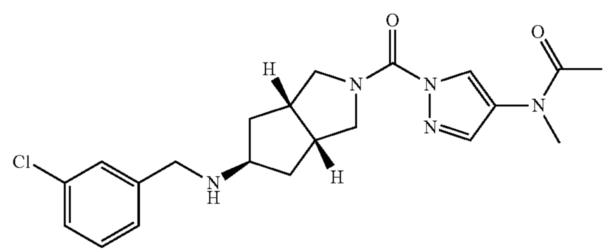 [SMILES: CC(=O)N(C)c1cnn(C(=O)N2C[C@H]3C[C@H](NCc4cccc(Cl)c4)C[C@H]3C2)c1] |
| 138 | N-(1-(trans-5-((4-chlorobenzyl)amino)octahydrocyclopenta[c]pyrrole-2-carbonyl)-1H-pyrazol-4-yl)-N-methylacetamide | 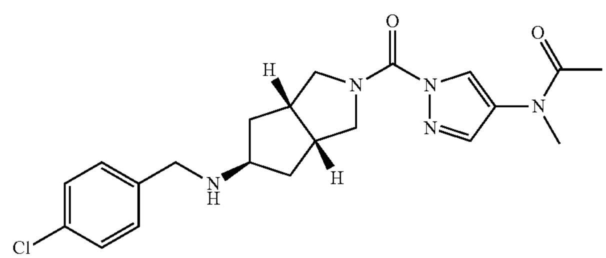 |
| 139 | N-(1-(trans-5-((2-chlorobenzyl)(methyl)amino)octahydrocyclopenta[c]pyrrole-2-carbonyl)-1H-pyrazol-4-yl)-N-methylacetamide | 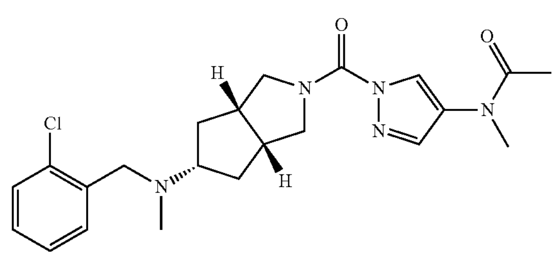 [SMILES: CC(=O)N(C)c1cnn(C(=O)N2C[C@H]3C[C@@H](N(C)Cc4ccccc4Cl)C[C@H]3C2)c1] |
| 140 | N-(1-(cis-5-((2,5-bis(trifluoromethyl)benzyl)(methyl)amino)octahydrocyclopenta[c]pyrrole-2-carbonyl)-1H-pyrazol-4-yl)-N-methylacetamide | 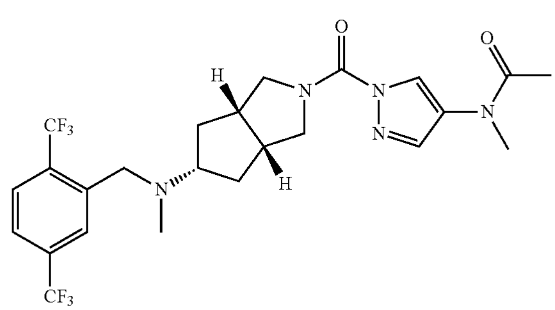 |

TABLE 1-continued

| Ex. | Names |
|---|---|
| 141 | N-(1-(m-5-((3-chlorobenzyl)(methyl)amino)octahydrocyclopenta[c]pyrrole-2-carbonyl)-1H-pyrazol-4-yl)-N-methylacetamide |
| 142 | N-methyl-N-(1-(trans-5-(methyl(5-(pyrrolidin-1-yl)-2-(trifluoromethyl)benzyl)amino)octahydrocyclopenta[c]pyrrole-2-carbonyl)-1H-pyrazol-4-yl)acetamide |
| 143 | N-(1-(cis-5-((4-chlorobenzyl)(methyl)amino)octahydrocyclopenta[c]pyrrole-2-carbonyl)-1H-pyrazol-4-yl)-N-methylacetamide |
| 144 | N-methyl-N-(1-(trans-5-(methyl(2-(pyrrolidin-1-yl)-5-(trifluoromethyl)benzyl)amino)octahydrocyclopenta[c]pyrrole-2-carbonyl)-1H-pyrazol-4-yl)acetamide |
| 145 | N-(1-(trans-5-((2-chlorobenzyl)(methyl)amino)octahydrocyclopenta[c]pyrrole-2-carbonyl)-1H-pyrazol-4-yl)-N-methylacetamide |

TABLE 1-continued

| Ex. | Names |
|---|---|
| 146 | N-(1-(trans-5-((2,5-bis(trifluoromethyl)benzyl)(methyl)amino)octahydrocyclopenta[c]pyrrole-2-carbonyl)-1H-pyrazol-4-yl)-N-methylacetamide |
| 147 | N-(1-(trans-5-((3-chlorobenzyl)(methyl)amino)octahydrocyclopenta[c]pyrrole-2-carbonyl)-1H-pyrazol-4-yl)-N-methylacetamide |
| 148 | N-(1-(trans-5-((4-chlorobenzyl)(methyl)amino)octahydrocyclopenta[c]pyrrole-2-carbonyl)-1H-pyrazol-4-yl)-N-methylacetamide |
| 149 | N-(1-(cis-5-((4-(3-oxa-8-azabicyclo[3.2.1]octan-8-yl)-2-(trifluoromethyl)benzyl)(methyl)amino)octahydrocyclopenta[c]pyrrole-2-carbonyl)-1H-pyrazol-4-yl)-N-methylacetamide |
| 150 | N-(1-(cis-5-((4-(3-oxa-8-azabicyclo[3.2.1]octan-8-yl)-3-(trifluoromethyl)benzyl)(methyl)amino)octahydrocyclopenta[c]pyrrole-2-carbonyl)-1H-pyrazol-4-yl)-N-methylacetamide |

TABLE 1-continued

| Ex. | Names | Structures |
|---|---|---|
| 151 | N-(1-(cis-5-((3-(3-oxa-8-azabicyclo[3.2.1]octan-8-yl)-5-(trifluoromethyl)benzyl)(methyl)amino)octahydrocyclopenta[c]pyrrole-2-carbonyl)-1H-pyrazol-4-yl)-N-methylacetamide | 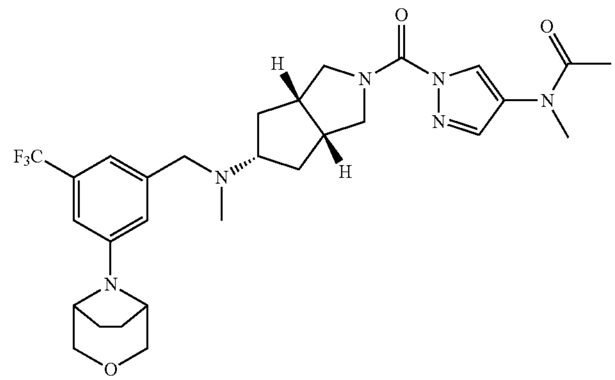 [SMILES: CC(=O)N(C)c1cnn(C(=O)N2C[C@H]3C[C@@H](N(C)Cc4cc(N5C6CCC5COC6)cc(C(F)(F)F)c4)C[C@H]3C2)c1] |
| 152 | N-methyl-N-(1-(cis-5-(methyl(4-(pyrrolidin-1-yl)-2-(trifluoromethyl)benzyl)amino)octahydrocyclopenta[c]pyrrole-2-carbonyl)-1H-pyrazol-4-yl)acetamide | 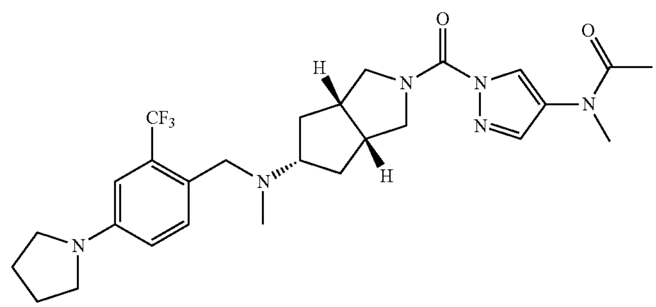 [SMILES: CC(=O)N(C)c1cnn(C(=O)N2C[C@H]3C[C@@H](N(C)Cc4ccc(N5CCCC5)cc4C(F)(F)F)C[C@H]3C2)c1] |
| 153 | N-methyl-N-(1-(cis-5-(methyl(4-(pyrrolidin-1-yl)-3-(trifluoromethyl)benzyl)amino)octahydrocyclopenta[c]pyrrole-2-carbonyl)-1H-pyrazol-4-yl)acetamide | 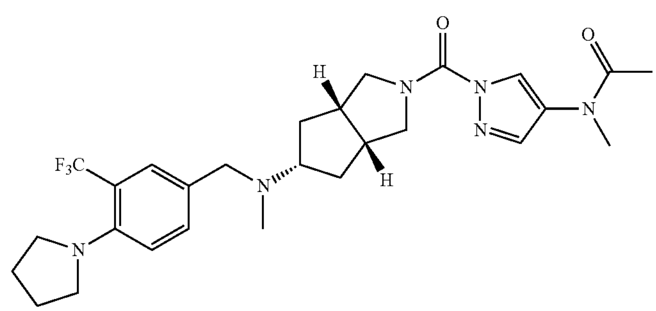 [SMILES: CC(=O)N(C)c1cnn(C(=O)N2C[C@H]3C[C@@H](N(C)Cc4ccc(N5CCCC5)c(C(F)(F)F)c4)C[C@H]3C2)c1] |
| 154 | N-methyl-N-(1-(cis-5-(methyl(3-(pyrrolidin-1-yl)-5-(trifluoromethyl)benzyl)amino)octahydrocyclopenta[c]pyrrole-2-carbonyl)-1H-pyrazol-4-yl)acetamide | 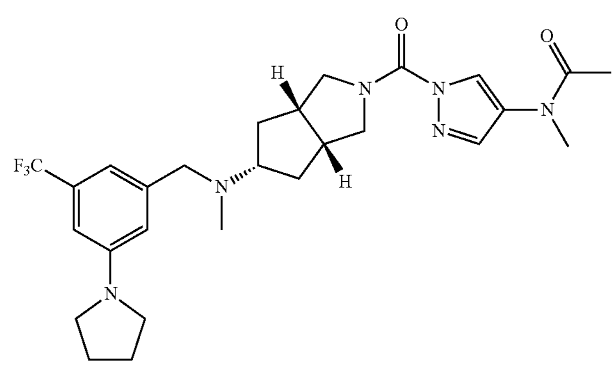 [SMILES: CC(=O)N(C)c1cnn(C(=O)N2C[C@H]3C[C@@H](N(C)Cc4cc(N5CCCC5)cc(C(F)(F)F)c4)C[C@H]3C2)c1] |

TABLE 1-continued

| Ex. | Names | Structures |
|---|---|---|
| 155 | N-(1-(trans-5-((4-(3-oxa-8-azabicyclo[3.2.1]octan-8-yl)-2-(trifluoromethyl)benzyl)(methyl)amino)octahydrocyclopenta[c]pyrrole-2-carbonyl)-1H-pyrazol-4-yl)-N-methylacetamide | 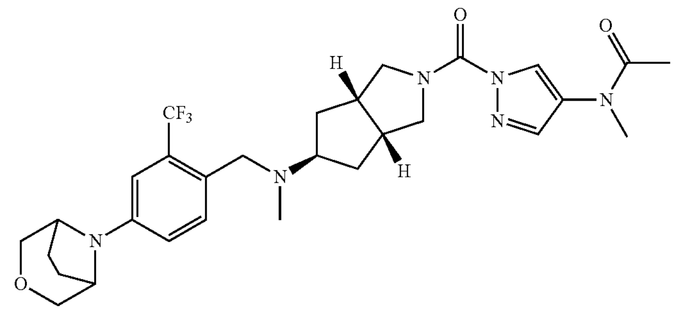 [SMILES: CC(=O)N(C)c1cnn(C(=O)N2C[C@H]3C[C@H](N(C)Cc4ccc(N5C6CCC5COC6)cc4C(F)(F)F)C[C@H]3C2)c1] |
| 156 | N-(1-(trans-5-((4-(3-oxa-8-azabicyclo[3.2.1]octan-8-yl)-3-(trifluoromethyl)benzyl)(methyl)amino)octahydrocyclopenta[c]pyrrole-2-carbonyl)-1H-pyrazol-4-yl)-N-methylacetamide | 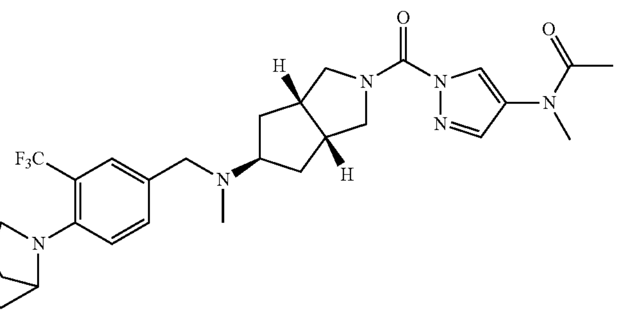 |
| 157 | N-(1-(trans-5-((3-(3-oxa-8-azabicyclo[3.2.1]octan-8-yl)-5-(trifluoromethyl)benzyl)(methyl)amino)octahydrocyclopenta[c]pyrrole-2-carbonyl)-1H-pyrazol-4-yl)-N-methylacetamide | 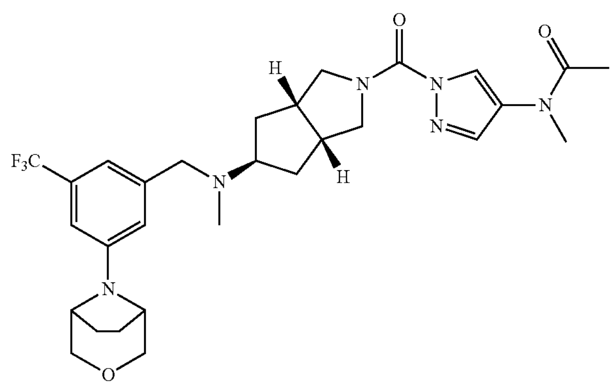 [SMILES: CC(=O)N(C)c1cnn(C(=O)N2C[C@H]3C[C@H](N(C)Cc4cc(N5C6CCC5COC6)cc(C(F)(F)F)c4)C[C@H]3C2)c1] |
| 158 | N-methyl-N-(1-(trans-5-(methyl(4-(pyrrolidin-1-yl)-2-(trifluoromethyl)benzyl)amino)octahydrocyclopenta[c]pyrrole-2-carbonyl)-1H-pyrazol-4-yl)acetamide | 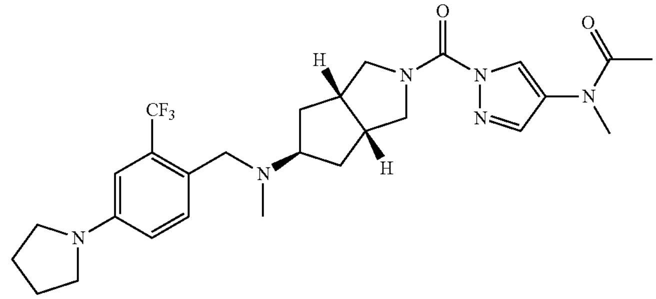 [SMILES: CC(=O)N(C)c1cnn(C(=O)N2C[C@H]3C[C@H](N(C)Cc4ccc(N5CCCC5)cc4C(F)(F)F)C[C@H]3C2)c1] |

TABLE 1-continued

| Ex. | Names | Structures |
|---|---|---|
| 159 | N-methyl-N-(1-(trans-5-(methyl(4-(pyrrolidin-1-yl)-3-(trifluoromethyl)benzyl)amino)octahydrocyclopenta[c]pyrrole-2-carbonyl)-1H-pyrazol-4-yl)acetamide | 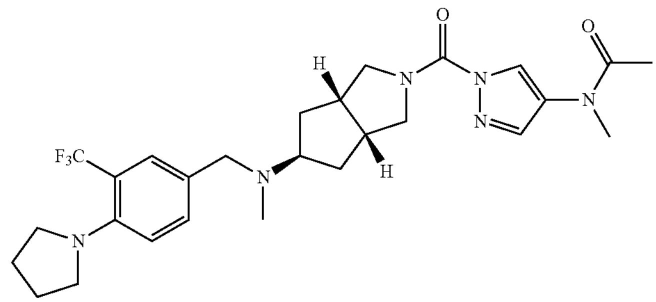 [SMILES: CC(=O)N(C)c1cnn(C(=O)N2C[C@H]3C[C@H](N(C)Cc4ccc(N5CCCC5)c(C(F)(F)F)c4)C[C@H]3C2)c1] |
| 160 | N-methyl-N-(1-(trans-5-(methyl(3-(pyrrolidin-1-yl)-5-(trifluoromethyl)benzyl)amino)octahydrocyclopenta[c]pyrrole-2-carbonyl)-1H-pyrazol-4-yl)acetamide | 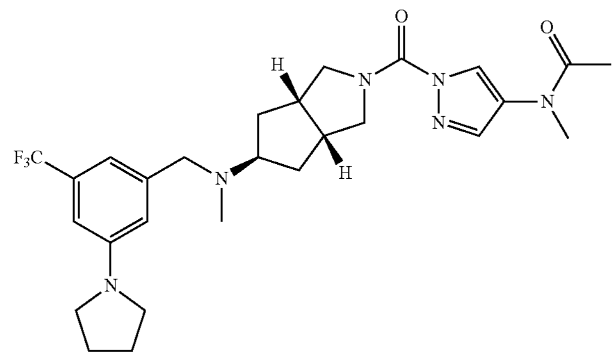 [SMILES: CC(=O)N(C)c1cnn(C(=O)N2C[C@H]3C[C@H](N(C)Cc4cc(N5CCCC5)cc(C(F)(F)F)c4)C[C@H]3C2)c1] |
| 161 | N-(1-(cis-5-((5-chloro-2-(trifluoromethyl)benzyl)(methyl)amino)octahydrocyclopenta[c]pyrrole-2-carbonyl)-1H-pyrazol-4-yl)-N-methylacetamide | 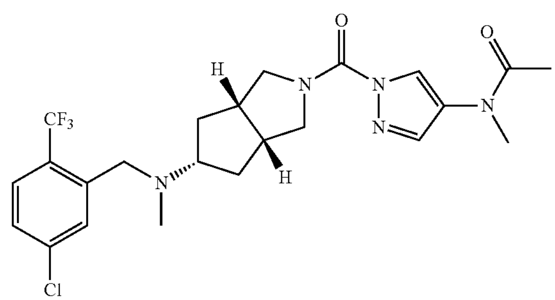 [SMILES: CC(=O)N(C)c1cnn(C(=O)N2C[C@H]3C[C@@H](N(C)Cc4cc(Cl)ccc4C(F)(F)F)C[C@H]3C2)c1] |
| 162 | N-(1-(cis-5-((2,5-dichlorobenzyl)(methyl)amino)octahydrocyclopenta[c]pyrrole-2-carbonyl)-1H-pyrazol-4-yl)-N-methylacetamide | 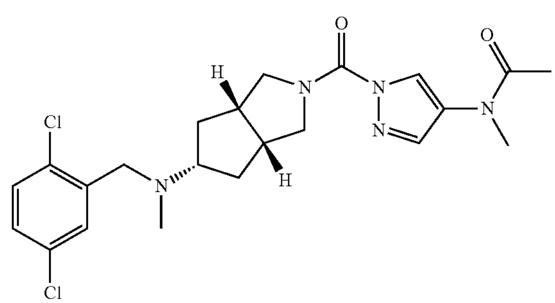 [SMILES: CC(=O)N(C)c1cnn(C(=O)N2C[C@H]3C[C@@H](N(C)Cc4cc(Cl)ccc4Cl)C[C@H]3C2)c1] |
| 163 | N-(1-(cis-5-((2-chloro-5-(trifluoromethyl)benzyl)(methyl)amino)octahydrocyclopenta[c]pyrrole-2-carbonyl)-1H-pyrazol-4-yl)-N-methylacetamide | 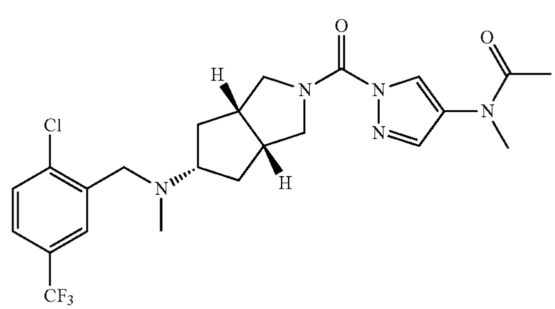 [SMILES: CC(=O)N(C)c1cnn(C(=O)N2C[C@H]3C[C@@H](N(C)Cc4cc(C(F)(F)F)ccc4Cl)C[C@H]3C2)c1] |

TABLE 1-continued

| Ex. | Names |
|---|---|
| 164 | N-(1-(trans-5-((5-chloro-2-(trifluoromethyl)benzyl)(methyl)amino)octahydrocyclopenta[c]pyrrole-2-carbonyl)-1H-pyrazol-4-yl)-N-methylacetamide |
| 165 | N-(1-(trans-5-((2,5-dichlorobenzyl)(methyl)amino)octahydrocyclopenta[c]pyrrole-2-carbonyl)-1H-pyrazol-4-yl)-N-methylacetamide |
| 166 | N-(1-(trans-5-((2-chloro-5-(trifluoromethyl)benzyl)(methyl)amino)octahydrocyclopenta[c]pyrrole-2-carbonyl)-1H-pyrazol-4-yl)-N-methylacetamide |
| 167 | N-methyl-N-(1-(cis-5-(methyl(5-(pyrrolidin-1-yl)-2-(trifluoromethyl)benzyl)amino)octahydrocyclopenta[c]pyrrole-2-carbonyl)-1H-pyrazol-4-yl)acetamide |
| 168 | N-methyl-N-(1-(cis-5-(methyl(2-(pyrrolidin-1-yl)-5-(trifluoromethyl)benzyl)amino)octahydrocyclopenta[c]pyrrole-2-carbonyl)-1H-pyrazol-4-yl)acetamide |

TABLE 1-continued

| Ex. | Names | Structures |
|---|---|---|
| 169 | N-(2-chlorobenzyl)-N-(cis-2-(4-(N-methylacetamido)-1H-pyrazole-1-carbonyl)octahydrocyclopenta[c]pyrrol-5-yl)acetamide | 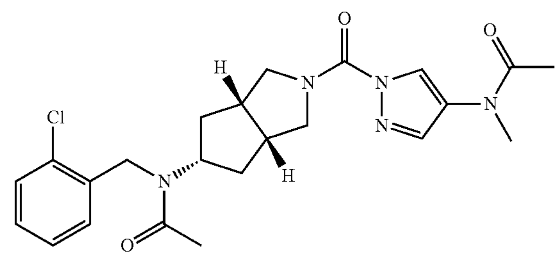 [SMILES: CC(=O)N(C)c1cnn(C(=O)N2C[C@H]3C[C@@H](N(Cc4ccccc4Cl)C(C)=O)C[C@H]3C2)c1] |
| 170 | N-(3-chlorobenzyl)-N-(cis-2-(4-(N-methylacetamido)-1H-pyrazole-1-carbonyl)octahydrocyclopenta[c]pyrrol-5-yl)acetamide | 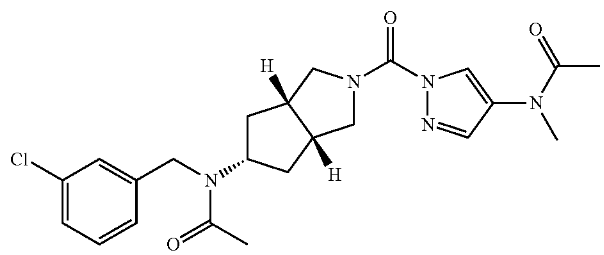 [SMILES: CC(=O)N(C)c1cnn(C(=O)N2C[C@H]3C[C@@H](N(Cc4cccc(Cl)c4)C(C)=O)C[C@H]3C2)c1] |
| 171 | N-(4-chlorobenzyl)-N-(cis-2-(4-(N-methylacetamido)-1H-pyrazole-1-carbonyl)octahydrocyclopenta[c]pyrrol-5-yl)acetamide | 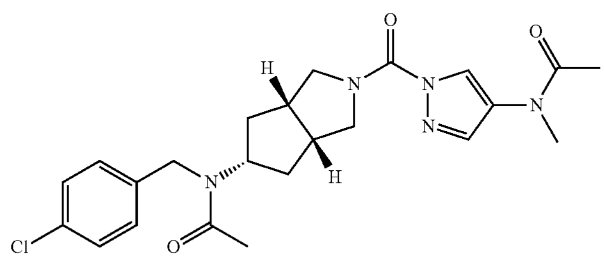 [SMILES: CC(=O)N(C)c1cnn(C(=O)N2C[C@H]3C[C@@H](N(Cc4ccc(Cl)cc4)C(C)=O)C[C@H]3C2)c1] |
| 172 | N-(1-(trans-5-((2-chlorobenzyl)(methyl)amino)octahydrocyclopenta[c]pyrrole-2-carbonyl)-1H-pyrazol-yl)-N-methylacetamide | 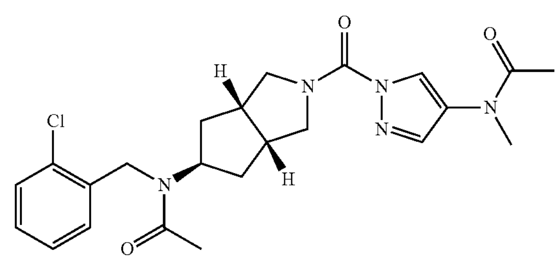 [SMILES: CC(=O)N(C)c1cnn(C(=O)N2C[C@H]3C[C@H](N(Cc4ccccc4Cl)C(C)=O)C[C@H]3C2)c1] |
| 173 | N-(3-chlorobenzyl)-N-(trans-2-(4-(N-methylacetamido)-1H-pyrazole-1-carbonyl)octahydrocyclopenta[c]pyrrol-5-yl)acetamide | 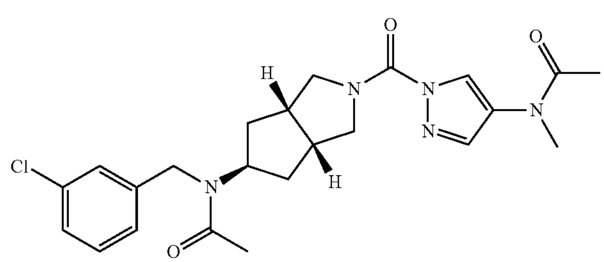 [SMILES: CC(=O)N(C)c1cnn(C(=O)N2C[C@H]3C[C@H](N(Cc4cccc(Cl)c4)C(C)=O)C[C@H]3C2)c1] |
| 174 | N-(4-chlorobenzyl)-N-(trans-2-(4-(N-methylacetamido)-1H-pyrazole-1-carbonyl)octahydrocyclopenta[c]pyrrol-5-yl)acetamide | 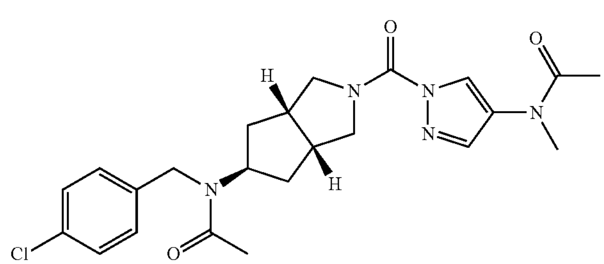 [SMILES: CC(=O)N(C)c1cnn(C(=O)N2C[C@H]3C[C@H](N(Cc4ccc(Cl)cc4)C(C)=O)C[C@H]3C2)c1] |

TABLE 1-continued

| Ex. | Names | Structures |
|---|---|---|
| 175 | N-(1-(7-(2,5-dichlorobenzyl)-2,7-diazaspiro[4.4]nonane-2-carbonyl)-1H-pyrazol-4-yl)-N-methylacetamide | 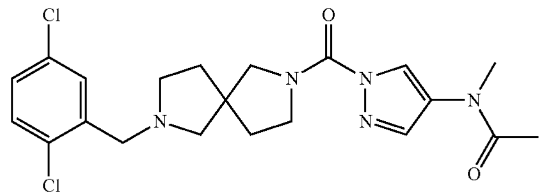 [SMILES: CC(=O)N(C)c1cnn(C(=O)N2CCC3(CCN(Cc4cc(Cl)ccc4Cl)C3)C2)c1] |
| 176 | N-(1-(7-(2,5-dichlorobenzyl)-2,7-diazaspiro[4.4]nonane-2-carbonyl)-1H-pyrazol-4-yl)-N-methylacetamide (single enantiomer) | 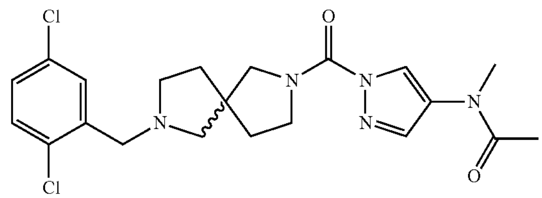 [SMILES: CC(=O)N(C)c1cnn(C(=O)N2CCC3(CCN(Cc4cc(Cl)ccc4Cl)C3)C2)c1] |
| 177 | N-(1-(7-(2,5-dichlorobenzyl)-2,7-diazaspiro[4.4]nonane-2-carbonyl)-1H-pyrazol-4-yl)-N-methylacetamide (single enantiomer) | 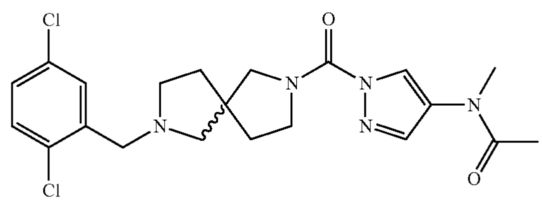 [SMILES: CC(=O)N(C)c1cnn(C(=O)N2CCC3(CCN(Cc4cc(Cl)ccc4Cl)C3)C2)c1] |
| 178 | N-(1-(5-(4-fluorobenzyl)octahydropyrrolo[3,4-c]pyrrole-2-carbonyl)-1H-pyrazol-4-yl) N-methylacetamide | 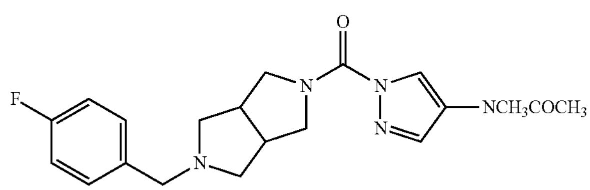 |
| 179 | N-(1-(5-(4-methoxybenzyl)octahydropyrrolo[3,4-c]pyrrole-2-carbonyl)-1H-pyrazol-4-yl)-N-methylacetamide | 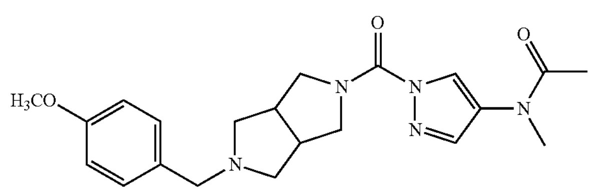 [SMILES: COc1ccc(CN2CC3CN(C(=O)n4cc(N(C)C(C)=O)cn4)CC3C2)cc1] |
| 180 | N-(1-(5-(3-fluorobenzyl)octahydropyrrolo[3,4-c]pyrrole-2-carbonyl)-1H-pyrazol-4-yl)-N-methylacetamide | 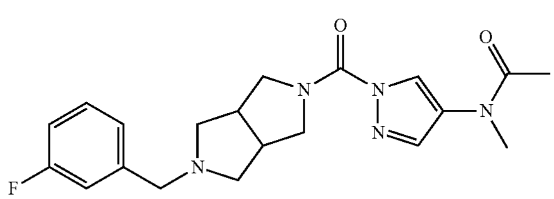 [SMILES: CC(=O)N(C)c1cnn(C(=O)N2CC3CN(Cc4cccc(F)c4)CC3C2)c1] |
| 181 | N-(1-(5-(3-methoxybenzyl)octahydropyrrolo[3,4-c]pyrrole-2-carbonyl)-1H-pyrazol-4-yl)-N-methylacetamide | 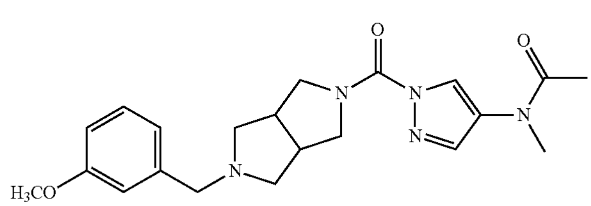 [SMILES: COc1cccc(CN2CC3CN(C(=O)n4cc(N(C)C(C)=O)cn4)CC3C2)c1] |

TABLE 1-continued

| Ex. | Names | Structures |
|-----|-------|------------|
| 182 | N-(1-(5-(2-fluorobenzyl)octahydropyrrolo[3,4-c]pyrrole-2-carbonyl)-1H-pyrazol-4-yl)-N-methylacetamide | 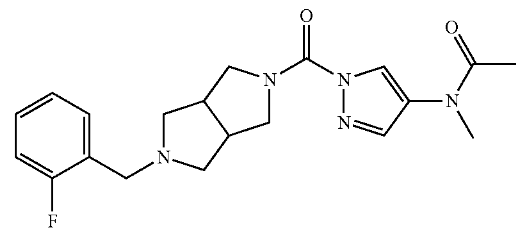 [SMILES: CC(=O)N(C)c1cnn(C(=O)N2CC3CN(Cc4ccccc4F)CC3C2)c1] |
| 183 | N-(1-(5-(2-methoxybenzyl)octahydropyrrolo[3,4-c]pyrrole-2-carbonyl)-1H-pyrazol-4-yl)-N-methylacetamide | 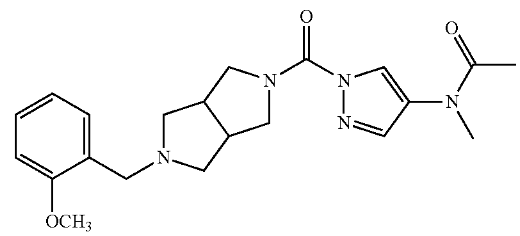 [SMILES: COc1ccccc1CN1CC2CN(C(=O)n3cc(N(C)C(C)=O)cn3)CC2C1] |
| 184 | N-methyl-N-(1-(5-(2-(pyrrolidin-1-yl)benzyl)octahydropyrrolo[3,4-c]pyrrole-2-carbonyl)-1H-pyrazol-4-yl)acetamide | 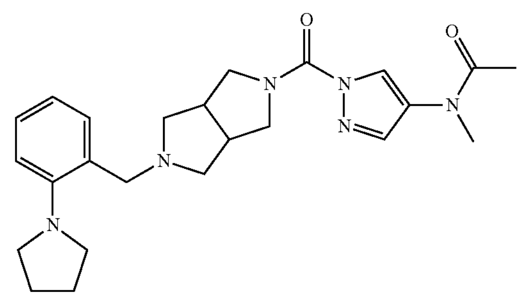 [SMILES: CC(=O)N(C)c1cnn(C(=O)N2CC3CN(Cc4ccccc4N4CCCC4)CC3C2)c1] |
| 185 | N-methyl-N-(1-(5-(2-morpholinobenzyl)octahydropyrrolo[3,4-c]pyrrole-2-carbonyl)-1H-pyrazol-4-yl)acetamide | 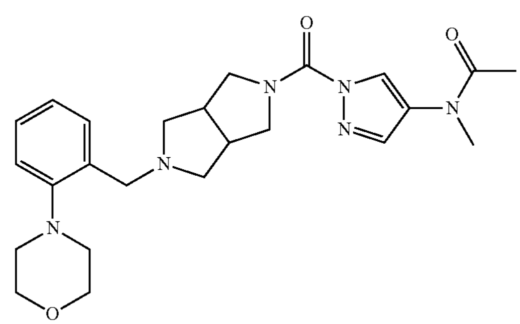 [SMILES: CC(=O)N(C)c1cnn(C(=O)N2CC3CN(Cc4ccccc4N4CCOCC4)CC3C2)c1] |
| 186 | N-(1-(2-(2-chlorobenzyl)-2,8-diazaspiro[4.5]decane-8-carbonyl)-1H-pyrazol-4-yl)-N-methylacetamide | 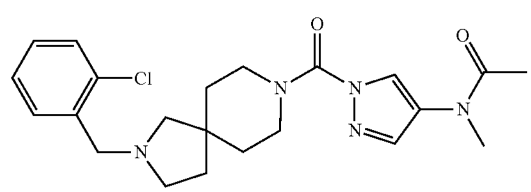 [SMILES: CC(=O)N(C)c1cnn(C(=O)N2CCC3(CCN(Cc4ccccc4Cl)C3)CC2)c1] |
| 187 | N-(1-(2-(3-chlorobenzyl)-2,8-diazaspiro[4.5]decane-8-carbonyl)-1H-pyrazol-4-yl)-N-methylacetamide | 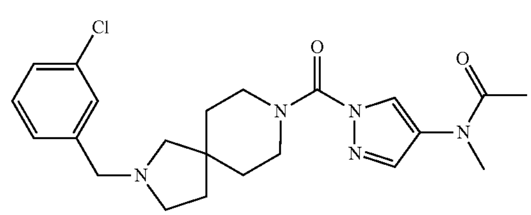 [SMILES: CC(=O)N(C)c1cnn(C(=O)N2CCC3(CCN(Cc4cccc(Cl)c4)C3)CC2)c1] |

TABLE 1-continued

| Ex. | Names | Structures |
|---|---|---|
| 188 | N-(1-(2-(4-chlorobenzyl)-2,8-diazaspiro[4.5]decane-8-carbonyl)-1H-pyrazol-4-yl)-N-methylacetamide | 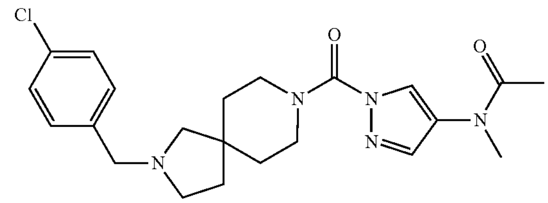 [SMILES: CC(=O)N(C)c1cnn(C(=O)N2CCC3(CCN(Cc4ccc(Cl)cc4)C3)CC2)c1] |
| 189 | N-(1-(5-(2-chloro-4-(2-oxo-2-(pyrrolidin-1-yl)ethoxy)benzyl)octahydropyrrolo[3,4-c]pyrrole-2-carbonyl)-1H-pyrazol-4-yl)-N-methylacetamide | 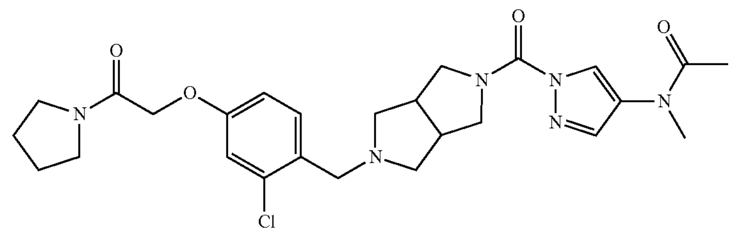 [SMILES: CC(=O)N(C)c1cnn(C(=O)N2CC3CN(Cc4ccc(OCC(=O)N5CCCC5)cc4Cl)CC3C2)c1] |
| 190 | N-methyl-N-(1-(4-(3-(pyrrolidin-1-yl)-5-(trifluoromethyl)benzyl)piperazine-1-carbonyl)-1H-pyrazol-4-yl)acetamide | 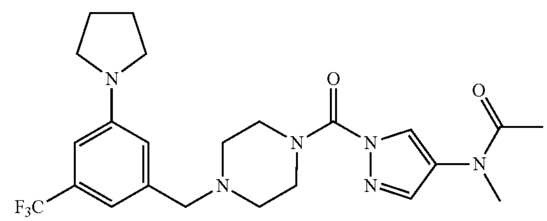 [SMILES: CC(=O)N(C)c1cnn(C(=O)N2CCN(Cc3cc(N4CCCC4)cc(C(F)(F)F)c3)CC2)c1] |
| 191 | N-methyl-N-(1-(4-(2-(pyrrolidin-1-yl)-4-(trifluoromethyl)benzyl)piperazine-1-carbonyl)-1H-pyrazol-4-yl)acetamide | 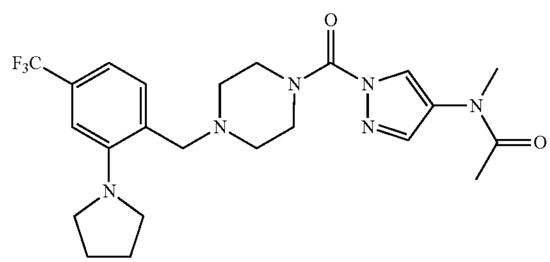 [SMILES: CC(=O)N(C)c1cnn(C(=O)N2CCN(Cc3ccc(C(F)(F)F)cc3N3CCCC3)CC2)c1] |
| 192 | N-(1-(4-(2-chlorobenzyl)piperazine-1-carbonyl)-1H-pyrazol-4-yl)-N-methylacetamide | 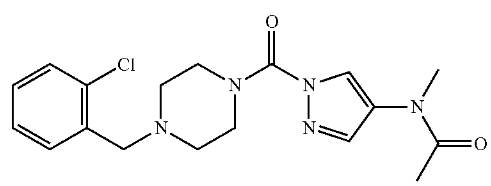 [SMILES: CC(=O)N(C)c1cnn(C(=O)N2CCN(Cc3ccccc3Cl)CC2)c1] |
| 193 | N-(1-(4-(3-chlorobenzyl)piperazine-1-carbonyl)-1H-pyrazol-4-yl)-N-methylacetamide | 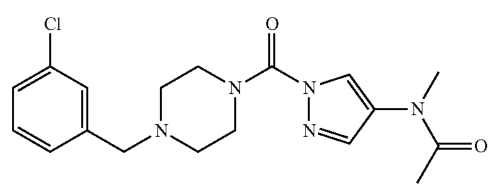 [SMILES: CC(=O)N(C)c1cnn(C(=O)N2CCN(Cc3cccc(Cl)c3)CC2)c1] |
| 194 | N-(1-(4-(4-chlorobenzyl)piperazine-1-carbonyl)-1H-pyrazol-4-yl)-N-methylacetamide | 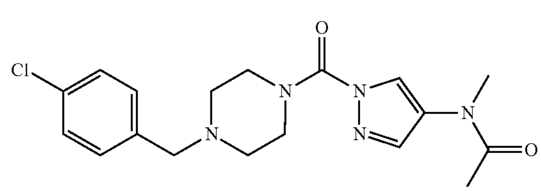 [SMILES: CC(=O)N(C)c1cnn(C(=O)N2CCN(Cc3ccc(Cl)cc3)CC2)c1] |

TABLE 1-continued

| Ex. | Names | Structures |
|---|---|---|
| 195 | N-(1-(4-(2-(3-oxa-8-azabicyclo[3.2.1]octan-8-yl)-4-(trifluoromethyl)benzyl)piperazine-1-carbonyl)-1H-pyrazol-4-yl)-N-methylacetamide | 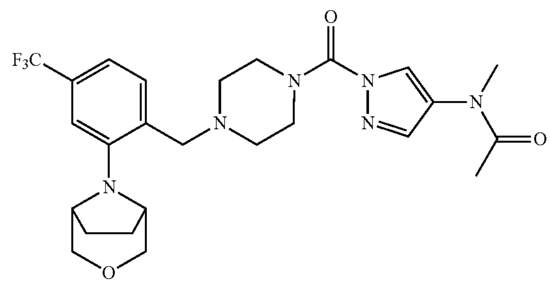 [SMILES: CC(=O)N(C)c1cnn(C(=O)N2CCN(Cc3ccc(C(F)(F)F)cc3N3C4CCC3COC4)CC2)c1] |
| 196 | N-(1-(4-(3,4-dichlorobenzyl)piperazine-1-carbonyl)-1H-pyrazol-4-yl)-N-methylacetamide | 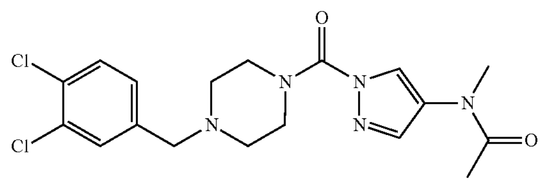 [SMILES: CC(=O)N(C)c1cnn(C(=O)N2CCN(Cc3ccc(Cl)c(Cl)c3)CC2)c1] |
| 197 | N-methyl-N-(1-(4-(4-(pyrrolidin-1-yl)benzyl)piperazine-1-carbonyl)-1H-pyrazol-4-yl)acetamide | 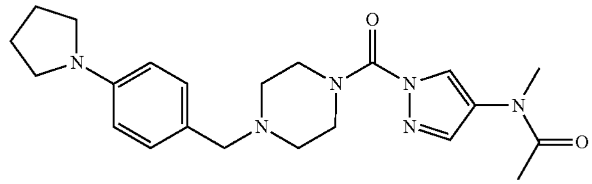 [SMILES: CC(=O)N(C)c1cnn(C(=O)N2CCN(Cc3ccc(N4CCCC4)cc3)CC2)c1] |
| 198 | N-methyl-N-(1-(4-(4-(trifluoromethyl)benzyl)piperazine-1-carbonyl)-1H-pyrazol-4-yl)acetamide | 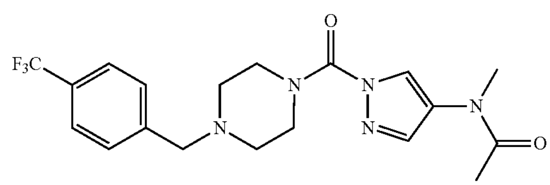 [SMILES: CC(=O)N(C)c1cnn(C(=O)N2CCN(Cc3ccc(C(F)(F)F)cc3)CC2)c1] |
| 199 | N-methyl-N-(1-(4-(4-(morpholinomethyl)benzyl)piperazine-1-carbonyl)-1H-pyrazol-4-yl)acetamide | 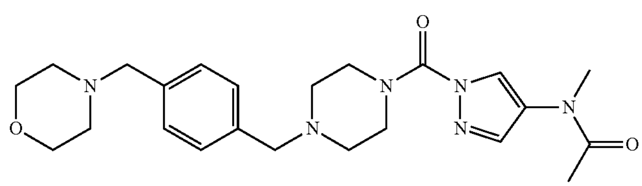 [SMILES: CC(=O)N(C)c1cnn(C(=O)N2CCN(Cc3ccc(CN4CCOCC4)cc3)CC2)c1] |
| 200 | N-methyl-N-(1-(4-(4-morpholinobenzyl)piperazine-1-carbonyl)-1H-pyrazol-4-yl)acetamide | 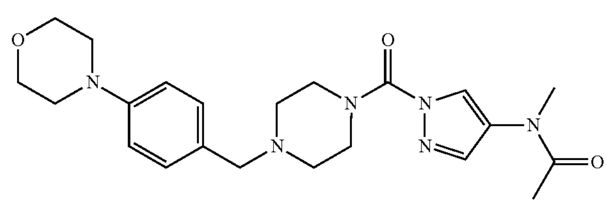 [SMILES: CC(=O)N(C)c1cnn(C(=O)N2CCN(Cc3ccc(N4CCOCC4)cc3)CC2)c1] |
| 201 | N-methyl-N-(1-(4-((3-methylbiphenyl-4-yl)methyl)piperazine-1-carbonyl)-1H-pyrazol-4-yl)acetamide | 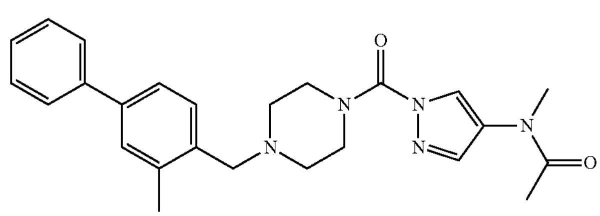 [SMILES: CC(=O)N(C)c1cnn(C(=O)N2CCN(Cc3ccc(-c4ccccc4)cc3C)CC2)c1] |

TABLE 1-continued

| Ex. | Names |
|---|---|
| 202 | N-methyl-N-(1-(4-(3-phenoxybenzyl)piperazine-1-carbonyl)-1H-pyrazol-4-yl)acetamide |
| 203 | N-(1-(4-(2-chloro-4-morpholinobenzyl)piperazine-1-carbonyl)-1H-pyrazol-4-yl)-N-methylacetamide |
| 204 | N-methyl-N-(1-(4-(2-methyl-4-morpholinobenzyl)piperazine-1-carbonyl)-1H-pyrazol-4-yl)acetamide |
| 205 | N-(1-(4-(3-fluorobenzyl)piperazine-1-carbonyl)-1H-pyrazol-4-yl)-N-methylacetamide |
| 206 | N-methyl-N-(1-(4-(3-methylbenzyl)piperazine-1-carbonyl)-1H-pyrazol-4-yl)acetamide |
| 207 | N-(1-(4-(3-methoxybenzyl)piperazine-1-carbonyl)-1H-pyrazol-4-yl)-N-methylacetamide |
| 208 | N-methyl-N-(1-(4-(3-(pyrrolidin-1-yl)benzyl)piperazine-1-carbonyl)-1H-pyrazol-4-yl)acetamide |
| 209 | N-methyl-N-(1-(4-(3-(trifluoromethyl)benzyl)piperazine-1-carbonyl)-1H-pyrazol-4-yl)acetamide |

TABLE 1-continued

| Ex. | Names | Structures |
|---|---|---|
| 210 | N-methyl-N-(1-(4-(3-morpholinobenzyl)piperazine-1-carbonyl)-1H-pyrazol-4-yl)acetamide | 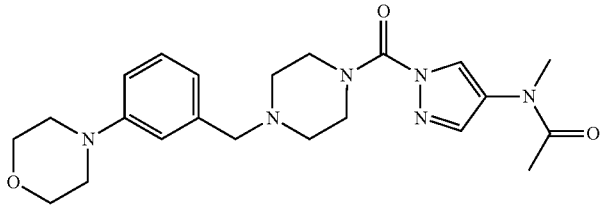 [SMILES: CC(=O)N(C)c1cnn(C(=O)N2CCN(Cc3cccc(N4CCOCC4)c3)CC2)c1] |
| 211 | N-(1-(4-(2-fluorobenzyl)piperazine-1-carbonyl)-1H-pyrazol-4-yl)-N-methylacetamide | 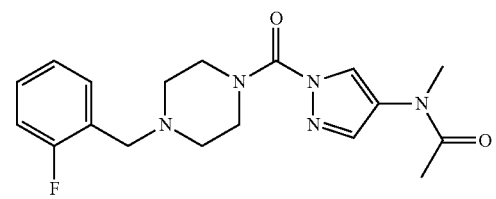 [SMILES: CC(=O)N(C)c1cnn(C(=O)N2CCN(Cc3ccccc3F)CC2)c1] |
| 212 | N-methyl-N-(1-(4-(2-methylbenzyl)piperazine-1-carbonyl)-1H-pyrazol-4-yl)acetamide | 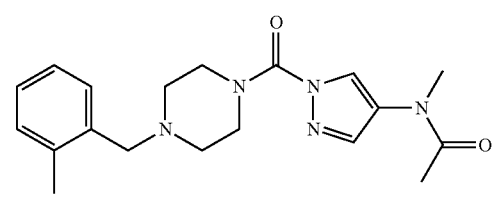 [SMILES: CC(=O)N(C)c1cnn(C(=O)N2CCN(Cc3ccccc3C)CC2)c1] |
| 213 | N-(1-(4-(2-methoxybenzyl)piperazine-1-carbonyl)-1H-pyrazol-4-yl)-N-methylacetamide | 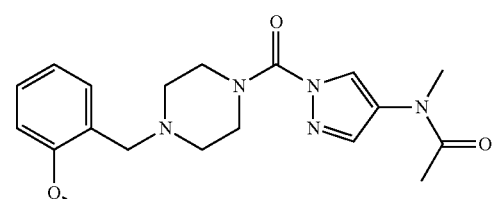 |
| 214 | N-methyl-N-(1-(4-(2-(trifluoromethyl)benzyl)piperazine-1-carbonyl)-1H-pyrazol-4-yl)acetamide | 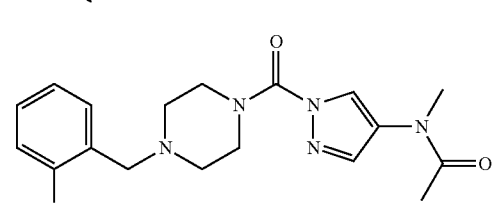 |
| 215 | N-methyl-N-(1-(4-(2-(pyrrolidin-1-yl)benzyl)piperazine-1-carbonyl)-1H-pyrazol-4-yl)acetamide | 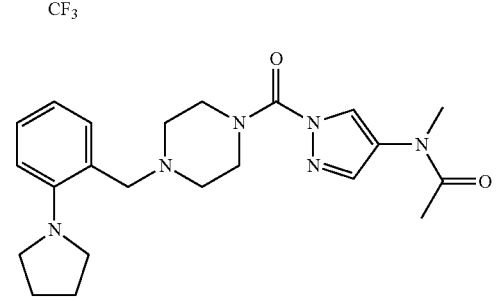 |
| 216 | N-methyl-N-(1-(4-(2-morpholinobenzyl)piperazine-1-carbonyl)-1H-pyrazol-4-yl)acetamide | 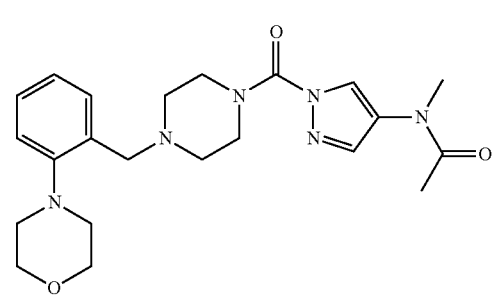 [SMILES: CC(=O)N(C)c1cnn(C(=O)N2CCN(Cc3ccccc3N3CCOCC3)CC2)c1] |

TABLE 1-continued

| Ex. | Names |
|---|---|
| 217 | N-(1-(4-(2-(pyrrolidin-1-yl)-4-(trifluoromethyl)benzyl)piperazine-1-carbonyl)-1H-pyrazol-4-yl)acetamide |
| 218 | N-methyl-N-(1-(4-(2-(pyrrolidin-1-yl)-4-(trifluoromethyl)benzyl)piperazine-1-carbonyl)-1H-pyrazol-4-yl)methanesulfonamide |
| 219 | N-(1-(4-((3-methyl-[1,1'-biphenyl]-4-yl)methyl)piperazine-1-carbonyl)-1H-pyrazol-4-yl)methanesulfonamide |
| 220 | N-(1-(4-((3-methoxy-[1,1'-biphenyl]-4-yl)methyl)piperazine-1-carbonyl)-1H-pyrazol-4-yl)methanesulfonamide |
| 221 | N-(1-(4-((3-chloro-[1,1'-biphenyl]-4-yl)methyl)piperazine-1-carbonyl)-1H-pyrazol-4-yl)methanesulfonamide |
| 222 | N-methyl-N-(1-(7-((3-methyl-[1,1'-biphenyl]-4-yl)methyl)-2,7-diazaspiro[3.5]nonane-2-carbonyl)-1H-pyrazol-4-yl)acetamide |

TABLE 1-continued

| Ex. | Names |
|---|---|
| 223 | N-methyl-N-(1-(5-((3-methyl-[1,1'-biphenyl]-4-yl)methyl)octahydropyrrolo[3,4-c]pyrrole-2-carbonyl)-1H-pyrazol-4-yl)acetamide |
| 224 | N-(1-(4-((3-(benzyloxy)-[1,1'-biphenyl]-4-yl)methyl)piperazine-1-carbonyl)-1H-pyrazol-4-yl)methanesulfonamide |
| 225 | N-methyl-N-(1-(5-(4-(morpholinomethyl)benzyl)octahydropyrrolo[3,4-c]pyrrole-2-carbonyl)-1H-pyrazol-4-yl)acetamide |
| 226 | N-methyl-N-(1-(2-((3-methyl-[1,1-biphenyl]-4-yl)methyl)-2,7-diazaspiro[3.5]nonane-7-carbonyl)-1H-pyrazol-4-yl)acetamide |
| 227 | N-(1-(4-(3-(pyrrolidin-1-yl])-5-(trifluoromethyl)benzyl)piperazine-1-carbonyl)-1H-pyrazol-4-yl)acetamide |
| 228 | N-(1-(4-(2-(3-oxa-8-azabicyclo[3.2.1]octan-8-yl)-4-(trifluoromethyl)benzyl)piperazine-1-carbonyl)-1H-pyrazol-4-yl)acetamide |
| 229 | N-methyl-N-(1-(7-(3-phenoxybenzyl)-2,7-diazaspiro[3.5]nonane-2-carbonyl)-1H-pyrazol-4-yl)acetamide |

TABLE 1-continued

| Ex. | Names | Structures |
|---|---|---|
| 230 | N-methyl-N-(1-(7-(4-(morpholinomethyl)benzyl)-2,7-diazaspiro[3.5]nonane-2-carbonyl)-1H-pyrazol-4-yl)acetamide | 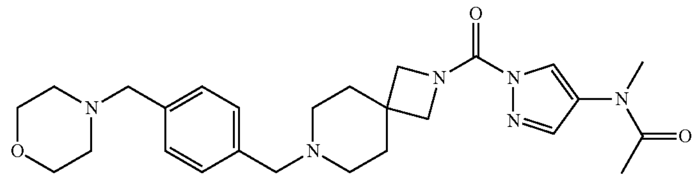 [SMILES: CC(=O)N(C)c1cnn(C(=O)N2CC3(CCN(Cc4ccc(CN5CCOCC5)cc4)CC3)C2)c1] |
| 231 | N-methyl-N-(1-(7-(4-(morpholinomethyl)benzyl)-2,7-diazaspiro[4.4]nonane-2-carbonyl)-1H-pyrazol-4-yl)acetamide | 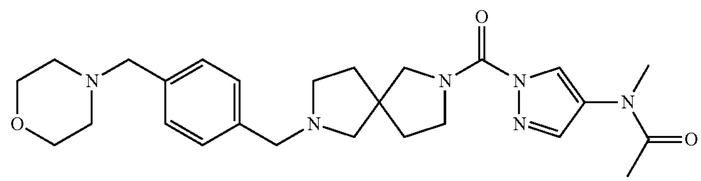 [SMILES: CC(=O)N(C)c1cnn(C(=O)N2CCC3(CCN(Cc4ccc(CN5CCOCC5)cc4)C3)C2)c1] |
| 232 | N-methyl-N-(1-(7-((3-methyl-[1,1'-biphenyl]-4-yl)methyl)-2,7-diazaspiro[4.4]nonane-2-carbonyl)-1H-pyrazol-4-yl)acetamide | 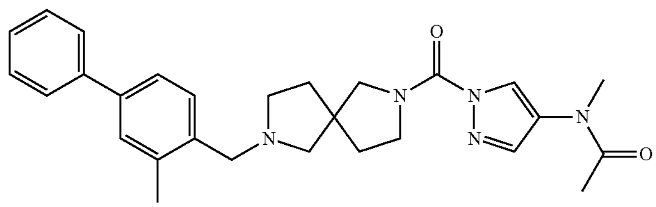 [SMILES: CC(=O)N(C)c1cnn(C(=O)N2CCC3(CCN(Cc4ccc(-c5ccccc5)cc4C)C3)C2)c1] |
| 233 | N-methyl-N-(1-(2-(4-(morpholinomethyl)benzyl)-2,7-diazaspiro[3.5]nonane-7-carbonyl)-1H-pyrazol-4-yl)acetamide | 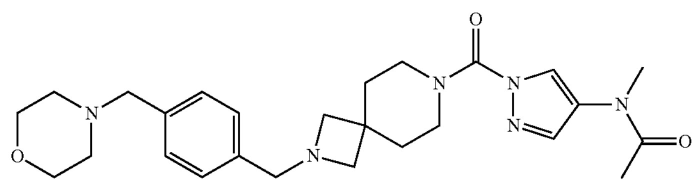 [SMILES: CC(=O)N(C)c1cnn(C(=O)N2CCC3(CC2)CN(Cc2ccc(CN4CCOCC4)cc2)C3)c1] |
| 234 | N-methyl-N-(1-(5-(3-phenoxybenzyl)octahydropyrrolo[3,4-c]pyrrole-2-carbonyl)-1H-pyrazol-4-yl)acetamide | 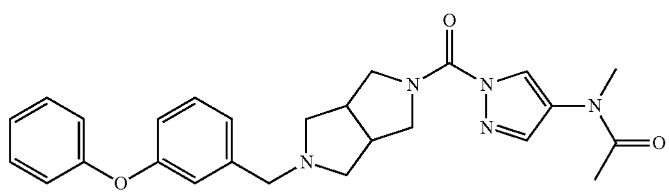 [SMILES: CC(=O)N(C)c1cnn(C(=O)N2CC3CN(Cc4cccc(Oc5ccccc5)c4)CC3C2)c1] |
| 235 | N-methyl-N-(1-(2-(3-phenoxybenzyl)-2,7-diazaspiro[3.5]nonane-7-carbonyl)-1H-pyrazol-4-yl)acetamide | 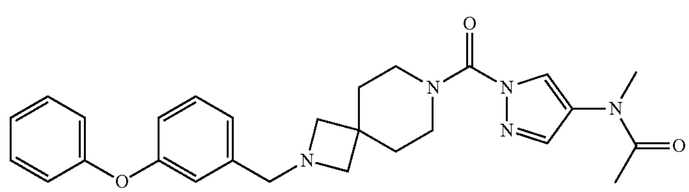 [SMILES: CC(=O)N(C)c1cnn(C(=O)N2CCC3(CC2)CN(Cc2cccc(Oc4ccccc4)c2)C3)c1] |
| 236 | N-methyl-N-(1-(7-(3-phenoxybenzyl)-2,7-diazaspiro[4.4]nonane-2-carbonyl)-1H-pyrazol-4-yl)acetamide | 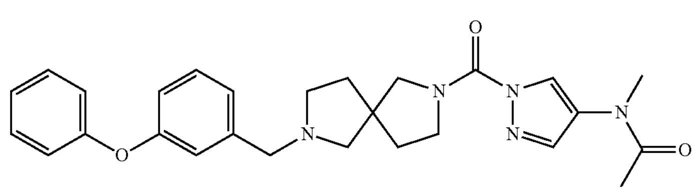 [SMILES: CC(=O)N(C)c1cnn(C(=O)N2CCC3(CCN(Cc4cccc(Oc5ccccc5)c4)C3)C2)c1] |
| 237 | N-(1-(5-(3-(4-chlorophenoxy)benzyl)octahydropyrrolo[3,4-c]pyrrole-2-carbonyl)-1H-pyrazol-4-yl)-N-methylacetamide | 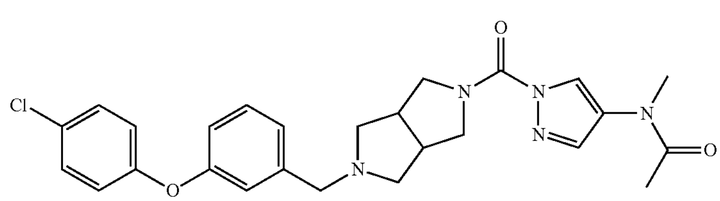 [SMILES: CC(=O)N(C)c1cnn(C(=O)N2CC3CN(Cc4cccc(Oc5ccc(Cl)cc5)c4)CC3C2)c1] |

TABLE 1-continued

| Ex. | Names | Structures |
|---|---|---|
| 238 | N-methyl-N-(1-(5-(3-(pyridin-2-yloxy)benzyl)octahydropyrrolo[3,4-c]pyrrole-2-carbonyl)-1H-pyrazol-4-yl)acetamide | 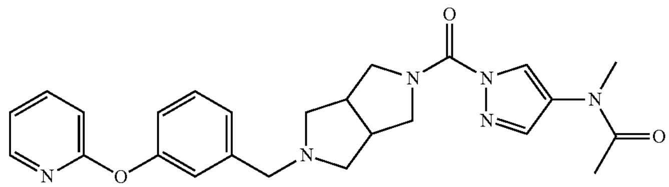 |
| 239 | N-(1-(5-(3-(benzyloxy)benzyl)octahydropyrrolo[3,4-c]pyrrole-2-carbonyl)-1H-pyrazol-4-yl)-N-methylacetamide | 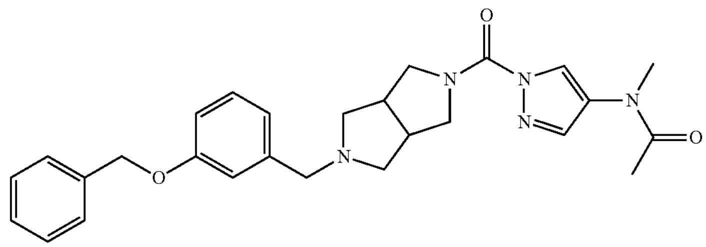 [SMILES: CC(=O)N(C)c1cnn(C(=O)N2CC3CN(Cc4cccc(OCc5ccccc5)c4)CC3C2)c1] |
| 240 | N-(1-(5-(3-(2-chlorophenoxy)benzyl)octahydropyrrolo[3,4-c]pyrrole-2-carbonyl)-1H-pyrazol-4-yl)-N-methylacetamide | 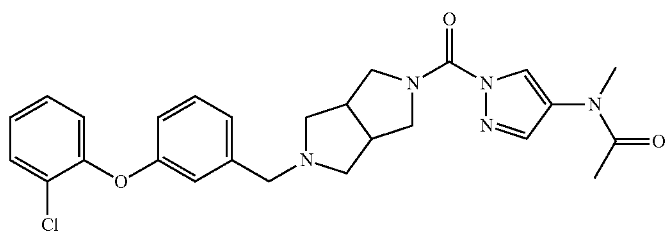 [SMILES: CC(=O)N(C)c1cnn(C(=O)N2CC3CN(Cc4cccc(Oc5ccccc5Cl)c4)CC3C2)c1] |
| 241 | N-methyl-N-(1-(5-(4-phenoxybenzyl)octahydropyrrolo[3,4-c]pyrrole-2-carbonyl)-1H-pyrazol-4-yl)acetamide | 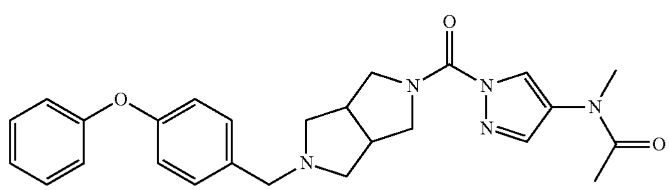 [SMILES: CC(=O)N(C)c1cnn(C(=O)N2CC3CN(Cc4ccc(Oc5ccccc5)cc4)CC3C2)c1] |
| 242 | N-(1-(5-((2,2-difluorobenzo[d][1,3]dioxol-5-yl)methyl)octahydropyrrolo[3,4-c]pyrrole-2-carbonyl)-1H-pyrazol-4-yl)-N-methylacetamide | 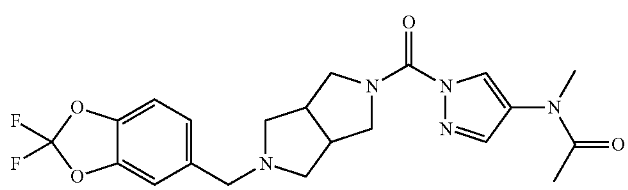 [SMILES: CC(=O)N(C)c1cnn(C(=O)N2CC3CN(Cc4ccc5c(c4)OC(F)(F)O5)CC3C2)c1] |
| 243 | N-(1-(5-(3-(4-methoxyphenoxy)benzyl)octahydropyrrolo[3,4-c]pyrrole-2-carbonyl)-1H-pyrazol-4-yl)-N-methylacetamide | 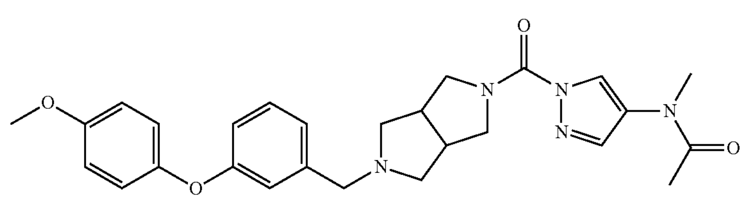 [SMILES: COc1ccc(Oc2cccc(CN3CC4CN(C(=O)n5cc(N(C)C(C)=O)cn5)CC4C3)c2)cc1] |
| 244 | N-(1-(5-(3-(3-chlorophenoxy)benzyl)octahydropyrrolo[3,4-c]pyrrole-2-carbonyl)-1H-pyrazol-4-yl)-N-methylacetamide | 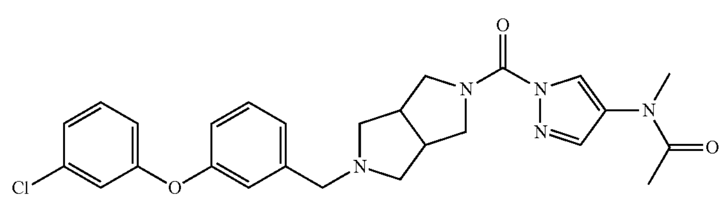 [SMILES: CC(=O)N(C)c1cnn(C(=O)N2CC3CN(Cc4cccc(Oc5cccc(Cl)c5)c4)CC3C2)c1] |

TABLE 1-continued

| Ex. | Names |
|---|---|
| 245 | N-(1-(5-(4-(4-chlorophenoxy)benzyl)octahydropyrrolo[3,4-c]pyrrole-2-carbonyl)-1H-pyrazol-4-yl)-N-methylacetamide |
| 246 | N-methyl-N-(1-(5-(2,4,5-trifluorobenzyl)octahydropyrrolo[3,4-c]pyrrole-2-carbonyl)-1H-pyrazol-4-yl)acetamide |
| 247 | N-(1-(5-(3-chloro-5-(8-oxa-2-azaspiro[4.5]decan-2-yl)benzyl)octahydropyrrolo[3,4-c]pyrrole-2-carbonyl)-1H-pyrazol-4-yl)-N-methylacetamide |
| 248 | N-(1-(5-(4-(benzyloxy)benzyl)octahydropyrrolo[3,4-c]pyrrole-2-carbonyl)-1H-pyrazol-4-yl)-N-methylacetamide |
| 249 | N-(1-(5-(3-((4-chlorobenzyl)oxy)benzyl)octahydropyrrolo[3,4-c]pyrrole-2-carbonyl)-1H-pyrazol-4-yl)-N-methylacetamide |
| 250 | N-methyl-N-(1-(5-(4-((1S,4S)-5-methyl-2,5-diazabicyclo[2.2.1]heptan-2-yl)-2-(trifluoromethyl)benzyl)octahydropyrrolo[3,4-c]pyrrole-2-carbonyl)-1H-pyrazol-4-yl)acetamide |

TABLE 1-continued

| Ex. | Names | Structures |
|---|---|---|
| 251 | N-(1-(5-(3-(benzyloxy)-5-chlorobenzyl)octahydropyrrolo[3,4-c]pyrrole-2-carbonyl)-1H-pyrazol-4-yl)-N-methylacetamide | 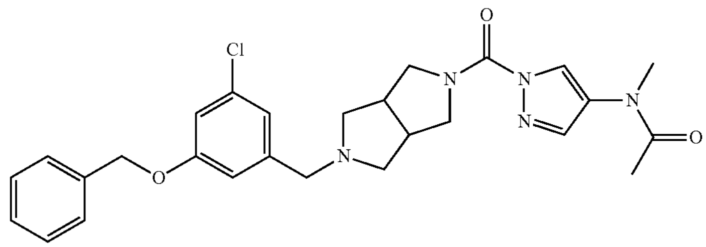 [SMILES: CC(=O)N(C)c1cnn(C(=O)N2CC3CN(Cc4cc(Cl)cc(OCc5ccccc5)c4)CC3C2)c1] |
| 252 | N-(1-(5-(4-(benzo[d]thiazol-2-yloxy)-2-chlorobenzyl)octahydropyrrolo[3,4-c]pyrrole-2-carbonyl)-1H-pyrazol-4-yl)-N-methylacetamide | 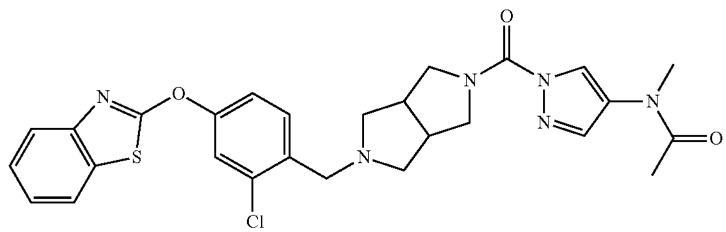 [SMILES: CC(=O)N(C)c1cnn(C(=O)N2CC3CN(Cc4ccc(Oc5nc6ccccc6s5)cc4Cl)CC3C2)c1] |
| 253 | N-(1-(5-(2-chloro-4-isopropoxybenzyl)octahydropyrrolo[3,4-c]pyrrole-2-carbonyl)-1H-pyrazol-4-yl)-N-methylacetamide | 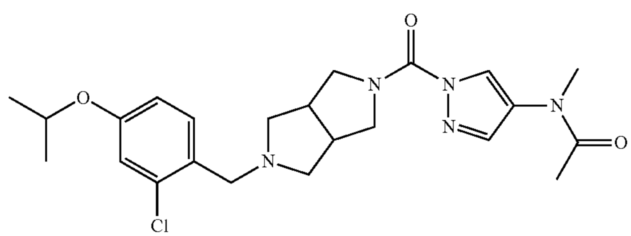 [SMILES: CC(=O)N(C)c1cnn(C(=O)N2CC3CN(Cc4ccc(OC(C)C)cc4Cl)CC3C2)c1] |
| 254 | N-(1-(5-(4-(benzo[d]thiazol-2-yloxy)-2-(trifluoromethyl)benzyl)octahydropyrrolo[3,4-c]pyrrole-2-carbonyl)-1H-pyrazol-4-yl)-N-methylacetamide | 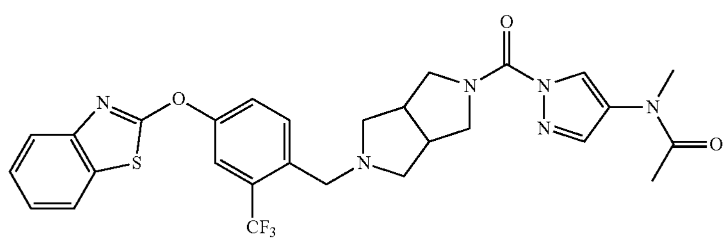 [SMILES: CC(=O)N(C)c1cnn(C(=O)N2CC3CN(Cc4ccc(Oc5nc6ccccc6s5)cc4C(F)(F)F)CC3C2)c1] |
| 255 | N-(1-(5-(4-isopropoxy-2-(trifluoromethyl)benzyl)octahydropyrrolo[3,4-c]pyrrole-2-carbonyl)-1H-pyrazol-4-yl)-N-methylacetamide | 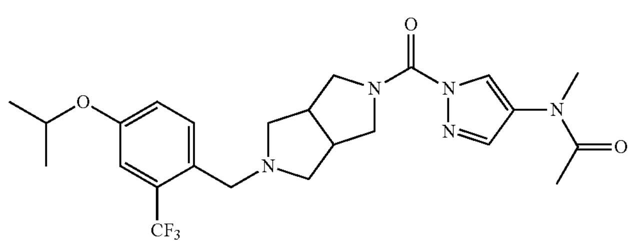 [SMILES: CC(=O)N(C)c1cnn(C(=O)N2CC3CN(Cc4ccc(OC(C)C)cc4C(F)(F)F)CC3C2)c1] |
| 256 | N-methyl-N-(1-(5-(4-(2-oxo-2-(pyrrolidin-1-yl)ethoxy)-2-(trifluoromethyl)benzyl)octahydropyrrolo[3,4-c]pyrrole-2-carbonyl)-1H-pyrazol-4-yl)acetamide | 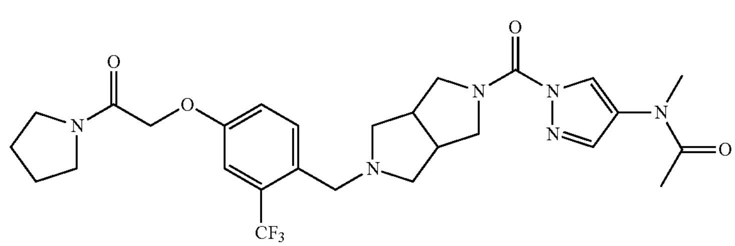 [SMILES: CC(=O)N(C)c1cnn(C(=O)N2CC3CN(Cc4ccc(OCC(=O)N5CCCC5)cc4C(F)(F)F)CC3C2)c1] |

TABLE 1-continued

| Ex. | Names |
|---|---|
| 257 | N-(1-(5-(2-chloro-4-(pyridazin-4-yloxy)benzyl)octahydropyrrolo[3,4-c]pyrrole-2-carbonyl)-1H-pyrazol-4-yl)-N-methylacetamide |
| 258 | N-methyl-N-(1-(5-(4-(pyridazin-4-yloxy)-2-(trifluoromethyl)benzyl)octahydropyrrolo[3,4-c]pyrrole-2-carbonyl)-1H-pyrazol-4-yl)acetamide |
| 259 | N-(1-(5-(2-chloro-4-(pyrimidin-5-yl)benzyl)octahydropyrrolo[3,4-c]pyrrole-2-carbonyl)-1H-pyrazol-4-yl)-N-methylacetamide |
| 260 | N-(1-(5-(2-chloro-4-(pyridazin-3-yl)benzyl)octahydropyrrolo[3,4-c]pyrrole-2-carbonyl)-1H-pyrazol-4-yl)-N-methylacetamide |
| 261 | N-(1-(5-(2-chloro-4-(pyrimidin-2-yl)benzyl)octahydropyrrolo[3,4-c]pyrrole-2-carbonyl)-1H-pyrazol-4-yl)-N-methylacetamide |
| 262 | N-(1-(7-(2-chloro-4-(pyrimidin-5-yl)benzyl)-2,7-diazaspiro[4.4]nonane-2-carbonyl)-1H-pyrazol-4-yl)-N-methylacetamide |

TABLE 1-continued

| Ex. | Names | Structures |
|---|---|---|
| 263 | N-(1-(7-(2-chloro-4-(pyridazin-3-yl)benzyl)-2,7-diazaspiro[4.4]nonane-2-carbonyl)-1H-pyrazol-4-yl)-N-methylacetamide | 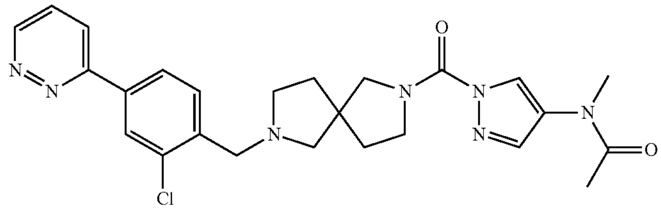 [SMILES: CC(=O)N(C)c1cnn(C(=O)N2CCC3(CCN(Cc4ccc(-c5cccnn5)cc4Cl)C3)C2)c1] |
| 264 | N-(1-(7-(2-chloro-4-(pyrazin-2-yl)benzyl)-2,7-diazaspiro[4.4]nonane-2-carbonyl)-1H-pyrazol-4-yl)-N-methylacetamide | 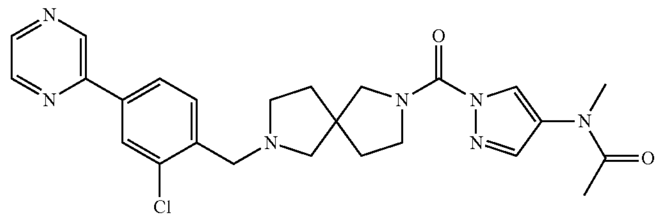 [SMILES: CC(=O)N(C)c1cnn(C(=O)N2CCC3(CCN(Cc4ccc(-c5cnccn5)cc4Cl)C3)C2)c1] |
| 265 | N-methyl-N-(1-(5-(4-(pyrimidin-5-yloxy)-2-(trifluoromethyl)benzyl)octahydropyrrolo[3,4-c]pyrrole-2-carbonyl)-1H-pyrazol-4-yl)acetamide | 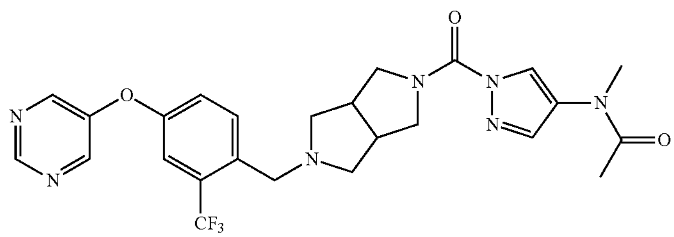 |
| 266 | N-(1-(5-(2-chloro-4-(pyrazin-2-yl)benzyl)octahydropyrrolo[3,4-c]pyrrole-2-carbonyl)-1H-pyrazol-4-yl)-N-methylacetamide | 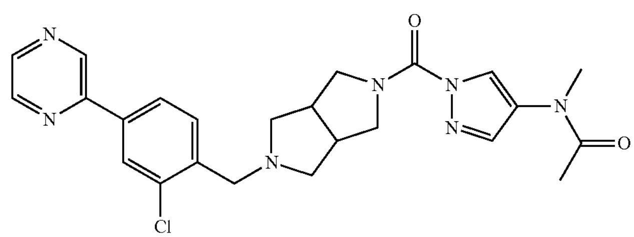 [SMILES: CC(=O)N(C)c1cnn(C(=O)N2CC3CN(Cc4ccc(-c5cnccn5)cc4Cl)CC3C2)c1] |
| 267 | N-(1-(5-(2-chloro-4-(thiazol-2-yl)benzyl)octahydropyrrolo[3,4-c]pyrrole-2-carbonyl)-1H-pyrazol-4-yl)-N-methylacetamide | 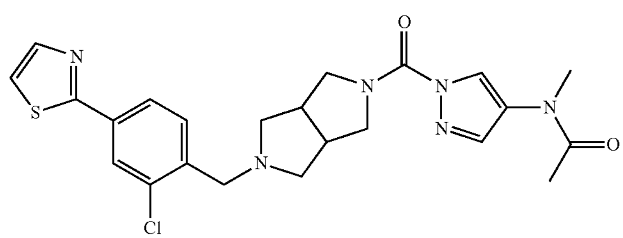 [SMILES: CC(=O)N(C)c1cnn(C(=O)N2CC3CN(Cc4ccc(-c5nccs5)cc4Cl)CC3C2)c1] |
| 268 | N-(1-(7-(2-chloro-4-(pyrimidin-2-yl)benzyl)-2,7-diazaspiro[4.4]nonane-2-carbonyl)-1H-pyrazol-4-yl)-N-methylacetamide | 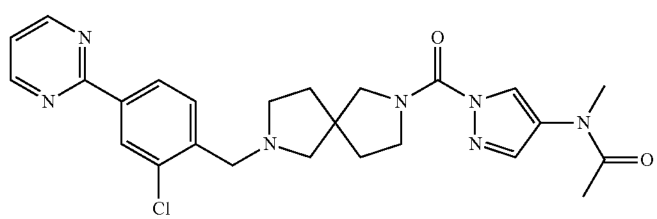 [SMILES: CC(=O)N(C)c1cnn(C(=O)N2CCC3(CCN(Cc4ccc(-c5ncccn5)cc4Cl)C3)C2)c1] |
| 269 | N-(1-(7-(2-chloro-4-(thiazol-2-yl)benzyl)-2,7-diazaspiro[4.4]nonane-2-carbonyl)-1H-pyrazol-4-yl)-N-methylacetamide | 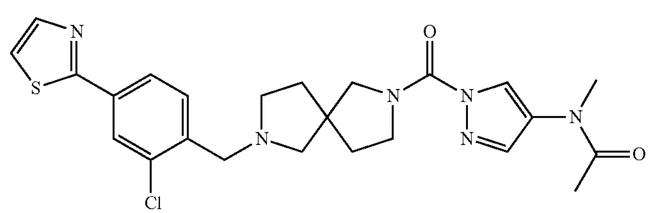 [SMILES: CC(=O)N(C)c1cnn(C(=O)N2CCC3(CCN(Cc4ccc(-c5nccs5)cc4Cl)C3)C2)c1] |

TABLE 1-continued

| Ex. | Names |
|---|---|
| 270 | N-(1-(5-(2-chloro-4-((1-cyclopropylpiperidin-4-yl)oxy)benzyl)octahydropyrrolo[3,4-c]pyrrole-2-carbonyl)-1H-pyrazol-4-yl)-N-methylacetamide |
| 271 | N-(1-(5-(4-((1-cyclopropylpiperidin-4-yl)oxy)-2-(trifluoromethyl)benzyl)octahydropyrrolo[3,4-c]pyrrole-2-carbonyl)-1H-pyrazol-4-yl)-N-methylacetamide |
| 272 | N-(1-(5-(2-chloro-4-(pyrimidin-4-yl)benzyl)octahydropyrrolo[3,4-c]pyrrole-2-carbonyl)-1H-pyrazol-4-yl)-N-methylacetamide |
| 273 | N-(1-(7-(2-chloro-4-(pyrimidin-4-yl)benzyl)-2,7-diazaspiro[4.4]nonane-2-carbonyl)-1H-pyrazol-4-yl)-N-methylacetamide |
| 274 | N-(1-(5-(2-chloro-4-(pyrimidin-5-yloxy)benzyl)octahydropyrrolo[3,4-c]pyrrole-2-carbonyl)-1H-pyrazol-4-yl)-N-methylacetamide |
| 275 | N-(1-(5-(5-chloro-2-(trifluoromethyl)benzyl)octahydropyrrolo[3,4-c]pyrrole-2-carbonyl)-1H-pyrazol-4-yl)methanesulfonamide |

TABLE 1-continued

| Ex. | Names |
|---|---|
| 276 | N-(1-(2-(5-chloro-2-(trifluoromethyl)benzyl)-2,8-diazaspiro[4.5]decane-8-carbonyl)-1H-pyrazol-4-yl)methanesulfonamide |
| 277 | N-(1-(2-(5-chloro-2-(trifluoromethyl)benzyl)-2,7-diazaspiro[3.5]nonane-7-carbonyl)-1H-pyrazol-4-yl)methanesulfonamide |
| 278 | N-(1-[[trans-5-([[5-chloro-2-(trifluoromethyl)phenyl]methyl](methyl)amino)-octahydrocyclopenta[c]pyrrol-2-yl]carbonyl]-1H-pyrazol-4-yl)methanesulfonamide |
| 279 | N-(1-(5-(4-(pyrrolidin-1-yl)-2-(trifluoromethyl)benzyl)octahydropyrrolo[3,4-c]pyrrole-2-carbonyl)-1H-pyrazol-4-yl)methanesulfonamide |
| 280 | N-(1-(2-(4-(pyrrolidin-1-yl)-2-(trifluoromethyl)benzyl)-2,8-diazaspiro[4.5]decane-8-carbonyl)-1H-pyrazol-4-yl)methanesulfonamide |
| 281 | N-(1-(2-(4-(pyrrolidin-1-yl)-2-(trifluoromethyl)benzyl)-2,7-diazaspiro[3.5]nonane-7-carbonyl)-1H-pyrazol-4-yl)methanesulfonamide |

TABLE 1-continued

| Ex. | Names | Structures |
|---|---|---|
| 282 | N-(1-(trans-5-(methyl(4-(pyrrolidin-1-yl)-2-(trifluoromethyl)benzyl)amino)octahydrocyclopenta[c]pyrrole-2-carbonyl)-1H-pyrazol-4-yl)methanesulfonamide | 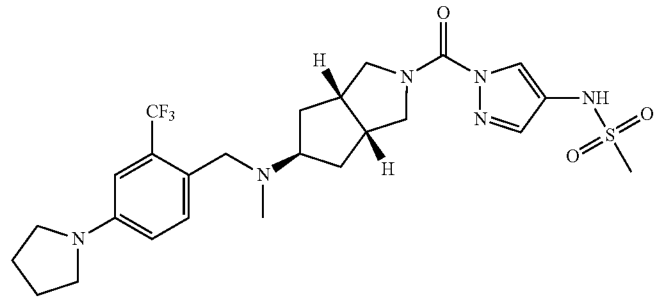 [SMILES: CN(Cc1ccc(N2CCCC2)cc1C(F)(F)F)[C@H]1C[C@@H]2CN(C(=O)n3cc(NS(C)(=O)=O)cn3)C[C@@H]2C1] |
| 283 | N-(1-(7-(3,4-dichlorobenzyl)-2,7-diazaspiro[4.4]nonane-2-carbonyl)-1H-pyrazol-4-yl)methanesulfonamide | 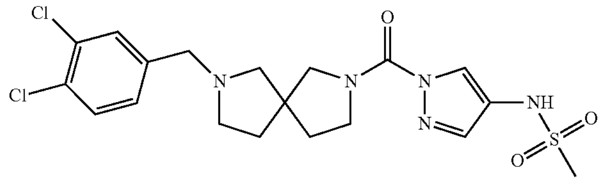 [SMILES: CS(=O)(=O)Nc1cnn(C(=O)N2CCC3(CCN(Cc4ccc(Cl)c(Cl)c4)C3)C2)c1] |
| 284 | N-[1-[(7-[[5-chloro-2-(trifluoromethyl)phenyl]methyl]-2,7-diazaspiro[4.4]nonan-2-yl)carbonyl]-1H-pyrazol-4-yl]methanesulfonamide | 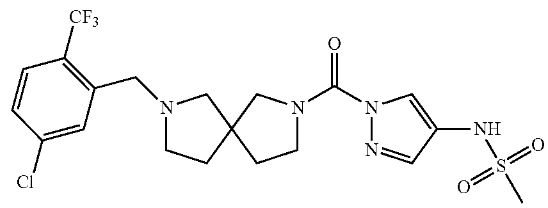 [SMILES: CS(=O)(=O)Nc1cnn(C(=O)N2CCC3(CCN(Cc4cc(Cl)ccc4C(F)(F)F)C3)C2)c1] |
| 285 | N-(1-(7-(4-(pyrrolidin-1-yl)-2-(trifluoromethyl)benzyl)-2,7-diazaspiro[4.4]nonane-2-carbonyl)-1H-pyrazol-4-yl)methanesulfonamide | 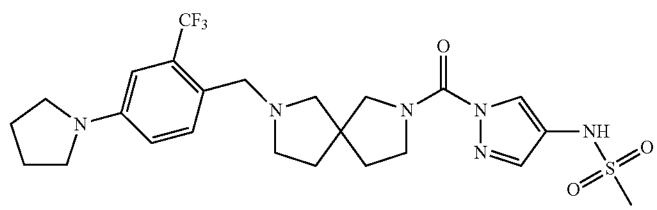 [SMILES: CS(=O)(=O)Nc1cnn(C(=O)N2CCC3(CCN(Cc4ccc(N5CCCC5)cc4C(F)(F)F)C3)C2)c1] |
| 286 | N-(1-(7-(3-chloro-5-(trifluoromethyl)benzyl)-2,7-diazaspiro[4.4]nonane-2-carbonyl)-1H-pyrazol-4-yl)methanesulfonamide | 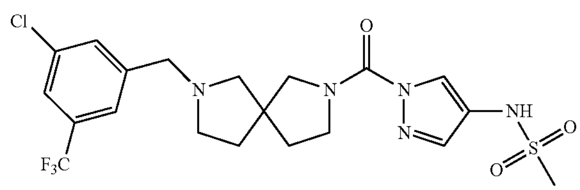 [SMILES: CS(=O)(=O)Nc1cnn(C(=O)N2CCC3(CCN(Cc4cc(Cl)cc(C(F)(F)F)c4)C3)C2)c1] |
| 287 | N-(1-(7-(2-chloro-4-(thiazol-2-yl)benzyl)-2,7-diazaspiro[4.4]nonane-2-carbonyl)-1H-pyrazol-4-yl)methanesulfonamide | 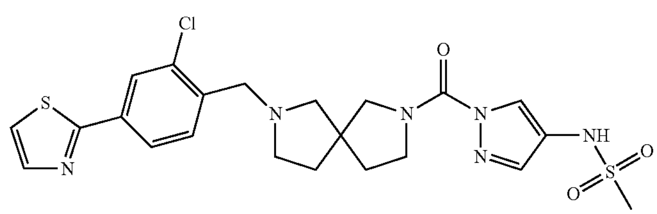 [SMILES: CS(=O)(=O)Nc1cnn(C(=O)N2CCC3(CCN(Cc4ccc(-c5nccs5)cc4Cl)C3)C2)c1] |
| 288 | N-(1-(7-(2,3-dichlorobenzyl)-2,7-diazaspiro[4.4]nonane-2-carbonyl)-1H-pyrazol-4-yl)methanesulfonamide | 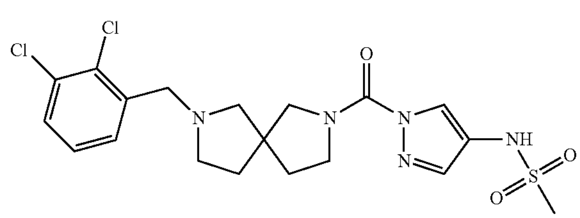 [SMILES: CS(=O)(=O)Nc1cnn(C(=O)N2CCC3(CCN(Cc4cccc(Cl)c4Cl)C3)C2)c1] |

TABLE 1-continued

| Ex. | Names | Structures |
|---|---|---|
| 289 | N-(1-(4-(4-(pyrazin-2-yl)-2-(trifluoromethyl)benzyl)piperazine-1-carbonyl)-1H-pyrazol-4-yl)methanesulfonamide | 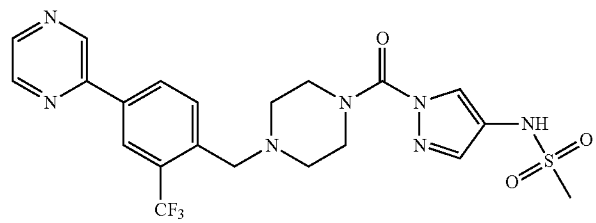 [SMILES: CS(=O)(=O)Nc1cnn(C(=O)N2CCN(Cc3ccc(-c4cnccn4)cc3C(F)(F)F)CC2)c1] |
| 290 | N-(1-(4-(4-(pyrimidin-5-yl)-2-(trifluoromethyl)benzyl)piperazine-1-carbonyl)-1H-pyrazol-4-yl)methanesulfonamide | 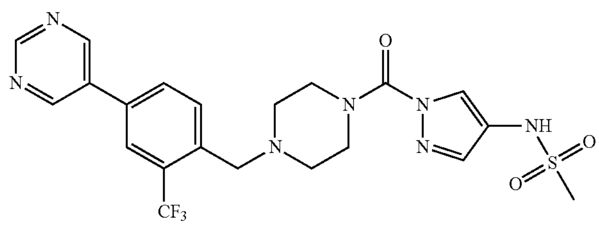 [SMILES: CS(=O)(=O)Nc1cnn(C(=O)N2CCN(Cc3ccc(-c4cncnc4)cc3C(F)(F)F)CC2)c1] |
| 291 | N-(1-(4-(4-(thiazol-2-yl)-2-(trifluoromethyl)benzyl)piperazine-1-carbonyl)-1H-pyrazol-4-yl)methanesulfonamide | 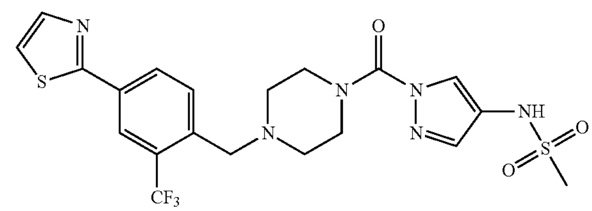 |
| 292 | N-(1-(4-(4-(pyrrolidin-1-yl)-2-(trifluoromethyl)benzyl)piperazine-1-carbonyl)-1H-pyrazol-4-yl)methanesulfonamide | 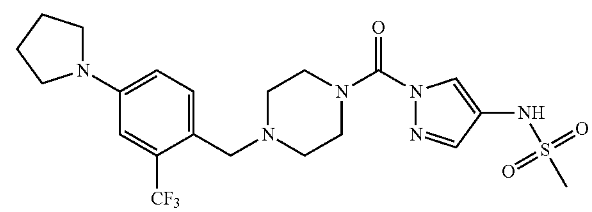 [SMILES: CS(=O)(=O)Nc1cnn(C(=O)N2CCN(Cc3ccc(N4CCCC4)cc3C(F)(F)F)CC2)c1] |
| 293 | N-(1-(4-(5-chloro-2-(trifluoromethyl)benzyl)piperazine-1-carbonyl)-1H-pyrazol-4-yl)methanesulfonamide | 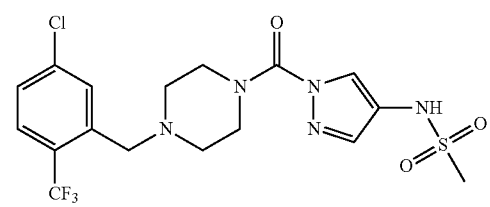 [SMILES: CS(=O)(=O)Nc1cnn(C(=O)N2CCN(Cc3cc(Cl)ccc3C(F)(F)F)CC2)c1] |
| 294 | N-(1-(4-(3-chloro-5-(trifluoromethyl)benzyl)piperazine-1-carbonyl)-1H-pyrazol-4-yl)methanesulfonamide | 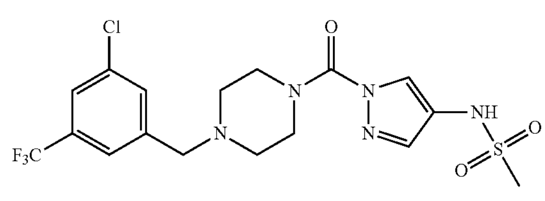 [SMILES: CS(=O)(=O)Nc1cnn(C(=O)N2CCN(Cc3cc(Cl)cc(C(F)(F)F)c3)CC2)c1] |
| 295 | N-(1-(4-(3-(pyrrolidin-1-yl)-5-(trifluoromethyl)benzyl)piperazine-1-carbonyl)-1H-pyrazol-4-yl)methanesulfonamide | 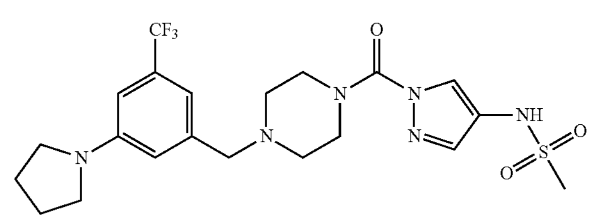 [SMILES: CS(=O)(=O)Nc1cnn(C(=O)N2CCN(Cc3cc(N4CCCC4)cc(C(F)(F)F)c3)CC2)c1] |

TABLE 1-continued

| Ex. | Names | Structures |
|---|---|---|
| 296 | N-(1-(4-(3-(4-chlorophenoxy)benzyl)piperazine-1-carbonyl)-1H-pyrazol-4-yl)methanesulfonamide | 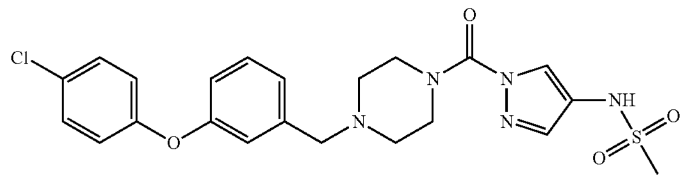 [SMILES: CS(=O)(=O)Nc1cnn(C(=O)N2CCN(Cc3cccc(Oc4ccc(Cl)cc4)c3)CC2)c1] |
| 297 | N-(1-(2-(3-chloro-5-(trifluoromethyl)benzyl)-2,8-diazaspiro[4.5]decane-8-carbonyl)-1H-pyrazol-4-yl)methanesulfonamide | 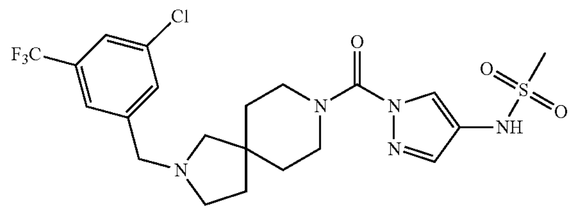 [SMILES: CS(=O)(=O)Nc1cnn(C(=O)N2CCC3(CCN(Cc4cc(Cl)cc(C(F)(F)F)c4)C3)CC2)c1] |
| 298 | N-(1-(2-(3-chloro-4-(pyrrolidin-1-yl)benzyl)-2,8-diazaspiro[4.5]decane-8-carbonyl)-1H-pyrazol-4-yl)methanesulfonamide | 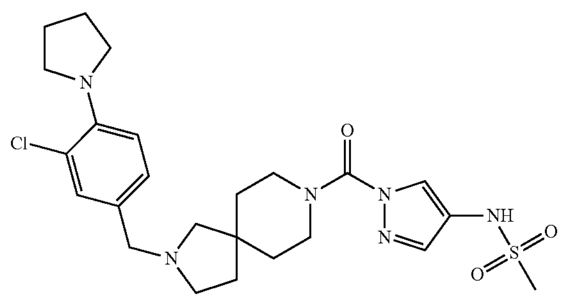 [SMILES: CS(=O)(=O)Nc1cnn(C(=O)N2CCC3(CCN(Cc4ccc(N5CCCC5)c(Cl)c4)C3)CC2)c1] |
| 299 | N-(1-(trans-5-(methyl(2-(trifluoromethyl)benzyl)amino)octahydrocyclopenta[c]pyrrole-2-carbonyl)-1H-pyrazol-4-yl)methanesulfonamide | 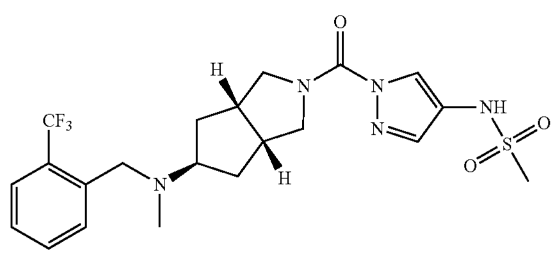 [SMILES: CN(Cc1ccccc1C(F)(F)F)[C@H]1C[C@@H]2CN(C(=O)n3cc(NS(C)(=O)=O)cn3)C[C@@H]2C1] |
| 300 | N-(1-(cis-5-(methyl(2-(trifluoromethyl)benzyl)amino)octahydrocyclopenta[c]pyrrole-2-carbonyl)-1H-pyrazol-4-yl)methanesulfonamide | 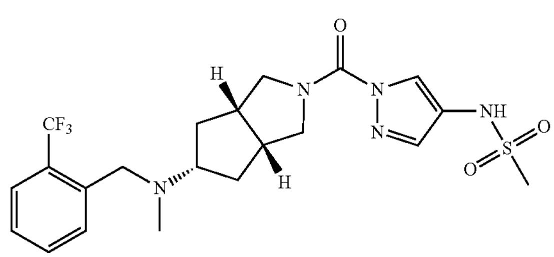 [SMILES: CN(Cc1ccccc1C(F)(F)F)[C@@H]1C[C@@H]2CN(C(=O)n3cc(NS(C)(=O)=O)cn3)C[C@@H]2C1] |
| 301 | N-(1-(4-(2-(trifluoromethyl)-4-(6-(trifluoromethyl)pyridin-3-yl)benzyl)piperazine-1-carbonyl)-1H-pyrazol-4-yl)methanesulfonamide | 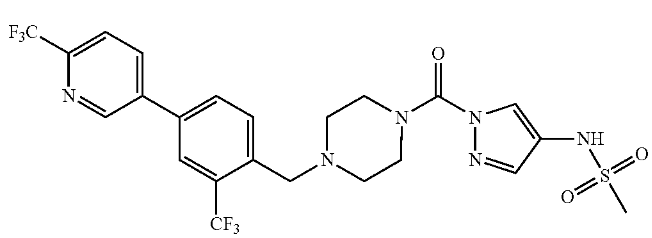 [SMILES: CS(=O)(=O)Nc1cnn(C(=O)N2CCN(Cc3ccc(-c4ccc(C(F)(F)F)nc4)cc3C(F)(F)F)CC2)c1] |

TABLE 1-continued

| Ex. | Names |
|---|---|
| 302 | 5-(4-((4-(4-(methylsulfonamido)-1H-pyrazole-1-carbonyl)piperazin-1-yl)methyl)-3-trifluoromethyl)phenyl)picolinamide |
| 303 | N-(1-(4-(4-(oxazol-2-yl)-2-(trifluoromethyl)benzy)piperazine-1-carbonyl)-1H-pyrazol-4-yl)methanesulfonamide |
| 304 | N-(1-(4-(4-(benzo[d]oxazol-2-yl)-2-(trifluoromethyl)benzyl)piperazine-1-carbonyl)-1H-pyrazol-4-yl)methanesulfonamide |
| 305 | N-(1-(4-(4-(benzo[d]thiazol-2-yl)-2-(trifluoromethyl)benzyl)piperazine-1-carbonyl)-1H-pyrazol-4-yl)methanesulfonamide |
| 306 | N-(1-(4-(4-(5-methyl-1,3,4-oxadiazol-2-yl)-2-(trifluoromethyl)benzyl)piperazine-1-carbonyl)-1H-pyrazol-4-yl)methanesulfonamide |
| 307 | N-(1-(4-(4-(3-methyl-1,2,4-oxadiazol-5-yl)-2-(trifluoromethyl)benzyl)piperazine-1-carbonyl)-1H-pyrazol-4-yl)methanesulfonamide |

TABLE 1-continued

| Ex. | Names | Structures |
|---|---|---|
| 308 | N-(1-(4-(4-(2-methyl-1H-imidazol-1-yl)-2-(trifluoromethyl)benzyl)piperazine-1-carbonyl)-1H-pyrazol-4-yl)methanesulfonamide | 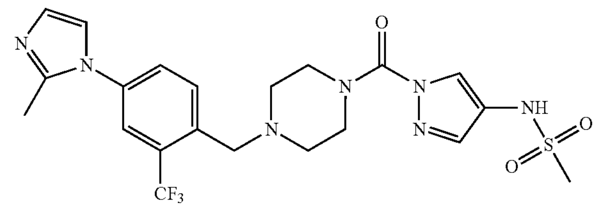 [SMILES: Cc1nccn1-c1ccc(CN2CCN(C(=O)n3cc(NS(C)(=O)=O)cn3)CC2)c(C(F)(F)F)c1] |
| 309 | N-(1-(4-(4-(pyrimidin-4-yl)-2-(trifluoromethyl)benzyl)piperazine-1-carbonyl)-1H-pyrazol-4-yl)methanesulfonamide | 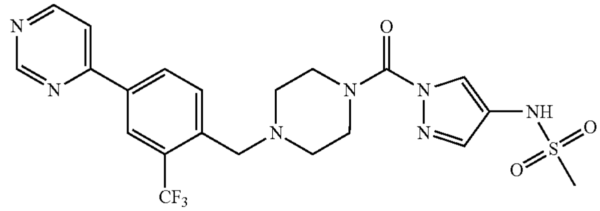 [SMILES: CS(=O)(=O)Nc1cnn(C(=O)N2CCN(Cc3ccc(-c4ccncn4)cc3C(F)(F)F)CC2)c1] |
| 310 | N-(1-(4-(4-(pyrimidin-2-yl)-2-(trifluoromethyl)benzylpiperazine-1-carbonyl)-1H-pyrazol-4-yl)methanesulfonamide | 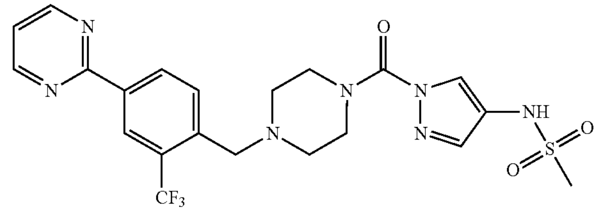 [SMILES: CS(=O)(=O)Nc1cnn(C(=O)N2CCN(Cc3ccc(-c4ncccn4)cc3C(F)(F)F)CC2)c1] |
| 311 | N-(1-(4-(4-(pyridazin-3-yl)-2-(trifluoromethyl)benzyl)piperazine-1-carbonyl)-1H-pyrazol-4-yl)methanesulforamide | 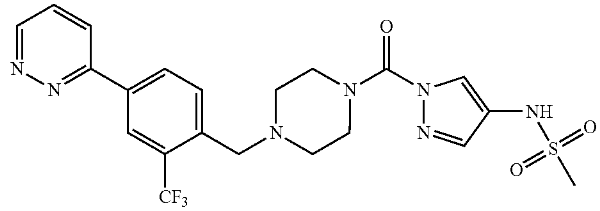 [SMILES: CS(=O)(=O)Nc1cnn(C(=O)N2CCN(Cc3ccc(-c4cccnn4)cc3C(F)(F)F)CC2)c1] |
| 312 | N-(1-(4-(4-(pyridazin-4-yl)-2-(trifluoromethyl)benzyl)piperazine-1-carbonyl)-1H-pyrazol-4-yl)methanesulfonamide | 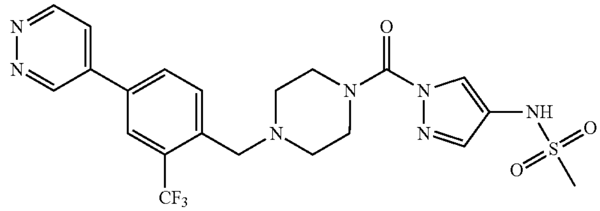 [SMILES: CS(=O)(=O)Nc1cnn(C(=O)N2CCN(Cc3ccc(-c4ccnnc4)cc3C(F)(F)F)CC2)c1] |
| 313 | N-(1-(2-(3-chloro-5-(trifluoromethyl)benzyl)-2,8-diazaspiro[4.5]decane-8-carbonyl)-1H-pyrazol-4-yl)acetamide | 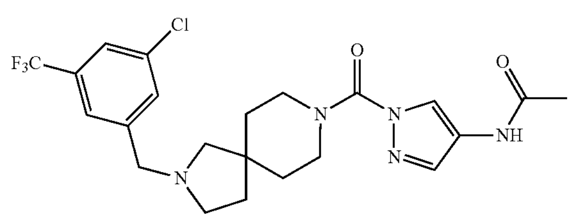 [SMILES: CC(=O)Nc1cnn(C(=O)N2CCC3(CCN(Cc4cc(Cl)cc(C(F)(F)F)c4)C3)CC2)c1] |
| 314 | N-(1-(4-(5-chloro-2-(trifluoromethyl)benzyl)piperazine-1-carbonyl)-1H-pyrazol-4-yl)acetamide | 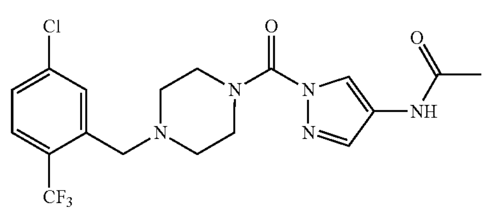 [SMILES: CC(=O)Nc1cnn(C(=O)N2CCN(Cc3cc(Cl)ccc3C(F)(F)F)CC2)c1] |

TABLE 1-continued

| Ex. | Names |
|---|---|
| 315 | N-(1-(5-(3-chloro-5-(trifluoromethyl)benzyl)octahydropyrrolo[3,4-c]pyrrole-2-carbonyl)-1H-pyrazol-4-yl)acetamide |
| 316 | N-(1-(5-(3-(4-chlorophenoxy)benzyl)octahydropyrrolo[3,4-c]pyrrole-2-carbonyl)-1H-pyrazol-4-yl)acetamide |
| 317 | N-(1-(4-(4-ethynylbenzyl)piperazine-1-carbonyl)-1H-pyrazol-4-yl)-N-methylacetamide |
| 318 | N-(1-(4-(4-ethynylbenzyl)piperazine-1-carbonyl)-1H-pyrazol-4-yl)methanesulfonamide |

Preparation of the Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the pyrazole compounds described herein is P. H. Stahl & C. G. Wermuth "Handbook of Pharmaceutical Salts", Verlag Helvetica Chimica Acta, Zurich, 2002.

Further Forms of Pyrazole Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The exocyclic diamine compounds described herein are capable of cis-trans isomerism. The fused 5,5-ring system has two distinct faces, and any substituent on the ring system is attached to one of two faces. When a substituent is attached to the concave surface of the ring system, the substituent is cis. When a substituent is attached to the convex surface of the ring system, the substituent is trans. Like the cases of cis-trans isomerism in alkenes, these isomers have the same atomic connectivities but differ in their spatial arrangement of atoms. Hence, they are stereoisomers.

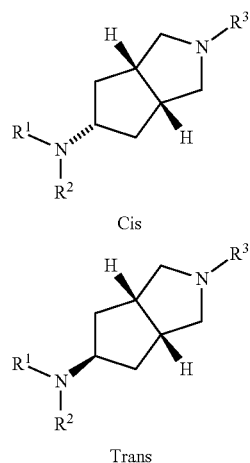

Cis

Trans

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in Advanced Drug Delivery Reviews 1996, 19, 115.

Amine derived prodrugs include, but are not limited to the following groups and combinations of groups:

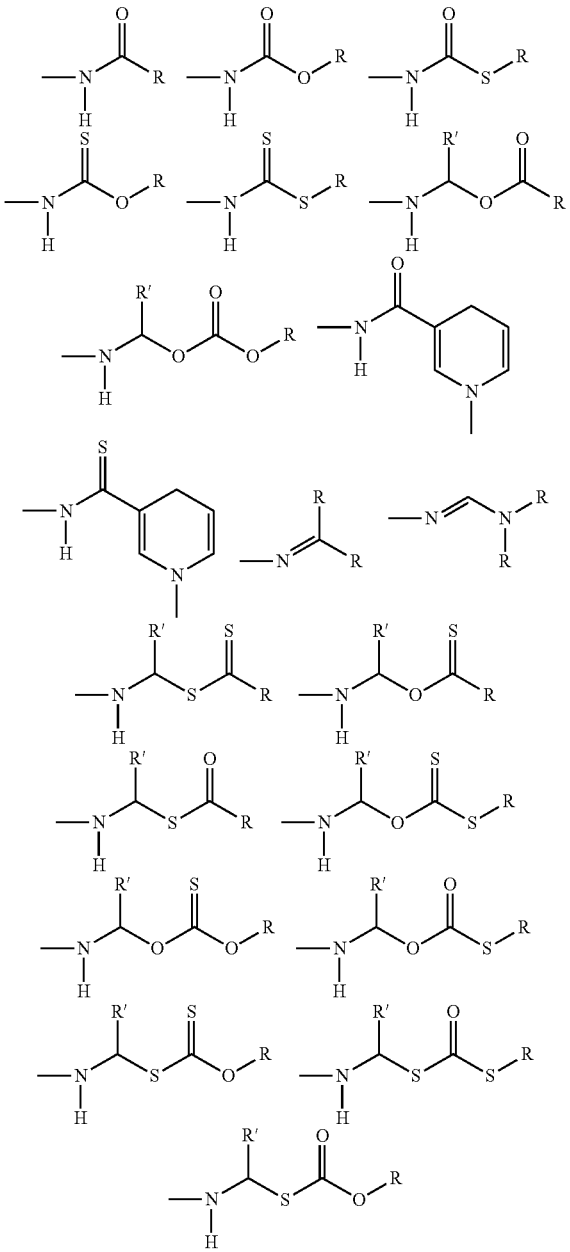

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Metabolites

In some embodiments, pyrazole compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, pyrazole compounds described herein are metabolized upon administration to an organism in need to produce a metabolite that is then used to produce a desired effect, including a desired therapeutic effect.

Pharmaceutical Compositions

In certain embodiments, the compound of Formula (I), (Ia), (II), (IIa), (IIb), (IIc), (IId), (III), (IIIa), (IV), or (IVa) as described herein is administered as a pure chemical. In some embodiments, the compound of Formula (I), (Ia), (II), (IIa), (IIb), (IIc), (IId), (III), (IIIa), (IV), or (IVa) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound of Formula (I), (Ia), (II), (IIa), (IIb), (IIc), (IId), (III), (IIIa), (IV), or (IVa) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof. One embodiment provides a pharmaceutical composition comprising a pharmaceutically acceptable excipient and a compound of Formula (Ia), or a pharmaceutically acceptable salt thereof.

One embodiment provides a pharmaceutical composition comprising a pharmaceutically acceptable excipient and a compound of Formula (II), or a pharmaceutically acceptable salt thereof. One embodiment provides a pharmaceutical composition comprising a pharmaceutically acceptable excipient and a compound of Formula (IIa), or a pharmaceutically acceptable salt thereof. One embodiment provides a pharmaceutical composition comprising a pharmaceutically acceptable excipient and a compound of Formula (IIb), or a pharmaceutically acceptable salt thereof. One embodiment provides a pharmaceutical composition comprising a pharmaceutically acceptable excipient and a compound of Formula (IIc), or a pharmaceutically acceptable salt thereof. One embodiment provides a pharmaceutical composition comprising a pharmaceutically acceptable excipient and a compound of Formula (IId), or a pharmaceutically acceptable salt thereof.

One embodiment provides a pharmaceutical composition comprising a pharmaceutically acceptable excipient and a compound of Formula (III), or a pharmaceutically acceptable salt thereof. One embodiment provides a pharmaceutical composition comprising a pharmaceutically acceptable excipient and a compound of Formula (IIIa), or a pharmaceutically acceptable salt thereof.

One embodiment provides a pharmaceutical composition comprising a pharmaceutically acceptable excipient and a compound of Formula (IV), or a pharmaceutically acceptable salt thereof. One embodiment provides a pharmaceutical composition comprising a pharmaceutically acceptable excipient and a compound of Formula (IVa), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (II), or a pharmaceutically acceptable salt thereof. Another embodiment provides a pharmaceutical composition consisting essentially of a pharmaceutically acceptable excipient and a compound of Formula (III), or a pharmaceutically acceptable salt thereof. Another embodiment provides a pharmaceutical composition consisting essentially of a pharmaceutically acceptable excipient and a compound of Formula (IV), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (IIa), or a pharmaceutically acceptable salt thereof. Another embodiment provides a pharmaceutical composition consisting essentially of a pharmaceutically acceptable excipient and a compound of Formula (IIb), or a pharmaceutically acceptable salt thereof. Another embodiment provides a pharmaceutical composition consisting essentially of a pharmaceutically acceptable excipient and a compound of Formula (IIc), or a pharmaceutically acceptable salt thereof. Another embodiment provides a pharmaceutical composition consisting essentially of a pharmaceutically acceptable excipient and a compound of Formula (IId), or a pharmaceutically acceptable salt thereof. Another embodiment provides a pharmaceutical composition consisting essentially of a pharmaceutically acceptable excipient and a compound of Formula (IIIa), or a pharmaceutically acceptable salt thereof. Another embodiment provides a pharmaceutical composition consisting essentially of a pharmaceutically acceptable excipient and a compound of Formula (IVa), or a pharmaceutically acceptable salt thereof.

In certain embodiments, the compound of Formula (I), (Ia), (II), (IIa), (IIb), (IIc), (IId), (III), (IIIa), (IV), or (IVa) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S 100, Kollicoat EMM30D, Estacryl 30D, Coateric, and Aquateric). The solubility of each of the above materials is either known or is readily determinable in vitro.

The dose of the composition comprising at least one compound of Formula (I), (Ia), (II), (IIa), (IIb), (IIc), (IId), (III), (IIIa), (IV), or (IVa) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of MAGL and/or FAAH. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), (II), (IIa), (IIb), (IIc), (IId), (III), (IIIa), (IV), or (IVa). The ability of compounds described herein to modulate or inhibit MAGL and FAAH is evaluated by procedures known in the art and/or described herein. Another aspect of this disclosure provides methods of treating a disease associated with expression or activity of MAGL and/or FAAH in a patient. For example, provided herein are compounds that are selective in inhibiting MAGL or FAAH, or both, as compared to inhibition of other serine hydrolases e.g., PLA2G7, e.g., 10, 100, 1000 or more fold inhibition of MAGL and/or FAAH over PLA2G7.

In another embodiment is a method of treating a disease or disorder selected from the group consisting of multiple sclerosis, Alzheimer's disease, and inflammatory bowel disease, comprising administering a therapeutically effective amount of a compound of Formula (I), (Ia), (II), (IIa), (IIb), (IIc), (IId), (III), (IIIa), (IV), or (IVa) described herein, or a solvate, hydrate, tautomer, N-oxide, or a pharmaceutically acceptable salt thereof, to a patient in need thereof. In another embodiment is a method of treating multiple sclerosis, comprising administering a therapeutically effective amount of a compound of Formula (I), (Ia), (II), (IIa), (IIb), (IIc), (IId), (III), (IIIa), (IV), or (IVa) described herein, or a solvate, hydrate, tautomer, N-oxide, or a pharmaceutically acceptable salt thereof, to a patient in need thereof. In another embodiment is a method of treating Alzheimer's disease, comprising administering a therapeutically effective amount of a compound of Formula (I), (Ia), (II), (IIa), (IIb), (IIc), (IId), (III), (IIIa), (IV), or (IVa) described herein, or a solvate, hydrate, tautomer, N-oxide, or a pharmaceutically acceptable salt thereof, to a patient in need thereof. In another embodiment is a method of treating inflammatory bowel disease, comprising administering a therapeutically effective amount of a compound of Formula (I), (Ia), (II), (IIa), (IIb), (IIc), (IId), (III), (IIIa), (IV), or (IVa) described herein, or a solvate, hydrate, tautomer, N-oxide, or a pharmaceutically acceptable salt thereof, to a patient in need thereof.

In another embodiment is a method of treating pain in a patient, comprising administering a therapeutically effective amount of a compound of Formula (I), (Ia), (II), (IIa), (IIb), (IIc), (IId), (III), (IIIa), (IV), or (IVa) described herein, or a solvate, hydrate, tautomer, N-oxide, or a pharmaceutically acceptable salt thereof, to a patient in need thereof to treat said pain. In another embodiment is a method of treating neuropathic pain in a patient, comprising administering a therapeutically effective amount of a compound of Formula (I), (Ia), (II), (IIa), (IIb), (IIc), (IId), (III), (IIIa), (IV), or (IVa) described herein, or a solvate, hydrate, tautomer, N-oxide, or a pharmaceutically acceptable salt thereof, to a patient in need thereof to treat said neuropathic pain. In another embodiment is a method of treating inflammatory pain in a patient, comprising administering a therapeutically effective amount of a compound of Formula (I), (Ia), (II), (IIa), (IIb), (IIc), (IId), (III), (IIIa), (IV), or (IVa) described herein, or a solvate, hydrate, tautomer, N-oxide, or a pharmaceutically acceptable salt thereof, to a patient in need thereof to treat said inflammatory pain.

Also contemplated herein in some embodiments are methods of treating and/or preventing in a patient in need thereof a disorder such as one or more of acute or chronic pain, bone cancer pain, rheumatoid arthritis pain, pruitis, vomiting or nausea, Down's syndrome, Parkinson's disease, epilepsy, NSAID-induced ulcers, opioid withdrawal, cannabis withdrawal, nicotine withdrawal, traumatic brain injury, ischemia, renal ischaemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g., myeloid, lymphoid or monocytic cancers), liver injury, lung injury, skeletal muscle contusions, inflammatory disorders, and/or anxiety disorders. Contemplated methods include administering a pharmaceutically effective amount of a disclosed compound.

In some embodiments, provided herein is a method for treating, ameliorating and/or preventing damage from ischemia, for example, hepatic ischemia or reperfusion in a patient in need thereof, comprising administering a disclosed compound. Methods of treating patients with liver conditions resulting from oxidative stress and/or inflammatory damage are contemplated herein, e.g., contemplated herein are methods of treating liver fibrosis, iron overload, and/or corticosteroid therapy that result in liver damage, in a patient in need thereof.

In some embodiments, provide herein is a method for treating chronic pain such as inflammatory pain, visceral pain, back pain, post operative pain, and pain related to migraine, osteoarthritis, or rheumatoid arthritis.

In some embodiments, provided herein are methods for ameliorating cognitive function in a patient suffering from Down's syndrome or Alzheimer's disease, comprising administering an effective amount of a disclosed compound. Exemplary patients suffering from Down's syndrome are a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). In some embodiments, such patients also suffer from further cognitive impairment and/or dementia, and/or seizures which, in some embodiments are due to production of prostaglandins and/or amyloid beta. For example, such patients also are suffering from, or have one or more of the following symptoms associated with early-mid or late stage cognitive impairment: loss of language, impairment of social skills, progressive loss of activities of daily living, and include psychotic behavior. Provided herein, for example, is a method for treating a patient having Down's syndrome or Alzheimer's disease with cognitive impairment, comprising administering an effective amount of a disclosed compound. Such disclosed methods result in cognitive improvement, for example, measured by IQ or the Arizona Cognitive Test Battery (e.g., measured with a cognitive test battery designed for use in individuals with Down's syndrome). For example, a treated patient using a disclosed method has at least one of: increased memory, improved memory or improved speech. In some embodiments, such disclosed methods result in a patient having an increased quality of life as measured by an adaptive behavior scale after said administration.

In other embodiments, a method for at least partially providing a Down's syndrome patient a neuroprotective (such as a disclosed compounds), that results in delayed onset of neurodegeneration or substantially prevents neurodegeneration, is provided. Administration to a patient is initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

In another embodiment is a method of treating a disease or disorder in a patient in need thereof, comprising administering to the patient in need thereof a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof, wherein the disease or disorder is selected from the group consisting of epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating epilepsy/seizure disorder in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating neuromyelitis optica (NMO) in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating Tourette syndrome in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating persistent motor tic disorder in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating persistent vocal tic disorder in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating abdominal pain associated with irritable bowel syndrome in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In another embodiment is a method of treating cancer pain, pain caused by peripheral neuropathy, central pain, fibromyalgia, migraine, vasoocclussive painful crises in sickle cell disease, functional chest pain, rheumatoid arthritis, osteoarthritis, functional dyspepsia, or spasticity, pain, sleep disturbance, or bladder dysfunction associated with multiple sclerosis in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating cancer pain in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating pain caused by peripheral neuropathy in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating central pain in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating fibromyalgia in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating migraine in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating vasoocclussive painful crises in sickle cell disease in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating spasticity, pain, sleep disturbance, or bladder dysfunction associated with multiple sclerosis in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating functional chest pain in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating rheumatoid arthritis in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating osteoarthritis in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating functional dyspepsia in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In another embodiment is a method of lowering intraocular eye pressure (IOP) in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In another embodiment is a method of treating glaucoma in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In another embodiment is a method of treating atopic dermatitis in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In another embodiment is a method of treating pruritis in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating a skeletal muscle contusion in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating attention deficit and hyperactivity disorder in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating obsessive-compulsive disorder in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating trichotillomania in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating trigeminal neuralgia in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In some embodiments, disclosed herein is a method of treating glossophyryngeal neuralgia in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating traumatic brain injury in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating progressive supranuclear palsy in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In some embodiments, disclosed herein is a method of treating corticobasal degeneration in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In some embodiments, disclosed herein is a method of treating frontotemporal dementia in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of improving functional outcome following stroke in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating Amyotrophic Lateral Sclerosis (ALS) or ALS-related symptoms in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating Huntington's Disease in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of Parkinson's Disease in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of treating autism in a patient in need thereof, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In some embodiments, disclosed herein is a method of synergistically potentiating the activity of an opioid analgesic in a patient being treated with an opioid analgesic, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of a compound of Formula (I), (Ia), (II), (IIa), (IIb), (IIc), (IId), (III), (IIIa), (IV), or (IVa) described herein, or a pharmaceutically acceptable salt or solvate thereof.

In certain embodiments, a disclosed compound utilized by one or more of the foregoing methods is one of the generic, subgeneric, or specific compounds described herein, such as a compound of Formula (I), (Ia), (II), (IIa), (IIb), (IIc), (IId), (III), (IIIa), (IV), or (IVa).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Combination Therapies

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain or other contemplated indications (e.g., Alzheimer's disease), a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a tricyclic antidepressant, such as imipramine, amitriptyline, or desipramine. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a serotonin-norepinephrine reuptake inhibitor, such as duloxetine, milnacipran, venlafaxine, or clomipramine. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with an alpha-2-delta inhibitor, such as gabapentin or pregabalin. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with an antiepileptic drug, such as topiramate, lamotrigine, levetiracetam, valproate, clonazepam, oxcarbazine, or carbamazepine.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with an opioid, such as morphine, codeine, oxycodone, oxymorphone, tramadol, tapentadol, methadone, or fentanyl.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with acetaminophen. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a nonsteroidal anti-inflammatory drug, such as ibuprofen, naproxen, celecoxib, or diclofenac. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a disease-modifying antirheumatic drug, such as tofacitinib, leflunomide, or methotrexate.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with exo-cannabinoids, such as oral delta-9-THC and nabiximols (Sativex).

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a muscle relaxant such as baclofen and tizanidine. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with diazepam.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a prokinetic agent, such as metoclopramide, domperidone, or itopride. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a 5-HT4 agonist, such as tegaserod or mosapride. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with buspirone.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a neuroleptic, such as pimozide, olanzapine, risperidone, or quetiapine.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a cholinesterase inhibitor, such as donepezil, rivastigmine, or galantamine. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a NMDA antagonist, such as memantine.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with dopamine replacement therapy, such as levodopa or carbidopa-levodopa. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a catechol-O-methyl transferase (COMT) inhibitor, such as tolcapone or entacapone. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a dopamine agonist, such as bromocriptine, pramipexole, or ropinirole. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a monamine oxidase (MAO) B inhibitor, such as selegiline or rasagiline. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with an anticholinergic agent, such as benztropine, trihexyphenidyl, or procyclidine.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a dopamine antagonist, such as haloperidol, pimozide, or fluphenazine. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a VMAT2 inhibitor which depletes dopamine, such as tetrabenazine. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with an alpha adrenergic agonist, such as clonidine or guanfacine.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a selective serotonin reuptake inhibitors (SSRI), such as fluoxetine, sertraline, paroxetine, citalopram or escitalopram.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a stimulant, such as methylphenidate, dextroamphetamine, or lisdexamfetamine. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with an antidepressant, such as bupropion or atomoxetine.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a serotonin 1b/1d agonist. In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a triptan, such as sumatriptan or zolmitriptan.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with a glutamate inhibitor, such as riluzole.

In some embodiments, a compound of Formula (I), (Ia), (II), (IIa), (IIb), (IIc), (IId), (III), (IIIa), (IV), or (IVa) described herein, or a pharmaceutically acceptable salt or solvate thereof, is co-administered with an H1 antihistamine, such as diphenhydramine, hydroxyzine, cetirizine, loratadine, or desloratadine.

In certain embodiments, a disclosed compound utilized by one or more of the foregoing methods is one of the generic, subgeneric, or specific compounds described herein, such as a compound of Formula (I), (Ia), (II), (IIa), (IIb), (IIc), (IId), (III), (IIIa), (IV), or (IVa).

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

| | |
|---|---|
| ACN or MeCN | acetonitrile |
| Bn | benzyl |
| BOC or Boc | tert-butyl carbamate |
| t-Bu | tert-butyl |
| Cy | cyclohexyl |
| DCE | dichloroethane |
| DCM | dichloromethane |
| DIPEA or DIEA | diisopropylethylamine |
| DMAP | 4-(N,N-dimethylamino)pyridine |
| DMF | dimethylformamide |
| DMA | N,N-dimethylacetamide |
| DMSO | dimethylsulfoxide |
| Dppf or dppf | 1,1'-bis(diphenylphosphino)ferrocene |
| equiv or eq | equivalent(s) |
| Et | ethyl |
| Et$_2$O | diethyl ether |
| EtOH | ethanol |
| EtOAc | ethyl acetate |
| HPLC | high performance liquid chromatography |
| LAH | lithium aluminum anhydride |
| Me | methyl |
| MeOH | methanol |
| MS | mass spectroscopy |
| NMM | N-methyl-morpholine |
| NMP | N-methyl-pyrrolidin-2-one |
| NMR | nuclear magnetic resonance |
| RP-HPLC | reverse phase-high pressure liquid chromatography |
| TFA | trifluoroacetic acid |
| THF | tetrahydrofuran |
| TLC | thin layer chromatography |

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. In some instances, compounds were purified using preparative HPLC on a Waters 2767-5 Chromatograph. Spectra are given in ppm (δ) and coupling constants (J) are reported in Hertz. For proton spectra the solvent peak was used as the reference peak.

Example 1: N-(1-(7-(3,4-dichlorobenzyl)-2,7-diaz-aspiro[4.4]nonane-2-carbonyl)-1H-pyrazol-4-yl)-N-methylacetamide

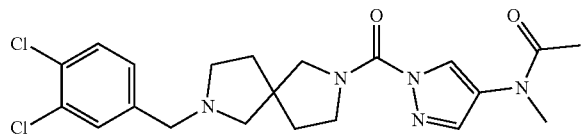 [SMILES: CC(=O)N(C)c1cnn(C(=O)N2CCC3(CCN(Cc4ccc(Cl)c(Cl)c4)C3)C2)c1]

Step 1: Synthesis of 4-nitrophenyl 4-acetamido-1H-pyrazole-1-carboxylate

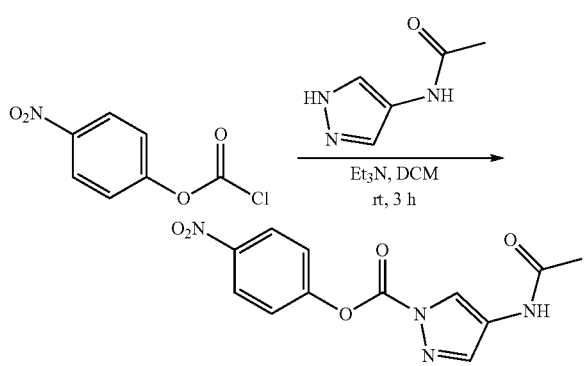

A 100-mL round-bottom flask was charged with N-(1H-pyrazol-4-yl)acetamide (600 mg, 4.80 mmol, 1.00 equiv), 4-nitrophenyl chloroformate (1.01 g, 5.01 mmol, 1.05 equiv), DCM (20 mL), and triethylamine (1.45 g, 14.3 mmol, 3.00 equiv). The resulting solution was stirred for 3 h at room temperature and concentrated under reduced pressure to yield 3.02 g (crude) of 4-nitrophenyl 4-acetamido-1H-pyrazole-1-carboxylate as a yellow solid. LCMS (ESI, m/z): 291 [M+H]$^+$.

Step 2: Synthesis of Tert-butyl 7-(3,4-dichlorobenzyl)-2,7-diazaspiro[4.4]nonane-2-carboxylate

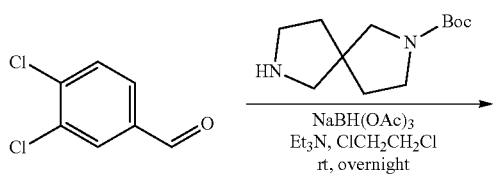

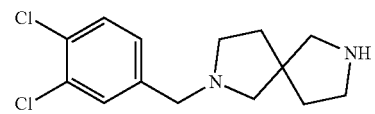

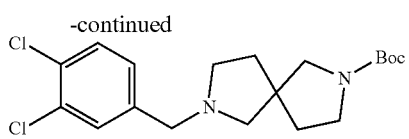

A 250-mL round-bottom flask was charged with 3,4-dichlorobenzaldehyde (800 mg, 4.57 mmol, 1.00 equiv), 1,2-dichloroethane (20 mL), tert-butyl 2,7-diazaspiro[4.4]nonane-2-carboxylate (1.04 g, 4.60 mmol, 1.00 equiv), and triethylamine (1.39 g, 13.7 mmol, 3.00 equiv). The resulting solution was stirred for 30 min at room temperature. Sodium triacetoxyborohydride (2.92 g, 13.8 mmol, 3.00 equiv) was added. The resulting solution was stirred overnight at room temperature and quenched with water (10 mL). The resulting solution was extracted with DCM (3×20 mL) and the organic layers were combined, washed with brine (2×20 mL), dried over anhydrous sodium sulfate, filtered and concentrated under reduced pressure. The residue was chromatographed on a silica gel column to yield 1.70 g (97% yield) of tert-butyl 7-(3,4-dichlorobenzyl)-2,7-diazaspiro[4.4]nonane-2-carboxylate as a yellow oil. LCMS (ESI, m/z): 385 [M+H]$^+$.

Step 3: Synthesis of 2-(3,4-dichlorobenzyl)-2,7-diazaspiro[4.4]nonane

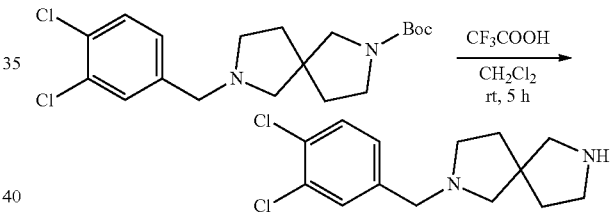

A 100-mL round-bottom flask was charged with tert-butyl 7-(3,4-dichlorobenzyl)-2,7-diazaspiro[4.4]nonane-2-carboxylate (1.70 g, 4.41 mmol, 1.00 equiv) in DCM (20 mL), and TFA (5 mL) was added. The resulting solution was stirred for 5 h at room temperature and concentrated under reduced pressure to yield 1.89 g (crude) of 2-(3,4-dichlorobenzyl)-2,7-diazaspiro[4.4]nonane as a yellow oil. LCMS (ESI, m/z): 285 [M+H]$^+$.

Step 4: Synthesis of N-(1-(7-(3,4-dichlorobenzyl)-2,7-diazaspiro[4.4]nonane-2-carbonyl)-1H-pyrazol-4-yl)acetamide

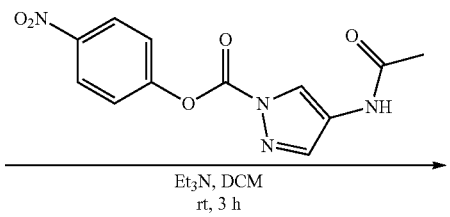

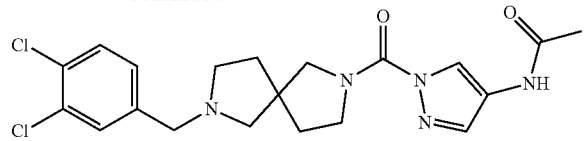

A 100-mL round-bottom flask was charged with 2-(3,4-dichlorobenzyl)-2,7-diazaspiro[4.4]nonane (300 mg, 1.05 mmol, 1.00 equiv), 4-nitrophenyl 4-acetamido-1H-pyrazole-1-carboxylate (461 mg, 1.59 mmol, 1.50 equiv), DCM (10 mL), and triethylamine (321 mg, 3.17 mmol, 3.00 equiv). The resulting solution was stirred for 3 h at room temperature and quenched with water (10 mL). The resulting solution was extracted with DCM (3×10 mL) and the organic layers were combined, washed with brine (2×10 mL), dried over anhydrous sodium sulfate, filtered and concentrated under reduced pressure. The residue was chromatographed on a silica gel column to yield 446 mg (97% yield) of N-(1-(7-(3,4-dichlorobenzyl)-2,7-diazaspiro[4.4]nonane-2-carbonyl)-1H-pyrazol-4-yl)acetamide as a yellow oil. LCMS (ESI, m/z): 436 [M+H]$^+$.

Step 5: Synthesis of N-(1-(7-(3,4-dichlorobenzyl)-2,7-diazaspiro[4.4]nonane-2-carbonyl)-1H-pyrazol-4-yl)-N-methylacetamide

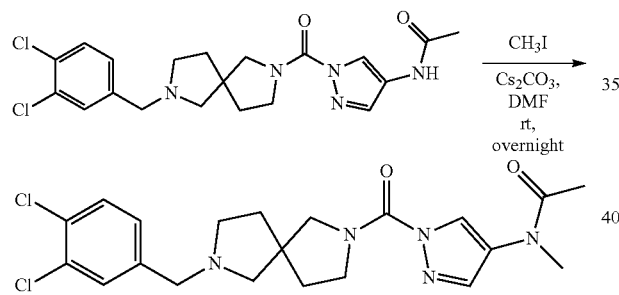

A 40-mL round-bottom flask was charged with N-(1-(7-(3,4-dichlorobenzyl)-2,7-diazaspiro[4.4]nonane-2-carbonyl)-1H-pyrazol-4-yl)acetamide (446 mg, 1.02 mmol, 1.00 equiv), cesium carbonate (998 mg, 3.06 mmol, 3.00 equiv), and DMF (10 mL). The resulting solution was stirred for 30 min at 0° C. Iodomethane (217 mg, 1.53 mmol, 1.50 equiv) was added dropwise at 0° C. The resulting solution was stirred overnight at room temperature and quenched with water (10 mL). The mixture was extracted with EtOAc (3×10 mL) and the organic layers were combined, washed with brine (2×10 mL), dried over anhydrous sodium sulfate, filtered and concentrated under reduced pressure. The crude product (400 mg) was purified by preparative HPLC. Purification resulted in 158.4 mg (34% yield) of N-(1-(7-(3,4-dichlorobenzyl)-2,7-diazaspiro[4.4]nonane-2-carbonyl)-1H-pyrazol-4-yl)-N-methylacetamide as a brown oil. $^1$H NMR (300 MHz, Chloroform-d) δ 8.29 (s, 0.3H), 8.20 (s, 0.7H), 8.04 (s, 0.3H), 7.57 (s, 0.7H), 7.34-7.50 (m, 2H), 7.20 (br, 1H), 3.81-4.15 (m, 2H), 3.51-3.80 (m, 4H), 3.36 (s, 1H), 3.21 (s, 2H), 2.41-2.85 (m, 4H), 2.28 (s, 1H), 1.99 (s, 2H), 1.80-1.95 (m, 4H). LCMS (ESI, m/z): 450 [M+H]$^+$.

Example 2: N-methyl-N-(1-(7-(4-(trifluoromethyl)benzyl)-2,7-diazaspiro[4.4]nonane-2-carbonyl)-1H-pyrazol-4-yl)acetamide

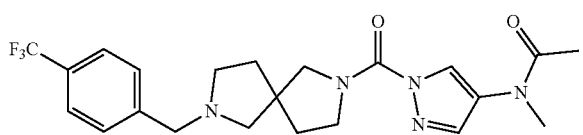 [SMILES: CC(=O)N(C)c1cnn(C(=O)N2CCC3(CCN(Cc4ccc(C(F)(F)F)cc4)C3)C2)c1]

The title compound was synthesized as described in Example 1 using 4-(trifluoromethyl)benzaldehyde in Step 2. Purification resulted in 114.7 mg of N-methyl-N-(1-(7-(4-(trifluoromethyl)benzyl)-2,7-diazaspiro[4.4]nonane-2-carbonyl)-1H-pyrazol-4-yl)acetamide as a yellow oil. $^1$H NMR (300 MHz, Chloroform-d) δ 8.28 (s, 0.3H), 8.20 (s, 0.7H), 8.04 (s, 0.3H), 7.59 (s, 0.7H), 7.40-7.58 (m, 4H), 3.85-4.15 (m, 2H), 3.55-3.82 (m, 4H), 3.36 (s, 1H), 3.21 (s, 2H), 2.45-2.85 (m, 4H), 2.28 (s, 1H), 2.00 (s, 2H), 1.80-1.99 (m, 4H). LCMS (ESI, m/z): 450 [M+H]$^+$.

Example 3: N-methyl-N-(1-(7-(4-morpholinobenzyl)-2,7-diazaspiro[4.4]nonane-2-carbonyl)-1H-pyrazol-4-yl)acetamide

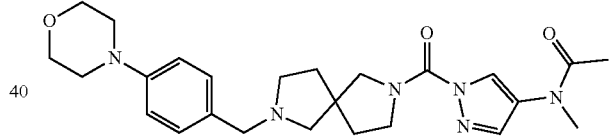

The title compound was synthesized as described in Example 1 using 4-morpholinobenzaldehyde in Step 2. Purification resulted in 63.1 mg of N-methyl-N-(1-(7-(4-morpholinobenzyl)-2,7-diazaspiro[4.4]nonane-2-carbonyl)-1H-pyrazol-4-yl)acetamide as a white solid. $^1$H NMR (300 MHz, Chloroform-d) δ 8.27 (s, 0.3H), 8.18 (s, 0.7H), 8.04 (s, 0.3H), 7.54 (s, 0.7H), 7.20-7.22 (m, 2H), 6.85-6.91 (m, 2H), 3.90-4.11 (m, 2H), 3.86 (t, (t, J=4.8 Hz, 4H), 3.55-3.78 (m, 4H), 3.35 (s, 1H), 3.21 (s, 2H), 3.15 (t, (t, J=4.5 Hz, 4H), 2.44-2.78 (m, 4H), 2.28 (s, 1H), 1.84-1.99 (m, 6H). LCMS (ESI, m/z): 467 [M+H]$^+$.

Example 4: N-(1-(7-(2-chloro-4-morpholinobenzyl)-2,7-diazaspiro[4.4]nonane-2-carbonyl)-1H-pyrazol-4-yl)-N-methylacetamide

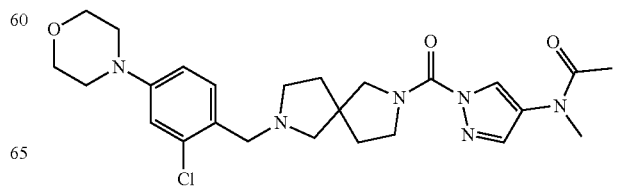

The title compound was synthesized as described in Example 1 using 2-chloro-4-morpholinobenzaldehyde in Step 2. Purification resulted in 259.7 mg of N-(1-(7-(2-chloro-4-morpholinobenzyl)-2,7-diazaspiro[4.4]nonane-2-carbonyl)-1H-pyrazol-4-yl)-N-methylacetamide as a white solid. $^1$H NMR (300 MHz, Chloroform-d) δ 8.25 (s, 0.3H), 8.16 (s, 0.7H), 8.01 (s, 0.3H), 7.76 (s, 0.7H), 7.23-7.30 (m, 1H), 6.83 (s, 1H), 6.73-6.75 (m, 1H), 3.93-4.04 (m, 2H), 3.83 (t, J=4.5 Hz, 4H), 3.52-3.80 (m, 4H), 3.32 (s, 1H), 3.18 (s, 2H), 3.11 (t, J=4.8 Hz, 4H), 2.48-2.68 (m, 4H), 2.25 (s, 1H), 1.96 (s, 2H), 1.81-1.91 (m, 4H). LCMS (ESI, m/z): 501 [M+H]$^+$.

Example 5: N-methyl-N-(1-(7-(2-methyl-4-morpholinobenzyl)-2,7-diazaspiro[4.4]nonane-2-carbonyl)-1H-pyrazol-4-yl)acetamide

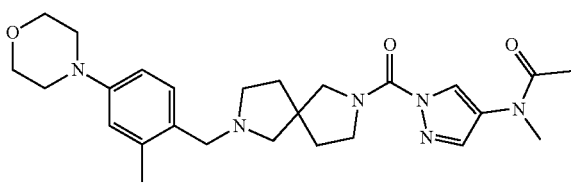 [SMILES: CC(=O)N(C)c1cnn(C(=O)N2CCC3(CCN(Cc4ccc(N5CCOCC5)cc4C)C3)C2)c1]

Step 1: Synthesis of 2-methyl-4-morpholinobenzaldehyde

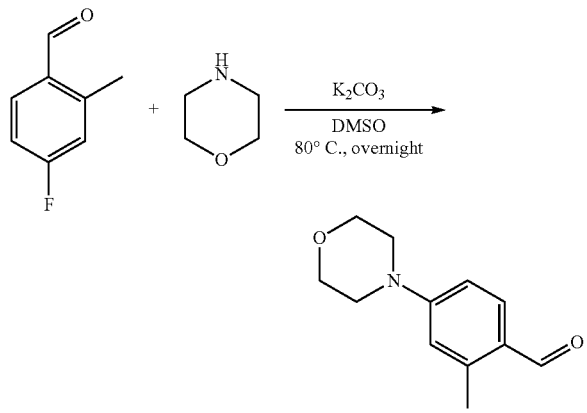

A 100-mL round-bottom flask was charged with 4-fluoro-2-methylbenzaldehyde (7.00 g, 50.7 mmol, 1.00 equiv), potassium carbonate (13.2 g, 152 mmol, 3.00 equiv), DMSO (50 mL), and morpholine (13.2 g, 152 mmol, 3.00 equiv). The resulting solution was stirred overnight at 80° C. and quenched with water (20 mL). The mixture was extracted with DCM (3×40 mL) and the organic layers were combined, washed with brine (30 mL), dried over anhydrous sodium sulfate, filtered and concentrated under reduced pressure. The residue was chromatographed on a silica gel column to provide 9.80 g (94% yield) of 2-methyl-4-morpholinobenzaldehyde as a yellow solid. LCMS (ESI, m/z): 206 [M+H]$^+$.

Step 2: Synthesis of N-methyl-N-(1-(7-(2-methyl-4-morpholinobenzyl)-2,7-diazaspiro[4.4]nonane-2-carbonyl)-1H-pyrazol-4-yl)acetamide

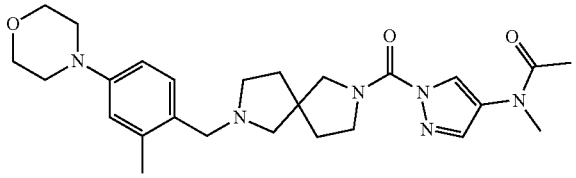 [SMILES: CC(=O)N(C)c1cnn(C(=O)N2CCC3(CCN(Cc4ccc(N5CCOCC5)cc4C)C3)C2)c1]

The title compound was synthesized as described in Example 1 using 2-methyl-4-morpholinobenzaldehyde in Step 2. Purification resulted in 211.9 mg (46% yield) of N-methyl-N-(1-(7-(2-methyl-4-morpholinobenzyl)-2,7-diazaspiro[4.4]nonane-2-carbonyl)-1H-pyrazol-4-yl)acetamide as a white solid. $^1$H NMR (300 MHz, Chloroform-d) δ 8.24 (s, 0.3H), 8.16 (s, 0.7H), 8.02 (s, 0.3H), 7.51 (s, 0.7H), 7.08-7.10 (m, 1H), 6.64-6.68 (m, 2H), 3.91-4.05 (m, 1H), 3.82 (t, J=4.8 Hz, 5H), 3.48-3.74 (m, 4H), 3.32 (s, 1H), 3.18 (s, 2H), 3.11 (t, J=4.8 Hz, 4H), 2.40-2.64 (m, 4H), 2.25-2.31 (m, 4H), 1.76-1.96 (m, 6H). LCMS (ESI, m/z): 481 [M+H]$^+$.

Example 6: N-(1-(5-(2-chlorobenzyl)octahydropyrrolo[3,4-c]pyrrole-2-carbonyl)-1H-pyrazol-4-yl)methanesulfonamide

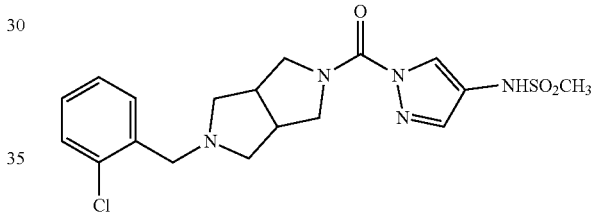

Step 1: Synthesis of 4-nitrophenyl 4-(methylsulfonamido)-1H-pyrazole-1-carboxylate

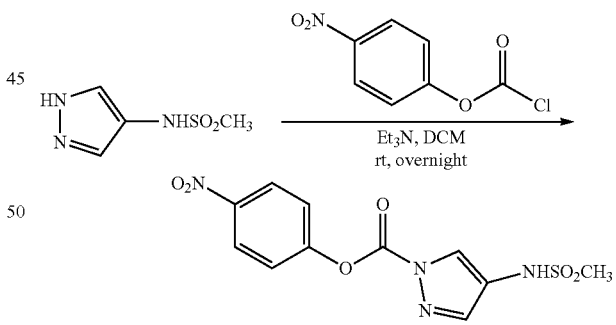

A 100-mL round-bottom flask was charged with N-(1H-pyrazol-4-yl)methanesulfonamide (1.20 g, 7.45 mmol, 1.00 equiv), DCM (20 mL), and triethylamine (2.26 g, 22.3 mmol, 3.00 equiv). 4-Nitrophenyl chloroformate (1.81 g, 8.98 mmol, 1.20 equiv) was added at 0° C. The resulting solution was stirred overnight at room temperature and then quenched with water (20 mL). The resulting mixture was extracted with DCM (3×30 mL) and the organic layers were combined, washed with brine (100 mL), dried over anhydrous sodium sulfate, filtered and concentrated under reduced pressure to provide 2.40 g (crude) of 4-nitrophenyl 4-(methylsulfonamido)-1H-pyrazole-1-carboxylate as a yellow oil. LCMS (ESI, m/z): 327 [M+H]$^+$.

Step 2: Synthesis of Tert-butyl 5-(2-chlorobenzyl)hexahydropyrrolo[3,4-c]pyrrole-2(1H)-carboxylate

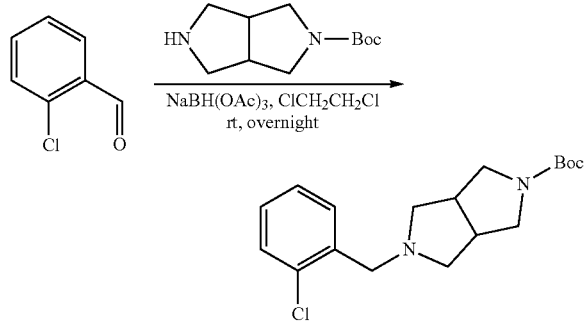

A 250-mL round-bottom flask was charged with 2-chlorobenzaldehyde (1.30 g, 9.25 mmol, 1.00 equiv), tert-butyl hexahydropyrrolo[3,4-c]pyrrole-2(1H)-carboxylate (2.70 g, 12.7 mmol, 1.40 equiv), and 1,2-dichloroethane (30 mL). The mixture was stirred for 1 h at room temperature. Sodium triacetoxyborohydride (5.90 g, 27.8 mmol, 3.00 equiv) was added. The resulting solution was stirred overnight at room temperature and then quenched with water (30 mL). The resulting mixture was extracted with DCM (3×30 mL) and the organic layers were combined, washed with brine (100 mL), dried over anhydrous sodium sulfate, filtered and concentrated under reduced pressure. The residue was chromatographed on a silica gel column to provide 2.40 g (77% yield) of tert-butyl 5-(2-chlorobenzyl)hexahydropyrrolo[3,4-c]pyrrole-2(1H)-carboxylate as a yellow oil. LCMS (ESI, m/z): 337 [M+H]$^+$.

Step 3: Synthesis of 2-(2-chlorobenzyl)octahydropyrrolo[3,4-c]pyrrole

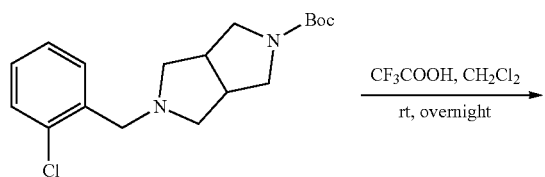

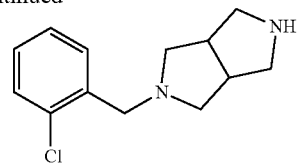

A 100-mL round-bottom flask was charged with tert-butyl 5-(2-chlorobenzyl)hexahydropyrrolo[3,4-c]pyrrole-2(1H)-carboxylate (2.40 g, 7.12 mmol, 1.00 equiv), TFA (8 mL), and DCM (15 mL). The resulting solution was stirred overnight at room temperature and concentrated under reduced pressure. The crude product was dissolved in 1M NaOH solution (10 mL) and extracted with DCM (3×20 mL). The organic layers were combined, washed with brine (10 mL), dried over anhydrous sodium sulfate, filtered and concentrated under reduced pressure to provide 1.40 g (83% yield) of 2-(2-chlorobenzyl)octahydropyrrolo[3,4-c]pyrrole as a yellow oil. LCMS (ESI, m/z): 237 [M+H]$^+$.

Step 4: Synthesis of N-(1-(5-(2-chlorobenzyl)octahydropyrrolo[3,4-c]pyrrole-2-carbonyl)-1H-pyrazol-4-yl)methanesulfonamide

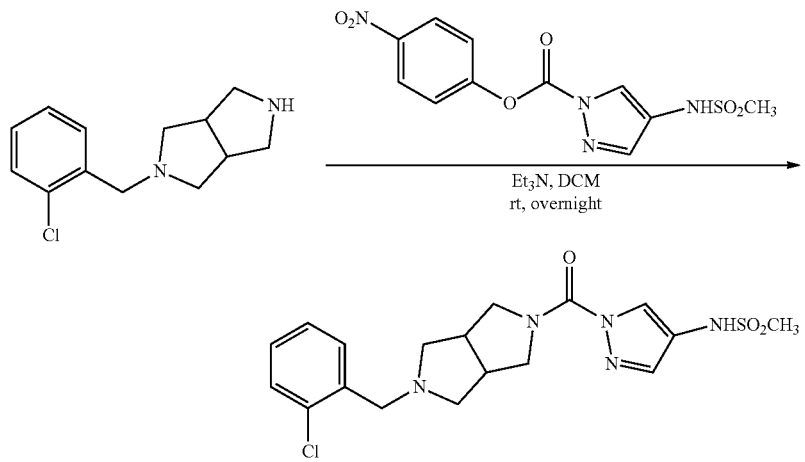

A 100-mL round-bottom flask was charged with 2-(2-chlorobenzyl)octahydropyrrolo[3,4-c]pyrrole (200 mg, 0.840 mmol, 1.00 equiv), 4-nitrophenyl 4-(methylsulfonamido)-1H-pyrazole-1-carboxylate (414 mg, 1.27 mmol, 1.50 equiv), triethylamine (171 mg, 1.69 mmol, 2.00 equiv), and DCM (5 mL). The resulting solution was stirred overnight at room temperature and concentrated under reduced pressure. The crude product (800 mg) was purified by preparative HPLC. Purification resulted in 60.6 mg of N-(1-(5-(2-chlorobenzyl)octahydropyrrolo[3,4-c]pyrrole-2-carbonyl)-1H-pyrazol-4-yl)methanesulfonamide as a white solid. $^1$H NMR (300 MHz, Chloroform-d) δ 8.22 (s, 1H), 7.64 (s, 1H), 7.41-7.44 (m, 1H), 7.31-7.34 (m, 1H), 7.14-7.25 (m, 2H), 4.12 (br, 2H), 3.73-3.95 (m, 4H), 2.99 (s, 3H), 2.90 (br, 2H), 2.65-2.70 (m, 4H). LCMS (ESI, m/z): 424 [M+H]$^+$.

Example 7: N-(1-(5-(3-chlorobenzyl)octahydropyrrolo[3,4-c]pyrrole-2-carbonyl)-1H-pyrazol-4-yl)methanesulfonamide

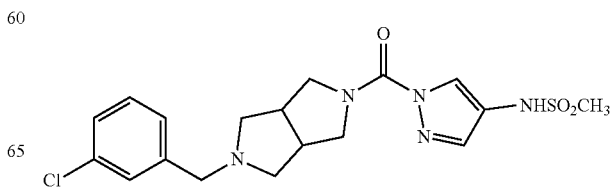

The title compound was synthesized as described in Example 6 using 3-chlorobenzaldehyde in Step 2. Purification resulted in 123.4 mg of N-(1-(5-(3-chlorobenzyl)octahydropyrrolo[3,4-c]pyrrole-2-carbonyl)-1H-pyrazol-4-yl)methanesulfonamide as a light yellow semi-solid. ¹H NMR (300 MHz, Chloroform-d) δ 8.22 (s, 1H), 7.65 (s, 1H), 7.29 (s, 1H), 7.17-7.24 (m, 3H), 4.07 (br, 2H), 3.79 (br, 2H), 3.57 (s, 2H), 2.99 (s, 3H), 2.89 (br, 2H), 2.53-2.66 (m, 4H). LCMS (ESI, m/z): 424 [M+H]⁺.

Example 8: N-(1-(5-(4-chlorobenzyl)octahydropyrrolo[3,4-c]pyrrole-2-carbonyl)-1H-pyrazol-4-yl)methanesulfonamide

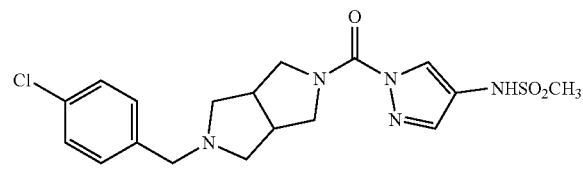

The title compound was synthesized as described in Example 6 using 4-chlorobenzaldehyde in Step 2. Purification resulted in 147.4 mg of N-(1-(5-(4-chlorobenzyl)octahydropyrrolo[3,4-c]pyrrole-2-carbonyl)-1H-pyrazol-4-yl)methanesulfonamide as a light yellow solid. ¹H NMR (300 MHz, Chloroform-d) δ 8.22 (s, 1H), 7.64 (s, 1H), 7.21-7.28 (m, 4H), 4.08 (br, 2H), 3.78 (br, 2H), 3.56 (s, 2H), 3.00 (s, 3H), 2.88 (br, 2H), 2.52-2.62 (m, 4H). LCMS (ESI, m/z): 424 [M+H]⁺.

Example 9: N-(1-(5-(2-chlorobenzyl)octahydropyrrolo[3,4-c]pyrrole-2-carbonyl)-1H-pyrazol-4-yl)-N-methylacetamide

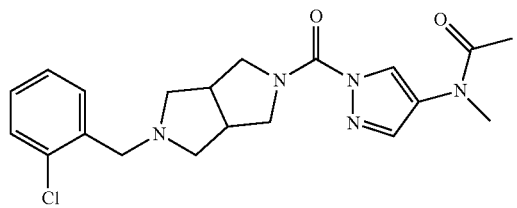 [SMILES: CC(=O)N(C)c1cnn(C(=O)N2CC3CN(Cc4ccccc4Cl)CC3C2)c1]

The title compound was synthesized as described in Example 1 using 2-chlorobenzaldehyde and tert-butyl hexahydropyrrolo[3,4-c]pyrrole-2(1H)-carboxylate in Step 2. Purification resulted in 283.8 mg of N-(1-(5-(2-chlorobenzyl)octahydropyrrolo[3,4-c]pyrrole-2-carbonyl)-1H-pyrazol-4-yl)-N-methylacetamide as a light yellow oil. ¹H NMR (300 MHz, Chloroform-d) δ 8.20-8.30 (m, 1H), 8.05 (s, 0.3H), 7.56 (s, 0.7H), 7.44 (d, J=7.2 Hz, 1H), 7.31-7.34 (m, 1H), 7.14-7.25 (m, 2H), 3.73-4.13 (m, 6H), 3.36 (s, 1H), 3.22 (s, 2H), 2.90 (br, 2H), 2.66 (br, 4H), 2.28 (s, 1H), 1.99 (s, 2H). LCMS (ESI, m/z): 402 [M+H]⁺.

Example 10: N-(1-(5-(3-chlorobenzyl)octahydropyrrolo[3,4-c]pyrrole-2-carbonyl)-1H-pyrazol-4-yl)-N-methylacetamide

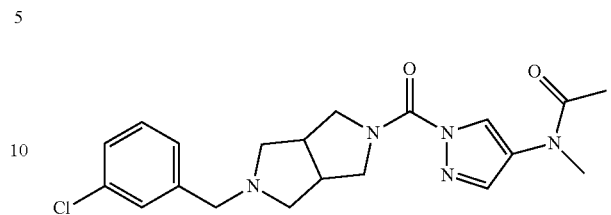

The title compound was synthesized as described in Example 1 using 3-chlorobenzaldehyde and tert-butyl hexahydropyrrolo[3,4-c]pyrrole-2(1H)-carboxylate in Step 2. Purification resulted in 52.1 mg of N-(1-(5-(3-chlorobenzyl)octahydropyrrolo[3,4-c]pyrrole-2-carbonyl)-1H-pyrazol-4-yl)-N-methylacetamide as a light yellow oil. ¹H NMR (300 MHz, Chloroform-d) δ 8.20-8.29 (m, 1H), 8.04 (s, 0.3H), 7.55 (s, 0.7H), 7.30 (s, 1H), 7.17-7.24 (m, 3H), 3.79-4.08 (m, 4H), 3.57 (s, 2H), 3.36 (s, 1H), 3.22 (s, 2H), 2.90 (br, 2H), 2.51-2.62 (m, 4H), 2.28 (s, 1H), 2.00 (s, 2H). LCMS (ESI, m/z): 402 [M+H]⁺.

Example 11: N-(1-(5-(4-chlorobenzyl)octahydropyrrolo[3,4-c]pyrrole-2-carbonyl)-1H-pyrazol-4-yl)-N-methylacetamide

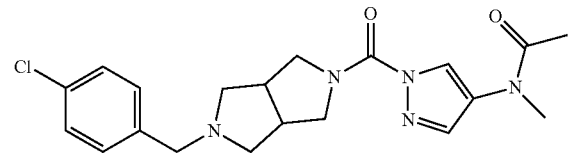 [SMILES: CC(=O)N(C)c1cnn(C(=O)N2CC3CN(Cc4ccc(Cl)cc4)CC3C2)c1]

Step 1: Synthesis of Tert-butyl 5-(chlorocarbonyl)hexahydropyrrolo[3,4-c]pyrrole-2(1H)-carboxylate

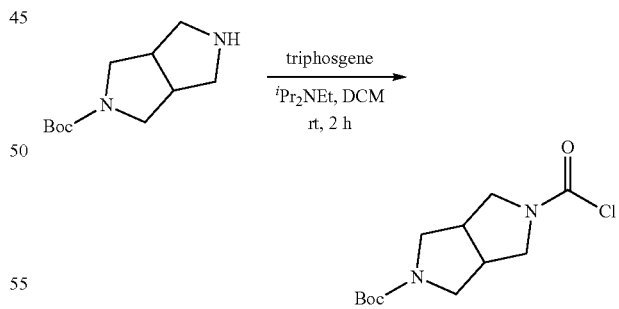

A 250-mL round-bottom flask was charged with triphosgene (2.10 g, 7.07 mmol, 0.50 equiv) and DCM (20 mL). tert-Butyl hexahydropyrrolo[3,4-c]pyrrole-2(1H)-carboxylate (3.00 g, 14.1 mmol, 1.00 equiv) was added at 0° C. N,N-diisopropylethylamine (5.48 g, 42.4 mmol, 3.00 equiv) was added at 0° C. The resulting solution was stirred for 2 h at room temperature and then quenched with water (20 mL). The resulting solution was extracted with DCM (3×20 mL) and the organic layers were combined, washed with brine (2×20 mL), dried over anhydrous sodium sulfate, filtered and concentrated under reduced pressure to provide 3.80 g (98% yield) of tert-butyl 5-(chlorocarbonyl)hexahydropyrrolo[3,4-c]pyrrole-2(1H)-carboxylate as a yellow oil. LCMS (ESI, m/z): 275 [M+H]+.

Step 2: Synthesis of Tert-butyl 5-(4-acetamido-1H-pyrazole-1-carbonyl)hexahydropyrrolo[3,4-c]pyrrole-2(1H)-carboxylate

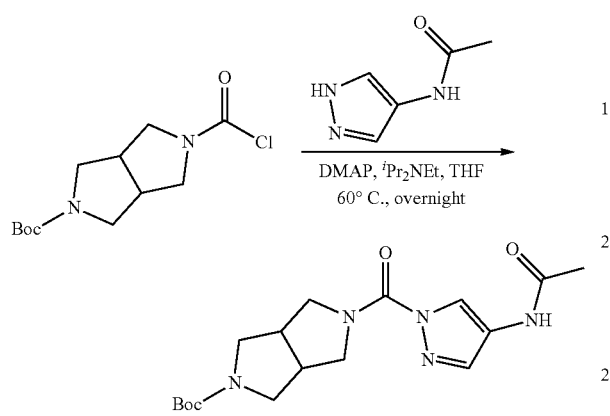

A 250-mL round-bottom flask was charged with tert-butyl 5-(chlorocarbonyl)hexahydropyrrolo[3,4-c]pyrrole-2(1H)-carboxylate (3.80 g, 13.8 mmol, 1.00 equiv), N-(1H-pyrazol-4-yl)acetamide (1.90 g, 15.2 mmol, 1.10 equiv), 4-dimethylaminopyridine (0.850 g, 6.96 mmol, 0.50 equiv), N,N-diisopropylethylamine (3.60 g, 27.9 mmol, 2.00 equiv), and tetrahydrofuran (30 mL). The resulting solution was stirred overnight at 60° C. and then quenched with water (20 mL). The resulting solution was extracted with DCM (3×20 mL) and the organic layers were combined, washed with brine (2×20 mL), dried over anhydrous sodium sulfate, filtered and concentrated under reduced pressure. The residue was chromatographed on a silica gel column to provide 3.43 g (68% yield) of tert-butyl 5-(4-acetamido-1H-pyrazole-1-carbonyl)hexahydropyrrolo[3,4-c]pyrrole-2(1H)-carboxylate as a yellow oil. LCMS (ESI, m/z): 364 [M+H]+.

Step 3: Synthesis of Tert-butyl 5-(4-(N-methylacetamido)-1H-pyrazole-1-carbonyl)hexahydropyrrolo[3,4-c]pyrrole-2(1H)-carboxylate

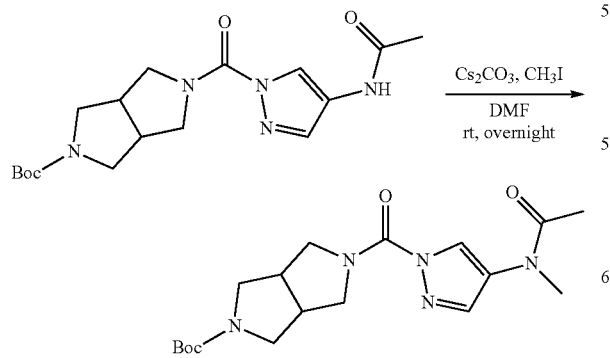

A 250-mL round-bottom flask was charged with tert-butyl 5-(4-acetamido-1H-pyrazole-1-carbonyl)hexahydropyrrolo[3,4-c]pyrrole-2(1H)-carboxylate (3.43 g, 9.44 mmol, 1.00 equiv) and DMF (20 mL). Cesium carbonate (6.16 g, 18.9 mmol, 2.00 equiv) was added at 0° C. The mixture was stirred for 30 min at room temperature. Iodomethane (2.40 g, 16.9 mmol, 1.50 equiv) was added. The resulting solution was stirred overnight at room temperature and then quenched with water (20 mL). The resulting solution was extracted with DCM (3×20 mL) and the organic layers were combined, washed with brine (2×20 mL), dried over anhydrous sodium sulfate, filtered and concentrated under reduced pressure. The residue was chromatographed on a silica gel column to provide 2.84 g (80% yield) of tert-butyl 5-(4-(N-methylacetamido)-1H-pyrazole-1-carbonyl)hexahydropyrrolo[3,4-c]pyrrole-2(1H)-carboxylate as a yellow oil. LCMS (ESI, m/z): 378 [M+H]+.

Step 4: Synthesis of N-methyl-N-(1-(octahydropyrrolo[3,4-c]pyrrole-2-carbonyl)-1H-pyrazol-4-yl)acetamide

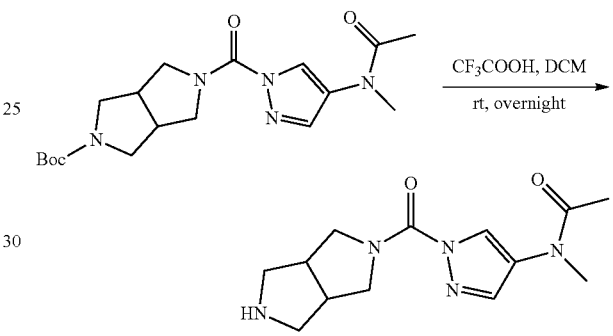

A 250-mL round-bottom flask was charged with tert-butyl 5-(4-(N-methylacetamido)-1H-pyrazole-1-carbonyl)hexahydropyrrolo[3,4-c]pyrrole-2(1H)-carboxylate (2.84 g, 7.52 mmol, 1.00 equiv), TFA (10 mL), and DCM (20 mL). The resulting solution was stirred overnight at room temperature and concentrated under reduced pressure to provide 3.80 g (crude) of N-methyl-N-(1-(octahydropyrrolo[3,4-c]pyrrole-2-carbonyl)-1H-pyrazol-4-yl)acetamide as a yellow oil. LCMS (ESI, m/z): 278 [M+H]+.

Step 5: Synthesis of N-(1-(5-(4-chlorobenzyl)octahydropyrrolo[3,4-c]pyrrole-2-carbonyl)-1H-pyrazol-4-yl)-N-methylacetamide

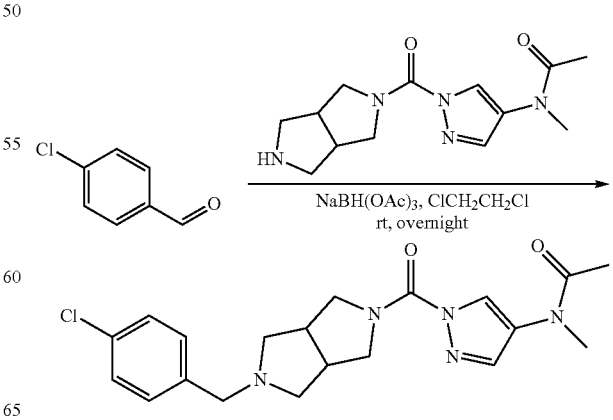

PH-ABI-LIB108-021-0

A 100-mL round-bottom flask was charged with 4-chlorobenzaldehyde (0.334 g, 2.38 mmol, 1.10 equiv), N-methyl-N-(1-(octahydropyrrolo[3,4-c]pyrrole-2-carbonyl)-1H-pyrazol-4-yl)acetamide (0.600 g, 2.16 mmol, 1.00 equiv), and 1,2-dichloroethane (10 mL). The mixture was stirred for 1 h at room temperature. Sodium triacetoxyborohydride (1.40 g, 6.61 mmol, 3.00 equiv) was added. The resulting solution was stirred overnight at room temperature and then quenched with water (10 mL). The resulting mixture was extracted with DCM (3×15 mL) and the organic layers were combined, washed with brine (1×30 mL), dried over anhydrous sodium sulfate, filtered and concentrated under reduced pressure. The crude product (980 mg) was purified by preparative HPLC. Purification resulted in 0.2536 g (29% yield) of N-(1-(5-(4-chlorobenzyl)octahydropyrrolo[3,4-c]pyrrole-2-carbonyl)-1H-pyrazol-4-yl)-N-methylacetamide as a white semi-solid. $^1$H NMR (300 MHz, Chloroform-d) δ 8.29 (s, 0.3H), 8.19 (s, 0.7H), 8.04 (s, 0.3H), 7.55 (s, 0.7H), 7.22-7.26 (m, 4H), 3.78-4.07 (m, 4H), 3.56 (s, 2H), 3.36 (s, 1H), 3.22 (s, 2H), 2.89 (br, 2H), 2.50-2.62 (m, 4H), 2.28 (s, 1H), 2.00 (s, 2H). LCMS (ESI, m/z): 402 [M+H]$^+$.

Example 12: N-(1-(5-(3,4-dichlorobenzyl)octahydropyrrolo[3,4-c]pyrrole-2-carbonyl)-1H-pyrazol-4-yl)-N-methylacetamide

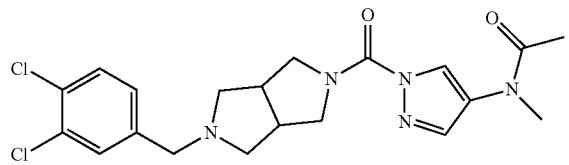 [SMILES: CC(=O)N(C)c1cnn(C(=O)N2CC3CN(Cc4ccc(Cl)c(Cl)c4)CC3C2)c1]

The title compound was synthesized as described in Example 1 using tert-butyl hexahydropyrrolo[3,4-c]pyrrole-2(1H)-carboxylate in Step 2. Purification resulted in 115.7 mg of N-(1-(5-(3,4-dichlorobenzyl)octahydropyrrolo[3,4-c]pyrrole-2-carbonyl)-1H-pyrazol-4-yl)-N-methylacetamide as a yellow oil. $^1$H NMR (300 MHz, Chloroform-d) δ 8.29 (s, 0.3H), 8.20 (s, 0.7H), 8.04 (s, 0.3H), 7.55 (s, 0.7H), 7.36-7.41 (m, 2H), 7.16 (d, J=9.0 Hz, 1H), 3.83-4.30 (m, 4H), 3.56 (br, 2H), 3.36 (s, 1H), 3.22 (s, 2H), 2.92 (br, 2H), 2.52-2.59 (m, 4H), 2.28 (s, 1H), 2.00 (s, 2H). LCMS (ESI, m/z): 436 [M+H]$^+$.

Example 13: N-methyl-N-(1-(5-(4-(pyrrolidin-1-yl)benzyl)octahydropyrrolo[3,4-c]pyrrole-2-carbonyl)-1H-pyrazol-4-yl)acetamide

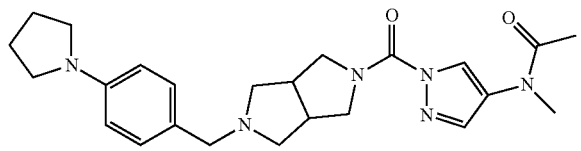 [SMILES: CC(=O)N(C)c1cnn(C(=O)N2CC3CN(Cc4ccc(N5CCCC5)cc4)CC3C2)c1]

The title compound was synthesized as described in Example 1 using 4-(pyrrolidin-1-yl)benzaldehyde and tert-butyl hexahydropyrrolo[3,4-c]pyrrole-2(1H)-carboxylate in Step 2. Purification resulted in 24.4 mg of N-methyl-N-(1-(5-(4-(pyrrolidin-1-yl)benzyl)octahydropyrrolo[3,4-c]pyrrole-2-carbonyl)-1H-pyrazol-4-yl)acetamide as a yellow oil. $^1$H NMR (300 MHz, Chloroform-d) δ 8.28 (s, 0.3H), 8.18 (s, 0.7H), 8.03 (s, 0.3H), 7.54 (s, 0.7H), 7.15 (d, J=6.0 Hz, 2H), 6.50 (d, J=9.0 Hz, 2H), 3.42-4.40 (m, 6H), 3.38 (s, 1H), 3.27 (t, J=6.0 Hz, 4H), 3.21 (s, 2H), 2.65-3.10 (m, 4H), 2.45-2.60 (m, 2H), 2.28 (s, 1H), 1.99-2.10 (m, 6H). LCMS (ESI, m/z): 437 [M+H]$^+$.

Example 14: N-methyl-N-(1-(5-(4-(trifluoromethyl)benzyl)octahydropyrrolo[3,4-c]pyrrole-2-carbonyl)-1H-pyrazol-4-yl)acetamide

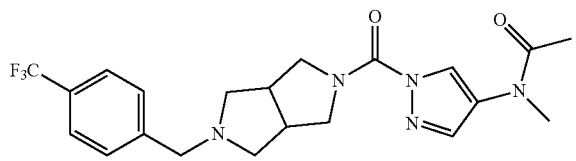 [SMILES: CC(=O)N(C)c1cnn(C(=O)N2CC3CN(Cc4ccc(C(F)(F)F)cc4)CC3C2)c1]

The title compound was synthesized as described in Example 1 using 4-(trifluoromethyl)benzaldehyde and tert-butyl hexahydropyrrolo[3,4-c]pyrrole-2(1H)-carboxylate in Step 2. Purification resulted in 56.0 mg of N-methyl-N-(1-(5-(4-(trifluoromethyl)benzyl)octahydropyrrolo[3,4-c]pyrrole-2-carbonyl)-1H-pyrazol-4-yl)acetamide as a yellow oil. $^1$H NMR (300 MHz, Chloroform-d) δ 8.30 (s, 0.3H), 8.19 (s, 0.7H), 8.04 (s, 0.3H), 7.57 (s, 0.7H), 7.56 (d, J=9.0 Hz, 2H), 7.42 (d, J=9.0 Hz, 2H), 3.61-4.40 (m, 6H), 3.36 (s, 1H), 3.22 (s, 2H), 2.91 (br, 2H), 2.60 (br, 4H), 2.29 (s, 1H), 2.00 (s, 2H). LCMS (ESI, m/z): 436 [M+H]$^+$.

Example 15: N-methyl-N-(1-(5-(4-morpholinobenzyl)octahydropyrrolo[3,4-c]pyrrole-2-carbonyl)-1H-pyrazol-4-yl)acetamide

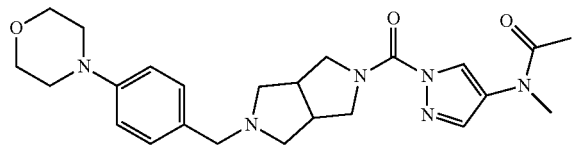 [SMILES: CC(=O)N(C)c1cnn(C(=O)N2CC3CN(Cc4ccc(N5CCOCC5)cc4)CC3C2)c1]

The title compound was synthesized as described in Example 1 using morpholinobenzaldehyde and tert-butyl hexahydropyrrolo[3,4-c]pyrrole-2(1H)-carboxylate in Step 2. Purification resulted in 77.5 mg of N-methyl-N-(1-(5-(4-morpholinobenzyl)octahydropyrrolo[3,4-c]pyrrole-2-carbonyl)-1H-pyrazol-4-yl)acetamide as a yellow solid. $^1$H NMR (300 MHz, Chloroform-d) δ 8.30 (s, 0.3H), 8.19 (s, 0.7H), 8.04 (s, 0.3H), 7.22 (d, J=8.4 Hz, 2H), 6.86 (d, J=8.7 Hz, 2H), 4.04 (br, 3H), 3.87 (t, J=5.1 Hz, 4H), 3.57 (br, 2H), 3.37 (s, 1H), 3.22 (s, 2H), 3.15 (t, J=4.8 Hz, 4H), 2.92 (br, 2H), 2.67 (br, 2H), 2.53-2.56 (m, 2H), 2.29 (s, 1H), 2.00 (s, 2H). LCMS (ESI, m/z): 475 [M+Na]$^+$.

Example 16: N-(1-(5-(2-chloro-4-morpholinobenzyl)octahydropyrrolo[3,4-c]pyrrole-2-carbonyl)-1H-pyrazol-4-yl)-N-methylacetamide

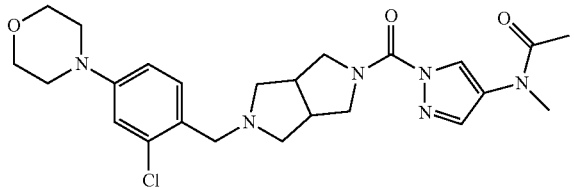 [SMILES: CC(=O)N(C)c1cnn(C(=O)N2CC3CN(Cc4ccc(N5CCOCC5)cc4Cl)CC3C2)c1]

The title compound was synthesized as described in Example 1 using 2-chloro-4-morpholinobenzaldehyde and tert-butyl hexahydropyrrolo[3,4-c]pyrrole-2(1H)-carboxylate in Step 2. Purification resulted in 83.9 mg of N-(1-(5-(2-chloro-4-morpholinobenzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.29 (s, 0.3H), 8.19 (s, 0.7H), 8.04 (s, 0.3H), 7.55 (s, 0.7H), 7.31 (s, 1H), 6.86 (s, 1H), 6.78 (d, J=8.7 Hz, 1H), 4.10 (br, 2H), 3.68-3.87 (m, 8H), 3.36 (s, 1H), 3.22 (s, 2H), 3.14 (t, J=4.8 Hz, 4H), 2.91 (br, 2H), 2.64 (br, 4H), 2.29 (s, 1H), 2.00 (s, 2H). LCMS (ESI, m/z): 487 [M+H]$^+$.

Example 17: N-methyl-N-(1-(5-(2-methyl-4-morpholinobenzyl)octahydropyrrolo[3,4-c]pyrrole-2-carbonyl)-1H-pyrazol-4-yl)acetamide

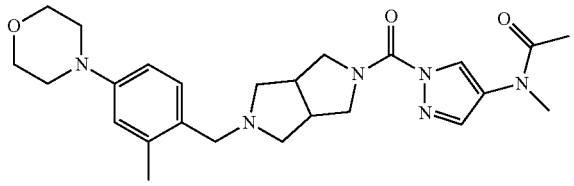 [SMILES: CC(=O)N(C)c1cnn(C(=O)N2CC3CN(Cc4ccc(N5CCOCC5)cc4C)CC3C2)c1]

The title compound was synthesized as described in Example 1 using 2-methyl-4-morpholinobenzaldehyde and tert-butyl hexahydropyrrolo[3,4-c]pyrrole-2(1H)-carboxylate in Step 2. Purification resulted in 70.9 mg of N-methyl-N-(1-(5-(2-methyl-4-morpholinobenzyl)octahydropyrrolo [3,4-c]pyrrole-2-carbonyl)-1H-pyrazol-4-yl)acetamide as an off-white solid. $^1$H NMR (300 MHz, Chloroform-d) δ 8.28 (s, 0.3H), 8.18 (s, 0.7H), 8.04 (s, 0.3H), 7.54 (s, 0.7H), 7.12 (d, J=8.4 Hz, 1H), 6.66-6.72 (m, 2H), 4.10 (br, 2H), 3.87 (t, J=5.1 Hz, 5H), 3.74 (br, 1H), 3.52 (br, 2H), 3.36 (s, 1H), 3.22 (s, 2H), 3.14 (t, J=4.8 Hz, 4H), 2.88 (br, 2H), 2.57 (br, 4H), 2.32 (s, 3H), 2.29 (s, 1H), 2.00 (s, 2H). LCMS (ESI, m/z): 489 [M+Na]$^+$.

Example 18: N-(1-(7-(3,4-dichlorobenzyl)-2,7-diazaspiro[3.5]nonane-2-carbonyl)-1H-pyrazol-4-yl)-N-methylacetamide

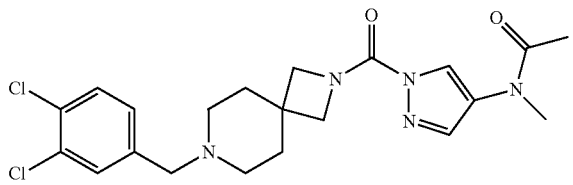 [SMILES: CC(=O)N(C)c1cnn(C(=O)N2CC3(CCN(Cc4ccc(Cl)c(Cl)c4)CC3)C2)c1]

The title compound was synthesized as described in Example 1 using tert-butyl 2,7-diazaspiro[3.5]nonane-2-carboxylate in Step 2. Purification resulted in 78.0 mg of N-(1-(7-(3,4-dichlorobenzyl)-2,7-diazaspiro[3.5]nonane-2-carbonyl)-1H-pyrazol-4-yl)-N-methylacetamide as a light yellow oil. $^1$H NMR (300 MHz, Chloroform-d) δ 8.26 (s, 0.3H), 8.17 (s, 0.7H), 8.06 (s, 0.3H), 7.54 (s, 0.7H), 7.37-7.45 (m, 2H), 7.16 (d, J=9.0 Hz, 1H), 4.35 (br, 2H), 3.90 (br, 2H), 3.43 (s, 2H), 3.35 (s, 1H), 3.20 (s, 2H), 2.38 (br, 4H), 2.28 (s, 1H), 1.98 (s, 2H), 1.84 (br, 4H). LCMS (ESI, m/z): 450 [M+H]$^+$.

Example 19: N-methyl-N-(1-(7-(4-(pyrrolidin-1-yl)benzyl)-2,7-diazaspiro[3.5]nonane-2-carbonyl)-1H-pyrazol-4-yl)acetamide

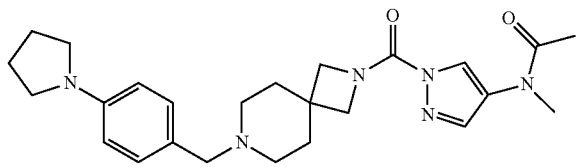 [SMILES: CC(=O)N(C)c1cnn(C(=O)N2CC3(CCN(Cc4ccc(N5CCCC5)cc4)CC3)C2)c1]

The title compound was synthesized as described in Example 1 using 4-(pyrrolidin-1-yl)benzaldehyde and tert-butyl 2,7-diazaspiro[3.5]nonane-2-carboxylate in Step 2. Purification resulted in 30.5 mg of N-methyl-N-(1-(7-(4-(pyrrolidin-1-yl)benzyl)-2,7-diazaspiro[3.5]nonane-2-carbonyl)-1H-pyrazol-4-yl)acetamide as a brown oil. $^1$H NMR (300 MHz, Chloroform-d) δ 8.25 (s, 0.3H), 8.16 (s, 0.7H), 8.05 (s, 0.3H), 7.53 (s, 0.7H), 7.14 (d, J=9.0 Hz, 2H), 6.52 (d, J=9.0 Hz, 2H), 4.33 (br, 2H), 3.88 (br, 2H), 3.47 (br, 2H), 3.34 (s, 1H), 3.28 (t, J=6.0 Hz, 4H), 3.20 (s, 2H), 2.43 (br, 4H), 2.28 (s, 1H), 1.99-2.10 (m, 4H), 1.97 (s, 2H), 1.86 (br, 4H). LCMS (ESI, m/z): 451 [M+H]$^+$.

Example 20: N-methyl-N-(1-(7-(4-(trifluoromethyl)benzyl)-2,7-diazaspiro[3.5]nonane-2-carbonyl)-1H-pyrazol-4-yl)acetamide

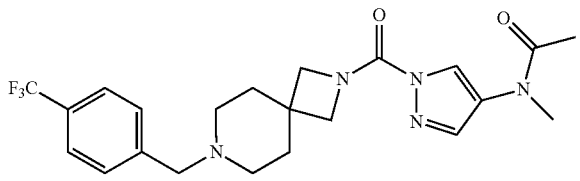 [SMILES: CC(=O)N(C)c1cnn(C(=O)N2CC3(CCN(Cc4ccc(C(F)(F)F)cc4)CC3)C2)c1]

The title compound was synthesized as described in Example 1 using 4-(trifluoromethyl)benzaldehyde and tert-butyl 2,7-diazaspiro[3.5]nonane-2-carboxylate in Step 2. Purification resulted in 62.0 mg of N-methyl-N-(1-(7-(4-(trifluoromethyl)benzyl)-2,7-diazaspiro[3.5]nonane-2-carbonyl)-1H-pyrazol-4-yl)acetamide as a white solid. $^1$H NMR (300 MHz, Chloroform-d) δ 8.26 (s, 0.3H), 8.17 (s, 0.7H), 8.06 (s, 0.3H), 7.59 (s, 0.7H), 7.55 (d, J=6.0 Hz, 2H), 7.45 (d, J=6.0 Hz, 2H), 4.36 (br, 2H), 3.91 (br, 2H), 3.54 (br, 2H), 3.35 (s, 1H), 3.20 (s, 2H), 2.41 (br, 4H), 2.28 (s, 1H), 1.98 (s, 2H), 1.85 (br, 4H). LCMS (ESI, m/z): 450 [M+H]$^+$.

Example 21: N-methyl-N-(1-(7-(4-morpholinobenzyl)-2,7-diazaspiro[3.5]nonane-2-carbonyl)-1H-pyrazol-4-yl)acetamide

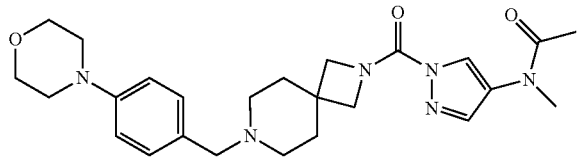 [SMILES: CC(=O)N(C)c1cnn(C(=O)N2CC3(CCN(Cc4ccc(N5CCOCC5)cc4)CC3)C2)c1]

The title compound was synthesized as described in Example 1 using 4-morpholinobenzaldehyde and tert-butyl 2,7-diazaspiro[3.5]nonane-2-carboxylate in Step 2. Purification resulted in 51.1 mg of N-methyl-N-(1-(7-(4-morpholinobenzyl)-2,7-diazaspiro[3.5]nonane-2-carbonyl)-1H-pyrazol-4-yl)acetamide as a white solid. $^1$H NMR (300 MHz, Chloroform-d) δ 8.25 (s, 0.3H), 8.17 (s, 0.7H), 8.05 (s, 0.3H), 7.53 (s, 0.7H), 7.21 (d, J=8.7 Hz, 2H), 6.87 (d, J=8.4 Hz, 2H), 4.34 (br, 2H), 3.86 (t, J=4.8 Hz, 6H), 3.46 (br, 2H), 3.25 (s, 1H), 3.20 (s, 2H), 3.16 (t, J=4.8 Hz, 4H), 2.59 (br, 4H), 2.41 (s, 1H), 1.97 (s, 2H), 1.85 (br, 4H). LCMS (ESI, m/z): 489 [M+Na]$^+$.

Example 22: N-(1-(7-(2-chloro-4-morpholinobenzyl)-2,7-diazaspiro[3.5]nonane-2-carbonyl)-1H-pyrazol-4-yl)-N-methylacetamide

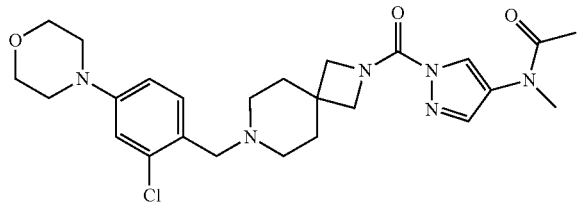 [SMILES: CC(=O)N(C)c1cnn(C(=O)N2CC3(CCN(Cc4ccc(N5CCOCC5)cc4Cl)CC3)C2)c1]

The title compound was synthesized as described in Example 1 using 2-chloro-4-morpholinobenzaldehyde and tert-butyl 2,7-diazaspiro[3.5]nonane-2-carboxylate in Step 2. Purification resulted in 98.6 mg of N-(1-(7-(2-chloro-4-morpholinobenzyl)-2,7-diazaspiro[3.5]nonane-2-carbonyl)-1H-pyrazol-4-yl)-N-methylacetamide as a white solid. $^1$H NMR (300 MHz, Chloroform-d) δ 8.26 (s, 0.3H), 8.17 (s, 0.7H), 8.05 (s, 0.3H), 7.54 (s, 0.7H), 7.33 (br, 1H), 6.87 (s, 1H), 6.77-6.81 (m, 1H), 4.53 (br, 2H), 3.83-3.99 (m, 6H), 3.56 (br, 2H), 3.35 (s, 1H), 3.14-3.20 (m, 6H), 2.47 (br, 4H), 2.28 (s, 1H), 1.98 (s, 2H), 1.86 (br, 4H). LCMS (ESI, m/z): 501 [M+H]$^+$.

Example 23: N-methyl-N-(1-(7-(2-methyl-4-morpholinobenzyl)-2,7-diazaspiro[3.5]nonane-2-carbonyl)-1H-pyrazol-4-yl)acetamide

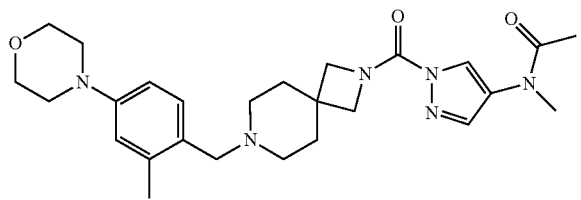 [SMILES: CC(=O)N(C)c1cnn(C(=O)N2CC3(CCN(Cc4ccc(N5CCOCC5)cc4C)CC3)C2)c1]

The title compound was synthesized as described in Example 1 using 2-methyl-4-morpholinobenzaldehyde and tert-butyl 2,7-diazaspiro[3.5]nonane-2-carboxylate in Step 2. Purification resulted in 84.3 mg of N-methyl-N-(1-(7-(2-methyl-4-morpholinobenzyl)-2,7-diazaspiro[3.5]nonane-2-carbonyl)-1H-pyrazol-4-yl)acetamide as a light yellow oil. $^1$H NMR (300 MHz, Chloroform-d) δ 8.26 (s, 0.3H), 8.17 (s, 0.7H), 8.06 (s, 0.3H), 7.54 (s, 0.7H), 7.11-7.14 (m, 1H), 6.67-6.72 (m, 2H), 4.34 (br, 2H), 3.84-3.89 (m, 6H), 3.36-3.39 (m, 3H), 3.20 (s, 2H), 3.14 (t, J=4.8 Hz, 4H), 2.33-2.41 (m, 7H), 2.28 (s, 1H), 1.98 (s, 2H), 1.80 (br, 4H). LCMS (ESI, m/z): 481 [M+H]$^+$.

Example 24: N-(1-(2-(3,4-dichlorobenzyl)-2,7-diazaspiro[3.5]nonane-7-carbonyl)-1H-pyrazol-4-yl)-N-methylacetamide

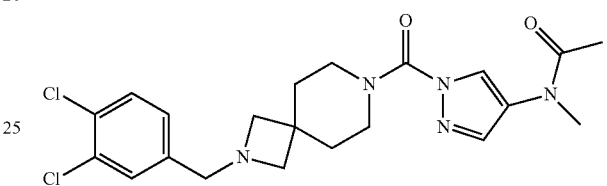

The title compound was synthesized as described in Example 1 using tert-butyl 2,7-diazaspiro[3.5]nonane-7-carboxylate in Step 2. Purification resulted in 68.2 mg of N-(1-(2-(3,4-dichlorobenzyl)-2,7-diazaspiro[3.5]nonane-7-carbonyl)-1H-pyrazol-4-yl)-N-methylacetamide as a yellow solid. $^1$H NMR (300 MHz, Chloroform-d) δ 8.18 (s, 0.3H), 8.04 (s, 0.7H), 7.98 (s, 0.3H), 7.55 (s, 0.7H), 7.32-7.45 (m, 2H), 7.14 (d, J=9.0 Hz, 1H), 3.73 (br, 4H), 3.61 (s, 2H), 3.36 (s, 1H), 3.21 (s, 2H), 3.10 (s, 4H), 2.28 (s, 1H), 2.00 (s, 2H), 1.85-1.95 (m, 4H). LCMS (ESI, m/z): 450 [M+H]$^+$.

Example 25: N-methyl-N-(1-(2-(4-(pyrrolidin-1-yl)benzyl)-2,7-diazaspiro[3.5]nonane-7-carbonyl)-1H-pyrazol-4-yl)acetamide

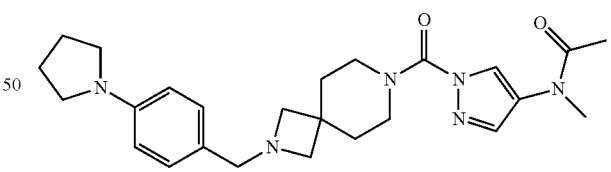

The title compound was synthesized as described in Example 1 using 4-(pyrrolidin-1-yl)benzaldehyde and tert-butyl 2,7-diazaspiro[3.5]nonane-7-carboxylate in Step 2. Purification resulted in 77.8 mg of N-methyl-N-(1-(2-(4-(pyrrolidin-1-yl)benzyl)-2,7-diazaspiro[3.5]nonane-7-carbonyl)-1H-pyrazol-4-yl)acetamide as an off-white solid. $^1$H NMR (300 MHz, Chloroform-d) δ 8.17 (s, 0.3H), 8.02 (s, 0.7H), 7.97 (s, 0.3H), 7.54 (s, 0.7H), 7.14 (d, J=9.0 Hz, 2H), 6.52 (d, J=9.0 Hz, 2H), 3.70 (br, 4H), 3.55 (s, 2H), 3.35 (s, 1H), 3.27 (t, J=6.0 Hz, 4H), 3.21 (s, 2H), 3.06 (s, 4H), 2.27 (s, 1H), 1.95-2.05 (m, 6H), 1.81-1.91 (m, 4H). LCMS (ESI, m/z): 473 [M+Na]$^+$.

Example 26: N-methyl-N-(1-(2-(4-(trifluoromethyl)benzyl)-2,7-diazaspiro[3.5]nonane-7-carbonyl)-1H-pyrazol-4-yl)acetamide

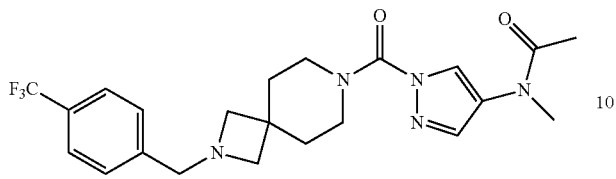

The title compound was synthesized as described in Example 1 using 4-(trifluoromethyl)benzaldehyde and tert-butyl 2,7-diazaspiro[3.5]nonane-7-carboxylate in Step 2. Purification resulted in 60.5 mg of N-methyl-N-(1-(2-(4-(trifluoromethyl)benzyl)-2,7-diazaspiro[3.5]nonane-7-carbonyl)-1H-pyrazol-4-yl)acetamide as a yellow oil. $^1$H NMR (300 MHz, Chloroform-d) δ 8.18 (s, 0.3H), 8.04 (s, 0.7H), 7.98 (s, 0.3H), 7.59 (s, 0.7H), 7.50-7.58 (m, 2H), 7.42 (d, J=9.0 Hz, 2H), 3.72 (br, 6H), 3.35 (s, 1H), 3.21 (s, 2H), 3.12 (s, 4H), 2.28 (s, 1H), 1.99 (s, 2H), 1.85-1.95 (m, 4H). LCMS (ESI, m/z): 450 [M+H]$^+$.

Example 27: N-methyl-N-(1-(2-(4-morpholinobenzyl)-2,7-diazaspiro[3.5]nonane-7-carbonyl)-1H-pyrazol-4-yl)acetamide

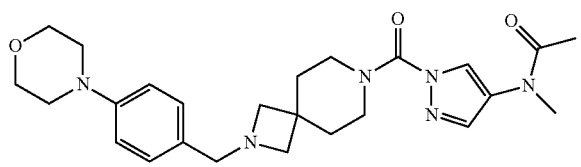 [SMILES: CC(=O)N(C)c1cnn(C(=O)N2CCC3(CC2)CN(Cc2ccc(N4CCOCC4)cc2)C3)c1]

Step 1: Synthesis of Tert-butyl 7-(4-acetamido-1H-pyrazole-1-carbonyl)-2,7-diazaspiro[3.5]nonane-2-carboxylate

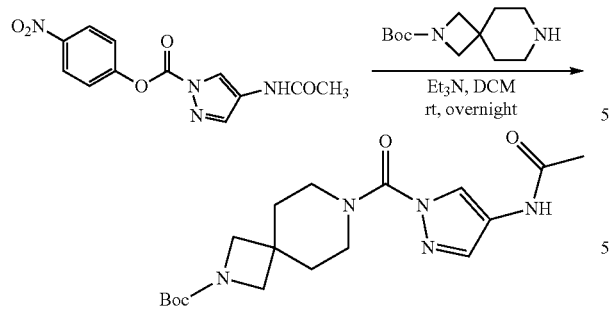

A 100-mL round-bottom flask was charged with tert-butyl 2,7-diazaspiro[3.5]nonane-2-carboxylate (500 mg, 2.21 mmol, 1.00 equiv), 4-nitrophenyl 4-acetamido-1H-pyrazole-1-carboxylate (956 mg, 3.29 mmol, 1.50 equiv), DCM (20 mL), and triethylamine (670 mg, 6.62 mmol, 3.00 equiv). The resulting solution was stirred overnight at room temperature and quenched with water (10 mL). The mixture was extracted with DCM (3×20 mL) and the organic layers were combined, washed with brine (15 mL), dried over anhydrous sodium sulfate, filtered and concentrated under reduced pressure. The residue was chromatographed on a silica gel column to provide 730 mg (84% yield) of tert-butyl 7-(4-acetamido-1H-pyrazole-1-carbonyl)-2,7-diazaspiro[3.5]nonane-2-carboxylate as a yellow solid. LCMS (ESI, m/z): 378 [M+H]$^+$.

Step 2: Synthesis of Tert-butyl 7-(4-(N-methylacetamido)-1H-pyrazole-1-carbonyl)-2,7-diazaspiro[3.5]nonane-2-carboxylate

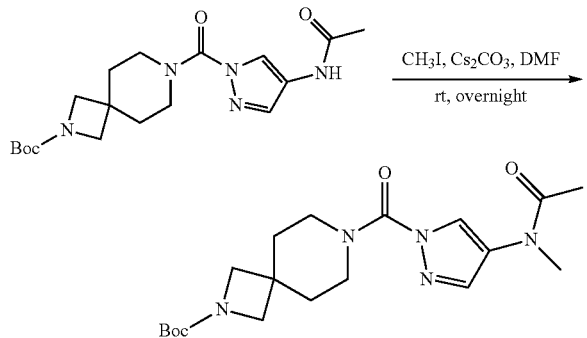

A 100-mL round-bottom flask was charged with tert-butyl 7-(4-acetamido-1H-pyrazole-1-carbonyl)-2,7-diazaspiro[3.5]nonane-2-carboxylate (1.09 g, 2.89 mmol, 1.00 equiv), DMF (20 mL), and cesium carbonate (2.82 g, 8.66 mmol, 3.00 equiv). The resulting solution was stirred for 1 h at 0° C. Iodomethane (491 mg, 3.46 mmol, 1.20 equiv) was added dropwise. The resulting solution was stirred overnight room temperature and quenched with water (20 mL). The mixture was extracted with EtOAc (3×40 mL) and the organic layers were combined, washed with brine (30 mL), dried over anhydrous sodium sulfate, filtered and concentrated under reduced pressure. The residue was chromatographed on a silica gel column to provide 607 mg (54% yield) of tert-butyl 7-(4-(N-methylacetamido)-1H-pyrazole-1-carbonyl)-2,7-diazaspiro[3.5]nonane-2-carboxylate as a yellow solid. LCMS (ESI, m/z): 392 [M+H]$^+$.

Step 3: Synthesis of N-(1-(2,7-diazaspiro[3.5]nonane-7-carbonyl)-1H-pyrazol-4-yl)-N-methylacetamide

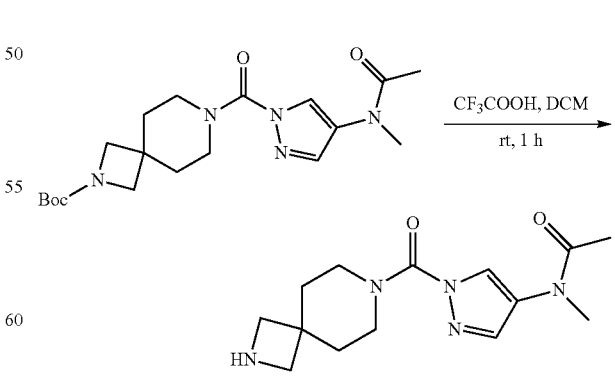

A 100-mL round-bottom flask was charged with tert-butyl 7-(4-(N-methylacetamido)-1H-pyrazole-1-carbonyl)-2,7-diazaspiro[3.5]nonane-2-carboxylate (607 mg, 1.55 mmol, 1.00 equiv), DCM (20 mL), and TFA (5 mL). The resulting solution was stirred for 1 h at room temperature and concentrated under reduced pressure. The pH value of the solution was adjusted to 9 with NaOH solution (1M). The mixture was extracted with DCM (3×20 mL) and the organic layers were combined, washed with brine (15 mL), dried over anhydrous sodium sulfate, filtered and concentrated under reduced pressure to yield 446 mg (99% yield) of N-(1-(2,7-diazaspiro[3.5]nonane-7-carbonyl)-1H-pyrazol-4-yl)-N-methylacetamide as a yellow oil. LCMS (ESI, m/z): 292 [M+H]⁺.

Step 4: Synthesis of N-methyl-N-(1-(2-(4-morpholinobenzyl)-2,7-diazaspiro[3.5]nonane-7-carbonyl)-1H-pyrazol-4-yl)acetamide

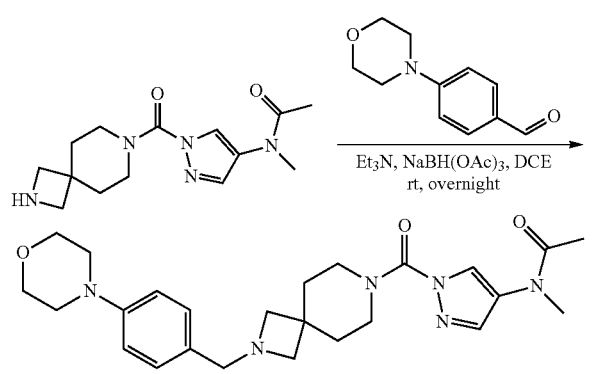

A 40 mL round-bottom flask was charged with 4-(morpholin-4-yl)benzaldehyde (92.3 mg, 0.483 mmol, 1.00 equiv), N-(1-(2,7-diazaspiro[3.5]nonane-7-carbonyl)-1H-pyrazol-4-yl)-N-methylacetamide (148 mg, 0.483 mmol, 1.00 equiv), 1,2-dichloroethane (10 mL), and triethylamine (146 mg, 1.44 mmol, 2.99 equiv). The resulting solution was stirred for 1 h at room temperature. Sodium triacetoxyborohydride (307 mg, 3.00 equiv) was added. The resulting solution was stirred overnight at room temperature and quenched with water (10 mL). The mixture was extracted with DCM (3×20 mL) and the organic layers were combined, washed with brine (15 mL), dried over anhydrous sodium sulfate, filtered and concentrated under reduced pressure. The crude product (300 mg) was purified by preparative HPLC. Purification resulted in 135.5 mg (60% yield) of N-methyl-N-(1-(2-(4-morpholinobenzyl)-2,7-diazaspiro[3.5]nonane-7-carbonyl)-1H-pyrazol-4-yl)acetamide as a white solid. ¹H NMR (300 MHz, Chloroform-d) δ 8.17 (s, 0.3H), 8.03 (s, 0.7H), 7.98 (s, 0.3H), 7.54 (s, 0.7H), 7.20 (d, J=8.7 Hz, 2H), 6.87 (d, J=8.4 Hz, 2H), 3.86 (t, J=4.8 Hz, 4H), 3.71 (br, 4H), 3.60 (s, 2H), 3.35 (s, 1H), 3.21 (s, 2H), 3.14 (t, J=4.8 Hz, 4H), 3.09 (s, 4H), 2.28 (s, 1H), 1.99 (s, 2H), 1.87-1.91 (m, 4H). LCMS (ESI, m/z): 467 [M+H]⁺.

Example 28: N-(1-(2-(2-chloro-4-morpholinobenzyl)-2,7-diazaspiro[3.5]nonane-7-carbonyl)-1H-pyrazol-4-yl)-N-methylacetamide

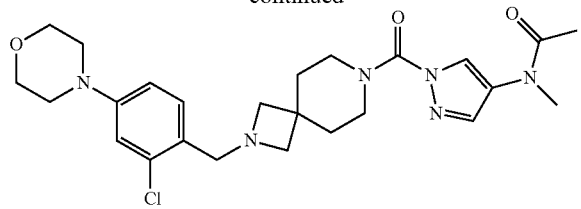

The title compound was synthesized as described in Example 27, Step 4 using 2-chloro-4-morpholinobenzaldehyde as the starting material. Purification resulted in 148.6 mg of N-(1-(2-(2-chloro-4-morpholinobenzyl)-2,7-diazaspiro[3.5]nonane-7-carbonyl)-1H-pyrazol-4-yl)-N-methylacetamide as a white solid. ¹H NMR (300 MHz, Chloroform-d) δ 8.18 (s, 0.3H), 8.03 (s, 0.7H), 7.98 (s, 0.3H), 7.55 (s, 0.7H), 7.27-7.29 (m, 1H), 6.88 (s, 1H), 6.77-6.81 (m, 1H), 3.84 (t, J=4.8 Hz, 4H), 3.73 (br, 6H), 3.36 (s, 1H), 3.21 (s, 2H), 3.12-3.17 (m, 8H), 2.28 (s, 1H), 2.01 (s, 2H), 1.90-1.93 (m, 4H). LCMS (ESI, m/z): 467 [M+H]⁺.

Example 29: N-methyl-N-(1-(2-(2-methyl-4-morpholinobenzyl)-2,7-diazaspiro[3.5]nonane-7-carbonyl)-1H-pyrazol-4-yl)acetamide

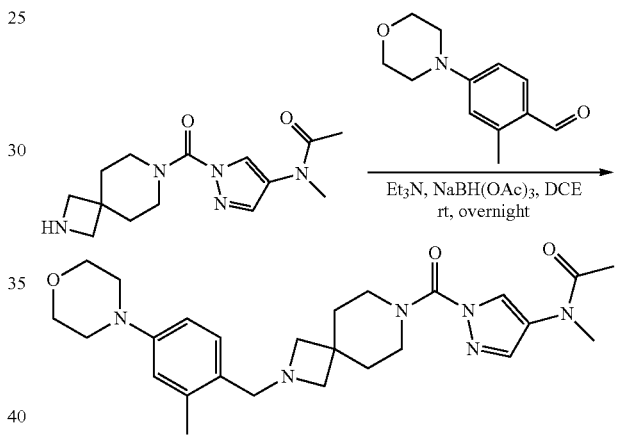

The title compound was synthesized as described in Example 27, Step 4 using 2-methyl-4-morpholinobenzaldehyde as the starting material. Purification resulted in 133.8 mg of N-methyl-N-(1-(2-(2-methyl-4-morpholinobenzyl)-2,7-diazaspiro[3.5]nonane-7-carbonyl)-1H-pyrazol-4-yl)acetamide as a white solid. ¹H NMR (300 MHz, Chloroform-d) δ 8.18 (s, 0.3H), 8.03 (s, 0.7H), 7.98 (s, 0.3H), 7.54 (s, 0.7H), 7.15 (d, J=8.1 Hz, 1H), 6.69-6.72 (m, 2H), 3.85 (t, J=4.5 Hz, 4H), 3.71 (br, 4H), 3.57 (s, 2H), 3.35 (s, 1H), 3.21 (s, 2H), 3.13 (t, J=4.8 Hz, 4H), 3.08 (br, 4H), 2.30 (s, 3H), 2.28 (s, 1H), 1.99 (s, 2H), 1.88-1.89 (m, 4H). LCMS (ESI, m/z): 481 [M+H]⁺.

Example 30: N-methyl-N-(1-(2-(3-(pyrrolidin-1-yl)benzyl)-2,7-diazaspiro[3.5]nonane-7-carbonyl)-1H-pyrazol-4-yl)acetamide

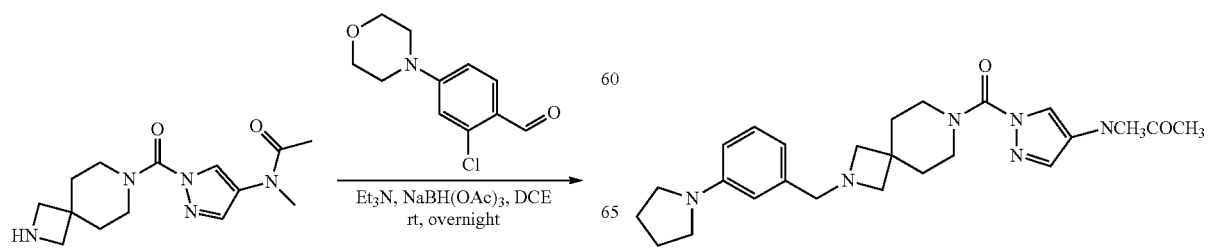

The title compound was synthesized as described in Example 27, Step 4 using 3-(pyrrolidin-1-yl)benzaldehyde as the starting material. Purification resulted in 100.3 mg of N-methyl-N-(1-(2-(3-(pyrrolidin-1-yl)benzyl)-2,7-diazaspiro[3.5]nonane-7-carbonyl)-1H-pyrazol-4-yl)acetamide as a light yellow solid. $^1$H NMR (300 MHz, Chloroform-d) δ 8.21 (s, 0.4H), 8.06 (s, 0.6H), 8.01 (s, 0.4H), 7.57 (s, 0.6H), 7.20 (t, J=7.8 Hz, 1H), 6.50-6.62 (m, 3H), 3.69-3.74 (m, 6H), 3.19-3.38 (m, 11H), 2.31 (s, 1H), 2.00-2.05 (m, 6H), 1.94 (br, 4H). LCMS (ESI, m/z): 451 [M+H]$^+$.

Example 31: N-(1-(2-(4-fluorobenzyl)-2,7-diazaspiro[3.5]nonane-7-carbonyl)-1H-pyrazol-4-yl)-N-methylacetamide

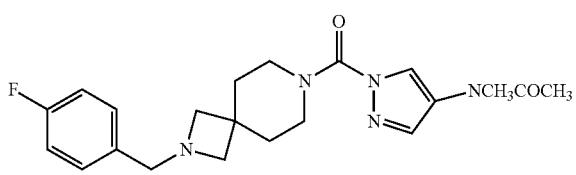

The title compound was synthesized as described in Example 27, Step 4 using 4-fluorobenzaldehyde as the starting material. Purification resulted in 131.8 mg of N-(1-(2-(4-fluorobenzyl)-2,7-diazaspiro[3.5]nonane-7-carbonyl)-1H-pyrazol-4-yl)-N-methylacetamide as a light yellow oil. $^1$H NMR (300 MHz, Chloroform-d) δ 8.17 (s, 0.4H), 8.03 (s, 0.6H), 7.98 (s, 0.4H), 7.54 (s, 0.6H), 7.22-7.25 (m, 2H), 7.00 (t, J=8.7 Hz, 2H), 3.72 (br, 4H), 3.62 (s, 2H), 3.35 (s, 1H), 3.21 (s, 2H), 3.08 (s, 4H), 2.28 (s, 1H), 1.99 (s, 2H), 1.89 (t, J=5.7 Hz, 4H). LCMS (ESI, m/z): 400 [M+H]$^+$.

Example 32: N-methyl-N-(1-(2-(4-methylbenzyl)-2,7-diazaspiro[3.5]nonane-7-carbonyl)-1H-pyrazol-4-yl)acetamide

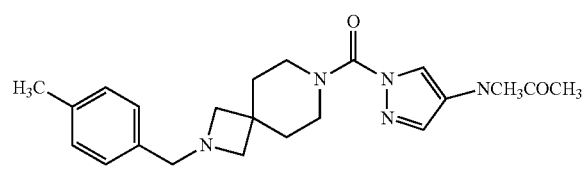

The title compound was synthesized as described in Example 27, Step 4 using 4-methylbenzaldehyde as the starting material. Purification resulted in 75.4 mg of N-methyl-N-(1-(2-(4-methylbenzyl)-2,7-diazaspiro[3.5]nonane-7-carbonyl)-1H-pyrazol-4-yl)acetamide as a light yellow semi-solid. $^1$H NMR (300 MHz, Chloroform-d) δ 8.17 (s, 0.3H), 8.02 (s, 0.7H), 7.98 (s, 0.3H), 7.54 (s, 0.7H), 7.11-7.19 (m, 4H), 3.71 (br, 4H), 3.62 (s, 2H), 3.35 (s, 1H), 3.21 (s, 2H), 3.09 (s, 4H), 2.36 (s, 3H), 2.27 (s, 1H), 1.99 (s, 2H), 1.89 (t, J=5.7 Hz, 4H). LCMS (ESI, m/z): 396 [M+H]$^+$.

Example 33: N-(1-(2-(4-methoxybenzyl)-2,7-diazaspiro[3.5]nonane-7-carbonyl)-1H-pyrazol-4-yl)-N-methylacetamide

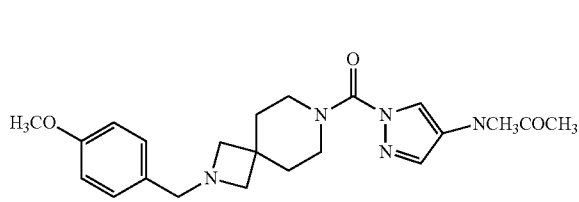

The title compound was synthesized as described in Example 27, Step 4 using 4-methoxybenzaldehyde as the starting material. Purification resulted in 153.7 mg of N-(1-(2-(4-methoxybenzyl)-2,7-diazaspiro[3.5]nonane-7-carbonyl)-1H-pyrazol-4-yl)-N-methylacetamide as a light yellow oil. $^1$H NMR (300 MHz, Chloroform-d) δ 8.17 (s, 0.3H), 8.02 (s, 0.7H), 7.98 (s, 0.3H), 7.54 (s, 0.7H), 7.20 (d, J=8.4 Hz, 2H), 6.85 (d, J=8.7 Hz, 2H), 3.80 (s, 3H), 3.71 (br, 4H), 3.59 (s, 2H), 3.35 (s, 1H), 3.21 (s, 2H), 3.07 (s, 4H), 2.27 (s, 1H), 1.99 (s, 2H), 1.88 (t, J=5.7 Hz, 4H). LCMS (ESI, m/z): 412 [M+H]$^+$.

Example 34: N-(1-(2-(3-chlorobenzyl)-2,7-diazaspiro[3.5]nonane-7-carbonyl)-1H-pyrazol-4-yl)-N-methylacetamide

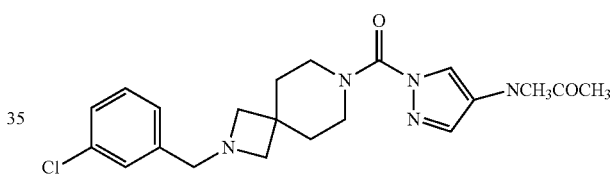

The title compound was synthesized as described in Example 27, Step 4 using 3-chlorobenzaldehyde as the starting material. Purification resulted in 55.7 mg of N-(1-(2-(3-chlorobenzyl)-2,7-diazaspiro[3.5]nonane-7-carbonyl)-1H-pyrazol-4-yl)-N-methylacetamide as a light yellow semi-solid. $^1$H NMR (300 MHz, Chloroform-d) δ 8.18 (s, 0.3H), 8.03 (s, 0.7H), 7.98 (s, 0.3H), 7.54 (s, 0.7H), 7.15-7.29 (m, 4H), 3.73 (br, 4H), 3.63 (s, 2H), 3.35 (s, 1H), 3.21 (s, 2H), 3.10 (s, 4H), 2.28 (s, 1H), 1.99 (s, 2H), 1.88 (t, J=5.7 Hz, 4H). LCMS (ESI, m/z): 416 [M+H]$^+$.

Example 35: N-(1-(2-(3-fluorobenzyl)-2,7-diazaspiro[3.5]nonane-7-carbonyl)-1H-pyrazol-4-yl)-N-methylacetamide

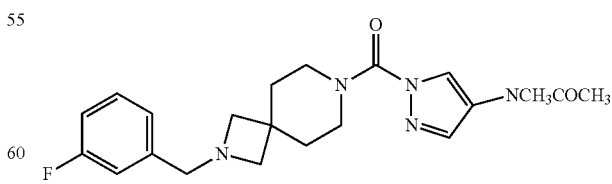

The title compound was synthesized as described in Example 27, Step 4 using 3-fluorobenzaldehyde as the starting material. Purification resulted in 79.6 mg of N-(1-(2-(3-fluorobenzyl)-2,7-diazaspiro[3.5]nonane-7-carbonyl)-1H-pyrazol-4-yl)-N-methylacetamide as in light yellow solid. ¹H NMR (300 MHz, Chloroform-d) δ 8.18 (s, 0.3H), 8.03 (s, 0.7H), 7.98 (s, 0.3H), 7.54 (s, 0.7H), 7.23-7.30 (m, 1H), 6.91-7.06 (m, 3H), 3.73 (br, 4H), 3.64 (s, 2H), 3.35 (s, 1H), 3.21 (s, 2H), 3.10 (s, 4H), 2.28 (s, 1H), 1.99 (s, 2H), 1.88 (t, J=5.7 Hz, 4H). LCMS (ESI, m/z): 400 [M+H]⁺.

Example 36: N-methyl-N-(1-(2-(3-methylbenzyl)-2,7-diazaspiro[3.5]nonane-7-carbonyl)-1H-pyrazol-4-yl)acetamide

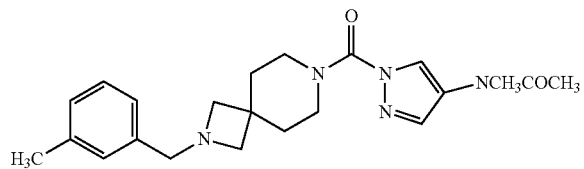

The title compound was synthesized as described in Example 27, Step 4 using 3-methylbenzaldehyde as the starting material. Purification resulted in 50.8 mg of N-methyl-N-(1-(2-(3-methylbenzyl)-2,7-diazaspiro[3.5]nonane-7-carbonyl)-1H-pyrazol-4-yl)acetamide as a light yellow semi-solid. ¹H NMR (300 MHz, Chloroform-d) δ 8.17 (s, 0.3H), 8.03 (s, 0.7H), 7.98 (s, 0.3H), 7.54 (s, 0.7H), 7.06-7.23 (m, 4H), 3.72 (br, 4H), 3.63 (s, 2H), 3.35 (s, 1H), 3.21 (s, 2H), 3.10 (s, 4H), 2.34 (s, 3H), 2.27 (s, 1H), 1.99 (s, 2H), 1.90 (t, J=5.7 Hz, 4H). LCMS (ESI, m/z): 396 [M+H]⁺.

Example 37: N-(1-(2-(3-methoxybenzyl)-2,7-diazaspiro[3.5]nonane-7-carbonyl)-1H-pyrazol-4-yl)-N-methylacetamide

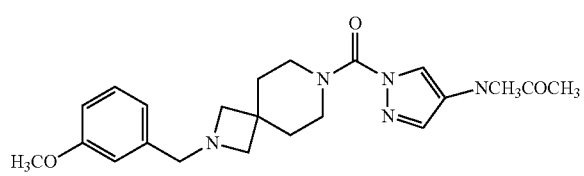

The title compound was synthesized as described in Example 27, Step 4 using 3-methoxybenzaldehyde as the starting material. Purification resulted in 142.7 mg of N-(1-(2-(3-methoxybenzyl)-2,7-diazaspiro[3.5]nonane-7-carbonyl)-1H-pyrazol-4-yl)-N-methylacetamide as a light yellow oil. ¹H NMR (300 MHz, Chloroform-d) δ 8.18 (s, 0.3H), 8.03 (s, 0.7H), 7.98 (s, 0.3H), 7.54 (s, 0.7H), 7.20-7.23 (m, 1H), 6.78-6.88 (m, 3H), 3.81 (s, 3H), 3.72 (br, 4H), 3.64 (s, 2H), 3.35 (s, 1H), 3.21 (s, 2H), 3.10 (s, 4H), 2.27 (s, 1H), 1.99 (s, 2H), 1.89 (t, J=5.7 Hz, 4H). LCMS (ESI, m/z): 412 [M+H]⁺.

Example 38: N-methyl-N-(1-(2-(3-(trifluoromethyl)benzyl)-2,7-diazaspiro[3.5]nonane-7-carbonyl)-1H-pyrazol-4-yl)acetamide

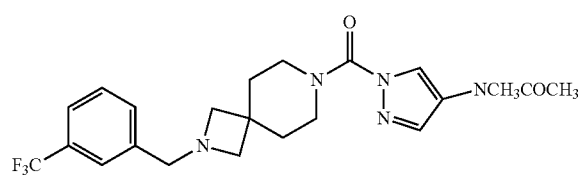

The title compound was synthesized as described in Example 27, Step 4 using 3-(trifluoromethyl)benzaldehyde as the starting material. Purification resulted in 159.5 mg of N-methyl-N-(1-(2-(3-(trifluoromethyl)benzyl)-2,7-diazaspiro[3.5]nonane-7-carbonyl)-1H-pyrazol-4-yl)acetamide as a light yellow oil. ¹H NMR (300 MHz, Chloroform-d) δ 8.21 (s, 0.4H), 8.06 (s, 0.6H), 8.01 (s, 0.4H), 7.58 (s, 0.6H), 7.45-7.55 (m, 4H), 3.76 (br, 6H), 3.38 (s, 1H), 3.24 (s, 2H), 3.16 (br, 4H), 2.31 (s, 1H), 2.02 (s, 2H), 1.95 (br, 4H). LCMS (ESI, m/z): 450 [M+H]⁺.

Example 39: N-methyl-N-(1-(2-(3-morpholinobenzyl)-2,7-diazaspiro[3.5]nonane-7-carbonyl)-1H-pyrazol-4-yl)acetamide

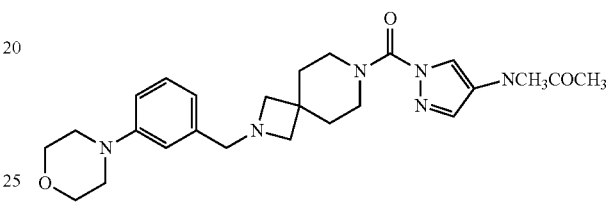

The title compound was synthesized as described in Example 27, Step 4 using 3-morpholinobenzaldehyde as the starting material. Purification resulted in 121.5 mg of N-methyl-N-(1-(2-(3-morpholinobenzyl)-2,7-diazaspiro[3.5]nonane-7-carbonyl)-1H-pyrazol-4-yl)acetamide as a white solid. ¹H NMR (300 MHz, Chloroform-d) δ 8.20 (s, 0.4H), 8.06 (s, 0.6H), 8.00 (s, 0.4H), 7.57 (s, 0.6H), 7.22-7.29 (m, 1H), 6.82-6.89 (m, 3H), 3.89 (t, J=4.8 Hz, 4H), 3.75 (br, 4H), 3.66 (s, 2H), 3.38 (s, 1H), 3.14-3.29 (m, 10H), 2.30 (s, 1H), 2.02 (s, 2H), 1.91-1.95 (m, 4H). LCMS (ESI, m/z): 467 [M+H]⁺.

Example 40: N-(1-(2-(2-chlorobenzyl)-2,7-diazaspiro[3.5]nonane-7-carbonyl)-1H-pyrazol-4-yl)-N-methylacetamide

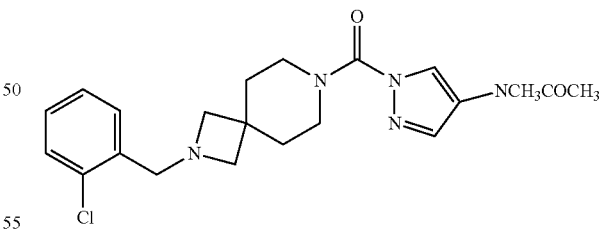

The title compound was synthesized as described in Example 27, Step 4 using 2-chlorobenzaldehyde as the starting material. Purification resulted in 186.3 mg of N-(1-(2-(2-chlorobenzyl)-2,7-diazaspiro[3.5]nonane-7-carbonyl)-1H-pyrazol-4-yl)-N-methylacetamide as a light yellow oil. ¹H NMR (300 MHz, Chloroform-d) δ 8.21 (s, 0.4H), 8.07 (s, 0.6H), 8.02 (s, 0.4H), 7.58 (s, 0.6H), 7.36-7.45 (m, 2H), 7.19-7.30 (m, 2H), 3.77-3.82 (m, 6H), 3.39 (s, 1H), 3.23 (d, J=7.8 Hz, 6H), 2.31 (s, 1H), 2.02 (s, 2H), 1.94-1.98 (m, 4H). LCMS (ESI, m/z): 416 [M+H]⁺.

Example 41: N-(1-(2-(2-fluorobenzyl)-2,7-diazaspiro[3.5]nonane-7-carbonyl)-1H-pyrazol-4-yl)-N-methylacetamide

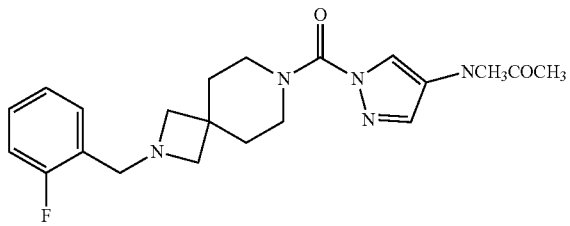

The title compound was synthesized as described in Example 27, Step 4 using 2-fluorobenzaldehyde as the starting material. Purification resulted in 180.0 mg of N-(1-(2-(2-fluorobenzyl)-2,7-diazaspiro[3.5]nonane-7-carbonyl)-1H-pyrazol-4-yl)-N-methylacetamide as a light yellow oil. $^1$H NMR (300 MHz, Chloroform-d) δ 8.21 (s, 0.4H), 8.06 (s, 0.6H), 8.01 (s, 0.4H), 7.57 (s, 0.6H), 7.34-7.39 (m, 1H), 7.23-7.29 (m, 1H), 7.02-7.16 (m, 2H), 3.74 (br, 6H), 3.38 (s, 1H), 3.24 (s, 2H), 3.17 (s, 4H), 2.31 (s, 1H), 2.02 (s, 2H), 1.91-1.94 (m, 4H). LCMS (ESI, m/z): 400 [M+H]$^+$.

Example 42: N-methyl-N-(1-(2-(2-methylbenzyl)-2,7-diazaspiro[3.5]nonane-7-carbonyl)-1H-pyrazol-4-yl)acetamide

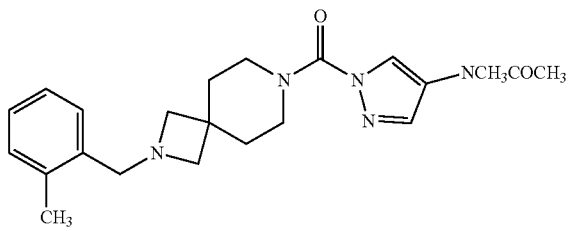

The title compound was synthesized as described in Example 27, Step 4 using 2-methylbenzaldehyde as the starting material. Purification resulted in 162.6 mg of N-methyl-N-(1-(2-(2-methylbenzyl)-2,7-diazaspiro[3.5]nonane-7-carbonyl)-1H-pyrazol-4-yl)acetamide as a light yellow oil. $^1$H NMR (300 MHz, Chloroform-d) δ 8.21 (s, 0.4H), 8.06 (s, 0.6H), 8.01 (s, 0.4H), 7.58 (s, 0.6H), 7.29 (s, 1H), 7.18-7.21 (m, 3H), 3.76 (br, 4H), 3.66 (s, 2H), 3.38 (s, 1H), 3.24 (s, 2H), 3.14 (s, 4H), 2.31-2.35 (m, 4H), 2.02 (s, 2H), 1.92-1.95 (m, 4H). LCMS (ESI, m/z): 396 [M+H]$^+$.

Example 43: N-(1-(2-(2-methoxybenzyl)-2,7-diazaspiro[3.5]nonane-7-carbonyl)-1H-pyrazol-4-yl)-N-methylacetamide

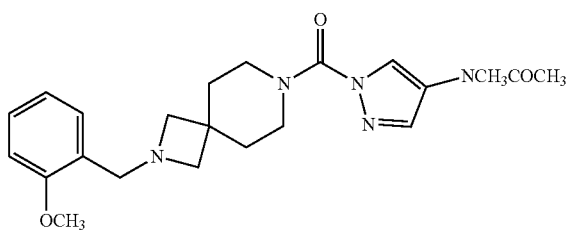

The title compound was synthesized as described in Example 27, Step 4 using 2-methoxybenzaldehyde as the starting material. Purification resulted in 90.1 mg of N-(1-(2-(2-methoxybenzyl)-2,7-diazaspiro[3.5]nonane-7-carbonyl)-1H-pyrazol-4-yl)-N-methylacetamide a light yellow solid. $^1$H NMR (300 MHz, Chloroform-d) δ 8.21 (s, 0.4H), 8.08 (s, 0.6H), 8.00 (s, 0.4H), 7.57 (s, 0.6H), 7.24-7.34 (m, 2H), 6.88-7.00 (m, 2H), 3.86 (s, 3H), 3.76 (br, 6H), 3.38 (s, 1H), 3.24 (s, 6H), 2.30 (s, 1H), 2.02 (s, 2H), 1.89-1.96 (m, 4H). LCMS (ESI, m/z): 412 [M+H]$^+$.

Example 44: N-methyl-N-(1-(2-(2-(trifluoromethyl)benzyl)-2,7-diazaspiro[3.5]nonane-7-carbonyl)-1H-pyrazol-4-yl)acetamide

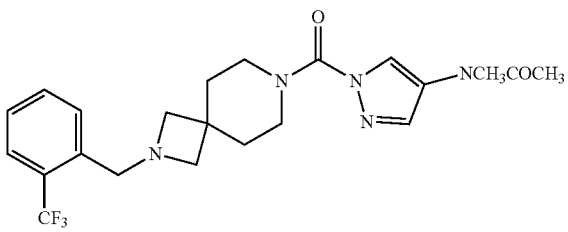

The title compound was synthesized as described in Example 27, Step 4 using 2-(trifluoromethyl)benzaldehyde as the starting material. Purification resulted in 106.4 mg of N-methyl-N-(1-(2-(2-(trifluoromethyl)benzyl)-2,7-diazaspiro[3.5]nonane-7-carbonyl)-1H-pyrazol-4-yl)acetamide as an off-white solid. $^1$H NMR (300 MHz, Chloroform-d) δ 8.21 (s, 0.4H), 8.07 (s, 0.6H), 8.02 (s, 0.4H), 7.63-7.72 (m, 2H), 7.58 (s, 0.6H), 7.33-7.55 (m, 1H), 7.29 (s, 1H), 3.88 (s, 2H), 3.77 (br, 4H), 3.39 (s, 1H), 3.24 (s, 2H), 3.18 (s, 4H), 2.31 (s, 1H), 2.02 (s, 2H), 1.92-1.98 (m, 4H). LCMS (ESI, m/z): 450 [M+H]$^+$.

Example 45: N-methyl-N-(1-(2-(2-(pyrrolidin-1-yl)benzyl)-2,7-diazaspiro[3.5]nonane-7-carbonyl)-1H-pyrazol-4-yl)acetamide

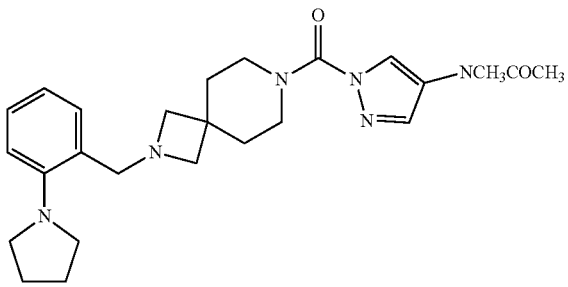

The title compound was synthesized as described in Example 27, Step 4 using 2-(pyrrolidin-1-yl)benzaldehyde as the starting material. Purification resulted in 88.5 mg of N-methyl-N-(1-(2-(2-(pyrrolidin-1-yl)benzyl)-2,7-diazaspiro[3.5]nonane-7-carbonyl)-1H-pyrazol-4-yl)acetamide as a white solid. $^1$H NMR (300 MHz, Chloroform-d) δ 8.21 (s, 0.4H), 8.06 (s, 0.6H), 8.01 (s, 0.4H), 7.57 (s, 0.6H), 7.40 (d, J=7.2 Hz, 1H), 7.21 (t, J=7.5 Hz, 1H), 6.96 (t, J=7.8 Hz, 2H), 3.78 (br, 6H), 3.38 (s, 1H), 3.24 (s, 2H), 3.17-3.21 (m, 8H), 2.31 (s, 1H), 2.04 (s, 2H), 1.94-1.98 (m, 8H). LCMS (ESI, m/z): 451 [M+H]$^+$.

Example 46: N-methyl-N-(1-(2-(2-morpholinobenzyl)-2,7-diazaspiro[3.5]nonane-7-carbonyl)-1H-pyrazol-4-yl)acetamide

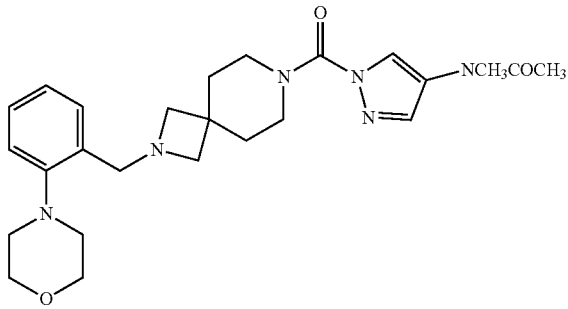

The title compound was synthesized as described in Example 27, Step 4 using 2-morpholinobenzaldehyde as the starting material. Purification resulted in 97.1 mg of N-methyl-N-(1-(2-(2-morpholinobenzyl)-2,7-diazaspiro[3.5]nonane-7-carbonyl)-1H-pyrazol-4-yl)acetamide as a white solid. $^1$H NMR (300 MHz, Chloroform-d) δ 8.21 (s, 0.4H), 8.06 (s, 0.6H), 8.01 (s, 0.4H), 7.57 (s, 0.6H), 7.43 (d, J=7.8 Hz, 1H), 7.33 (s, 1H), 7.14 (t, J=7.8 Hz, 2H), 3.88 (t, J=4.5 Hz, 4H), 3.76 (br, 6H), 3.38 (s, 1H), 3.24 (s, 6H), 2.97-2.98 (m, 4H), 2.31 (s, 1H), 2.02 (s, 2H), 1.93-1.94 (m, 4H). LCMS (ESI, m/z): 467 [M+H]$^+$.

Example 47: N-methyl-N-(1-(7-(4-(pyrrolidin-1-yl)benzyl)-2,7-diazaspiro[4.4]nonane-2-carbonyl)-1H-pyrazol-4-yl)acetamide

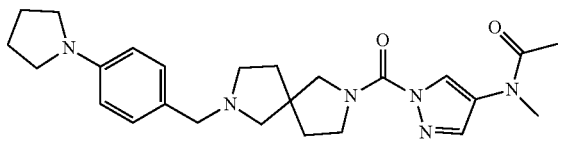 [SMILES: CC(=O)N(C)c1cnn(C(=O)N2CCC3(CCN(Cc4ccc(N5CCCC5)cc4)C3)C2)c1]

The title compound was synthesized as described in Example 27 using tert-butyl 2,7-diazaspiro[4.4]nonane-2-carboxylate in Step 1 and 4-(pyrrolidin-1-yl)benzaldehyde in Step 4. Purification resulted in 91.6 mg of N-methyl-N-(1-(7-(4-(pyrrolidin-1-yl)benzyl)-2,7-diazaspiro[4.4]nonane-2-carbonyl)-1H-pyrazol-4-yl)acetamide as a pink solid. $^1$H NMR (300 MHz, Chloroform-d) δ 8.27 (s, 0.3H), 8.17 (s, 0.7H), 8.04 (s, 0.3H), 7.54 (s, 0.7H), 7.12-7.20 (m, 2H), 6.51 (d, J=6.0 Hz, 2H), 3.82-4.10 (m, 2H), 3.50-3.80 (m, 4H), 3.35 (s, 1H), 3.27 (t, J=6.0 Hz, 4H), 3.21 (s, 2H), 2.40-2.80 (m, 4H), 2.28 (s, 1H), 2.01 (s, 2H), 1.96-2.00 (m, 4H), 1.75-1.95 (m, 4H). LCMS (ESI, m/z): 451 [M+H]$^+$.

Example 48: N-methyl-N-(1-(7-(3-morpholinobenzyl)-2,7-diazaspiro[4.4]nonane-2-carbonyl)-1H-pyrazol-4-yl)acetamide

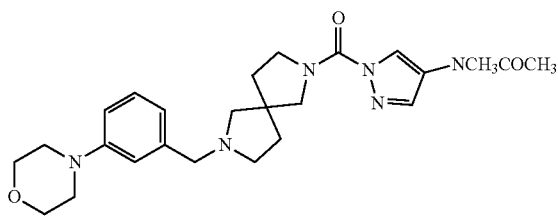

The title compound was synthesized as described in Example 27 using tert-butyl 2,7-diazaspiro[4.4]nonane-2-carboxylate in Step 1 and 3-morpholinobenzaldehyde in Step 4. Purification resulted in 98.4 mg of N-methyl-N-(1-(7-(3-morpholinobenzyl)-2,7-diazaspiro[4.4]nonane-2-carbonyl)-1H-pyrazol-4-yl)acetamide as a white solid. $^1$H NMR (300 MHz, Chloroform-d) δ 8.27 (s, 0.3H), 8.19 (s, 0.7H), 8.05 (br, 0.3H), 7.54 (s, 0.7H), 7.21 (t, J=7.8 Hz, 1H), 6.80-6.91 (m, 3H), 3.91-4.08 (m, 2H), 3.86 (br, 4H), 3.59-3.79 (m, 4H), 3.35 (s, 1H), 3.21 (s, 2H), 3.16 (br, 4H), 2.45-2.70 (m, 4H), 2.28 (s, 1H), 1.86-1.99 (m, 6H). LCMS (ESI, m/z): 467 [M+H]$^+$.

Example 49: N-(1-(7-(2,6-dichlorobenzyl)-2,7-diazaspiro[4.4]nonane-2-carbonyl)-1H-pyrazol-4-yl)-N-methylacetamide

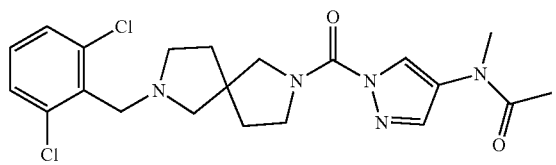 [SMILES: CC(=O)N(C)c1cnn(C(=O)N2CCC3(CCN(Cc4c(Cl)cccc4Cl)C3)C2)c1]

The title compound was synthesized as described in Example 27 using tert-butyl 2,7-diazaspiro[4.4]nonane-2-carboxylate in Step 1 and 2,6-dichlorobenzaldehyde in Step 4. Purification resulted in 100.6 mg of N-(1-(7-(2,6-dichlorobenzyl)-2,7-diazaspiro[4.4]nonane-2-carbonyl)-1H-pyrazol-4-yl)-N-methylacetamide as a white solid. $^1$H NMR (300 MHz, Chloroform-d) δ 8.28 (s, 0.3H), 8.17-8.19 (m, 0.7H), 8.04 (s, 0.3H), 7.61 (s, 0.7H), 7.28-7.31 (m, 2H), 7.14-7.21 (m, 1H), 3.81-4.04 (m, 4H), 3.44-3.71 (m, 2H), 3.35 (s, 1H), 3.21 (s, 2H), 2.49-2.97 (m, 4H), 2.28 (s, 1H), 1.68-1.99 (m, 6H). LCMS (ESI, m/z): 450 [M+H]$^+$.

Example 50: N-(1-(7-(2-chlorobenzyl)-2,7-diazaspiro[4.4]nonane-2-carbonyl)-1H-pyrazol-4-yl)-N-methylacetamide

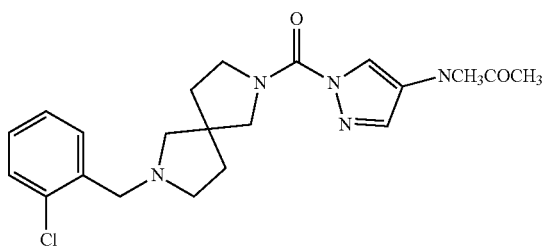

The title compound was synthesized as described in Example 27 using tert-butyl 2,7-diazaspiro[4.4]nonane-2-carboxylate in Step 1 and 2-chlorobenzaldehyde in Step 4. Purification resulted in 63.4 mg of N-(1-(7-(2-chlorobenzyl)-2,7-diazaspiro[4.4]nonane-2-carbonyl)-1H-pyrazol-4-yl)-N-methylacetamide as a light yellow semi-solid. $^1$H NMR (300 MHz, Chloroform-d) δ 8.28 (s, 0.3H), 8.19 (s, 0.7H), 8.05 (s, 0.3H), 7.54-7.56 (m, 0.7H), 7.43-7.49 (m, 1H), 7.32-7.35 (m, 1H), 7.15-7.24 (m, 2H), 3.87-4.07 (m, 2H), 3.58-3.74 (m, 4H), 3.36 (s, 1H), 3.22 (s, 2H), 2.52-2.77 (m, 4H), 2.28 (s, 1H), 1.86-1.99 (m, 6H). LCMS (ESI, m/z): 416 [M+H]$^+$.

Example 51: N-(1-(7-(2,4-dichlorobenzyl)-2,7-diazaspiro[4.4]nonane-2-carbonyl)-1H-pyrazol-4-yl)-N-methylacetamide

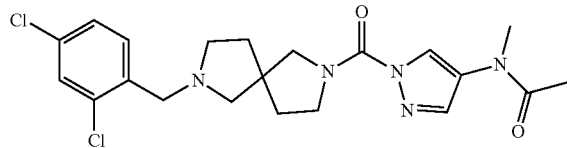 [SMILES: CC(=O)N(C)c1cnn(C(=O)N2CCC3(CCN(Cc4ccc(Cl)cc4Cl)C3)C2)c1]

The title compound was synthesized as described in Example 27 using tert-butyl 2,7-diazaspiro[4.4]nonane-2-carboxylate in Step 1 and 2,4-dichlorobenzaldehyde in Step 4. Purification resulted in 103.6 mg of N-(1-(7-(2,4-dichlorobenzyl)-2,7-diazaspiro[4.4]nonane-2-carbonyl)-1H-pyrazol-4-yl)-N-methylacetamide as a white solid. $^1$H NMR (400 MHz, Chloroform-d) δ 8.29 (s, 0.3H), 8.20 (s, 0.7H), 8.06 (s, 0.3H), 7.56-7.57 (m, 0.7H), 7.39-7.44 (m, 1H), 7.36 (s, 1H), 7.21-7.24 (m, 1H), 3.87-4.13 (m, 2H), 3.54-3.72 (m, 4H), 3.37 (s, 1H), 3.22 (s, 2H), 2.45-2.78 (m, 4H), 2.29 (s, 1H), 1.86-2.00 (m, 6H). LCMS (ESI, m/z): 450 [M+H]$^+$.

Example 52: N-(1-(7-(2-fluorobenzyl)-2,7-diazaspiro[4.4]nonane-2-carbonyl)-1H-pyrazol-4-yl)-N-methylacetamide

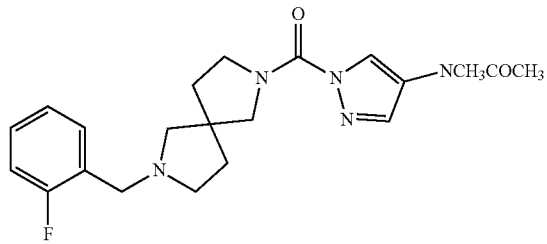

The title compound was synthesized as described in Example 27 using tert-butyl 2,7-diazaspiro[4.4]nonane-2-carboxylate in Step 1 and 2-fluorobenzaldehyde in Step 4. Purification resulted in 110.0 mg of N-(1-(7-(2-fluorobenzyl)-2,7-diazaspiro[4.4]nonane-2-carbonyl)-1H-pyrazol-4-yl)-N-methylacetamide as a light yellow oil. $^1$H NMR (300 MHz, Chloroform-d) δ 8.28 (s, 0.3H), 8.18 (s, 0.7H), 8.04 (s, 0.3H), 7.54 (s, 0.7H), 7.38-7.40 (m, 1H), 7.22-7.24 (m, 1H), 6.91-7.13 (m, 2H), 3.91-4.12 (m, 2H), 3.56-3.72 (m, 4H), 3.35 (s, 1H), 3.21 (s, 2H), 2.53-2.73 (m, 4H), 2.28 (s, 1H), 1.86-1.99 (m, 6H). LCMS (ESI, m/z): 400 [M+H]$^+$.

Example 53: N-(1-(7-(3,5-dichlorobenzyl)-2,7-diazaspiro[4.4]nonane-2-carbonyl)-1H-pyrazol-4-yl)-N-methylacetamide

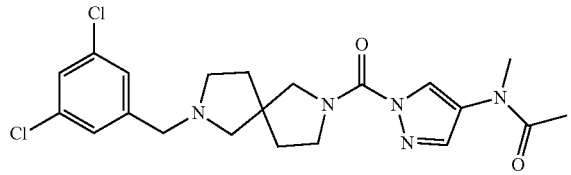 [SMILES: CC(=O)N(C)c1cnn(C(=O)N2CCC3(CCN(Cc4cc(Cl)cc(Cl)c4)C3)C2)c1]

The title compound was synthesized as described in Example 27 using tert-butyl 2,7-diazaspiro[4.4]nonane-2-carboxylate in Step 1 and 3,5-dichlorobenzaldehyde in Step 4. Purification resulted in 87.6 mg of N-(1-(7-(3,5-dichlorobenzyl)-2,7-diazaspiro[4.4]nonane-2-carbonyl)-1H-pyrazol-4-yl)-N-methylacetamide as a white solid. $^1$H NMR (400 MHz, Chloroform-d) δ 8.30 (s, 0.3H), 8.21 (s, 0.7H), 8.06 (s, 0.3H), 7.54-7.59 (m, 0.7H), 7.29 (br, 3H), 3.94-4.10 (m, 2H), 3.62-3.77 (m, 4H), 3.38 (s, 1H), 3.23 (s, 2H), 2.64-2.93 (m, 4H), 2.30 (s, 1H), 1.80-2.01 (m, 6H). LCMS (ESI, m/z): 450 [M+H]$^+$.

Example 54: N-methyl-N-(1-(7-(2-methylbenzyl)-2,7-diazaspiro[4.4]nonane-2-carbonyl)-1H-pyrazol-4-yl)acetamide

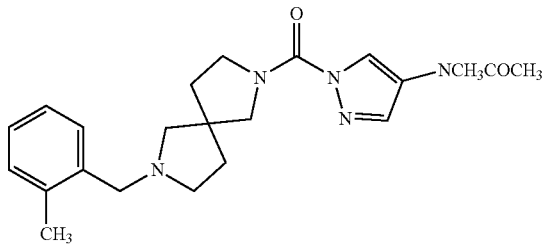

The title compound was synthesized as described in Example 27 using tert-butyl 2,7-diazaspiro[4.4]nonane-2-carboxylate in Step 1 and 2-methylbenzaldehyde in Step 4. Purification resulted in 55.3 mg of N-methyl-N-(1-(7-(2-methylbenzyl)-2,7-diazaspiro[4.4]nonane-2-carbonyl)-1H-pyrazol-4-yl)acetamide as a light yellow solid. $^1$H NMR (300 MHz, Chloroform-d) δ 8.27 (s, 0.3H), 8.18 (s, 0.7H), 8.05 (s, 0.3H), 7.54-7.55 (m, 0.7H), 7.26 (br, 1H), 7.15 (br, 3H), 3.85-4.07 (m, 2H), 3.55-3.74 (m, 4H), 3.35 (s, 1H), 3.21 (s, 2H), 2.49-2.68 (m, 4H), 2.34 (s, 3H), 2.28 (s, 1H), 1.84-1.99 (m, 6H). LCMS (ESI, m/z): 396 [M+H]$^+$.

Example 55: N-(1-(7-(2-chloro-4-methylbenzyl)-2,7-diazaspiro[4.4]nonane-2-carbonyl)-1H-pyrazol-4-yl)-N-methylacetamide

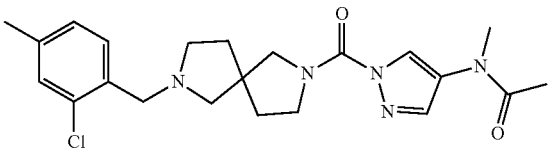 [SMILES: CC(=O)N(C)c1cnn(C(=O)N2CCC3(CCN(Cc4ccc(C)cc4Cl)C3)C2)c1]

The title compound was synthesized as described in Example 27 using tert-butyl 2,7-diazaspiro[4.4]nonane-2-carboxylate in Step 1 and 2-chloro-4-methylbenzaldehyde in Step 4. Purification resulted in 76.8 mg of N-(1-(7-(2-chloro-4-methylbenzyl)-2,7-diazaspiro[4.4]nonane-2-carbonyl)-1H-pyrazol-4-yl)-N-methylacetamide as a white solid. $^1$H NMR (300 MHz, Chloroform-d) δ 8.28 (s, 0.3H), 8.19 (s, 0.7H), 8.05 (s, 0.3H), 7.56 (s, 0.7H), 7.30-7.35 (m, 1H), 7.17 (s, 1H), 7.04 (br, 1H), 3.87-4.06 (m, 2H), 3.57-3.72 (m, 4H), 3.36 (s, 1H), 3.21 (s, 2H), 2.54-2.74 (m, 4H), 2.31 (s, 3H), 2.28 (s, 1H), 1.86-1.99 (m, 6H). LCMS (ESI, m/z): 430 [M+H]$^+$.

Example 56: N-(1-(7-(2-methoxybenzyl)-2,7-diazaspiro[4.4]nonane-2-carbonyl)-1H-pyrazol-4-yl)-N-methylacetamide

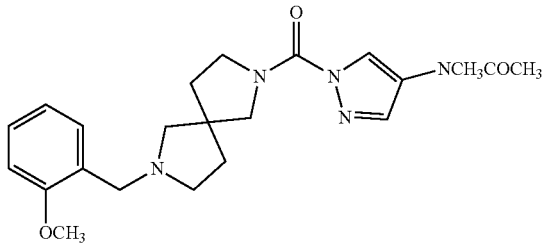

The title compound was synthesized as described in Example 27 using tert-butyl 2,7-diazaspiro[4.4]nonane-2-carboxylate in Step 1 and 2-methoxybenzaldehyde in Step 4. Purification resulted in 67.7 mg of N-(1-(7-(2-methoxybenzyl)-2,7-diazaspiro[4.4]nonane-2-carbonyl)-1H-pyrazol-4-yl)-N-methylacetamide as an off-white solid. $^1$H NMR (300 MHz, Chloroform-d) δ 8.28 (s, 0.3H), 8.18 (s, 0.7H), 8.04 (s, 0.3H), 7.54 (s, 0.7H), 7.32-7.39 (m, 1H), 7.22 (d, J=8.1 Hz, 1H), 6.85-6.94 (m, 2H), 3.87-4.05 (m, 2H), 3.82 (s, 3H), 3.57-3.69 (m, 4H), 3.35 (s, 1H), 3.21 (s, 2H), 2.53-2.75 (m, 4H), 2.28 (s, 1H), 1.85-1.99 (m, 6H). LCMS (ESI, m/z): 412 [M+H]$^+$.

Example 57: N-(1-(7-(3-chloro-2-methylbenzyl)-2,7-diazaspiro[4.4]nonane-2-carbonyl)-1H-pyrazol-4-yl)-N-methylacetamide

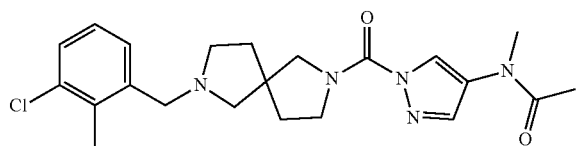 [SMILES: CC(=O)N(C)c1cnn(C(=O)N2CCC3(CCN(Cc4cccc(Cl)c4C)C3)C2)c1]

The title compound was synthesized as described in Example 27 using tert-butyl 2,7-diazaspiro[4.4]nonane-2-carboxylate in Step 1 and 3-chloro-2-methylbenzaldehyde in Step 4. Purification resulted in 86.7 mg of N-(1-(7-(3-chloro-2-methylbenzyl)-2,7-diazaspiro[4.4]nonane-2-carbonyl)-1H-pyrazol-4-yl)-N-methylacetamide as a white solid. $^1$H NMR (300 MHz, Chloroform-d) δ 8.28 (s, 0.3H), 8.19 (s, 0.7H), 8.04 (s, 0.3H), 7.55 (s, 0.7H), 7.28-7.30 (m, 1H), 7.07-7.17 (m, 2H), 3.80-4.05 (m, 2H), 3.45-3.72 (m, 4H), 3.36 (s, 1H), 3.21 (s, 2H), 2.40-2.90 (m, 7H), 2.28 (s, 1H), 1.72-2.18 (m, 6H). LCMS (ESI, m/z): 430 [M+H]$^+$.

Example 58: N-methyl-N-(1-(7-(2-(trifluoromethyl)benzyl)-2,7-diazaspiro[4.4]nonane-2-carbonyl)-1H-pyrazol-4-yl)acetamide

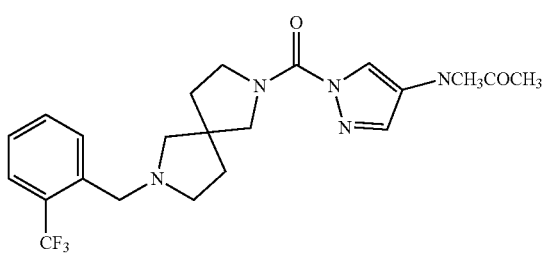

The title compound was synthesized as described in Example 27 using tert-butyl 2,7-diazaspiro[4.4]nonane-2-carboxylate in Step 1 and 2-(trifluoromethyl)benzaldehyde in Step 4. Purification resulted in 112.8 mg of N-methyl-N-(1-(7-(2-(trifluoromethyl)benzyl)-2,7-diazaspiro[4.4]nonane-2-carbonyl)-1H-pyrazol-4-yl)acetamide as a light yellow oil. $^1$H NMR (300 MHz, Chloroform-d) δ 8.28 (s, 0.3H), 8.19 (s, 0.7H), 8.06 (s, 0.3H), 7.60-7.79 (m, 1H), 7.47-7.57 (m, 2.7H), 7.33 (t, J=7.5 Hz, 1H), 3.87-4.13 (m, 2H), 3.58-3.78 (m, 4H), 3.36 (s, 1H), 3.22 (s, 2H), 2.49-2.80 (m, 4H), 2.28 (s, 1H), 1.85-2.00 (m, 6H). LCMS (ESI, m/z): 450 [M+H]$^+$.

Example 59: N-(1-(7-(2,3-dichlorobenzyl)-2,7-diazaspiro[4.4]nonane-2-carbonyl)-1H-pyrazol-4-yl)-N-methylacetamide

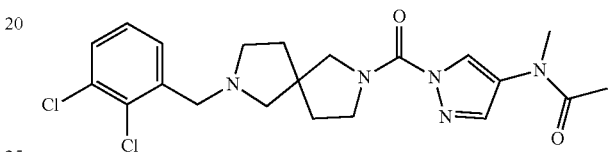

The title compound was synthesized as described in Example 27 using tert-butyl 2,7-diazaspiro[4.4]nonane-2-carboxylate in Step 1 and 2,3-dichlorobenzaldehyde in Step 4. Purification resulted in 78.6 mg of N-(1-(7-(2,3-dichlorobenzyl)-2,7-diazaspiro[4.4]nonane-2-carbonyl)-1H-pyrazol-4-yl)-N-methylacetamide as a white solid. $^1$H NMR (400 MHz, MeOH-d$_4$) δ 8.43 (s, 0.3H), 8.36 (s, 0.7H), 7.99 (s, 0.3H), 7.78 (s, 0.7H), 7.44-7.46 (m, 2H), 7.28-7.29 (m, 1H), 3.56-4.02 (m, 6H), 3.43 (s, 1H), 3.22 (s, 2H), 2.58-2.81 (m, 4H), 2.30 (s, 1H), 1.88-2.00 (m, 6H). LCMS (ESI, m/z): 450 [M+H]$^+$.

Example 60: N-methyl-N-(1-(7-(2-(pyrrolidin-1-yl)benzyl)-2,7-diazaspiro[4.4]nonane-2-carbonyl)-1H-pyrazol-4-yl)acetamide

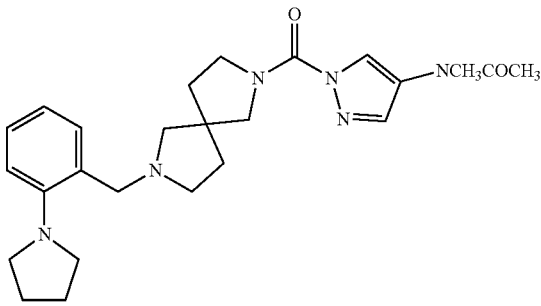

The title compound was synthesized as described in Example 27 using tert-butyl 2,7-diazaspiro[4.4]nonane-2-carboxylate in Step 1 and 2-(pyrrolidin-1-yl)benzaldehyde in Step 4. Purification resulted in 66.4 mg of N-methyl-N-(1-(7-(2-(pyrrolidin-1-yl)benzyl)-2,7-diazaspiro[4.4]nonane-2-carbonyl)-1H-pyrazol-4-yl)acetamide as an off-white solid. $^1$H NMR (300 MHz, Chloroform-d) δ 8.27 (s, 0.3H), 8.19 (s, 0.7H), 8.05 (br, 0.3H), 7.55 (s, 0.7H), 7.38 (br, 1H), 7.14-7.16 (m, 1H), 6.90-6.91 (m, 2H), 3.84-4.05 (m, 2H), 3.56-3.78 (m, 4H), 3.35 (s, 1H), 3.19-3.21 (m, 2H), 2.39-2.73 (m, 4H), 2.28 (s, 1H), 1.90-2.12 (m, 10H). LCMS (ESI, m/z): 451 [M+H]$^+$.

Example 61: N-methyl-N-(1-(7-(3-morpholino-4-(trifluoromethyl)benzyl)-2,7-diazaspiro[4.4]nonane-2-carbonyl)-1H-pyrazol-4-yl)acetamide

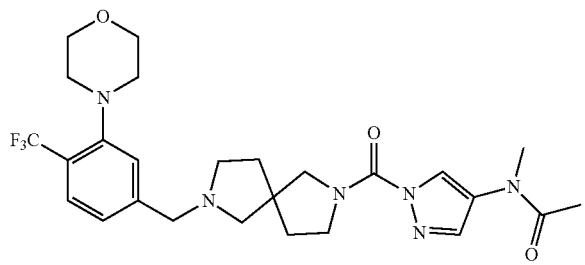 [SMILES: CC(=O)N(C)c1cnn(C(=O)N2CCC3(CCN(Cc4ccc(C(F)(F)F)c(N5CCOCC5)c4)C3)C2)c1]

Step 1: Synthesis of 3-morpholino-4-(trifluoromethyl)benzaldehyde

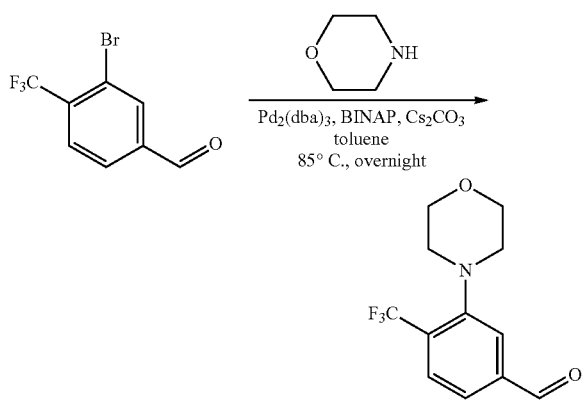

A 250-mL round-bottom flask was charged with 3-bromo-4-(trifluoromethyl)benzaldehyde (3.00 g, 11.9 mmol, 1.00 equiv), 2,2'-bis(diphenylphosphino)-1,1'-binaphthyl (1.11 g, 1.78 mmol, 0.15 equiv), cesium carbonate (11.6 g, 35.6 mmol, 3.00 equiv), tris(dibenzylideneacetone)dipalladium (0.545 g, 0.600 mmol, 0.05 equiv), toluene (60 mL), and morpholine (1.55 g, 17.8 mmol, 1.50 equiv) under nitrogen. The resulting solution was stirred overnight at 85° C. and quenched with water (80 mL). The resulting solution was extracted with EtOAc (2×150 mL) and the organic layers were combined, dried over anhydrous sodium sulfate, filtered and concentrated under reduced pressure. The residue was chromatographed on a silica gel column to provide 2.00 g (65% yield) of 3-morpholino-4-(trifluoromethyl)benzaldehyde as a yellow solid. LCMS (ESI, m/z): 260 [M+H]$^+$.

Step 2: Synthesis of N-methyl-N-(1-(7-(3-morpholino-4-(trifluoromethyl)benzyl)-2,7-diazaspiro[4.4]nonane-2-carbonyl)-1H-pyrazol-4-yl)acetamide

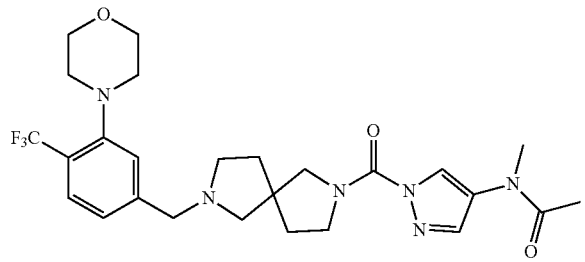 [SMILES: CC(=O)N(C)c1cnn(C(=O)N2CCC3(CCN(Cc4ccc(C(F)(F)F)c(N5CCOCC5)c4)C3)C2)c1]

The title compound was synthesized as described in Example 27 using tert-butyl 2,7-diazaspiro[4.4]nonane-2-carboxylate in Step 1 and 3-morpholino-4-(trifluoromethyl)benzaldehyde in Step 4. Purification resulted in 155.0 mg of N-methyl-N-(1-(7-(3-morpholino-4-(trifluoromethyl)benzyl)-2,7-diazaspiro[4.4]nonane-2-carbonyl)-1H-pyrazol-4-yl)acetamide as a white solid. $^1$H NMR (300 MHz, Chloroform-d) δ 8.30 (s, 0.3H), 8.20 (s, 0.7H), 8.05 (s, 0.3H), 7.54-7.57 (m, 1.7H), 7.34 (s, 1H), 7.18 (br, 1H), 3.90-4.05 (m, 2H), 3.82 (s, 4H), 3.58-3.77 (m, 4H), 3.36 (s, 1H), 3.21 (s, 2H), 2.92 (s, 4H), 2.45-2.71 (m, 4H), 2.28 (s, 1H), 1.87-1.99 (m, 6H). LCMS (ESI, m/z): 535 [M+H]$^+$.

Example 62: N-methyl-N-(1-(7-(2-morpholinobenzyl)-2,7-diazaspiro[4.4]nonane-2-carbonyl)-1H-pyrazol-4-yl)acetamide

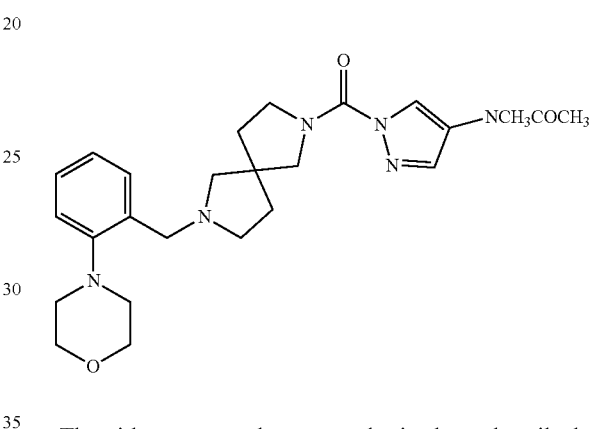

The title compound was synthesized as described in Example 27 using tert-butyl 2,7-diazaspiro[4.4]nonane-2-carboxylate in Step 1 and 2-morpholinobenzaldehyde in Step 4. Purification resulted in 50.0 mg of N-methyl-N-(1-(7-(2-morpholinobenzyl)-2,7-diazaspiro[4.4]nonane-2-carbonyl)-1H-pyrazol-4-yl)acetamide as a white solid. $^1$H NMR (300 MHz, Chloroform-d) δ 8.28 (s, 0.3H), 8.19 (s, 0.7H), 8.04 (br, 0.3H), 7.54 (s, 0.7H), 7.33-7.39 (m, 1H), 7.18 (br, 1H), 7.07-7.09 (m, 2H), 3.91-4.06 (m, 2H), 3.81-3.83 (m, 4H), 3.54-3.70 (m, 4H), 3.35 (s, 1H), 3.21 (s, 2H), 3.00 (br, 4H), 2.49-2.73 (m, 4H), 2.28 (s, 1H), 1.83-1.99 (m, 6H). LCMS (ESI, m/z): 467 [M+H]$^+$.

Example 63: N-(1-(7-(3-chloro-5-morpholinobenzyl)-2,7-diazaspiro[4.4]nonane-2-carbonyl)-1H-pyrazol-4-yl)-N-methylacetamide

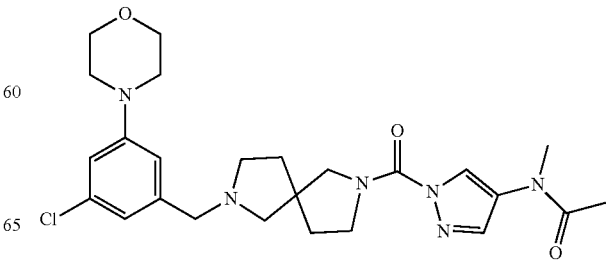

Step 1: Synthesis of 3-chloro-5-morpholinobenzaldehyde

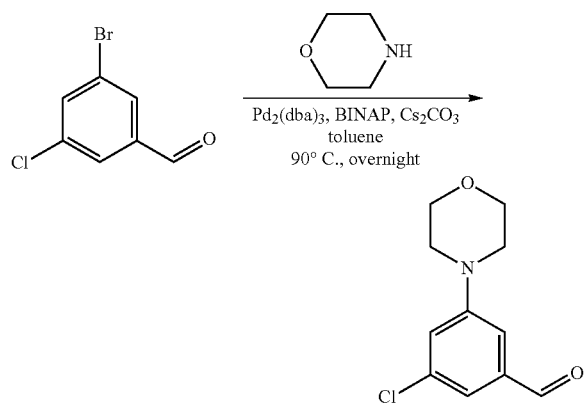

A 250-mL round-bottom flask was charged with 3-bromo-5-chlorobenzaldehyde (1.50 g, 6.83 mmol, 1.00 equiv), tris(dibenzylideneacetone)dipalladium (0.315 g, 0.340 mmol, 0.05 equiv), 2,2'-bis(diphenylphosphino)-1,1'-binaphthyl (0.643 g, 1.03 mmol, 0.15 equiv), cesium carbonate (6.72 g, 20.6 mmol, 3.00 equiv), morpholine (0.896 g, 10.3 mmol, 1.50 equiv), and toluene (20 mL) under nitrogen. The resulting solution was stirred overnight at 90° C. and quenched with water (50 mL). The resulting solution was extracted with EtOAc (2×80 mL) and the organic layers were combined, dried over anhydrous sodium sulfate, filtered and concentrated under reduced pressure. The residue was chromatographed on a silica gel column to provide 800 mg (52% yield) of 3-chloro-5-morpholinobenzaldehyde as a yellow solid. LCMS (ESI, m/z): 226 [M+H]$^+$.

Step 2: Synthesis of N-(1-(7-(3-chloro-5-morpholinobenzyl)-2,7-diazaspiro[4.4]nonane-2-carbonyl)-1H-pyrazol-4-yl)-N-methylacetamide

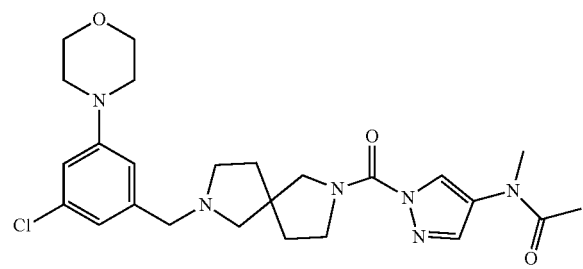 [SMILES: CC(=O)N(C)c1cnn(C(=O)N2CCC3(CCN(Cc4cc(Cl)cc(N5CCOCC5)c4)C3)C2)c1]

The title compound was synthesized as described in Example 27 using tert-butyl 2,7-diazaspiro[4.4]nonane-2-carboxylate in Step 1 and 3-chloro-5-morpholinobenzaldehyde in Step 4. Purification resulted in 146.5 mg of N-(1-(7-(3-chloro-5-morpholinobenzyl)-2,7-diazaspiro[4.4]nonane-2-carbonyl)-1H-pyrazol-4-yl)-N-methylacetamide as a white solid. $^1$H NMR (300 MHz, Chloroform-d) δ 8.28 (s, 0.3H), 8.19 (s, 0.7H), 8.05 (s, 0.3H), 7.55 (s, 0.7H), 6.75-6.81 (m, 3H), 3.84-4.06 (m, 6H), 3.41-3.71 (m, 4H), 3.35 (s, 1H), 3.21 (s, 2H), 3.15 (s, 4H), 2.45-2.69 (m, 4H), 2.28 (s, 1H), 1.87-1.99 (m, 6H). LCMS (ESI, m/z): 501 [M+H]$^+$.

Example 64: N-methyl-N-(1-(7-(3-(trifluoromethyl)benzyl)-2,7-diazaspiro[4.4]nonane-2-carbonyl)-1H-pyrazol-4-yl)acetamide

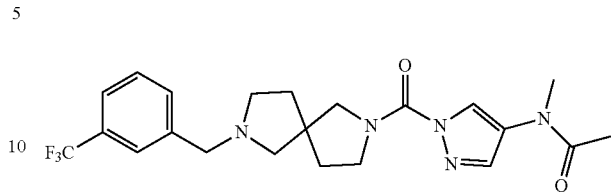

The title compound was synthesized as described in Example 27 using tert-butyl 2,7-diazaspiro[4.4]nonane-2-carboxylate in Step 1 and 3-trifluromethylbenzaldehyde in Step 4. Purification resulted in 137.6 mg of N-methyl-N-(1-(7-(3-(trifluoromethyl)benzyl)-2,7-diazaspiro[4.4]nonane-2-carbonyl)-1H-pyrazol-4-yl)acetamide as a yellow oil. $^1$H NMR (300 MHz, Chloroform-d) δ 8.28 (s, 0.3H), 8.19 (s, 0.7H), 8.05 (s, 0.3H), 7.39-7.58 (m, 4.7H), 3.87-4.08 (m, 2H), 3.57-3.75 (m, 4H), 3.36 (s, 1H), 3.22 (s, 2H), 2.41-2.74 (m, 4H), 2.28 (s, 1H), 1.84-1.99 (m, 6H). LCMS (ESI, m/z): 450 [M+H]$^+$.

Example 65: N-methyl-N-(1-(7-(3-(trifluoromethyl)benzyl)-2,7-diazaspiro[4.4]nonane-2-carbonyl)-1H-pyrazol-4-yl)acetamide (Single Enantiomer)

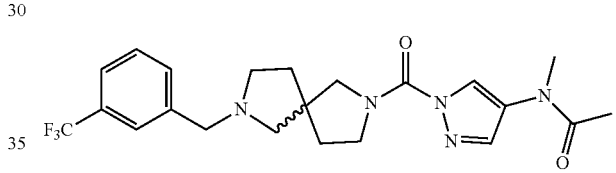

One enantiomer of racemic N-methyl-N-(1-(7-(3-(trifluoromethyl)benzyl)-2,7-diazaspiro[4.4]nonane-2-carbonyl)-1H-pyrazol-4-yl)acetamide (Example 64, 700 mg, 1.56 mmol, 1.00 equiv) was separated by SFC using the following gradient conditions: Column: Chiralpak AD-H 2*25 cm; Mobile Phase A: CO$_2$ (50%), Mobile Phase B: ACN (50%); Flow rate: 40 mL/min; Detector: UV 220 nm; RT: 6.87 min. SFC separation resulted in 260.8 mg (37% yield) of one enantiomer of N-methyl-N-(1-(7-(3-(trifluoromethyl)benzyl)-2,7-diazaspiro[4.4]nonane-2-carbonyl)-1H-pyrazol-4-yl)acetamide as a yellow oil. $^1$H NMR (300 MHz, Chloroform-d) δ 8.25 (s, 0.3H), 8.16 (s, 0.7H), 8.02 (s, 0.3H), 7.40-7.56 (m, 4.7H), 3.85-4.33 (m, 2H), 3.55-3.76 (m, 4H), 3.32 (s, 1H), 3.18 (s, 2H), 2.32-2.79 (m, 4H), 2.25 (s, 1H), 1.75-1.96 (m, 6H). LCMS (ESI, m/z): 450 [M+H]$^+$.

Example 66: N-methyl-N-(1-(7-(3-(trifluoromethyl)benzyl)-2,7-diazaspiro[4.4]nonane-2-carbonyl)-1H-pyrazol-4-yl)acetamide (Single Enantiomer)

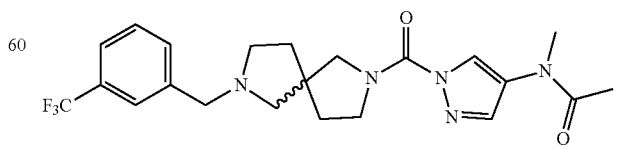

The second enantiomer of racemic N-methyl-N-(1-(7-(3-(trifluoromethyl)benzyl)-2,7-diazaspiro[4.4]nonane-2-carbonyl)-1H-pyrazol-4-yl)acetamide (Example 64, 700 mg, 1.56 mmol, 1.00 equiv) was separated by SFC using the following gradient conditions: Column: Chiralpak AD-H 2*25 cm; Mobile Phase A: CO$_2$ (50%), Mobile Phase B: ACN (50%); Flow rate: 40 mL/min; Detector: UV 220 nm; RT: 16.48 min. SFC separation resulted in 214.1 mg (31% yield) of the second enantiomer of N-methyl-N-(1-(7-(3-(trifluoromethyl)benzyl)-2,7-diazaspiro[4.4]nonane-2-carbonyl)-1H-pyrazol-4-yl)acetamide as a yellow oil. $^1$H NMR (300 MHz, Chloroform-d) δ 8.25 (s, 0.3H), 8.16 (s, 0.7H), 8.02 (s, 0.3H), 7.42-7.56 (m, 4.7H), 3.79-4.34 (m, 2H), 3.51-3.76 (m, 4H), 3.33 (s, 1H), 3.18 (s, 2H), 2.42-2.68 (m, 4H), 2.25 (s, 1H), 1.75-1.99 (m, 6H). LCMS (ESI, m/z): 450 [M+H]$^+$.

Example 67: N-(1-(7-(3-chloro-4-(pyrrolidin-1-yl)benzyl)-2,7-diazaspiro[4.4]nonane-2-carbonyl)-1H-pyrazol-4-yl)-N-methylacetamide

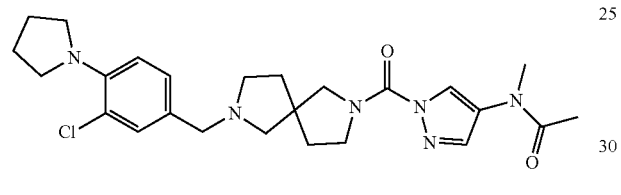

Step 1: Synthesis of 3-chloro-4-(pyrrolidin-1-yl)benzaldehyde

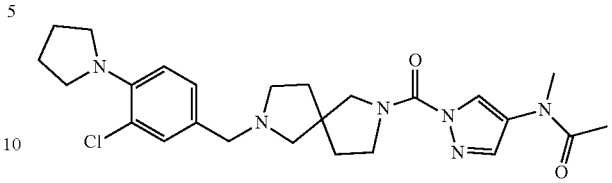

A 50-mL round-bottom flask was charged with 3-chloro-4-fluorobenzaldehyde (1.00 g, 6.31 mmol, 1.00 equiv), DMSO (10 mL), potassium carbonate (2.62 g, 19.0 mmol, 3.00 equiv), and pyrrolidine (0.674 g, 9.48 mmol, 1.50 equiv) under nitrogen. The resulting solution was stirred overnight at 90° C. and quenched with water (50 mL). The resulting solution was extracted with EtOAc (2×80 mL) and the organic layers were combined, dried over anhydrous sodium sulfate, filtered and concentrated under reduced pressure. The residue was chromatographed on a silica gel column to provide 1.10 g (83% yield) of 3-chloro-4-(pyrrolidin-1-yl)benzaldehyde as a yellow oil. LCMS (ESI, m/z): 210 [M+H]$^+$.

Step 2: Synthesis of N-(1-(7-(3-chloro-4-(pyrrolidin-1-yl)benzyl)-2,7-diazaspiro[4.4]nonane-2-carbonyl)-1H-pyrazol-4-yl)-N-methylacetamide

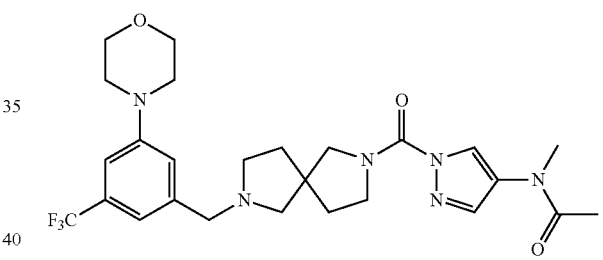

The title compound was synthesized as described in Example 27 using tert-butyl 2,7-diazaspiro[4.4]nonane-2-carboxylate in Step 1 and 3-chloro-4-(pyrrolidin-1-yl)benzaldehyde in Step 4. Purification resulted in 137.2 mg of N-(1-(7-(3-chloro-4-(pyrrolidin-1-yl)benzyl)-2,7-diazaspiro[4.4]nonane-2-carbonyl)-1H-pyrazol-4-yl)-N-methylacetamide as a light yellow solid. $^1$H NMR (300 MHz, Chloroform-d) δ 8.28 (s, 0.3H), 8.18 (s, 0.7H), 8.05 (s, 0.3H), 7.54-7.56 (m, 0.7H), 7.24-7.26 (m, 1H), 7.05-7.10 (m, 1H), 6.81-6.83 (m, 1H), 3.86-4.05 (m, 2H), 3.50-3.73 (m, 4H), 3.34-3.38 (m, 5H), 3.21 (s, 2H), 2.42-2.67 (m, 4H), 2.28 (s, 1H), 1.85-2.00 (m, 10H). LCMS (ESI, m/z): 507 [M+Na]$^+$.

Example 68: N-methyl-N-(1-(7-(3-morpholino-5-(trifluoromethyl)benzyl)-2,7-diazaspiro[4.4]nonane-2-carbonyl)-1H-pyrazol-4-yl)acetamide

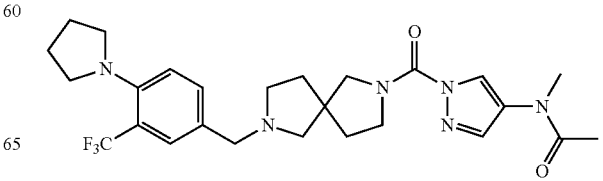

The title compound was synthesized as described in Example 27 using tert-butyl 2,7-diazaspiro[4.4]nonane-2-carboxylate in Step 2 and 3-morpholino-5-(trifluoromethyl)benzaldehyde (Example 63, Step 1) in Step 4. Purification resulted in 109.7 mg of N-methyl-N-(1-(7-(3-morpholino-5-(trifluoromethyl)benzyl)-2,7-diazaspiro[4.4]nonane-2-carbonyl)-1H-pyrazol-4-yl)acetamide as a white solid. $^1$H NMR (300 MHz, Chloroform-d) δ 8.28 (s, 0.3H), 8.19 (s, 0.7H), 8.05 (s, 0.3H), 7.55 (s, 0.7H), 6.99-7.06 (m, 3H), 4.00-4.07 (m, 2H), 3.86 (s, 4H), 3.44-3.68 (m, 4H), 3.35 (s, 1H), 3.21 (s, 6H), 2.43-2.71 (m, 4H), 2.28 (s, 1H), 1.88-1.99 (m, 6H). LCMS (ESI, m/z): 535 [M+H]$^+$.

Example 69: N-methyl-N-(1-(7-(4-(pyrrolidin-1-yl)-3-(trifluoromethyl)benzyl)-2,7-diazaspiro[4.4]nonane-2-carbonyl)-1H-pyrazol-4-yl)acetamide The title compound was synthesized as described in Example 27 using tert-butyl 2,7-diazaspiro[4.4]nonane-2-carboxylate in Step 1 and 4-(pyrrolidin-1-yl)-3-(trifluoromethyl)benzaldehyde (synthesized as described in Example 67, Step 1) in Step 4. Purification resulted in 111.5 mg of N-methyl-N-(1-(7-(4-(pyrrolidin-1-yl)-3-(trifluoromethyl)benzyl)-2,7-diazaspiro[4.4]nonane-2-carbonyl)-1H-pyrazol-4-yl)acetamide as a light yellow solid. $^1$H NMR (300 MHz, Chloroform-d) δ 8.28 (s, 0.3H), 8.18 (s, 0.7H), 8.04 (s, 0.3H), 7.55 (s, 0.7H), 7.48 (s, 1H), 7.31-7.34 (m, 1H), 6.92-6.94 (m, 1H), 3.86-4.05 (m, 2H), 3.55-3.71 (m, 4H), 3.29-3.35 (m, 5H), 3.21 (s, 2H), 2.37-2.68 (m, 4H), 2.28 (s, 1H), 1.88-1.99 (m, 10H). LCMS (ESI, m/z): 541 [M+Na]$^+$.

Example 70: N-(1-(7-(5-chloro-2-(trifluoromethyl)benzyl)-2,7-diazaspiro[4.4]nonane-2-carbonyl)-1H-pyrazol-4-yl)-N-methylacetamide

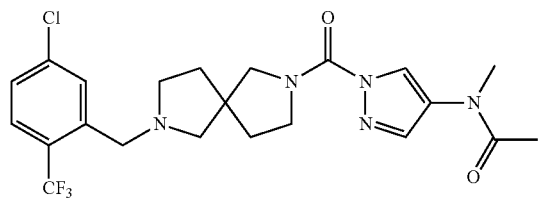 [SMILES: CC(=O)N(C)c1cnn(C(=O)N2CCC3(CCN(Cc4cc(Cl)ccc4C(F)(F)F)C3)C2)c1]

The title compound was synthesized as described in Example 27 using tert-butyl 2,7-diazaspiro[4.4]nonane-2-carboxylate in Step 1 and 5-chloro-2-(trifluoromethyl)benzaldehyde in Step 4. Purification resulted in 152.7 mg of N-(1-(7-(5-chloro-2-(trifluoromethyl)benzyl)-2,7-diazaspiro[4.4]nonane-2-carbonyl)-1H-pyrazol-4-yl)-N-methylacetamide as a colorless oil. $^1$H NMR (300 MHz, Chloroform-d) δ 8.29 (s, 0.3H), 8.20 (s, 0.7H), 8.06 (s, 0.3H), 7.76-7.78 (m, 1H), 7.53-7.58 (m, 1.7H), 7.29-7.31 (m, 1H), 3.88-4.08 (m, 2H), 3.60-3.76 (m, 4H), 3.36 (s, 1H), 3.22 (s, 2H), 2.47-2.80 (m, 4H), 2.28 (s, 1H), 1.78-1.99 (m, 6H). LCMS (ESI, m/z): 484 [M+H]$^+$.

Example 71: N-(1-(7-(2-chloro-5-(trifluoromethyl)benzyl)-2,7-diazaspiro[4.4]nonane-2-carbonyl)-1H-pyrazol-4-yl)-N-methylacetamide

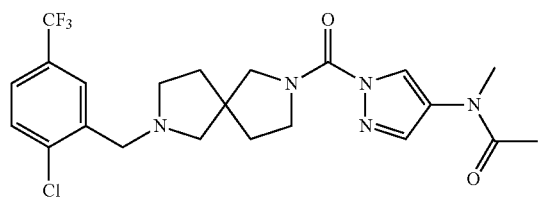

The title compound was synthesized as described in Example 27 using tert-butyl 2,7-diazaspiro[4.4]nonane-2-carboxylate in Step 1 and 2-chloro-5-(trifluoromethyl)benzaldehyde in Step 4. Purification resulted in 115.4 mg of N-(1-(7-(2-chloro-5-(trifluoromethyl)benzyl)-2,7-diazaspiro[4.4]nonane-2-carbonyl)-1H-pyrazol-4-yl)-N-methylacetamide as a colorless oil. $^1$H NMR (300 MHz, Chloroform-d) δ 8.29 (s, 0.3H), 8.19 (s, 0.7H), 8.04 (s, 0.3H), 7.86 (br, 1H), 7.56 (s, 0.7H), 7.48 (br, 2H), 3.69-4.06 (m, 6H), 3.36 (s, 1H), 3.21 (s, 2H), 2.73-2.98 (m, 4H), 2.28 (s, 1H), 1.99 (br, 6H). LCMS (ESI, m/z): 484 [M+H]$^+$.

Example 72: N-(1-(7-(2,5-bis(trifluoromethyl)benzyl)-2,7-diazaspiro[4.4]nonane-2-carbonyl)-1H-pyrazol-4-yl)-N-methylacetamide

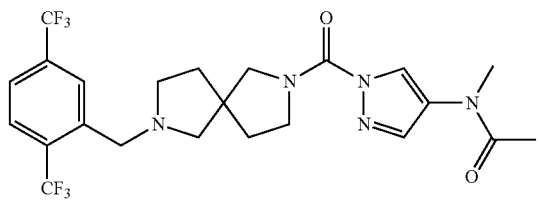

The title compound was synthesized as described in Example 27 using tert-butyl 2,7-diazaspiro[4.4]nonane-2-carboxylate in Step 1 and 2,5-bis(trifluoromethyl)benzaldehyde in Step 4. Purification resulted in 175.4 mg of N-(1-(7-(2,5-bis(trifluoromethyl)benzyl)-2,7-diazaspiro[4.4]nonane-2-carbonyl)-1H-pyrazol-4-yl)-N-methylacetamide as a colorless oil. $^1$H NMR (300 MHz, Chloroform-d) δ 8.39 (s, 0.3H), 8.32 (s, 0.7H), 8.18 (br, 1H), 7.74-7.95 (m, 3H), 4.03-4.80 (m, 4H), 3.66 (br, 2H), 3.38 (s, 1H), 2.74-3.29 (m, 6H), 2.25 (s, 1H), 2.00 (br, 4H), 1.92 (s, 2H). LCMS (ESI, m/z): 518 [M+H]$^+$.

Example 73: N-methyl-N-(1-(7-(5-(pyrrolidin-1-yl)-2-(trifluoromethyl)benzyl)-2,7-diazaspiro[4.4]nonane-2-carbonyl)-1H-pyrazol-4-yl)acetamide

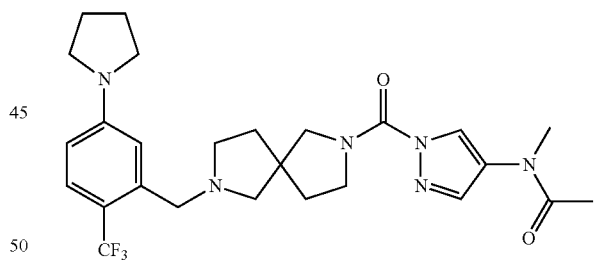

The title compound was synthesized as described in Example 27 using tert-butyl 2,7-diazaspiro[4.4]nonane-2-carboxylate in Step 1 and 5-(pyrrolidin-1-yl)-2-(trifluoromethyl)benzaldehyde (synthesized as described in Example 67, Step 1) in Step 4. Purification resulted in 165.1 mg of N-methyl-N-(1-(7-(5-(pyrrolidin-1-yl)-2-(trifluoromethyl)benzyl)-2,7-diazaspiro[4.4]nonane-2-carbonyl)-1H-pyrazol-4-yl)acetamide as a white solid. $^1$H NMR (300 MHz, Chloroform-d) δ 8.27 (s, 0.3H), 8.19 (s, 0.7H), 8.04-8.08 (m, 0.3H), 7.54 (s, 0.7H), 7.42 (d, J=8.7 Hz, 1H), 6.87-6.91 (m, 1H), 6.37-6.40 (m, 1H), 3.88-4.06 (m, 2H), 3.57-3.72 (m, 4H), 3.32-3.35 (m, 5H), 3.21 (s, 2H), 2.57-2.81 (m, 3H), 2.47 (br, 1H), 2.28 (s, 1H), 1.88-2.01 (m, 10H). LCMS (ESI, m/z): 311 [M+Na]$^+$.

Example 74: N-methyl-N-(1-(7-(2-(pyrrolidin-1-yl)-5-(trifluoromethyl)benzyl)-2,7-diazaspiro[4.4]nonane-2-carbonyl)-1H-pyrazol-4-yl)acetamide

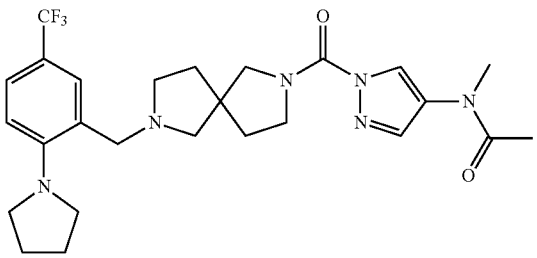 [SMILES: CC(=O)N(C)c1cnn(C(=O)N2CCC3(CCN(Cc4cc(C(F)(F)F)ccc4N4CCCC4)C3)C2)c1]

The title compound was synthesized as described in Example 27 using tert-butyl 2,7-diazaspiro[4.4]nonane-2-carboxylate in Step 1 and 2-(pyrrolidin-1-yl)-5-(trifluoromethyl)benzaldehyde (synthesized as described in Example 67, Step 1) in Step 4. Purification resulted in 145.0 mg of N-methyl-N-(1-(7-(2-(pyrrolidin-1-yl)-5-(trifluoromethyl)benzyl)-2,7-diazaspiro[4.4]nonane-2-carbonyl)-1H-pyrazol-4-yl)acetamide as a white solid. $^1$H NMR (300 MHz, MeOH-$d_4$) δ 8.38 (s, 0.3H), 8.31 (s, 0.7H), 7.95 (s, 0.3H), 7.74 (s, 0.7H), 7.59 (br, 1H), 7.42 (br, 1H), 7.00 (br, 1H), 3.85-4.04 (m, 4H), 3.61 (br, 2H), 3.28-3.38 (m, 5H), 3.17 (s, 2H), 2.70-2.95 (m, 4H), 2.25 (s, 1H), 1.95 (br, 10H). LCMS (ESI, m/z): 519 [M+H]$^+$.

Example 75: N-(1-(7-(4-fluorobenzyl)-2,7-diazaspiro[4.4]nonane-2-carbonyl)-1H-pyrazol-4-yl)-N-methylacetamide

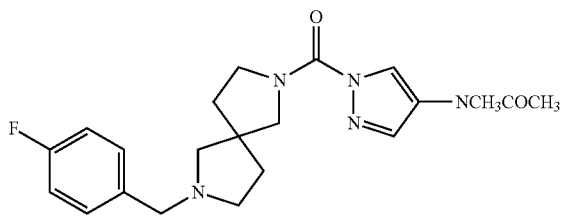

The title compound was synthesized as described in Example 27 using tert-butyl 2,7-diazaspiro[4.4]nonane-2-carboxylate in Step 1 and 4-fluorobenzaldehyde in Step 4. Purification resulted in 71.0 mg of N-(1-(7-(4-fluorobenzyl)-2,7-diazaspiro[4.4]nonane-2-carbonyl)-1H-pyrazol-4-yl)-N-methylacetamide as a white solid. $^1$H NMR (300 MHz, Chloroform-d) δ 8.27 (s, 0.3H), 8.19 (s, 0.7H), 8.05 (s, 0.3H), 7.55 (br, 0.7H), 7.27 (br, 2H), 6.99 (t, J=8.4 Hz, 2H), 3.84-4.06 (m, 2H), 3.59-3.78 (m, 4H), 3.35 (s, 1H), 3.21 (s, 2H), 2.36-2.66 (m, 4H), 2.28 (s, 1H), 1.85-2.09 (m, 6H). LCMS (ESI, m/z): 400 [M+H]$^+$.

Example 76: N-methyl-N-(1-(7-(4-methylbenzyl)-2,7-diazaspiro[4.4]nonane-2-carbonyl)-1H-pyrazol-4-yl)acetamide

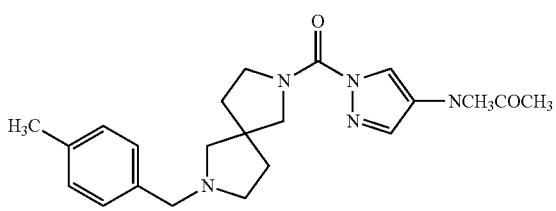

The title compound was synthesized as described in Example 27 using tert-butyl 2,7-diazaspiro[4.4]nonane-2-carboxylate in Step 1 and 4-methylbenzaldehyde in Step 4. Purification resulted in 73.5 mg of N-methyl-N-(1-(7-(4-methylbenzyl)-2,7-diazaspiro[4.4]nonane-2-carbonyl)-1H-pyrazol-4-yl)acetamide as a white solid. $^1$H NMR (300 MHz, Chloroform-d) δ 8.27 (s, 0.3H), 8.18 (s, 0.7H), 8.04 (br, 0.3H), 7.54 (br, 0.7H), 7.21 (br, 2H), 7.12-7.14 (m, 2H), 3.91-4.05 (m, 2H), 3.51-3.71 (m, 4H), 3.35 (s, 1H), 3.21 (s, 2H), 2.40-2.70 (m, 4H), 2.34 (s, 3H), 2.28 (s, 1H), 1.78-2.04 (m, 6H). LCMS (ESI, m/z): 396 [M+H]$^+$.

Example 77: N-(1-(7-(4-methoxybenzyl)-2,7-diazaspiro[4.4]nonane-2-carbonyl)-1H-pyrazol-4-yl)-N-methylacetamide

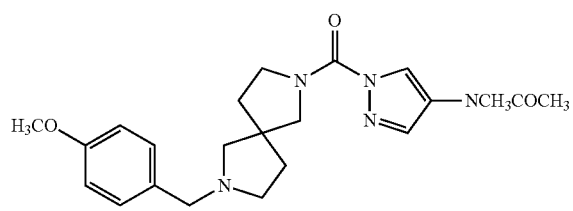

The title compound was synthesized as described in Example 27 using tert-butyl 2,7-diazaspiro[4.4]nonane-2-carboxylate in Step 1 and 4-methoxybenzaldehyde in Step 4. Purification resulted in 79.1 mg of N-(1-(7-(4-methoxybenzyl)-2,7-diazaspiro[4.4]nonane-2-carbonyl)-1H-pyrazol-4-yl)-N-methylacetamide as an off-white solid. $^1$H NMR (300 MHz, Chloroform-d) δ 8.27 (s, 0.3H), 8.18 (s, 0.7H), 8.04 (br, 0.3H), 7.55 (br, 0.7H), 7.20-7.22 (m, 2H), 6.84 (d, J=8.1 Hz, 2H), 3.86-4.07 (m, 2H), 3.80 (s, 3H), 3.55-3.73 (m, 4H), 3.35 (s, 1H), 3.21 (s, 2H), 2.40-2.67 (m, 4H), 2.28 (s, 1H), 1.84-1.99 (m, 6H). LCMS (ESI, m/z): 412 [M+H]$^+$.

Example 78: N-(1-(7-(3-chlorobenzyl)-2,7-diazaspiro[4.4]nonane-2-carbonyl)-1H-pyrazol-4-yl)-N-methylacetamide

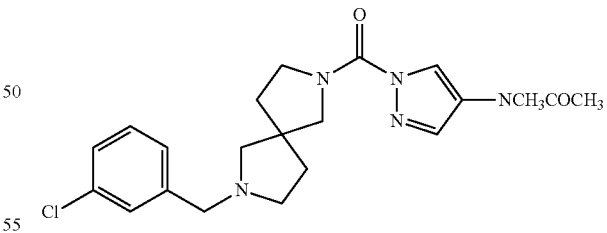

The title compound was synthesized as described in Example 27 using tert-butyl 2,7-diazaspiro[4.4]nonane-2-carboxylate in Step 1 and 3-chlorobenzaldehyde in Step 4. Purification resulted in 76.0 mg of N-(1-(7-(3-chlorobenzyl)-2,7-diazaspiro[4.4]nonane-2-carbonyl)-1H-pyrazol-4-yl)-N-methylacetamide as a light yellow semi-solid. $^1$H NMR (300 MHz, Chloroform-d) δ 8.28 (s, 0.3H), 8.19 (s, 0.7H), 8.05 (br, 0.3H), 7.54-7.56 (m, 0.7H), 7.32 (s, 1H), 7.19-7.22 (m, 3H), 3.90-4.08 (m, 2H), 3.58-3.87 (m, 4H), 3.36 (s, 1H), 3.21 (s, 2H), 2.42-2.73 (m, 4H), 2.28 (s, 1H), 1.80-1.99 (m, 6H). LCMS (ESI, m/z): 416 [M+H]$^+$.

Example 79: N-(1-(7-(3-fluorobenzyl)-2,7-diazaspiro[4.4]nonane-2-carbonyl)-1H-pyrazol-4-yl)-N-methylacetamide

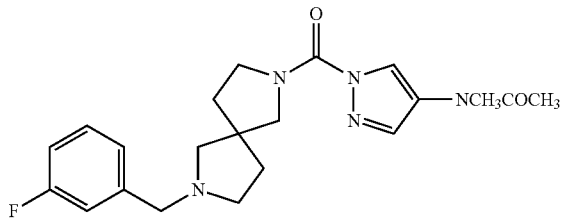

The title compound was synthesized as described in Example 27 using tert-butyl 2,7-diazaspiro[4.4]nonane-2-carboxylate in Step 1 and 3-fluorobenzaldehyde in Step 4. Purification resulted in 76.1 mg of N-(1-(7-(3-fluorobenzyl)-2,7-diazaspiro[4.4]nonane-2-carbonyl)-1H-pyrazol-4-yl)-N-methylacetamide as a light yellow semi-solid. $^1$H NMR (300 MHz, Chloroform-d) δ 8.28 (s, 0.3H), 8.19 (s, 0.7H), 8.05 (br, 0.3H), 7.54-7.56 (m, 0.7H), 7.22-7.29 (m, 1H), 7.07-7.10 (m, 2H), 6.93 (t, J=8.4 Hz, 1H), 3.90-4.08 (m, 2H), 3.60-3.87 (m, 4H), 3.36 (s, 1H), 3.22 (s, 2H), 2.41-2.74 (m, 4H), 2.28 (s, 1H), 1.84-2.01 (m, 6H). LCMS (ESI, m/z): 400 [M+H]$^+$.

Example 80: N-methyl-N-(1-(7-(3-methylbenzyl)-2,7-diazaspiro[4.4]nonane-2-carbonyl)-1H-pyrazol-4-yl)acetamide

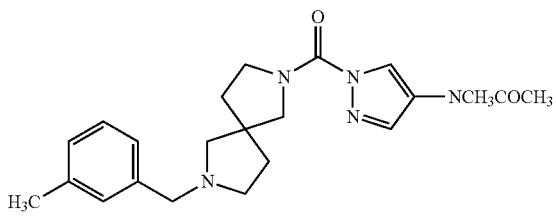

The title compound was synthesized as described in Example 27 using tert-butyl 2,7-diazaspiro[4.4]nonane-2-carboxylate in Step 1 and 3-methylbenzaldehyde in Step 4. Purification resulted in 52.3 mg of N-methyl-N-(1-(7-(3-methylbenzyl)-2,7-diazaspiro[4.4]nonane-2-carbonyl)-1H-pyrazol-4-yl)acetamide as a light yellow semi-solid. $^1$H NMR (300 MHz, Chloroform-d) δ 8.28 (s, 0.3H), 8.18 (s, 0.7H), 8.05 (br, 0.3H), 7.54-7.55 (m, 0.7H), 7.05-7.22 (m, 4H), 3.90-4.12 (m, 2H), 3.57-3.86 (m, 4H), 3.35 (s, 1H), 3.21 (s, 2H), 2.41-2.74 (m, 4H), 2.33 (s, 3H), 2.28 (s, 1H), 1.84-1.99 (m, 6H). LCMS (ESI, m/z): 396 [M+H]$^+$.

Example 81: N-(1-(7-(3-methoxybenzyl)-2,7-diazaspiro[4.4]nonane-2-carbonyl)-1H-pyrazol-4-yl)-N-methylacetamide

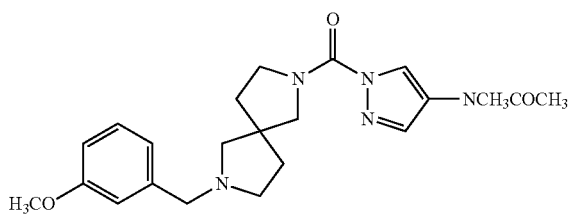

The title compound was synthesized as described in Example 27 using tert-butyl 2,7-diazaspiro[4.4]nonane-2-carboxylate in Step 1 and 3-methoxybenzaldehyde in Step 4. Purification resulted in 78.9 mg of N-(1-(7-(3-methoxybenzyl)-2,7-diazaspiro[4.4]nonane-2-carbonyl)-1H-pyrazol-4-yl)-N-methylacetamide as a light yellow semi-solid. $^1$H NMR (300 MHz, Chloroform-d) δ 8.27 (s, 0.3H), 8.19 (s, 0.7H), 8.05 (br, 0.3H), 7.54-7.55 (m, 0.7H), 7.22 (t, J=7.8 Hz, 1H), 6.89 (br, 2H), 6.79 (d, J=8.1 Hz, 1H), 3.86-4.08 (m, 2H), 3.79 (s, 3H), 3.58-3.74 (m, 4H), 3.35 (s, 1H), 3.21 (s, 2H), 2.42-2.75 (m, 4H), 2.28 (s, 1H), 1.80-1.99 (m, 6H). LCMS (ESI, m/z): 412 [M+H]$^+$.

Example 82: N-methyl-N-(1-(7-(3-(pyrrolidin-1-yl)benzyl)-2,7-diazaspiro[4.4]nonane-2-carbonyl)-1H-pyrazol-4-yl)acetamide

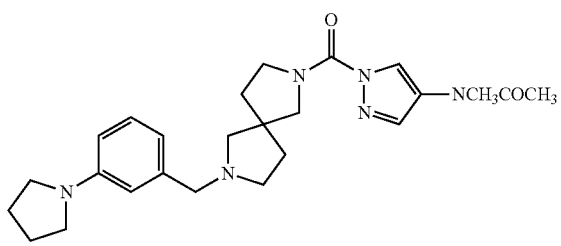

The title compound was synthesized as described in Example 27 using tert-butyl 2,7-diazaspiro[4.4]nonane-2-carboxylate in Step 1 and 3-(pyrrolidin-1-yl)benzaldehyde in Step 4. Purification resulted in 87.6 mg of N-methyl-N-(1-(7-(3-(pyrrolidin-1-yl)benzyl)-2,7-diazaspiro[4.4]nonane-2-carbonyl)-1H-pyrazol-4-yl)acetamide as a white solid. $^1$H NMR (300 MHz, Chloroform-d) δ 8.27 (s, 0.3H), 8.18 (s, 0.7H), 8.05 (br, 0.3H), 7.54 (s, 0.7H), 7.15 (t, J=7.8 Hz, 1H), 6.45-6.60 (m, 3H), 3.82-4.07 (m, 2H), 3.59-3.71 (m, 4H), 3.36 (s, 1H), 3.28 (br, 4H), 3.21 (s, 2H), 2.46-2.73 (m, 4H), 2.28 (s, 1H), 1.86-1.99 (m, 10H). LCMS (ESI, m/z): 451 [M+H]$^+$.

Example 83: N-methyl-N-(1-(7-(3-methylbenzyl)-2,7-diazaspiro[3.5]nonane-2-carbonyl)-1H-pyrazol-4-yl)acetamide

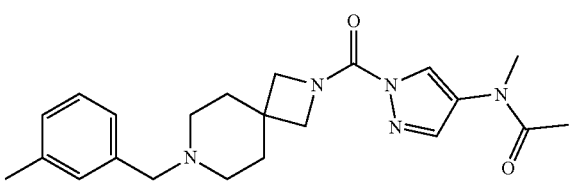 [SMILES: CC(=O)N(C)c1cnn(C(=O)N2CC3(CCN(Cc4cccc(C)c4)CC3)C2)c1]

Step 1: Synthesis of Tert-butyl 2-(4-acetamido-1H-pyrazole-1-carbonyl)-2,7-diazaspiro[3.5]nonane-7-carboxylate

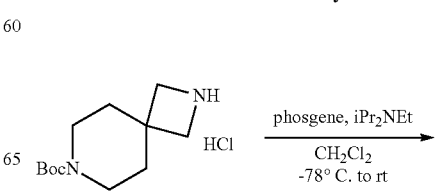

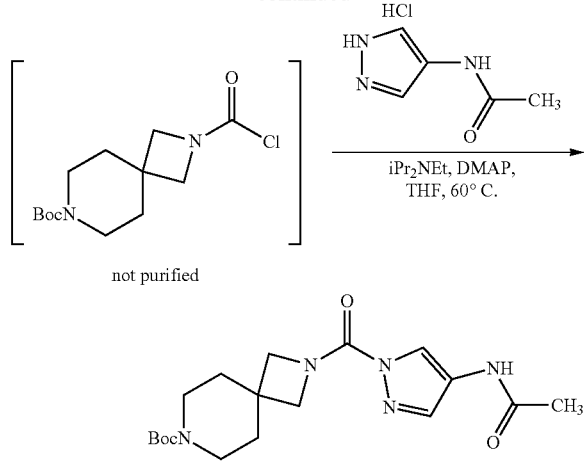

To a −78° C. solution of tert-butyl 2,7-diazaspiro[3.5] nonane-7-carboxylate hydrochloride (1 g, 3.81 mmol) in DCM (12 mL) was added N,N-diisopropylethylamine (1.4 mL, 8 mmol, 2.1 eq). Following this, a 15 wt % solution of phosgene in toluene (2.7 mL, 3.8 mmol) was added dropwise. The mixture was stirred at −78° C. for 5 min, then warmed to r.t. and stirred for 1 h. Following this time, the solution was diluted with H$_2$O (20 mL) and the biphasic mixture was transferred to a separatory funnel. The layers were separated and the aqueous phase was extracted with DCM (2×10 mL). The combined organic layers were dried over Na$_2$SO$_4$, filtered, and concentrated.

The unpurified carbamoyl chloride (TLC R$_f$=0.57, 3:2 n-Hexane/EtOAc) was dissolved in THF (12 mL), then N,N-diisopropylethylamine (1.4 mL, 8 mmol, 2.1 eq) and 4-dimethylaminopyridine (465 mg, 3.81 mmol) were added. The mixture was stirred at r.t. for 5 min, then N-(1H-pyrazol-4-yl)acetamide hydrochloride (615 mg, 3.81 mmol) was added. The resulting mixture was heated at 60° C. for 20 h, then cooled to r.t., concentrated, and applied directly onto a silica gel column. Purification by column chromatography on silica gel afforded tert-butyl 2-(4-acetamido-1H-pyrazole-1-carbonyl)-2,7-diazaspiro[3.5]nonane-7-carboxylate (1.16 g, 3.08 mmol, 81%) as a dark brown oil. $^1$H NMR (CD$_3$CN, 400 MHz) δ 8.38 (br s, 1H), 8.32 (s, 1H), 7.68 (s, 1H), 4.26 (br s, 2H), 3.81 (br s, 2H), 3.37-3.29 (m, 4H), 2.01 (s, 3H), 1.73-1.67 (m, 4H), 1.41 (s, 9H); LCMS (ESI, m/z): 278 (M-Boc); 322 (M-tBu); 400 [M+Na].

Step 2: Synthesis of Tert-butyl 2-(4-(N-methylacetamido)-1H-pyrazole-1-carbonyl)-2,7-diazaspiro[3.5]nonane-7-carboxylate

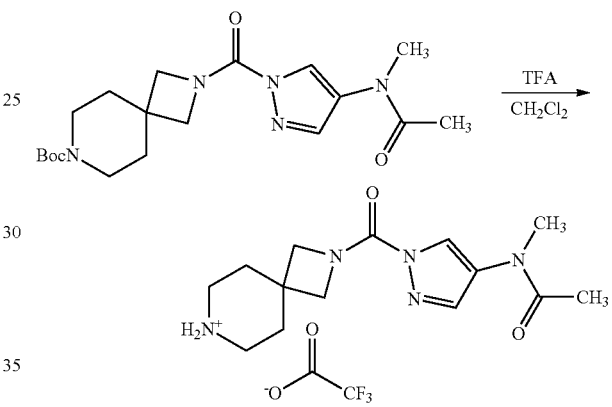

To a solution of tert-butyl 2-(4-acetamido-1H-pyrazole-1-carbonyl)-2,7-diazaspiro[3.5]nonane-7-carboxylate (1.16 g, 3.07 mmol) in DMF (4.4 mL) were added sequentially cesium carbonate (1.2 g, 3.7 mmol, 1.2 eq) and iodomethane (0.23 mL, 3.7 mmol, 1.2 eq). The reaction mixture was stirred at r.t. for 18 h. Following this time, the reaction mixture was diluted with H$_2$O (50 mL), causing a white solid to precipitate. The solid was collected via filtration, and was was rinsed with H$_2$O (20 mL), then dried under vacuum to afford tert-butyl 2-(4-(N-methylacetamido)-1H-pyrazole-1-carbonyl)-2,7-diazaspiro[3.5]nonane-7-carboxylate (895 mg, 2.29 mmol, 74%). $^1$H NMR (CD$_3$CN, 400 MHz) δ 8.32 (s, 0.5H), 8.19 (s, 0.5H), 7.92 (s, 0.5H), 7.64 (s, 0.5H), 4.34-4.24 (m, 2H), 3.88-3.79 (m, 2H), 3.28-3.27 (m, 5.5H), 3.11 (s, 1.5H), 2.19 (s, 1.5H), 1.88 (s, 1.5H), 1.43-1.39 (m, 9H); LCMS (ESI, m/z): 292 (M-Boc); 336 (M-tBu); 392 [M+H]$^+$.

Step 3: Synthesis of N-(1-(2,7-diazaspiro[3.5]nonane-2-carbonyl)-1H-pyrazol-4-yl)-N-methylacetamide

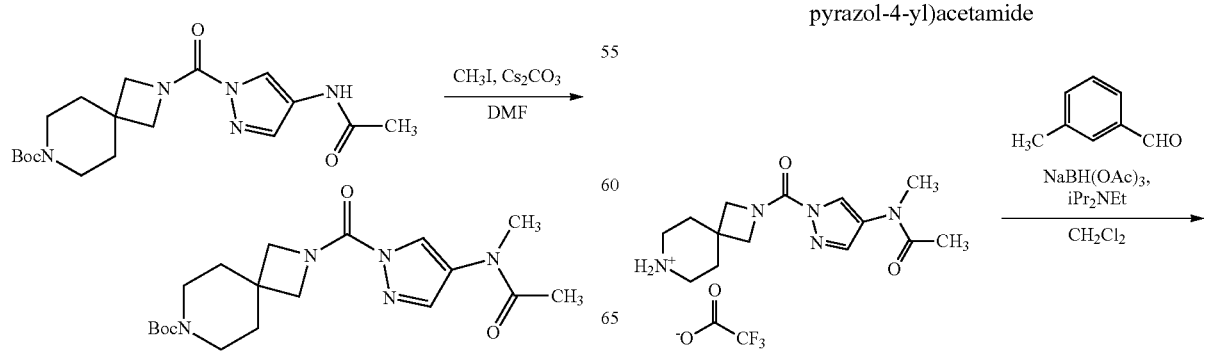

To an ice-cold solution of tert-butyl 2-(4-(N-methylacetamido)-1H-pyrazole-1-carbonyl)-2,7-diazaspiro[3.5]nonane-7-carboxylate (250 mg, 0.64 mmol) in DCM (6 mL) was added TFA (0.49 mL, 6.4 mmol, 10 eq). The reaction mixture was stirred at this temperature for 4 h, then warmed to r.t. and stirred for an addition 16 h. Following this time, the reaction mixture was concentrated to give a brown oil. This material was suspended in 10 mL of toluene, then concentrated to ensure removal of excess TFA. This process was repeated an additional two times, yielding N-(1-(2,7-diazaspiro[3.5]nonane-2-carbonyl)-1H-pyrazol-4-yl)-N-methylacetamide; 2,2,2-trifluoroacetate (255 mg, 0.629 mmol, 99%) as a brown oil, which was used without further purification. LCMS (ESI, m/z): 292 [M+H]$^+$.

Step 4: Synthesis of N-methyl-N-(1-(7-(3-methylbenzyl)-2,7-diazaspiro[3.5]nonane-2-carbonyl)-1H-pyrazol-4-yl)acetamide

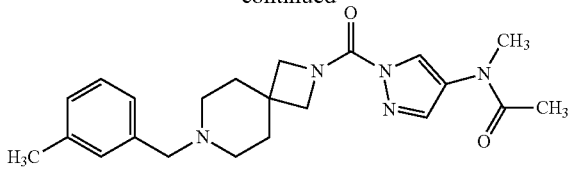

To a solution of N-[1-(2-aza-7-azoniaspiro[3.5]nonane-2-carbonyl)pyrazol-4-yl]-N-methylacetamide; 2,2,2-trifluoroacetate (72 mg, 0.18 mmol) in DCM (1 mL) were added sequentially N,N-diisopropylethylamine (34 μL, 0.2 mmol, 1.1 eq), 3-methylbenzaldehyde (41 μL, 0.36 mmol, 2 eq), and sodium triacetoxyborohydride (75 mg, 0.36 mmol, 2 eq). The reaction mixture was stirred at r.t. for 3 h. Following this time, the mixture was diluted to 5 mL with DCM, then quenched by the addition of saturated aqueous NaHCO₃ (5 mL). The biphasic mixture was stirred vigorously for 5 min, then transferred to a separatory funnel. The layers were separated and the aqueous layer was extracted with DCM (2×5 mL). The organic layers were combined, dried over Na₂SO₄, filtered, and concentrated. Purification by column chromatography on silica gel afforded N-methyl-N-(1-(7-(3-methylbenzyl)-2,7-diazaspiro[3.5]nonane-2-carbonyl)-1H-pyrazol-4-yl)acetamide (62 mg, 0.15 mmol, 86%) as a white foamy solid. H NMR (400 MHz, DMSO-d6, 100° C.) δ 8.32 (s, 1H), 7.87 (s, 1H), 7.19 (t, 1H, J=7.5 Hz), 7.13-7.02 (m, 3H), 4.02 (br s, 4H), 3.43 (s, 2H), 3.22 (s, 3H), 2.39-2.33 (m, 4H), 2.31 (s, 3H), 2.05 (s, 3H), 1.80-1.74 (m, 4H); LCMS (ESI, m/z): 396 [M+H]⁺.

Example 84: N-(1-(7-(4-chlorobenzyl)-2,7-diazaspiro[3.5]nonane-2-carbonyl)-1H-pyrazol-4-yl)-N-methylacetamide

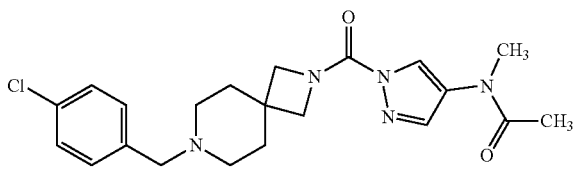 [SMILES: CC(=O)N(C)c1cnn(C(=O)N2CC3(CCN(Cc4ccc(Cl)cc4)CC3)C2)c1]

The title compound was synthesized as described in Example 83 using 4-chlorobenzaldehyde in Step 4. ¹H NMR (400 MHz, DMSO-d6, 100° C.) δ 8.32 (s, 1H), 7.87 (s, 1H), 7.37-7.285 (m, 4H), 4.02 (br s, 4H), 3.46 (s, 2H), 3.22 (s, 3H), 2.39-2.30 (m, 4H), 2.05 (s, 3H), 1.80-1.71 (m, 4H); LCMS (ESI, m/z): 416 [M+H]⁺.

Example 85: N-(1-(7-(3-chlorobenzyl)-2,7-diazaspiro[3.5]nonane-2-carbonyl)-1H-pyrazol-4-yl)-N-methylacetamide

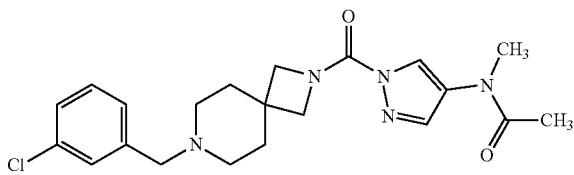 [SMILES: CC(=O)N(C)c1cnn(C(=O)N2CC3(CCN(Cc4cccc(Cl)c4)CC3)C2)c1]

The title compound was synthesized as described in Example 83 using 3-chlorobenzaldehyde in Step 4. ¹H NMR (400 MHz, CD₃CN) δ 8.30 (s, 0.5H), 8.18 (s, 0.5H), 7.92 (s, 0.5H), 7.64 (s, 0.5H), 7.36-7.20 (m, 4H), 4.32-4.19 (m, 2H), 3.85-3.74 (m, 2H), 3.43 (s, 2H), 3.30 (s, 1.5H), 3.10 (s, 1.5H), 2.48-2.22 (m, 4H), 2.18 (s, 1.5H, overlapping with water peak), 1.87 (s, 1.5H), 1.81-1.73 (m, 4H); LCMS (ESI, m/z): 416 [M+H]⁺.

Example 86: N-(1-(7-(2-chlorobenzyl)-2,7-diazaspiro[3.5]nonane-2-carbonyl)-1H-pyrazol-4-yl)-N-methylacetamide

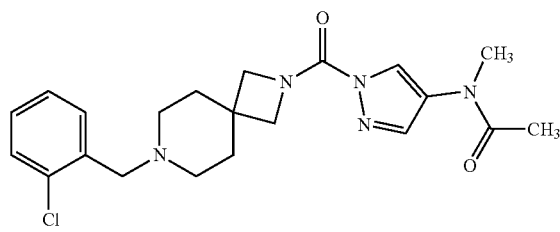 [SMILES: CC(=O)N(C)c1cnn(C(=O)N2CC3(CCN(Cc4ccccc4Cl)CC3)C2)c1]

The title compound was synthesized as described in Example 83 using 2-chlorobenzaldehyde in Step 4. ¹H NMR (400 MHz, DMSO-d6, 100° C.) δ 8.32 (s, 1H), 7.87 (s, 1H), 7.52-7.46 (m, 1H), 7.41-7.36 (m, 1H), 7.34-7.23 (m, 2H), 4.03 (br s, 4H), 3.58 (s, 2H), 3.22 (s, 3H), 2.46-2.39 (m, 4H—partially overlapping with DMSO peak), 2.05 (s, 3H), 1.82-1.74 (m, 4H); LCMS (ESI, m/z): 416 [M+H]⁺.

Example 87: N-methyl-N-(1-(7-(4-methylbenzyl)-2,7-diazaspiro[3.5]nonane-2-carbonyl)-1H-pyrazol-4-yl)acetamide

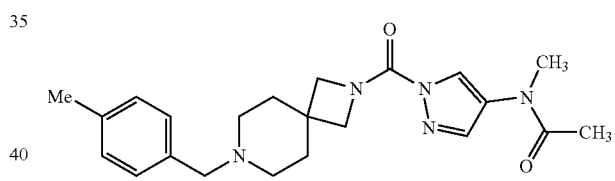

The title compound was synthesized as described in Example 83 using 4-methylbenzaldehyde in Step 4. ¹H NMR (400 MHz, DMSO-d6, 100° C.) δ 8.32 (s, 1H), 7.87 (s, 1H), 7.17 (d, 2H, J=8.0 Hz), 7.11 (d, 2H, J=8.0 Hz), 4.02 (br s, 4H), 3.42 (s, 2H), 3.22 (s, 3H), 2.37-2.31 (m, 4H), 2.29 (s, 3H), 2.05 (s, 3H), 1.80-1.72 (m, 4H); LCMS (ESI, m/z): 396 [M+H]⁺.

Example 88: N-methyl-N-(1-(7-(3-(trifluoromethyl)benzyl)-2,7-diazaspiro[3.5]nonane-2-carbonyl)-1H-pyrazol-4-yl)acetamide

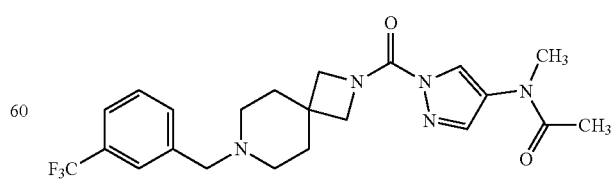

The title compound was synthesized as described in Example 83 using 3-(trifluoromethyl)benzaldehyde in Step 4. ¹H NMR (400 MHz, DMSO-d6, 100° C.) δ 8.32 (s, 1H), 7.87 (s, 1H), 7.64-7.53 (m, 4H), 4.03 (br s, 4H), 3.58 (s, 2H), 3.22 (s, 3H), 2.41-2.35 (m, 4H), 2.05 (s, 3H), 1.82-1.74 (m, 4H); LCMS (ESI, m/z): 450 [M+H]+.

Example 89: N-methyl-N-(1-(7-(2-methylbenzyl)-2,7-diazaspiro[3.5]nonane-2-carbonyl)-1H-pyrazol-4-yl)acetamide

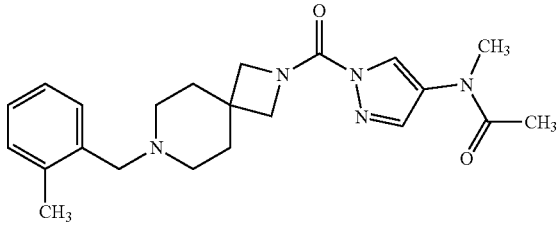

The title compound was synthesized as described in Example 83 using 2-methylbenzaldehyde in Step 4. ¹H NMR (400 MHz, DMSO-d6, 100° C.) δ 8.32 (s, 1H), 7.87 (s, 1H), 7.26-7.21 (m, 1H), 7.16-7.08 (m, 3H), 4.03 (br s, 4H), 3.44 (s, 2H), 3.22 (s, 3H), 2.40-2.34 (m, 4H), 2.33 (s, 3H), 2.05 (s, 3H), 1.80-1.72 (m, 4H); LCMS (ESI, m/z): 396 [M+H]+.

Example 90: N-methyl-N-(1-(7-(2-(trifluoromethyl)benzyl)-2,7-diazaspiro[3.5]nonane-2-carbonyl)-1H-pyrazol-4-yl)acetamide

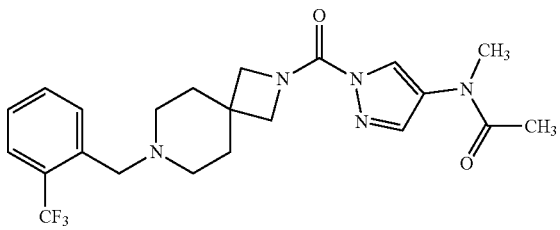 [SMILES: CC(=O)N(C)c1cnn(C(=O)N2CC3(CCN(Cc4ccccc4C(F)(F)F)CC3)C2)c1]

The title compound was synthesized as described in Example 83 using 2-(trifluoromethyl)benzaldehyde in Step 4. ¹H NMR (400 MHz, CD₃CN) δ 8.31 (s, 0.5H), 8.18 (s, 0.5H), 7.92 (s, 0.5H), 7.79 (d, 1H, J=7.8 Hz), 7.66 (s, 0.5H), 7.64 (s, 1H), 7.58 (t, 1H, J=7.6 Hz), 7.38 (t, 1H, J=7.6 Hz), 4.31-4.22 (m, 2H), 3.85-3.76 (m, 2H), 3.60 (s, 2H), 3.30 (s, 1.5H), 3.10 (s, 1.5H), 2.36 (br s, 4H), 2.18 (s, 1.5H), 1.87 (s, 1.5H), 1.82-1.74 (m, 4H); LCMS (ESI, m/z): 450 [M+H]+.

Example 91: N-methyl-N-(1-(5-(4-methylbenzyl)octahydropyrrolo[3,4-c]pyrrole-2-carbonyl)-1H-pyrazol-4-yl)acetamide

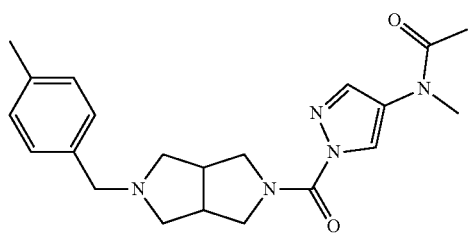 [SMILES: CC(=O)N(C)c1cnn(C(=O)N2CC3CN(Cc4ccc(C)cc4)CC3C2)c1]

The title compound was synthesized as described in Example 83 using tert-butyl hexahydropyrrolo[3,4-c]pyrrole-2(1H)-carboxylate in Step 1 and 4-methylbenzaldehyde in Step 4. ¹H NMR (400 MHz, Acetonitrile-d₃) δ 8.33 (s, 1H), 8.19 (s, 1H), 7.92 (s, 1H), 7.64 (s, 1H), 7.20-7.07 (m, 8H), 4.10-3.62 (m, 8H), 3.51 (s, 4H), 3.32 (s, 3H), 3.13 (s, 3H), 2.83 (s, 4H), 2.56-2.44 (m, 8H), 2.29 (s, 6H), 2.20 (s, 3H), 1.90 (s, 3H). LCMS (ESI, m/z): 382 [M+H]+.

Example 92: N-methyl-N-(1-(5-(3-methylbenzyl)octahydropyrrolo[3,4-c]pyrrole-2-carbonyl)-1H-pyrazol-4-yl)acetamide

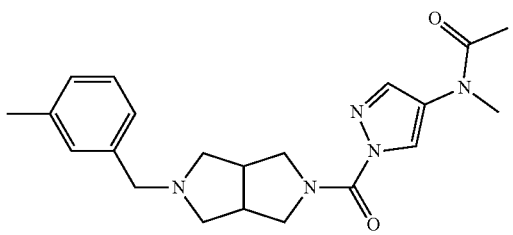 [SMILES: CC(=O)N(C)c1cnn(C(=O)N2CC3CN(Cc4cccc(C)c4)CC3C2)c1]

The title compound was synthesized as described in Example 83 using tert-butyl hexahydropyrrolo[3,4-c]pyrrole-2(1H)-carboxylate in Step 1 and 3-methylbenzaldehyde in Step 4 to provide N-methyl-N-(1-(5-(3-methylbenzyl)octahydropyrrolo[3,4-c]pyrrole-2-carbonyl)-1H-pyrazol-4-yl)acetamide as a white solid. ¹H NMR (400 MHz, DMSO-d, 100° C.) δ 8.54 (s, 1H), 8.07 (s, 1H), 7.38 (t, J=7.4 Hz, 1H), 7.34-7.21 (m, 3H), 4.15 (dd, J=11.6, 8.3 Hz, 2H), 3.91 (dd, J=12.0, 3.5 Hz, 2H), 3.77 (s, 2H), 3.44 (s, 3H), 3.11-3.00 (m, 2H), 2.82 (dd, J=9.2, 6.3 Hz, 2H), 2.77-2.67 (m, 5H), 2.26 (s, 3H). LCMS (ESI, m/z): 382 [M+H]+.

Example 93: N-methyl-N-(1-(5-(4-(pyrrolidin-1-yl)-2-(trifluoromethyl)benzyl)octahydropyrrolo[3,4-c]pyrrole-2-carbonyl)-1H-pyrazol-4-yl)acetamide

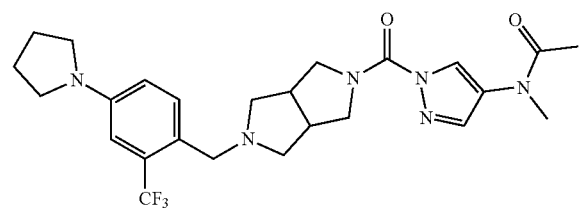 [SMILES: CC(=O)N(C)c1cnn(C(=O)N2CC3CN(Cc4ccc(N5CCCC5)cc4C(F)(F)F)CC3C2)c1]

The title compound was synthesized as described in Example 83 using tert-butyl hexahydropyrrolo[3,4-c]pyrrole-2(1H)-carboxylate in Step 1 and 4-(pyrrolidin-1-yl)-2-(trifluoromethyl)benzaldehyde (synthesized as described in Example 67, Step 1) in Step 4. Purification resulted in 140 mg of N-methyl-N-(1-(5-(4-(pyrrolidin-1-yl)-2-(trifluoromethyl)benzyl)octahydropyrrolo[3,4-c]pyrrole-2-carbonyl)-1H-pyrazol-4-yl)acetamide as a white solid. ¹H NMR (300 MHz, Chloroform-d) δ 8.29 (s, 0.3H), 8.19 (s, 0.7H), 8.04 (s, 0.3H), 7.54 (s, 0.7H), 7.44-7.47 (m, 1H), 6.74-6.75 (m, 1H), 6.62-6.65 (m, 1H), 3.67-4.12 (m, 6H), 3.22-3.36 (m, 7H), 2.63-2.98 (m, 6H), 2.28 (s, 1H), 2.00-2.04 (m, 6H). LCMS (ESI, m/z): 505 [M+H]+.

Example 94: N-methyl-N-(1-(5-(2-methylbenzyl)octahydropyrrolo[3,4-c]pyrrole-2-carbonyl)-1H-pyrazol-4-yl)acetamide

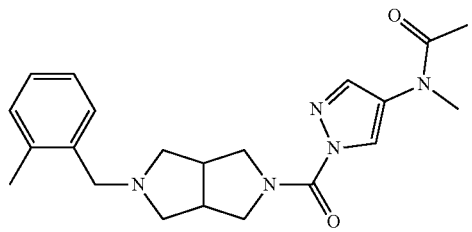 [SMILES: CC(=O)N(C)c1cnn(C(=O)N2CC3CN(Cc4ccccc4C)CC3C2)c1]

The title compound was synthesized as described in Example 83 using tert-butyl hexahydropyrrolo[3,4-c]pyrrole-2(1H)-carboxylate in Step 1 and 2-methylbenzaldehyde in Step 4 to provide N-methyl-N-(1-(5-(2-methylbenzyl)octahydropyrrolo[3,4-c]pyrrole-2-carbonyl)-1H-pyrazol-4-yl)acetamide as an off-white solid. $^1$H NMR (400 MHz, DMSO-d$_6$, 100° C.) δ 8.51 (d, J=0.9 Hz, 1H), 8.05 (s, 1H), 7.46-7.39 (m, 1H), 7.39-7.25 (m, 3H), 4.14 (dd, J=11.8, 8.0 Hz, 2H), 3.87 (dd, J=12.0, 3.4 Hz, 2H), 3.77 (s, 2H), 3.42 (s, 3H), 3.08-3.00 (m, 2H), 2.84-2.62 (m, 7H), 2.25 (s, 3H). LCMS (ESI, m/z): 382 [M+H]$^+$.

Example 95: N-(1-(5-(3-chloro-4-morpholinobenzyl)octahydropyrrolo[3,4-c]pyrrole-2-carbonyl)-1H-pyrazol-4-yl)-N-methylacetamide

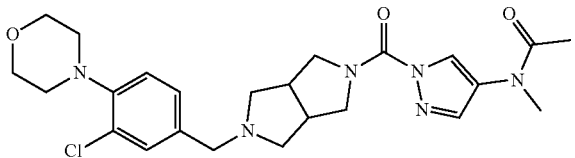 [SMILES: CC(=O)N(C)c1cnn(C(=O)N2CC3CN(Cc4ccc(N5CCOCC5)c(Cl)c4)CC3C2)c1]

The title compound was synthesized as described in Example 83 using tert-butyl hexahydropyrrolo[3,4-c]pyrrole-2(1H)-carboxylate in Step 1 and 3-chloro-4-morpholinobenzaldehyde (synthesized as described in Example 67, Step 1) in Step 4. Purification resulted in 189.2 mg of N-(1-(5-(3-chloro-4-morpholinobenzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.29 (s, 0.3H), 8.20 (s, 0.7H), 8.04 (s, 0.3H), 7.55 (s, 0.7H), 7.32 (s, 1H), 7.16-7.18 (m, 1H), 6.97 (d, J=8.4 Hz, 1H), 4.06 (br, 2H), 3.62-3.91 (m, 6H), 3.53 (s, 2H), 3.36 (s, 1H), 3.22 (s, 2H), 3.02-3.06 (m, 4H), 2.90 (br, 2H), 2.50-2.63 (m, 4H), 2.28 (s, 1H), 2.00 (s, 2H). LCMS (ESI, m/z): 487 [M+H]$^+$.

Example 96: N-methyl-N-(1-(5-(2-(trifluoromethyl)benzyl)octahydropyrrolo[3,4-c]pyrrole-2-carbonyl)-1H-pyrazol-4-yl)acetamide

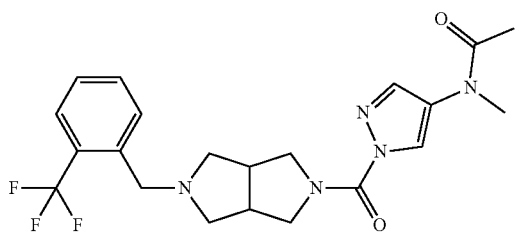 [SMILES: CC(=O)N(C)c1cnn(C(=O)N2CC3CN(Cc4ccccc4C(F)(F)F)CC3C2)c1]

The title compound was synthesized as described in Example 83 using tert-butyl hexahydropyrrolo[3,4-c]pyrrole-2(1H)-carboxylate in Step 1 and 2-(trifluoromethyl)benzaldehyde in Step 4 to provide N-methyl-N-(1-(5-(2-(trifluoromethyl)benzyl)octahydropyrrolo[3,4-c]pyrrole-2-carbonyl)-1H-pyrazol-4-yl)acetamide as a colorless resin. $^1$H NMR (400 MHz, Acetonitrile-d$_3$) δ 8.34 (s, 1H), 8.19 (s, 1H), 7.93 (s, 1H), 7.76 (d, J=7.8 Hz, 2H), 7.65 (d, J=7.2 Hz, 3H), 7.57 (t, J=7.7 Hz, 2H), 7.39 (t, J=7.8 Hz, 2H), 3.98 (s, 4H), 3.75 (s, 8H), 3.32 (d, J=2.0 Hz, 3H), 3.13 (s, 3H), 2.87 (s, 4H), 2.63 (d, J=9.2 Hz, 4H), 2.53 (t, J=7.4 Hz, 4H), 2.23-2.16 (m, 3H), 1.90 (s, 3H). LCMS (ESI, m/z): 436 [M+H]$^+$.

Example 97: N-methyl-N-(1-(5-(4-(pyrrolidin-1-yl)-3-(trifluoromethyl)benzyl)octahydropyrrolo[3,4-c]pyrrole-2-carbonyl)-1H-pyrazol-4-yl)acetamide

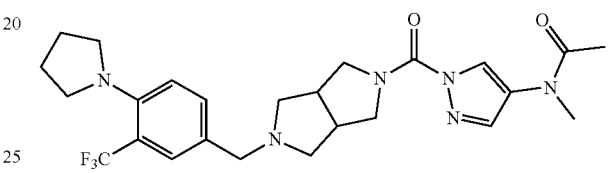

The title compound was synthesized as described in Example 83 using tert-butyl hexahydropyrrolo[3,4-c]pyrrole-2(1H)-carboxylate in Step 1 and 4-(pyrrolidin-1-yl)-3-(trifluoromethyl)benzaldehyde (synthesized as described in Example 67, Step 1) in Step 4. Purification resulted in 143.9 mg of N-methyl-N-(1-(5-(4-(pyrrolidin-1-yl)-3-(trifluoromethyl)benzyl)octahydropyrrolo[3,4-c]pyrrole-2-carbonyl)-1H-pyrazol-4-yl)acetamide as an orange oil. $^1$H NMR (400 MHz, Chloroform-d) δ 8.30 (s, 0.3H), 8.20 (s, 0.7H), 8.05 (s, 0.3H), 7.56 (s, 0.7H), 7.48 (s, 1H), 7.31-7.33 (m, 1H), 6.93 (d, J=8.8 Hz, 1H), 3.76-4.20 (m, 4H), 3.54 (s, 2H), 3.37 (s, 1H), 3.30-3.33 (m, 4H), 3.23 (s, 2H), 2.91 (br, 2H), 2.50-2.64 (m, 4H), 2.30 (s, 1H), 1.84-2.10 (m, 6H). LCMS (ESI, m/z): 505 [M+H]$^+$.

Example 98: N-(1-(5-(4-chloro-3-(trifluoromethyl)benzyl)octahydropyrrolo[3,4-c]pyrrole-2-carbonyl)-1H-pyrazol-4-yl)-N-methylacetamide

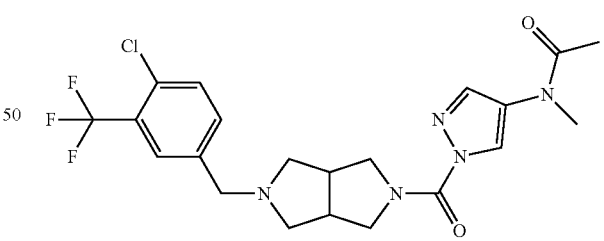

The title compound was synthesized as described in Example 83 using tert-butyl hexahydropyrrolo[3,4-c]pyrrole-2(1H)-carboxylate in Step 1 and 4-chloro-3-(trifluoromethyl)benzaldehyde in Step 4 to provide N-(1-(5-(4-chloro-3-(trifluoromethyl)benzyl)octahydropyrrolo[3,4-c]pyrrole-2-carbonyl)-1H-pyrazol-4-yl)-N-methylacetamide as a white foam. $^1$H NMR (400 MHz, CDCl$_3$) δ 8.31-8.25 (m, 0.33H), 8.21-8.16 (m, 0.66H), 8.03 (s, 0.33H), 7.64-7.57 (m, 1H), 7.54 (d, J=1.0 Hz, 0.66H), 7.45-7.40 (m, 2H), 4.33-3.70 (m, 4H), 3.63-3.56 (m, 2H), 3.35 (s, 1H), 3.21 (s, 2H), 2.90 (s, 2H), 2.67-2.47 (m, 4H), 2.28 (s, 1H), 1.99 (s, 2H). LCMS (ESI, m/z): 470 [M+H]$^+$.

Example 99: N-methyl-N-(1-(5-(4-morpholino-3-(trifluoromethyl)benzyl)octahydropyrrolo[3,4-c]pyrrole-2-carbonyl)-1H-pyrazol-4-yl)acetamide

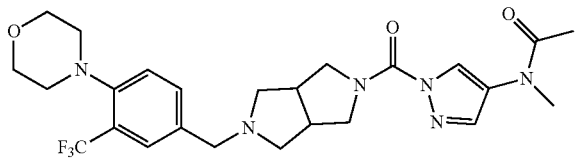 [SMILES: CC(=O)N(C)c1cnn(C(=O)N2CC3CN(Cc4ccc(N5CCOCC5)c(C(F)(F)F)c4)CC3C2)c1]

The title compound was synthesized as described in Example 83 using tert-butyl hexahydropyrrolo[3,4-c]pyrrole-2(1H)-carboxylate in Step 1 and 4-morpholino-3-(trifluoromethyl)benzaldehyde (synthesized as described in Example 67, Step 1) in Step 4. Purification resulted in 111.7 mg of N-methyl-N-(1-(5-(4-morpholino-3-(trifluoromethyl)benzyl)octahydropyrrolo[3,4-c]pyrrole-2-carbonyl)-1H-pyrazol-4-yl)acetamide as an off-white solid. $^1$H NMR (400 MHz, Chloroform-d) δ 8.30 (s, 0.3H), 8.21 (s, 0.7H), 8.06 (s, 0.3H), 7.55-7.57 (m, 1.7H), 7.49-7.50 (m, 1H), 7.32 (d, J=8.4 Hz, 1H), 3.68-4.24 (m, 8H), 3.60-3.61 (m, 2H), 3.38 (s, 1H), 3.23 (s, 2H), 2.91-2.93 (m, 6H), 2.53-2.64 (m, 4H), 2.30 (s, 1H), 2.01 (s, 2H). LCMS (ESI, m/z): 521 [M+H]$^+$.

Example 100: N-(1-(5-(4-fluoro-3-(pyrrolidin-1-yl)benzyl)octahydropyrrolo[3,4-c]pyrrole-2-carbonyl)-1H-pyrazol-4-yl)-N-methylacetamide

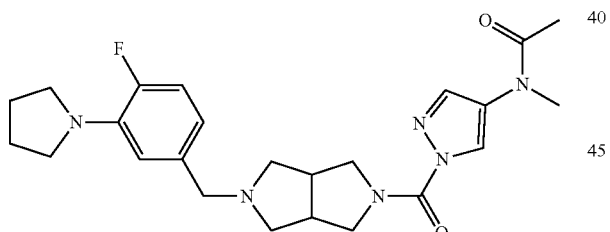

The title compound was synthesized as described in Example 83 using tert-butyl hexahydropyrrolo[3,4-c]pyrrole-2(1H)-carboxylate in Step 1 and 4-fluoro-3-(pyrrolidin-1-yl)benzaldehyde (synthesized as described in Example 63, Step 1) in Step 4 to provide N-(1-(5-(4-fluoro-3-(pyrrolidin-1-yl)benzyl)octahydropyrrolo[3,4-c]pyrrole-2-carbonyl)-1H-pyrazol-4-yl)-N-methylacetamide as a pale yellow resin. $^1$H NMR (400 MHz, Chloroform-d) δ 8.28 (s, 0.33H), 8.18 (s, 0.66H), 8.03 (s, 0.33H), 7.54 (s, 0.66H), 6.87 (dd, J=13.6, 8.0 Hz, 1H), 6.61 (dd, J=9.0, 2.0 Hz, 1H), 6.59-6.51 (m, 1H), 4.34-3.57 (m, 4H), 3.52-3.46 (m, 2H), 3.42-3.28 (m, 5H), 3.21 (s, 2H), 2.87 (s, 2H), 2.64-2.47 (m, 4H), 2.28 (s, 1H), 1.98 (s, 2H), 1.94-1.88 (m, 4H). LCMS (ESI, m/z): 455 [M+H]$^+$.

Example 101: N-(1-(5-(4-(8-oxa-3-azabicyclo[3.2.1]octan-3-yl)-2-(trifluoromethyl)benzyl)octahydropyrrolo[3,4-c]pyrrole-2-carbonyl)-1H-pyrazol-4-yl)-N-methylacetamide

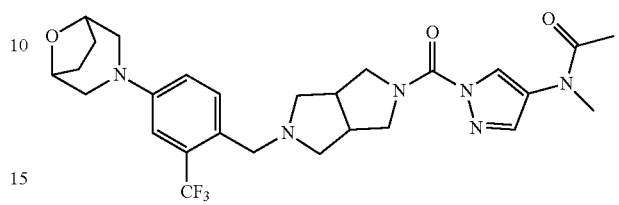

The title compound was synthesized as described in Example 83 using tert-butyl hexahydropyrrolo[3,4-c]pyrrole-2(1H)-carboxylate in Step 1 and 4-(8-oxa-3-azabicyclo[3.2.1]octan-3-yl)-2-(trifluoromethyl)benzaldehyde (synthesized as described in Example 67, Step 1) in Step 4. Purification resulted in 149.8 mg of N-(1-(5-(4-(8-oxa-3-azabicyclo[3.2.1]octan-3-yl)-2-(trifluoromethyl)benzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.30 (s, 0.3H), 8.19 (s, 0.7H), 8.04 (s, 0.3H), 7.51-7.55 (m, 1.7H), 7.00 (s, 1H), 6.88-6.91 (m, 1H), 4.50 (s, 2H), 3.54-4.24 (m, 6H), 3.32-3.36 (m, 3H), 3.22 (s, 2H), 3.01-3.05 (m, 2H), 2.90 (br, 2H), 2.56-2.66 (m, 4H), 2.28 (s, 1H), 1.88-2.00 (m, 6H). LCMS (ESI, m/z): 547 [M+H]$^+$.

Example 102: N-(1-(5-(4-(3-oxa-8-azabicyclo[3.2.1]octan-8-yl)-2-(trifluoromethyl)benzyl)octahydropyrrolo[3,4-c]pyrrole-2-carbonyl)-1H-pyrazol-4-yl)-N-methylacetamide

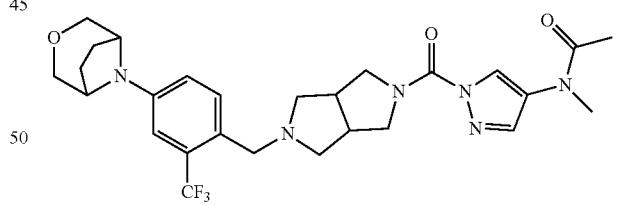

The title compound was synthesized as described in Example 83 using tert-butyl hexahydropyrrolo[3,4-c]pyrrole-2(1H)-carboxylate in Step 1 and 4-(3-oxa-8-azabicyclo[3.2.1]octan-8-yl)-2-(trifluoromethyl)benzaldehyde (synthesized as described in Example 67, Step 1) in Step 4. Purification resulted in 58 mg of N-(1-(5-(4-(3-oxa-8-azabicyclo[3.2.1]octan-8-yl)-2-(trifluoromethyl)benzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.30 (s, 0.3H), 8.19 (s, 0.7H), 8.04 (s, 0.3H), 7.49-7.61 (m, 1.7H), 6.97 (s, 1H), 6.86-6.89 (m, 1H), 4.07-4.38 (m, 4H), 3.66-3.89 (m, 6H), 3.53-3.57 (m, 2H), 3.36 (s, 1H), 3.22 (s, 2H), 2.90 (br, 2H), 2.64-2.67 (m, 2H), 2.56 (br, 2H), 2.28 (s, 1H), 2.00-2.13 (m, 6H). LCMS (ESI, m/z): 547 [M+H]⁺.

Example 103: N-(1-(5-(3-chloro-2-methylbenzyl) octahydropyrrolo[3,4-c]pyrrole-2-carbonyl)-1H-pyrazol-4-yl)-N-methylacetamide

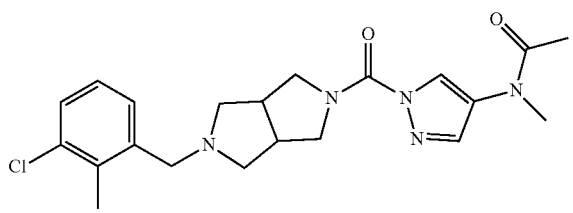 [SMILES: CC(=O)N(C)c1cnn(C(=O)N2CC3CN(Cc4cccc(Cl)c4C)CC3C2)c1]

The title compound was synthesized as described in Example 83 using tert-butyl hexahydropyrrolo[3,4-c]pyrrole-2(1H)-carboxylate in Step 1 and 3-chloro-2-methylbenzaldehyde in Step 4. Purification resulted in 54.4 mg of N-(1-(5-(3-chloro-2-methylbenzyl)octahydropyrrolo[3,4-c]pyrrole-2-carbonyl)-1H-pyrazol-4-yl)-N-methylacetamide as a white solid. ¹H NMR (300 MHz, Chloroform-d) δ 8.27 (s, 0.3H), 8.18 (s, 0.7H), 8.04 (s, 0.3H), 7.54 (s, 0.7H), 7.28 (d, J=7.8 Hz, 1H), 7.03-7.15 (m, 2H), 3.62-4.06 (m, 6H), 3.36 (s, 1H), 3.22 (s, 2H), 2.90 (br, 2H), 2.60 (br, 4H), 2.38 (s, 3H), 2.28 (s, 1H), 1.99 (s, 2H). LCMS (ESI, m/z): 416 [M+H]⁺.

Example 104: N-(1-(5-(5-chloro-2-(trifluoromethyl)benzyl)octahydropyrrolo[3,4-c]pyrrole-2-carbonyl)-1H-pyrazol-4-yl)-N-methylacetamide

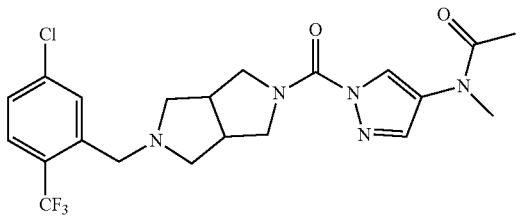 [SMILES: CC(=O)N(C)c1cnn(C(=O)N2CC3CN(Cc4cc(Cl)ccc4C(F)(F)F)CC3C2)c1]

The title compound was synthesized as described in Example 83 using tert-butyl hexahydropyrrolo[3,4-c]pyrrole-2(1H)-carboxylate in Step 1 and 5-chloro-2-(trifluoromethyl)benzaldehyde in Step 4. Purification resulted in 102.3 mg of N-(1-(5-(5-chloro-2-(trifluoromethyl)benzyl)octahydropyrrolo[3,4-c]pyrrole-2-carbonyl)-1H-pyrazol-4-yl)-N-methylacetamide as an off-white semi-solid. ¹H NMR (400 MHz, Chloroform-d) δ 8.30 (s, 0.3H), 8.22 (s, 0.7H), 8.07 (s, 0.3H), 7.74 (s, 1H), 7.56-7.57 (m, 1H), 7.54 (s, 0.7H), 7.30-7.32 (m, 1H), 3.75-4.26 (m, 6H), 3.37 (s, 1H), 3.22 (s, 2H), 2.94 (br, 2H), 2.65-2.66 (m, 4H), 2.29 (s, 1H), 2.00 (s, 2H). LCMS (ESI, m/z): 470 [M+H]⁺.

Example 105: N-(1-(5-(3,5-dichlorobenzyl)octahydropyrrolo[3,4-c]pyrrole-2-carbonyl)-1H-pyrazol-4-yl)-N-methylacetamide

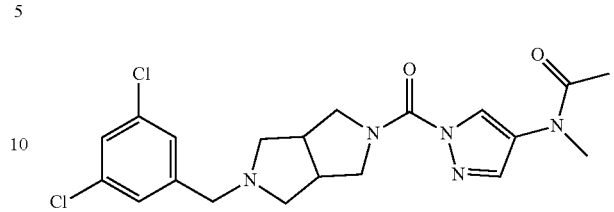

The title compound was synthesized as described in Example 83 using tert-butyl hexahydropyrrolo[3,4-c]pyrrole-2(1H)-carboxylate in Step 1 and 3,5-dichlorobenzaldehyde in Step 4. Purification resulted in 144.6 mg of N-(1-(5-(3,5-dichlorobenzyl)octahydropyrrolo[3,4-c]pyrrole-2-carbonyl)-1H-pyrazol-4-yl)-N-methylacetamide as a light yellow oil. ¹H NMR (400 MHz, Chloroform-d) δ 8.31 (s, 0.3H), 8.22 (s, 0.7H), 8.08 (s, 0.3H), 7.57 (s, 0.7H), 7.25 (s, 1H), 7.22 (s, 2H), 3.74-4.25 (m, 4H), 3.55-3.56 (m, 2H), 3.38 (s, 1H), 3.24 (s, 2H), 2.92 (br, 2H), 2.53-2.62 (m, 4H), 2.30 (s, 1H), 2.01 (s, 2H). LCMS (ESI, m/z): 436 [M+H]⁺.

Example 106: N-(1-(5-(2-chloro-5-(trifluoromethyl)benzyl)octahydropyrrolo[3,4-c]pyrrole-2-carbonyl)-1H-pyrazol-4-yl)-N-methylacetamide

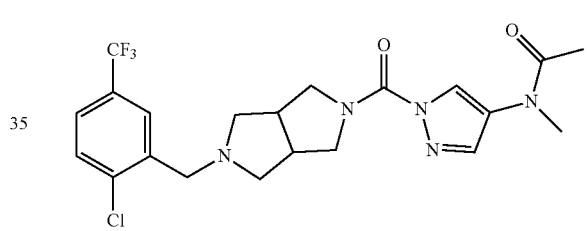

The title compound was synthesized as described in Example 83 using tert-butyl hexahydropyrrolo[3,4-c]pyrrole-2(1H)-carboxylate in Step 1 and 2-chloro-5-(trifluoromethyl)benzaldehyde in Step 4. Purification resulted in 188.3 mg of N-(1-(5-(2-chloro-5-(trifluoromethyl)benzyl)octahydropyrrolo[3,4-c]pyrrole-2-carbonyl)-1H-pyrazol-4-yl)-N-methylacetamide as a yellow oil. ¹H NMR (300 MHz, Chloroform-d) δ 8.28 (s, 0.3H), 8.20 (s, 0.7H), 8.05 (s, 0.3H), 7.73 (s, 1H), 7.55 (s, 0.7H), 7.42-7.48 (m, 2H), 3.77-4.08 (m, 6H), 3.36 (s, 1H), 3.22 (s, 2H), 2.94 (br, 2H), 2.60-2.68 (m, 4H), 2.28 (s, 1H), 2.00 (s, 2H). LCMS (ESI, m/z): 470 [M+H]⁺.

Example 107: N-(1-(5-(2,3-dichlorobenzyl)octahydropyrrolo[3,4-c]pyrrole-2-carbonyl)-1H-pyrazol-4-yl)-N-methylacetamide

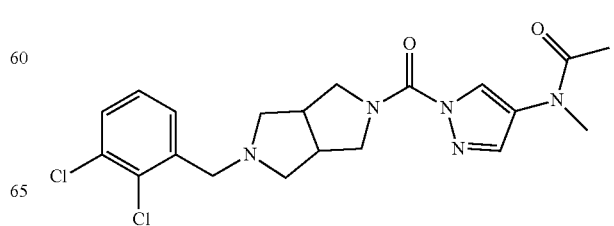

The title compound was synthesized as described in Example 83 using tert-butyl hexahydropyrrolo[3,4-c]pyrrole-2(1H)-carboxylate in Step 1 and 2,3-dichlorobenzaldehyde in Step 4. Purification resulted in 164.0 mg of N-(1-(5-(2,3-dichlorobenzyl)octahydropyrrolo[3,4-c]pyrrole-2-carbonyl)-1H-pyrazol-4-yl)-N-methylacetamide as a light yellow oil. $^1$H NMR (400 MHz, Chloroform-d) δ 8.31 (s, 0.3H), 8.21 (s, 0.7H), 8.07 (s, 0.3H), 7.57 (s, 0.7H), 7.36-7.41 (m, 2H), 7.19 (t, J=7.8 Hz, 1H), 3.90-4.30 (m, 3H), 3.76-3.77 (m, 3H), 3.38 (s, 1H), 3.24 (s, 2H), 2.93 (br, 2H), 2.68-2.69 (m, 4H), 2.30 (s, 1H), 2.02 (s, 2H). LCMS (ESI, m/z): 436 [M+H]$^+$.

Example 108: N-(1-(5-(3,5-dimethylbenzyl)octahydropyrrolo[3,4-c]pyrrole-2-carbonyl)-1H-pyrazol-4-yl)-N-methylacetamide

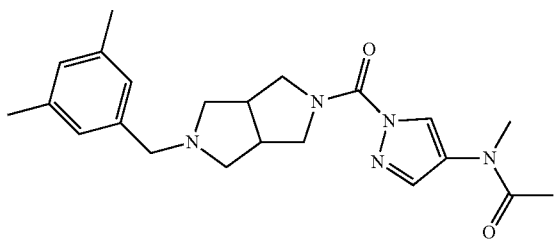 [SMILES: CC(=O)N(C)c1cnn(C(=O)N2CC3CN(Cc4cc(C)cc(C)c4)CC3C2)c1]

The title compound was synthesized as described in Example 83 using tert-butyl hexahydropyrrolo[3,4-c]pyrrole-2(1H)-carboxylate in Step 1 and 3,5-dimethylbenzaldehyde in Step 4 to provide N-(1-(5-(3,5-dimethylbenzyl)octahydropyrrolo[3,4-c]pyrrole-2-carbonyl)-1H-pyrazol-4-yl)-N-methylacetamide as a yellow oil. $^1$H NMR (400 MHz, Chloroform-d) δ 8.48-7.45 (m, 2H), 6.96-6.87 (m, 3H), 4.33-3.63 (m, 4H), 3.57-3.47 (m, 2H), 3.37 (s, 1H), 3.22 (s, 2H), 2.99-2.79 (m, 2H), 2.77-2.62 (m, 2H), 2.58-2.43 (m, 2H), 2.38-2.23 (m, 7H), 2.05-1.94 (m, 2H). LCMS (ESI, m/z): 396 [M+H]$^+$.

Example 109: N-(1-(5-(2,5-dichlorobenzyl)octahydropyrrolo[3,4-c]pyrrole-2-carbonyl)-1H-pyrazol-4-yl)-N-methylacetamide

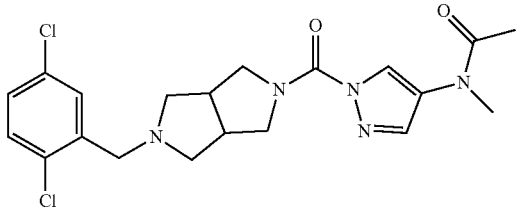 [SMILES: CC(=O)N(C)c1cnn(C(=O)N2CC3CN(Cc4cc(Cl)ccc4Cl)CC3C2)c1]

The title compound was synthesized as described in Example 83 using tert-butyl hexahydropyrrolo[3,4-c]pyrrole-2(1H)-carboxylate in Step 1 and 2,5-dichlorobenzaldehyde in Step 4. Purification resulted in 167.9 mg of N-(1-(5-(2,5-dichlorobenzyl)octahydropyrrolo[3,4-c]pyrrole-2-carbonyl)-1H-pyrazol-4-yl)-N-methylacetamide as a light yellow oil. $^1$H NMR (400 MHz, Chloroform-d) δ 8.30 (s, 0.3H), 8.22 (s, 0.7H), 8.08 (s, 0.3H), 7.57 (s, 0.7H), 7.45-7.46 (m, 1H), 7.27 (s, 1H), 7.16-7.19 (m, 1H), 3.77-4.27 (m, 4H), 3.70-3.71 (m, 2H), 3.38 (s, 1H), 3.23 (s, 2H), 2.94 (br, 2H), 2.62-2.71 (m, 4H), 2.30 (s, 1H), 2.02 (s, 2H). LCMS (ESI, m/z): 436 [M+H]$^+$.

Example 110: N-(1-(5-(3-chloro-5-(pyrrolidin-1-yl)benzyl)octahydropyrrolo[3,4-c]pyrrole-2-carbonyl)-1H-pyrazol-4-yl)-N-methylacetamide

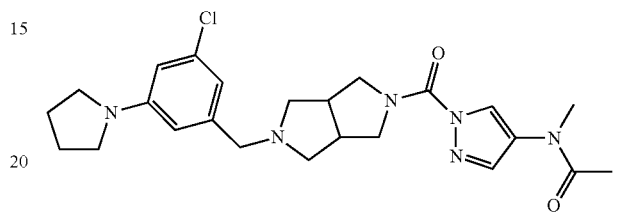

The title compound was synthesized as described in Example 83 using tert-butyl hexahydropyrrolo[3,4-c]pyrrole-2(1H)-carboxylate in Step 1 and 3-chloro-5-(pyrrolidin-1-yl)benzaldehyde (synthesized as described in Example 67, Step 1) in Step 4 to provide N-(1-(5-(3-chloro-5-(pyrrolidin-1-yl)benzyl)octahydropyrrolo[3,4-c]pyrrole-2-carbonyl)-1H-pyrazol-4-yl)-N-methylacetamide as a yellow oil. $^1$H NMR (400 MHz, Chloroform-d) δ 8.43-7.44 (m, 2H), 6.57 (s, 1H), 6.47-6.35 (m, 2H), 4.27-3.67 (m, 4H), 3.53 (s, 2H), 3.37 (s, 1H), 3.32-3.17 (m, 6H), 3.00-2.77 (m, 2H), 2.76-2.49 (m, 4H), 2.30 (s, 1H), 2.09-1.94 (m, 6H). LCMS (ESI, m/z): 471 [M+H]$^+$.

Example 111: N-(1-(5-(2,6-dichlorobenzyl)octahydropyrrolo[3,4-c]pyrrole-2-carbonyl)-1H-pyrazol-4-yl)-N-methylacetamide

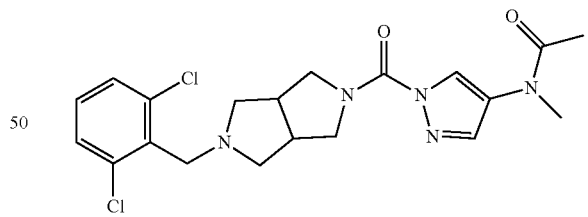

The title compound was synthesized as described in Example 83 using tert-butyl hexahydropyrrolo[3,4-c]pyrrole-2(1H)-carboxylate in Step 1 and 2,6-dichlorobenzaldehyde in Step 4. Purification resulted in 99.5 mg of N-(1-(5-(2,6-dichlorobenzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.26 (s, 0.3H), 8.16 (s, 0.7H), 8.03 (s, 0.3H), 7.53 (s, 0.7H), 7.29 (d, J=8.1 Hz, 2H), 7.11-7.17 (m, 1H), 3.72-4.09 (m, 6H), 3.35 (s, 1H), 3.21 (s, 2H), 2.67-2.97 (m, 6H), 2.28 (s, 1H), 1.99 (s, 2H). LCMS (ESI, m/z): 436 [M+H]$^+$.

Example 112: N-methyl-N-(1-(5-(3-(pyrrolidin-1-yl)-5-(trifluoromethyl)benzyl)octahydropyrrolo[3,4-c]pyrrole-2-carbonyl)-1H-pyrazol-4-yl)acetamide

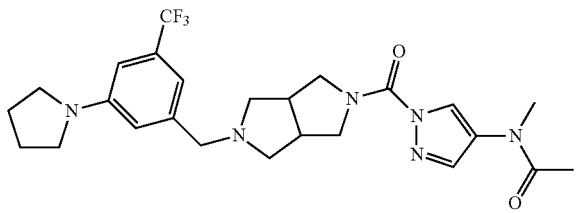

The title compound was synthesized as described in Example 83 using tert-butyl hexahydropyrrolo[3,4-c]pyrrole-2(1H)-carboxylate in Step 1 and 3-(pyrrolidin-1-yl)-5-(trifluoromethyl)benzaldehyde (synthesized as described in Example 67, Step 1) in Step 4 to provide N-methyl-N-(1-(5-(3-(pyrrolidin-1-yl)-5-(trifluoromethyl)benzyl)octahydropyrrolo[3,4-c]pyrrole-2-carbonyl)-1H-pyrazol-4-yl)acetamide as a yellow oil. $^1$H NMR (400 MHz, Chloroform-d) δ 8.39-7.45 (m, 2H), 6.87-6.79 (m, 1H), 6.73-6.60 (m, 2H), 4.35-3.69 (m, 4H), 3.64-3.53 (m, 2H), 3.44-3.17 (m, 6H), 3.03-2.83 (m, 2H), 2.79-2.49 (m, 4H), 2.30 (s, 2H), 2.12-1.94 (m, 6H). LCMS (ESI, m/z): 505 [M+H]$^+$.

Example 113: N-(1-(5-(2,4-dichlorobenzyl)octahydropyrrolo[3,4-c]pyrrole-2-carbonyl)-1H-pyrazol-4-yl)-N-methylacetamide

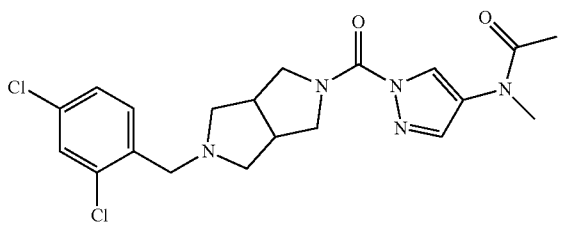 [SMILES: CC(=O)N(C)c1cnn(C(=O)N2CC3CN(Cc4ccc(Cl)cc4Cl)CC3C2)c1]

The title compound was synthesized as described in Example 83 using tert-butyl hexahydropyrrolo[3,4-c]pyrrole-2(1H)-carboxylate in Step 1 and 2,4-dichlorobenzaldehyde in Step 4. Purification resulted in 80.9 mg of N-(1-(5-(2,4-dichlorobenzyl)octahydropyrrolo[3,4-c]pyrrole-2-carbonyl)-1H-pyrazol-4-yl)-N-methylacetamide as a white solid. $^1$H NMR (400 MHz, Chloroform-d) δ 8.30 (s, 0.3H), 8.20 (s, 0.7H), 8.06 (s, 0.3H), 7.57 (s, 0.7H), 7.37-7.41 (m, 2H), 7.21-7.23 (m, 1H), 3.71-4.27 (m, 6H), 3.38 (s, 1H), 3.23 (s, 2H), 2.92 (br, 2H), 2.67 (br, 4H), 2.30 (s, 1H), 2.01 (s, 2H). LCMS (ESI, m/z): 436 [M+H]$^+$.

Example 114: N-methyl-N-(1-(5-(3-morpholino-5-(trifluoromethyl)benzyl)octahydropyrrolo[3,4-c]pyrrole-2-carbonyl)-1H-pyrazol-4-yl)acetamide

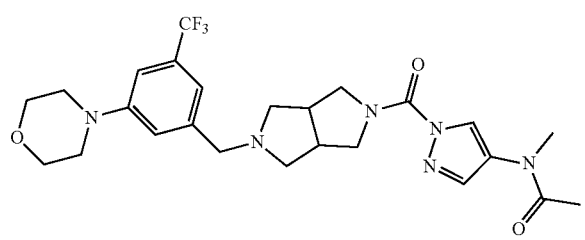 [SMILES: CC(=O)N(C)c1cnn(C(=O)N2CC3CN(Cc4cc(N5CCOCC5)cc(C(F)(F)F)c4)CC3C2)c1]

The title compound was synthesized as described in Example 83 using tert-butyl hexahydropyrrolo[3,4-c]pyrrole-2(1H)-carboxylate in Step 1 and 3-morpholino-5-(trifluoromethyl)benzaldehyde (synthesized as described in Example 67, Step 1) in Step 4 to provide N-methyl-N-(1-(5-(3-morpholino-5-(trifluoromethyl)benzyl)octahydropyrrolo[3,4-c]pyrrole-2-carbonyl)-1H-pyrazol-4-yl)acetamide as a yellow oil. $^1$H NMR (400 MHz, Chloroform-d) δ 8.37-7.46 (m, 2H), 7.10-7.01 (m, 2H), 7.00 (s, 1H), 4.30-3.71 (m, 8H), 3.60 (s, 2H), 3.38 (s, 1H), 3.27-3.15 (m, 6H), 2.99-2.85 (m, 2H), 2.70-2.50 (m, 4H), 2.30 (s, 1H), 2.05-1.96 (m, 2H). LCMS (ESI, m/z): 521 [M+H]$^+$.

Example 115: N-(1-(5-(2-chloro-4-methylbenzyl)octahydropyrrolo[3,4-c]pyrrole-2-carbonyl)-1H-pyrazol-4-yl)-N-methylacetamide

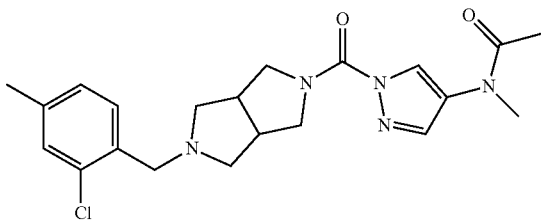 [SMILES: CC(=O)N(C)c1cnn(C(=O)N2CC3CN(Cc4ccc(C)cc4Cl)CC3C2)c1]

The title compound was synthesized as described in Example 83 using tert-butyl hexahydropyrrolo[3,4-c]pyrrole-2(1H)-carboxylate in Step 1 and 2-chloro-4-methylbenzaldehyde in Step 4. Purification resulted in 87.7 mg of N-(1-(5-(2-chloro-4-methylbenzyl)octahydropyrrolo[3,4-c]pyrrole-2-carbonyl)-1H-pyrazol-4-yl)-N-methylacetamide as a light yellow solid. $^1$H NMR (400 MHz, Chloroform-d) δ 8.30 (s, 0.3H), 8.20 (s, 0.7H), 8.06 (s, 0.3H), 7.57 (s, 0.7H), 7.30-7.33 (m, 1H), 7.18 (s, 1H), 7.04 (d, J=7.6 Hz, 1H), 3.73-4.25 (m, 6H), 3.38 (s, 1H), 3.24 (s, 2H), 2.92 (br, 2H), 2.67 (br, 4H), 2.30-2.32 (m, 4H), 2.01 (s, 2H). LCMS (ESI, m/z): 416 [M+H]$^+$.

Example 116: N-(1-(5-(3,5-bis(trifluoromethyl)benzyl)octahydropyrrolo[3,4-c]pyrrole-2-carbonyl)-1H-pyrazol-4-yl)-N-methylacetamide

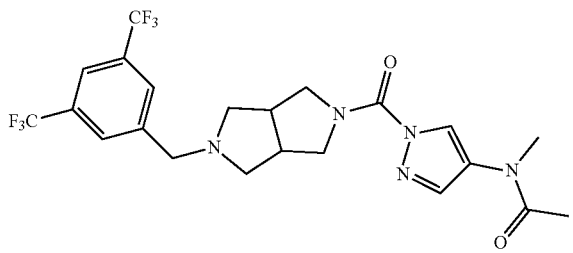 [SMILES: CC(=O)N(C)c1cnn(C(=O)N2CC3CN(Cc4cc(C(F)(F)F)cc(C(F)(F)F)c4)CC3C2)c1]

The title compound was synthesized as described in Example 83 using tert-butyl hexahydropyrrolo[3,4-c]pyrrole-2(1H)-carboxylate in Step 1 and 3,5-bis(trifluoromethyl)benzaldehyde in Step 4 to provide N-(1-(5-(3,5-bis(trifluoromethyl)benzyl)octahydropyrrolo[3,4-c]pyrrole-2-carbonyl)-1H-pyrazol-4-yl)-N-methylacetamide as a yellow oil. $^1$H NMR (400 MHz, Chloroform-d) δ 8.47-7.43 (m, 5H), 4.39-3.59 (m, 6H), 3.38 (s, 1H), 3.23 (s, 2H), 2.95 (s, 2H), 2.76-2.49 (m, 4H), 2.30 (s, 1H), 2.01 (s, 2H). LCMS (ESI, m/z): 504 [M+H]$^+$.

Example 117: N-methyl-N-(1-(5-(3-(trifluoromethyl)benzyl)octahydropyrrolo[3,4-c]pyrrole-2-carbonyl)-1H-pyrazol-4-yl)acetamide

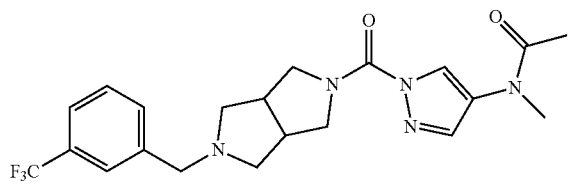 [SMILES: CC(=O)N(C)c1cnn(C(=O)N2CC3CN(Cc4cccc(C(F)(F)F)c4)CC3C2)c1]

The title compound was synthesized as described in Example 83 using tert-butyl hexahydropyrrolo[3,4-c]pyrrole-2(1H)-carboxylate in Step 1 and 3-(trifluoromethyl)benzaldehyde in Step 4. Purification resulted in 190 mg of N-methyl-N-(1-(5-(3-(trifluoromethyl)benzyl)octahydropyrrolo[3,4-c]pyrrole-2-carbonyl)-1H-pyrazol-4-yl)acetamide as a light yellow oil. $^1$H NMR (400 MHz, Chloroform-d) δ 8.31 (s, 0.3H), 8.21 (s, 0.7H), 8.06 (s, 0.3H), 7.51-7.58 (m, 3.7H), 7.42-7.46 (m, 1H), 3.74-4.24 (m, 4H), 3.66-3.67 (m, 2H), 3.38 (s, 1H), 3.24 (s, 2H), 2.93 (br, 2H), 2.54-2.65 (m, 4H), 2.30 (s, 1H), 2.01 (s, 2H). LCMS (ESI, m/z): 436 [M+H]$^+$.

Example 118: N-(1-(5-(3-chloro-5-(tetrahydro-1H-furo[3,4-c]pyrrol-5(3H)-yl)benzyl)octahydropyrrolo[3,4-c]pyrrole-2-carbonyl)-1H-pyrazol-4-yl)-N-methylacetamide

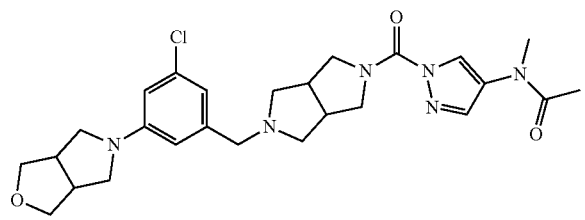 [SMILES: CC(=O)N(C)c1cnn(C(=O)N2CC3CN(Cc4cc(Cl)cc(N5CC6COCC6C5)c4)CC3C2)c1]

The title compound was synthesized as described in Example 83 using tert-butyl hexahydropyrrolo[3,4-c]pyrrole-2(1H)-carboxylate in Step 1 and 3-chloro-5-(tetrahydro-1H-furo[3,4-c]pyrrol-5(3H)-yl)benzaldehyde (synthesized as described in Example 63, Step 1) in Step 4 to provide N-(1-(5-(3-chloro-5-(tetrahydro-1H-furo[3,4-c]pyrrol-5(3H)-yl)benzyl)octahydropyrrolo[3,4-c]pyrrole-2-carbonyl)-1H-pyrazol-4-yl)-N-methylacetamide as a yellow oil. $^1$H NMR (400 MHz, Chloroform-d) δ 8.31 (s, OH), 8.20 (s, 1H), 8.06 (s, OH), 7.56 (s, 1H), 7.28 (s, 1H), 6.66 (s, 1H), 6.49 (s, 2H), 4.35-3.59 (m, 8H), 3.55 (s, 2H), 3.49-3.39 (m, 2H), 3.38 (s, 1H), 3.28-3.17 (m, 4H), 3.11-3.01 (m, 2H), 3.00-2.85 (m, 2H), 2.80-2.47 (m, 3H), 2.30 (s, 1H), 2.05-2.00 (m, 2H). LCMS (ESI, m/z): 514 [M+H]$^+$.

Example 119: N-methyl-N-(1-(5-(3-(pyrrolidin-1-yl)benzyl)octahydropyrrolo[3,4-c]pyrrole-2-carbonyl)-1H-pyrazol-4-yl)acetamide

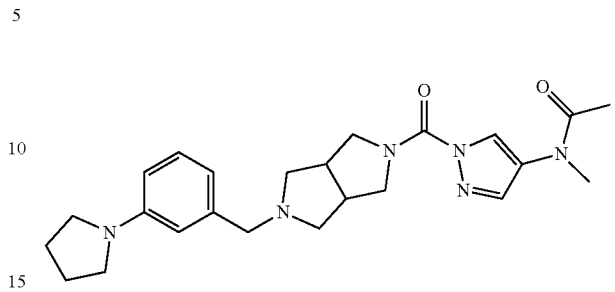

The title compound was synthesized as described in Example 83 using tert-butyl hexahydropyrrolo[3,4-c]pyrrole-2(1H)-carboxylate in Step 1 and 3-(pyrrolidin-1-yl)benzaldehyde in Step 4. Purification resulted in 123.3 mg of N-methyl-N-(1-(5-(3-(pyrrolidin-1-yl)benzyl)octahydropyrrolo[3,4-c]pyrrole-2-carbonyl)-1H-pyrazol-4-yl)acetamide as a white solid. $^1$H NMR (400 MHz, Chloroform-d) δ 8.30 (s, 0.3H), 8.20 (s, 0.7H), 8.06 (s, 0.3H), 7.56 (s, 0.7H), 7.16 (t, J=7.8 Hz, 1H), 6.61 (d, J=7.2 Hz, 1H), 6.56 (s, 1H), 6.48 (d, J=8.0 Hz, 1H), 3.77-4.19 (m, 4H), 3.61 (br, 2H), 3.37 (s, 1H), 3.27-3.30 (m, 4H), 3.23 (s, 2H), 2.93 (br, 2H), 2.63-2.70 (m, 4H), 2.30 (s, 1H), 1.97-2.01 (m, 6H). LCMS (ESI, m/z): 437 [M+H]$^+$.

Example 120: N-(1-(5-(3-chloro-5-(4-cyclopropylpiperazin-1-yl)benzyl)octahydropyrrolo[3,4-c]pyrrole-2-carbonyl)-1H-pyrazol-4-yl)-N-methylacetamide

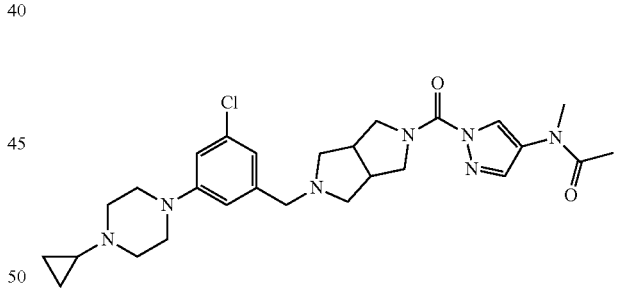

The title compound was synthesized as described in Example 83 using tert-butyl hexahydropyrrolo[3,4-c]pyrrole-2(1H)-carboxylate in Step 1 and 3-chloro-5-(4-cyclopropylpiperazin-1-yl)benzaldehyde (synthesized as described in Example 63, Step 1) in Step 4 to provide N-(1-(5-(3-chloro-5-(4-cyclopropylpiperazin-1-yl)benzyl)octahydropyrrolo[3,4-c]pyrrole-2-carbonyl)-1H-pyrazol-4-yl)-N-methylacetamide as a yellow oil. $^1$H NMR (400 MHz, Chloroform-d) δ 8.23-8.15 (m, 1H), 7.60-7.51 (m, 1H), 7.28 (s, 1H), 6.88-6.70 (m, 3H), 4.35-3.63 (m, 4H), 3.55 (s, 2H), 3.38 (s, 1H), 3.27-3.12 (m, 6H), 3.06-2.85 (m, 2H), 2.85-2.49 (m, 8H), 2.30 (s, 1H), 2.01 (s, 2H), 1.69 (s, 1H), 0.58-0.39 (m, 4H). LCMS (ESI, m/z): 526 [M+H]$^+$.

Example 121: N-methyl-N-(1-(5-(3-morpholinobenzyl)octahydropyrrolo[3,4-c]pyrrole-2-carbonyl)-1H-pyrazol-4-yl)acetamide

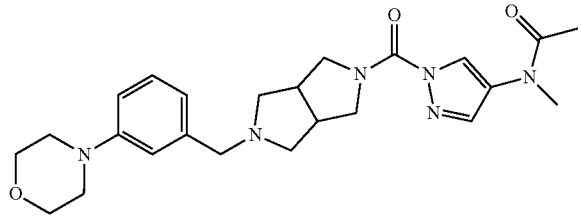 [SMILES: CC(=O)N(C)c1cnn(C(=O)N2CC3CN(Cc4cccc(N5CCOCC5)c4)CC3C2)c1]

The title compound was synthesized as described in Example 83 using tert-butyl hexahydropyrrolo[3,4-c]pyrrole-2(1H)-carboxylate in Step 1 and 3-morpholinobenzaldehyde in Step 4. Purification resulted in 103.8 mg of N-methyl-N-(1-(5-(3-morpholinobenzyl)octahydropyrrolo[3,4-c]pyrrole-2-carbonyl)-1H-pyrazol-4-yl)acetamide as a white solid. $^1$H NMR (400 MHz, Chloroform-d) δ 8.30 (s, 0.3H), 8.20 (s, 0.7H), 8.05 (s, 0.3H), 7.56 (s, 0.7H), 7.22 (t, J=7.8 Hz, 1H), 6.93 (s, 1H), 6.82-6.84 (m, 2H), 3.78-4.19 (m, 8H), 3.55-3.62 (m, 2H), 3.37 (s, 1H), 3.23 (s, 2H), 3.16-3.17 (m, 4H), 2.94 (br, 2H), 2.58-2.69 (m, 4H), 2.30 (s, 1H), 2.01 (s, 2H). LCMS (ESI, m/z): 453 [M+H]$^+$.

Example 122: N-(1-(5-(3-chloro-4 fluorobenzyl)octahydropyrrolo[3,4-c]pyrrole-2-carbonyl)-1H-pyrazol-4-yl)-N-methylacetamide

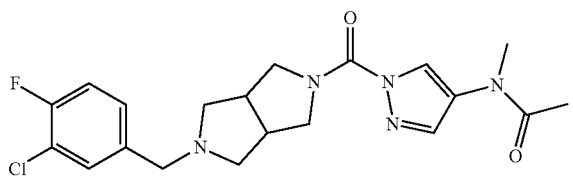 [SMILES: CC(=O)N(C)c1cnn(C(=O)N2CC3CN(Cc4ccc(F)c(Cl)c4)CC3C2)c1]

The title compound was synthesized as described in Example 83 using tert-butyl hexahydropyrrolo[3,4-c]pyrrole-2(1H)-carboxylate in Step 1 and 3-chloro-4-fluorobenzaldehyde in Step 4 to provide N-(1-(5-(3-chloro-4 fluorobenzyl)octahydropyrrolo[3,4-c]pyrrole-2-carbonyl)-1H-pyrazol-4-yl)-N-methylacetamide as a yellow oil. $^1$H NMR (400 MHz, Chloroform-d) δ 8.25-8.18 (m, 1H), 7.61-7.52 (m, 1H), 7.40-7.34 (m, 1H), 7.24-7.13 (m, 1H), 7.13-7.01 (m, 1H), 4.42-3.63 (m, 4H), 3.57 (s, 2H), 3.38 (s, 1H), 3.23 (s, 2H), 3.06-2.82 (m, 2H), 2.77-2.48 (m, 4H), 2.30 (s, 1H), 2.01 (s, 2H). LCMS (ESI, m/z): 420 [M+H]$^+$.

Example 123: N-(1-(5-(3-chloro-4-(pyrrolidin-1-yl)benzyl)octahydropyrrolo[3,4-c]pyrrole-2-carbonyl)-1H-pyrazol-4-yl)-N-methylacetamide

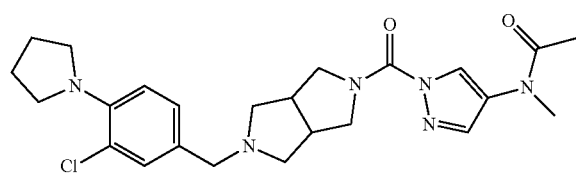 [SMILES: CC(=O)N(C)c1cnn(C(=O)N2CC3CN(Cc4ccc(N5CCCC5)c(Cl)c4)CC3C2)c1]

The title compound was synthesized as described in Example 83 using tert-butyl hexahydropyrrolo[3,4-c]pyrrole-2(1H)-carboxylate in Step 1 and 3-chloro-4-(pyrrolidin-1-yl)benzaldehyde (synthesized as described in Example 67, Step 1) in Step 4. Purification resulted in 75.3 mg of N-(1-(5-(3-chloro-4-(pyrrolidin-1-yl)benzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.19-8.28 (m, 1H), 7.55-8.04 (m, 1H), 7.22 (s, 1H), 7.06 (d, J=8.1 Hz, 1H), 6.81 (d, J=8.1 Hz, 1H), 3.60-4.38 (m, 4H), 3.49 (s, 2H), 3.30-3.42 (m, 5H), 3.21 (s, 2H), 2.90 (br, 2H), 2.62 (br, 2H), 2.44-2.57 (m, 2H), 2.28 (s, 1H), 2.00 (s, 2H), 1.89-1.97 (m, 4H). LCMS (ESI, m/z): 471 [M+H]$^+$.

Example 124: N-methyl-N-(1-(5-(3-morpholino-4-(trifluoromethyl)benzyl)octahydropyrrolo[3,4-c]pyrrole-2-carbonyl)-1H-pyrazol-4-yl)acetamide

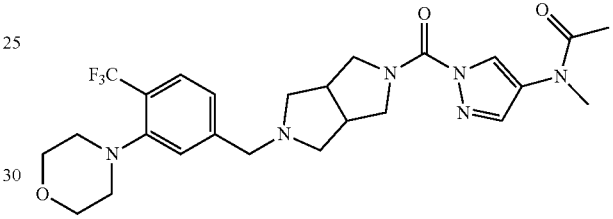

The title compound was synthesized as described in Example 83 using tert-butyl hexahydropyrrolo[3,4-c]pyrrole-2(1H)-carboxylate in Step 1 and 3-morpholino-4-(trifluoromethyl)benzaldehyde (synthesized as described in Example 63, Step 1) in Step 4. Purification resulted in 176.2 mg of N-methyl-N-(1-(5-(3-morpholino-4-(trifluoromethyl)benzyl)octahydropyrrolo[3,4-c]pyrrole-2-carbonyl)-1H-pyrazol-4-yl)acetamide as a yellow oil. $^1$H NMR (300 MHz, Chloroform-d) δ 8.21-8.30 (m, 1H), 7.61-8.05 (m, 2H), 7.34 (s, 1H), 7.18 (d, J=8.1 Hz, 1H), 3.52-4.30 (m, 10H), 3.36 (s, 1H), 3.22 (s, 2H), 2.90-2.93 (m, 6H), 2.50-2.62 (m, 4H), 2.28 (s, 1H), 2.00 (s, 2H). LCMS (ESI, m/z): 521 [M+H]$^+$.

Example 125: N-(1-(5-(3-chloro-5-morpholinobenzyl)octahydropyrrolo[3,4-c]pyrrole-2-carbonyl)-1H-pyrazol-4-yl)-N-methylacetamide

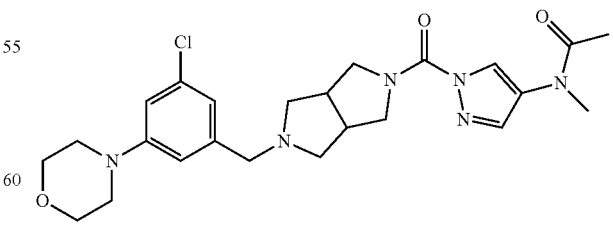

The title compound was synthesized as described in Example 83 using tert-butyl hexahydropyrrolo[3,4-c]pyrrole-2(1H)-carboxylate in Step 1 and 3-chloro-5-morpholinobenzaldehyde (synthesized as described in Example 63, Step 1) in Step 4. Purification resulted in 88.7 mg of N-(1-(5-(3-chloro-5-morpholinobenzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.19-8.29 (m, 1H), 7.56-8.04 (m, 1H), 6.78-7.27 (m, 3H), 3.32-4.37 (m, 12H), 2.40-3.28 (m, 11H), 2.29 (s, 1H), 1.99 (s, 2H). LCMS (ESI, m/z): 487 [M+H]$^+$.

Example 126: N-(1-(5-(2,5-bis(trifluoromethyl)benzyl)octahydropyrrolo[3,4-c]pyrrole-2-carbonyl)-1H-pyrazol-4-yl)-N-methylacetamide

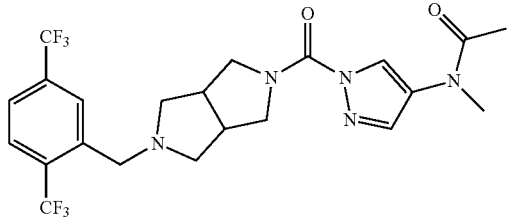 [SMILES: CC(=O)N(C)c1cnn(C(=O)N2CC3CN(Cc4cc(C(F)(F)F)ccc4C(F)(F)F)CC3C2)c1]

The title compound was synthesized as described in Example 83 using tert-butyl hexahydropyrrolo[3,4-c]pyrrole-2(1H)-carboxylate in Step 1 and 2,5-bis(trifluoromethyl)benzaldehyde in Step 4. Purification resulted in 94.1 mg of N-(1-(5-(2,5-bis(trifluoromethyl)benzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.28 (s, 0.3H), 8.21 (s, 0.7H), 8.06 (s, 0.3H), 8.04 (s, 1H), 7.75 (d, J=8.1 Hz, 1H), 7.60 (d, J=8.1 Hz, 1H), 7.55 (s, 0.7H), 3.83-4.05 (m, 6H), 3.36 (s, 1H), 3.22 (s, 2H), 2.95 (br, 2H), 2.61-2.68 (m, 4H), 2.28 (s, 1H), 2.00 (s, 2H). LCMS (ESI, m/z): 504 [M+H]$^+$.

Example 127: N-methyl-N-(1-(5-(5-(pyrrolidin-1-yl)-2-(trifluoromethyl)benzyl)octahydropyrrolo[3,4-c]pyrrole-2-carbonyl)-1H-pyrazol-4-yl)acetamide

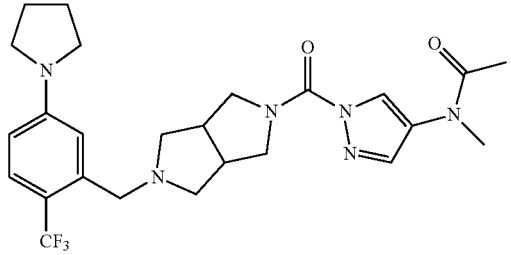 [SMILES: CC(=O)N(C)c1cnn(C(=O)N2CC3CN(Cc4cc(N5CCCC5)ccc4C(F)(F)F)CC3C2)c1]

The title compound was synthesized as described in Example 83 using tert-butyl hexahydropyrrolo[3,4-c]pyrrole-2(1H)-carboxylate in Step 1 and 5-(pyrrolidin-1-yl)-2-(trifluoromethyl)benzaldehyde (synthesized as described in Example 67, Step 1) in Step 4. Purification resulted in 83.8 mg of N-methyl-N-(1-(5-(5-(pyrrolidin-1-yl)-2-(trifluoromethyl)benzyl)octahydropyrrolo[3,4-c]pyrrole-2-carbonyl)-1H-pyrazol-4-yl)acetamide as a white solid. $^1$H NMR (400 MHz, Chloroform-d) δ 8.31 (s, 0.3H), 8.20 (s, 0.7H), 8.06 (s, 0.3H), 7.60 (s, 0.7H), 7.42-7.45 (m, 1H), 6.89-6.92 (m, 1H), 6.40-6.42 (m, 1H), 3.90-4.25 (m, 4H), 3.73 (s, 2H), 3.38 (s, 1H), 3.30-3.32 (m, 4H), 3.24 (s, 2H), 2.92 (br, 2H), 2.75-2.78 (m, 2H), 2.57-2.61 (m, 2H), 2.30 (s, 1H), 2.01 (s, 6H). LCMS (ESI, m/z): 505 [M+H]$^+$.

Example 128: N-methyl-N-(1-(5-(2-(pyrrolidin-1-yl)-5-(trifluoromethyl)benzyl)octahydropyrrolo[3,4-c]pyrrole-2-carbonyl)-1H-pyrazol-4-yl)acetamide

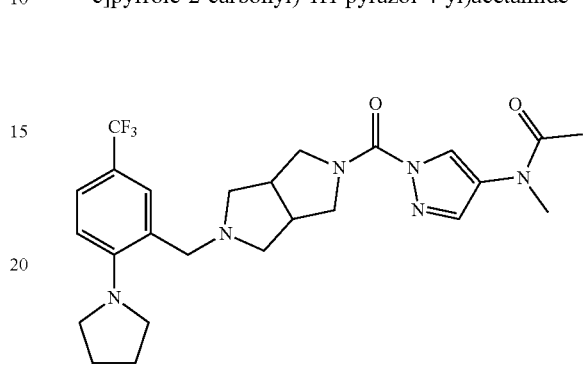

The title compound was synthesized as described in Example 83 using tert-butyl hexahydropyrrolo[3,4-c]pyrrole-2(1H)-carboxylate in Step 1 and 2-(pyrrolidin-1-yl)-5-(trifluoromethyl)benzaldehyde (synthesized as described in Example 67, Step 1) in Step 4. Purification resulted in 67.6 mg of N-methyl-N-(1-(5-(2-(pyrrolidin-1-yl)-5-(trifluoromethyl)benzyl)octahydropyrrolo[3,4-c]pyrrole-2-carbonyl)-1H-pyrazol-4-yl)acetamide as an off-white solid. $^1$H NMR (300 MHz, Chloroform-d) δ 8.28 (s, 0.3H), 8.18 (s, 0.7H), 8.03 (s, 0.3H), 7.49-7.54 (m, 1.7H), 7.35 (d, J=8.4 Hz, 1H), 6.79 (d, J=8.4 Hz, 1H), 3.65-4.22 (m, 6H), 3.35-3.44 (m, 5H), 3.21 (s, 2H), 2.90 (br, 2H), 2.58-2.61 (m, 4H), 2.28 (s, 1H), 1.88-2.06 (m, 6H). LCMS (ESI, m/z): 505 [M+H]$^+$.

Example 129: N-(1-(5-(4-chloro-3-morpholinobenzyl)octahydropyrrolo[3,4-c]pyrrole-2-carbonyl)-1H-pyrazol-4-yl)-N-methylacetamide

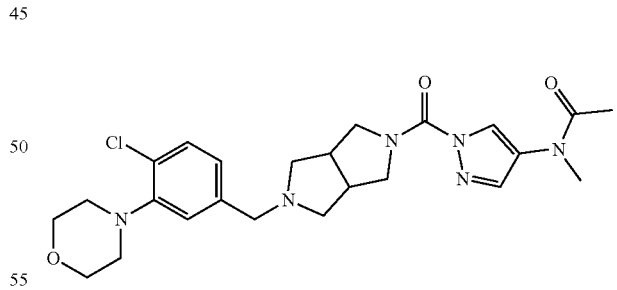

The title compound was synthesized as described in Example 83 using tert-butyl hexahydropyrrolo[3,4-c]pyrrole-2(1H)-carboxylate in Step 1 and 4-chloro-3-morpholinobenzaldehyde (synthesized as described in Example 63, Step 1) in Step 4. Purification resulted in 63.1 mg of N-(1-(5-(4-chloro-3-morpholinobenzyl)octahydropyrrolo[3,4-c]pyrrole-2-carbonyl)-1H-pyrazol-4-yl)-N-methylacetamide as a light yellow solid. $^1$H NMR (400 MHz, Chloroform-d) δ 8.31 (s, 0.3H), 8.21 (s, 0.7H), 8.05 (s, 0.3H), 7.57 (s, 0.7H), 7.30 (s, 1H), 7.01 (s, 1H), 6.93-6.95 (m, 1H), 3.70-4.23 (m, 8H), 3.58 (s, 2H), 3.37 (s, 1H), 3.23 (s, 2H), 3.06 (br, 4H), 2.91 (br, 2H), 2.54-2.63 (m, 4H), 2.30 (s, 1H), 2.01 (s, 2H). LCMS (ESI, m/z): 487 [M+H]⁺.

Example 130: N-methyl-N-(1-(5-(3-(pyrrolidin-1-yl)-4-(trifluoromethyl)benzyl)octahydropyrrolo[3,4-c]pyrrole-2-carbonyl)-1H-pyrazol-4-yl)acetamide

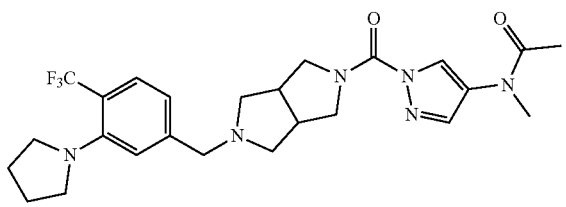 [SMILES: CC(=O)N(C)c1cnn(C(=O)N2CC3CN(Cc4ccc(C(F)(F)F)c(N5CCCC5)c4)CC3C2)c1]

The title compound was synthesized as described in Example 83 using tert-butyl hexahydropyrrolo[3,4-c]pyrrole-2(1H)-carboxylate in Step 1 and 3-(pyrrolidin-1-yl)-4-(trifluoromethyl)benzaldehyde (synthesized as described in Example 63, Step 1) in Step 4. Purification resulted in 134.6 mg of N-methyl-N-(1-(5-(3-(pyrrolidin-1-yl)-4-(trifluoromethyl)benzyl)octahydropyrrolo[3,4-c]pyrrole-2-carbonyl)-1H-pyrazol-4-yl)acetamide as an off-white solid. ¹H NMR (300 MHz, Chloroform-d) δ 8.29 (s, 0.3H), 8.19 (s, 0.7H), 8.03 (s, 0.3H), 7.54 (s, 0.7H), 7.49 (d, J=8.1 Hz, 1H), 6.93 (s, 1H), 6.77 (d, J=8.1 Hz, 1H), 3.84-4.08 (m, 4H), 3.58 (s, 2H), 3.30-3.36 (m, 5H), 3.22 (s, 2H), 2.90-2.98 (m, 2H), 2.61 (br, 4H), 2.28 (s, 1H), 1.88-1.99 (m, 6H). LCMS (ESI, m/z): 505 [M+H]⁺.

Example 131: N-methyl-N-(1-(5-(4-morpholino-2-(trifluoromethyl)benzyl)octahydropyrrolo[3,4-c]pyrrole-2-carbonyl)-1H-pyrazol-4-yl)acetamide

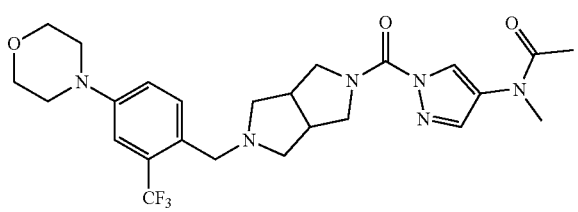 [SMILES: CC(=O)N(C)c1cnn(C(=O)N2CC3CN(Cc4ccc(N5CCOCC5)cc4C(F)(F)F)CC3C2)c1]

The title compound was synthesized as described in Example 83 using tert-butyl hexahydropyrrolo[3,4-c]pyrrole-2(1H)-carboxylate in Step 1 and 4-morpholino-2-(trifluoromethyl)benzaldehyde (synthesized as described in Example 67, Step 1) in Step 4. Purification resulted in 170.2 mg of N-methyl-N-(1-(5-(4-morpholino-2-(trifluoromethyl)benzyl)octahydropyrrolo[3,4-c]pyrrole-2-carbonyl)-1H-pyrazol-4-yl)acetamide as a white solid. ¹H NMR (300 MHz, Chloroform-d) δ 8.30 (s, 0.3H), 8.19 (s, 0.7H), 8.04 (s, 0.3H), 7.55-7.58 (m, 1.7H), 7.11 (s, 1H), 7.00-7.02 (m, 1H), 4.11-4.23 (m, 2H), 3.85-3.88 (m, 5H), 3.70 (br, 3H), 3.36 (s, 1H), 3.16-3.22 (m, 6H), 2.91 (br, 2H), 2.58-2.64 (m, 4H), 2.28 (s, 1H), 2.00 (s, 2H). LCMS (ESI, m/z): 521 [M+H]⁺.

Example 132: N-(1-(5-(2-chloro-4-(pyrrolidin-1-yl)benzyl)octahydropyrrolo[3,4-c]pyrrole-2-carbonyl)-1H-pyrazol-4-yl)-N-methylacetamide

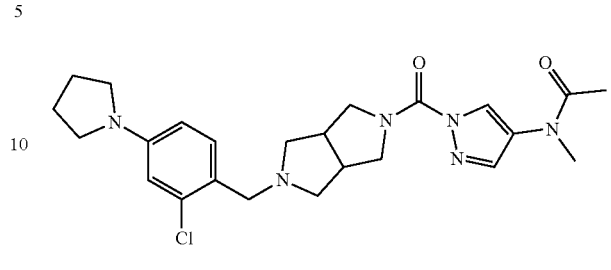

The title compound was synthesized as described in Example 83 using tert-butyl hexahydropyrrolo[3,4-c]pyrrole-2(1H)-carboxylate in Step 1 and 2-chloro-4-(pyrrolidin-1-yl)benzaldehyde (synthesized as described in Example 67, Step 1) in Step 4. Purification resulted in 160.9 mg of N-(1-(5-(2-chloro-4-(pyrrolidin-1-yl)benzyl)octahydropyrrolo[3,4-c]pyrrole-2-carbonyl)-1H-pyrazol-4-yl)-N-methylacetamide as a white solid. ¹H NMR (300 MHz, Chloroform-d) δ 8.28 (s, 0.3H), 8.18 (s, 0.7H), 8.04 (s, 0.3H), 7.54 (s, 0.7H), 7.18-7.20 (m, 1H), 6.51-6.52 (m, 1H), 6.39-6.42 (m, 1H), 3.66-4.08 (m, 6H), 3.21-3.35 (m, 7H), 2.59-2.89 (m, 6H), 2.28 (s, 1H), 1.97-2.02 (m, 6H). LCMS (ESI, m/z): 471 [M+H]⁺.

Example 133: N-(1-(cis-5-(2-chlorobenzylamino)octahydrocyclopenta[c]pyrrole-2-carbonyl)-1H-pyrazol-4-yl)-N-methylacetamide

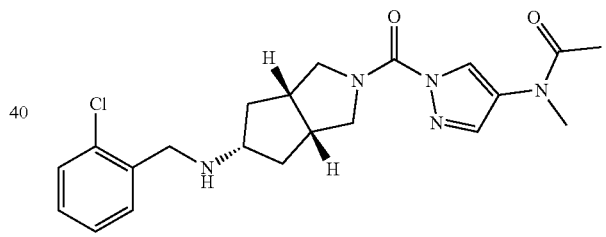

Step 1: Synthesis of 4-nitrophenyl 4-acetamido-1H-pyrazole-1-carboxylate

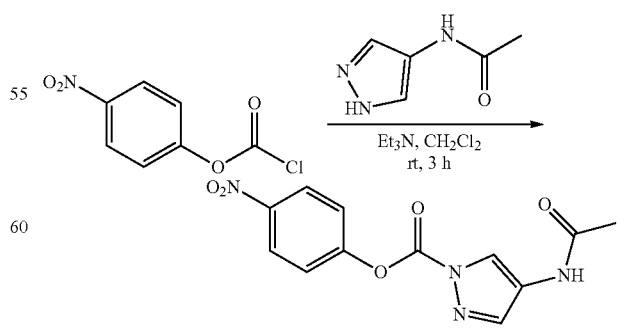

A 100-mL round-bottom flask was charged with N-(1H-pyrazol-4-yl)acetamide (690 mg, 5.51 mmol, 1.00 equiv) in DCM (10 mL), 4-nitrophenyl chloroformate (1.16 g, 5.75 mmol, 1.05 equiv), and triethylamine (1.67 g, 16.5 mmol, 3.00 equiv) under nitrogen. The resulting solution was stirred for 3 h at room temperature. The reaction progress was monitored by LCMS. The resulting mixture was concentrated under reduced pressure to yield 2.25 g (crude) of 4-nitrophenyl 4-acetamido-1H-pyrazole-1-carboxylate as a yellow solid. LCMS (ESI, m/z): 291 [M+H]$^+$.

Step 2: Synthesis of cis-tert-butyl 5-(2-chlorobenzylamino)hexahydrocyclopenta[c]pyrrole-2(1H)-carboxylate

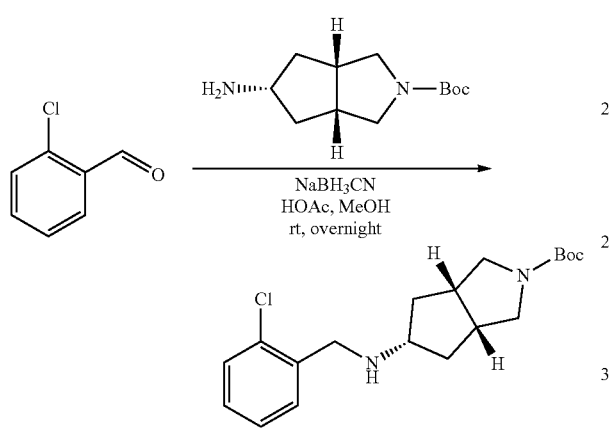

A 100-mL round-bottom flask was charged with 2-chlorobenzaldehyde (2.80 g, 19.9 mmol, 1.00 equiv) in MeOH (30 mL), cis-tert-butyl 5-aminohexahydrocyclopenta[c]pyrrole-2(1H)-carboxylate (5.42 g, 24.0 mmol, 1.20 equiv), and acetic acid (3.60 g, 60.0 mmol, 3.00 equiv). The resulting solution was stirred for 30 min at room temperature. Sodium cyanoborohydride (3.78 g, 60.0 mmol, 3.00 equiv) was added. The resulting solution was stirred overnight at room temperature and quenched with water (30 mL). The resulting solution was extracted with DCM (3×30 mL) and the organic layers were combined, washed with brine (2×30 mL), dried over anhydrous sodium sulfate, filtered and concentrated under reduced pressure. The residue was chromatographed on a silica gel column to yield 5.00 g (72% yield) of cis-tert-butyl 5-(2-chlorobenzylamino)hexahydrocyclopenta[c]pyrrole-2(1H)-carboxylate as a yellow oil. LCMS (ESI, m/z): 351 [M+H]$^+$.

Step 3: Synthesis of cis-N-(2-chlorobenzyl)octahydrocyclopenta[c]pyrrol-5-amine

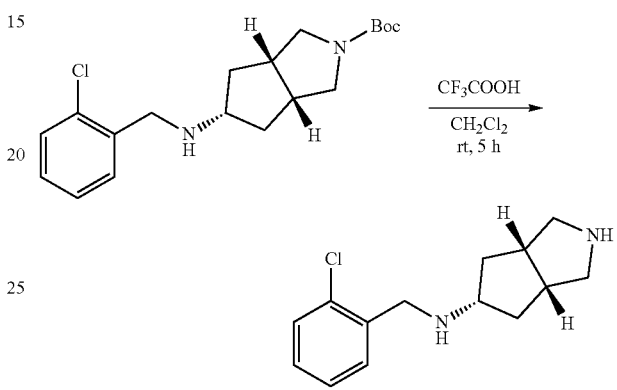

A 100-mL round-bottom flask was charged with cis-tert-butyl 5-(2-chlorobenzylamino)hexahydrocyclopenta[c]pyrrole-2(1H)-carboxylate (1.60 g, 4.56 mmol, 1.00 equiv) in DCM (20 mL), and TFA (5 mL). The resulting solution was stirred for 5 h at room temperature. The reaction progress was monitored by LCMS. The resulting mixture was concentrated under reduced pressure to yield 1.90 g (crude) of cis-N-(2-chlorobenzyl)octahydrocyclopenta[c]pyrrol-5-amine as a yellow oil. LCMS (ESI, m/z): 251 [M+H]$^+$.

Step 4: Synthesis of N-(1-(cis-5-(2-chlorobenzylamino)octahydrocyclopenta[c]pyrrole-2-carbonyl)-1H-pyrazol-4-yl)acetamide

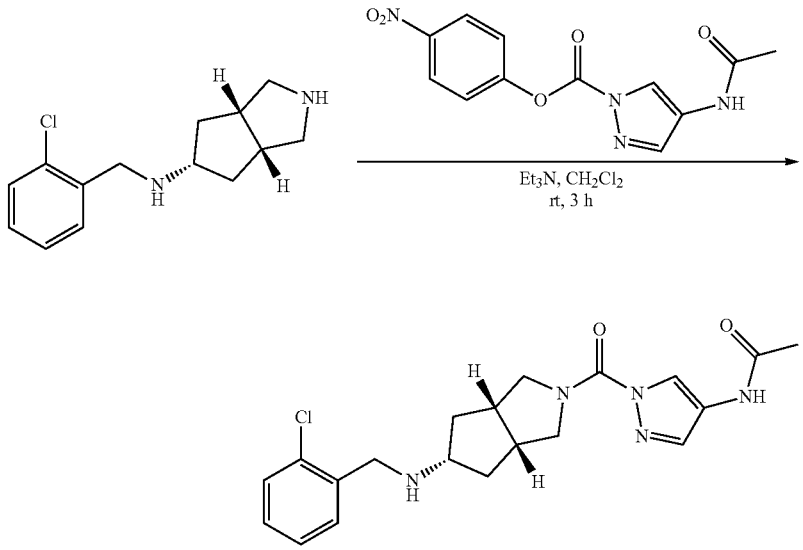

A 100-mL round-bottom flask was charged with cis-N-(2-chlorobenzyl)octahydrocyclopenta[c]pyrrol-5-amine (600 mg, 2.39 mmol, 1.00 equiv) in DCM (20 mL), 4-nitrophenyl 4-acetamido-1H-pyrazole-1-carboxylate (1044 mg, 3.60 mmol, 1.50 equiv), and triethylamine (727 mg, 7.20 mmol, 3.00 equiv) under nitrogen. The resulting solution was stirred for 3 h at room temperature and quenched with water (20 mL). The resulting solution was extracted with DCM (3×20 mL) and the organic layers were combined, washed with brine (2×20 mL), dried over anhydrous sodium sulfate, filtered and concentrated under reduced pressure. The residue was chromatographed on a silica gel column to yield 800 mg (83% yield) of N-(1-(cis-5-(2-chlorobenzylamino)octahydrocyclopenta[c]pyrrole-2-carbonyl)-1H-pyrazol-4-yl)acetamide as a yellow oil. LCMS (ESI, m/z): 402 [M+H]+.

Step 5: Synthesis of Tert-butyl cis-2-(4-acetamido-1H-pyrazole-1-carbonyl)octahydrocyclopenta[c]pyrrol-5-yl(2-chlorobenzyl)carbamate

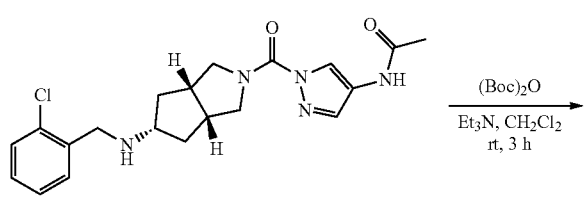

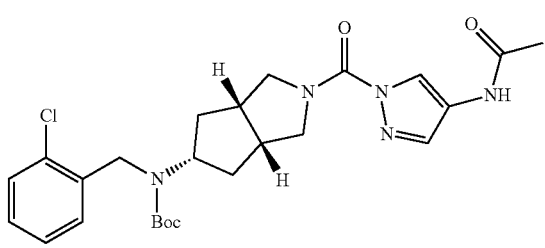

A 100-mL round-bottom flask was charged with N-(1-(cis-5-(2-chlorobenzylamino)octahydrocyclopenta[c]pyrrole-2-carbonyl)-1H-pyrazol-4-yl)acetamide (700 mg, 1.74 mmol, 1.00 equiv) in DCM (10 mL), di-tert-butyl dicarbonate (571 mg, 2.62 mmol, 1.30 equiv), and triethylamine (529 mg, 5.24 mmol, 3.00 equiv) under nitrogen. The resulting solution was stirred for 3 h at room temperature and quenched with water (10 mL). The resulting solution was extracted with DCM (3×10 mL) and the organic layers were combined, washed with brine (2×10 mL), dried over anhydrous sodium sulfate, filtered and concentrated under reduced pressure. The residue was chromatographed on a silica gel column to yield 850 mg (97% yield) of tert-butyl cis-2-(4-acetamido-1H-pyrazole-1-carbonyl)octahydrocyclopenta[c]pyrrol-5-yl(2-chlorobenzyl)carbamate as a white solid. LCMS (ESI, m/z): 502 [M+H]+.

Step 6: Synthesis of Tert-butyl 2-chlorobenzyl(cis-2-(4-(N-methylacetamido)-1H-pyrazole-1-carbonyl)octahydrocyclopenta[c]pyrrol-5-yl)carbamate

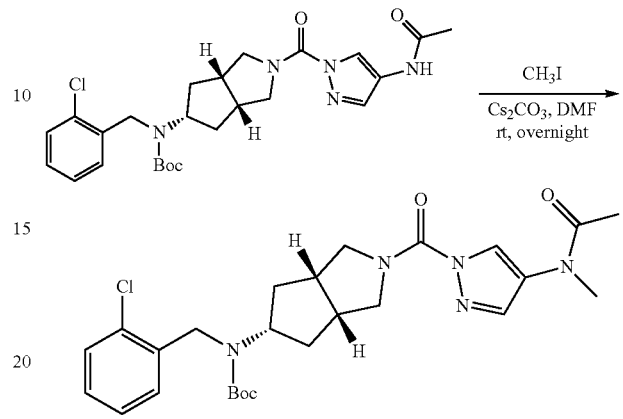

A 100-mL round-bottom flask was charged with tert-butyl cis-2-(4-acetamido-1H-pyrazole-1-carbonyl)octahydrocyclopenta[c]pyrrol-5-yl(2-chlorobenzyl)carbamate (500 mg, 1.00 mmol, 1.00 equiv) in DMF (10 mL), and cesium carbonate (978 mg, 3.00 mmol, 3.00 equiv) under nitrogen. The resulting solution was stirred for 1 h at 0° C. Then iodomethane (213 mg, 1.50 mmol, 1.50 equiv) was added dropwise at 0° C. The resulting solution was stirred overnight at room temperature and quenched with water (10 mL). The resulting solution was extracted with EtOAc (3×10 mL) and the organic layers were combined, washed with brine (2×10 mL), dried over sodium sulfate, filtered and concentrated under reduced pressure. The residue was chromatographed on a silica gel column to yield 500 mg (97% yield) of tert-butyl 2-chlorobenzyl(cis-2-(4-(N-methylacetamido)-1H-pyrazole-1-carbonyl)octahydrocyclopenta[c]pyrrol-5-yl)carbamate as a yellow oil. LCMS (ESI, m/z): 516 [M+H]+.

Step 7: Synthesis of N-(1-(cis-5-(2-chlorobenzylamino)octahydrocyclopenta[c]pyrrole-2-carbonyl)-1H-pyrazol-4-yl)-N-methylacetamide

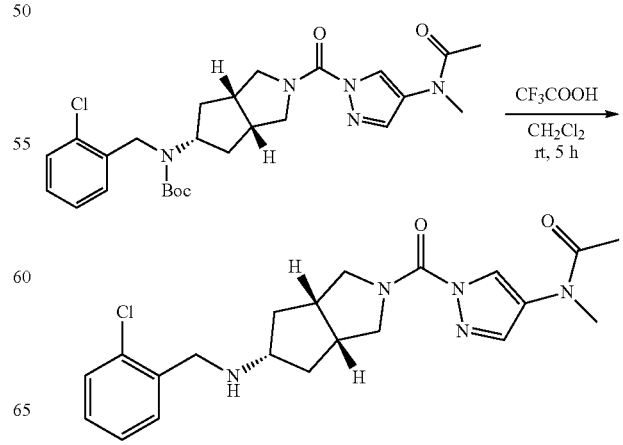

A 100-mL round-bottom flask was charged with tert-butyl 2-chlorobenzyl(cis-2-(4-(N-methylacetamido)-1H-pyrazole-1-carbonyl)octahydrocyclopenta[c]pyrrol-5-yl)carbamate (500 mg, 0.97 mmol, 1.00 equiv) in DCM (20 mL), and TFA (5 mL). The resulting solution was stirred for 5 h at room temperature. The reaction progress was monitored by LCMS. The mixture was concentrated under reduced pressure. The crude product (400 mg) was purified by preparative HPLC. Purification resulted in 126.7 mg (31% yield) of N-(1-(cis-5-(2-chlorobenzylamino)octahydrocyclopenta[c]pyrrole-2-carbonyl)-1H-pyrazol-4-yl)-N-methylacetamide as a white semi-solid. $^1$H NMR (300 MHz, Chloroform-d) δ 8.27 (s, 0.3H), 8.18 (s, 0.7H), 8.05 (s, 0.3H), 7.54 (s, 0.7H), 7.34-7.38 (m, 2H), 7.17-7.27 (m, 2H), 3.86-4.08 (m, 6H), 3.35 (s, 1H), 3.19-3.29 (m, 3H), 2.70 (br, 2H), 2.24-2.28 (m, 3H), 2.01 (s, 2H), 1.34-1.43 (m, 2H). LCMS (ESI, m/z): 416 [M+H]$^+$.

Example 134: N-(1-(cis-5-(3-chlorobenzylamino) octahydrocyclopenta[c]pyrrole-2-carbonyl)-1H-pyrazol-4-yl)-N-methylacetamide

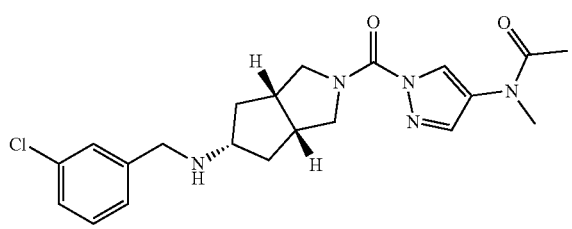 [SMILES: CC(=O)N(C)c1cnn(C(=O)N2C[C@H]3C[C@@H](NCc4cccc(Cl)c4)C[C@H]3C2)c1]

The title compound was synthesized as described in Example 133 using 3-chlorobenzaldehyde in Step 2. Purification resulted in 165.6 mg of N-(1-(cis-5-(3-chlorobenzylamino)octahydrocyclopenta[c]pyrrole-2-carbonyl)-1H-pyrazol-4-yl)-N-methylacetamide as a light brown oil. $^1$H NMR (300 MHz, Chloroform-d) δ 8.27 (s, 0.3H), 8.18 (s, 0.7H), 8.05 (s, 0.3H), 7.54 (s, 0.7H), 7.31 (s, 1H), 7.16-7.24 (m, 3H), 3.86-4.19 (m, 4H), 3.74 (s, 2H), 3.35 (s, 1H), 3.18-3.28 (m, 3H), 2.69 (br, 2H), 2.23-2.28 (m, 3H), 1.99 (s, 2H), 1.31-1.41 (m, 2H). LCMS (ESI, m/z): 416 [M+H]$^+$.

Example 135: N-(1-(cis-5-(4-chlorobenzylamino) octahydrocyclopenta[c]pyrrole-2-carbonyl)-1H-pyrazol-4-yl)-N-methylacetamide

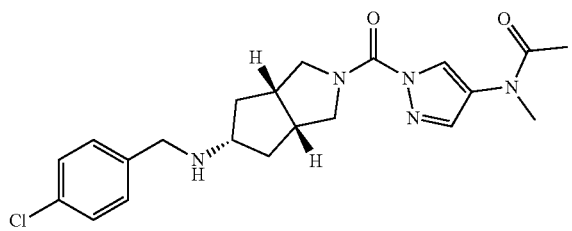 [SMILES: CC(=O)N(C)c1cnn(C(=O)N2C[C@H]3C[C@@H](NCc4ccc(Cl)cc4)C[C@H]3C2)c1]

The title compound was synthesized as described in Example 133 using 4-chlorobenzaldehyde in Step 2. Purification resulted in 93.7 mg of N-(1-(cis-5-(4-chlorobenzylamino)octahydrocyclopenta[c]pyrrole-2-carbonyl)-1H-pyrazol-4-yl)-N-methylacetamide as an off-white solid. $^1$H NMR (300 MHz, Chloroform-d) δ 8.26 (s, 0.3H), 8.19 (s, 0.7H), 8.05 (s, 0.3H), 7.55 (s, 0.7H), 7.28-7.31 (m, 3H), 7.24-7.25 (m, 1H), 3.96 (br, 4H), 3.75 (s, 2H), 3.36 (s, 1H), 3.22 (s, 3H), 2.69 (br, 2H), 2.29 (s, 1H), 2.24-2.26 (m, 2H), 2.00 (s, 2H), 1.37-1.44 (m, 2H). LCMS (ESI, m/z): 416 [M+H]$^+$.

Example 136: N-(1-(trans-5-(2-chlorobenzylamino) octahydrocyclopenta[c]pyrrole-2-carbonyl)-1H-pyrazol-4-yl)-N-methylacetamide

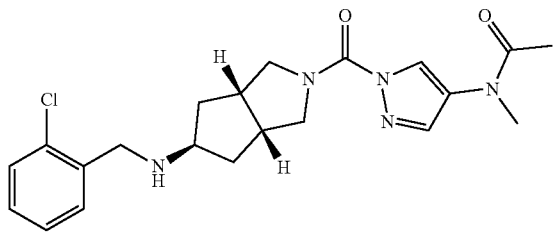 [SMILES: CC(=O)N(C)c1cnn(C(=O)N2C[C@H]3C[C@H](NCc4ccccc4Cl)C[C@H]3C2)c1]

The title compound was synthesized as described in Example 133 using 2-chlorobenzaldehyde and trans-tert-butyl 5-aminohexahydrocyclopenta[c]pyrrole-2(1H)-carboxylate in Step 2. Purification resulted in 75.1 mg of N-(1-(trans-5-(2-chlorobenzylamino)octahydrocyclopenta[c]pyrrole-2-carbonyl)-1H-pyrazol-4-yl)-N-methylacetamide as a white semi-solid. $^1$H NMR (300 MHz, Chloroform-d) δ 8.27 (s, 0.3H), 8.18 (s, 0.7H), 8.04 (s, 0.3H), 7.54 (s, 0.7H), 7.34-7.37 (m, 2H), 7.17-7.26 (m, 2H), 3.99-4.06 (m, 2H), 3.58-3.84 (m, 4H), 3.36-3.44 (m, 2H), 3.21 (s, 2H), 2.90 (br, 2H), 2.28 (s, 1H), 1.99 (s, 2H), 1.71-1.82 (m, 4H). LCMS (ESI, m/z): 416 [M+H]$^+$.

Example 137: N-(1-(trans-5-(3-chlorobenzylamino) octahydrocyclopenta[c]pyrrole-2-carbonyl)-1H-pyrazol-4-yl)-N-methylacetamide

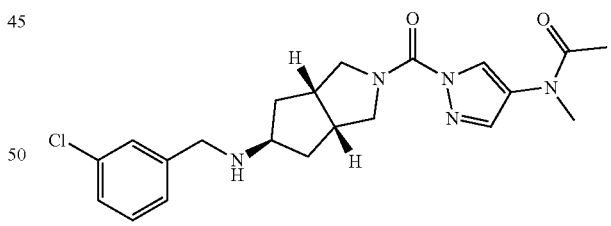

The title compound was synthesized as described in Example 133 using 3-chlorobenzaldehyde and trans-tert-butyl 5-aminohexahydrocyclopenta[c]pyrrole-2(1H)-carboxylate in Step 2. Purification resulted in 69.0 mg of N-(1-(trans-5-(3-chlorobenzylamino)octahydrocyclopenta[c]pyrrole-2-carbonyl)-1H-pyrazol-4-yl)-N-methylacetamide as an off-white solid. $^1$H NMR (300 MHz, Chloroform-d) δ 8.28 (s, 0.3H), 8.19 (s, 0.7H), 8.05 (s, 0.3H), 7.55 (s, 0.7H), 7.33 (s, 1H), 7.17-7.26 (m, 3H), 3.61-4.10 (m, 6H), 3.39-3.45 (m, 1H), 3.36 (s, 1H), 3.22 (s, 2H), 2.91 (br, 2H), 2.29 (s, 1H), 2.00 (s, 2H), 1.78-1.82 (m, 4H). LCMS (ESI, m/z): 416 [M+H]$^+$.

Example 138: N-(1-(trans-5-(4-chlorobenzylamino)octahydrocyclopenta[c]pyrrole-2-carbonyl)-1H-pyrazol-4-yl)-N-methylacetamide

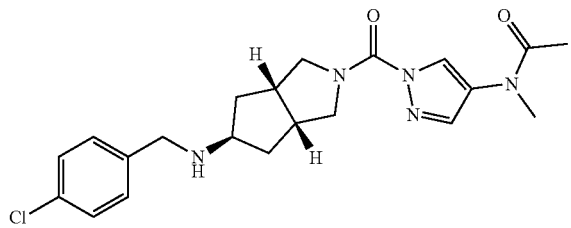 [SMILES: CC(=O)N(C)c1cnn(C(=O)N2C[C@H]3C[C@H](NCc4ccc(Cl)cc4)C[C@H]3C2)c1]

The title compound was synthesized as described in Example 133 using 4-chlorobenzaldehyde and trans-tert-butyl 5-aminohexahydrocyclopenta[c]pyrrole-2(1H)-carboxylate in Step 2. Purification resulted in 70.3 mg of N-(1-(trans-5-(4-chlorobenzylamino)octahydrocyclopenta[c]pyrrole-2-carbonyl)-1H-pyrazol-4-yl)-N-methylacetamide as a white solid. $^1$H NMR (300 MHz, Chloroform-d) δ 8.27 (s, 0.3H), 8.18 (s, 0.7H), 8.05 (s, 0.3H), 7.55 (s, 0.7H), 7.28-7.31 (m, 2H), 7.23-7.26 (m, 2H), 3.73-4.19 (m, 6H), 3.38-3.42 (m, 1H), 3.36 (s, 1H), 3.22 (s, 2H), 2.90 (br, 2H), 2.29 (s, 1H), 2.00 (s, 2H), 1.77-1.81 (m, 4H). LCMS (ESI, m/z): 416 [M+H]$^+$.

Example 139: N-(1-(cis-5-((2-chlorobenzyl)(methyl)amino)octahydrocyclopenta[c]pyrrole-2-carbonyl)-1H-pyrazol-4-yl)-N-methylacetamide

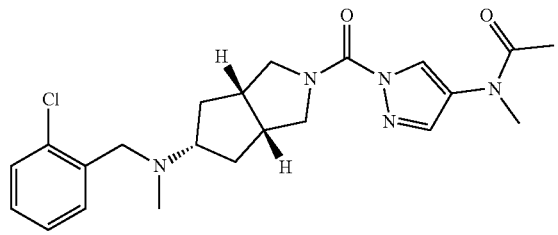 [SMILES: CC(=O)N(C)c1cnn(C(=O)N2C[C@H]3C[C@@H](N(C)Cc4ccccc4Cl)C[C@H]3C2)c1]

Step 1: Synthesis of 4-nitrophenyl 4-acetamido-1H-pyrazole-1-carboxylate

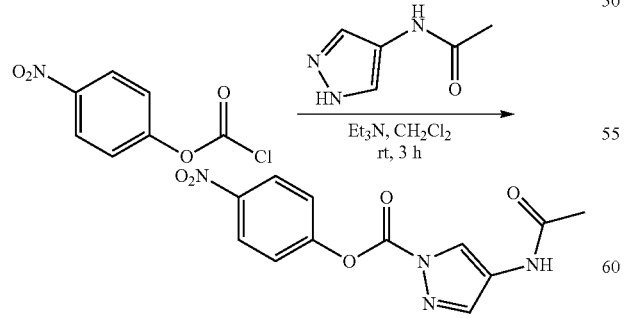

A 100-mL round-bottom flask was charged with N-(1H-pyrazol-4-yl)acetamide (690 mg, 5.51 mmol, 1.00 equiv) in DCM (10 mL), 4-nitrophenyl chloroformate (1.16 g, 5.75 mmol, 1.05 equiv), and triethylamine (1.67 g, 16.5 mmol, 3.00 equiv) under nitrogen. The resulting solution was stirred for 3 h at room temperature. The reaction progress was monitored by LCMS. The resulting mixture was concentrated under reduced pressure to yield 2.25 g (crude) of 4-nitrophenyl 4-acetamido-1H-pyrazole-1-carboxylate as a yellow solid. LCMS (ESI, m/z): 291 [M+H]$^+$.

Step 2: Synthesis of cis-tert-butyl 5-(2-chlorobenzylamino)hexahydrocyclopenta[c]pyrrole-2(1H)-carboxylate

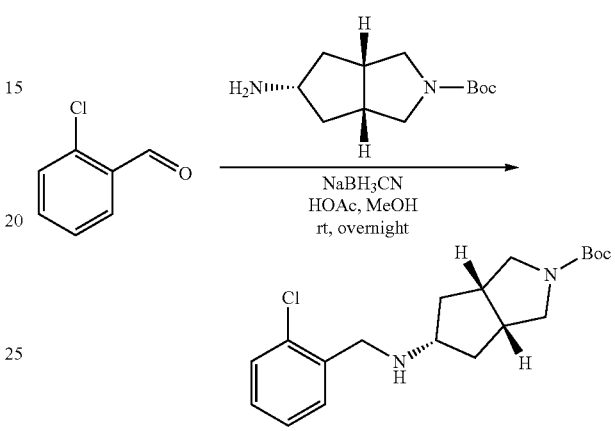

A 100-mL round-bottom flask was charged with 2-chlorobenzaldehyde (2.80 g, 19.9 mmol, 1.00 equiv) in MeOH (30 mL), cis-tert-butyl 5-aminohexahydrocyclopenta[c]pyrrole-2(1H)-carboxylate (5.42 g, 24.0 mmol, 1.20 equiv), and acetic acid (3.60 g, 60.0 mmol, 3.00 equiv). The resulting solution was stirred for 30 min at room temperature. Sodium cyanoborohydride (3.78 g, 60.0 mmol, 3.00 equiv) was added. The resulting solution was stirred overnight at room temperature and quenched with water (30 mL). The resulting solution was extracted with DCM (3×30 mL) and the organic layers were combined, washed with brine (2×30 mL), dried over anhydrous sodium sulfate, filtered and concentrated under reduced pressure. The residue was chromatographed on a silica gel column to yield 5.00 g (72% yield) of cis-tert-butyl 5-(2-chlorobenzylamino)hexahydrocyclopenta[c]pyrrole-2(1H)-carboxylate as a yellow oil. LCMS (ESI, m/z): 351 [M+H]$^+$.

Step 3: Synthesis of cis-tert-butyl 5-((2-chlorobenzyl)(methyl)amino)hexahydrocyclopenta[c]pyrrole-2(1H)-carboxylate

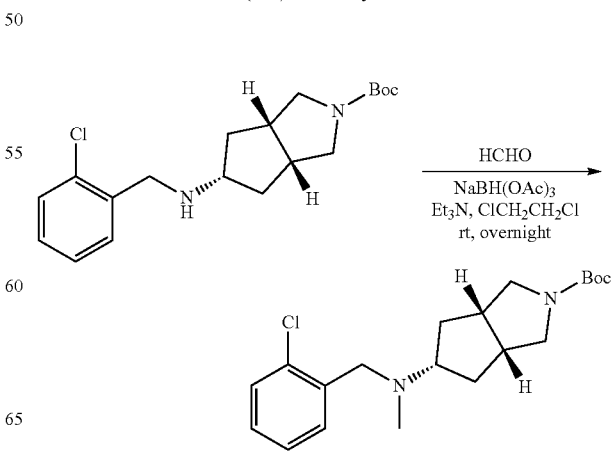

A 100-mL round-bottom flask was charged with cis-tert-butyl 5-(2-chlorobenzylamino)hexahydrocyclopenta[c]pyrrole-2(1H)-carboxylate (1.40 g, 3.99 mmol, 1.00 equiv) in dichloroethane (30 mL), paraformaldehyde (1.20 g, 39.9 mmol, 10.0 equiv), and triethylamine (1.21 g, 12.0 mmol, 3.00 equiv). The resulting solution was stirred for 30 min at room temperature. Sodium triacetoxyborohydride (2.54 g, 12.0 mmol, 3.00 equiv) was added. The resulting solution was stirred overnight at room temperature and quenched with water (30 mL). The resulting solution was extracted with DCM (3×30 mL) and the organic layers were combined, washed with brine (2×30 mL), dried over anhydrous sodium sulfate, filtered and concentrated under reduced pressure. The residue was chromatographed on a silica gel column to yield 1.30 g (89% yield) of tert-butyl cis-tert-butyl 5-((2-chlorobenzyl)(methyl)amino)hexahydrocyclopenta[c]pyrrole-2(1H)-carboxylate as a yellow oil. LCMS (ESI, m/z): 365 [M+H]$^+$.

Step 4: Synthesis of cis-N-(2-chlorobenzyl)-N-methyloctahydrocyclopenta[c]pyrrol-5-amine A 100-mL round-bottom flask was charged with cis-tert-butyl 5-((2-chlorobenzyl)(methyl)amino)hexahydrocyclopenta[c]pyrrole-2(1H)-carboxylate (1.20 g, 3.29 mmol, 1.00 equiv) in DCM (20 mL), and TFA (5 mL). The resulting solution was stirred for 5 h at room temperature. The reaction progress was monitored by LCMS. The resulting solution was concentrated under reduced pressure to yield 1.45 g (crude) of cis-N-(2-chlorobenzyl)-N-methyloctahydrocyclopenta[c]pyrrol-5-amine as a yellow oil. LCMS (ESI, m/z): 265 [M+H]$^+$.

Step 5: Synthesis of N-(1-(cis-5-((2-chlorobenzyl)(methyl)amino)octahydrocyclopenta[c]pyrrole-2-carbonyl)-1H-pyrazol-4-yl)acetamide

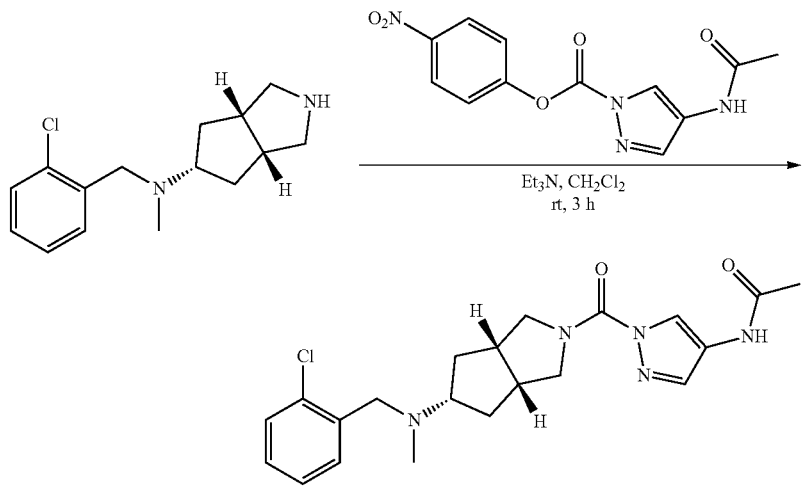

A 100-mL round-bottom flask was charged with cis-N-(2-chlorobenzyl)-N-methyloctahydrocyclopenta[c]pyrrol-5-amine (340 mg, 1.28 mmol, 1.00 equiv) in DCM (20 mL), 4-nitrophenyl 4-acetamido-1H-pyrazole-1-carboxylate (560 mg, 1.93 mmol, 1.50 equiv), and triethylamine (390 mg, 3.86 mmol, 3.00 equiv) under nitrogen. The resulting solution was stirred for 3 h at room temperature and quenched with water (20 mL). The resulting solution was extracted with DCM (3×20 mL) and the organic layers were combined, washed with brine (2×20 mL), dried over anhydrous sodium sulfate, filtered and concentrated under reduced pressure. The residue was chromatographed on a silica gel column to yield 500 mg (94% yield) of N-(1-(cis-5-((2-chlorobenzyl)(methyl)amino)octahydrocyclopenta[c]pyrrole-2-carbonyl)-1H-pyrazol-4-yl)acetamide as a yellow oil. LCMS (ESI, m/z): 416 [M+H]$^+$.

Step 6: Synthesis of N-(1-(cis-5-((2-chlorobenzyl)(methyl)amino)octahydrocyclopenta[c]pyrrole-2-carbonyl)-1H-pyrazol-4-yl)-N-methylacetamide

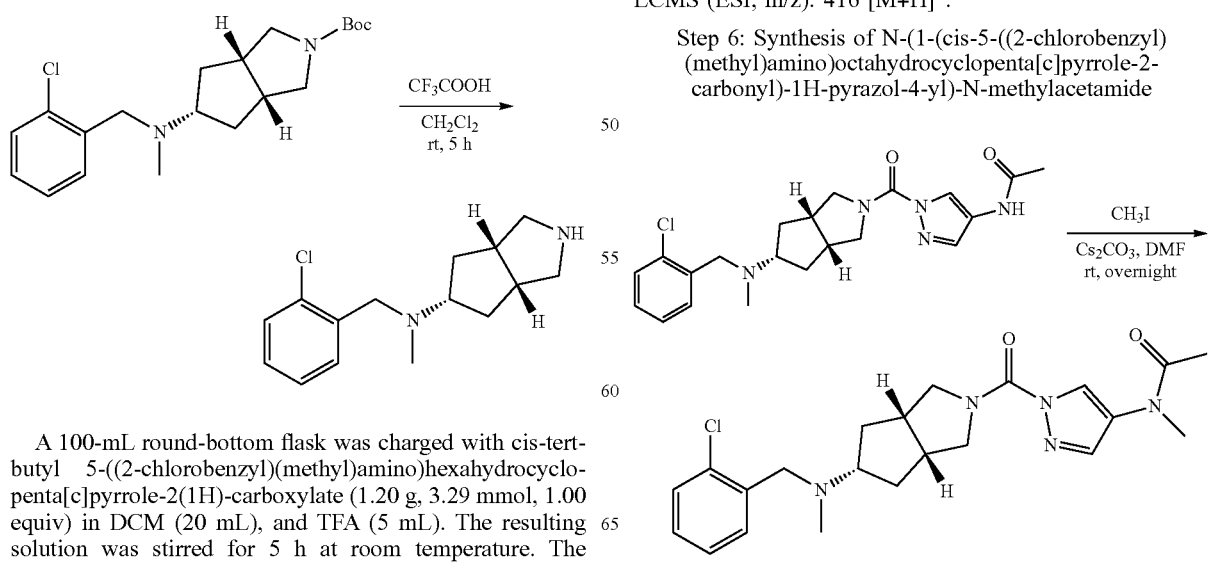

A 40-mL round-bottom flask was charged with N-(1-(cis-5-((2-chlorobenzyl)(methyl)amino)octahydrocyclopenta[c]pyrrole-2-carbonyl)-1H-pyrazol-4-yl)acetamide (500 mg, 1.20 mmol, 1.00 equiv) in DMF (10 mL), and cesium carbonate (1.18 g, 3.62 mmol, 3.00 equiv) under nitrogen. The resulting solution was stirred for 1 h at 0° C. Then iodomethane (257 mg, 1.81 mmol, 1.50 equiv) was added dropwise at 0° C. The resulting solution was stirred overnight at room temperature and quenched with water (10 mL). The mixture was extracted with EtOAc (3×10 mL) and the organic layers were combined, washed with brine (2×10 mL), dried over anhydrous sodium sulfate, filtered and concentrated under reduced pressure. The crude product (300 mg) was purified by preparative HPLC. Purification resulted in 137.4 mg (27% yield) of N-(1-(cis-5-((2-chlorobenzyl)(methyl)amino)octahydrocyclopenta[c]pyrrole-2-carbonyl)-1H-pyrazol-4-yl)-N-methylacetamide as a light yellow oil. $^1$H NMR (300 MHz, Chloroform-d) δ 8.28 (s, 0.3H), 8.20 (s, 0.7H), 8.05 (s, 0.3H), 7.54 (s, 0.7H), 7.51 (br, 1H), 7.34-7.40 (m, 1H), 7.23-7.26 (m, 2H), 3.65-3.98 (m, 6H), 3.36 (s, 1H), 3.22 (s, 2H), 3.00 (br, 1H), 2.72 (br, 2H), 2.21-2.28 (m, 6H), 2.00 (s, 2H), 1.61 (br, 2H). LCMS (ESI, m/z): 430 [M+H]$^+$.

Example 140 N-(1-(cis-5-((2,5-bis(trifluoromethyl)benzyl)(methyl)amino)octahydrocyclopenta[c]pyrrole-2-carbonyl)-1H-pyrazol-4-yl)-N-methylacetamide

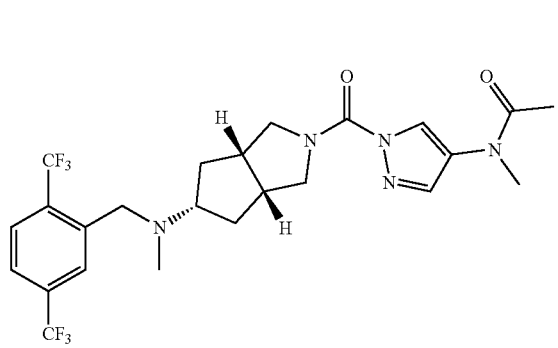 [SMILES: CC(=O)N(C)c1cnn(C(=O)N2C[C@H]3C[C@@H](N(C)Cc4cc(C(F)(F)F)ccc4C(F)(F)F)C[C@H]3C2)c1]

The title compound was synthesized as described in Example 139 using 2,5-bis(trifluoromethyl)benzaldehyde in Step 2. Purification resulted in 117.8 mg of N-(1-(cis-5-((2,5-bis(trifluoromethyl)benzyl)(methyl)amino)octahydrocyclopenta[c]pyrrole-2-carbonyl)-1H-pyrazol-4-yl)-N-methylacetamide as a light yellow oil. $^1$H NMR (300 MHz, Chloroform-d) δ 8.30 (s, 0.3H), 8.22 (s, 0.7H), 8.17 (s, 1H), 8.07 (s, 0.3H), 7.74-7.76 (m, 1H), 7.61 (s, 1H), 7.56 (s, 0.7H), 4.03 (br, 4H), 3.73 (s, 2H), 3.37 (s, 1H), 3.23 (s, 2H), 3.00-3.02 (m, 1H), 2.73 (br, 2H), 2.29 (s, 1H), 2.15-2.23 (m, 5H), 2.01 (s, 2H), 1.52 (br, 2H). LCMS (ESI, m/z): 532 [M+H]$^+$.

Example 141 N-(1-(cis-5-((3-chlorobenzyl)(methyl)amino)octahydrocyclopenta[c]pyrrole-2-carbonyl)-1H-pyrazol-4-yl)-N-methylacetamide

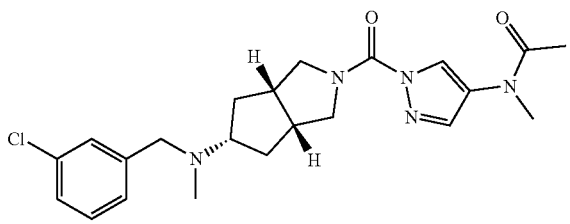 [SMILES: CC(=O)N(C)c1cnn(C(=O)N2C[C@H]3C[C@@H](N(C)Cc4cccc(Cl)c4)C[C@H]3C2)c1]

The title compound was synthesized as described in Example 139 using 3-chlorobenzaldehyde benzaldehyde in Step 2. Purification resulted in 65.1 mg of N-(1-(cis-5-((3-chlorobenzyl)(methyl)amino)octahydrocyclopenta[c]pyrrole-2-carbonyl)-1H-pyrazol-4-yl)-N-methylacetamide as an off-white semi-solid. $^1$H NMR (300 MHz, Chloroform-d) δ 8.29 (s, 0.3H), 8.21 (s, 0.7H), 8.07 (s, 0.3H), 7.56 (s, 0.7H), 7.32 (s, 1H), 7.19-7.24 (m, 3H), 3.71-4.19 (m, 4H), 3.48 (s, 2H), 3.37 (s, 1H), 3.23 (s, 2H), 2.85-2.96 (m, 1H), 2.71 (br, 2H), 2.13-2.29 (m, 6H), 2.00 (s, 2H), 1.52-1.58 (m, 2H). LCMS (ESI, m/z): 430 [M+H]$^+$.

Example 142: N-methyl-N-(1-(trans-5-(methyl(5-(pyrrolidin-1-yl)-2-(trifluoromethyl)benzyl)amino)octahydrocyclopenta[c]pyrrole-2-carbonyl)-1H-pyrazol-4-yl)acetamide

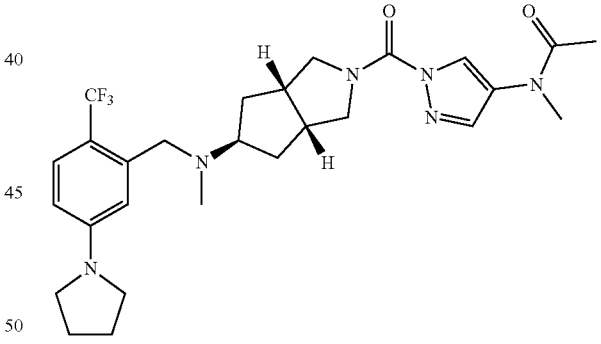

The title compound was synthesized as described in Example 139 using 5-(pyrrolidin-1-yl)-2-(trifluoromethyl)benzaldehyde (synthesized as described in Example 67, Step 1) and trans-tert-butyl 5-aminohexahydrocyclopenta[c]pyrrole-2(1H)-carboxylate in Step 2. Purification resulted in 58.6 mg of N-methyl-N-(1-(trans-5-(methyl(5-(pyrrolidin-1-yl)-2-(trifluoromethyl)benzyl)amino)octahydrocyclopenta[c]pyrrole-2-carbonyl)-1H-pyrazol-4-yl)acetamide as a white solid. $^1$H NMR (300 MHz, Chloroform-d) δ 8.28 (s, 0.3H), 8.19 (s, 0.7H), 8.05 (s, 0.3H), 7.55 (s, 0.7H), 7.42 (d, J=8.7 Hz, 1H), 6.94 (br, 1H), 6.39 (d, J=8.1 Hz, 1H), 4.04 (br, 2H), 3.60 (br, 4H), 3.33-3.36 (m, 5H), 3.22 (s, 3H), 2.86 (br, 2H), 2.28 (s, 1H), 2.17 (s, 3H), 2.00-2.06 (m, 6H), 1.85-1.90 (m, 4H). LCMS (ESI, m/z): 533 [M+H]$^+$.

Example 143: N-(1-(cis-5-((4-chlorobenzyl)(methyl)amino)octahydrocyclopenta[c]pyrrole-2-carbonyl)-1H-pyrazol-4-yl)-N-methylacetamide

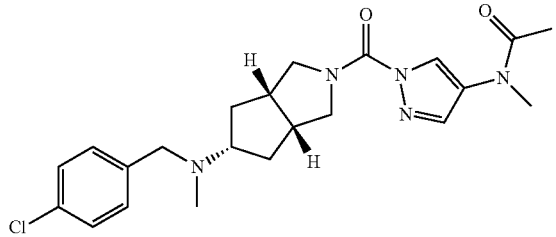 [SMILES: CC(=O)N(C)c1cnn(C(=O)N2C[C@H]3C[C@@H](N(C)Cc4ccc(Cl)cc4)C[C@H]3C2)c1]

The title compound was synthesized as described in Example 139 using 4-chlorobenzaldehyde benzaldehyde in Step 2. Purification resulted in 16.0 mg of N-(1-(cis-5-((4-chlorobenzyl)(methyl)amino)octahydrocyclopenta[c]pyrrole-2-carbonyl)-1H-pyrazol-4-yl)-N-methylacetamide as a light yellow semi-solid. $^1$H NMR (300 MHz, Chloroform-d) δ 8.28 (s, 0.3H), 8.20 (s, 0.7H), 8.06 (s, 0.3H), 7.55 (s, 0.7H), 7.29 (s, 1H), 7.22-7.24 (m, 3H), 3.77-4.19 (m, 4H), 3.46 (s, 2H), 3.36 (s, 1H), 3.22 (s, 2H), 2.85-2.94 (m, 1H), 2.70 (br, 2H), 2.28 (s, 0.8H), 2.17 (br, 2H), 2.10 (s, 3.2H), 2.00 (s, 2H), 1.46-1.53 (m, 2H). LCMS (ESI, m/z): 430 [M+H]$^+$.

Example 144: N-methyl-N-(1-(trans-5-(methyl(2-(pyrrolidin-1-yl)-5-(trifluoromethyl)benzyl)amino)octahydrocyclopenta[c]pyrrole-2-carbonyl)-1H-pyrazol-4-yl)acetamide

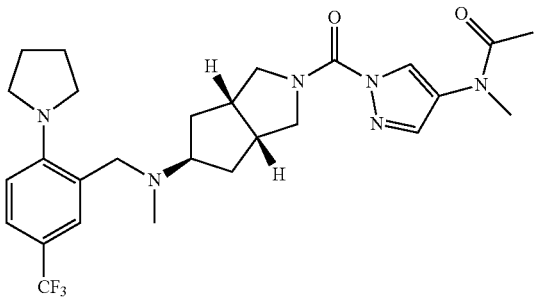 [SMILES: CC(=O)N(C)c1cnn(C(=O)N2C[C@H]3C[C@H](N(C)Cc4cc(C(F)(F)F)ccc4N4CCCC4)C[C@H]3C2)c1]

The title compound was synthesized as described in Example 139 using 2-(pyrrolidin-1-yl)-5-(trifluoromethyl)benzaldehyde (synthesized as described in Example 67, Step 1) and trans-tert-butyl 5-aminohexahydrocyclopenta[c]pyrrole-2(1H)-carboxylate in Step 2. Purification resulted in 72.5 mg of N-methyl-N-(1-(trans-5-(methyl(2-(pyrrolidin-1-yl)-5-(trifluoromethyl)benzyl)amino)octahydrocyclopenta[c]pyrrole-2-carbonyl)-1H-pyrazol-4-yl)acetamide as a yellow semi-solid. $^1$H NMR (300 MHz, Chloroform-d) δ 8.30 (s, 0.3H), 8.20 (s, 0.7H), 8.05 (s, 0.3H), 7.77 (s, 1H), 7.56 (s, 0.7H), 7.36 (d, J=8.1 Hz, 1H), 6.87 (d, J=8.4 Hz, 1H), 4.02 (br, 4H), 3.54 (br, 2H), 3.37 (s, 1H), 3.16-3.29 (m, 7H), 2.87 (br, 2H), 2.29 (s, 1H), 2.10 (s, 3H), 1.80-1.97 (m, 10H). LCMS (ESI, m/z): 533 [M+H]$^+$.

Example 145: N-(1-(trans-5-((2-chlorobenzyl)(methyl)amino)octahydrocyclopenta[c]pyrrole-2-carbonyl)-1H-pyrazol-4-yl)-N-methylacetamide

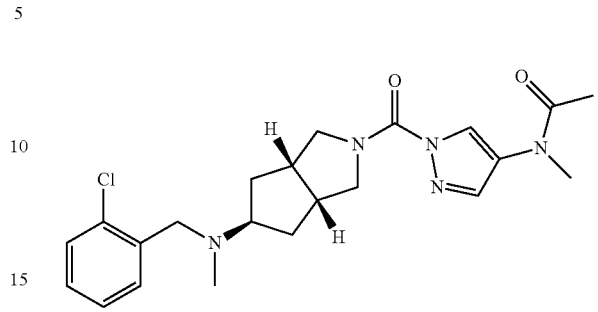

The title compound was synthesized as described in Example 139 using trans-tert-butyl 5-aminohexahydrocyclopenta[c]pyrrole-2(1H)-carboxylate in Step 2. Purification resulted in 163.7 mg of N-(1-(trans-5-((2-chlorobenzyl)(methyl)amino)octahydrocyclopenta[c]pyrrole-2-carbonyl)-1H-pyrazol-4-yl)-N-methylacetamide as a light yellow oil. $^1$H NMR (300 MHz, Chloroform-d) δ 8.29 (s, 0.3H), 8.20 (s, 0.7H), 8.05 (s, 0.3H), 7.56 (s, 0.7H), 7.44-7.47 (m, 1H), 7.32-7.35 (m, 1H), 7.15-7.23 (m, 2H), 3.60-4.05 (m, 6H), 3.36 (s, 1H), 3.17-3.22 (m, 3H), 2.88 (br, 2H), 2.28 (s, 1H), 2.17 (s, 3H), 1.84-2.00 (m, 6H). LCMS (ESI, m/z): 430 [M+H]$^+$.

Example 146: N-(1-(trans-5-((2,5-bis(trifluoromethyl)benzyl)(methyl)amino)octahydrocyclopenta[c]pyrrole-2-carbonyl)-1H-pyrazol-4-yl)-N-methylacetamide

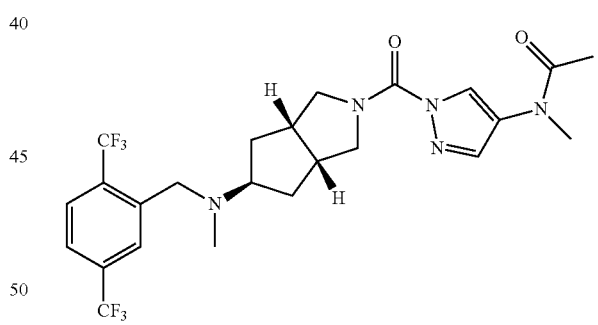

The title compound was synthesized as described in Example 139 using 2,5-bis(trifluoromethyl)benzaldehyde and trans-tert-butyl 5-aminohexahydrocyclopenta[c]pyrrole-2(1H)-carboxylate in Step 2. Purification resulted in 206.0 mg of N-(1-(trans-5-((2,5-bis(trifluoromethyl)benzyl)(methyl)amino)octahydrocyclopenta[c]pyrrole-2-carbonyl)-1H-pyrazol-4-yl)-N-methylacetamide as a white solid. $^1$H NMR (300 MHz, Chloroform-d) δ 8.30 (s, 0.3H), 8.20 (s, 0.7H), 8.17 (s, 1H), 8.06 (s, 0.3H), 7.75 (d, J=8.1 Hz, 1H), 7.59 (d, J=8.4 Hz, 1H), 7.56 (s, 0.7H), 4.12 (br, 4H), 3.72 (br, 2H), 3.37 (s, 1H), 3.23 (s, 3H), 2.90 (br, 2H), 2.30 (s, 1H), 2.17 (s, 3H), 2.01 (s, 2H), 1.88 (br, 4H). LCMS (ESI, m/z): 532 [M+H]$^+$.

Example 147: N-(1-(trans-5-((3-chlorobenzyl)(methyl)amino)octahydrocyclopenta[c]pyrrole-2-carbonyl)-1H-pyrazol-4-yl)-N-methylacetamide

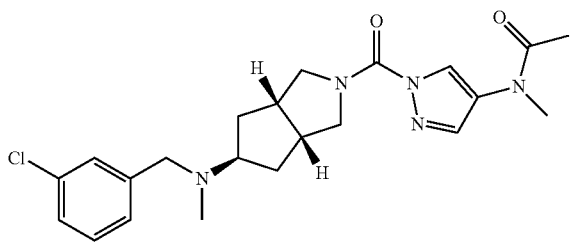 [SMILES: CC(=O)N(C)c1cnn(C(=O)N2C[C@H]3C[C@H](N(C)Cc4cccc(Cl)c4)C[C@H]3C2)c1]

The title compound was synthesized as described in Example 139 using 3-chlorobenzaldehyde benzaldehyde and trans-tert-butyl 5-aminohexahydrocyclopenta[c]pyrrole-2(1H)-carboxylate in Step 2. Purification resulted in 51.0 mg of N-(1-(trans-5-((3-chlorobenzyl)(methyl)amino) octahydrocyclopenta[c]pyrrole-2-carbonyl)-1H-pyrazol-4-yl)-N-methylacetamide as a white solid. $^1$H NMR (300 MHz, Chloroform-d) δ 8.29 (s, 0.3H), 8.19 (s, 0.7H), 8.05 (s, 0.3H), 7.56 (s, 0.7H), 7.32 (s, 1H), 7.16-7.24 (m, 3H), 3.62-4.26 (m, 4H), 3.47 (s, 2H), 3.36 (s, 1H), 3.22 (s, 2H), 3.06-3.17 (m, 1H), 2.88 (br, 2H), 2.29 (s, 1H), 2.18 (s, 3H), 2.00 (s, 2H), 1.89 (br, 4H). LCMS (ESI, m/z): 430 [M+H]$^+$.

Example 148: N-(1-(trans-5-((4-chlorobenzyl)(methyl)amino)octahydrocyclopenta[c]pyrrole-2-carbonyl)-1H-pyrazol-4-yl)-N-methylacetamide

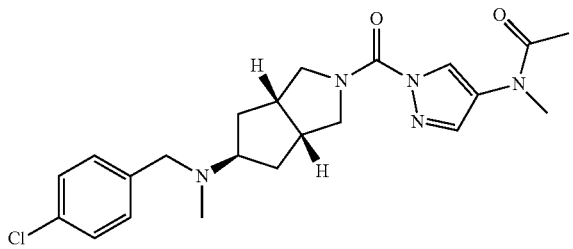 [SMILES: CC(=O)N(C)c1cnn(C(=O)N2C[C@H]3C[C@H](N(C)Cc4ccc(Cl)cc4)C[C@H]3C2)c1]

The title compound was synthesized as described in Example 139 using 4-chlorobenzaldehyde benzaldehyde and trans-tert-butyl 5-aminohexahydrocyclopenta[c]pyrrole-2(1H)-carboxylate in Step 2. Purification resulted in 23.0 mg of N-(1-(trans-5-((4-chlorobenzyl)(methyl)amino) octahydrocyclopenta[c]pyrrole-2-carbonyl)-1H-pyrazol-4-yl)-N-methylacetamide as a light yellow semi-solid. $^1$H NMR (300 MHz, Chloroform-d) δ 8.28 (s, 0.3H), 8.19 (s, 0.7H), 8.05 (s, 0.3H), 7.55 (s, 0.7H), 7.29 (s, 1H), 7.21-7.24 (m, 3H), 3.61-4.18 (m, 4H), 3.45 (s, 2H), 3.36 (s, 1H), 3.22 (s, 2H), 3.04-3.12 (m, 1H), 2.87 (br, 2H), 2.28 (s, 1H), 2.10 (s, 3H), 2.00 (s, 2H), 1.87 (br, 4H). LCMS (ESI, m/z): 430 [M+H]$^+$.

Example 149: N-(1-(cis-5-((4-(3-oxa-8-azabicyclo[3.2.1]octan-8-yl)-2-(trifluoromethyl)benzyl)(methyl)amino)octahydrocyclopenta[c]pyrrole-2-carbonyl)-1H-pyrazol-4-yl)-N-methylacetamide

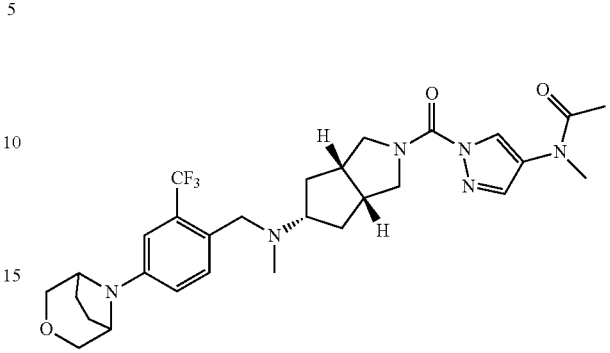

The title compound was synthesized as described in Example 139 using 4-(3-oxa-8-azabicyclo[3.2.1]octan-8-yl)-2-(trifluoromethyl)benzaldehyde (synthesized as described in Example 67, Step 1) in Step 2. Purification resulted in 70.1 mg of N-(1-(cis-5-((4-(3-oxa-8-azabicyclo [3.2.1]octan-8-yl)-2-(trifluoromethyl)benzyl)(methyl) amino)octahydrocyclopenta[c]pyrrole-2-carbonyl)-1H-pyrazol-4-yl)-N-methylacetamide as a white solid. $^1$H NMR (300 MHz, Chloroform-d) δ 8.29 (s, 0.3H), 8.20 (s, 0.7H), 8.05 (s, 0.3H), 7.56-7.65 (m, 1H), 7.55 (s, 0.7H), 6.85-7.00 (m, 2H), 3.70-4.20 (m, 8H), 3.50-3.60 (m, 4H), 3.36 (s, 1H), 3.22 (s, 2H), 2.60-3.10 (m, 3H), 2.28 (s, 1H), 1.95-2.22 (m, 11H), 1.40-1.58 (m, 2H). LCMS (ESI, m/z): 575 [M+H]$^+$.

Example 150: N-(1-(cis-5-((4-(3-oxa-8-azabicyclo[3.2.1]octan-8-yl)-3-(trifluoromethyl)benzyl)(methyl)amino)octahydrocyclopenta[c]pyrrole-2-carbonyl)-1H-pyrazol-4-yl)-N-methylacetamide

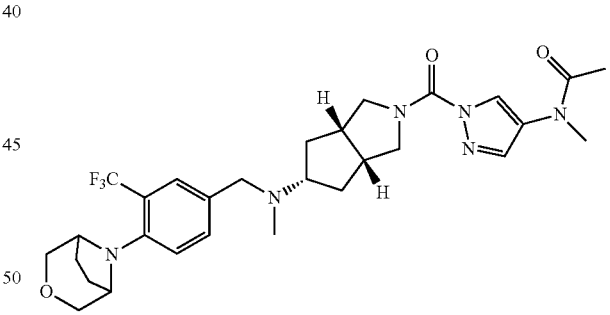

The title compound was synthesized as described in Example 139 using 4-(3-oxa-8-azabicyclo[3.2.1]octan-8-yl)-3-(trifluoromethyl)benzaldehyde (synthesized as described in Example 67, Step 1) in Step 2. Purification resulted in 62.7 mg of N-(1-(cis-5-((4-(3-oxa-8-azabicyclo [3.2.1]octan-8-yl)-3-(trifluoromethyl)benzyl)(methyl) amino)octahydrocyclopenta[c]pyrrole-2-carbonyl)-1H-pyrazol-4-yl)-N-methylacetamide as a white solid. $^1$H NMR (300 MHz, Chloroform-d) δ 8.28 (s, 0.3H), 8.20 (s, 0.7H), 8.06 (s, 0.3H), 7.55 (s, 0.7H), 7.51 (s, 1H), 7.36 (br, 1H), 6.94 (d, J=9.0 Hz, 1H), 3.55-4.20 (m, 10H), 3.47 (br, 2H), 3.36 (s, 1H), 3.22 (s, 2H), 2.60-3.00 (m, 3H), 2.29 (s, 1H), 1.90-2.25 (m, 11H), 1.40-1.60 (m, 2H). LCMS (ESI, m/z): 575 [M+H]$^+$.

Example 151: N-(1-(cis-5-((3-(3-oxa-8-azabicyclo[3.2.1]octan-8-yl)-5-(trifluoromethyl)benzyl)(methyl)amino)octahydrocyclopenta[c]pyrrole-2-carbonyl)-1H-pyrazol-4-yl)-N-methylacetamide

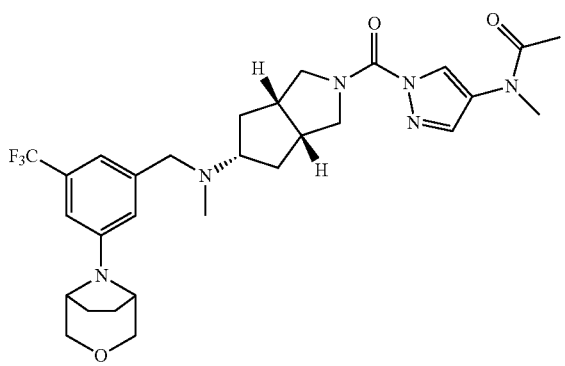 [SMILES: CC(=O)N(C)c1cnn(C(=O)N2C[C@H]3C[C@@H](N(C)Cc4cc(N5C6CCC5COC6)cc(C(F)(F)F)c4)C[C@H]3C2)c1]

The title compound was synthesized as described in Example 139 using 3-(3-oxa-8-azabicyclo[3.2.1]octan-8-yl)-5-(trifluoromethyl)benzaldehyde (synthesized as described in Example 63, Step 1) in Step 2. Purification resulted in 111.3 mg of N-(1-(cis-5-((3-(3-oxa-8-azabicyclo[3.2.1]octan-8-yl)-5-(trifluoromethyl)benzyl)(methyl)amino)octahydrocyclopenta[c]pyrrole-2-carbonyl)-1H-pyrazol-4-yl)-N-methylacetamide as a white solid. $^1$H NMR (300 MHz, Chloroform-d) δ 8.29 (s, 0.3H), 8.20 (s, 0.7H), 8.06 (s, 0.3H), 7.56 (s, 0.7H), 6.80-7.00 (m, 3H), 3.12 (br, 4H), 3.70-3.98 (m, 4H), 3.40-3.60 (m, 4H), 3.36 (s, 1H), 3.22 (s, 2H), 2.60-3.00 (m, 3H), 2.28 (s, 1H), 1.95-2.25 (m, 11H), 1.45-1.60 (m, 2H). LCMS (ESI, m/z): 575 [M+H]$^+$.

Example 152: N-methyl-N-(1-(cis-5-(methyl(4-(pyrrolidin-1-yl)-2-(trifluoromethyl)benzyl)amino)octahydrocyclopenta[c]pyrrole-2-carbonyl)-1H-pyrazol-4-yl)acetamide

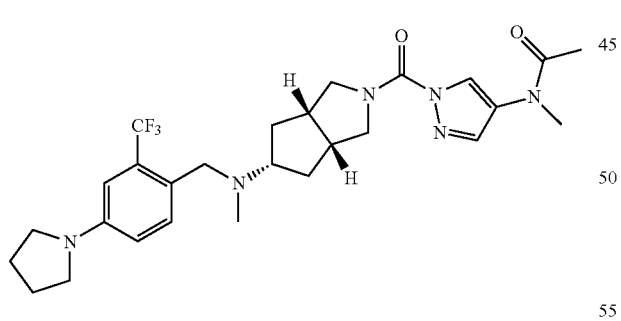

The title compound was synthesized as described in Example 139 using 4-(pyrrolidin-1-yl)-2-(trifluoromethyl)benzaldehyde (synthesized as described in Example 67, Step 1) in Step 2. Purification resulted in 17.8 mg of N-methyl-N-(1-(cis-5-(methyl(4-(pyrrolidin-1-yl)-2-(trifluoromethyl)benzyl)amino)octahydrocyclopenta[c]pyrrole-2-carbonyl)-1H-pyrazol-4-yl)acetamide as a white solid. $^1$H NMR (300 MHz, Chloroform-d) δ 8.28 (s, 0.3H), 8.20 (s, 0.7H), 8.06 (s, 0.3H), 7.55 (s, 0.7H), 7.49-7.54 (m, 1H), 6.71-6.80 (m, 1H), 6.60-6.70 (m, 1H), 4.00 (br, 4H), 3.54 (br, 2H), 3.36 (s, 1H), 3.30 (t, J=7.5 Hz, 4H), 3.22 (s, 2H), 2.92 (br, 1H), 2.69 (br, 2H), 2.28 (s, 1H), 1.95-2.25 (m, 11H), 1.40-1.60 (m, 2H). LCMS (ESI, m/z): 533 [M+H]$^+$.

Example 153: N-methyl-N-(1-(cis-5-(methyl(4-(pyrrolidin-1-yl)-3-(trifluoromethyl)benzyl)amino)octahydrocyclopenta[c]pyrrole-2-carbonyl)-1H-pyrazol-4-yl)acetamide

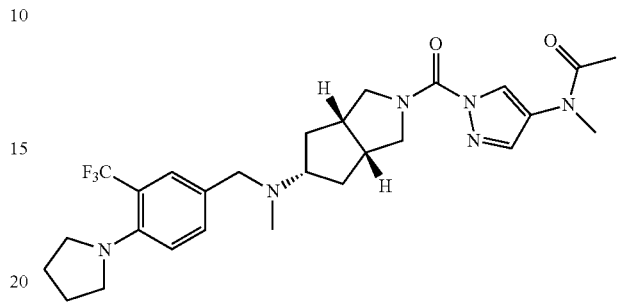

The title compound was synthesized as described in Example 139 using 4-(pyrrolidin-1-yl)-3-(trifluoromethyl)benzaldehyde (synthesized as described in Example 67, Step 1) in Step 2. Purification resulted in 76.3 mg of N-methyl-N-(1-(cis-5-(methyl(4-(pyrrolidin-1-yl)-3-(trifluoromethyl)benzyl)amino)octahydrocyclopenta[c]pyrrole-2-carbonyl)-1H-pyrazol-4-yl)acetamide as a yellow oil. $^1$H NMR (300 MHz, Chloroform-d) δ 8.28 (s, 0.3H), 8.20 (s, 0.7H), 8.06 (s, 0.3H), 7.55 (s, 0.7H), 7.45 (s, 1H), 7.31 (br, 1H), 6.94 (d, J=9.0 Hz, 1H), 3.93 (br, 4H), 3.47 (br, 2H), 3.36 (s, 1H), 3.25-3.35 (m, 4H), 3.22 (s, 2H), 2.60-2.98 (m, 3H), 2.28 (s, 1H), 1.90-2.25 (m, 11H), 1.50-1.70 (m, 2H). LCMS (ESI, m/z): 533 [M+H]$^+$.

Example 154: N-methyl-N-(1-(cis-5-(methyl(3-(pyrrolidin-1-yl)-5-(trifluoromethyl)benzyl)amino)octahydrocyclopenta[c]pyrrole-2-carbonyl)-1H-pyrazol-4-yl)acetamide

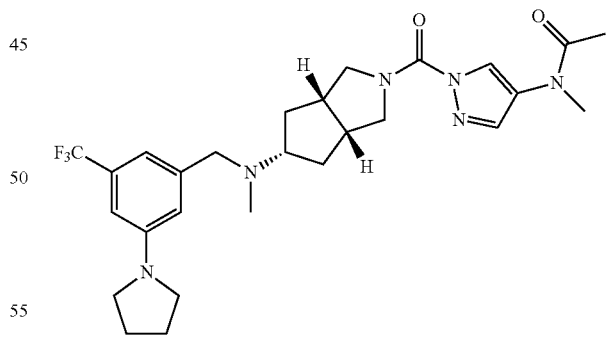

The title compound was synthesized as described in Example 139 using 3-(pyrrolidin-1-yl)-5-(trifluoromethyl)benzaldehyde (synthesized as described in Example 63, Step 1) in Step 2. Purification resulted in 64.7 mg of N-methyl-N-(1-(cis-5-(methyl(3-(pyrrolidin-1-yl)-5-(trifluoromethyl)benzyl)amino)octahydrocyclopenta[c]pyrrole-2-carbonyl)-1H-pyrazol-4-yl)acetamide as an off-white solid. $^1$H NMR (300 MHz, Chloroform-d) δ 8.28 (s, 0.3H), 8.20 (s, 0.7H), 8.06 (s, 0.3H), 7.55 (s, 0.7H), 6.81 (br, 1H), 6.63 (br, 2H), 3.98 (br, 4H), 3.49 (br, 2H), 3.36 (s, 1H), 3.25-3.35 (m, 4H), 3.22 (s, 2H), 2.91 (br, 1H), 2.70 (br, 2H), 2.28 (s, 1H), 2.10-2.25 (m, 5H), 1.95-2.05 (m, 6H), 1.55-1.75 (m, 2H). LCMS (ESI, m/z): 533 [M+H]⁺.

Example 155: N-(1-(trans-5-((4-(3-oxa-8-azabicyclo[3.2.1]octan-8-yl)-2-(trifluoromethyl)benzyl)(methyl)amino)octahydrocyclopenta[c]pyrrole-2-carbonyl)-1H-pyrazol-4-yl)-N-methylacetamide

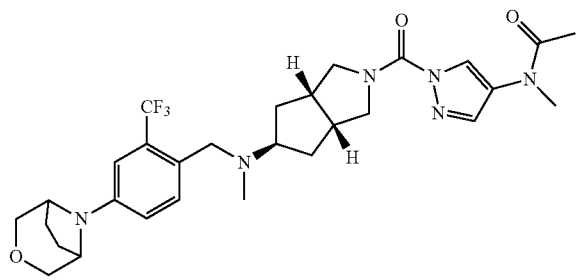 [SMILES: CC(=O)N(C)c1cnn(C(=O)N2C[C@H]3C[C@H](N(C)Cc4ccc(N5C6CCC5COC6)cc4C(F)(F)F)C[C@H]3C2)c1]

The title compound was synthesized as described in Example 139 using 4-(3-oxa-8-azabicyclo[3.2.1]octan-8-yl)-2-(trifluoromethyl)benzaldehyde (synthesized as described in Example 67, Step 1) and trans-tert-butyl 5-aminohexahydrocyclopenta[c]pyrrole-2(1H)-carboxylate in Step 2. Purification resulted in 107.5 mg of N-(1-(trans-5-((4-(3-oxa-8-azabicyclo[3.2.1]octan-8-yl)-2-(trifluoromethyl)benzyl)(methyl)amino)octahydrocyclopenta[c]pyrrole-2-carbonyl)-1H-pyrazol-4-yl)-N-methylacetamide as a light green solid. ¹H NMR (300 MHz, Chloroform-d) δ 8.28 (s, 0.3H), 8.19 (s, 0.7H), 8.05 (s, 0.3H), 7.55-7.61 (m, 1.7H), 6.98 (s, 1H), 6.89 (d, J=8.7 Hz, 1H), 3.53-4.07 (m, 12H), 3.13-3.36 (m, 4H), 2.86 (br, 2H), 2.28 (s, 1H), 1.87-2.21 (m, 13H). LCMS (ESI, m/z): 575 [M+H]⁺.

Example 156: N-(1-(trans-5-((4-(3-oxa-8-azabicyclo[3.2.1]octan-8-yl)-3-(trifluoromethyl)benzyl)(methyl)amino)octahydrocyclopenta[c]pyrrole-2-carbonyl)-1H-pyrazol-4-yl)-N-methylacetamide

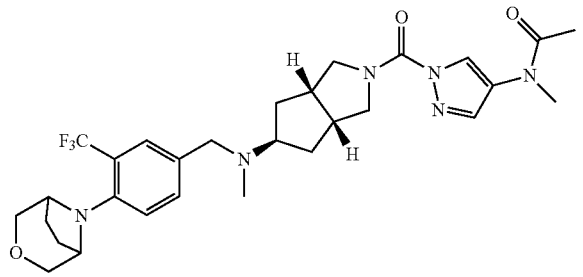 [SMILES: CC(=O)N(C)c1cnn(C(=O)N2C[C@H]3C[C@H](N(C)Cc4ccc(N5C6CCC5COC6)c(C(F)(F)F)c4)C[C@H]3C2)c1]

The title compound was synthesized as described in Example 139 using 4-(3-oxa-8-azabicyclo[3.2.1]octan-8-yl)-3-(trifluoromethyl)benzaldehyde (synthesized as described in Example 67, Step 1) and trans-tert-butyl 5-aminohexahydrocyclopenta[c]pyrrole-2(1H)-carboxylate in Step 2. Purification resulted in 29.1 mg of N-(1-(trans-5-((4-(3-oxa-8-azabicyclo[3.2.1]octan-8-yl)-3-(trifluoromethyl)benzyl)(methyl)amino)octahydrocyclopenta[c]pyrrole-2-carbonyl)-1H-pyrazol-4-yl)-N-methylacetamide as a white solid. ¹H NMR (300 MHz, Chloroform-d) δ 8.32 (s, 0.3H), 8.22 (s, 0.7H), 8.07 (s, 0.3H), 7.55-7.59 (m, 1.7H), 7.45 (br, 1H), 6.99 (d, J=9.0 Hz, 1H), 3.93-3.96 (m, 5H), 3.63-3.71 (m, 7H), 3.39 (s, 1H), 3.25 (s, 3H), 2.96 (br, 2H), 2.21-2.28 (m, 4H), 1.96-2.12 (m, 10H). LCMS (ESI, m/z): 575 [M+H]⁺.

Example 157: N-(1-(trans-5-((3-(3-oxa-8-azabicyclo[3.2.1]octan-8-yl)-5-(trifluoromethyl)benzyl)(methyl)amino)octahydrocyclopenta[c]pyrrole-2-carbonyl)-1H-pyrazol-4-yl)-N-methylacetamide

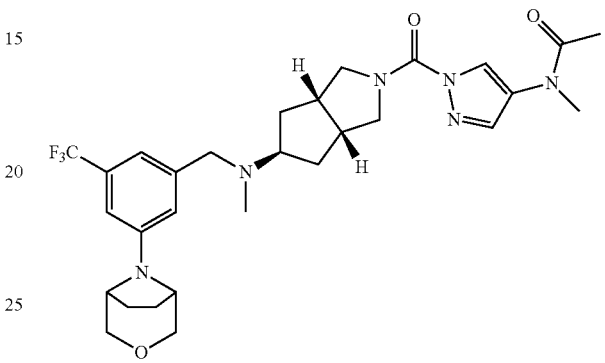

The title compound was synthesized as described in Example 139 using 3-(3-oxa-8-azabicyclo[3.2.1]octan-8-yl)-5-(trifluoromethyl)benzaldehyde (synthesized as described in Example 63, Step 1) and trans-tert-butyl 5-aminohexahydrocyclopenta[c]pyrrole-2(1H)-carboxylate in Step 2. Purification resulted in 57.6 mg of N-(1-(trans-5-((3-(3-oxa-8-azabicyclo[3.2.1]octan-8-yl)-5-(trifluoromethyl)benzyl)(methyl)amino)octahydrocyclopenta[c]pyrrole-2-carbonyl)-1H-pyrazol-4-yl)-N-methylacetamide as a yellow oil. ¹H NMR (300 MHz, Chloroform-d) δ 8.26 (s, 0.3H), 8.16 (s, 0.7H), 8.01 (s, 0.3H), 7.52 (s, 0.7H), 6.82-6.89 (m, 3H), 4.00-4.07 (m, 4H), 3.63-3.86 (m, 4H), 3.46-3.53 (m, 4H), 3.33 (s, 1H), 3.18 (s, 2H), 3.12 (br, 1H), 2.86 (br, 2H), 2.25 (s, 1H), 2.03-2.12 (m, 5H), 1.96-2.01 (m, 5H), 1.74-1.87 (m, 3H). LCMS (ESI, m/z): 575 [M+H]⁺.

Example 158: N-methyl-N-(1-(trans-5-(methyl(4-(pyrrolidin-1-yl)-2-(trifluoromethyl)benzyl)amino)octahydrocyclopenta[c]pyrrole-2-carbonyl)-1H-pyrazol-4-yl)acetamide

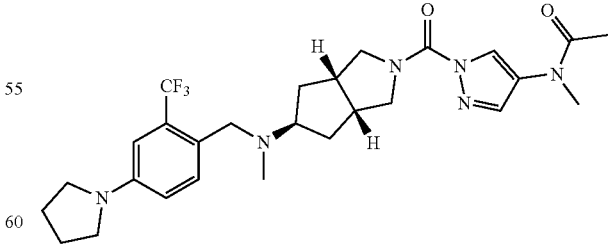

The title compound was synthesized as described in Example 139 using 4-(pyrrolidin-1-yl)-2-(trifluoromethyl)benzaldehyde (synthesized as described in Example 67, Step 1) and trans-tert-butyl 5-aminohexahydrocyclopenta[c]pyrrole-2(1H)-carboxylate in Step 2. Purification resulted in 182.0 mg of N-methyl-N-(1-(trans-5-(methyl(4-(pyrrolidin-1-yl)-2-(trifluoromethyl)benzyl)amino)octahydrocyclopenta[c]pyrrole-2-carbonyl)-1H-pyrazol-4-yl)acetamide as a yellow oil. $^1$H NMR (300 MHz, Chloroform-d) δ 8.28 (s, 0.3H), 8.19 (s, 0.7H), 8.05 (s, 0.3H), 7.55 (s, 0.7H), 7.52 (br, 1H), 6.74 (s, 1H), 6.67 (d, J=8.7 Hz, 1H), 3.57-4.07 (m, 6H), 3.15-3.45 (m, 8H), 2.87 (br, 2H), 2.28 (s, 1H), 1.83-2.11 (m, 13H). LCMS (ESI, m/z): 533 [M+H]$^+$.

Example 159: N-methyl-N-(1-(trans-5-(methyl(4-(pyrrolidin-1-yl)-3-(trifluoromethyl)benzyl)amino)octahydrocyclopenta[c]pyrrole-2-carbonyl)-1H-pyrazol-4-yl)acetamide

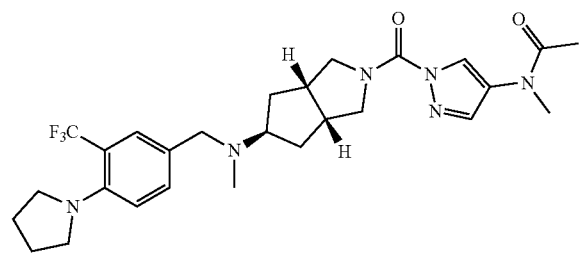 [SMILES: CC(=O)N(C)c1cnn(C(=O)N2C[C@H]3C[C@H](N(C)Cc4ccc(N5CCCC5)c(C(F)(F)F)c4)C[C@H]3C2)c1]

The title compound was synthesized as described in Example 139 using 4-(pyrrolidin-1-yl)-3-(trifluoromethyl)benzaldehyde (synthesized as described in Example 67, Step 1) and trans-tert-butyl 5-aminohexahydrocyclopenta[c]pyrrole-2(1H)-carboxylate in Step 2. Purification resulted in 115.2 mg of N-methyl-N-(1-(trans-5-(methyl(4-(pyrrolidin-1-yl)-3-(trifluoromethyl)benzyl)amino)octahydrocyclopenta[c]pyrrole-2-carbonyl)-1H-pyrazol-4-yl)acetamide as a yellow oil. $^1$H NMR (300 MHz, Chloroform-d) δ 8.28 (s, 0.3H), 8.19 (s, 0.7H), 8.04 (s, 0.3H), 7.55 (s, 0.7H), 7.46 (s, 1H), 7.27-7.31 (m, 1H), 6.93 (d, J=8.7 Hz, 1H), 3.54-4.25 (m, 4H), 3.22-3.34 (m, 9H), 3.08-3.16 (m, 1H), 2.88 (br, 2H), 2.28 (s, 1H), 2.11 (s, 3H), 1.83-1.99 (m, 10H). LCMS (ESI, m/z): 555 [M+Na]$^+$.

Example 160: N-methyl-N-(1-(trans-5-(methyl(3-(pyrrolidin-1-yl)-5-(trifluoromethyl)benzyl)amino)octahydrocyclopenta[c]pyrrole-2-carbonyl)-1H-pyrazol-4-yl)acetamide

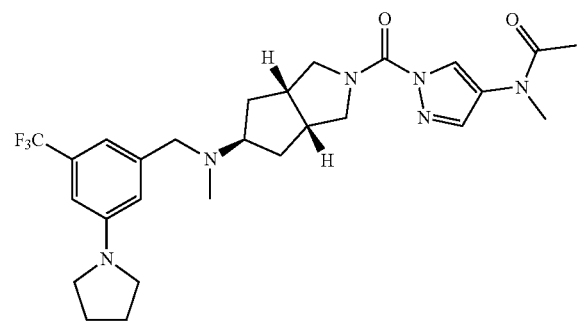 [SMILES: CC(=O)N(C)c1cnn(C(=O)N2C[C@H]3C[C@H](N(C)Cc4cc(N5CCCC5)cc(C(F)(F)F)c4)C[C@H]3C2)c1]

The title compound was synthesized as described in Example 139 using 3-(pyrrolidin-1-yl)-5-(trifluoromethyl)benzaldehyde (synthesized as described in Example 63, Step 1) and trans-tert-butyl 5-aminohexahydrocyclopenta[c]pyrrole-2(1H)-carboxylate in Step 2. Purification resulted in 114.3 mg of N-methyl-N-(1-(trans-5-(methyl(3-(pyrrolidin-1-yl)-5-(trifluoromethyl)benzyl)amino)octahydrocyclopenta[c]pyrrole-2-carbonyl)-1H-pyrazol-4-yl)acetamide as a light green solid. $^1$H NMR (300 MHz, Chloroform-d) δ 8.28 (s, 0.3H), 8.19 (s, 0.7H), 8.04 (s, 0.3H), 7.55 (s, 0.7H), 8.33 (s, 1H), 6.62 (br, 2H), 3.58-4.04 (m, 4H), 3.48 (br, 2H), 3.13-3.36 (m, 8H), 2.88 (br, 2H), 2.28 (s, 1H), 1.87-2.21 (m, 13H). LCMS (ESI, m/z): 533 [M+H]$^+$.

Example 161: N-(1-(cis-5-((5-chloro-2-(trifluoromethyl)benzyl)(methyl)amino)octahydrocyclopenta[c]pyrrole-2-carbonyl)-1H-pyrazol-4-yl)-N-methylacetamide

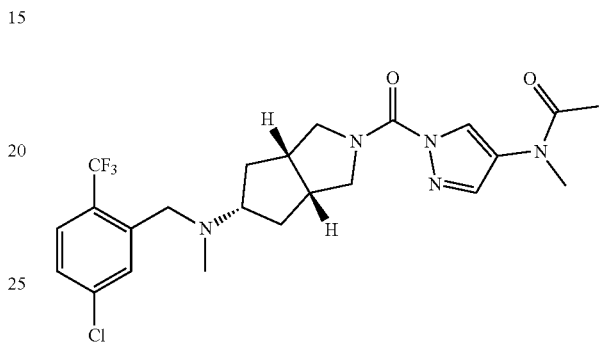

The title compound was synthesized as described in Example 139 using 5-chloro-2-(trifluoromethyl)benzaldehyde in Step 2. Purification resulted in 73.4 mg of N-(1-(cis-5-((5-chloro-2-(trifluoromethyl)benzyl)(methyl)amino)octahydrocyclopenta[c]pyrrole-2-carbonyl)-1H-pyrazol-4-yl)-N-methylacetamide as a light yellow semi-solid. $^1$H NMR (300 MHz, Chloroform-d) δ 8.30 (s, 0.3H), 8.22 (s, 0.7H), 8.07 (s, 0.3H), 7.88 (s, 1H), 7.57 (s, 1H), 7.53 (s, 0.7H), 7.32 (s, 1H), 4.01 (br, 4H), 3.65 (s, 2H), 3.37 (s, 1H), 3.23 (s, 2H), 2.92-3.04 (m, 1H), 2.72 (br, 2H), 2.29 (s, 1H), 2.20 (br, 2H), 2.16 (s, 3H), 2.01 (s, 2H), 1.52 (br, 2H). LCMS (ESI, m/z): 498 [M+H]$^+$.

Example 162: N-(1-(cis-5-((2,5-dichlorobenzyl)(methyl)amino)octahydrocyclopenta[c]pyrrole-2-carbonyl)-1H-pyrazol-4-yl)-N-methylacetamide

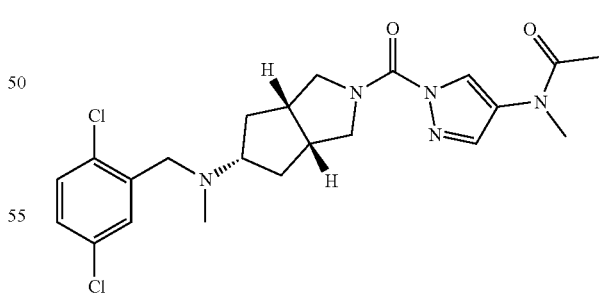

The title compound was synthesized as described in Example 139 using 2,5-dichlorobenzaldehyde in Step 2. Purification resulted in 117.3 mg of N-(1-(cis-5-((2,5-dichlorobenzyl)(methyl)amino)octahydrocyclopenta[c]pyrrole-2-carbonyl)-1H-pyrazol-4-yl)-N-methylacetamide as a colorless oil. $^1$H NMR (300 MHz, Chloroform-d) δ 8.28 (s, 0.3H), 8.20 (s, 0.7H), 8.06 (s, 0.3H), 7.55 (s, 0.7H), 7.51 (s, 1H), 7.24 (s, 1H), 7.13-7.17 (m, 1H), 3.99 (br, 4H), 3.57 (s, 2H), 3.36 (s, 1H), 3.22 (s, 2H), 2.94-3.05 (m, 1H), 2.72 (br, 2H), 2.28 (s, 1H), 2.23 (br, 2H), 2.18 (s, 3H), 2.00 (s, 2H), 1.53 (br, 2H). LCMS (ESI, m/z): 464 [M+H]+.

Example 163: N-(1-(cis-5-((2-chloro-5-(trifluoromethyl)benzyl)(methyl)amino)octahydrocyclopenta[c]pyrrole-2-carbonyl)-1H-pyrazol-4-yl)-N-methylacetamide

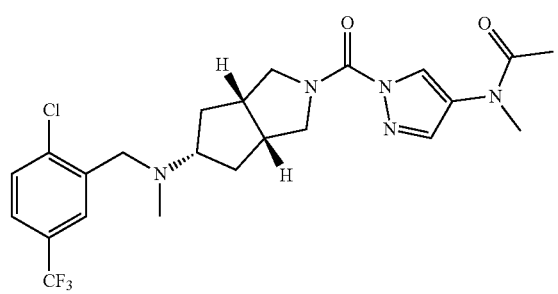 [SMILES: CC(=O)N(C)c1cnn(C(=O)N2C[C@H]3C[C@@H](N(C)Cc4cc(C(F)(F)F)ccc4Cl)C[C@H]3C2)c1]

The title compound was synthesized as described in Example 139 using 2-chloro-5-(trifluoromethyl)benzaldehyde in Step 2. Purification resulted in 111.3 mg of N-(1-(cis-5-((2-chloro-5-(trifluoromethyl)benzyl)(methyl)amino)octahydrocyclopenta[c]pyrrole-2-carbonyl)-1H-pyrazol-4-yl)-N-methylacetamide as a white solid. 1H NMR (300 MHz, Chloroform-d) δ 8.29 (s, 0.3H), 8.21 (s, 0.7H), 8.07 (s, 0.3H), 7.80 (s, 1H), 7.56 (s, 0.7H), 7.46 (s, 2H), 4.00 (br, 4H), 3.66 (s, 2H), 3.37 (s, 1H), 3.23 (s, 2H), 2.98-3.08 (m, 1H), 2.73 (br, 2H), 2.29 (s, 1H), 2.19 (s, 5H), 2.00 (s, 2H), 1.58 (br, 2H). LCMS (ESI, m/z): 498 [M+H]+.

Example 164: N-(1-(trans-5-((5-chloro-2-(trifluoromethyl)benzyl)(methyl)amino)octahydrocyclopenta[c]pyrrole-2-carbonyl)-1H-pyrazol-4-yl)-N-methylacetamide

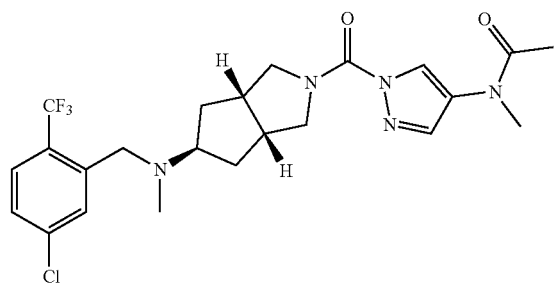 [SMILES: CC(=O)N(C)c1cnn(C(=O)N2C[C@H]3C[C@H](N(C)Cc4cc(Cl)ccc4C(F)(F)F)C[C@H]3C2)c1]

The title compound was synthesized as described in Example 139 using 5-chloro-2-(trifluoromethyl)benzaldehyde and trans-tert-butyl 5-aminohexahydrocyclopenta[c]pyrrole-2(1H)-carboxylate in Step 2. Purification resulted in 73.9 mg of N-(1-(trans-5-((5-chloro-2-(trifluoromethyl)benzyl)(methyl)amino)octahydrocyclopenta[c]pyrrole-2-carbonyl)-1H-pyrazol-4-yl)-N-methylacetamide as a white semisolid. 1H NMR (300 MHz, Chloroform-d) δ 8.29 (s, 0.3H), 8.20 (s, 0.7H), 8.06 (s, 0.3H), 7.87 (s, 1H), 7.56 (s, 1H), 7.53 (s, 0.7H), 7.31 (s, 1H), 4.05 (br, 3H), 3.64 (s, 3H), 3.37 (s, 1H), 3.23 (s, 2H), 3.18-3.20 (m, 1H), 2.88 (br, 2H), 2.29 (s, 1H), 2.16 (s, 3H), 2.00 (s, 2H), 1.87 (br, 4H). LCMS (ESI, m/z): 498 [M+H]+.

Example 165: N-(1-(trans-5-((2,5-dichlorobenzyl)(methyl)amino)octahydrocyclopenta[c]pyrrole-2-carbonyl)-1H-pyrazol-4-yl)-N-methylacetamide

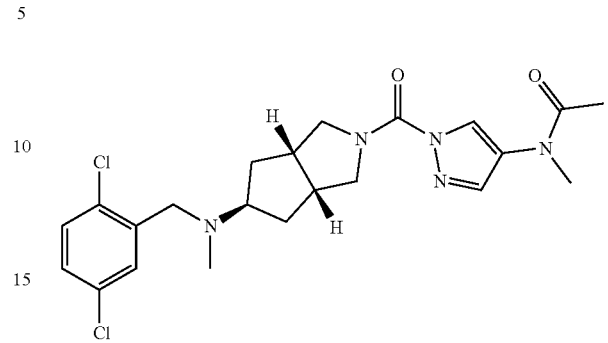

The title compound was synthesized as described in Example 139 using 2,5-dichlorobenzaldehyde and trans-tert-butyl 5-aminohexahydrocyclopenta[c]pyrrole-2(1H)-carboxylate in Step 2. Purification resulted in 37.9 mg of N-(1-(trans-5-((2,5-dichlorobenzyl)(methyl)amino)octahydrocyclopenta[c]pyrrole-2-carbonyl)-1H-pyrazol-4-yl)-N-methylacetamide as a white solid. 1H NMR (300 MHz, Chloroform-d) δ 8.29 (s, 0.3H), 8.19 (s, 0.7H), 8.05 (s, 0.3H), 7.56 (s, 0.7H), 7.51 (br, 1H), 7.28 (s, 1H), 7.15-7.17 (m, 1H), 3.66-4.21 (m, 4H), 3.56 (br, 2H), 3.36 (s, 1H), 3.22 (s, 3H), 2.89 (br, 2H), 2.28 (s, 1H), 2.18 (s, 3H), 2.00 (s, 2H), 1.90 (br, 4H). LCMS (ESI, m/z): 464 [M+H]+.

Example 166: N-(1-(trans-5-((2-chloro-5-(trifluoromethyl)benzyl)(methyl)amino)octahydrocyclopenta[c]pyrrole-2-carbonyl)-1H-pyrazol-4-yl)-N-methylacetamide

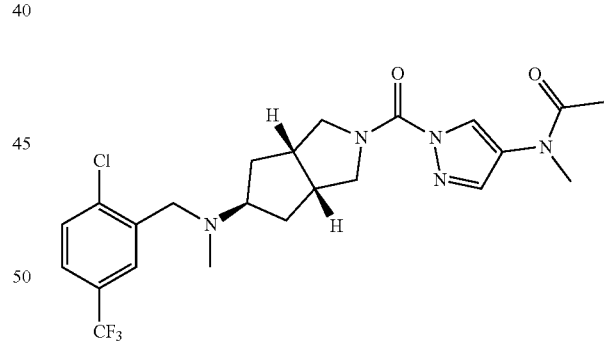

The title compound was synthesized as described in Example 139 using 2-chloro-5-(trifluoromethyl)benzaldehyde and trans-tert-butyl 5-aminohexahydrocyclopenta[c]pyrrole-2(1H)-carboxylate in Step 2. Purification resulted in 182.3 mg of N-(1-(trans-5-((2-chloro-5-(trifluoromethyl)benzyl)(methyl)amino)octahydrocyclopenta[c]pyrrole-2-carbonyl)-1H-pyrazol-4-yl)-N-methylacetamide as a white solid. 1H NMR (300 MHz, Chloroform-d) δ 8.30 (s, 0.3H), 8.20 (s, 0.7H), 8.06 (s, 0.3H), 7.80 (s, 1H), 7.56 (s, 0.7H), 7.45-7.48 (m, 2H), 3.76-4.05 (m, 4H), 3.64 (s, 2H), 3.37 (s, 1H), 3.22 (s, 3H), 2.90 (br, 2H), 2.29 (s, 1H), 2.19 (s, 3H), 2.01 (s, 2H), 1.91 (br, 4H). LCMS (ESI, m/z): 498 [M+H]+.

Example 167: N-methyl-N-(1-(cis-5-(methyl(5-(pyrrolidin-1-yl)-2-(trifluoromethyl)benzyl)amino)octahydrocyclopenta[c]pyrrole-2-carbonyl)-1H-pyrazol-4-yl)acetamide

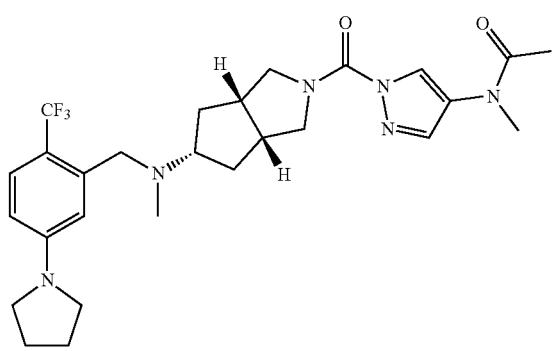 [SMILES: CC(=O)N(C)c1cnn(C(=O)N2C[C@H]3C[C@@H](N(C)Cc4cc(N5CCCC5)ccc4C(F)(F)F)C[C@H]3C2)c1]

The title compound was synthesized as described in Example 139 using 5-(pyrrolidin-1-yl)-2-(trifluoromethyl)benzaldehyde (synthesized as described in Example 67, Step 1) in Step 2. Purification resulted in 164.8 mg of N-methyl-N-(1-(cis-5-(methyl(5-(pyrrolidin-1-yl)-2-(trifluoromethyl)benzyl)amino)octahydrocyclopenta[c]pyrrole-2-carbonyl)-1H-pyrazol-4-yl)acetamide as a white solid. $^1$H NMR (300 MHz, Chloroform-d) δ 8.29 (s, 0.3H), 8.20 (s, 0.7H), 8.05 (s, 0.3H), 7.55 (s, 0.7H), 7.42 (d, J=8.7 Hz, 1H), 6.96 (s, 1H), 6.38 (d, J=8.4 Hz, 1H), 3.99 (br, 4H), 3.61 (s, 2H), 3.28-3.36 (m, 5H), 3.22 (s, 2H), 2.92-3.03 (m, 1H), 2.69 (br, 2H), 2.28 (s, 1H), 2.18 (s, 5H), 1.99-2.04 (m, 6H), 1.53 (br, 2H). LCMS (ESI, m/z): 533 [M+H]$^+$.

Example 168: N-methyl-N-(1-(cis-5-(methyl(2-(pyrrolidin-1-yl)-5-(trifluoromethyl)benzyl)amino)octahydrocyclopenta[c]pyrrole-2-carbonyl)-1H-pyrazol-4-yl)acetamide

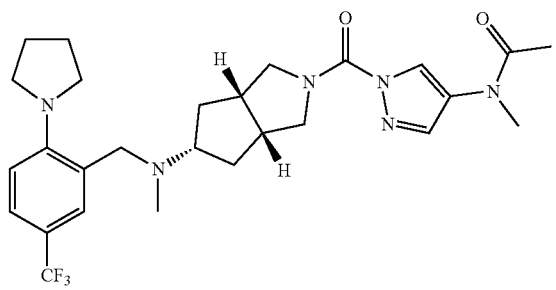 [SMILES: CC(=O)N(C)c1cnn(C(=O)N2C[C@H]3C[C@@H](N(C)Cc4cc(C(F)(F)F)ccc4N4CCCC4)C[C@H]3C2)c1]

The title compound was synthesized as described in Example 139 using 2-(pyrrolidin-1-yl)-5-(trifluoromethyl)benzaldehyde (synthesized as described in Example 67, Step 1) in Step 2. Purification resulted in 43.4 mg of N-methyl-N-(1-(cis-5-(methyl(2-(pyrrolidin-1-yl)-5-(trifluoromethyl)benzyl)amino)octahydrocyclopenta[c]pyrrole-2-carbonyl)-1H-pyrazol-4-yl)acetamide as a light yellow semi-solid. $^1$H NMR (300 MHz, Chloroform-d) δ 8.28 (s, 0.3H), 8.20 (s, 0.7H), 8.06 (s, 0.3H), 7.73 (s, 1H), 7.55 (s, 0.7H), 7.36 (d, J=8.7 Hz, 1H), 6.86 (d, J=8.7 Hz, 1H), 3.97 (br, 4H), 3.55 (s, 2H), 3.36 (s, 1H), 3.22-3.29 (m, 6H), 2.98 (br, 1H), 2.68 (br, 2H), 2.28 (s, 1H), 2.10-2.15 (m, 5H), 1.92-2.00 (m, 6H), 1.54 (br, 2H). LCMS (ESI, m/z): 533 [M+H]$^+$.

Example 169: N-(2-chlorobenzyl)-N-(cis-2-(4-(N-methylacetamido)-1H-pyrazole-1-carbonyl)octahydrocyclopenta[c]pyrrol-5-yl)acetamide

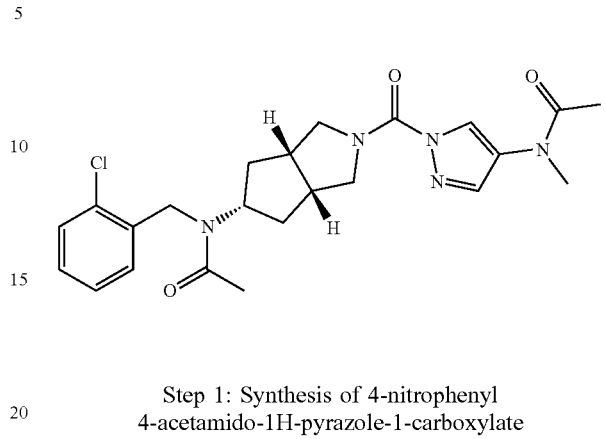

Step 1: Synthesis of 4-nitrophenyl 4-acetamido-1H-pyrazole-1-carboxylate

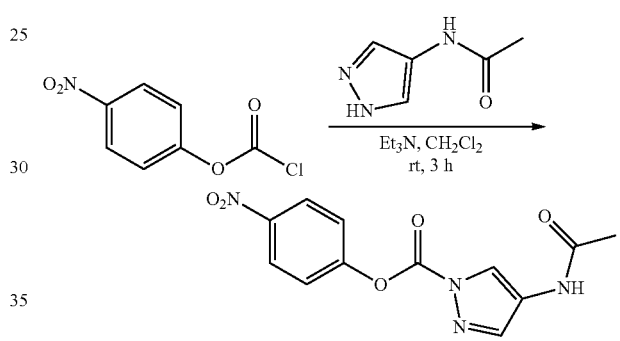

A 100-mL round-bottom flask was charged with N-(1H-pyrazol-4-yl)acetamide (690 mg, 5.51 mmol, 1.00 equiv) in DCM (10 mL), 4-nitrophenyl chloroformate (1.16 g, 5.75 mmol, 1.05 equiv), and triethylamine (1.67 g, 16.5 mmol, 3.00 equiv) under nitrogen. The resulting solution was stirred for 3 h at room temperature. The reaction progress was monitored by LCMS. The resulting mixture was concentrated under reduced pressure to yield 2.25 g (crude) of 4-nitrophenyl 4-nitrophenyl 4-acetamido-1H-pyrazole-1-carboxylate as a yellow solid. LCMS (ESI, m/z): 291 [M+H]$^+$.

Step 2: Synthesis of cis-tert-butyl 5-(2-chlorobenzylamino)hexahydrocyclopenta[c]pyrrole-2(1H)-carboxylate

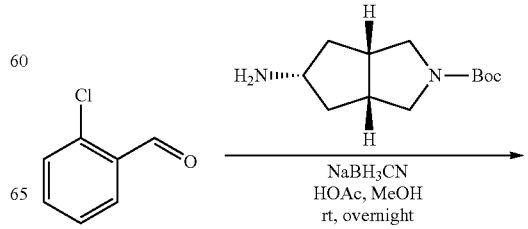

-continued

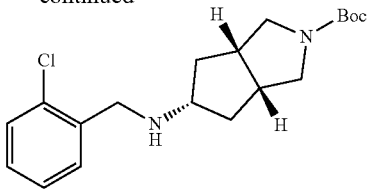

A 100-mL round-bottom flask was charged with 2-chlorobenzaldehyde (2.80 g, 19.9 mmol, 1.00 equiv) in MeOH (30 mL), cis-tert-butyl 5-aminohexahydrocyclopenta[c]pyrrole-2(1H)-carboxylate (5.42 g, 24.0 mmol, 1.20 equiv), and acetic acid (3.60 g, 60.0 mmol, 3.00 equiv). The resulting solution was stirred for 30 min at room temperature. Sodium cyanoborohydride (3.78 g, 60.0 mmol, 3.00 equiv) was added. The resulting solution was stirred overnight at room temperature and quenched with water (30 mL). The resulting solution was extracted with DCM (3×30 mL) and the organic layers were combined, washed with brine (2×30 mL), dried over anhydrous sodium sulfate, filtered and concentrated under reduced pressure. The residue was chromatographed on a silica gel column to yield 5.00 g (72% yield) of cis-tert-butyl 5-(2-chlorobenzylamino)hexahydrocyclopenta[c]pyrrole-2(1H)-carboxylate as a yellow oil. LCMS (ESI, m/z): 351 [M+H]+.

Step 3: Synthesis of cis-tert-butyl 5-(N-(2-chlorobenzyl)acetamido)hexahydrocyclopenta[c]pyrrole-2(1H)-carboxylate

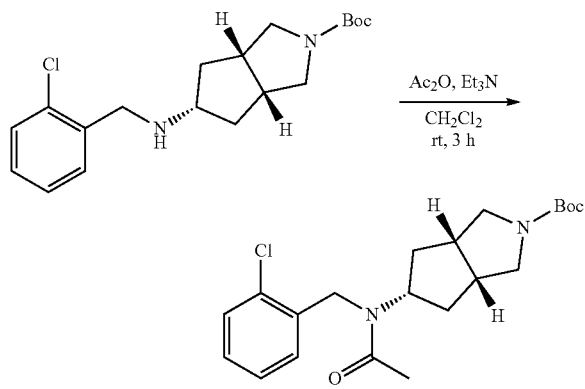

A 100-mL round-bottom flask was charged with cis-tert-butyl 5-(2-chlorobenzylamino)hexahydrocyclopenta[c]pyrrole-2(1H)-carboxylate (2.00 g, 5.70 mmol, 1.00 equiv) in DCM (30 mL), triethylamine (1.73 g, 17.1 mmol, 3.00 equiv), and acetic anhydride (0.874 g, 8.57 mmol, 1.50 equiv) under nitrogen. The resulting solution was stirred for 3 h at room temperature and quenched with water (30 mL). The resulting solution was extracted with DCM (3×30 mL) and the organic layers were combined, washed with brine (2×30 mL), dried over anhydrous sodium sulfate, filtered and concentrated under reduced pressure. The residue was chromatographed on a silica gel column to yield 1.80 g (80% yield) of cis-tert-butyl 5-(N-(2-chlorobenzyl)acetamido)hexahydrocyclopenta[c]pyrrole-2(1H)-carboxylate as a light yellow oil. LCMS (ESI, m/z): 393 [M+H]+.

Step 4: Synthesis of N-(2-chlorobenzyl)-N-(cis-octahydrocyclopenta[c]pyrrol-5-yl)acetamide

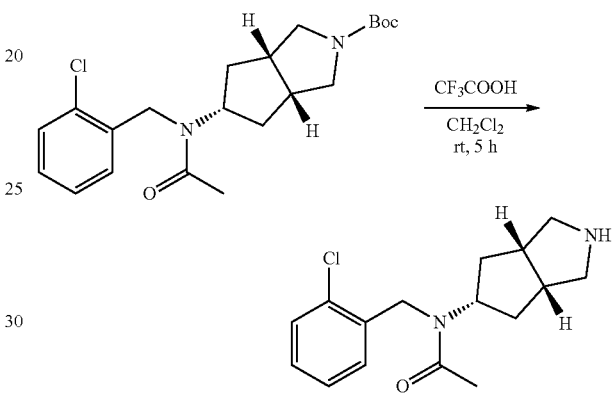

A 100-mL round-bottom flask was charged with cis-tert-butyl 5-(N-(2-chlorobenzyl)acetamido)hexahydrocyclopenta[c]pyrrole-2(1H)-carboxylate (1.60 g, 4.07 mmol, 1.00 equiv) in DCM (20 mL), and TFA (5 mL). The resulting solution was stirred for 5 h at room temperature. The reaction progress was monitored by LCMS. The resulting solution was concentrated under reduced pressure to yield 1.85 g (crude) of N-(2-chlorobenzyl)-N-(cis-octahydrocyclopenta[c]pyrrol-5-yl)acetamide as a yellow oil. LCMS (ESI, m/z): 293 [M+H]+.

Step 5: Synthesis of N-(cis-2-(4-acetamido-1H-pyrazole-1-carbonyl)octahydrocyclopenta[c]pyrrol-5-yl)-N-(2-chlorobenzyl)acetamide

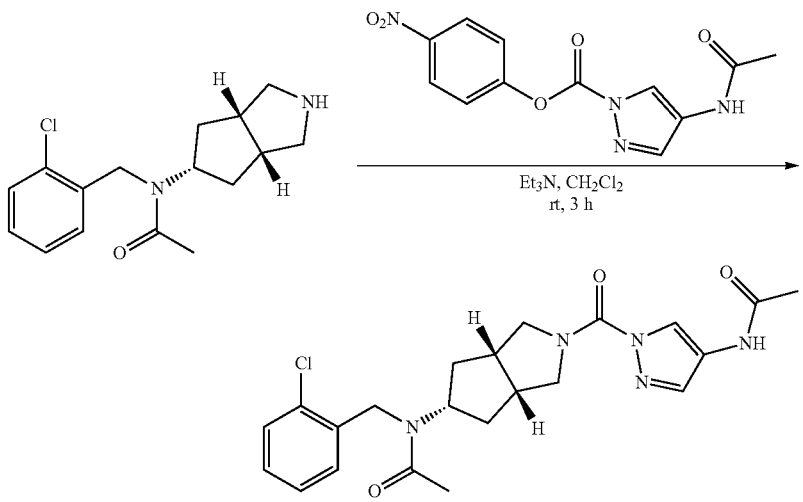

A 100-mL round-bottom flask was charged with N-(2-chlorobenzyl)-N-(cis-octahydrocyclopenta[c]pyrrol-5-yl)acetamide (570 mg, 1.95 mmol, 1.00 equiv) in DCM (20 mL), 4-nitrophenyl 4-acetamido-1H-pyrazole-1-carboxylate (849 mg, 2.93 mmol, 1.50 equiv), and triethylamine (591 mg, 5.85 mmol, 3.00 equiv) under nitrogen. The resulting solution was stirred for 3 h at room temperature and quenched with water (20 mL). The resulting solution was extracted with DCM (3×20 mL) and the organic layers were combined, washed with brine (2×20 mL), dried over anhydrous sodium sulfate, filtered and concentrated under reduced pressure. The residue was chromatographed on a silica gel column to yield 800 mg (93% yield) of N-(cis-2-(4-acetamido-1H-pyrazole-1-carbonyl)octahydrocyclopenta[c]pyrrol-5-yl)-N-(2-chlorobenzyl)acetamide as a yellow oil. LCMS (ESI, m/z): 444 [M+H]$^+$.

Step 6: Synthesis of N-(2-chlorobenzyl)-N-(cis-2-(4-(N-methylacetamido)-1H-pyrazole-1-carbonyl)octahydrocyclopenta[c]pyrrol-5-yl)acetamide

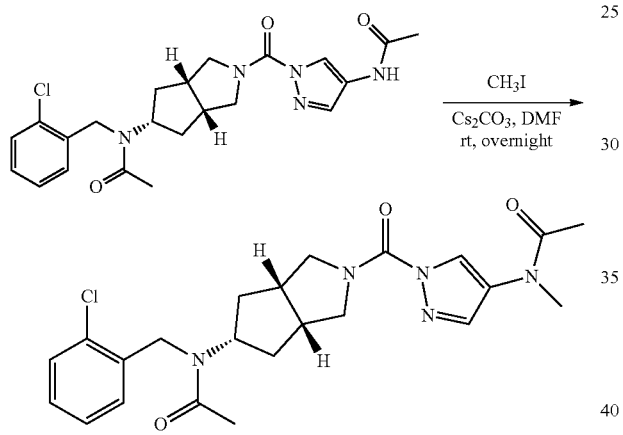

A 40-mL round-bottom flask was charged with N-(cis-2-(4-acetamido-1H-pyrazole-1-carbonyl)octahydrocyclopenta[c]pyrrol-5-yl)-N-(2-chlorobenzyl)acetamide (400 mg, 0.900 mmol, 1.00 equiv) in DMF (10 mL), and cesium carbonate (883 mg, 2.71 mmol, 3.00 equiv) under nitrogen. The resulting solution was stirred for 1 h at 0° C. Then iodomethane (192 mg, 1.35 mmol, 1.50 equiv) was added dropwise at 0° C. The resulting solution was stirred overnight at room temperature and quenched with water (10 mL). The mixture was extracted with EtOAc (3×10 mL) and the organic layers were combined, washed with brine (2×10 mL), dried over anhydrous sodium sulfate, filtered and concentrated under reduced pressure. The crude product (400 mg) was purified by preparative HPLC. Purification resulted in 178.6 mg of N-(2-chlorobenzyl)-N-(cis-2-(4-(N-methylacetamido)-1H-pyrazole-1-carbonyl)octahydrocyclopenta[c]pyrrol-5-yl)acetamide as a white solid. $^1$H NMR (300 MHz, Chloroform-d) δ 8.26 (s, 0.3H), 8.17 (s, 0.7H), 8.02 (s, 0.3H), 7.52 (s, 0.7H), 7.27-7.40 (m, 2H), 7.09-7.17 (m, 2H), 5.00 (br, 0.7H), 4.50-4.66 (m, 2H), 4.23-4.34 (m, 0.3H), 3.75-3.96 (m, 4H), 3.35 (s, 1H), 3.20 (s, 2H), 2.68 (br, 2H), 2.28-2.31 (m, 2H), 2.10 (br, 2H), 2.00 (s, 2H), 1.98 (s, 2H), 1.40-1.43 (m, 2H). LCMS (ESI, m/z): 458 [M+H]$^+$.

Example 170: N-(3-chlorobenzyl)-N-(cis-2-(4-(N-methylacetamido)-1H-pyrazole-1-carbonyl)octahydrocyclopenta[c]pyrrol-5-yl)acetamide

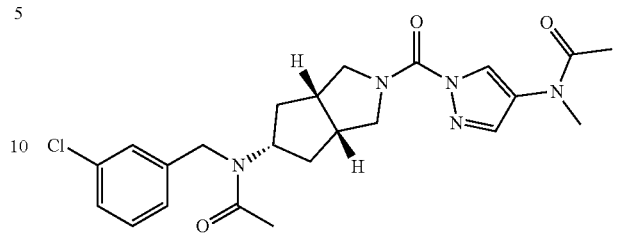

The title compound was synthesized as described in Example 169 using 3-chlorobenzaldehyde in Step 2. Purification resulted in 118.7 mg of N-(3-chlorobenzyl)-N-(cis-2-(4-(N-methylacetamido)-1H-pyrazole-1-carbonyl)octahydrocyclopenta[c]pyrrol-5-yl)acetamide as a white solid. $^1$H NMR (300 MHz, Chloroform-d) δ 8.28 (s, 0.3H), 8.17 (s, 0.7H), 8.02 (s, 0.3H), 7.54 (s, 0.7H), 7.30 (s, 1H), 7.17 (s, 2H), 7.06-7.08 (m, 1H), 4.97-5.00 (m, 0.6H), 4.47-4.54 (m, 2H), 4.29-4.30 (m, 0.4H), 3.62-3.93 (m, 4H), 3.36 (s, 1H), 3.21 (s, 2H), 2.69 (br, 2H), 2.29 (s, 2H), 1.99-2.12 (m, 6H), 1.43-1.45 (m, 2H). LCMS (ESI, m/z): 458 [M+H]$^+$.

Example 171: N-(4-chlorobenzyl)-N-(cis-2-(4-(N-methylacetamido)-1H-pyrazole-1-carbonyl)octahydrocyclopenta[c]pyrrol-5-yl)acetamide

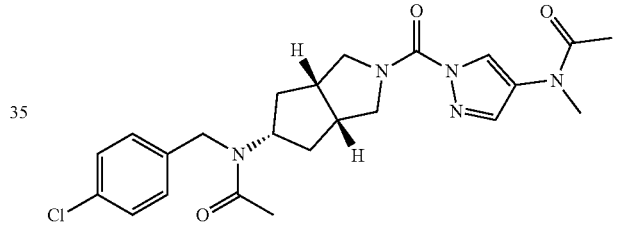

The title compound was synthesized as described in Example 169 using 4-chlorobenzaldehyde in Step 2. Purification resulted in 62.8 mg of N-(4-chlorobenzyl)-N-(cis-2-(4-(N-methylacetamido)-1H-pyrazole-1-carbonyl)octahydrocyclopenta[c]pyrrol-5-yl)acetamide as a white solid. $^1$H NMR (300 MHz, Chloroform-d) δ 8.28 (s, 0.3H), 8.17 (s, 0.7H), 8.01 (s, 0.3H), 7.62 (s, 0.7H), 7.32-7.35 (m, 1H), 7.22-7.25 (m, 1H), 7.11-7.13 (m, 2H), 4.93-5.05 (m, 0.6H), 4.46-4.53 (m, 2H), 4.27-4.30 (m, 0.4H), 3.75-3.92 (m, 4H), 3.36 (s, 1H), 3.21 (s, 2H), 2.68 (br, 2H), 2.28 (s, 2H), 2.09 (br, 2H), 2.02 (s, 2H), 1.99 (s, 2H), 1.44 (m, 2H). LCMS (ESI, m/z): 458 [M+H]$^+$.

Example 172: N-(2-chlorobenzyl)-N-(trans-2-(4-(N-methylacetamido)-1H-pyrazole-1-carbonyl)octahydrocyclopenta[c]pyrrol-5-yl)acetamide

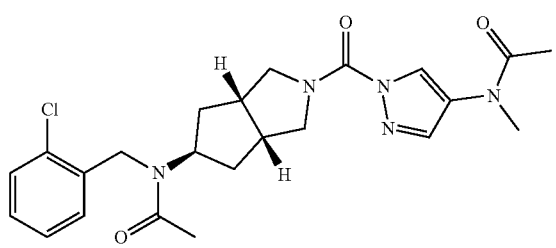 [SMILES: CC(=O)N(C)c1cnn(C(=O)N2C[C@H]3C[C@H](N(Cc4ccccc4Cl)C(C)=O)C[C@H]3C2)c1]

The title compound was synthesized as described in Example 169 using trans-tert-butyl 5-aminohexahydrocyclopenta[c]pyrrole-2(1H)-carboxylate in Step 2. Purification resulted in 116.0 mg of N-(2-chlorobenzyl)-N-(trans-2-(4-(N-methylacetamido)-1H-pyrazole-1-carbonyl)octahydrocyclopenta[c]pyrrol-5-yl)acetamide as a white solid. $^1$H NMR (300 MHz, Chloroform-d) δ 8.26 (s, 0.3H), 8.18 (s, 0.7H), 8.04 (s, 0.3H), 7.53 (s, 0.7H), 7.32-7.42 (m, 2H), 7.06-7.18 (m, 2H), 4.99-5.08 (m, 0.7H), 4.51-4.59 (m, 2.3H), 4.07-4.24 (m, 2H), 3.52-3.85 (m, 2H), 3.35 (s, 1H), 3.21 (m, 2H), 2.86 (br, 2H), 2.28 (br, 2H), 2.00 (s, 4H), 1.84-1.86 (m, 4H). LCMS (ESI, m/z): 458 [M+H]$^+$.

Example 173: N-(3-chlorobenzyl)-N-(trans-2-(4-(N-methylacetamido)-1H-pyrazole-1-carbonyl)octahydrocyclopenta[c]pyrrol-5-yl)acetamide

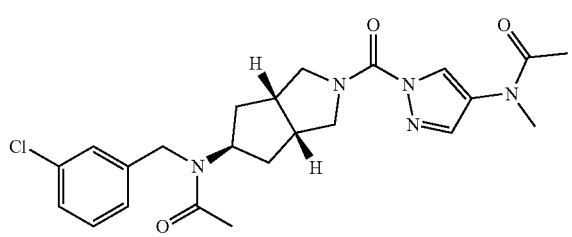 [SMILES: CC(=O)N(C)c1cnn(C(=O)N2C[C@H]3C[C@H](N(Cc4cccc(Cl)c4)C(C)=O)C[C@H]3C2)c1]

The title compound was synthesized as described in Example 169 using trans-tert-butyl 5-aminohexahydrocyclopenta[c]pyrrole-2(1H)-carboxylate and 3-chlorobenzaldehyde in Step 2. Purification resulted in 79.7 mg of N-(3-chlorobenzyl)-N-(trans-2-(4-(N-methylacetamido)-1H-pyrazole-1-carbonyl)octahydrocyclopenta[c]pyrrol-5-yl)acetamide as a white solid. $^1$H NMR (300 MHz, Chloroform-d) δ 8.26 (s, 0.3H), 8.18 (s, 0.7H), 8.04 (s, 0.3H), 7.53 (s, 0.7H), 7.28-7.31 (m, 1H), 7.06-7.23 (m, 3H), 4.86-4.94 (m, 0.6H), 4.47-4.52 (m, 2.4H), 4.04 (br, 2H), 3.61 (br, 2H), 3.35 (s, 1H), 3.21 (s, 2H), 2.86 (br, 2H), 2.28 (s, 2H), 2.04 (s, 2H), 1.99 (s, 2H), 1.79-1.90 (m, 4H). LCMS (ESI, m/z): 458 [M+H]$^+$.

Example 174: N-(4-chlorobenzyl)-N-(trans-2-(4-(N-methylacetamido)-1H-pyrazole-1-carbonyl)octahydrocyclopenta[c]pyrrol-5-yl)acetamide

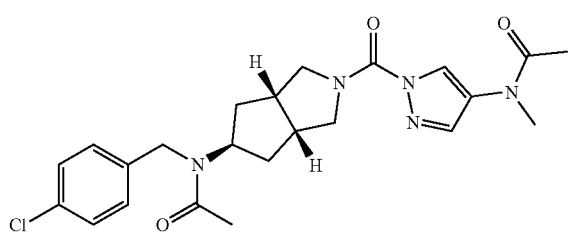 [SMILES: CC(=O)N(C)c1cnn(C(=O)N2C[C@H]3C[C@H](N(Cc4ccc(Cl)cc4)C(C)=O)C[C@H]3C2)c1]

The title compound was synthesized as described in Example 169 using trans-tert-butyl 5-aminohexahydrocyclopenta[c]pyrrole-2(1H)-carboxylate and 4-chlorobenzaldehyde in Step 2. Purification resulted in 75.3 mg of N-(4-chlorobenzyl)-N-(trans-2-(4-(N-methylacetamido)-1H-pyrazole-1-carbonyl)octahydrocyclopenta[c]pyrrol-5-yl)acetamide as a white solid. $^1$H NMR (300 MHz, Chloroform-d) δ 8.26 (s, 0.3H), 8.18 (s, 0.7H), 8.04 (s, 0.3H), 7.53 (s, 0.7H), 7.25-7.36 (m, 2H), 7.10-7.13 (m, 2H), 4.84-4.92 (m, 0.6H), 4.46-4.50 (m, 2.4H), 4.04 (br, 2H), 3.61 (br, 2H), 3.35 (s, 1H), 3.21 (s, 2H), 2.86 (br, 2H), 2.28 (s, 1H), 2.25 (s, 1H), 2.04 (s, 2H), 1.99 (s, 2H), 1.79-1.89 (m, 4H). LCMS (ESI, m/z): 458 [M+H]$^+$.

Example 175: N-(1-(7-(2,5-dichlorobenzyl)-2,7-diazaspiro[4.4]nonane-2-carbonyl)-1H-pyrazol-4-yl)-N-methylacetamide

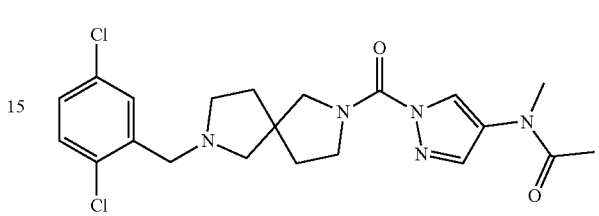

Step 1: Synthesis of Tert-butyl 7-(4-acetamido-1H-pyrazole-1-carbonyl)-2,7-diazaspiro[4.4]nonane-2-carboxylate

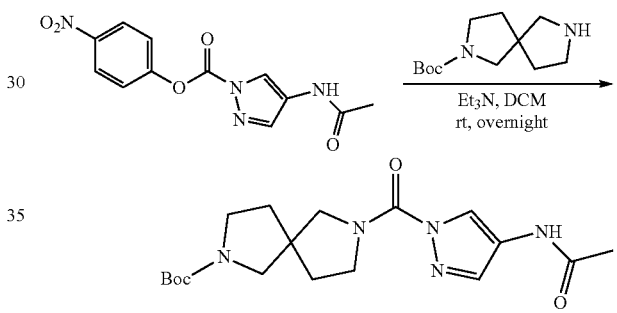

A 250-mL round-bottom flask was charged with tert-butyl 2,7-diazaspiro[4.4]nonane-2-carboxylate (2.00 g, 8.84 mmol, 1.00 equiv), DCM (50 mL), 4-nitrophenyl 4-acetamido-1H-pyrazole-1-carboxylate (3.85 g, 13.3 mmol, 1.50 equiv), and triethylamine (2.68 g, 26.5 mmol, 3.00 equiv). The resulting solution was stirred overnight at room temperature and quenched with water (80 mL). The resulting solution was extracted with DCM (2×150 mL) and the organic layers were combined, dried over anhydrous sodium sulfate, filtered and concentrated under reduced pressure. The residue was chromatographed on a silica gel column to provide 3.00 g (90% yield) of tert-butyl 7-(4-acetamido-1H-pyrazole-1-carbonyl)-2,7-diazaspiro[4.4]nonane-2-carboxylate as a yellow oil. LCMS (ESI, m/z): 378 [M+H]$^+$.

Step 2: Synthesis of tert-butyl 7-(4-(N-methylacetamido)-1H-pyrazole-1-carbonyl)-2,7-diazaspiro[4.4]nonane-2-carboxylate

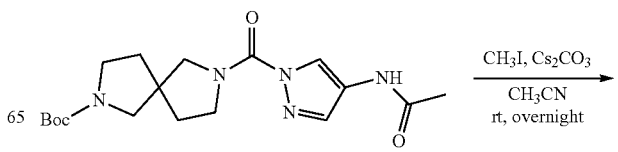

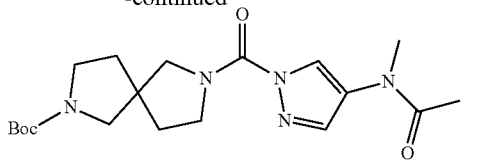

A 250-mL round-bottom flask was charged with tert-butyl 7-(4-acetamido-1H-pyrazole-1-carbonyl)-2,7-diazaspiro[4.4]nonane-2-carboxylate (3.00 g, 7.95 mmol, 1.00 equiv), acetonitrile (50 mL), cesium carbonate (7.79 g, 23.9 mmol, 3.00 equiv), and iodomethane (2.26 g, 15.9 mmol, 2.00 equiv). The resulting solution was stirred overnight at room temperature and quenched with water (50 mL). The resulting solution was extracted with DCM (2×80 mL) and the organic layers were combined, dried over anhydrous sodium sulfate, filtered and concentrated under reduced pressure. The residue was chromatographed on a silica gel column to 3.00 g (96% yield) of tert-butyl 7-(4-(N-methylacetamido)-1H-pyrazole-1-carbonyl)-2,7-diazaspiro[4.4]nonane-2-carboxylate as a yellow oil. LCMS (ESI, m/z): 392 [M+H]$^+$.

Step 3: Synthesis of N-(1-(2,7-diazaspiro[4.4]nonane-2-carbonyl)-1H-pyrazol-4-yl)-N-methylacetamide

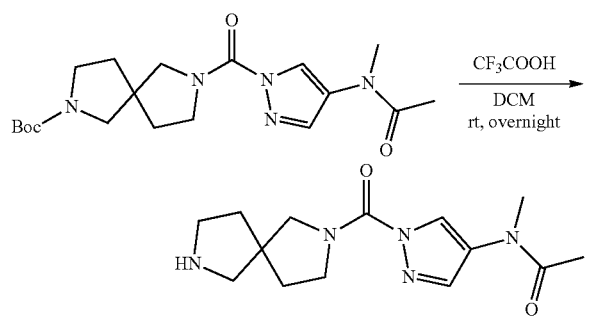

A 100-mL round-bottom flask was charged with tert-butyl 7-(4-(N-methylacetamido)-1H-pyrazole-1-carbonyl)-2,7-diazaspiro[4.4]nonane-2-carboxylate (3.00 g, 7.66 mmol, 1.00 equiv), DCM (30 mL), and TFA (6 mL). The resulting solution was stirred overnight at room temperature and concentrated under reduced pressure to provide 3.50 g (crude) of N-(1-(2,7-diazaspiro[4.4]nonane-2-carbonyl)-1H-pyrazol-4-yl)-N-methylacetamide as a brown oil. LCMS (ESI, m/z): 292 [M+H]$^+$.

Step 4: Synthesis of N-(1-(7-(2,5-dichlorobenzyl)-2,7-diazaspiro[4.4]nonane-2-carbonyl)-1H-pyrazol-4-yl)-N-methylacetamide

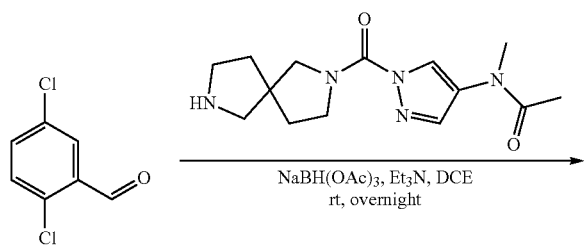

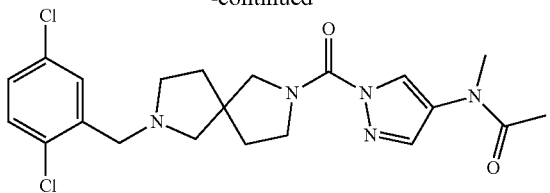

A 50-mL round-bottom flask was charged with 2,5-dichlorobenzaldehyde (84.0 mg, 0.480 mmol, 1.00 equiv), 1,2-dichloroethane (10 mL), triethylamine (145 mg, 1.43 mmol, 3.00 equiv), and N-(1-(2,7-diazaspiro[4.4]nonane-2-carbonyl)-1H-pyrazol-4-yl)-N-methylacetamide (140 mg, 0.480 mmol, 1.00 equiv). The mixture was stirred for 1 h at room temperature. Sodium triacetoxyborohydride (305 mg, 1.44 mmol, 3.00 equiv) was added. The resulting solution was stirred overnight at room temperature and quenched with water (30 mL). The resulting solution was extracted with DCM (2×50 mL) and the organic layers were combined, dried over anhydrous sodium sulfate, filtered and concentrated under reduced pressure. The crude product (300 mg) was purified by preparative HPLC. Purification resulted in 89.8 mg (42% yield) of N-(1-(7-(2,5-dichlorobenzyl)-2,7-diazaspiro[4.4]nonane-2-carbonyl)-1H-pyrazol-4-yl)-N-methylacetamide as a white solid. $^1$H NMR (400 MHz, Chloroform-d) δ 8.30 (s, 0.3H), 8.21 (s, 0.7H), 8.07 (s, 0.3H), 7.56-7.59 (m, 0.7H), 7.47-7.50 (m, 1H), 7.27 (s, 1H), 7.16-7.18 (m, 1H), 3.90-4.11 (m, 2H), 3.61-3.73 (m, 4H), 3.37 (s, 1H), 3.23 (s, 2H), 2.55-2.77 (m, 4H), 2.29 (s, 1H), 1.89-2.02 (m, 6H). LCMS (ESI, m/z): 450 [M+H]$^+$.

Example 176: N-(1-(7-(2,5-dichlorobenzyl)-2,7-diazaspiro[4.4]nonane-2-carbonyl)-1H-pyrazol-4-yl)-N-methylacetamide (Single Enantiomer)

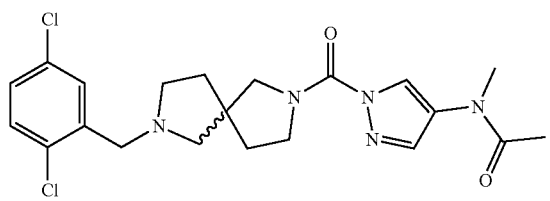 [SMILES: CC(=O)N(C)c1cnn(C(=O)N2CCC3(CCN(Cc4cc(Cl)ccc4Cl)C3)C2)c1]

One enantiomer of racemic N-(1-(7-(2,5-dichlorobenzyl)-2,7-diazaspiro[4.4]nonane-2-carbonyl)-1H-pyrazol-4-yl)-N-methylacetamide (Example 175, 500 mg, 1.11 mmol, 1.00 equiv) was separated by SFC using the following gradient conditions: Column: Chiralpak AD-H 2*25 cm; Mobile Phase A: CO$_2$ (60%), Mobile Phase B: EtOH (40%); Flow rate: 40 mL/min; Detector: UV 220 nm; RT1: 7.0 min. SFC separation resulted in 138.2 mg (28% yield) of (R)—N-(1-(7-(2,5-dichlorobenzyl)-2,7-diazaspiro[4.4]nonane-2-carbonyl)-1H-pyrazol-4-yl)-N-methylacetamide as a colorless oil. $^1$H NMR (300 MHz, Chloroform-d) δ 8.26 (s, 0.3H), 8.22 (s, 0.7H), 8.17 (s, 0.3H), 7.46-7.54 (m, 1.7H), 7.24-7.26 (m, 1H), 7.12-7.15 (m, 1H), 3.86-4.04 (m, 2H), 3.57-3.70 (m, 4H), 3.33 (s, 1H), 3.19 (s, 2H), 2.52-2.74 (m, 4H), 2.25 (s, 1H), 1.87-1.96 (m, 6H). LCMS (ESI, m/z): 450 [M+H]$^+$.

Example 177: N-(1-(7-(2,5-dichlorobenzyl)-2,7-diazaspiro[4.4]nonane-2-carbonyl)-1H-pyrazol-4-yl)-N-methylacetamide (Single Enantiomer)

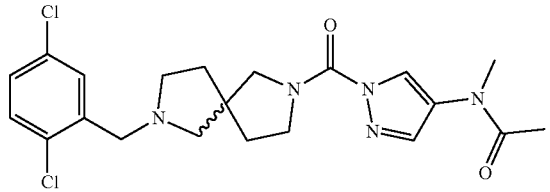 [SMILES: CC(=O)N(C)c1cnn(C(=O)N2CCC3(CCN(Cc4cc(Cl)ccc4Cl)C3)C2)c1]

The second enantiomer of racemic N-(1-(7-(2,5-dichlorobenzyl)-2,7-diazaspiro[4.4]nonane-2-carbonyl)-1H-pyrazol-4-yl)-N-methylacetamide (Example 175, 500 mg, 1.11 mmol, 1.00 equiv) was separated by SFC using the following gradient conditions: Column: Chiralpak AD-H 2*25 cm; Mobile Phase A: $CO_2$ (60%), Mobile Phase B: EtOH (40%); Flow rate: 40 mL/min; Detector: UV 220 nm; RT2: 11.81 min. SFC separation resulted in 136.1 mg (27% yield) of (S)—N-(1-(7-(2,5-dichlorobenzyl)-2,7-diazaspiro[4.4]nonane-2-carbonyl)-1H-pyrazol-4-yl)-N-methylacetamide as a light pink oil. $^1$H NMR (300 MHz, Chloroform-d) δ 8.26 (s, 0.3H), 8.17 (s, 0.7H), 8.03 (s, 0.3H), 7.46-7.58 (m, 1.7H), 7.23-7.26 (m, 1H), 7.13-7.15 (m, 1H), 3.90-4.03 (m, 2H), 3.50-3.70 (m, 4H), 3.33 (s, 1H), 3.19 (s, 2H), 2.64-2.73 (m, 4H), 2.25 (s, 1H), 1.87-1.96 (m, 6H). LCMS (ESI, m/z): 450 [M+H]$^+$.

Example 178: N-(1-(5-(4-fluorobenzyl)octahydropyrrolo[3,4-c]pyrrole-2-carbonyl)-1H-pyrazol-4-yl)-N-methylacetamide

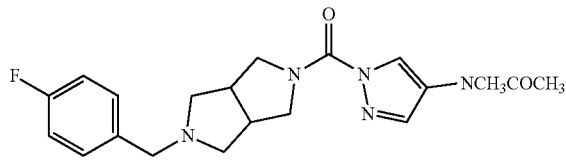

The title compound was synthesized as described in Example 27 using tert-butyl hexahydropyrrolo[3,4-c]pyrrole-2(1H)-carboxylate in Step 1 and 4-fluorobenzaldehyde in Step 4. Purification resulted in 156.8 mg of the title compound as a light yellow semi-solid. $^1$H NMR (400 MHz, Chloroform-d) δ 8.31 (s, 0.3H), 8.21 (s, 0.7H), 8.06 (s, 0.3H), 7.57 (s, 0.7H), 7.28-7.30 (m, 1H), 7.26-7.27 (m, 1H), 7.00 (t, J=8.8 Hz, 2H), 3.75-4.21 (m, 4H), 3.57-3.58 (m, 2H), 3.38 (s, 1H), 3.24 (s, 2H), 2.91 (br, 2H), 2.52-2.64 (m, 4H), 2.30 (s, 1H), 2.01 (s, 2H). LCMS (ESI, m/z): 386 [M+H]$^+$.

Example 179: N-(1-(5-(4-methoxybenzyl)octahydropyrrolo[3,4-c]pyrrole-2-carbonyl)-1H-pyrazol-4-yl)-N-methylacetamide

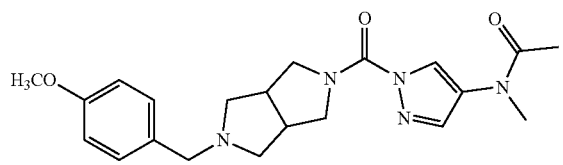 [SMILES: COc1ccc(CN2CC3CN(C(=O)n4cc(N(C)C(C)=O)cn4)CC3C2)cc1]

The title compound was synthesized as described in Example 27 using tert-butyl hexahydropyrrolo[3,4-c]pyrrole-2(1H)-carboxylate in Step 1 and 4-methoxybenzaldehyde in Step 4. Purification resulted in 130.5 mg of the title compound as a light yellow oil. $^1$H NMR (400 MHz, Chloroform-d) δ 8.30 (s, 0.3H), 8.20 (s, 0.7H), 8.06 (s, 0.3H), 7.56 (s, 0.7H), 7.23 (d, J=8.8 Hz, 2H), 6.84-6.87 (m, 2H), 3.81-4.38 (m, 7H), 3.55-3.56 (m, 2H), 3.38 (s, 1H), 3.24 (s, 2H), 2.90 (br, 2H), 2.62-2.65 (m, 2H), 2.49-2.56 (m, 2H), 2.30 (s, 1H), 2.01 (s, 2H). LCMS (ESI, m/z): 398 [M+H]$^+$

Example 180: N-(1-(5-(3-fluorobenzyl)octahydropyrrolo[3,4-c]pyrrole-2-carbonyl)-1H-pyrazol-4-yl)-N-methylacetamide

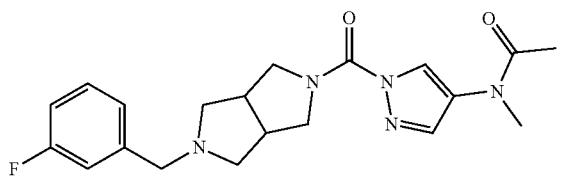 [SMILES: CC(=O)N(C)c1cnn(C(=O)N2CC3CN(Cc4cccc(F)c4)CC3C2)c1]

The title compound was synthesized as described in Example 27 using tert-butyl hexahydropyrrolo[3,4-c]pyrrole-2(1H)-carboxylate in Step 1 and 3-fluorobenzaldehyde in Step 4. Purification resulted in 178.8 mg of the title compound as a light yellow oil. $^1$H NMR (400 MHz, Chloroform-d) δ 8.31 (s, 0.3H), 8.22 (s, 0.7H), 8.07 (s, 0.3H), 7.57 (s, 0.7H), 7.24-7.28 (m, 1H), 7.04-7.09 (m, 2H), 6.92-6.97 (m, 1H), 3.76-4.25 (m, 4H), 3.60-3.61 (m, 2H), 3.38 (s, 1H), 3.24 (s, 2H), 2.92 (br, 2H), 2.54-2.61 (m, 4H), 2.30 (s, 1H), 2.02 (s, 2H). LCMS (ESI, m/z): 386 [M+H]$^+$.

Example 181: N-(1-(5-(3-methoxybenzyl)octahydropyrrolo[3,4-c]pyrrole-2-carbonyl)-1H-pyrazol-4-yl)-N-methylacetamide

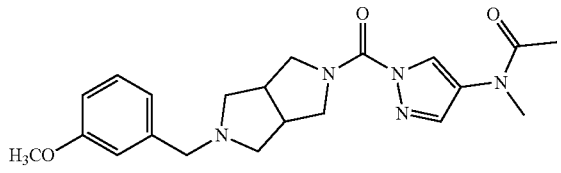 [SMILES: COc1cccc(CN2CC3CN(C(=O)n4cc(N(C)C(C)=O)cn4)CC3C2)c1]

The title compound was synthesized as described in Example 27 using tert-butyl hexahydropyrrolo[3,4-c]pyrrole-2(1H)-carboxylate in Step 1 and 3-methoxybenzaldehyde in Step 4. Purification resulted in 99.7 mg of the title compound as a light yellow oil. $^1$H NMR (400 MHz, Chloroform-d) δ 8.30 (s, 0.3H), 8.21 (s, 0.7H), 8.06 (s, 0.3H), 7.56 (s, 0.7H), 7.23 (t, J=8.2 Hz, 1H), 6.89-6.91 (m, 2H), 6.80-6.82 (m, 1H), 3.76-4.40 (m, 7H), 3.59-3.60 (m, 2H), 3.38 (s, 1H), 3.24 (s, 2H), 2.91 (br, 2H), 2.54-2.63 (m, 4H), 2.30 (s, 1H), 2.01 (s, 2H). LCMS (ESI, m/z): 398 [M+H]$^+$.

Example 182: N-(1-(5-(2-fluorobenzyl)octahydropyrrolo[3,4-c]pyrrole-2-carbonyl)-1H-pyrazol-4-yl)-N-methylacetamide

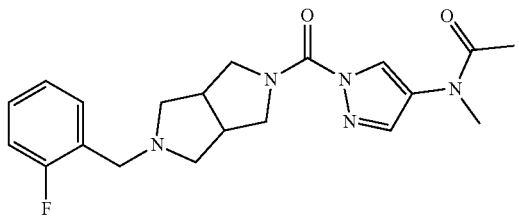 [SMILES: CC(=O)N(C)c1cnn(C(=O)N2CC3CN(Cc4ccccc4F)CC3C2)c1]

The title compound was synthesized as described in Example 27 using tert-butyl hexahydropyrrolo[3,4-c]pyrrole-2(1H)-carboxylate in Step 1 and 2-fluorobenzaldehyde in Step 4. Purification resulted in 111.5 mg of the title compound as a light yellow solid. $^1$H NMR (400 MHz, Chloroform-d) δ 8.30 (s, 0.3H), 8.20 (s, 0.7H), 8.06 (s, 0.3H), 7.56 (s, 0.7H), 7.38 (t, J=7.4 Hz, 1H), 7.23-7.26 (m, 1H), 7.10-7.13 (m, 1H), 7.04 (t, J=9.2 Hz, 1H), 3.70-4.21 (m, 6H), 3.38 (s, 1H), 3.24 (s, 2H), 2.91 (br, 2H), 2.68-2.72 (m, 2H), 2.56-2.62 (m, 2H), 2.30 (s, 1H), 2.01 (s, 2H). LCMS (ESI, m/z): 386 [M+H]$^+$.

Example 183: N-(1-(5-(2-methoxybenzyl)octahydropyrrolo[3,4-c]pyrrole-2-carbonyl)-1H-pyrazol-4-yl)-N-methylacetamide

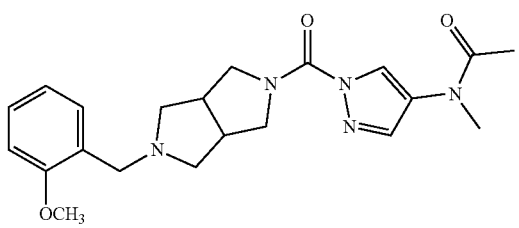 [SMILES: COc1ccccc1CN1CC2CN(C(=O)n3cc(N(C)C(C)=O)cn3)CC2C1]

The title compound was synthesized as described in Example 27 using tert-butyl hexahydropyrrolo[3,4-c]pyrrole-2(1H)-carboxylate in Step 1 and 2-methoxybenzaldehyde in Step 4. Purification resulted in 145.9 mg of the title compound as a light yellow solid. $^1$H NMR (400 MHz, Chloroform-d) δ 8.30 (s, 0.3H), 8.20 (s, 0.7H), 8.06 (s, 0.3H), 7.56 (s, 0.7H), 7.34-7.36 (m, 1H), 7.22-7.26 (m, 1H), 6.92-6.96 (m, 1H), 6.87 (d, J=8.0 Hz, 1H), 3.72-4.19 (m, 7H), 3.64-3.68 (m, 2H), 3.37 (s, 1H), 3.23 (s, 2H), 2.90 (br, 2H), 2.70-2.74 (m, 2H), 2.55-2.62 (m, 2H), 2.30 (s, 1H), 2.01 (s, 2H). LCMS (ESI, m/z): 398 [M+H]$^+$.

Example 184: N-methyl-N-(1-(5-(2-(pyrrolidin-1-yl)benzyl)octahydropyrrolo[3,4-c]pyrrole-2-carbonyl)-1H-pyrazol-4-yl)acetamide

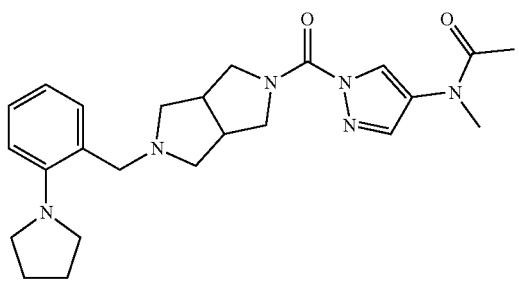 [SMILES: CC(=O)N(C)c1cnn(C(=O)N2CC3CN(Cc4ccccc4N4CCCC4)CC3C2)c1]

The title compound was synthesized as described in Example 27 using tert-butyl hexahydropyrrolo[3,4-c]pyrrole-2(1H)-carboxylate in Step 1 and 2-(pyrrolidin-1-yl)benzaldehyde in Step 4. Purification resulted in 124.7 mg of the title compound as a off-white solid. $^1$H NMR (400 MHz, Chloroform-d) δ 8.30 (s, 0.3H), 8.20 (s, 0.7H), 8.06 (s, 0.3H), 7.56 (s, 0.7H), 7.38 (d, J=7.2 Hz, 1H), 7.17 (t, J=7.8 Hz, 1H), 6.86-6.93 (m, 2H), 3.66-4.26 (m, 6H), 3.38 (s, 1H), 3.19-3.24 (m, 6H), 2.90 (br, 2H), 2.63-2.69 (m, 4H), 2.30 (s, 1H), 2.01 (s, 2H), 1.86-1.95 (m, 4H). LCMS (ESI, m/z): 437 [M+H]$^+$.

Example 185: N-methyl-N-(1-(5-(2-morpholinobenzyl)octahydropyrrolo[3,4-c]pyrrole-2-carbonyl)-1H-pyrazol-4-yl)acetamide

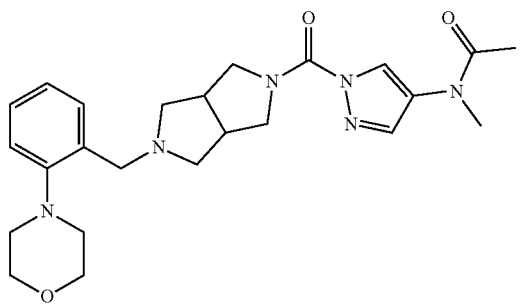 [SMILES: CC(=O)N(C)c1cnn(C(=O)N2CC3CN(Cc4ccccc4N4CCOCC4)CC3C2)c1]

The title compound was synthesized as described in Example 27 using tert-butyl hexahydropyrrolo[3,4-c]pyrrole-2(1H)-carboxylate in Step 1 and 2-morpholinobenzaldehyde in Step 4. Purification resulted in 123.3 mg of the title compound as a off-white solid. $^1$H NMR (400 MHz, Chloroform-d) δ 8.28 (s, 0.3H), 8.19 (s, 0.7H), 8.06 (s, 0.3H), 7.55 (s, 0.7H), 7.39-7.40 (m, 1H), 7.25-7.27 (m, 1H), 7.06-7.10 (m, 2H), 3.70-4.23 (m, 10H), 3.37 (s, 1H), 3.23 (s, 2H), 2.99-3.05 (m, 4H), 2.91 (br, 2H), 2.65-2.72 (m, 4H), 2.30 (s, 1H), 2.00 (s, 2H). LCMS (ESI, m/z): 453 [M+H]$^+$.

Example 186: N-(1-(2-(2-chlorobenzyl)-2,8-diazaspiro[4.5]decane-8-carbonyl)-1H-pyrazol-4-yl)-N-methylacetamide

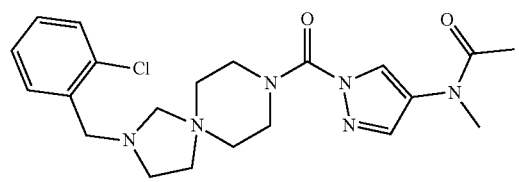

Step 1: Synthesis of Tert-butyl 2-(2-chlorobenzyl)-2,8-diazaspiro[4.5]decane-8-carboxylate

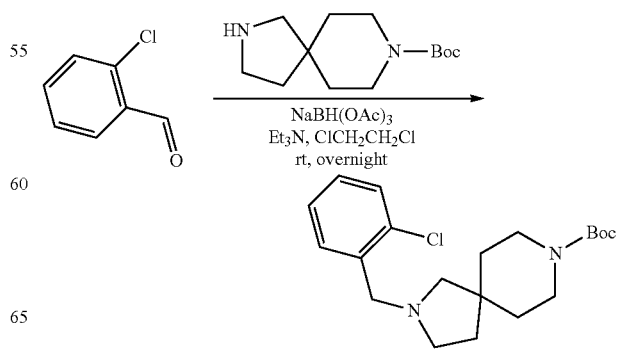

A 40-mL round-bottom flask was charged with 2-chlorobenzaldehyde (200 mg, 1.42 mmol, 1.00 equiv) in dichloroethane (10 mL), tert-butyl 2,8-diazaspiro[4.5]decane-8-carboxylate (514 mg, 2.14 mmol, 1.50 equiv), and triethylamine (433 mg, 4.29 mmol, 3.00 equiv). The resulting solution was stirred for 30 min at room temperature. Sodium triacetoxyborohydride (909 mg, 4.29 mmol, 3.00 equiv) was added. The resulting solution was stirred overnight at room temperature and quenched with water (10 mL). The resulting solution was extracted with DCM (3×10 mL) and the organic layers were combined, washed with brine (2×10 mL), dried over anhydrous sodium sulfate, filtered and concentrated under reduced pressure. The residue was chromatographed on a silica gel column to yield 500 mg (96% yield) of tert-butyl 2-(2-chlorobenzyl)-2,8-diazaspiro[4.5]decane-8-carboxylate as a colorless oil. LCMS (ESI, m/z): 365 [M+H]⁺.

Step 2: Synthesis of 2-(2-chlorobenzyl)-2,8-diazaspiro[4.5]decane

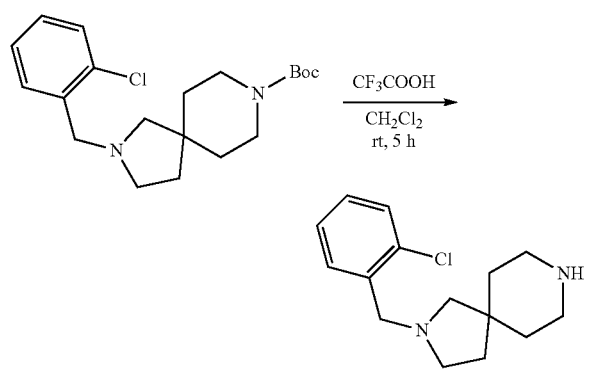

A 100-mL round-bottom flask was charged with tert-butyl 2-(2-chlorobenzyl)-2,8-diazaspiro[4.5]decane-8-carboxylate (500 mg, 1.37 mmol, 1.00 equiv) in DCM (10 mL), and TFA (2.5 mL). The resulting solution was stirred for 5 h at room temperature. The reaction progress was monitored by LCMS. The resulting mixture was concentrated under reduced pressure to yield 660 mg (crude) of 2-(2-chlorobenzyl)-2,8-diazaspiro[4.5]decane as a yellow oil. LCMS (ESI, m/z): 265 [M+H]⁺.

Step 3: Synthesis of N-(1-(2-(2-chlorobenzyl)-2,8-diazaspiro[4.5]decane-8-carbonyl)-1H-pyrazol-4-yl)acetamide

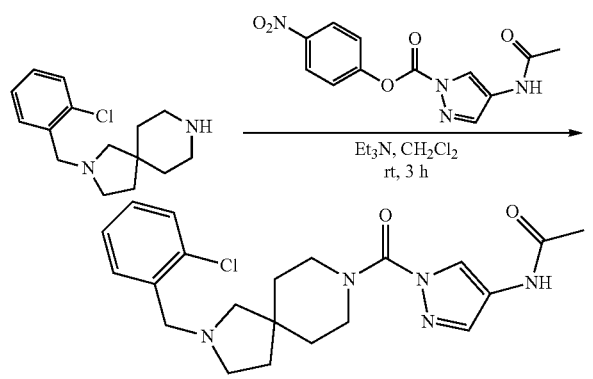

A 100-mL round-bottom flask was charged with 2-(2-chlorobenzyl)-2,8-diazaspiro[4.5]decane (360 mg, 1.36 mmol, 1.00 equiv) in DCM (10 mL), 4-nitrophenyl 4-acetamido-1H-pyrazole-1-carboxylate (593 mg, 2.04 mmol, 1.50 equiv), and triethylamine (413 mg, 4.09 mmol, 3.00 equiv) under nitrogen. The resulting solution was stirred for 3 h at room temperature and quenched with water (10 mL). The resulting solution was extracted with DCM (3×10 mL) and the organic layers were combined, washed with brine (2×10 mL), dried over anhydrous sodium sulfate, filtered and concentrated under reduced pressure. The residue was chromatographed on a silica gel column to yield 300 mg (53% yield) of N-(1-(2-(2-chlorobenzyl)-2,8-diazaspiro[4.5]decane-8-carbonyl)-1H-pyrazol-4-yl)acetamide as a yellow oil. LCMS (ESI, m/z): 416 [M+H]⁺.

Step 4: Synthesis of N-(1-(2-(2-chlorobenzyl)-2,8-diazaspiro[4.5]decane-8-carbonyl)-1H-pyrazol-4-yl)-N-methylacetamide

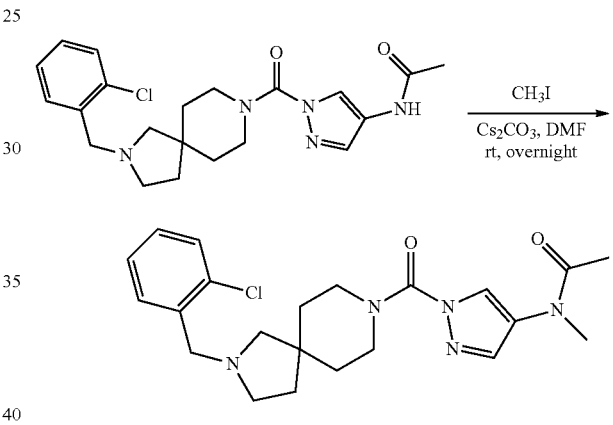

A 40-mL round-bottom flask was charged with N-(1-(2-(2-chlorobenzyl)-2,8-diazaspiro[4.5]decane-8-carbonyl)-1H-pyrazol-4-yl)acetamide (300 mg, 0.720 mmol, 1.00 equiv) in DMF (10 mL), and cesium carbonate (707 mg, 2.17 mmol, 3.00 equiv) under nitrogen. The resulting solution was stirred for 1 h at 0° C. Then iodomethane (154 mg, 1.08 mmol, 1.50 equiv) was added. The resulting solution was stirred overnight at room temperature and quenched with water (10 mL). The mixture was extracted with EtOAc (3×10 mL) and the organic layers were combined, washed with brine (2×10 mL), dried over anhydrous sodium sulfate, filtered and concentrated under reduced pressure. The crude product (200 mg) was purified by preparative HPLC. Purification resulted in 87.5 mg (28% yield) of N-(1-(2-(2-chlorobenzyl)-2,8-diazaspiro[4.5]decane-8-carbonyl)-1H-pyrazol-4-yl)-N-methylacetamide as a light yellow solid. ¹H NMR (300 MHz, Chloroform-d) δ 8.18 (s, 0.3H), 8.03 (s, 0.7H), 7.98 (s, 0.3H), 7.54 (s, 0.7H), 7.48 (br, 1H), 7.34-7.36 (m, 1H), 7.19-7.22 (m, 2H), 3.60-3.91 (m, 6H), 3.36 (s, 1H), 3.21 (s, 2H), 2.53-2.72 (m, 4H), 2.28 (s, 1H), 1.99 (s, 2H), 1.74 (br, 6H). LCMS (ESI, m/z): 430 [M+H]⁺.

Example 187: N-(1-(2-(3-chlorobenzyl)-2,8-diazaspiro[4.5]decane-8-carbonyl)-1H-pyrazol-4-yl)-N-methylacetamide

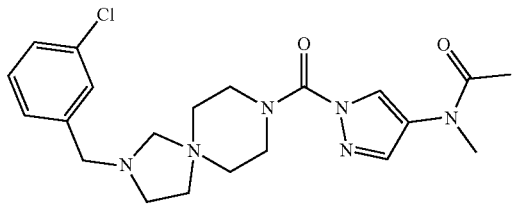

The title compound was synthesized as described in Example 186, using 3-chlorobenzaldehyde in Step 1. Purification resulted in 92.8 mg of N-(1-(2-(3-chlorobenzyl)-2,8-diazaspiro[4.5]decane-8-carbonyl)-1H-pyrazol-4-yl)-N-methylacetamide as a light yellow oil. $^1$H NMR (300 MHz, Chloroform-d) δ 8.18 (s, 0.3H), 8.03 (s, 0.7H), 7.97 (s, 0.3H), 7.54 (s, 0.7H), 7.33 (s, 1H), 7.21-7.27 (m, 3H), 3.70-3.79 (m, 4H), 3.57 (s, 2H), 3.35 (s, 1H), 3.21 (s, 2H), 2.61-2.65 (m, 2H), 2.44 (s, 2H), 2.28 (s, 1H), 1.99 (s, 2H), 1.71 (br, 6H). LCMS (ESI, m/z): 430 [M+H]$^+$.

Example 188: N-(1-(2-(4-chlorobenzyl)-2,8-diazaspiro[4.5]decane-8-carbonyl)-1H-pyrazol-4-yl)-N-methylacetamide

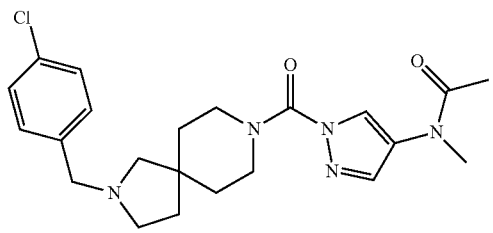 [SMILES: CC(=O)N(C)c1cnn(C(=O)N2CCC3(CCN(Cc4ccc(Cl)cc4)C3)CC2)c1]

The title compound was synthesized as described in Example 186, using 4-chlorobenzaldehyde in Step 1. Purification resulted in 43.2 mg of N-(1-(2-(4-chlorobenzyl)-2,8-diazaspiro[4.5]decane-8-carbonyl)-1H-pyrazol-4-yl)-N-methylacetamide as a light yellow oil. $^1$H NMR (300 MHz, Chloroform-d) δ 8.18 (s, 0.3H), 8.03 (s, 0.7H), 7.97 (s, 0.3H), 7.54 (s, 0.7H), 7.24-7.30 (m, 4H), 3.73-3.78 (m, 4H), 3.57 (s, 2H), 3.35 (s, 1H), 3.21 (s, 2H), 2.63 (br, 2H), 2.43 (s, 2H), 2.28 (s, 1H), 1.99 (s, 2H), 1.71 (br, 6H). LCMS (ESI, m/z): 430 [M+H]$^+$.

Example 189: N-(1-(5-(2-chloro-4-(2-oxo-2-(pyrrolidin-1-yl)ethoxy)benzyl)octahydropyrrolo[3,4-c]pyrrole-2-carbonyl)-1H-pyrazol-4-yl)-N-methylacetamide

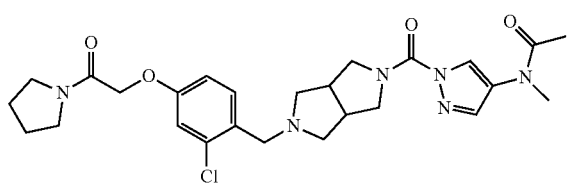 [SMILES: CC(=O)N(C)c1cnn(C(=O)N2CC3CN(Cc4ccc(OCC(=O)N5CCCC5)cc4Cl)CC3C2)c1]

Step 1: Synthesis of 2-chloro-1-(pyrrolidin-1-yl)ethanone

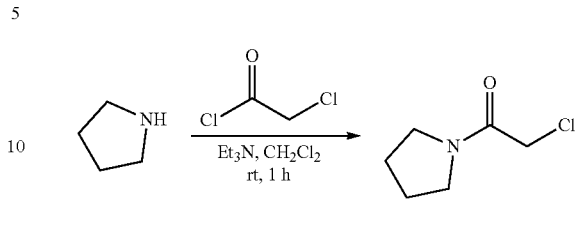

A 100-mL round-bottom flask was charged with pyrrolidine (0.500 g, 7.03 mmol, 1.00 equiv), triethylamine (2.13 g, 21.1 mmol, 3.00 equiv), and DCM (20 mL). 2-chloroacetyl chloride (1.18 g, 10.4 mmol, 1.50 equiv) was added at 0° C. The resulting solution was stirred for 1 h at room temperature and concentrated under reduced pressure. The residue was chromatographed on a silica gel column to provide 0.902 g (87% yield) of 2-chloro-1-(pyrrolidin-1-yl)ethanone as a yellow solid. LCMS (ESI, m/z): 148 [M+H]$^+$.

Step 2: Synthesis of 2-chloro-4-(2-oxo-2-(pyrrolidin-1-yl)ethoxy)benzaldehyde

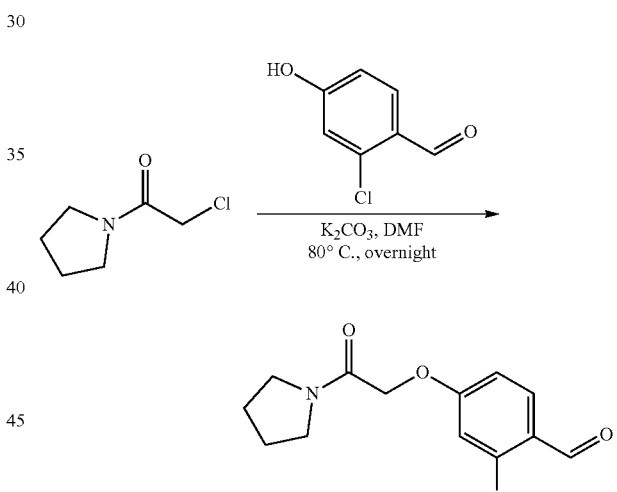

A 100-mL round-bottom flask was charged with 2-chloro-4-hydroxybenzaldehyde (0.400 g, 2.55 mmol, 1.00 equiv), 2-chloro-1-(pyrrolidin-1-yl)ethanone (0.565 g, 3.83 mmol, 1.50 equiv), potassium carbonate (1.10 g, 7.96 mmol, 3.00 equiv), and DMF (10 mL). The resulting solution was stirred overnight at 80° C. and then quenched with water (10 mL). The resulting solution was extracted with EtOAc (3×10 mL) and the organic layers were combined, washed with brine (1×50 mL), dried over anhydrous sodium sulfate, filtered and concentrated under reduced pressure. The residue was chromatographed on a silica gel column to provide 0.500 g (73% yield) of 2-chloro-4-(2-oxo-2-(pyrrolidin-1-yl)ethoxy)benzaldehyde as a yellow solid. LCMS (ESI, m/z): 268 [M+H]$^+$.

Step 3: Synthesis of N-(1-(5-(2-chloro-4-(2-oxo-2-(pyrrolidin-1-yl)ethoxy)benzyl)octahydropyrrolo[3,4-c]pyrrole-2-carbonyl)-1H-pyrazol-4-yl)-N-methylacetamide

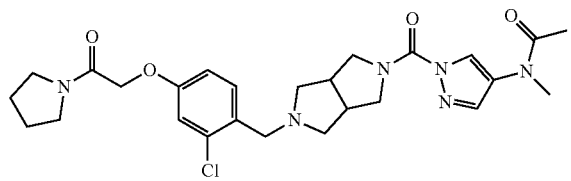 [SMILES: CC(=O)N(C)c1cnn(C(=O)N2CC3CN(Cc4ccc(OCC(=O)N5CCCC5)cc4Cl)CC3C2)c1]

The title compound was synthesized as described in Example 83 using tert-butyl hexahydropyrrolo[3,4-c]pyrrole-2(1H)-carboxylate in Step 1 and 2-chloro-4-(2-oxo-2-(pyrrolidin-1-yl)ethoxy)benzaldehyde in Step 4. Purification resulted in 74.0 mg of N-(1-(5-(2-chloro-4-(2-oxo-2-(pyrrolidin-1-yl)ethoxy)benzyl)octahydropyrrolo[3,4-c]pyrrole-2-carbonyl)-1H-pyrazol-4-yl)-N-methylacetamide as a white solid. $^1$H NMR (300 MHz, Chloroform-d) δ 8.29 (s, 0.3H), 8.19 (s, 0.7H), 8.04 (s, 0.3H), 7.56 (s, 0.7H), 7.32 (d, J=8.7 Hz, 1H), 6.94-6.95 (m, 1H), 6.81-6.85 (m, 1H), 4.60 (s, 2H), 4.09 (br, 2H), 3.66-3.87 (m, 4H), 3.48-3.55 (m, 4H), 3.36 (s, 1H), 3.22 (s, 2H), 2.89-2.98 (m, 2H), 2.63 (br, 4H), 2.28 (s, 1H), 1.95-2.04 (m, 5H), 1.85-1.90 (m, 1H). LCMS (ESI, m/z): 529 [M+H]$^+$.

Example 190: N-methyl-N-(1-(4-(3-(pyrrolidin-1-yl)-5-(trifluoromethyl)benzyl)piperazine-1-carbonyl)-1H-pyrazol-4-yl)acetamide

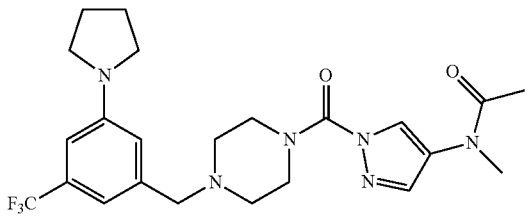 [SMILES: CC(=O)N(C)c1cnn(C(=O)N2CCN(Cc3cc(N4CCCC4)cc(C(F)(F)F)c3)CC2)c1]

The title compound was synthesized as describe in Example 190 using tert-butyl piperazine-1-carboxylate in Step 2. Purification resulted in 71.6 mg of N-methyl-N-(1-(4-(3-(pyrrolidin-1-yl)-5-(trifluoromethyl)benzyl)piperazine-1-carbonyl)-1H-pyrazol-4-yl)acetamide as a light yellow solid. $^1$H NMR (300 MHz, Chloroform-d) δ 7.95-8.32 (m, 1H), 7.48-7.62 (m, 2H), 7.00-7.20 (m, 2H), 3.80-4.00 (m, 4H), 3.55-3.70 (m, 2H), 3.30-3.45 (m, 1H), 3.12-3.32 (m, 6H), 2.48-2.70 (m, 4H), 2.22-2.38 (m, 1H), 1.88-2.08 (m, 6H). LCMS (ESI, m/z): 479 [M+H]$^+$.

Examples 191-318

(Table 2) were synthesized as described in the previous Examples using the appropriate starting materials.

TABLE 2

| Ex. | Structure | NMR | MS [M+H]$^+$ |
|---|---|---|---|
| 191 | ![structure] | $^1$H NMR (400 MHz, Chloroform-d) δ 7.98-8.21 (m, 1.4H), 7.53-7.54 (m, 1.6H), 7.09-7.11 (m, 2H), 3.87 (br, 4H), 3.60 (br, 2H), 3.36 (s, 1H), 3.21-3.26 (m, 6H), 2.57 (br, 4H), 2.28 (s, 1H), 1.99 (s, 2H), 1.94-1.97 (m, 4H). | 479 |
| 192 | ![structure] | $^1$H NMR (300 MHz, Chloroform-d) δ 8.20 (s, 0.3H), 8.07 (s, 0.7H), 7.99 (s, 0.3H), 7.54 (s, 0.7H), 7.46-7.48 (m, 1H), 7.36-7.38 (m, 1H), 7.19-7.28 (m, 2H), 3.90 (br, 4H), 3.69 (br, 2H), 3.36 (s, 1H), 3.21 (s, 2H), 2.64 (br, 4H), 2.28 (s, 1H), 1.99 (s, 2H). | 376 |
| 193 | ![structure] | $^1$H NMR (300 MHz, Chloroform-d) δ 8.20 (s, 0.3H), 8.06 (s, 0.7H), 7.98 (s, 0.3H), 7.54 (s, 0.7H), 7.35 (s, 1H), 7.19-7.26 (m, 3H), 3.88 (br, 4H), 3.52-3.53 (m, 2H), 3.36 (s, 1H), 3.21 (s, 2H), 2.52-2.58 (m, 4H), 2.28 (s, 1H), 1.99 (s, 2H). | 376 |
| 194 | ![structure] | $^1$H NMR (300 MHz, Chloroform-d) δ 8.20 (s, 0.3H), 8.06 (s, 0.7H), 7.98 (s, 0.3H), 7.54 (s, 0.7H), 7.25-7.32 (m, 4H), 3.87 (br, 4H), 3.51-3.52 (m, 2H), 3.35 (s, 1H), 3.21 (s, 2H), 2.53-2.56 (m, 4H), 2.28 (s, 1H), 1.99 (s, 2H). | 376 |

TABLE 2-continued

| Ex. | Structure | NMR | MS [M + H]+ |
|---|---|---|---|
| 195 | 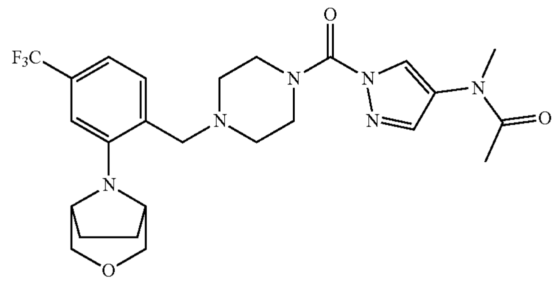 [SMILES: CC(=O)N(C)c1cnn(C(=O)N2CCN(Cc3ccc(C(F)(F)F)cc3N3C4CCC3COC4)CC2)c1] | ¹H NMR (400 MHz, Chloroform-d) δ 8.23 (m, 1H), 7.52-8.05 (m, 2H), 7.20-7.28 (m, 1H), 7.06 (m, 1H), 3.81-4.10 (m, 6H), 3.65-3.78 (m, 6H), 3.40 (s, 1H), 3.20 (s, 2H), 2.48-2.78 (m, 4H), 2.30 (s, 1H), 1.90-2.15 (m, 6H). | 521 |
| 196 | 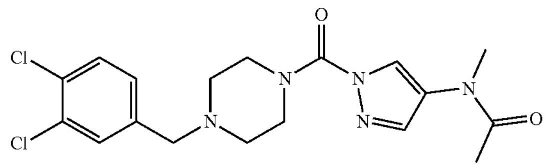 [SMILES: CC(=O)N(C)c1cnn(C(=O)N2CCN(Cc3ccc(Cl)c(Cl)c3)CC2)c1] | ¹H NMR (300 MHz, Chloroform-d) δ 8.20 (s, 0.3H), 8.07 (s, 0.7H), 7.99 (s, 0.3H), 7.54 (s, 0.7H), 7.45 (s, 1H), 7.40 (d, J = 8.1 Hz, 1H), 7.16-7.19 (m, 1H), 3.88 (br, 4H), 3.50 (s, 2H), 3.36 (s, 1H), 3.21 (s, 2H), 2.56 (t, J = 5.1 Hz, 4H), 2.28 (s, 1H), 1.99 (s, 2H). | 432 (+Na) |
| 197 | 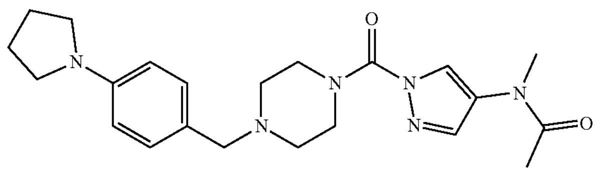 [SMILES: CC(=O)N(C)c1cnn(C(=O)N2CCN(Cc3ccc(N4CCCC4)cc3)CC2)c1] | ¹H NMR (300 MHz, Chloroform-d) δ 8.19 (s, 0.3H), 8.05 (s, 0.7H), 7.98 (s, 0.3H), 7.53 (s, 0.7H), 7.15 (d, J = 8.4 Hz, 2H), 6.53 (d, J = 8.4 Hz, 2H), 3.86 (br, 4H), 3.48 (s, 2H), 3.35 (s, 1H), 3.28 (t, J = 6.3 Hz, 4H), 3.21 (s, 2H), 2.55 (t, J = 4.8 Hz, 4H), 2.27 (s, 1H), 1.98-2.04 (m, 6H). | 433 (+Na) |
| 198 | 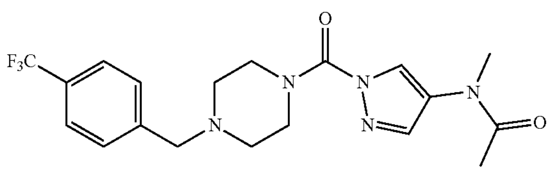 [SMILES: CC(=O)N(C)c1cnn(C(=O)N2CCN(Cc3ccc(C(F)(F)F)cc3)CC2)c1] | ¹H NMR (300 MHz, Chloroform-d) δ 8.21 (s, 0.3H), 8.07 (s, 0.7H), 7.99 (s, 0.3H), 7.54-7.70 (m, 2.7H), 7.47 (d, J = 8.1 Hz, 2H), 3.89 (br, 4H), 3.60 (s, 2H), 3.36 (s, 1H), 3.21 (s, 2H), 2.53-2.59 (m, 4H), 2.80 (s, 1H), 1.99 (s, 2H). | 432 (+Na) |
| 199 | 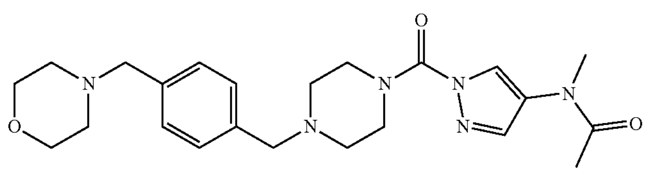 [SMILES: CC(=O)N(C)c1cnn(C(=O)N2CCN(Cc3ccc(CN4CCOCC4)cc3)CC2)c1] | ¹H NMR (300 MHz, Chloroform-d) δ 8.20 (s, 0.3H), 8.06 (s, 0.7H), 7.97 (s, 0.3H), 7.54 (s, 0.7H), 7.52-7.28 (m, 4H), 3.87 (br, 4H), 3.71 (t, J = 4.5 Hz, 4H), 3.44-3.57 (m, 4H), 3.35 (s, 1H), 3.27 (s, 2H), 2.52-2.58 (m, 4H), 2.44 (t, J = 4.5 Hz, 4H), 2.28 (s, 1H), 1.99 (s, 2H). | 463 (+Na) |
| 200 | 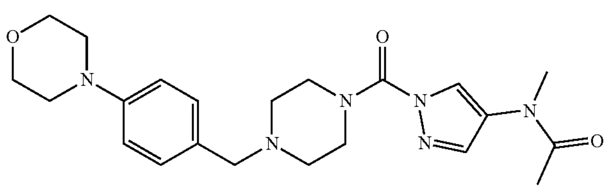 [SMILES: CC(=O)N(C)c1cnn(C(=O)N2CCN(Cc3ccc(N4CCOCC4)cc3)CC2)c1] | ¹H NMR (300 MHz, Chloroform-d) δ 8.19 (s, 0.3H), 8.05 (s, 0.7H), 7.98 (s, 0.3H), 7.54 (s, 0.7H), 7.22 (d, J = 8.4 Hz, 2H), 6.88 (d, J = 8.4 Hz, 2H), 3.86 (t, J = 4.5 Hz, 8H), 3.44 (s, 2H), 3.35 (s, 1H), 3.21 (s, 2H), 3.16 (t, J = 4.8 Hz, 4H), 2.54 (br, 4H), 2.28 (s, 1H), 1.99 (s, 2H). | 449 (+Na) |
| 201 | 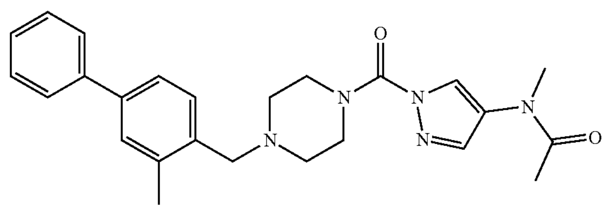 [SMILES: CC(=O)N(C)c1cnn(C(=O)N2CCN(Cc3ccc(-c4ccccc4)cc3C)CC2)c1] | ¹H NMR (300 MHz, Chloroform-d) δ 8.21 (s, 0.3H), 8.07 (s, 0.7H), 7.99 (s, 0.3H), 7.55-7.60 (m, 2.7H), 7.26-7.46 (m, 6H), 3.87 (br, 4H), 3.55 (s, 2H), 3.36 (s, 1H), 3.22 (s, 2H), 2.60 (t, J = 5.1 Hz, 4H), 2.45 (s, 3H), 2.24 (s, 1H), 2.00 (s, 2H). | 432 |
| 202 | 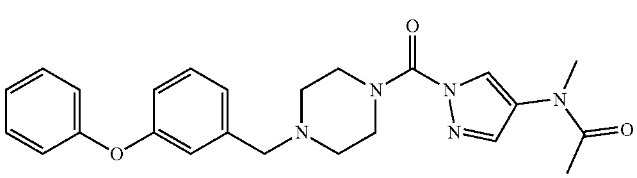 [SMILES: CC(=O)N(C)c1cnn(C(=O)N2CCN(Cc3cccc(Oc4ccccc4)c3)CC2)c1] | ¹H NMR (300 MHz, Chloroform-d) δ 8.20 (s, 0.3H), 8.06 (s, 0.7H), 7.99 (s, 0.3H), 7.54 (s, 0.7H), 7.26-7.37 (m, 3H), 6.89-7.13 (m, 6H), 3.86 (br, 4H), 3.53 (s, 2H), 3.35 (s, 1H), 3.21 (s, 2H), 2.52-2.58 (m, 4H), 2.28 (s, 1H), 2.00 (s, 2H). | 434 |

TABLE 2-continued

| Ex. | Structure | NMR | MS [M + H]+ |
|---|---|---|---|
| 203 | 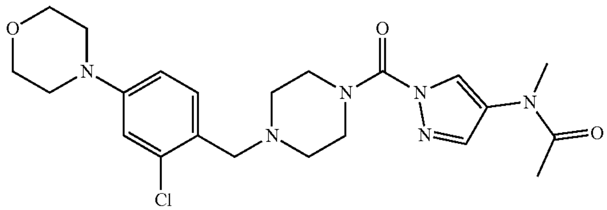 [SMILES: CC(=O)N(C)c1cnn(C(=O)N2CCN(Cc3ccc(N4CCOCC4)cc3Cl)CC2)c1] | ¹H NMR (300 MHz, Chloroform-d) δ 8.20 (s, 0.3H), 8.06 (s, 0.7H), 7.99 (s, 0.3H), 7.54 (s, 0.7H), 7.30 (d, J = 8.7 Hz, 1H), 6.88 (s, 1H), 6.77-6.81 (m, 1H), 3.85 (t, J = 4.5 Hz, 8H), 3.61 (s, 2H), 3.36 (s, 1H), 3.21 (s, 2H), 3.15 (t, J = 4.5 Hz, 4H), 2.61 (br, 4H), 2.28 (s, 1H), 1.99 (s, 2H). | 461 |
| 204 | 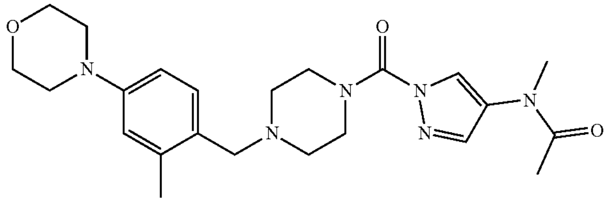 [SMILES: CC(=O)N(C)c1cnn(C(=O)N2CCN(Cc3ccc(N4CCOCC4)cc3C)CC2)c1] | ¹H NMR (300 MHz, Chloroform-d) δ 8.20 (s, 0.3H), 8.06 (s, 0.7H), 7.98 (s, 0.3H), 7.54 (s, 0.7H), 7.12 (d, J = 8.1 Hz, 1H), 6.68-6.74 (m, 2H), 3.86 (t, J = 4.8 Hz, 8H), 3.45 (br, 2H), 3.36 (s, 1H), 3.21 (s, 2H), 3.15 (t, J = 4.8 Hz, 4H), 2.54 (br, 4H), 2.36 (s, 3H), 2.28 (s, 1H), 1.99 (s, 2H). | 463 (+Na) |
| 205 | 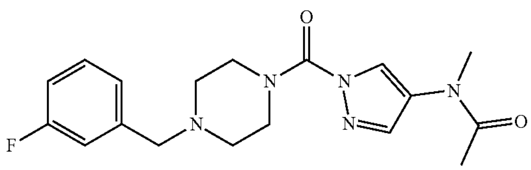 [SMILES: CC(=O)N(C)c1cnn(C(=O)N2CCN(Cc3cccc(F)c3)CC2)c1] | ¹H NMR (300 MHz, Chloroform-d) δ 8.20 (s, 0.4H), 8.06 (s, 0.6H), 7.98 (s, 0.4H), 7.54 (s, 0.6H), 7.30-7.32 (m, 1H), 7.08-7.10 (m, 2H), 6.94-6.99 (m, 1H), 4.10 (br, 4H), 3.54-3.55 (m, 2H), 3.36 (s, 1H), 3.21 (s, 2H), 2.55-2.58 (m, 4H), 2.28 (s, 1H), 1.99 (s, 2H). | 360 |
| 206 | 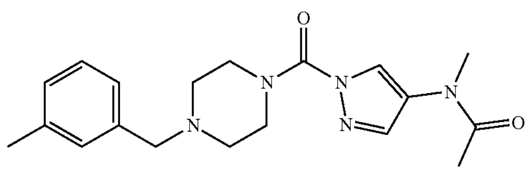 [SMILES: CC(=O)N(C)c1cnn(C(=O)N2CCN(Cc3cccc(C)c3)CC2)c1] | ¹H NMR (300 MHz, Chloroform-d) δ 8.20 (s, 0.4H), 8.06 (s, 0.6H), 7.98 (s, 0.4H), 7.54 (s, 0.6H), 7.08-7.25 (m, 4H), 3.88 (br, 4H), 3.76 (s, 2H), 3.53 (s, 1H), 3.21 (s, 2H), 2.56 (br, 4H), 2.35 (s, 3H), 2.28 (s, 1H), 1.99 (s, 2H). | 356 |
| 207 | 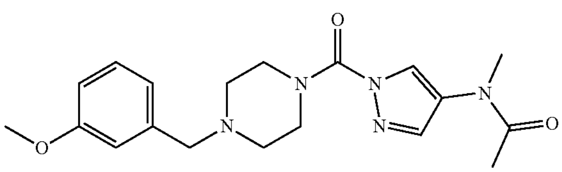 [SMILES: COc1cccc(CN2CCN(C(=O)n3cc(N(C)C(C)=O)cn3)CC2)c1] | ¹H NMR (300 MHz, Chloroform-d) δ 8.20 (s, 0.4H), 8.06 (s, 0.6H), 7.98 (s, 0.4H), 7.54 (s, 0.6H), 7.22-7.24 (m, 1H), 6.90-6.92 (m, 2H), 6.80-6.83 (m, 1H), 3.88 (br, 4H), 3.82 (s, 3H), 3.53 (s, 2H), 3.35 (s, 1H), 3.21 (s, 2H), 2.56 (t, J = 4.2 Hz, 4H), 2.28 (s, 1H), 1.99 (s, 2H). | 372 |
| 208 | 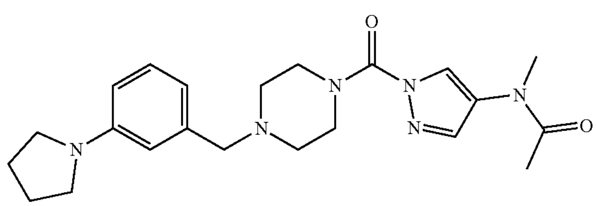 [SMILES: CC(=O)N(C)c1cnn(C(=O)N2CCN(Cc3cccc(N4CCCC4)c3)CC2)c1] | ¹H NMR (300 MHz, Chloroform-d) δ 8.22 (s, 0.4H), 8.08 (s, 0.6H), 8.02 (s, 0.4H), 7.57 (s, 0.6H), 7.18-7.29 (m, 1H), 6.64-6.66 (m, 1H), 6.51-6.57 (m, 2H), 3.92 (br, 4H), 3.56 (br, 2H), 3.30-3.38 (m, 5H), 3.24 (s, 2H), 2.62 (br, 4H), 2.31 (s, 1H), 2.02-2.06 (m, 6H). | 411 |
| 209 | 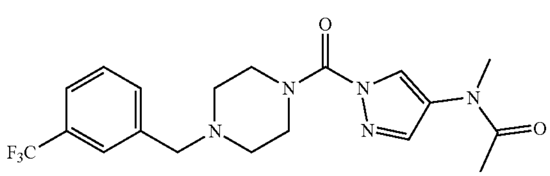 [SMILES: CC(=O)N(C)c1cnn(C(=O)N2CCN(Cc3cccc(C(F)(F)F)c3)CC2)c1] | ¹H NMR (300 MHz, Chloroform-d) δ 8.23 (s, 0.4H), 8.09 (s, 0.6H), 8.01 (s, 0.4H), 7.64 (s, 0.6H), 7.55-7.57 (m, 3H), 7.45-7.50 (m, 1H), 3.92 (br, 4H), 3.63 (s, 2H), 3.38 (s, 1H), 3.24 (s, 2H), 2.59-2.62 (m, 4H), 2.31 (s, 1H), 2.02 (s, 2H). | 410 |
| 210 | 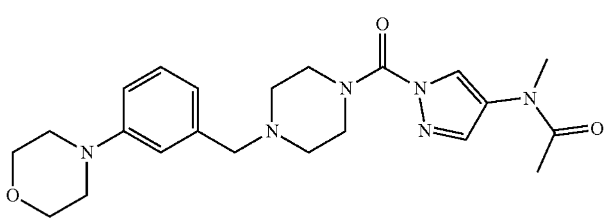 [SMILES: CC(=O)N(C)c1cnn(C(=O)N2CCN(Cc3cccc(N4CCOCC4)c3)CC2)c1] | ¹H NMR (300 MHz, Chloroform-d) δ 8.23 (s, 0.4H), 8.09 (s, 0.6H), 8.01 (s, 0.4H), 7.57 (s, 0.6H), 7.24-7.29 (m, 1H), 6.94 (s, 1H), 6.87 (d, J = 6.3 Hz, 2H), 3.90 (t, J = 4.8 Hz, 8H), 3.56 (s, 2H), 3.38 (s, 1H), 3.19-3.24 (m, 6H), 2.60 (br, 4H), 2.31 (s, 1H), 2.02 (s, 2H). | 427 |

TABLE 2-continued

| Ex. | Structure | NMR | MS [M + H]+ |
|---|---|---|---|
| 211 | 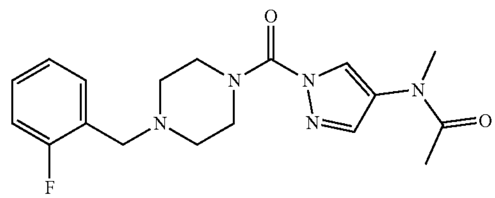 [SMILES: CC(=O)N(C)c1cnn(C(=O)N2CCN(Cc3ccccc3F)CC2)c1] | ¹H NMR (300 MHz, Chloroform-d) δ 8.22 (s, 0.4H), 8.08 (s, 0.6H), 8.02 (s, 0.4H), 7.56 (s, 0.6H), 7.37-7.42 (m, 1H), 7.26-7.33 (m, 1H), 7.04-7.18 (m, 2H), 3.91 (br, 4H), 3.68 (s, 2H), 3.38 (s, 1H), 3.24 (s, 2H), 2.64 (t, J = 4.5 Hz, 4H), 2.30 (s, 1H), 2.02 (s, 2H). | 360 |
| 212 | 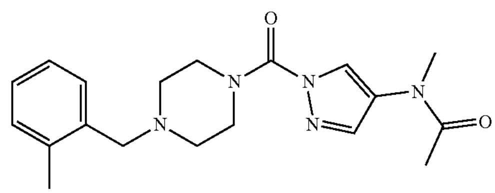 [SMILES: CC(=O)N(C)c1cnn(C(=O)N2CCN(Cc3ccccc3C)CC2)c1] | ¹H NMR (300 MHz, Chloroform-d) δ 8.23 (s, 0.4H), 8.09 (s, 0.6H), 8.02 (s, 0.4H), 7.57 (s, 0.6H), 7.15-7.29 (m, 4H), 3.88 (br, 4H), 3.55 (s, 2H), 3.39 (s, 1H), 3.24 (s, 2H), 2.58-2.60 (m, 4H), 2.42 (s, 3H), 2.31 (s, 1H), 2.02 (s, 2H). | 356 |
| 213 | 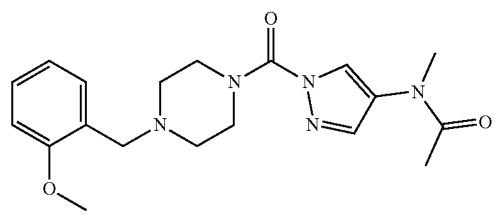 [SMILES: COc1ccccc1CN1CCN(C(=O)n2cc(N(C)C(C)=O)cn2)CC1] | ¹H NMR (300 MHz, Chloroform-d) δ 8.22 (s, 0.4H), 8.08 (s, 0.6H), 8.02 (s, 0.4H), 7.57 (s, 0.6H), 7.26-7.38 (m, 2H), 6.90-7.00 (m, 2H), 3.92 (br, 4H), 3.86 (s, 3H), 3.67 (s, 2H), 3.38 (s, 1H), 3.24 (s, 2H), 2.66 (br, 4H), 2.31 (s, 1H), 2.02 (s, 2H). | 372 |
| 214 | 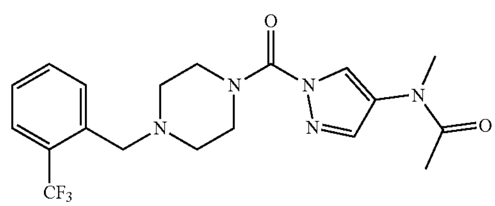 [SMILES: CC(=O)N(C)c1cnn(C(=O)N2CCN(Cc3ccccc3C(F)(F)F)CC2)c1] | ¹H NMR (300 MHz, Chloroform-d) δ 8.23 (s, 0.4H), 8.10 (s, 0.6H), 8.02 (s, 0.4H), 7.82 (s, 0.6H), 7.37-7.69 (m, 4H), 3.92 (br, 4H), 3.75 (s, 2H), 3.39 (s, 1H), 3.24 (s, 2H), 2.63 (t, J = 4.5 Hz, 4H), 2.31 (s, 1H), 2.02 (s, 2H). | 410 |
| 215 | 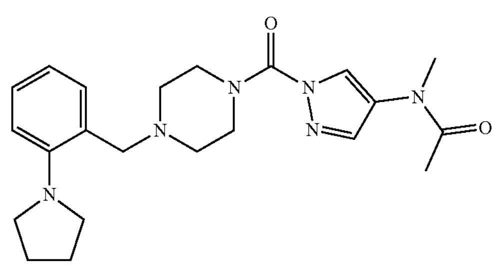 [SMILES: CC(=O)N(C)c1cnn(C(=O)N2CCN(Cc3ccccc3N3CCCC3)CC2)c1] | ¹H NMR (300 MHz, Chloroform-d) δ 8.23 (s, 0.4H), 8.09 (s, 0.6H), 8.01 (s, 0.4H), 7.56 (s, 0.6H), 7.44 (d, J = 7.5 Hz, 1H), 7.19-7.29 (m, 1H), 6.91-7.00 (m, 2H), 3.91 (br, 4H), 3.63 (br, 2H), 3.38 (s, 1H), 3.20-3.24 (m, 6H), 2.62 (br, 4H), 2.31 (s, 1H), 1.91-2.02 (m, 6H). | 411 |
| 216 | 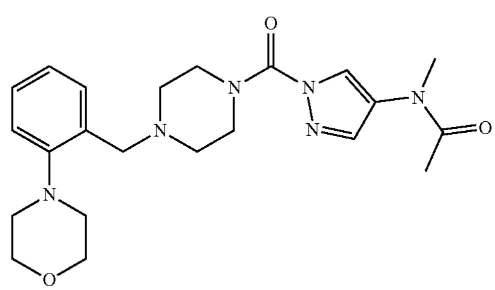 [SMILES: CC(=O)N(C)c1cnn(C(=O)N2CCN(Cc3ccccc3N3CCOCC3)CC2)c1] | ¹H NMR (300 MHz, Chloroform-d) δ 8.20 (s, 0.4H), 8.06 (s, 0.6H), 7.99 (s, 0.4H), 7.54 (s, 0.6H), 7.44 (d, J = 7.2 Hz, 1H), 7.26-7.31 (m, 1H), 7.08-7.14 (m, 2H), 4.07-4.09 (m, 8H), 3.82-3.85 (m, 2H), 3.64 (s, 1H), 3.36 (s, 2H), 2.98 (t, J = 4.2 Hz, 4H), 2.62 (br, 4H), 2.28 (s, 1H), 1.99 (s, 2H). | 427 |

TABLE 2-continued

| Ex. | Structure | NMR | MS [M + H]+ |
|---|---|---|---|
| 217 | 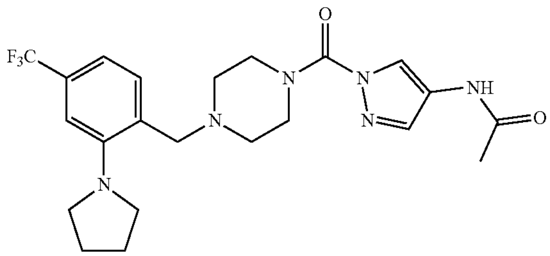 [SMILES: CC(=O)Nc1cnn(C(=O)N2CCN(Cc3ccc(C(F)(F)F)cc3N3CCCC3)CC2)c1] | ¹H NMR (300 MHz, Chloroform-d) δ 8.32 (s, 1H), 7.73 (s, 1H), 7.52-7.54 (m, 1H), 7.09-7.17 (m, 3H), 3.84 (br, 4H), 3.58 (s, 2H), 3.24 (br, 4H), 2.54 (br, 4H), 2.16 (s, 3H), 1.95 (br, 4H). | 465 |
| 218 | 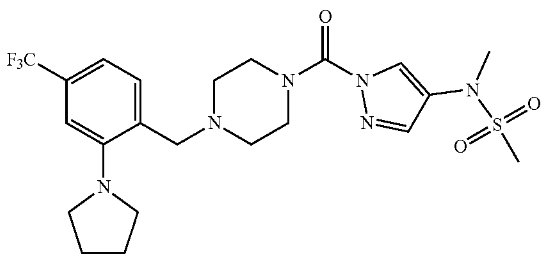 [SMILES: CN(c1cnn(C(=O)N2CCN(Cc3ccc(C(F)(F)F)cc3N3CCCC3)CC2)c1)S(C)(=O)=O] | ¹H NMR (300 MHz, Chloroform-d) δ 8.05 (s, 1H), 7.74 (s, 1H), 7.52-7.55 (m, 1H), 7.09-7.11 (m, 2H), 3.88 (br, 4H), 3.59 (s, 2H), 3.22-3.26 (m, 7H), 2.83 (s, 3H), 2.55 (br, 4H), 1.93-1.97 (m, 4H). | 515 |
| 219 | 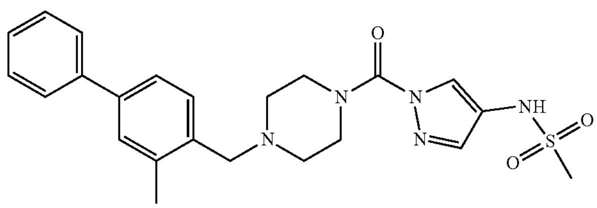 [SMILES: Cc1cc(-c2ccccc2)ccc1CN1CCN(C(=O)n2cc(NS(C)(=O)=O)cn2)CC1] | ¹H NMR (300 MHz, Chloroform-d) δ 8.11 (s, 1H), 7.57-7.63 (m, 3H), 7.26-7.46 (m, 6H), 6.32 (br, 1H), 3.86 (br, 4H), 3.55 (br, 2H), 3.00 (s, 3H), 2.59 (br, 4H), 2.44 (s, 3H). | 454 |
| 220 | 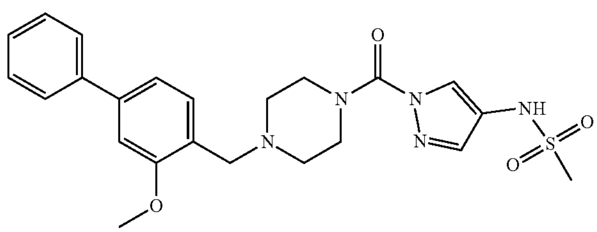 [SMILES: COc1cc(-c2ccccc2)ccc1CN1CCN(C(=O)n2cc(NS(C)(=O)=O)cn2)CC1] | ¹H NMR (300 MHz, Chloroform-d) δ 8.10 (d, J = 2.4 Hz, 1H), 7.57-7.62 (m, 3H), 7.33-7.46 (m, 4H), 7.15-7.18 (m, 1H), 7.08-7.09 (m, 1H), 6.24 (br, 1H), 3.89 (br, 7H), 3.67 (br, 2H), 3.00 (s, 3H), 2.64 (br, 4H). | 470 |
| 221 | 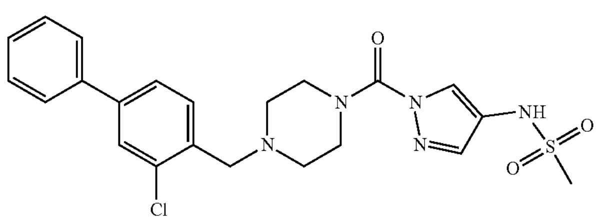 [SMILES: CS(=O)(=O)Nc1cnn(C(=O)N2CCN(Cc3ccc(-c4ccccc4)cc3Cl)CC2)c1] | ¹H NMR (300 MHz, Chloroform-d) δ 8.13 (s, 1H), 7.26-7.64 (m, 9H), 6.22 (s, 1H), 3.74-3.91 (m, 6H), 3.01 (s, 3H), 2.68-2.78 (m, 4H). | 474 |
| 222 | 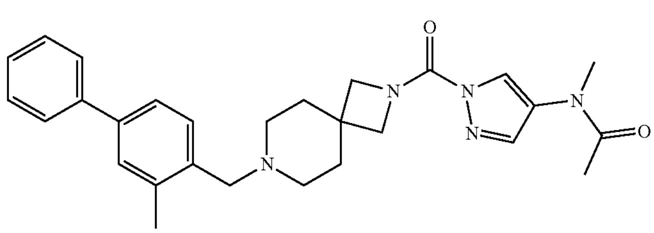 [SMILES: CC(=O)N(C)c1cnn(C(=O)N2CC3(CCN(Cc4ccc(-c5ccccc5)cc4C)CC3)C2)c1] | ¹H NMR (300 MHz, Chloroform-d) δ 8.26 (s, 0.3H), 8.18 (s, 0.7H), 8.06 (s, 0.3H), 7.57-7.60 (m, 2H), 7.54 (s, 0.7H), 7.30-7.45 (m, 6H), 4.36 (br, 2H), 3.91 (br, 2H), 3.46 (br, 2H), 3.34 (s, 1H), 3.20 (s, 2H), 2.42 (br, 7H), 2.28 (s, 1H), 1.98 (s, 2H), 1.83 (br, 4H). | 472 |

TABLE 2-continued

| Ex. | Structure | NMR | MS [M + H]+ |
|---|---|---|---|
| 223 | 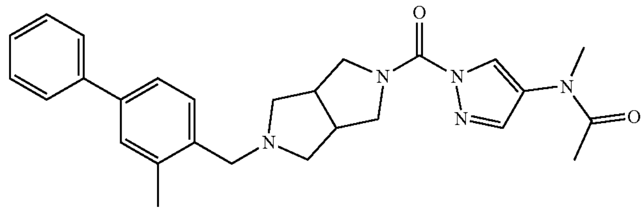 [SMILES: CC(=O)N(C)c1cnn(C(=O)N2CC3CN(Cc4ccc(-c5ccccc5)cc4C)CC3C2)c1] | ¹H NMR (300 MHz, Chloroform-d) δ 8.28 (s, 0.3H), 8.18 (s, 0.7H), 8.04 (s, 0.3H), 7.54-7.59 (m, 2.7H), 7.30-7.45 (m, 6H), 4.10 (br, 2H), 3.75 (br, 2H), 3.62 (br, 2H), 3.35 (s, 1H), 3.21 (s, 2H), 2.91 (br, 2H), 2.62 (br, 4H), 2.40 (s, 3H), 2.28 (s, 1H), 1.99 (s, 2H). | 458 |
| 224 | 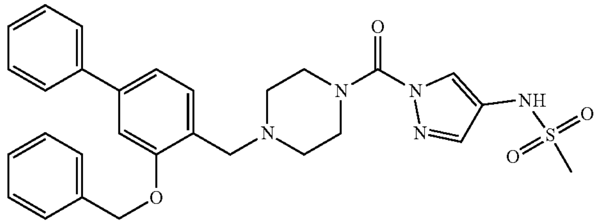 [SMILES: CS(=O)(=O)Nc1cnn(C(=O)N2CCN(Cc3ccc(-c4ccccc4)cc3OCc3ccccc3)CC2)c1] | ¹H NMR (300 MHz, Chloroform-d) δ 8.10 (s, 1H), 7.62 (s, 1H), 7.54-7.57 (m, 2H), 7.40-7.47 (m, 4H), 7.33-7.37 (m, 5H), 7.17-7.20 (m, 2H), 5.16 (s, 2H), 3.88 (br, 4H), 3.72 (br, 2H), 2.99 (s, 3H), 2.64 (br, 4H). | 546 |
| 225 | 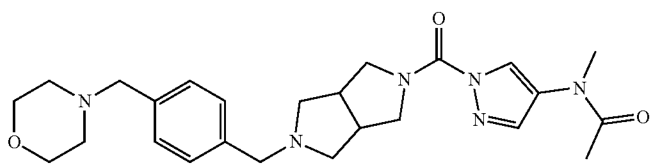 [SMILES: CC(=O)N(C)c1cnn(C(=O)N2CC3CN(Cc4ccc(CN5CCOCC5)cc4)CC3C2)c1] | ¹H NMR (300 MHz, Chloroform-d) δ 8.29 (s, 0.3H), 8.19 (s, 0.7H), 8.04 (s, 0.3H), 7.55 (s, 0.7H), 7.26-7.27 (m, 4H), 3.58-4.40 (m, 10H), 3.50 (s, 2H), 3.36 (s, 1H), 3.22 (s, 2H), 2.92 (br, 2H), 2.37-2.80 (m, 8H), 2.28 (s, 1H), 2.00 (s, 2H). | 467 |
| 226 | 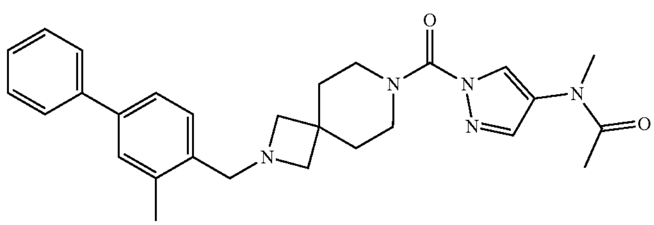 [SMILES: CC(=O)N(C)c1cnn(C(=O)N2CCC3(CC2)CN(Cc2ccc(-c4ccccc4)cc2C)C3)c1] | ¹H NMR (300 MHz, Chloroform-d) δ 8.18 (s, 0.3H), 8.03 (s, 0.7H), 7.98 (s, 0.3H), 7.56-7.59 (m, 2H), 7.54 (s, 0.7H), 7.30-7.45 (m, 6H), 3.74 (br, 6H), 3.35 (s, 1H), 3.21 (s, 6H), 2.40 (s, 3H), 2.28 (s, 1H), 1.99 (s, 2H), 1.93 (br, 4H). | 472 |
| 227 | 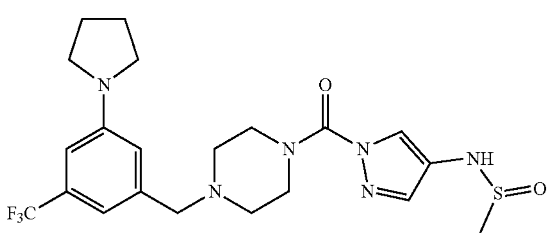 [SMILES: CS(=O)Nc1cnn(C(=O)N2CCN(Cc3cc(N4CCCC4)cc(C(F)(F)F)c3)CC2)c1] | ¹H NMR (300 MHz, Chloroform-d) δ 8.32 (s, 1H), 7.77 (s, 1H), 7.15-7.38 (m, 1H), 6.84 (m, 1H), 6.48-6.78 (m, 2H), 3.70-4.05 (m, 4H), 3.42-3.70 (m, 2H), 3.20-3.42 (m, 4H), 2.46-2.74 (m, 4H), 2.18 (s, 3H), 1.95-2.12 (m, 4H). | 465 |
| 228 | 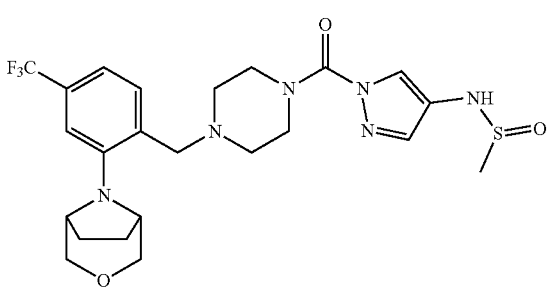 [SMILES: CS(=O)Nc1cnn(C(=O)N2CCN(Cc3ccc(C(F)(F)F)cc3N3C4CCC3COC4)CC2)c1] | ¹H NMR (300 MHz, Chloroform-d) δ 8.35 (s, 1H), 7.80 (s, 1H), 7.60 (m, 1H), 7.18-7.28 (m, 2H), 7.10 (s, 1H), 3.81-4.05 (m, 6H), 3.65-3.80 (m, 6H), 2.50-2.75 (m, 4H), 2.18 (s, 3H), 1.95-2.13 (m, 4H). | 507 |
| 229 | 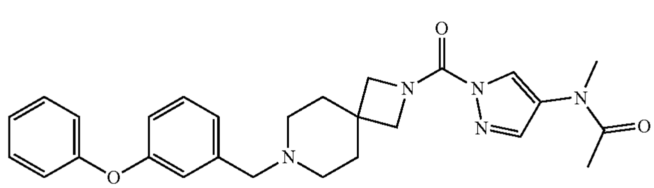 [SMILES: CC(=O)N(C)c1cnn(C(=O)N2CC3(CCN(Cc4cccc(Oc5ccccc5)c4)CC3)C2)c1] | ¹H NMR (300 MHz, Chloroform-d) δ 8.26 (s, 0.3H), 8.17 (s, 0.7H), 8.05 (s, 0.3H), 7.54 (s, 0.7H), 7.25-7.37 (m, 3H), 7.05-7.12 (m, 2H), 6.98-7.02 (m, 3H), 6.88-6.91 (m, 1H), 4.34 (br, 2H), 3.89 (br, 2H), 3.48 (s, 2H), 3.34 (s, 1H), 3.20 (s, 2H), 2.40 (br, 4H), 2.27 (s, 1H), 1.97 (s, 2H), 1.67 (br, 4H). | 474 |

TABLE 2-continued

| Ex. | Structure | NMR | MS [M + H]+ |
|---|---|---|---|
| 230 | 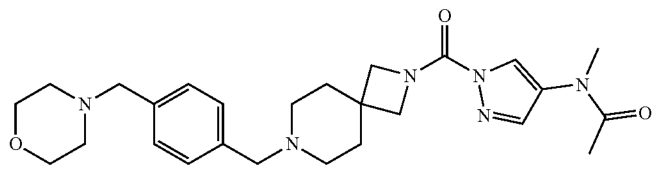 [SMILES: CC(=O)N(C)c1cnn(C(=O)N2CC3(CCN(Cc4ccc(CN5CCOCC5)cc4)CC3)C2)c1] | $^1$H NMR (300 MHz, Chloroform-d) δ 8.25 (s, 0.3H), 8.17 (s, 0.7H), 8.05 (s, 0.3H), 7.54 (s, 0.7H), 7.25-7.35 (m, 4H), 4.35 (br, 2H), 3.90 (br, 2H), 3.72 (t, J = 4.5 Hz, 4H), 3.50 (s, 4H), 3.34 (s, 1H), 3.20 (s, 2H), 2.34-2.55 (m, 8H), 2.28 (s, 1H), 1.97 (s, 2H), 1.85 (br, 4H). | 481 |
| 231 | 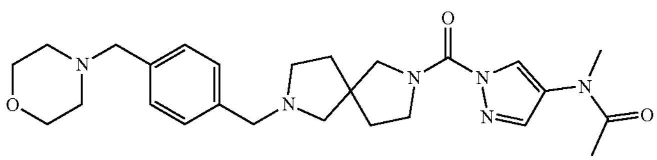 [SMILES: CC(=O)N(C)c1cnn(C(=O)N2CCC3(CCN(Cc4ccc(CN5CCOCC5)cc4)C3)C2)c1] | $^1$H NMR (300 MHz, Chloroform-d) δ 8.28 (s, 0.3H), 8.18 (s, 0.7H), 8.04 (s, 0.3H), 7.55 (s, 0.7H), 7.21-7.31 (m, 4H), 3.82-4.10 (m, 2H), 3.52-3.80 (m, 8H), 3.48 (s, 2H), 3.35 (s, 1H), 3.21 (s, 2H), 2.40-2.80 (m, 8H), 2.28 (s, 1H), 1.99 (s, 2H), 1.80-1.98 (m, 4H). | 481 |
| 232 | 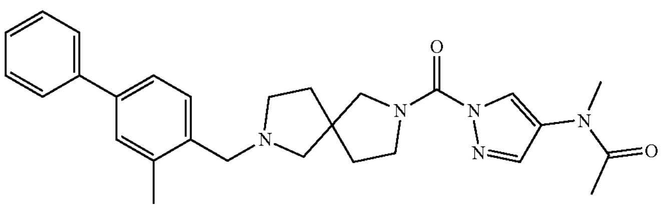 [SMILES: CC(=O)N(C)c1cnn(C(=O)N2CCC3(CCN(Cc4ccc(-c5ccccc5)cc4C)C3)C2)c1] | $^1$H NMR (300 MHz, Chloroform-d) δ 8.27 (s, 0.3H), 8.19 (s, 0.7H), 8.05 (s, 0.3H), 7.53-7.59 (s, 2.7H), 7.29-7.44 (m, 6H), 3.86-4.06 (m, 2H), 3.56-3.70 (m, 4H), 3.34 (s, 1H), 3.20 (s, 2H), 2.46-2.71 (m, 4H), 2.27-2.42 (m, 4H), 1.99 (s, 2H), 1.85-1.95 (m, 4H). | 472 |
| 233 | 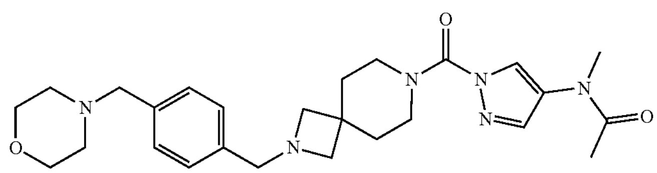 [SMILES: CC(=O)N(C)c1cnn(C(=O)N2CCC3(CC2)CN(Cc2ccc(CN4CCOCC4)cc2)C3)c1] | $^1$H NMR (300 MHz, Chloroform-d) δ 8.17 (s, 0.3H), 8.03 (s, 0.7H), 7.98 (s, 0.3H), 7.54 (s, 0.7H), 7.26-7.28 (m, 2H), 7.21-7.24 (m, 2H), 3.66-3.80 (m, 8H), 3.64 (s, 2H), 3.48 (s, 2H), 3.35 (s, 1H), 3.21 (s, 2H), 3.10 (s, 4H), 2.44 (t, J = 4.5 Hz, 4H), 2.28 (s, 1H), 1.99 (s, 2H), 1.82-1.92 (m, 4H). | 503 (+Na) |
| 234 | 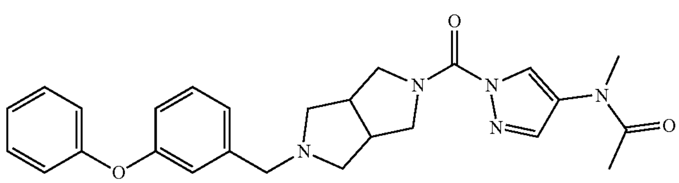 [SMILES: CC(=O)N(C)c1cnn(C(=O)N2CC3CN(Cc4cccc(Oc5ccccc5)c4)CC3C2)c1] | $^1$H NMR (300 MHz, Chloroform-d) δ 8.28 (s, 0.3H), 8.19 (s, 0.7H), 8.05 (s, 0.3H), 7.55 (s, 0.7H), 7.23-7.36 (m, 3H), 6.99-7.11 (m, 5H), 6.86-6.89 (m, 1H), 4.21 (br, 2H), 4.10 (br, 2H), 3.78 (s, 2H), 3.35 (s, 1H), 3.22 (s, 2H), 2.89 (br, 2H), 2.52-2.64 (m, 4H), 2.28 (s, 1H), 1.99 (s, 2H). | 460 |
| 235 | 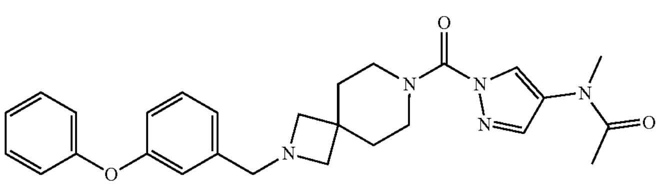 [SMILES: CC(=O)N(C)c1cnn(C(=O)N2CCC3(CC2)CN(Cc2cccc(Oc4ccccc4)c2)C3)c1] | $^1$H NMR (300 MHz, Chloroform-d) δ 8.18 (s, 0.3H), 8.03 (s, 0.7H), 7.98 (s, 0.3H), 7.55 (s, 0.7H), 7.24-7.36 (m, 3H), 7.10 (t, J = 7.5 Hz, 1H), 6.97-7.03 (m, 4H), 6.86-6.89 (m, 1H), 3.72 (br, 4H), 3.63 (s, 2H), 3.35 (s, 1H), 3.21 (s, 2H), 3.08 (s, 4H), 2.28 (s, 1H), 1.99 (s, 2H), 1.84-1.90 (m, 4H). | 474 |
| 236 | 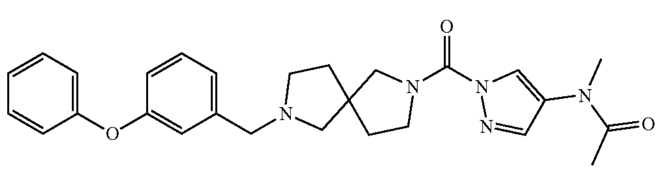 [SMILES: CC(=O)N(C)c1cnn(C(=O)N2CCC3(CCN(Cc4cccc(Oc5ccccc5)c4)C3)C2)c1] | $^1$H NMR (300 MHz, Chloroform-d) δ 8.25 (s, 0.3H), 8.14 (s, 0.7H), 8.02 (s, 0.3H), 7.58 (s, 0.7H), 7.21-7.52 (m, 2H), 6.97-7.03 (m, 1H), 6.96-7.10 (m, 5H), 6.84-6.87 (m, 1H), 3.83-4.02 (m, 2H), 3.58-3.71 (m, 4H), 3.32 (s, 1H), 3.18 (s, 2H), 2.51-2.65 (m, 4H), 2.25 (s, 1H), 1.96 (s, 2H), 1.56-1.92 (m, 4H). | 474 |
| 237 | 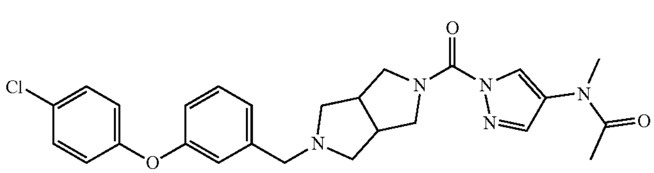 [SMILES: CC(=O)N(C)c1cnn(C(=O)N2CC3CN(Cc4cccc(Oc5ccc(Cl)cc5)c4)CC3C2)c1] | $^1$H NMR (400 MHz, Chloroform-d) δ 8.27 (s, 0.3H), 8.21-8.16 (m, 0.7H), 8.05 (s, 0.3H), 7.57-7.52 (m, 0.7H), 7.32-7.21 (m, 3H), 7.07 (d, J = 7.5 Hz, 1H), 7.01-6.94 (m, 1H), 6.97-6.88 (m, 2H), 6.86 (dd, J = 8.2, 2.9 Hz, 1H), 4.41-3.70 (m, 4H), 3.58 (s, 2H), 3.35 (s, 1H), 3.21 (s, 2H), 2.89 (s, 2H), 2.65-2.51 (m, 4H), 2.28 (s, 1H), 1.99 (s, 2H). | 494 |

TABLE 2-continued

| Ex. | Structure | NMR | MS [M + H]+ |
|---|---|---|---|
| 238 | 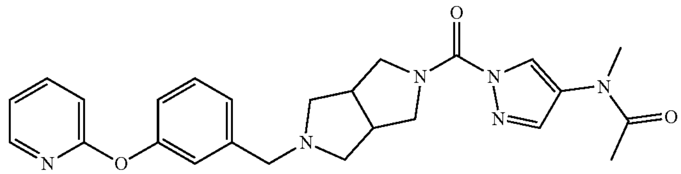 [SMILES: CC(=O)N(C)c1cnn(C(=O)N2CC3CN(Cc4cccc(Oc5ccccn5)c4)CC3C2)c1] | ¹H NMR (400 MHz, Chloroform-d) δ 8.29-8.24 (m, 0.3H), 8.21-8.14 (m, 1.7H), 8.03 (s, 0.3H), 7.72-7.62 (m, 1H), 7.55-7.50 (m, 0.7H), 7.31 (td, J = 7.9, 1.6 Hz, 1H), 7.16-7.05 (m, 2H), 7.04-6.92 (m, 2H), 6.88 (d, J = 8.4 Hz, 1H), 4.36-3.71 (m, 4H), 3.60 (s, 2H), 3.41-3.31 (m, 1H), 3.31-3.12 (m, 2H), 2.88 (s, 2H), 2.71-2.48 (m, 4H), 2.34-2.24 (m, 1H), 2.05-1.90 (m, 2H). | 460 |
| 239 | 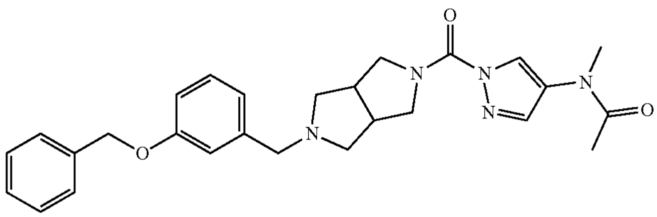 [SMILES: CC(=O)N(C)c1cnn(C(=O)N2CC3CN(Cc4cccc(OCc5ccccc5)c4)CC3C2)c1] | ¹H NMR (400 MHz, Chloroform-d) δ 8.27 (s, 0.33 H), 8.20-8.15 (m, 0.67H), 8.03 (s, 0.33 H), 7.55-7.49 (m, 0.67 H), 7.45-7.33 (m, 4H), 7.33-7.28 (m, 1H), 7.21 (t, J = 7.9 Hz, 1H), 7.00-6.94 (m, 1H), 6.93-6.83 (m, 2H), 5.10-4.97 (m, 2H), 4.34-3.63 (m, 4H), 3.60-3.55 (m, 2H), 3.31 (s, 1H), 3.19 (s, 2H), 2.88 (s, 2H), 2.71-2.45 (m, 4H), 2.26 (s, 1H), 1.97 (s, 2H). | 474 |
| 240 | 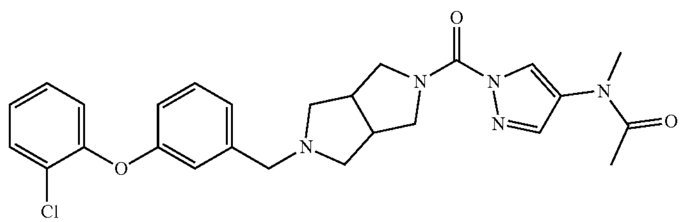 [SMILES: CC(=O)N(C)c1cnn(C(=O)N2CC3CN(Cc4cccc(Oc5ccccc5Cl)c4)CC3C2)c1] | ¹H NMR (400 MHz, Chloroform-d) δ 1H NMR (400 MHz, Chloroform-d) δ 8.28 (s, 0.3H), 8.18 (d, J = 1.0 Hz, 0.7H), 8.04 (s, 0.3H), 7.54 (d, J = 1.0 Hz, 0.7H), 7.47-7.39 (m, 1H), 7.29-7.15 (m, 2H), 7.10-7.00 (m, 2H), 7.00-6.88 (m, 2H), 6.81 (dt, J = 8.3, 1.5 Hz, 1H), 4.38-3.62 (m, 4H), 3.60-3.53 (m, 2H), 3.34 (s, 1H), 3.20 (s, 2H), 2.87 (s, 2H), 2.65-2.48 (m, 4H), 2.26 (s, 1H), 1.98 (s, 2H). | 494 |
| 241 | 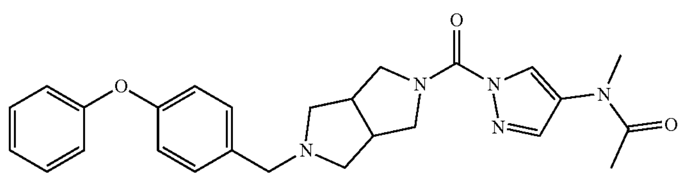 [SMILES: CC(=O)N(C)c1cnn(C(=O)N2CC3CN(Cc4ccc(Oc5ccccc5)cc4)CC3C2)c1] | ¹H NMR (400 MHz, Chloroform-d) δ 8.28 (s, 0.3H), 8.18 (d, J = 0.9 Hz, 0.7H), 8.03 (s, 0.3H), 7.54 (d, J = 1.0 Hz, 0.7H), 7.36-7.30 (m, 2H), 7.27-7.21 (m, 2H), 7.13-7.04 (m, 1H), 7.03-6.95 (m, 2H), 6.95-6.89 (m, 2H), 4.33-3.61 (m, 4H), 3.59-3.52 (m, 2H), 3.34 (s, 1H), 3.20 (s, 2H), 2.89 (s, 2H), 2.67-2.47 (m, 4H), 2.27 (s, 1H), 1.98 (s, 2H). | 460 |
| 242 | 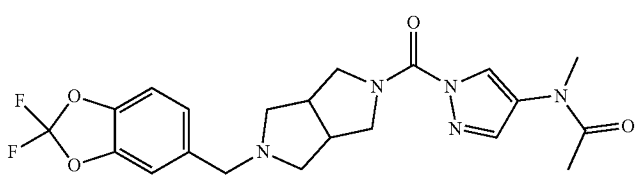 [SMILES: CC(=O)N(C)c1cnn(C(=O)N2CC3CN(Cc4ccc5c(c4)OC(F)(F)O5)CC3C2)c1] | ¹H NMR (400 MHz, Chloroform-d) δ 8.30 (s, 0H), 8.20 (s, 1H), 8.05 (s, 0H), 7.56 (s, 1H), 7.07 (s, 1H), 7.02-6.90 (m, 2H), 4.41-3.47 (m, 6H), 3.37 (s, 1H), 3.22 (s, 2H), 3.02-2.80 (m, 2H), 2.69-2.50 (m, 4H), 2.29 (s, 1H), 2.00 (s, 2H). | 448 |
| 243 | 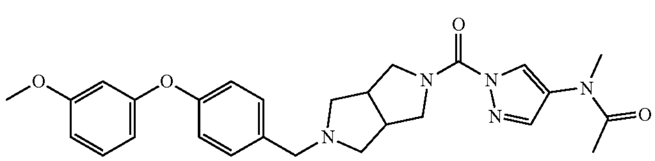 [SMILES: COc1cccc(Oc2ccc(CN3CC4CN(C(=O)n5cc(N(C)C(C)=O)cn5)CC4C3)cc2)c1] | ¹H NMR (400 MHz, Chloroform-d) δ 8.27 (s, 0H), 8.18 (s, 1H), 8.04 (s, 0H), 7.57-7.51 (m, 1H), 7.24-7.15 (m, 1H), 7.01-6.82 (m, 6H), 6.78 (dd, J = 8.3, 2.6 Hz, 1H), 4.36-3.59 (m, 7H), 3.58-3.51 (m, 2H), 3.33 (d, J = 1.6 Hz, 1H), 3.23-3.17 (m, 2H), 2.87 (s 2H), 2.65-2.47 (m, 4H), 2.29-2.24 (m, 1H), 2.01-1.95 (m, 2H). | 490 |
| 244 | 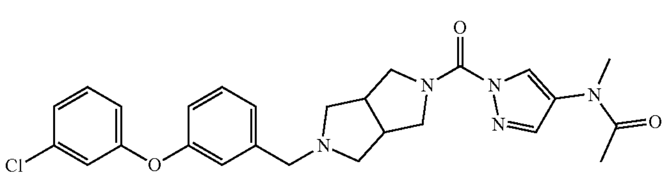 [SMILES: CC(=O)N(C)c1cnn(C(=O)N2CC3CN(Cc4cccc(Oc5cccc(Cl)c5)c4)CC3C2)c1] | ¹H NMR (400 MHz, Chloroform-d) δ 8.27 (s, 0.3H), 8.17 (s, 0.7H), 8.03 (s, 0.3H), 7.53 (s, 0.7H), 7.32-7.18 (m, 1H), 7.12-6.92 (m, 4H), 6.92-6.82 (m, 2H), 4.37-3.52 (m, 6H), 3.34 (s, 1H), 3.20 (s, 2H), 2.88 (s, 2H), 2.65-2.48 (m, 4H), 2.27 (s, 1H), 2.01-1.96 (m, 3H). | 494 |
| 245 | 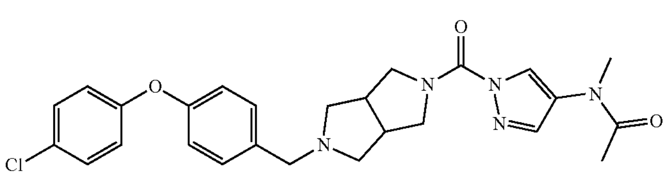 [SMILES: CC(=O)N(C)c1cnn(C(=O)N2CC3CN(Cc4ccc(Oc5ccc(Cl)cc5)cc4)CC3C2)c1] | ¹H NMR (400 MHz, Chloroform-d) δ 8.28 (s, 0.3H), 8.21-8.15 (m, 0.7H), 8.03 (s, 0.3H), 7.54 (s, 0.7H), 7.31-7.23 (m, 4H), 6.97-6.88 (m, 4H), 4.39-3.53 (m, 6H), 3.35 (s, 1H), 3.21 (s, 2H), 2.89 (s, 2H), 2.68-2.45 (m, 4H), 2.27 (s, 1H), 2.01-1.96 (m, 2H). | 494 |

TABLE 2-continued

| Ex. | Structure | NMR | MS [M + H]+ |
|---|---|---|---|
| 246 | 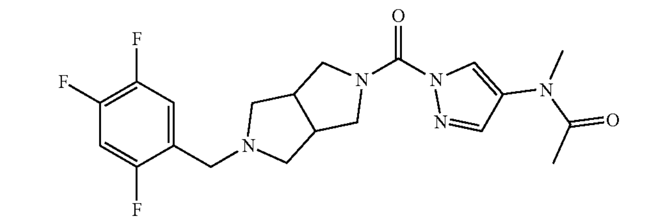 [SMILES: CC(=O)N(C)c1cnn(C(=O)N2CC3CN(Cc4cc(F)c(F)cc4F)CC3C2)c1] | ¹H NMR (400 MHz, Chloroform-d) δ 8.24-8.18 (m, 1H), 7.61-7.54 (m, 1H), 7.27 (s, 1H), 6.95-6.85 (m, 1H), 4.39-3.68 (m, 4H), 3.64 (s, 2H), 3.38 (s, 1H), 3.23 (s, 2H), 3.02-2.86 (m, 2H), 2.82-2.52 (m, 4H), 2.30 (s, 1H), 2.01 (s, 2H). | 422 |
| 247 | 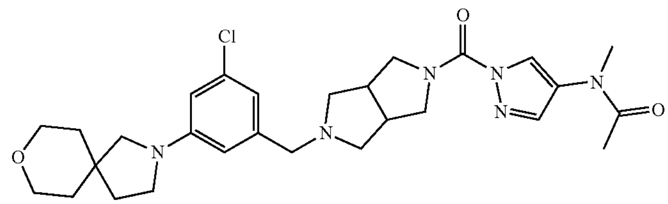 [SMILES: CC(=O)N(C)c1cnn(C(=O)N2CC3CN(Cc4cc(Cl)cc(N5CCC6(CCOCC6)C5)c4)CC3C2)c1] | ¹H NMR (400 MHz, Chloroform-d) δ 8.25-8.18 (m, 1H), 7.62-7.52 (m, 1H), 6.66-6.55 (m, 1H), 6.47-6.31 (m, 2H), 4.36-3.88 (m, 3H), 3.80-3.72 (m, 2H), 3.72-3.64 (m, 2H), 3.57-3.47 (m, 2H), 3.39-3.30 (m, 3H), 3.24-3.22 (m, 2H), 3.21-3.16 (m, 2H), 2.92 (s, 2H), 2.78-2.48 (m, 4H), 2.29 (s, 1H), 2.06-1.86 (m, 5H), 1.70-1.55 (m, 4H). | 542 |
| 248 | 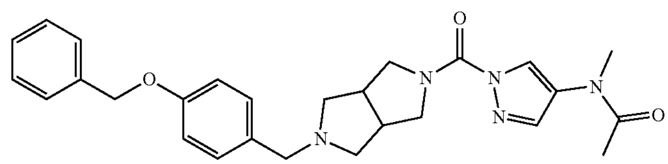 [SMILES: CC(=O)N(C)c1cnn(C(=O)N2CC3CN(Cc4ccc(OCc5ccccc5)cc4)CC3C2)c1] | ¹H NMR (400 MHz, Chloroform-d) δ 8.28 (s, 0.3H), 8.20-8.16 (m, 0.7H), 8.04 (s, 0.3H), 7.54 (s, 0.7H), 7.46-7.27 (m, 5H), 7.23-7.17 (m, 2H), 6.95-6.87 (m, 2H), 5.04 (s, 2H), 4.34-3.56 (m, 4H), 3.56-3.50 (m, 2H), 3.35 (s, 1H), 3.21 (s, 2H), 2.87 (br s, 2H), 2.65-2.56 (m, 2H), 2.56-2.44 (m, 2H), 2.28 (s, 1H), 1.99 (s, 2H). | 474 |
| 249 | 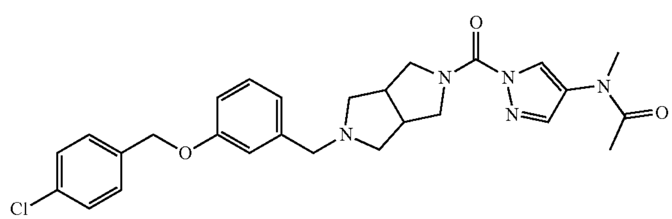 [SMILES: CC(=O)N(C)c1cnn(C(=O)N2CC3CN(Cc4cccc(OCc5ccc(Cl)cc5)c4)CC3C2)c1] | ¹H NMR (400 MHz, Chloroform-d) δ 8.27 (s, 0.3H), 8.20-8.14 (m, 0.6H), 8.02 (s, 0.3H), 7.55-7.50 (m, 0.6H), 7.40-7.30 (m, 4H), 7.25-7.16 (m, 1H), 6.97-6.79 (m, 3H), 5.04-4.97 (m, 2H), 4.34-3.60 (m, 4H), 3.60-3.54 (m, 2H), 3.34-3.27 (m, 1H), 3.22-3.17 (m, 2H), 2.88 (br s, 2H), 2.65-2.48 (m, 4H), 2.29-2.24 (m, 1H), 1.98 (s, 2H). | 508 |
| 250 | 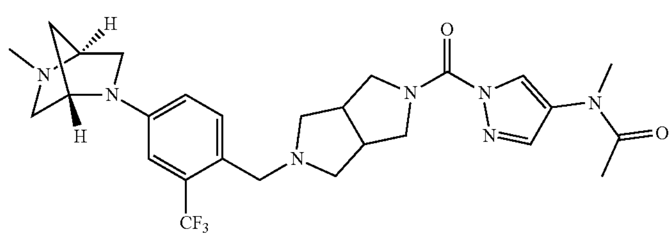 [SMILES: CC(=O)N(C)c1cnn(C(=O)N2CC3CN(Cc4ccc(N5C[C@@H]6C[C@H]5CN6C)cc4C(F)(F)F)CC3C2)c1] | 1H NMR (300 MHz, Chloroform-d) δ 8.30 (s, 0.3H), 8.19 (s, 0.7H), 8.04 (s, 0.3H), 7.55 (s, 0.7H), 7.42-7.48 (m, 1H), 6.73 (s, 1H), 6.62-6.65 (m, 1H), 3.54-4.39 (m, 8H), 3.31-3.42 (m, 3H), 3.22 (s, 2H), 2.88-2.98 (m, 3H), 2.55-2.69 (m, 5H), 2.41 (s, 3H), 2.28 (s, 1H), 2.00-2.04 (m, 3H), 1.89-1.92 (m, 1H). | 546 |
| 251 | 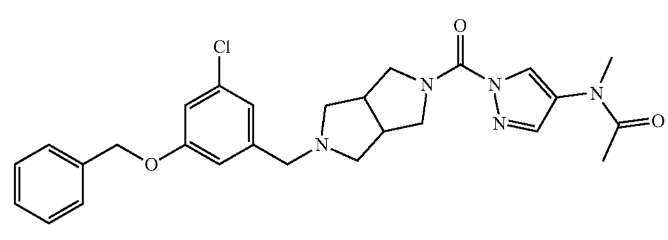 [SMILES: CC(=O)N(C)c1cnn(C(=O)N2CC3CN(Cc4cc(Cl)cc(OCc5ccccc5)c4)CC3C2)c1] | ¹H NMR (400 MHz, Chloroform-d) δ 8.27 (s, 0.3H), 8.17 (s, 0.7H), 8.04 (s, 0.3H), 7.52 (s, 0.7H), 7.43-7.28 (m, 5H), 6.92-6.81 (m, 3H), 5.04-4.99 (m, 2H), 4.36-3.57 (m, 4H), 3.54-3.48 (m, 2H), 3.30 (s, 1H), 3.19 (s, 2H), 2.87 (br s, 2H), 2.67-2.45 (m, 4H), 2.26 (s, 1H), 1.97 (s, 2H). | 508 |
| 252 | 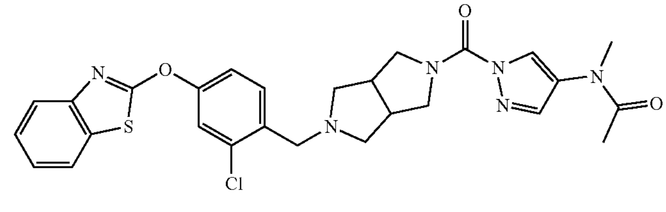 [SMILES: CC(=O)N(C)c1cnn(C(=O)N2CC3CN(Cc4ccc(Oc5nc6ccccc6s5)cc4Cl)CC3C2)c1] | ¹H NMR (400 MHz, Chloroform-d) δ 8.31 (s, 0.3H), 8.21 (s, 0.7H), 8.07 (s, 0.3H), 7.76 (d, J = 8.4 Hz, 1H), 7.71 (d, J = 8.0 Hz, 1H), 7.54-7.58 (m, 1.7H), 7.40-7.44 (m, 2H), 7.28-7.33 (m, 2H), 3.94-4.30 (m, 3H), 3.77 (br, 3H), 3.36 (s, 1H), 3.23 (s, 2H), 2.95 (br, 2H), 2.72 (br, 4H), 2.29 (s, 1H), 2.02 (s, 2H). | 551 |

TABLE 2-continued

| Ex. | Structure | NMR | MS [M + H]+ |
|---|---|---|---|
| 253 | 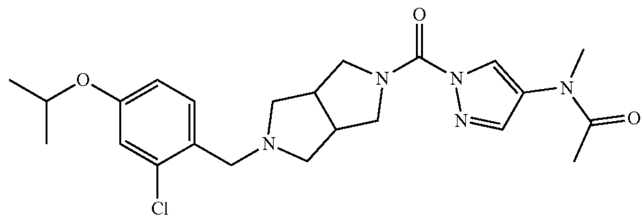 [SMILES: CC(=O)N(C)c1cnn(C(=O)N2CC3CN(Cc4ccc(OC(C)C)cc4Cl)CC3C2)c1] | ¹H NMR (300 MHz, Chloroform-d) δ 8.28 (s, 0.3H), 8.18 (s, 0.7H), 8.04 (s, 0.3H), 7.55 (s, 0.7H), 7.29 (s, 1H), 7.76 (d, J = 8.4 Hz, 1H), 6.73-6.76 (m, 1H), 4.46-4.54 (m, 1H), 3.97-4.27 (m, 2H), 3.66-3.94 (m, 4H), 3.36 (s, 1H), 3.22 (s, 2H), 2.85 (br, 2H), 2.60-2.63 (m, 4H), 2.28 (s, 1H), 1.99 (s, 2H), 1.33 (d, J = 6.0 Hz, 6H). | 460 |
| 254 | 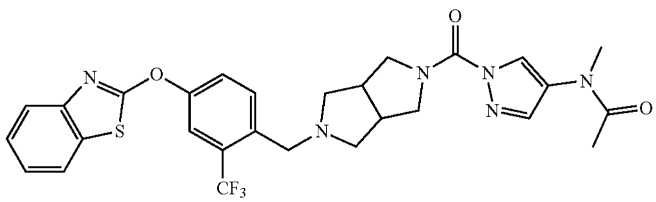 [SMILES: CC(=O)N(C)c1cnn(C(=O)N2CC3CN(Cc4ccc(Oc5nc6ccccc6s5)cc4C(F)(F)F)CC3C2)c1] | ¹H NMR (300 MHz, Chloroform-d) δ 8.30 (s, 0.3H), 8.20 (s, 0.7H), 8.05 (s, 0.4H), 7.82-7.85 (m, 1H), 7.75 (s, 0.6H), 7.72 (s, 1H), 7.56-7.70 (m, 3H), 7.39-7.44 (m, 1H), 7.28-7.33 (m, 1H), 3.98-4.30 (m, 3H), 3.80 (br, 3H), 3.35 (s, 1H), 3.21 (s, 2H), 2.94 (br, 2H), 2.64-2.71 (m, 4H), 2.26 (s, 1H), 1.99 (s, 2H). | 585 |
| 255 | 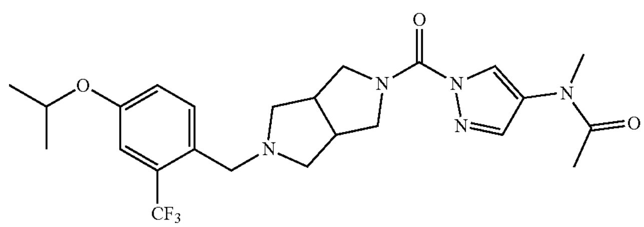 [SMILES: CC(=O)N(C)c1cnn(C(=O)N2CC3CN(Cc4ccc(OC(C)C)cc4C(F)(F)F)CC3C2)c1] | ¹H NMR (300 MHz, Chloroform-d) δ 8.30 (s, 0.3H), 8.20 (s, 0.7H), 8.05 (s, 0.3H), 7.5-7.61 (m, 1.7H), 7.11 (s, 1H), 6.97-7.00 (m, 1H), 4.52-4.60 (m, 1H), 4.0-4.30 (m, 2H), 3.68-3.81 (m, 4H), 3.36 (s, 1H), 3.22 (s, 2H), 2.90 (br, 2H), 2.54-2.67 (m, 4H), 2.29 (s, 1H), 2.00 (s, 2H), 1.36 (d, J = 6.0 Hz, 6H). | 494 |
| 256 | 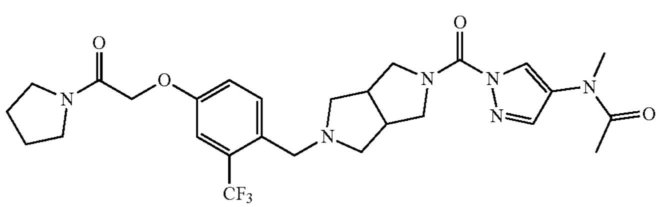 [SMILES: CC(=O)N(C)c1cnn(C(=O)N2CC3CN(Cc4ccc(OCC(=O)N5CCCC5)cc4C(F)(F)F)CC3C2)c1] | ¹H NMR (300 MHz, Chloroform-d) δ 8.31 (s, 0.3H), 8.20 (s, 0.7H), 8.04 (s, 0.3H), 7.59-7.64 (m, 1H), 7.56 (s, 0.7H), 7.18-7.19 (m, 1H), 7.05-7.09 (m, 1H), 4.64 (s, 2H), 4.09-4.22 (m, 2H), 3.69-4.03 (m, 4H), 3.50-3.60 (m, 4H), 3.37 (s, 1H), 3.22 (s, 2H), 2.90-2.99 (m, 2H), 2.64-2.67 (m, 2H), 2.54-2.59 (m, 2H), 2.29 (s, 1H), 1.96-2.05 (m, 4H), 1.88-1.93 (m, 2H). | 563 |
| 257 | 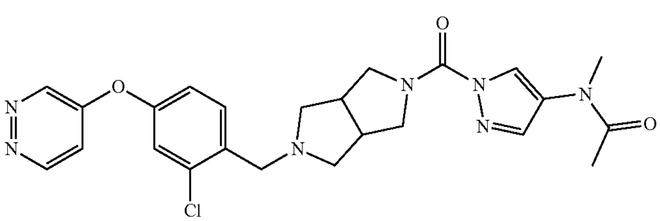 | ¹H NMR (300 MHz, Chloroform-d) δ 8.34 (s, 0.3H), 8.18-8.26 (m, 1.7H), 8.01-8.03 (m, 1.4H), 7.61-7.63 (m, 2H), 7.57 (s, 0.6H), 7.42-7.45 (m, 1H), 6.60-6.64 (m, 1H), 3.76-4.32 (m, 6H), 3.37 (s, 1H), 3.22 (s, 2H), 2.94 (br, 2H), 2.71 (br, 4H), 2.29 (s, 1H), 2.00 (s, 2H). | 496 |
| 258 | 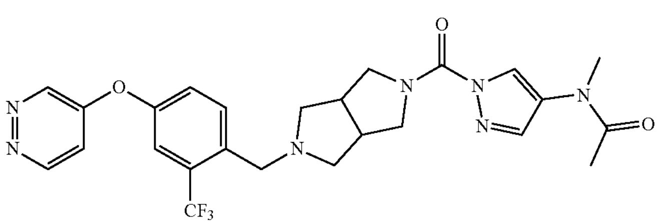 [SMILES: CC(=O)N(C)c1cnn(C(=O)N2CC3CN(Cc4ccc(Oc5ccnnc5)cc4C(F)(F)F)CC3C2)c1] | ¹H NMR (300 MHz, Chloroform-d) δ 8.34-8.39 (m, 1H), 8.24-8.29 (m, 0.6H), 8.21 (s, 0.4H), 8.04 (s, 1H), 7.99 (s, 0.4H), 7.78-7.96 (m, 2H), 7.68-7.74 (m, 1H), 7.57 (s, 0.6H), 6.63-6.66 (m, 1H), 3.52-4.83 (m, 6H), 3.38 (s, 1H), 3.22 (s, 2H), 2.93 (br, 2H), 2.61-2.73 (m, 4H), 2.29 (s, 1H), 2.00 (s, 2H). | 530 |
| 259 | 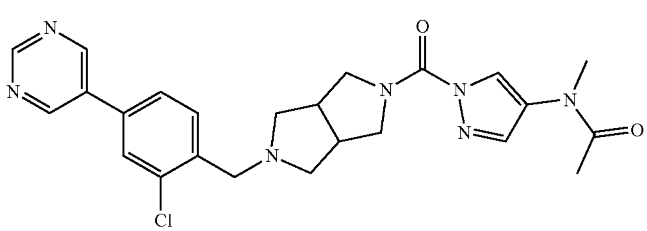 [SMILES: CC(=O)N(C)c1cnn(C(=O)N2CC3CN(Cc4ccc(-c5cncnc5)cc4Cl)CC3C2)c1] | ¹H NMR (400 MHz, Chloroform-d) δ 9.23 (s, 1H), 8.94 (s, 2H), 8.31 (s, 0.3H), 8.20 (s, 0.7H), 8.03 (s, 0.3H), 7.56-7.63 (m, 2.7H), 7.45-7.46 (m, 1H), 4.00 (br, 4H), 3.82 (s, 2H), 3.36 (s, 1H), 3.22 (s, 2H), 2.94 (br, 2H), 2.72 (br, 4H), 2.29 (s, 1H), 2.00 (s, 2H). | 480 |

TABLE 2-continued

| Ex. | Structure | NMR | MS [M + H]+ |
|---|---|---|---|
| 260 | 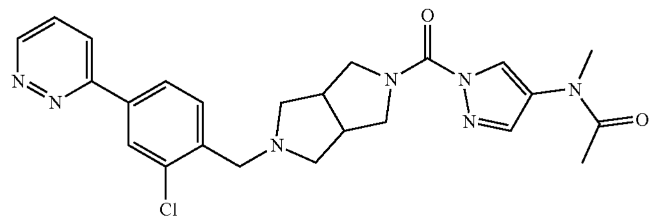 [SMILES: CC(=O)N(C)c1cnn(C(=O)N2CC3CN(Cc4ccc(-c5cccnn5)cc4Cl)CC3C2)c1] | ¹H NMR (400 MHz, Chloroform-d) δ 9.18 (s, 1H), 8.31 (s, 0.3H), 8.20 (s, 0.7H), 8.13 (s, 1H), 7.93 (s, 0.3H), 7.92 (d, J = 16 Hz, 1H), 7.85 (d, J = 14 Hz, 1H), 7.57-7.64 (m, 2.7H), 4.00 (br, 4H), 3.82 (s, 2H), 3.37 (s, 1H), 3.22 (s, 2H), 2.94 (br, 2H), 2.72 (br, 4H), 2.28 (s, 1H), 2.00 (s, 2H). | 480 |
| 261 | 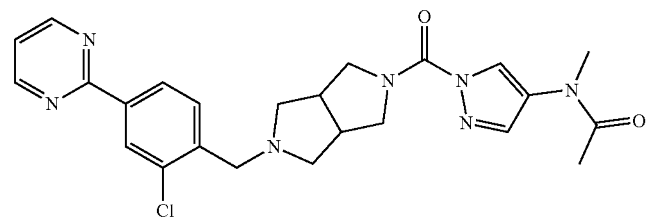 [SMILES: CC(=O)N(C)c1cnn(C(=O)N2CC3CN(Cc4ccc(-c5ncccn5)cc4Cl)CC3C2)c1] | ¹H NMR (400 MHz, Chloroform-d) δ 8.80 (d, J = 4.8 Hz, 2H), 8.44 (s, 1H), 8.29-8.30 (m, 1.3H), 8.20 (s, 0.7H), 8.06 (s, 0.3H), 7.55-7.59 (m, 1.7H), 7.21-7.23 (m, 1H), 4.02 (br, 6H), 3.37 (s, 1H), 3.22 (s, 2H), 2.93 (br, 2H), 2.71 (br, 4H), 2.28 (s, 1H), 2.00 (s, 2H). | 480 |
| 262 | 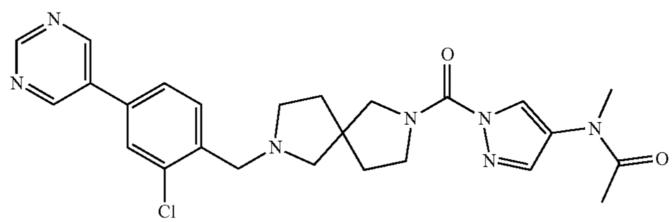 [SMILES: CC(=O)N(C)c1cnn(C(=O)N2CCC3(CCN(Cc4ccc(-c5cncnc5)cc4Cl)C3)C2)c1] | ¹H NMR (300 MHz, Chloroform-d) δ 9.22 (s, 1H), 8.94 (s, 2H), 8.28 (s, 0.3H), 8.20 (s, 0.7H), 8.05 (s, 0.3H), 7.64 (br, 1H), 7.58 (br, 1.7H), 7.40-7.50 (m, 1H), 3.90-4.15 (m, 2H), 3.55-3.85 (m, 4H), 3.36 (s, 1H), 3.21 (s, 2H), 2.50-2.90 (m, 4H), 2.28 (s, 1H), 1.80-2.10 (m, 6H). | 494 |
| 263 | 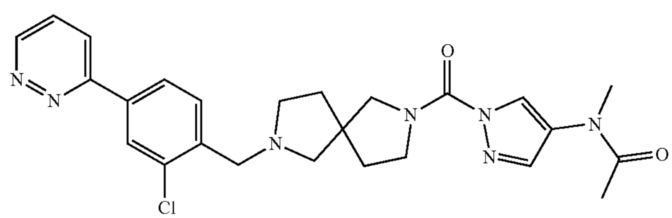 [SMILES: CC(=O)N(C)c1cnn(C(=O)N2CCC3(CCN(Cc4ccc(-c5cccnn5)cc4Cl)C3)C2)c1] | ¹H NMR (300 MHz, Chloroform-d) δ 9.18 (d, J = 6.0 Hz, 1H), 8.29 (s, 0.3H), 8.20 (s, 0.7H), 8.12 (br, 1H), 8.05 (br, 0.3H), 7.90-8.00 (m, 1H), 7.85 (d, J = 6.0 Hz, 1H), 7.65 (br, 1H), 7.50-7.60 (m, 1.7H), 3.55-4.16 (m, 6H), 3.36 (s, 1H), 3.21 (s, 2H), 2.53-2.90 (m, 4H), 2.28 (s, 1H), 1.80-2.10 (m, 6H). | 494 |
| 264 | 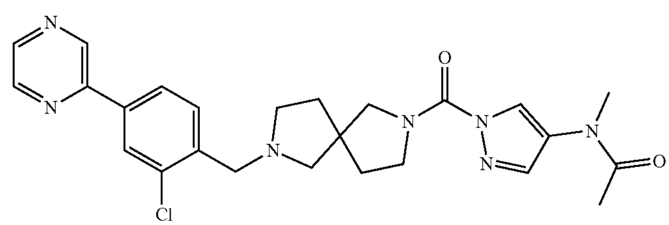 [SMILES: CC(=O)N(C)c1cnn(C(=O)N2CCC3(CCN(Cc4ccc(-c5cnccn5)cc4Cl)C3)C2)c1] | ¹H NMR (300 MHz, Chloroform-d) δ 9.02 (br, 1H), 8.64 (br, 1H), 8.50-8.58 (m, 1H), 8.28 (s, 0.3H), 8.20 (s, 0.7H), 8.05 (br, 1.3H), 7.80-7.92 (m, 1H), 7.50-7.70 (m, 1.7H), 3.91-4.18 (m, 2H), 3.58-3.89 (m, 4H), 3.36 (s, 1H), 3.21 (s, 2H), 2.50-2.90 (m, 4H), 2.28 (s, 1H), 1.85-2.10 (m, 6H). | 494 |
| 265 | 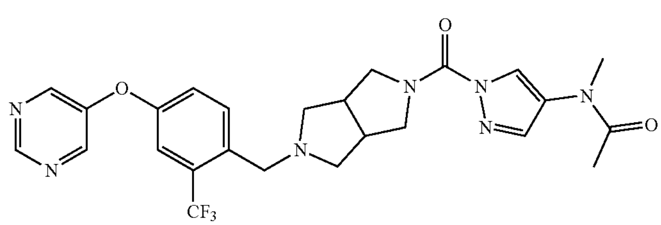 [SMILES: CC(=O)N(C)c1cnn(C(=O)N2CC3CN(Cc4ccc(Oc5cncnc5)cc4C(F)(F)F)CC3C2)c1] | ¹H NMR (400 MHz, Chloroform-d) δ 9.04 (s, 1H), 8.52 (s, 2H), 8.31 (s, 0.4H), 8.21 (s, 0.6H), 8.05 (s, 0.4H), 7.79-7.81 (m, 1H), 7.57 (s, 0.6H), 7.33-7.34 (m, 1H), 7.19-7.21 (m, 1H), 3.52-4.41 (m, 6H), 3.37 (s, 1H), 3.23 (s, 2H), 2.94 (br, 2H), 2.70-2.74 (m, 2H), 2.68 (br, 2H), 2.29 (s, 1H), 2.00 (s, 2H). | 530 |
| 266 | 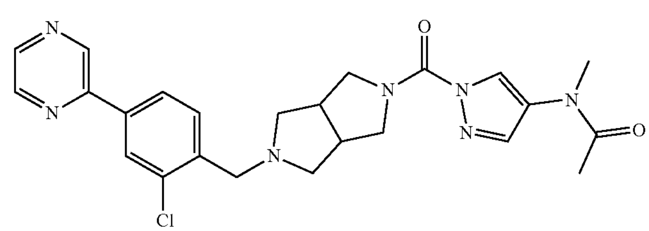 [SMILES: CC(=O)N(C)c1cnn(C(=O)N2CC3CN(Cc4ccc(-c5cnccn5)cc4Cl)CC3C2)c1] | ¹H NMR (400 MHz, Chloroform-d) δ 9.02 (s, 1H), 8.64 (s, 1H), 8.54 (s, 1H), 8.31 (s, 0.3H), 8.20 (s, 0.7H), 8.04 (s, 1.3H), 7.87 (d, J = 7.6 Hz, 1H), 7.61 (d, J = 8.0 Hz, 1H), 7.56 (s, 0.7H), 3.97 (br, 6H), 3.36 (s, 1H), 3.22 (s, 2H), 2.94 (br, 2H), 2.71 (br, 4H), 2.29 (s, 1H), 2.00 (s, 2H). | 480 |

TABLE 2-continued

| Ex. | Structure | NMR | MS [M + H]+ |
|---|---|---|---|
| 267 | 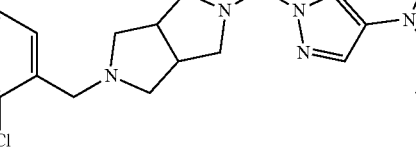 | ¹H NMR (400 MHz, Chloroform-d) δ 8.29 (s, 0.3H), 8.19 (s, 0.7H), 8.05 (s, 0.3H), 7.98 (s, 1H), 7.92 (s, 1H), 7.87 (d, J = 3.2 Hz, 1H), 7.52-7.55 (m, 1.7H), 7.36 (s, 1H), 4.04 (br, 6H), 3.39 (s, 1H), 3.22 (s, 2H), 2.94 (br, 2H), 2.70 (br, 4H), 2.28 (s, 1H), 2.00 (s, 2H). | 485 |
| 268 | 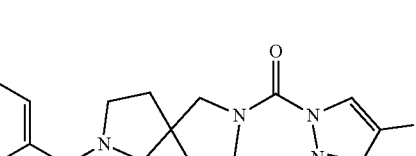 | ¹H NMR (300 MHz, Chloroform-d) δ 8.80 (d, J = 6.0 Hz, 2H), 8.44 (br, 1H), 8.29 (br, 1.3H), 8.19 (s, 0.7H), 8.05 (s, 0.3H), 7.50-7.65 (m, 1.7H), 7.18-7.24 (m, 1H), 3.85-4.18 (m, 2H), 3.55-3.84 (m, 4H), 3.35 (s, 1H), 3.22 (s, 2H), 2.55-2.85 (m, 4H), 2.28 (s, 1H), 1.85-2.10 (m, 6H). | 494 |
| 269 | 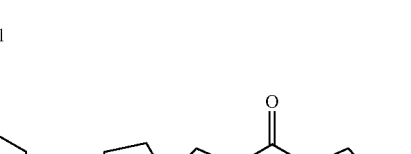 | ¹H NMR (300 MHz, Chloroform-d) δ 8.30 (s, 0.3H), 8.20 (s, 0.7H), 8.05 (s, 0.3H), 8.00 (s, 1H), 7.86-7.92 (m, 1H), 7.76-7.85 (m, 1H), 7.50-7.62 (m, 1.7H), 7.32-7.40 (m, 1H), 3.86-4.20 (m, 2H), 3.55-3.84 (m, 4H), 3.35 (s, 1H), 3.22 (s, 2H), 2.63-2.88 (m, 3H), 2.50-2.60 (m, 1H), 2.28 (s, 1H), 1.80-2.10 (m, 6H). | 499 |
| 270 | 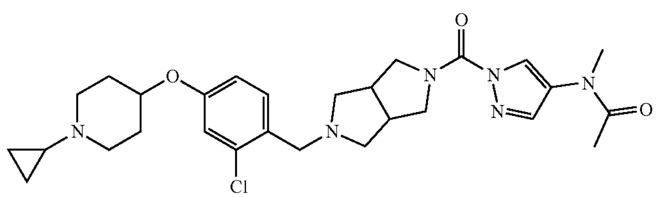 [SMILES: CC(=O)N(C)c1cnn(C(=O)N2CC3CN(Cc4ccc(OC5CCN(C6CC6)CC5)cc4Cl)CC3C2)c1] | ¹H NMR (300 MHz, Chloroform-d) δ 8.28 (s, 0.3H), 8.19 (s, 0.7H), 8.04 (s, 0.3H), 7.55 (s, 0.7H), 7.30 (s, 1H), 6.90 (s, 1H), 6.76-6.79 (m, 1H), 3.97-4.38 (m, 3H), 3.58-3.94 (m, 4H), 3.36 (s, 1H), 3.22 (s, 2H), 2.89 (br, 4H), 2.60-2.68 (m, 4H), 2.46-2.57 (m, 2H), 2.28 (s, 1H), 1.92-2.00 (m, 4H), 1.75-1.82 (m, 2H), 1.60-1.67 (m, 1H), 0.43-0.50 (m, 4H). | 541 |
| 271 | 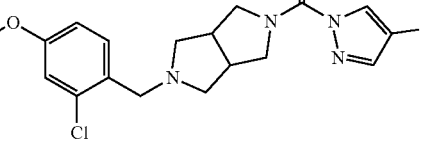 | ¹H NMR (300 MHz, Chloroform-d) δ 8.30 (s, 0.3H), 8.20 (s, 0.7H), 8.04 (s, 0.3H), 7.55-7.60 (m, 1.7H), 7.14 (s, 1H), 7.00-7.03 (m, 1H), 4.03-4.35 (m, 3H), 3.64-3.98 (m, 4H), 3.36 (s, 1H), 3.22 (s, 2H), 2.89 (br, 4H), 2.47-2.67 (m, 6H), 2.29 (s, 1H), 1.93-2.00 (m, 4H), 1.79-1.83 (m, 2H), 1.61 (br, 1H), 0.38-0.51 (m, 4H). | 575 |
| 272 | 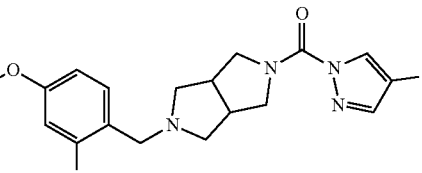 | ¹H NMR (400 MHz, Chloroform-d) δ 9.27 (s, 1H), 8.79 (d, J = 5.6 Hz, 1H), 8.31 (s, 0.3H), 8.20 (s, 0.7H), 8.12 (s, 1H), 8.07 (s, 0.3H), 7.94 (d, J = 8.0 Hz, 1H), 7.69-7.72 (m, 1H), 7.63 (d, J = 7.6 Hz, 1H), 7.53 (s, 0.7H), 4.03 (br, 6H), 3.37 (s, 1H), 3.22 (s, 2H), 2.97 (br, 2H), 2.71 (br, 4H), 2.29 (s, 1H), 2.00 (s, 2H). | 480 |
| 273 | 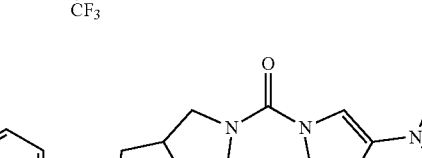 | ¹H NMR (400 MHz, Chloroform-d) δ 9.30 (s, 1H), 8.79 (d, J = 8.0 Hz, 1H), 8.29 (s, 0.3H), 8.20 (s, 0.7H), 8.12 (br, 1H), 8.06 (br, 0.3H), 7.90-8.00 (m, 1H), 7.70-7.80 (m, 1H), 7.50-7.69 (m, 1.7H), 3.60-4.18 (m, 6H), 3.36 (s, 1H), 3.22 (s, 2H), 2.50-2.90 (m, 4H), 2.28 (s, 1H), 1.85-2.10 (m, 6H). | 494 |

TABLE 2-continued

| Ex. | Structure | NMR | MS [M + H]+ |
|---|---|---|---|
| 274 | 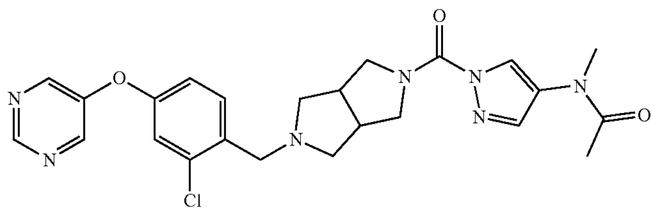 [SMILES: CC(=O)N(C)c1cnn(C(=O)N2CC3CN(Cc4ccc(Oc5cncnc5)cc4Cl)CC3C2)c1] | ¹H NMR (300 MHz, Chloroform-d) δ 9.02 (s, 1H), 8.51 (s, 2H), 8.29 (s, 0.3H), 8.19 (s, 0.7H), 8.04 (s, 0.3H), 7.61 (s, 0.7H), 7.50 (br, 1H), 7.07 (s, 1H), 6.92-6.97 (m, 1H), 3.74-4.70 (m, 6H), 3.36 (s, 1H), 3.21 (s, 2H), 2.96 (br, 2H), 2.69 (br, 4H), 2.28 (s, 1H), 1.99 (s, 2H). | 496 |
| 275 | 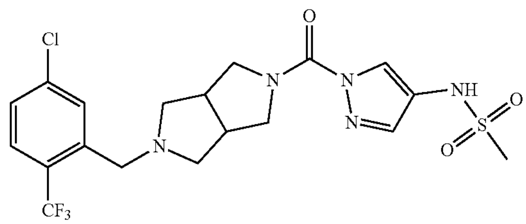 [SMILES: CS(=O)(=O)Nc1cnn(C(=O)N2CC3CN(Cc4cc(Cl)ccc4C(F)(F)F)CC3C2)c1] | . ¹H NMR (300 MHz, Chloroform-d) δ 8.09 (s, 1H), 7.77 (br, 1H), 7.64 (s, 1H), 7.55 (d, J = 8.4 Hz, 1H), 7.26-7.32 (m, 1H), 6.41 (br, 1H), 3.67-3.84 (m, 6H), 3.01 (s, 3H), 2.68 (m, 2H), 2.50 (br, 2H), 1.63-1.74 (m, 6H). | 492 |
| 276 | 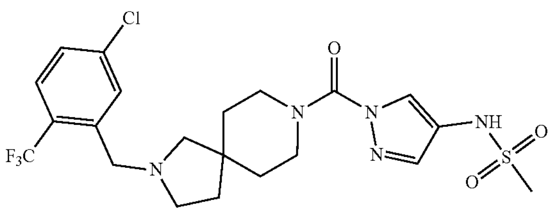 [SMILES: CS(=O)(=O)Nc1cnn(C(=O)N2CCC3(CCN(Cc4cc(Cl)ccc4C(F)(F)F)C3)CC2)c1] | ¹H NMR (300 MHz, Chloroform-d) δ 8.09 (s, 1H), 7.77 (br, 1H), 7.64 (s, 1H), 7.55 (d, J = 8.4 Hz, 1H), 7.26-7.32 (m, 1H), 6.41 (br, 1H), 3.67-3.84 (m, 6H), 3.01 (s, 3H), 2.68 (m, 2H), 2.50 (br, 2H), 1.63-1.74 (m, 6H). | 520 |
| 277 | 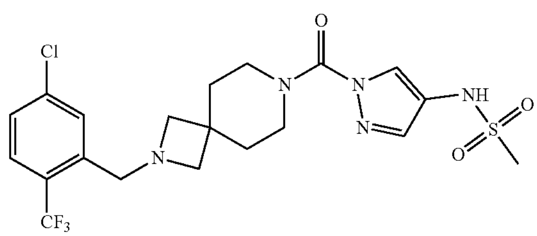 [SMILES: CS(=O)(=O)Nc1cnn(C(=O)N2CCC3(CC2)CN(Cc2cc(Cl)ccc2C(F)(F)F)C3)c1] | ¹H NMR (300 MHz, Chloroform-d) δ 8.09 (s, 1H), 7.69 (br, 1H), 7.64 (s, 1H), 7.54 (d, J = 8.5 Hz, 1H), 7.26-7.32 (m, 1H), 6.30 (br, 1H), 3.74-3.82 (m, 6H), 3.16 (br, 4H), 3.01 (s, 3H), 1.93 (t, J = 5.3 Hz, 4H). | 506 |
| 278 | 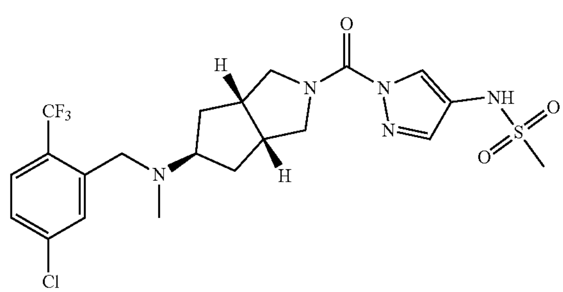 [SMILES: CN(Cc1cc(Cl)ccc1C(F)(F)F)[C@H]1C[C@@H]2CN(C(=O)n3cc(NS(C)(=O)=O)cn3)C[C@@H]2C1] | . ¹H NMR (300 MHz, Chloroform-d) δ 8.34 (s, 1H), 7.54 (s, 1H), 7.56 (s, 1H), 7.54 (d, J = 8.4 Hz, 1H), 7.28-7.30 (m, 1H), 6.34 (s, 1H), 3.63-4.11 (m, 6H), 3.13-3.23 (m, 1H), 3.01 (s, 3H), 2.87 (br, 2H), 2.14 (s, 3H), 1.85-1.90 (m, 4H). | 520 |
| 279 | 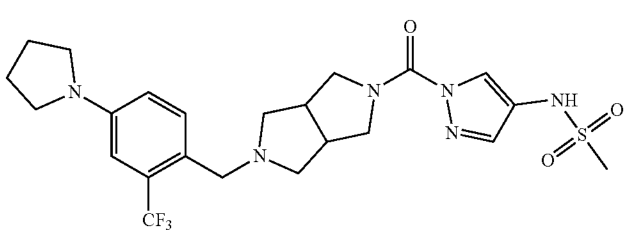 [SMILES: CS(=O)(=O)Nc1cnn(C(=O)N2CC3CN(Cc4ccc(N5CCCC5)cc4C(F)(F)F)CC3C2)c1] | . ¹H NMR (300 MHz, Chloroform-d) δ 8.23 (s, 1H), 7.64 (s, 1H), 7.45 (d, J = 7.7 Hz, 1H), 6.73 (s, 1H), 6.64-6.66 (m, 1H), 4.13 (br, 2H), 3.65 (br, 4H), 3.27-3.31 (m, 4H), 3.00 (s, 3H), 2.88 (br, 2H), 2.55-2.64 (m, 4H), 1.98-2.06 (m, 4H). | 527 |

TABLE 2-continued

| Ex. | Structure | NMR | MS [M + H]+ |
|---|---|---|---|
| 280 | 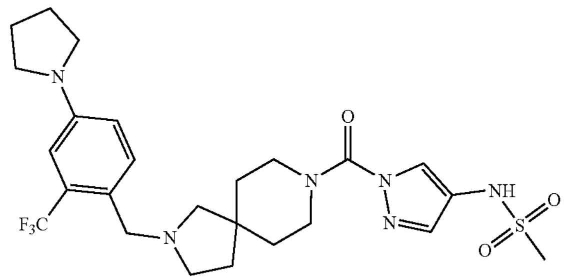 [SMILES: CS(=O)(=O)Nc1cnn(C(=O)N2CCC3(CCN(Cc4ccc(N5CCCC5)cc4C(F)(F)F)C3)CC2)c1] | ¹H NMR (300 MHz, Chloroform-d) δ 8.08 (s, 1H), 7.62 (s, 1H), 7.51 (br, 1H), 6.75 (s, 1H), 6.68 (br, 1H), 3.63 (br, 6H), 3.23-3.32 (m, 4H), 3.00 (s, 3H), 2.71 (br, 2H), 2.44 (br, 2H), 1.83-2.05 (m, 6H), 1.72 (br, 4H). | 555 |
| 281 | 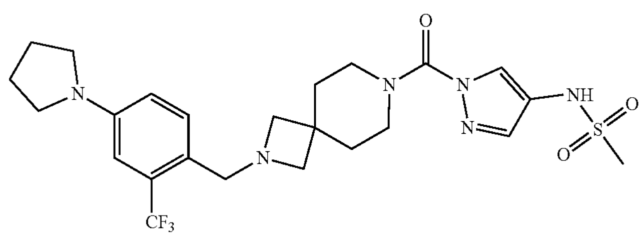 [SMILES: CS(=O)(=O)Nc1cnn(C(=O)N2CCC3(CC2)CN(Cc2ccc(N4CCCC4)cc2C(F)(F)F)C3)c1] | . ¹H NMR (300 MHz, Chloroform-d) δ 8.07 (s, 1H), 7.62 (s, 1H), 7.43 (d, J = 8.5 Hz, 1H), 6.77 (s, 1H), 6.66-6.68 (m, 1H), 3.70-3.75 (m, 6H), 3.22-3.31 (m, 4H), 3.12 (s, 4H), 2.99 (s, 3H), 1.98-2.07 (m, 4H), 1.87-1.91 (m, 4H). | 541 |
| 282 | 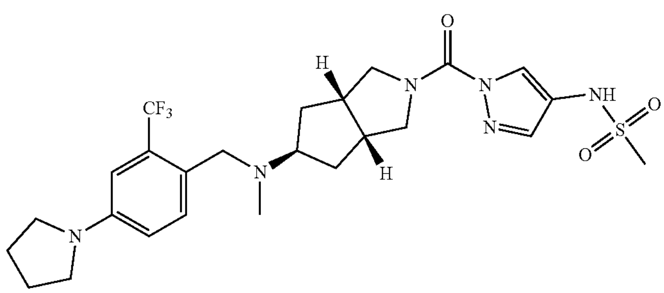 [SMILES: CN(Cc1ccc(N2CCCC2)cc1C(F)(F)F)[C@H]1C[C@@H]2CN(C(=O)n3cc(NS(C)(=O)=O)cn3)C[C@@H]2C1] | ¹H NMR (300 MHz, Chloroform-d) δ 8.24 (s, 1H), 7.65 (s, 1H), 7.52 (br, 1H), 6.74-6.75 (m, 1H), 6.66 (d, J = 8.8 Hz, 1H), 4.04 (br, 2H), 3.67 (br, 2H), 3.53 (br, 2H), 3.31-3.32 (m, 4H), 3.13 (br, 1H), 3.00 (s, 3H), 2.87 (br, 2H), 2.10 (br, 3H), 2.00-2.04 (m, 4H), 1.86 (br, 4H). | 555 |
| 283 | 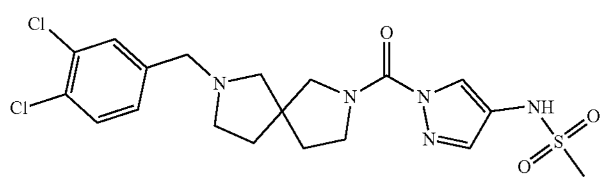 [SMILES: CS(=O)(=O)Nc1cnn(C(=O)N2CCC3(CCN(Cc4ccc(Cl)c(Cl)c4)C3)C2)c1] | ¹H NMR (300 MHz, Chloroform-d) δ 8.23 (s, 1H), 7.63-7.65 (m, 1H), 7.36-7.42 (m, 2H), 7.16 (br, 1H), 6.42 (br, 1H), 3.85-4.05 (m, 2H), 3.57-3.77 (m, 4H), 3.00 (s, 3H), 2.45-2.70 (m, 4H), 1.70-2.01 (m, 4H). | 472 |
| 284 | 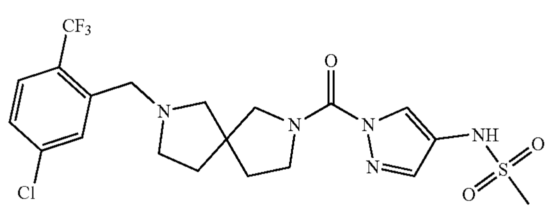 [SMILES: CS(=O)(=O)Nc1cnn(C(=O)N2CCC3(CCN(Cc4cc(Cl)ccc4C(F)(F)F)C3)C2)c1] | ¹H NMR (300 MHz, Chloroform-d) δ 8.25 (s, 1H), 7.75-7.78 (m, 1H), 7.61-7.67 (m, 1H), 7.53-7.56 (m, 1H), 7.29-7.31 (m, 1H), 5.87-6.09 (m, 1H), 3.85-4.04 (m, 2H), 3.58-3.75 (m, 4H), 3.00 (s, 3H), 2.48-2.72 (m, 4H), 1.78-2.01 (m, 4H). | 506 |
| 285 | 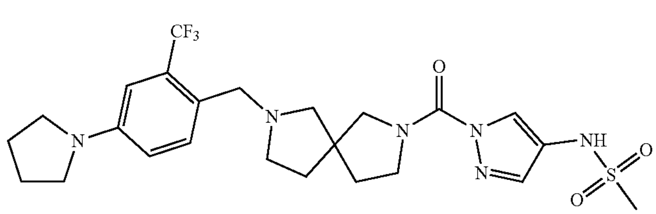 [SMILES: CS(=O)(=O)Nc1cnn(C(=O)N2CCC3(CCN(Cc4ccc(N5CCCC5)cc4C(F)(F)F)C3)C2)c1] | ¹H NMR: (400 MHz, Chloroform-d) δ 8.22 (s, 1H), 7.63-7.65 (d, J = 11.7 Hz, 2H), 7.44-7.51 (m, 1H), 6.74 (d, J = 1.8 Hz, 1H), 6.63-6.66 (s, 1H), 3.81-4.07 (m, 2H), 3.54-3.78 (m, 4H), 3.22-3.34 (m, 4H), 2.92-3.05 (d, J = 4.5 Hz, 3H), 2.39-2.77 (m, 4 H), 1.80-2.05 (m, 8H). | 541 |

TABLE 2-continued

| Ex. | Structure | NMR | MS [M + H]+ |
|---|---|---|---|
| 286 | 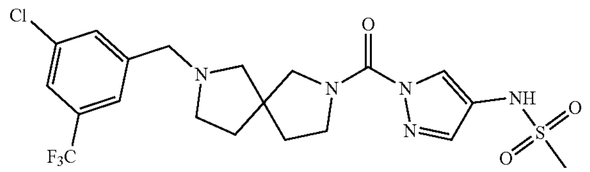 [SMILES: CS(=O)(=O)Nc1cnn(C(=O)N2CCC3(CCN(Cc4cc(Cl)cc(C(F)(F)F)c4)C3)C2)c1] | ¹H NMR (300 MHz, Chloroform-d) δ 8.24 (s, 1H), 7.61-7.66 (m, 1H), 7.47-7.49 (m, 3H), 6.19 (br, 1H), 3.85-4.04 (m, 2H), 3.63-3.76 (m, 4H), 3.00 (s, 3H), 2.43-2.77 (m, 4H), 1.70-2.05 (m, 4H). | 506 |
| 287 | 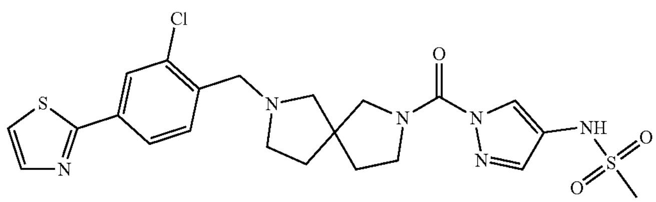 [SMILES: CS(=O)(=O)Nc1cnn(C(=O)N2CCC3(CCN(Cc4ccc(-c5nccs5)cc4Cl)C3)C2)c1] | ¹H NMR (300 MHz, Chloroform-d) δ 8.10-8.23 (m, 1H), 7.50-7.99 (m, 5H), 7.37-7.38 (m, 1H), 6.37-7.10 (m, 1H), 3.58-4.00 (m, 6H), 2.91-3.00 (m, 3H), 2.37-2.87 (m, 4H), 1.77-2.00 (m, 4H). | 521 |
| 288 | 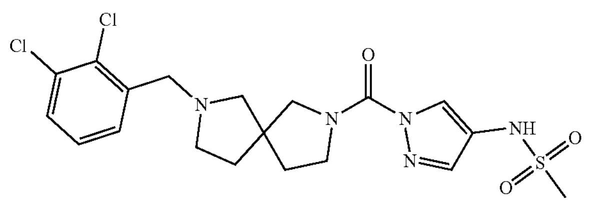 [SMILES: CS(=O)(=O)Nc1cnn(C(=O)N2CCC3(CCN(Cc4cccc(Cl)c4Cl)C3)C2)c1] | ¹H NMR: (300 MHz, Chloroform-d) δ 8.26 (s, 1H), 7.68 (s, 1H), 7.33-7.49 (d, J = 7.7 Hz, 2H), 7.13-7.28 (m, 1H), 6.33 (s, 1H), 3.86-4.22 (m, 2H), 3.55-3.85 (m, 4H), 3.03 (s, 3H), 2.49-2.89 (m, 4H), 1.78-2.14 (m, 4H). | 472 |
| 289 | 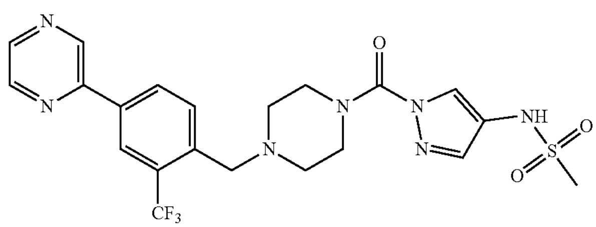 [SMILES: CS(=O)(=O)Nc1cnn(C(=O)N2CCN(Cc3ccc(-c4cnccn4)cc3C(F)(F)F)CC2)c1] | ¹H NMR (300 MHz, Chloroform-d) δ 9.09 (s, 1H), 8.69-8.70 (m, 1H), 8.59-8.60 (m, 1H), 8.36 (s, 1H), 8.14-8.22 (m, 2H), 7.97-8.00 (m, 1H), 7.66 (s, 1H), 6.80 (s, 1H), 3.80-3.92 (m, 6H), 3.03 (s, 3H), 2.64-2.82 (m, 4H). | 510 |
| 290 | 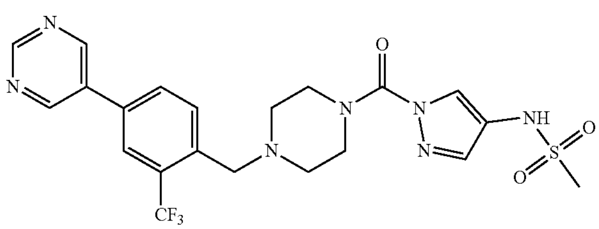 [SMILES: CS(=O)(=O)Nc1cnn(C(=O)N2CCN(Cc3ccc(-c4cncnc4)cc3C(F)(F)F)CC2)c1] | ¹H NMR (300 MHz, Chloroform-d) δ 9.29 (s, 1H), 9.00 (s, 2H), 8.15 (s, 1H), 8.00-8.03 (m, 1H), 7.87 (s, 1H), 7.78-7.80 (m, 1H), 7.66 (s, 1H), 6.48 (s, 1H), 3.81-3.94 (m, 6H), 3.04 (s, 3H), 2.65 (br, 4H). | 510 |
| 291 | 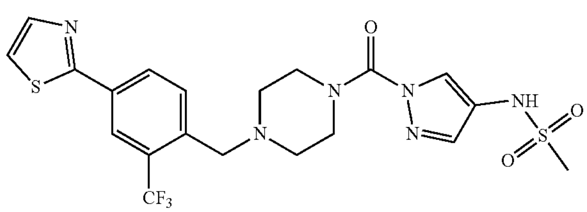 | ¹H NMR (300 MHz, Chloroform-d) δ 8.28 (s, 1H), 8.12-8.14 (m, 2H), 7.91-7.94 (m, 2H), 7.66 (s, 1H), 7.42-7.43 (m, 1H), 6.56 (s, 1H), 3.77-3.92 (m, 6H), 3.03 (s, 3H), 2.63 (br, 4H). | 515 |
| 292 | 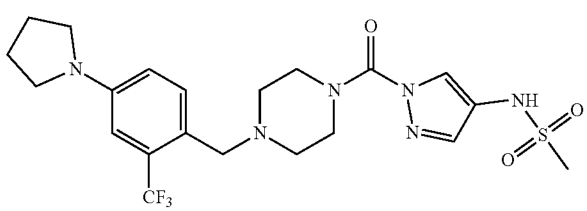 [SMILES: CS(=O)(=O)Nc1cnn(C(=O)N2CCN(Cc3ccc(N4CCCC4)cc3C(F)(F)F)CC2)c1] | ¹H NMR (300 MHz, Chloroform-d) δ 8.12 (s, 1H), 7.65 (s, 1H), 7.49-7.51 (m, 1H), 6.67-6.79 (m, 3H), 3.86 (br, 4H), 3.61 (br, 2H), 3.30-3.35 (m, 4H), 3.02 (s, 3H), 2.57 (br, 4H), 2.01-2.09 (m, 4H). | 501 |

TABLE 2-continued

| Ex. | Structure | NMR | MS [M + H]+ |
|---|---|---|---|
| 293 | 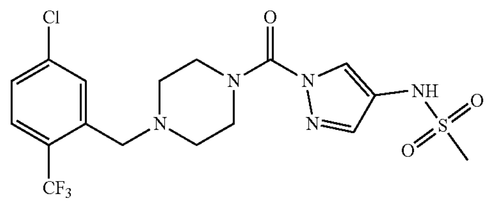 [SMILES: CS(=O)(=O)Nc1cnn(C(=O)N2CCN(Cc3cc(Cl)ccc3C(F)(F)F)CC2)c1] | ¹H NMR (300 MHz, Chloroform-d) δ 8.14 (s, 1H), 7.84 (s, 1H), 7.58-7.66 (m, 2H), 7.35-7.38 (m, 1H), 6.75 (s, 1H), 3.92 (br, 4H), 3.71 (br, 2H), 3.03 (s, 3H), 2.62 (br, 4H). | 466 |
| 294 | 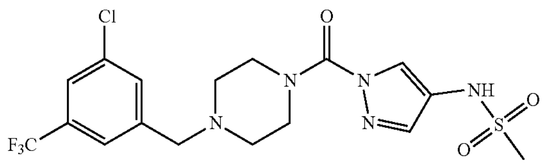 [SMILES: CS(=O)(=O)Nc1cnn(C(=O)N2CCN(Cc3cc(Cl)cc(C(F)(F)F)c3)CC2)c1] | ¹H NMR (300 MHz, Chloroform-d) δ 8.13 (s, 1H), 7.65 (s, 1H), 7.53-7.59 (m, 3H), 6.68 (s, 1H), 3.92 (br, 4H), 3.62 (s, 2H), 3.03 (s, 3H), 2.60 (br, 4H). | 466 |
| 295 | 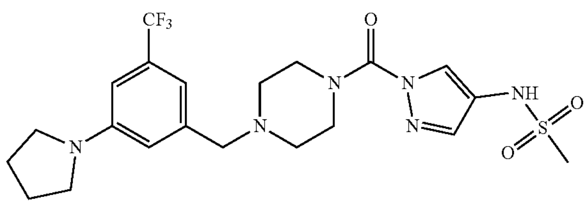 [SMILES: CS(=O)(=O)Nc1cnn(C(=O)N2CCN(Cc3cc(N4CCCC4)cc(C(F)(F)F)c3)CC2)c1] | ¹H NMR (300 MHz, Chloroform-d) δ 8.12 (s, 1H), 7.65 (s, 1H), 6.67-6.87 (m, 4H), 3.89 (br, 4H), 3.56 (s, 2H), 3.32-3.36 (m, 4H), 3.02 (s, 3H), 2.58 (br, 4H), 2.01-2.10 (m, 4H). | 501 |
| 296 | 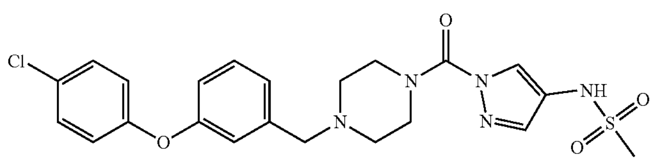 [SMILES: CS(=O)(=O)Nc1cnn(C(=O)N2CCN(Cc3cccc(Oc4ccc(Cl)cc4)c3)CC2)c1] | ¹H NMR (300 MHz, Chloroform-d) δ 8.13 (s, 1H), 7.65 (s, 1H), 7.30-7.35 (m, 3H), 7.10-7.13 (m, 1H), 7.04 (s, 1H), 6.90-6.99 (m, 3H), 6.58 (br, 1H), 3.89 (br, 4H), 3.58 (s, 2H), 3.02-3.06 (m, 3H), 2.58 (br, 4H). | 490 |
| 297 | 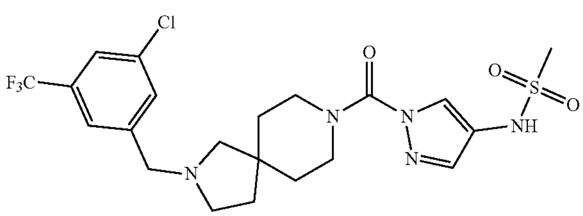 [SMILES: CS(=O)(=O)Nc1cnn(C(=O)N2CCC3(CCN(Cc4cc(Cl)cc(C(F)(F)F)c4)C3)CC2)c1] | ¹H NMR (300 MHz, Chloroform-d) δ 8.08 (s, 1H), 7.63 (s, 1H), 7.48-7.52 (m, 3H), 6.45 (br, 1H), 3.79-3.83 (m, 2H), 3.63-3.70 (m, 4H), 3.00 (s, 3H), 2.61-2.66 (m, 2H), 2.45 (s, 2H), 1.67-1.76 (m, 6H). | 520 |
| 298 | 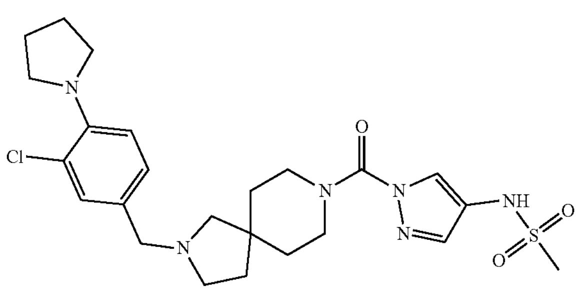 [SMILES: CS(=O)(=O)Nc1cnn(C(=O)N2CCC3(CCN(Cc4ccc(N5CCCC5)c(Cl)c4)C3)CC2)c1] | ¹H NMR (300 MHz, Chloroform-d) δ 8.03 (s, 1H), 7.59 (s, 1H), 7.25-7.27 (m, 1H), 7.06-7.09 (m, 1H), 6.81-6.84 (m, 1H), 5.62 (br, 1H), 3.64-3.73 (m, 4H), 3.50 (s, 2H), 3.33-3.38 (m, 4H), 2.98 (s, 3H), 2.60-2.65 (m, 2H), 2.43 (s, 2H), 1.90-1.98 (m, 4H), 1.62-1.72 (m, 6H). | 521 |
| 299 | 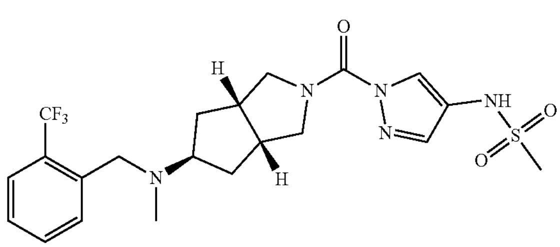 [SMILES: CN(Cc1ccccc1C(F)(F)F)[C@H]1C[C@@H]2CN(C(=O)n3cc(NS(C)(=O)=O)cn3)C[C@@H]2C1] | ¹H NMR (300 MHz, Chloroform-d) δ 8.24 (s, 1H), 7.80-7.83 (m, 1H), 7.66 (s, 1H), 7.59-7.62 (m, 1H), 7.48-7.54 (m, 1H), 7.27-7.34 (m, 1H), 7.04 (br, 1H), 4.04 (br, 2H), 3.66-3.88 (m, 4H), 3.13-3.23 (m, 1H), 3.02 (s, 3H), 2.86 (br, 2H), 2.13 (s, 3H), 1.81-1.96 (m, 4H). | 486 |

TABLE 2-continued

| Ex. | Structure | NMR | MS [M + H]+ |
|---|---|---|---|
| 300 | 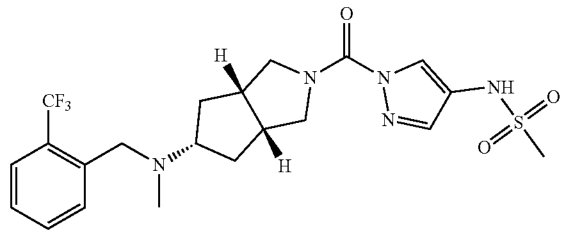 [SMILES: CN(Cc1ccccc1C(F)(F)F)[C@@H]1C[C@@H]2CN(C(=O)n3cc(NS(C)(=O)=O)cn3)C[C@@H]2C1] | ¹H NMR (300 MHz, Chloroform-d) δ 8.25 (s, 1H), 7.82-7.85 (m, 1H), 7.66 (s, 1H), 7.59-7.61 (m, 1H), 7.48-7.54 (m, 1H), 7.27-7.34 (m, 1H), 7.01 (br, 1H), 3.95 (br, 4H), 3.66 (s, 2H), 2.93-3.00 (m, 4H), 2.70 (br, 2H), 2.13-2.20 (m, 5H), 1.46-1.55 (m, 2H). | 486 |
| 301 | 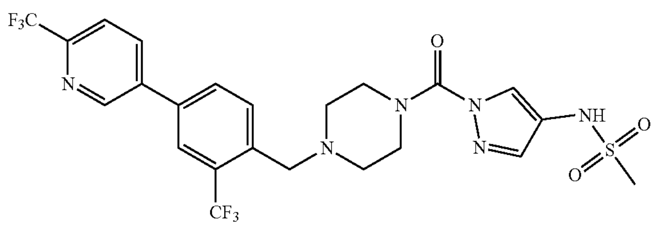 [SMILES: CS(=O)(=O)Nc1cnn(C(=O)N2CCN(Cc3ccc(-c4ccc(C(F)(F)F)nc4)cc3C(F)(F)F)CC2)c1] | ¹H NMR (300 MHz, Methanol-d4) δ 9.04 (d, J = 1.8 Hz, 1H), 8.33-8.36 (m, 1H), 8.02-8.08 (m, 4H), 7.95-8.02 (m, 1H), 7.63 (s, 1H), 3.87 (br, 4H), 3.81 (s, 2H), 2.96 (s, 3H), 2.61-2.64 (m, 4H). | 577 |
| 302 | 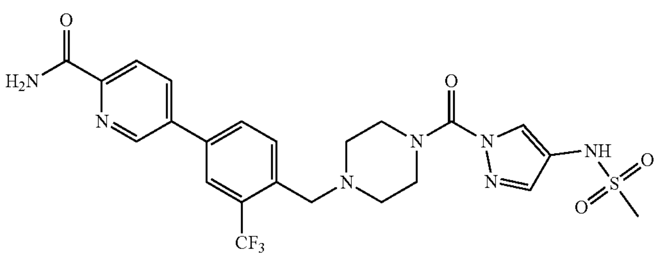 [SMILES: CS(=O)(=O)Nc1cnn(C(=O)N2CCN(Cc3ccc(-c4ccc(C(N)=O)nc4)cc3C(F)(F)F)CC2)c1] | ¹H NMR (300 MHz, Dimethyl sulfoxide-d6) δ 9.55 (br, 1H), 9.01 (s, 1H), 8.35-8.38 (m, 1H), 8.08-8.17 (m, 4H), 7.96-7.98 (m, 2H), 7.72 (br, 1H), 7.62 (s, 1H), 3.74 (br, 6H), 2.96 (s, 3H), 2.50-2.54 (m, 4H). | 552 |
| 303 | 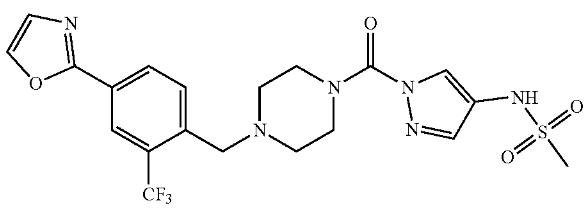 [SMILES: CS(=O)(=O)Nc1cnn(C(=O)N2CCN(Cc3ccc(-c4ncco4)cc3C(F)(F)F)CC2)c1] | ¹H NMR (300 MHz, Chloroform-d) δ 8.34 (s, 1H), 8.19-8.22 (m, 1H), 8.12 (s, 1H), 7.91-7.94 (m, 1H), 7.76 (s, 1H), 7.63 (s, 1H), 7.26-7.28 (m, 1H), 6.45 (s, 1H), 3.90 (br, 4H), 3.76 (s, 2H), 3.01 (s, 3H), 2.61 (br, 4H). | 499 |
| 304 | 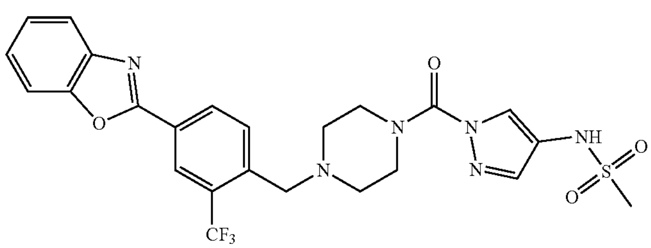 | ¹H NMR (300 MHz, Chloroform-d) δ 8.56 (s, 1H), 8.42-7.44 (m, 1H), 8.14 (s, 1H), 8.04 (br, 1H), 7.79-7.82 (m, 1H), 7.61-7.64 (m, 2H), 7.37-7.44 (m, 2H), 6.27 (br, 1H), 3.82-3.94 (br, 6H), 3.02 (s, 3H), 2.66 (br, 4H). | 549 |
| 305 | 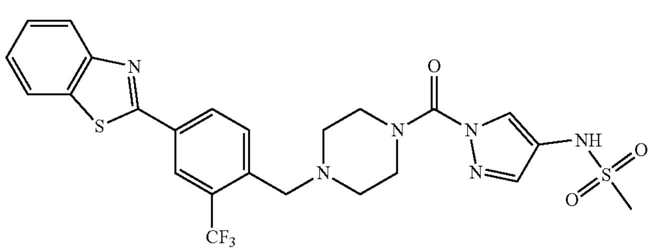 [SMILES: CS(=O)(=O)Nc1cnn(C(=O)N2CCN(Cc3ccc(-c4nc5ccccc5s4)cc3C(F)(F)F)CC2)c1] | ¹H NMR (300 MHz, Chloroform-d) δ 8.39 (s, 1H), 8.22-8.25 (m, 1H), 8.09-8.14 (m, 2H), 7.93-7.98 (m, 2H), 7.64 (s, 1H), 7.51-7.56 (m, 1H), 7.41-7.46 (m, 1H), 6.10 (s, 1H), 3.91 (br, 4H), 3.78 (s, 2H), 3.02 (s, 3H), 2.63 (br, 4H). | 565 |

| Ex. | Structure | NMR | MS [M + H]+ |
|---|---|---|---|
| 306 | 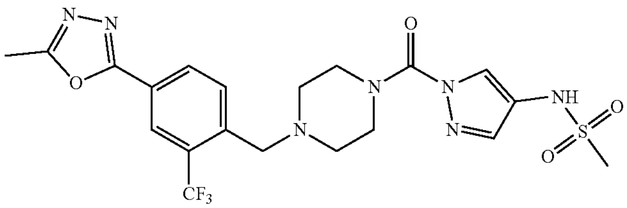 [SMILES: Cc1nnc(-c2ccc(CN3CCN(C(=O)n4cc(NS(C)(=O)=O)cn4)CC3)c(C(F)(F)F)c2)o1] | ¹H NMR (300 MHz, Chloroform-d) δ 8.28 (s, 1H), 8.20-8.23 (m, 1H), 8.12 (s, 1H), 7.99 (d, J = 8.4 Hz, 1H), 7.65 (s, 1H), 7.03 (s, 1H), 3.90 (br, 4H), 3.76 (s, 2H), 3.01 (s, 3H), 2.65 (s, 3H), 2.61 (br, 4H). | 514 |
| 307 | 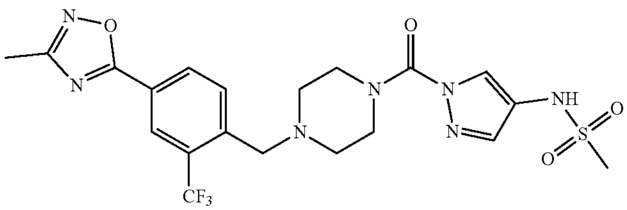 [SMILES: Cc1noc(-c2ccc(CN3CCN(C(=O)n4cc(NS(C)(=O)=O)cn4)CC3)c(C(F)(F)F)c2)n1] | ¹H NMR (300 MHz, Chloroform-d) δ 8.41 (s, 1H), 8.26-8.29 (m, 1H), 8.12 (s, 1H), 8.02-8.05 (m, 1H), 7.64 (s, 1H), 6.56 (s, 1H), 3.91 (br, 4H), 3.79 (br, 2H), 3.01 (s, 3H), 2.62 (br, 4H), 2.50 (s, 3H). | 514 |
| 308 | 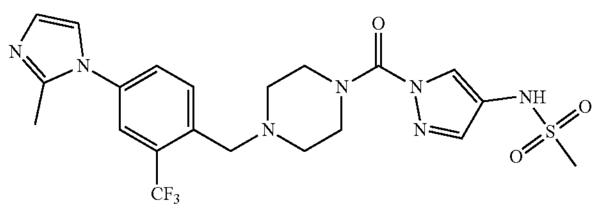 [SMILES: Cc1nccn1-c1ccc(CN2CCN(C(=O)n3cc(NS(C)(=O)=O)cn3)CC2)c(C(F)(F)F)c1] | ¹H NMR (300 MHz, Chloroform-d) δ 8.13 (s, 1H), 7.98 (d, J = 8.4 Hz, 1H), 7.66 (s, 1H), 7.60 (s, 1H), 7.48-7.52 (m, 2H), 7.06 (d, J = 11.7 Hz, 2H), 3.93 (br, 4H), 3.78 (s, 2H), 2.99 (s, 3H), 2.62-2.66 (m, 4H), 2.40 (s, 3H). | 512 |
| 309 | 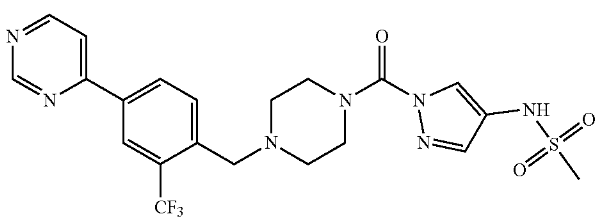 [SMILES: CS(=O)(=O)Nc1cnn(C(=O)N2CCN(Cc3ccc(-c4ccncn4)cc3C(F)(F)F)CC2)c1] | ¹H NMR (300 MHz, Chloroform-d) δ 9.31 (s, 1H), 8.83 (d, J = 5.1 Hz, 1H), 8.40 (br, 1H), 8.25-8.27 (m, 1H), 8.12 (s, 1H), 7.97-7.99 (m, 1H), 7.64 (d, J = 5.4 Hz, 1H), 7.64 (s, 1H), 6.58 (br, 1H), 3.90 (br, 4H), 3.78 (br, 2H), 3.01 (s, 3H), 2.62 (br, 4H). | 512 |
| 310 | 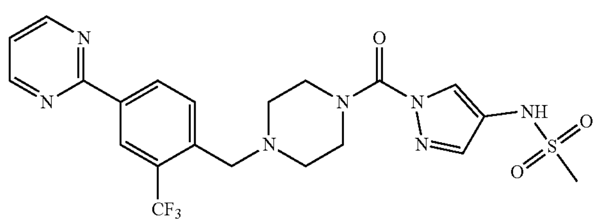 [SMILES: CS(=O)(=O)Nc1cnn(C(=O)N2CCN(Cc3ccc(-c4ncccn4)cc3C(F)(F)F)CC2)c1] | ¹H NMR (300 MHz, Chloroform-d) δ 8.82-8.84 (m, 2H), 8.75 (s, 1H), 8.58-8.61 (m, 1H), 8.10 (s, 1H), 7.92-7.95 (m, 1H), 7.62 (s, 1H), 7.23-7.26 (m, 1H), 6.87 (br, 1H), 3.90 (br, 4H), 3.79 (br, 2H), 3.00 (s, 3H), 2.62 (br, 4H). | 510 |
| 311 | 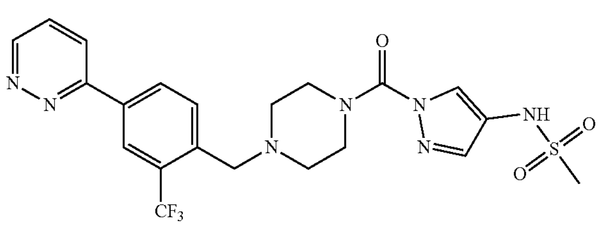 [SMILES: CS(=O)(=O)Nc1cnn(C(=O)N2CCN(Cc3ccc(-c4cccnn4)cc3C(F)(F)F)CC2)c1] | ¹H NMR (300 MHz, Chloroform-d) δ 9.21-9.23 (m, 1H), 8.34 (br, 1H), 8.26-8.28 (m, 1H), 8.12 (s, 1H), 7.92-8.00 (m, 2H), 7.57-7.66 (m, 3H), 3.89 (br, 4H), 3.78 (br, 2H), 3.00 (s, 3H), 2.62 (br, 4H). | 510 |
| 312 | 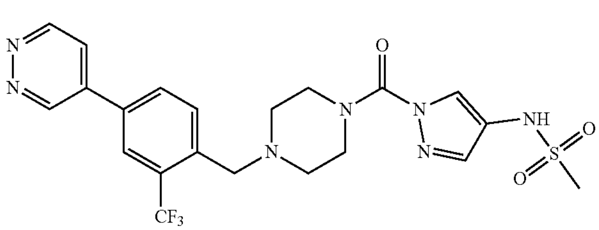 [SMILES: CS(=O)(=O)Nc1cnn(C(=O)N2CCN(Cc3ccc(-c4ccnnc4)cc3C(F)(F)F)CC2)c1] | ¹H NMR (300 MHz, Chloroform-d) δ 9.49 (s, 1H), 9.28-9.30 (m, 1H), 8.13 (s, 1H), 8.02-8.04 (m, 1H), 7.93 (s, 1H), 7.85-7.88 (m, 1H), 7.61-7.73 (m, 3H), 3.90 (br, 4H), 3.78 (br, 2H), 3.00 (s, 3H), 2.60-2.63 (m, 4H). | 510 |

TABLE 2-continued

| Ex. | Structure | NMR | MS [M + H]+ |
|---|---|---|---|
| 313 | 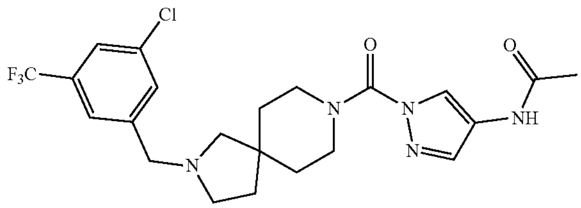 [SMILES: CC(=O)Nc1cnn(C(=O)N2CCC3(CCN(Cc4cc(Cl)cc(C(F)(F)F)c4)C3)CC2)c1] | ¹H NMR (400 MHz, Chloroform-d) δ 8.28 (s, 1H), 7.74 (s, 1H), 7.47-7.52 (m, 3H), 7.29 (s, 1H), 3.77-3.80 (m, 2H), 3.61-3.67 (m, 4H), 2.60-2.63 (m, 2H), 2.44 (s, 2H), 2.16 (s, 3H), 1.62-1.74 (m, 6H). | 484 |
| 314 | 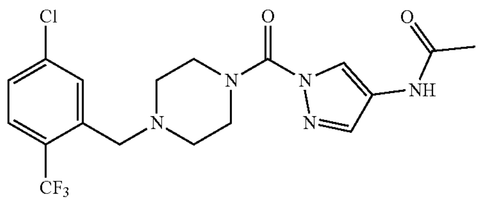 [SMILES: CC(=O)Nc1cnn(C(=O)N2CCN(Cc3cc(Cl)ccc3C(F)(F)F)CC2)c1] | ¹H NMR (400 MHz, Chloroform-d) δ 8.29 (s, 1H), 7.82 (s, 1H), 7.74-7.75 (m, 2H), 7.55-7.58 (m, 1H), 7.26-7.34 (m, 1H), 3.87 (br, 4H), 3.67 (s, 2H), 2.56-2.59 (m, 4H), 2.15 (s, 3H). | 430 |
| 315 | 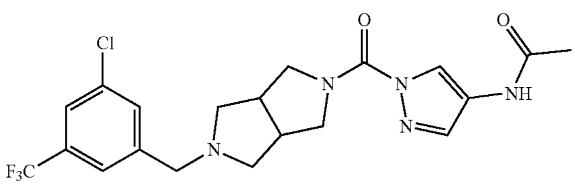 [SMILES: CC(=O)Nc1cnn(C(=O)N2CC3CN(Cc4cc(Cl)cc(C(F)(F)F)c4)CC3C2)c1] | ¹H NMR (400 MHz, Chloroform-d) δ 8.39 (s, 1H), 7.81 (s, 1H), 7.68 (s, 1H), 7.48-7.51 (m, 2H), 7.44 (s, 1H), 4.06 (br, 2H), 3.81 (br, 2H), 3.62 (s, 2H), 2.90 (br, 2H), 2.65 (br, 2H), 2.52-2.54 (m, 2H), 2.16 (s, 3H). | 456 |
| 316 | 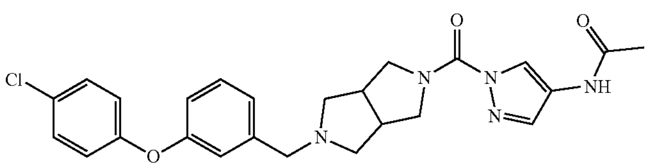 [SMILES: CC(=O)Nc1cnn(C(=O)N2CC3CN(Cc4cccc(Oc5ccc(Cl)cc5)c4)CC3C2)c1] | ¹H NMR (400 MHz, Chloroform-d) δ 8.36 (s, 1H), 7.79 (s, 1H), 7.50 (s, 1H), 7.24-7.28 (m, 3H), 7.06-7.08 (m, 1H), 6.97 (s, 1H), 6.91-6.93 (m, 2H), 6.85-6.87 (m, 1H), 4.05 (br, 2H), 3.77 (br, 2H), 3.58 (s, 2H), 2.88 (br, 2H), 2.64 (br, 2H), 2.52-2.54 (m, 2H), 2.15 (s, 3H). | 480 |
| 317 | 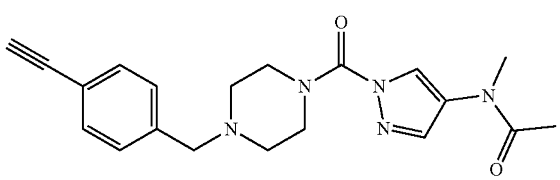 [SMILES: C#Cc1ccc(CN2CCN(C(=O)n3cc(N(C)C(C)=O)cn3)CC2)cc1] | ¹H NMR (400 MHz, Chloroform-d) δ 8.06-8.20 (m, 1H), 7.54-7.99 (m, 1H), 7.45-7.47 (m, 2H), 7.27-7.31 (m, 2H), 3.87 (br, 4H), 3.55-3.56 (m, 2H), 3.36 (s, 1H), 3.21 (s, 2H), 3.08-(s, 1H), 2.55-2.57 (m, 4H), 2.28 (s, 1H), 1.99 (s, 2H). | 366 |
| 318 | 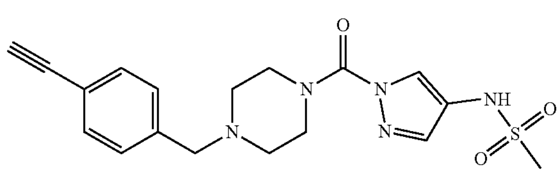 [SMILES: C#Cc1ccc(CN2CCN(C(=O)n3cc(NS(C)(=O)=O)cn3)CC2)cc1] | ¹H NMR (300 MHz, Chloroform-d) δ 8.10 (s, 1H), 7.62 (s, 1H), 7.44-7.47 (m, 2H), 7.26-7.30 (m, 2H), 6.35 (br, 1H), 3.86 (br, 4H), 3.54 (s, 2H), 3.00-3.07 (m, 4H), 2.52-2.55 (m, 4H). | 388 |

II. Biological Evaluation

Compounds are tested to assess their MAGL and FAAH activity using the following in vitro and in vivo assays.

In Vitro Competitive Activity-Based Protein Profiling.

Proteomes (mouse brain membrane fraction or cell lysates for mouse assays; human prefrontal cortex or cell membrane fractions for human assays) (50 μL, 1.0 mg/mL total protein concentration) were preincubated with varying concentrations of inhibitors at 37° C. After 30 min, FP—Rh or HT-01 (1.0 μL, 50 μM in DMSO) was added and the mixture was incubated for another 30 min at 37° C. Reactions were quenched with SDS loading buffer (15 μL-4×) and run on SDS-PAGE. Following gel imaging, serine hydrolase activity was determined by measuring fluorescent intensity of gel bands corresponding to MAGL and FAAH using ImageJ 1.43u software.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 3 and Table 4.

TABLE 3

| Ex | MAGL % inh. 1 μM (mouse) | FAAH % inh. 1 μM (mouse) | FAAH IC50 (mouse) | MAGL IC50 (mouse) | MAGL % inh. 5 mg/kg (mouse) |
|---|---|---|---|---|---|
| 1 | A | A | *** | ** | |
| 2 | A | A | ** | ** | |
| 3 | D | B | | | |
| 4 | A | A | *** | ** | |
| 5 | D | B | | | |
| 6 | D | A | ** | * | |
| 7 | D | A | ** | * | |
| 8 | D | A | ** | * | |
| 9 | A | A | *** | ** | B |
| 10 | A | A | ** | ** | |
| 11 | A | A | *** | ** | A |
| 12 | A | A | *** | ** | |
| 13 | A | A | ** | ** | |
| 14 | A | A | *** | *** | |
| 15 | D | C | | | |
| 16 | A | A | *** | *** | |
| 17 | A | A | | | |
| 18 | C | A | | | |
| 19 | B | C | | | |
| 20 | C | B | | | |
| 21 | D | C | | | |
| 22 | C | A | ** | * | |
| 23 | C | C | | | |
| 24 | A | A | *** | *** | |
| 25 | A | B | | | |
| 26 | A | A | ** | *** | |
| 27 | A | D | | | |
| 28 | A | A | | | |
| 29 | A | C | | | |
| 30 | A | A | | | |
| 31 | A | C | | | |
| 32 | A | C | | | |
| 33 | B | C | | | |
| 34 | A | A | *** | *** | |
| 35 | A | A | | | |
| 36 | A | A | | | |
| 37 | B | B | | | |
| 38 | A | A | ** | *** | |
| 39 | A | C | | | |
| 40 | A | A | ** | *** | |
| 41 | A | B | | | |
| 42 | A | A | | | |
| 43 | A | D | | | |
| 44 | A | A | *** | *** | |
| 45 | A | D | | | |
| 46 | B | D | | | |
| 47 | C | A | | | |
| 48 | D | C | | | |
| 49 | A | A | ** | ** | |
| 50 | B | A | *** | ** | A |
| 51 | A | A | *** | *** | |
| 52 | D | A | | | |
| 53 | A | A | *** | ** | |
| 54 | D | A | | | |
| 55 | A | A | *** | ** | |
| 56 | D | D | | | |

TABLE 3-continued

| Ex | MAGL % inh. 1 μM (mouse) | FAAH % inh. 1 μM (mouse) | FAAH IC50 (mouse) | MAGL IC50 (mouse) | MAGL % inh. 5 mg/kg (mouse) |
|---|---|---|---|---|---|
| 57 | A | A | *** | ** | |
| 58 | A | A | *** | ** | A |
| 59 | A | A | *** | ** | |
| 60 | D | D | | | |
| 61 | A | A | *** | *** | |
| 62 | D | D | | | |
| 63 | A | A | | | |
| 64 | A | A | *** | ** | |
| 65 | A | A | *** | ** | |
| 66 | A | A | *** | ** | |
| 67 | A | A | *** | ** | |
| 68 | A | A | *** | ** | |
| 69 | A | A | | | |
| 70 | A | A | *** | *** | |
| 71 | A | A | | | |
| 72 | A | A | | | |
| 73 | A | A | | | |
| 74 | A | B | | | |
| 75 | D | B | | | |
| 76 | D | B | | | |
| 77 | D | C | | | |
| 78 | B | A | *** | * | |
| 79 | D | A | | | |
| 80 | D | B | | | |
| 81 | D | B | | | |
| 82 | C | A | | | |
| 83 | C | C | | | |
| 84 | B | A | | | |
| 85 | B | A | | | |
| 86 | B | A | | | |
| 87 | B | C | | | |
| 88 | B | A | | | |
| 89 | C | C | | | |
| 90 | D | A | | | |
| 91 | B | A | ** | ** | |
| 92 | A | A | *** | ** | |
| 93 | A | A | *** | *** | |
| 94 | A | A | *** | ** | |
| 95 | A | A | | | |
| 96 | A | A | *** | *** | |
| 97 | A | A | | | |
| 98 | A | A | *** | *** | |
| 99 | A | A | | | |
| 100 | A | A | *** | *** | |
| 101 | A | A | | | |
| 102 | A | A | | | |
| 103 | A | A | *** | *** | |
| 104 | A | A | | | |
| 105 | A | A | *** | *** | |
| 106 | A | A | | | |
| 107 | A | A | *** | *** | |
| 108 | A | A | *** | ** | |
| 109 | A | A | *** | *** | |
| 110 | A | A | *** | *** | |
| 111 | A | A | *** | *** | |
| 112 | A | A | *** | *** | |
| 113 | A | A | *** | *** | |
| 114 | A | A | *** | *** | |
| 115 | A | A | *** | *** | |
| 116 | A | A | *** | *** | |
| 117 | A | A | *** | *** | |
| 118 | A | A | *** | *** | |
| 119 | A | A | *** | *** | |
| 120 | A | A | *** | *** | |
| 121 | A | B | | | |
| 122 | A | A | *** | ** | |
| 123 | A | A | *** | *** | |
| 124 | A | A | *** | *** | |
| 125 | A | A | *** | *** | |
| 126 | A | A | | | |
| 127 | A | A | | | |
| 128 | A | A | | | |
| 129 | A | A | | | |
| 130 | A | A | *** | *** | |
| 131 | A | A | *** | *** | |
| 132 | A | A | | | |

TABLE 3-continued

| Ex | MAGL % inh. 1 μM (mouse) | FAAH % inh. 1 μM (mouse) | FAAH IC50 (mouse) | MAGL IC50 (mouse) | MAGL % inh. 5 mg/kg (mouse) |
|---|---|---|---|---|---|
| 133 | C | A | | | |
| 134 | D | A | | | |
| 135 | A | A | | | |
| 136 | A | A | ** | ** | |
| 137 | A | A | ** | ** | |
| 138 | A | A | | | |
| 139 | C | A | ** | * | |
| 140 | A | A | | | |
| 141 | B | A | *** | ** | |
| 142 | A | A | | | |
| 143 | A | A | ** | ** | |
| 144 | A | B | | | |
| 145 | A | A | *** | *** | |
| 146 | A | A | | | |
| 147 | A | A | *** | *** | |
| 148 | A | A | *** | *** | A |
| 149 | A | A | | | |
| 150 | A | A | *** | ** | |
| 151 | A | A | ** | ** | |
| 152 | A | A | | | |
| 153 | A | A | | | |
| 154 | A | A | | | |
| 155 | A | A | | | |
| 156 | A | A | *** | ** | |
| 157 | A | A | | | |
| 158 | A | A | | | |
| 159 | A | A | | | |
| 160 | A | A | | | |
| 161 | A | A | *** | *** | |
| 162 | A | A | | | |
| 163 | A | A | | | |
| 164 | A | A | *** | *** | |
| 165 | A | A | | | |
| 166 | A | A | | | |
| 167 | A | A | | | |
| 168 | A | B | | | |
| 169 | A | C | | | |
| 170 | A | C | | | |
| 171 | A | C | | | |
| 172 | A | D | * | *** | D |
| 173 | A | D | | | |
| 174 | A | D | | | |
| 175 | A | A | *** | ** | |
| 176 | A | A | *** | *** | |
| 177 | A | A | *** | *** | |
| 178 | C | A | ** | * | |
| 179 | C | A | | | |
| 180 | B | A | ** | ** | |
| 181 | B | A | ** | * | |
| 182 | A | A | *** | ** | |
| 183 | D | A | | | |
| 184 | A | B | | | |
| 185 | B | D | | | |
| 186 | A | A | ** | *** | |
| 187 | A | A | ** | ** | |
| 188 | A | A | ** | ** | |
| 189 | A | D | ** | * | |
| 190 | A | B | * | *** | |
| 191 | A | C | ** | *** | |
| 192 | A | A | ** | ** | |
| 193 | A | A | ** | ** | |
| 194 | A | A | * | ** | |
| 195 | A | D | * | *** | |
| 196 | A | A | ** | *** | |
| 197 | A | A | ** | ** | |
| 198 | A | A | ** | *** | |
| 199 | B | D | | | |
| 200 | B | D | | | |
| 201 | A | A | *** | *** | |
| 202 | A | A | *** | *** | |
| 203 | A | A | ** | *** | |
| 204 | A | A | ** | ** | |
| 205 | A | A | ** | ** | |
| 206 | A | A | ** | *** | |
| 207 | A | A | | | |
| 208 | A | A | ** | *** | |
| 209 | A | A | *** | *** | |
| 210 | A | D | | | |
| 211 | A | A | | | |
| 212 | A | A | ** | ** | |
| 213 | A | D | | | |
| 214 | A | A | *** | *** | |
| 215 | A | C | | | |
| 216 | A | D | | | |
| 217 | A | C | * | *** | A |
| 218 | A | C | * | ** | |
| 219 | A | A | *** | * | A |
| 220 | A | A | *** | ** | |
| 221 | A | A | *** | ** | |
| 222 | D | A | | | |
| 223 | A | A | *** | *** | |
| 224 | A | B | | | |
| 225 | D | C | | | |
| 226 | A | A | ** | *** | |
| 227 | A | B | ** | ** | |
| 228 | A | D | * | ** | |
| 229 | B | A | *** | * | |
| 230 | C | D | | | |
| 231 | D | D | | | |
| 232 | A | A | *** | *** | |
| 233 | B | D | | | |
| 234 | A | A | *** | *** | |
| 235 | A | A | *** | *** | |
| 236 | A | A | *** | ** | C |
| 237 | A | A | *** | *** | |
| 238 | A | A | *** | ** | |
| 239 | A | A | *** | *** | |
| 240 | A | A | *** | *** | |
| 241 | A | A | *** | *** | |
| 242 | A | A | *** | *** | |
| 243 | A | A | *** | *** | |
| 244 | A | A | *** | *** | |
| 245 | A | A | *** | *** | |
| 246 | A | A | *** | ** | |
| 247 | A | A | *** | *** | |
| 248 | A | A | *** | *** | |
| 249 | A | A | | | |
| 250 | A | B | | | |
| 251 | A | A | *** | *** | |
| 252 | A | A | | | |
| 253 | A | A | | | |
| 254 | A | A | | | |
| 255 | A | A | | | |
| 256 | D | A | | | |
| 257 | B | A | | | |
| 258 | A | A | | | |
| 259 | A | A | | | |
| 260 | A | A | | | |
| 261 | A | A | | | |
| 262 | A | A | | | |
| 263 | A | A | | | |
| 264 | A | A | | | |
| 265 | A | A | | | |
| 266 | A | A | | | |
| 267 | A | A | | | |
| 268 | A | A | | | |
| 269 | A | A | | | |
| 270 | A | A | | | |
| 271 | A | A | | | |
| 272 | A | A | | | |
| 273 | A | A | *** | ** | |
| 274 | A | A | ** | *** | D |
| 275 | A | A | ** | *** | |
| 276 | A | A | | | |
| 277 | A | A | *** | *** | |
| 278 | A | A | | | |
| 279 | A | A | ** | *** | |
| 280 | A | A | | | |
| 281 | A | A | | | |
| 282 | B | A | | | |
| 284 | C | A | | | |
| 286 | C | A | | | |

TABLE 3-continued

| Ex | MAGL % inh. 1 μM (mouse) | FAAH % inh. 1 μM (mouse) | FAAH IC50 (mouse) | MAGL IC50 (mouse) | MAGL % inh. 5 mg/kg (mouse) |
|---|---|---|---|---|---|
| 287 | B | A | | | |
| 289 | C | A | | | |
| 291 | B | A | | | |
| 292 | C | A | * | *** | B |
| 293 | B | A | * | *** | |
| 294 | A | A | | | |
| 295 | A | A | | | |
| 296 | A | A | | | |
| 297 | A | A | *** | *** | A |
| 299 | A | A | | | |
| 302 | C | A | | | |
| 303 | B | A | * | *** | |
| 307 | C | A | | | |
| 309 | C | A | | | |
| 313 | A | A | | | A |
| 314 | A | A | | | |
| 315 | A | A | | | |
| 317 | A | A | | | |

*** IC$_{50}$ is less than or equal to 100 nM;
** IC$_{50}$ is greater than 100 nM and less than 1 μM;
* IC$_{50}$ is greater than or equal to 1 μM and less than 10 μM.
A = % inhibition greater than or equal to 75%;
B = % inhibition greater than or equal to 50% and less than 75%;
C = % inhibition greater than or equal to 25% and less than 50%;
D = % inhibition greater than or equal to 0% and less than 25%.

TABLE 4

| Ex | MAGL % inh. 1 μM (human) | FAAH % inh. 1 μM (human) | MAGL % inh. 10 μM (human) | FAAH % inh. 10 μM (human) |
|---|---|---|---|---|
| 3 | | | A | A |
| 5 | | | A | A |
| 15 | | | A | A |
| 21 | | | D | A |
| 48 | | | A | A |
| 52 | | | A | A |
| 54 | | | A | A |
| 56 | | | A | A |
| 60 | | | A | A |
| 62 | | | C | A |
| 75 | | | A | A |
| 76 | | | A | A |
| 77 | | | A | A |
| 79 | | | A | A |
| 80 | | | A | A |
| 81 | | | A | A |
| 90 | | | C | A |
| 134 | | | A | A |
| 183 | | | A | A |
| 222 | | | A | B |
| 225 | | | A | A |
| 231 | | | A | C |
| 283 | A | A | | |
| 285 | A | A | | |
| 288 | A | A | | |
| 290 | A | A | | |
| 298 | A | A | | |
| 300 | A | A | | |
| 301 | | | A | A |
| 304 | C | A | | |
| 305 | A | A | | |
| 306 | B | D | | |
| 308 | A | D | | |
| 310 | A | A | | |
| 311 | A | B | | |
| 312 | A | C | | |
| 316 | A | A | | |
| 318 | C | A | | |

A = % inhibition greater than or equal to 75%;
B = % inhibition greater than or equal to 50% and less than 75%;
C = % inhibition greater than or equal to 25% and less than 50%;
D = % inhibition greater than or equal to 0% and less than 25%.

We claim:

1. A compound of Formula (I):

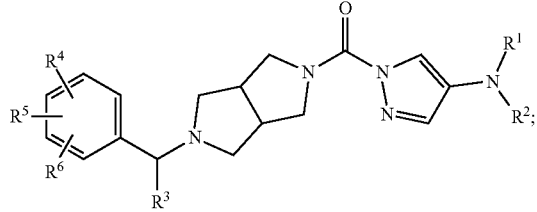

Formula (I)

wherein:

$R^1$ is $-C(O)R^{15}$ or $-SO_2R^{15}$;

$R^2$ is H or $C_{1-6}$alkyl;

$R^3$ is H or optionally substituted phenyl;

$R^4$ is H, halogen, $-OR^7$, $C_{1-6}$ alkyl, $C_{1-6}$haloalkyl, optionally substituted heterocycloalkyl, optionally substituted $C_{1-6}$ alkyl-heterocycloalkyl, optionally substituted phenyl, or optionally substituted heteroaryl;

$R^5$ is H, halogen, $C_{1-6}$alkyl, $C_{1-6}$haloalkyl, or phenyl; or $R^4$ and $R^5$ are combined to form a heterocycloalkyl ring;

$R^6$ is H, halogen or $C_{1-6}$alkyl;

$R^7$ is H, $C_{1-6}$alkyl, optionally substituted phenyl, optionally substituted $C_{1-6}$alkyl-phenyl, optionally substituted heteroaryl, optionally substituted heterocycloalkyl, or $-C_{1-6}$alkylC(O)NR$^{10}$R$^{11}$;

$R^{10}$ and $R^{11}$ are each independently H, or $C_{1-6}$alkyl; or $R^{10}$ and $R^{11}$ together with the nitrogen to which they are attached are combined to form a heterocycloalkyl ring; and $R^{15}$ is $C_{1-6}$alkyl;

or a solvate, hydrate, tautomer, N-oxide, or pharmaceutically acceptable salt thereof.

2. The compound of claim 1, or a solvate, hydrate, tautomer, N-oxide, or pharmaceutically acceptable salt thereof, wherein $R^4$ is optionally substituted heterocycloalkyl.

3. The compound of claim 2, or a solvate, hydrate, tautomer, N-oxide, or pharmaceutically acceptable salt thereof, wherein $R^4$ is

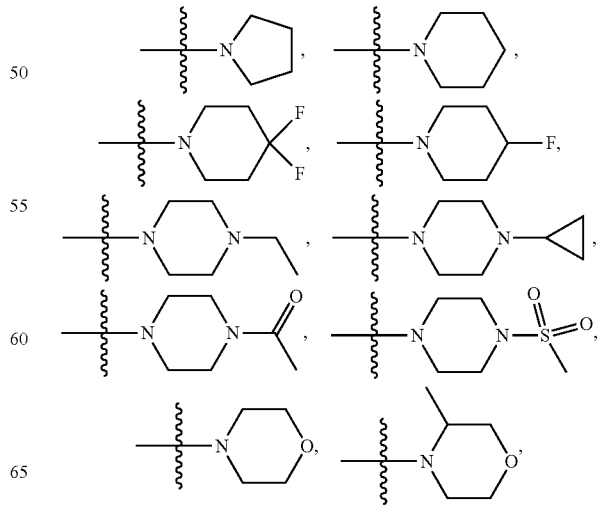

-continued

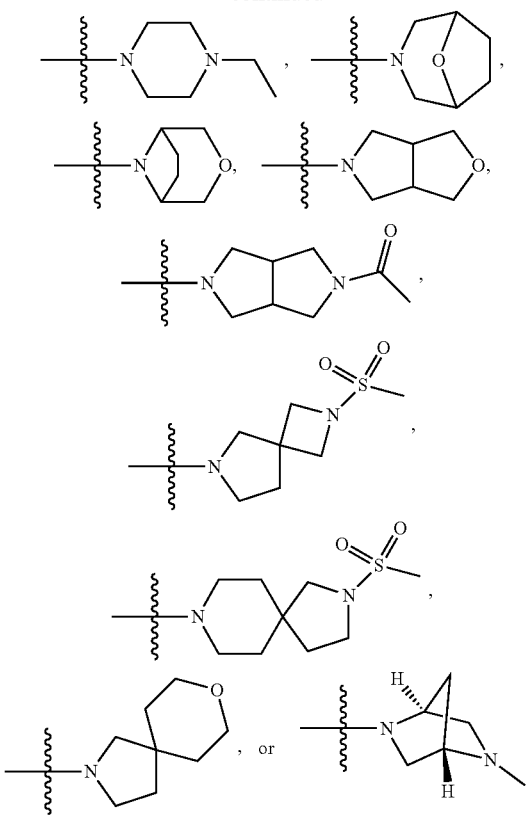

4. The compound of claim 1, or a solvate, hydrate, tautomer, N-oxide, or pharmaceutically acceptable salt thereof, wherein $R^4$ is —$OR^7$.

5. The compound of claim 4, or a solvate, hydrate, tautomer, N-oxide, or pharmaceutically acceptable salt thereof, wherein $R^7$ is $C_{1-6}$alkyl,

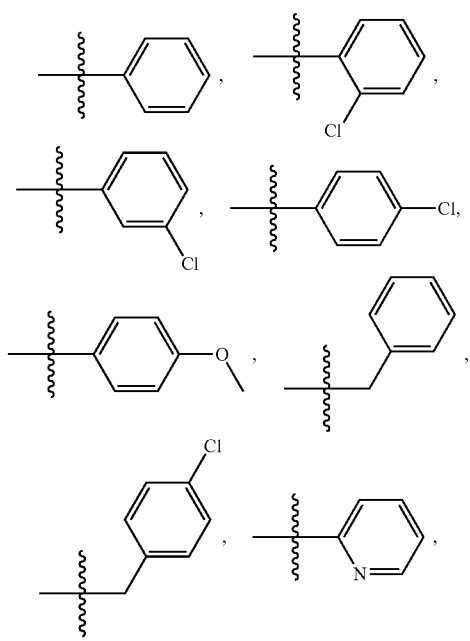

-continued

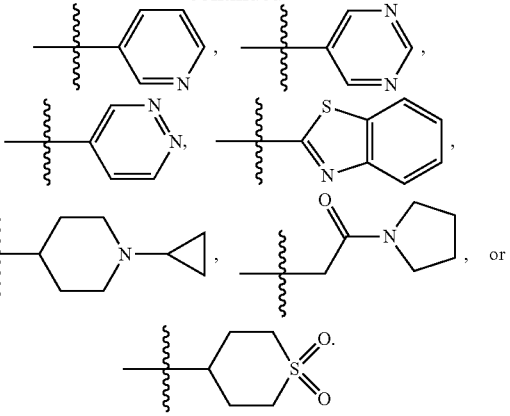

6. The compound of claim 1, or a solvate, hydrate, tautomer, N-oxide, or pharmaceutically acceptable salt thereof, wherein $R^4$ is optionally substituted heteroaryl.

7. The compound of claim 6, or a solvate, hydrate, tautomer, N-oxide, or pharmaceutically acceptable salt thereof, wherein $R^4$ is

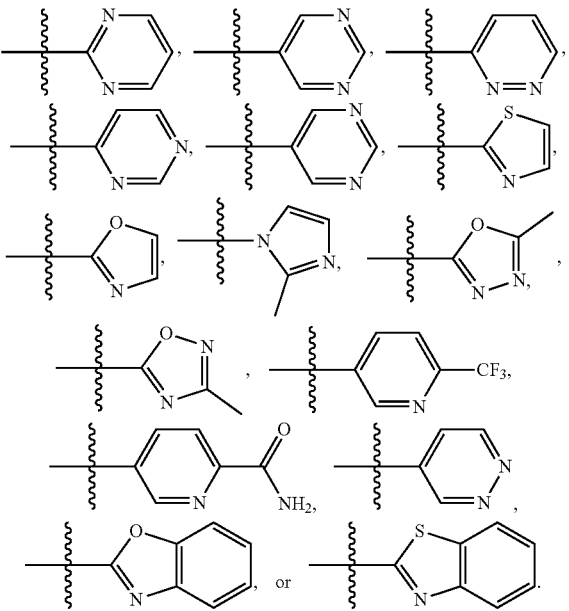

8. The compound of claim 1, or a solvate, hydrate, tautomer, N-oxide, or pharmaceutically acceptable salt thereof, wherein $R^4$ is halogen.

9. The compound of claim 1, or a solvate, hydrate, tautomer, N-oxide, or pharmaceutically acceptable salt thereof, wherein $R^4$ is $C_{1-6}$haloalkyl.

10. The compound of claim 1, or a solvate, hydrate, tautomer, N-oxide, or pharmaceutically acceptable salt thereof, wherein $R^5$ is H.

11. The compound of claim 1, or a solvate, hydrate, tautomer, N-oxide, or pharmaceutically acceptable salt thereof, wherein $R^5$ is halogen.

12. The compound of claim 1, or a solvate, hydrate, tautomer, N-oxide, or pharmaceutically acceptable salt thereof, wherein $R^5$ is $C_{1-6}$haloalkyl.

13. The compound of claim 1, or a solvate, hydrate, tautomer, N-oxide, or pharmaceutically acceptable salt thereof, wherein $R^6$ is H.

14. The compound of claim 1, or a solvate, hydrate, tautomer, N-oxide, or pharmaceutically acceptable salt thereof, wherein $R^3$ is H.

15. The compound of claim 1, or a solvate, hydrate, tautomer, N-oxide, or pharmaceutically acceptable salt thereof, wherein $R^2$ is H or —$CH_3$.

16. The compound of claim 1, or a solvate, hydrate, tautomer, N-oxide, or pharmaceutically acceptable salt thereof, wherein $R^1$ is —$C(O)R^{15}$.

17. The compound of claim 1, or a solvate, hydrate, tautomer, N-oxide, or pharmaceutically acceptable salt thereof, wherein $R^1$ is —$SO_2R^{15}$.

18. A compound selected from:

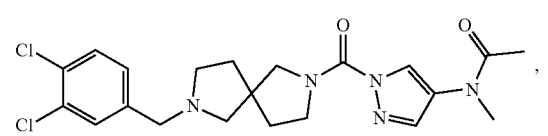

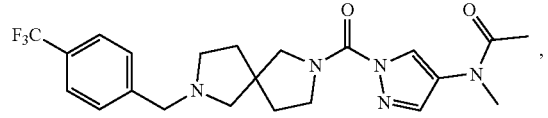

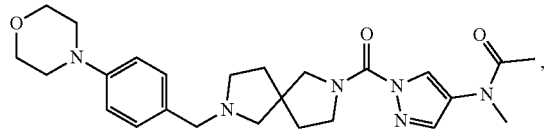

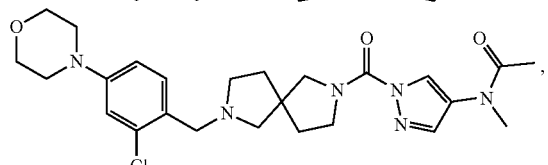

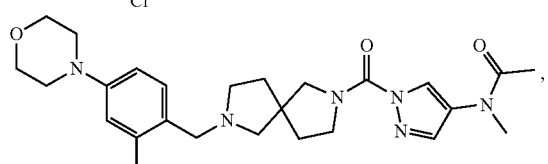

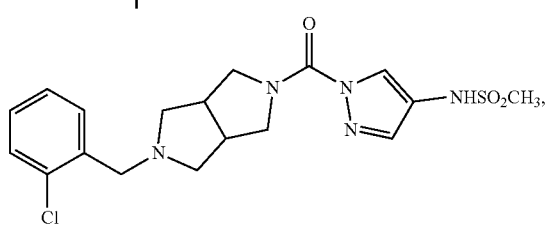

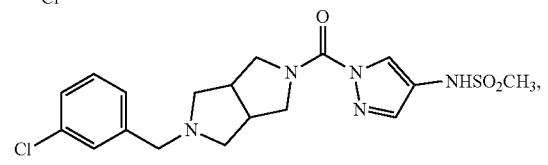

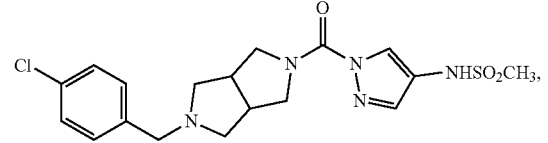

-continued

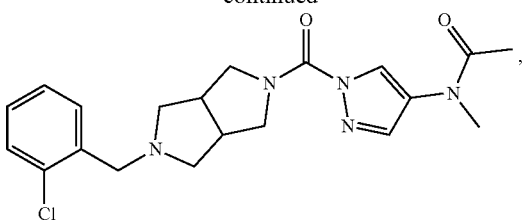

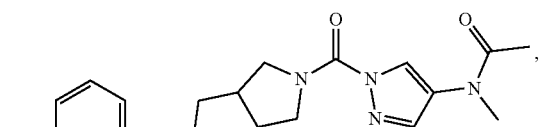

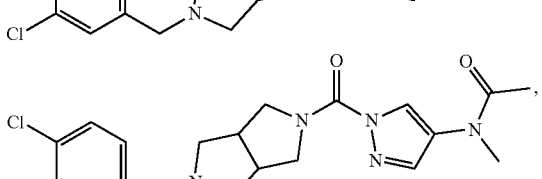

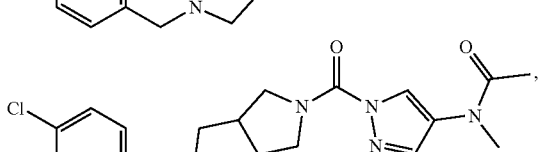

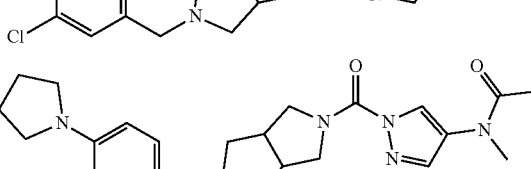

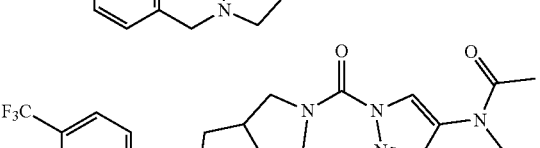

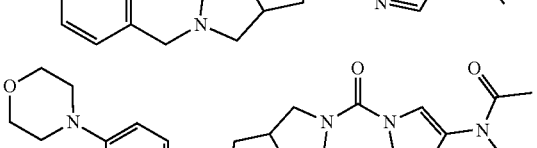

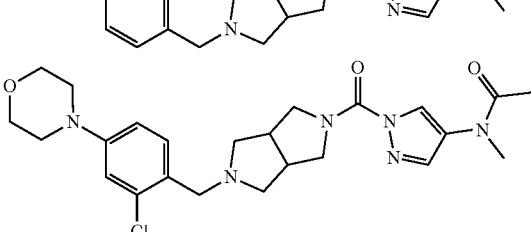

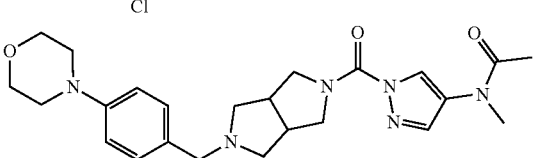

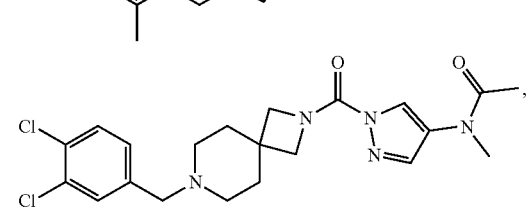

343
-continued
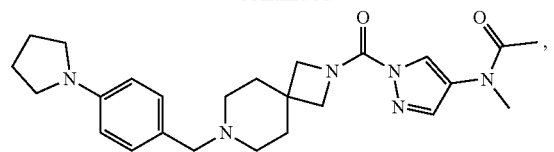
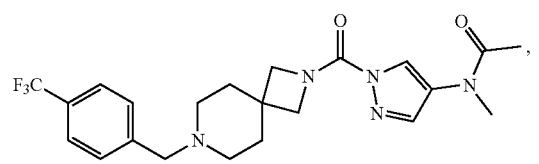
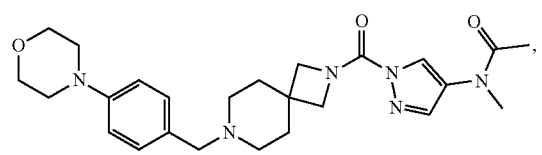
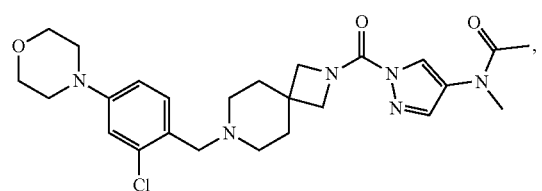
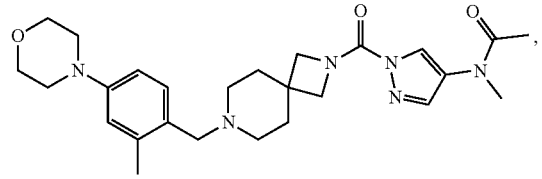
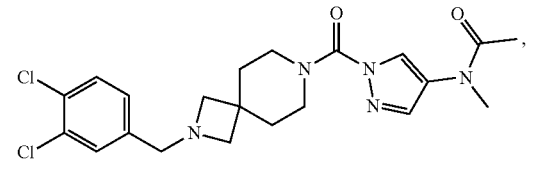
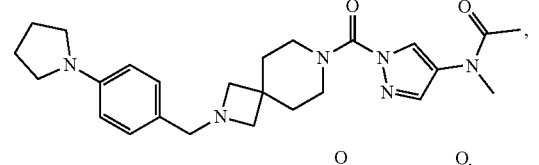
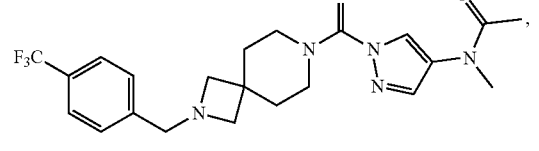
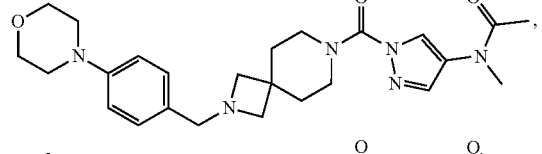
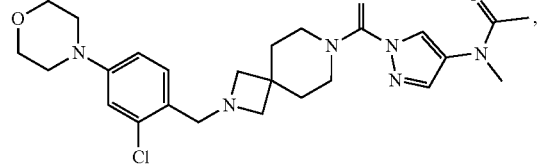
344
-continued
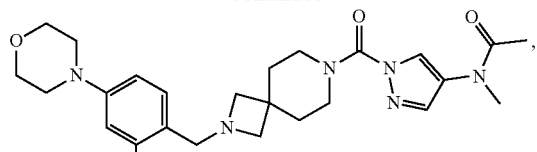
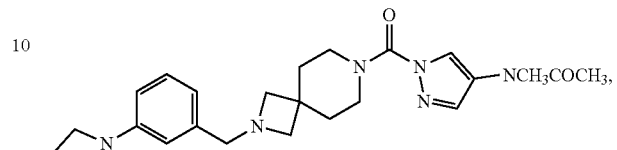
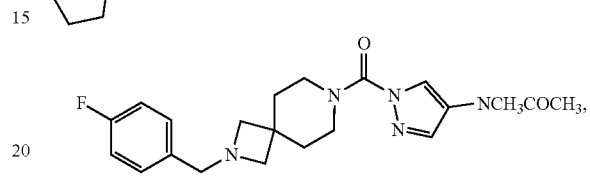
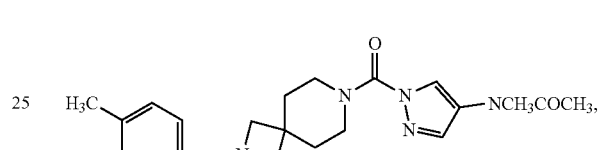
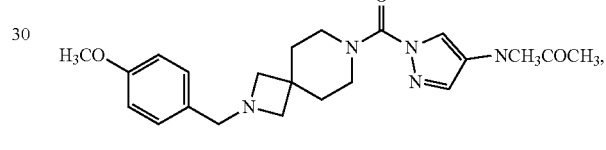
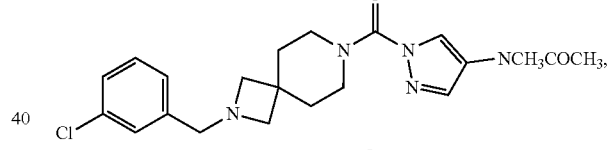
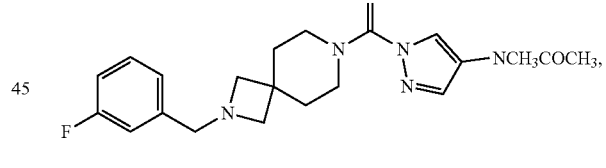
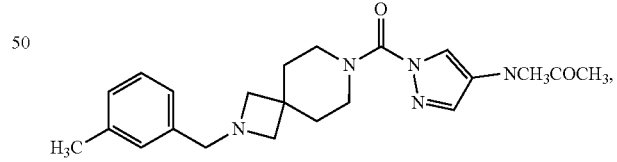
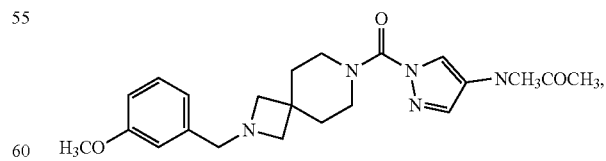
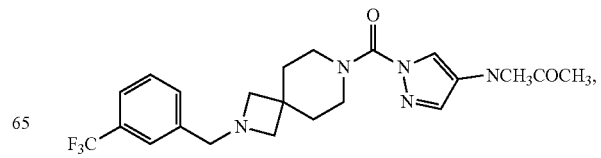

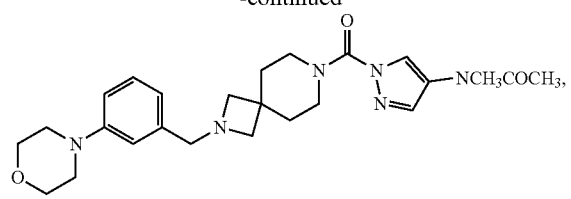
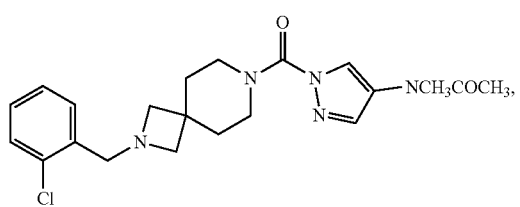
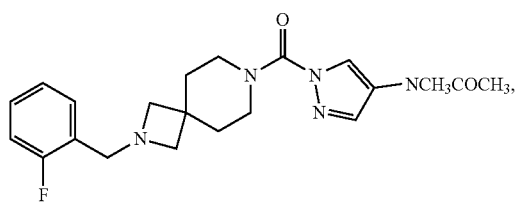
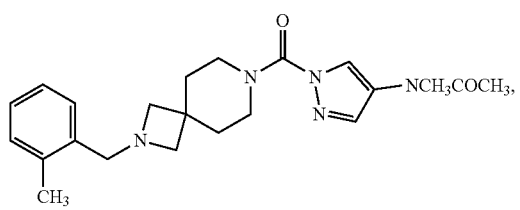
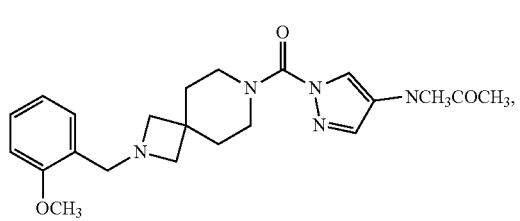
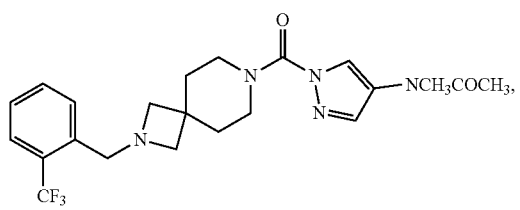
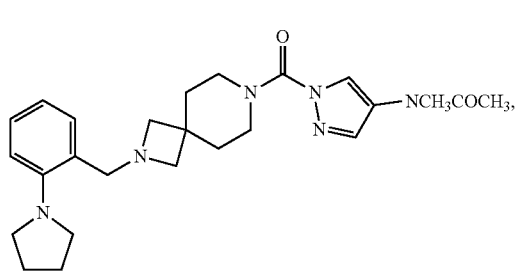
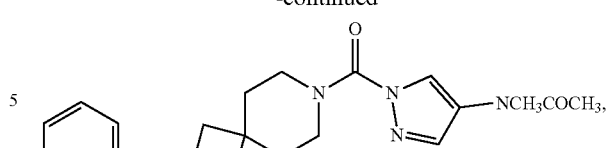
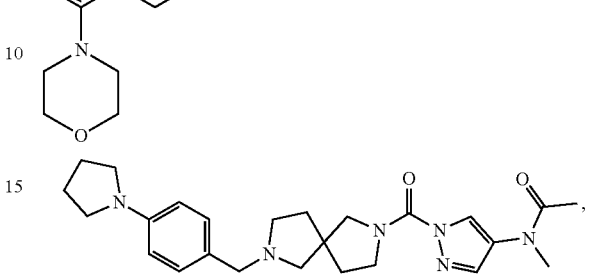
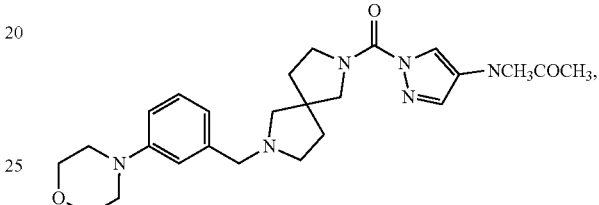
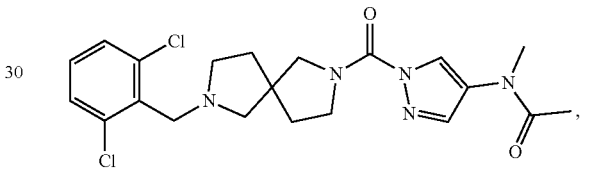
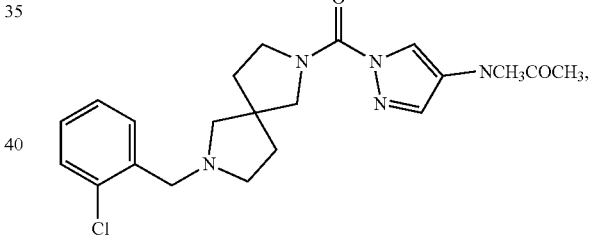
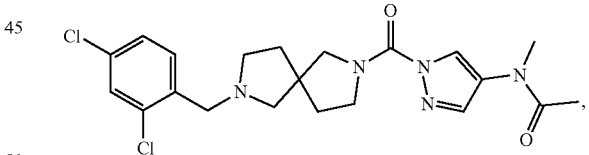
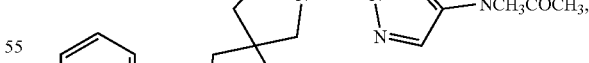
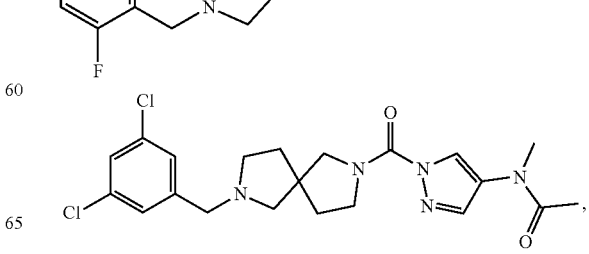

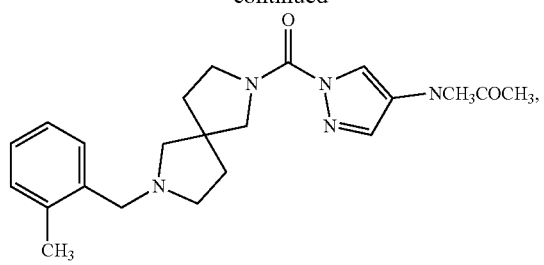
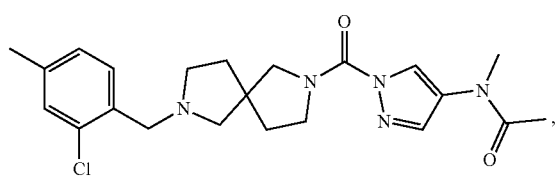
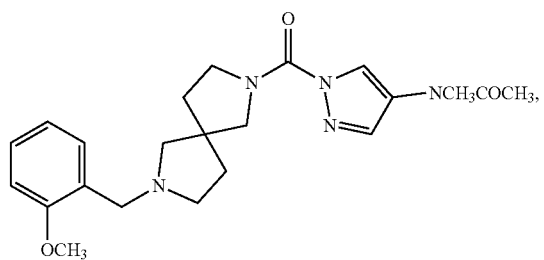
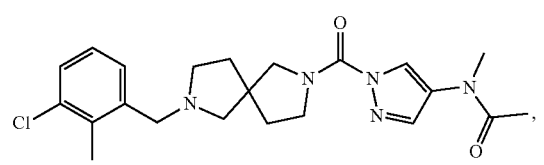
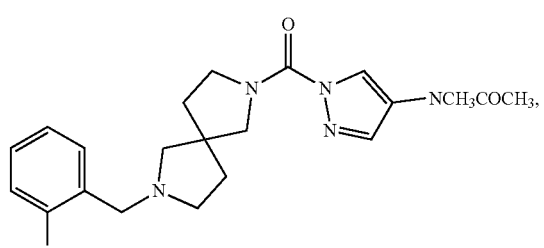
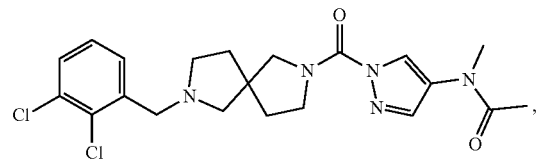
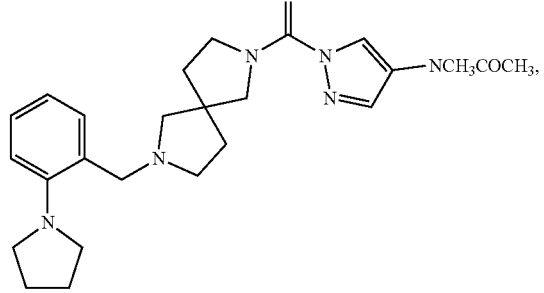
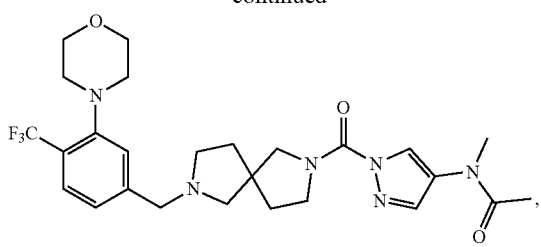
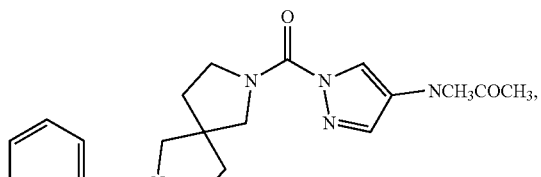
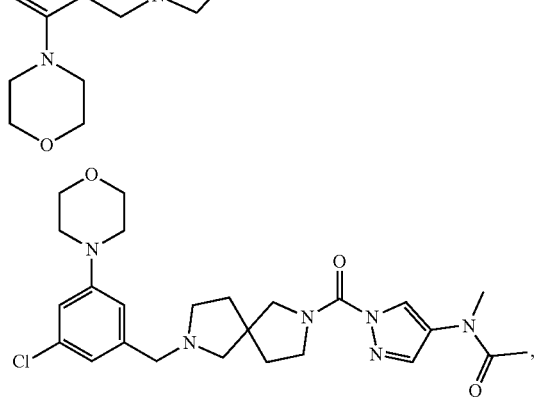
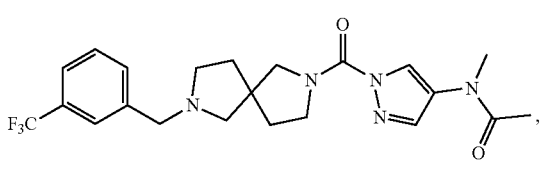
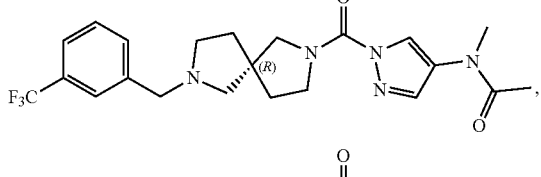
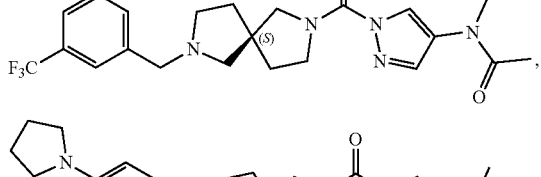
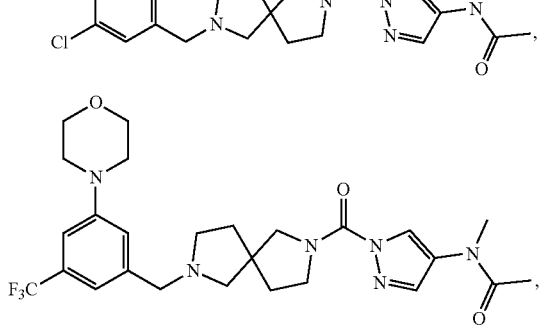

349
-continued

350
-continued

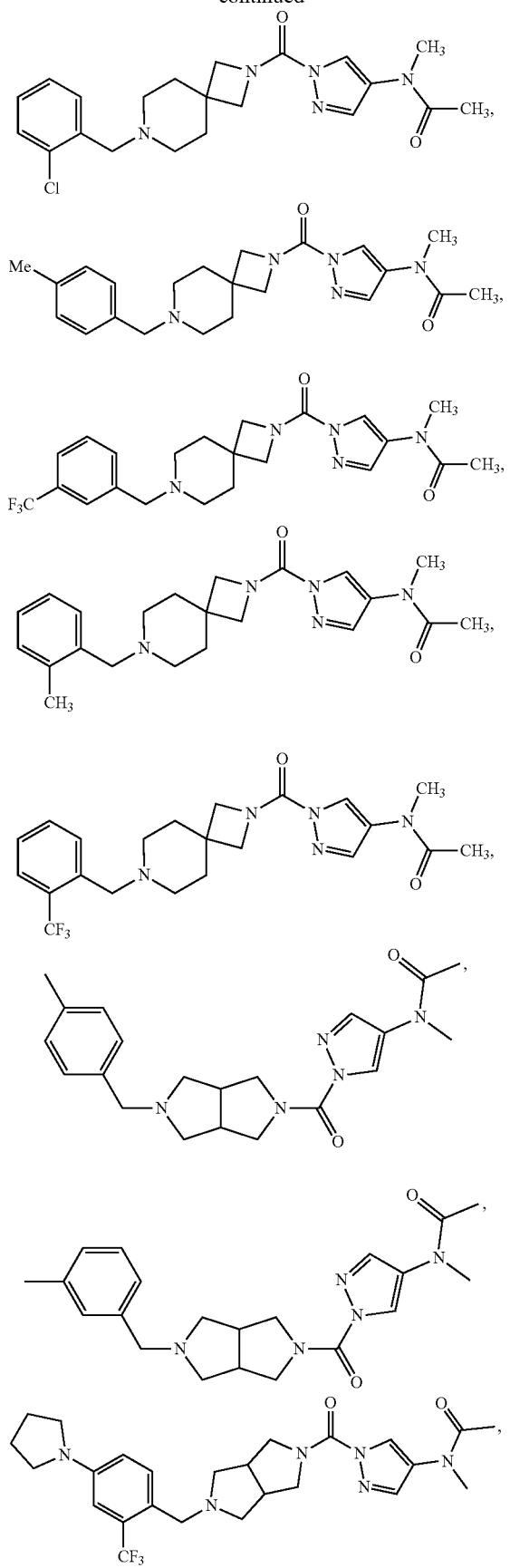
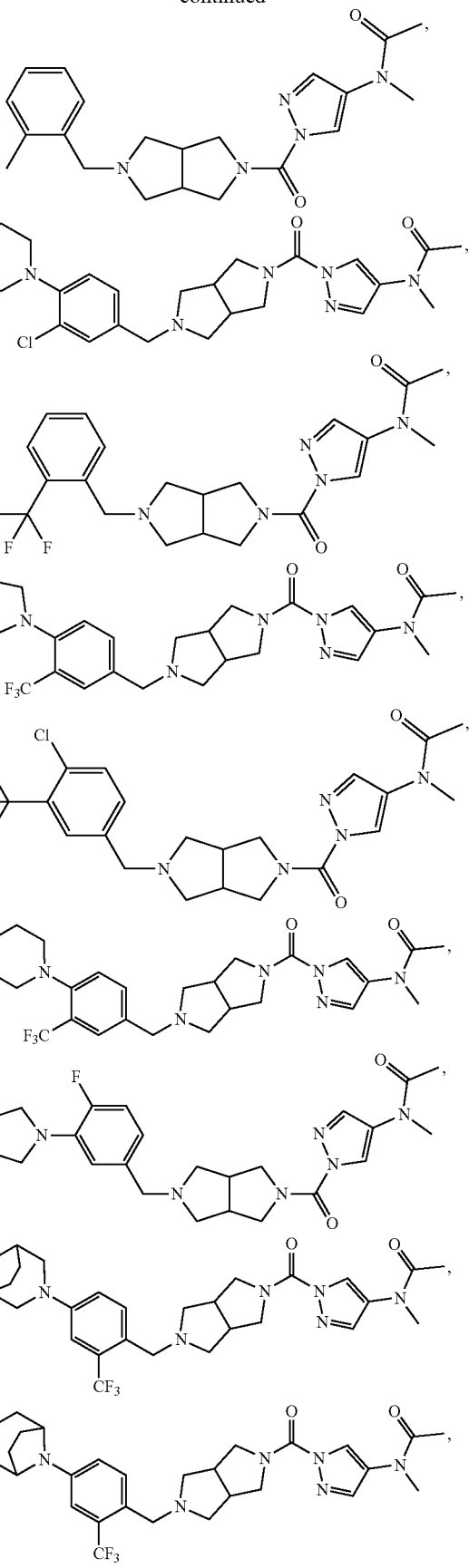

353
-continued
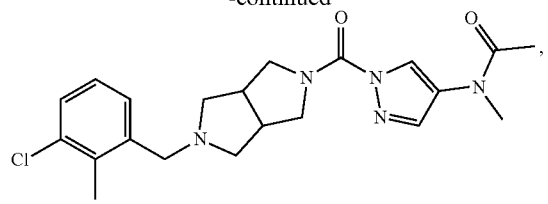
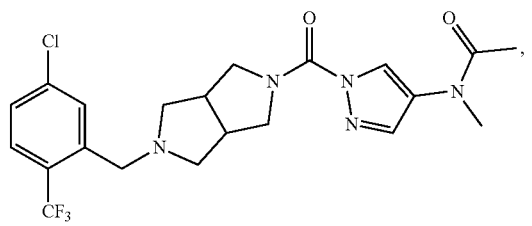
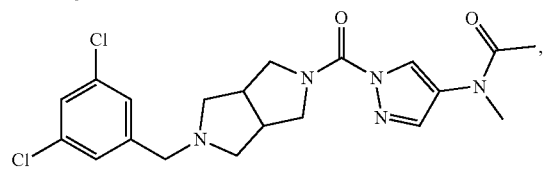
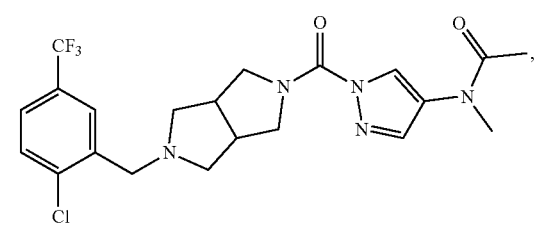
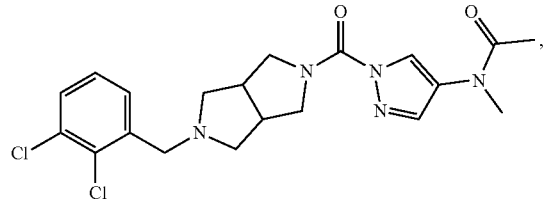
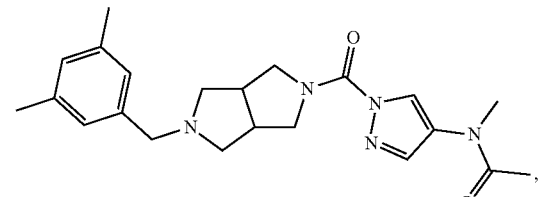
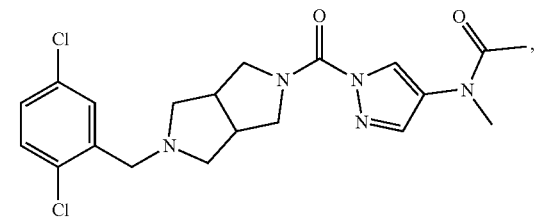
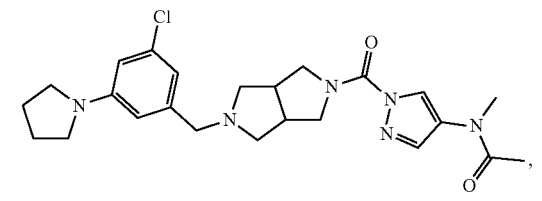
354
-continued
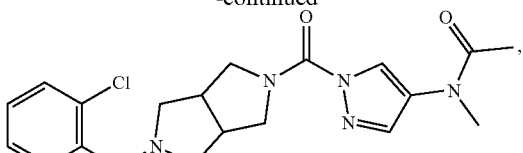
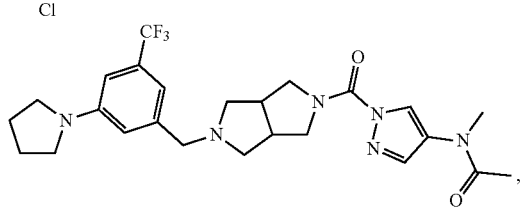
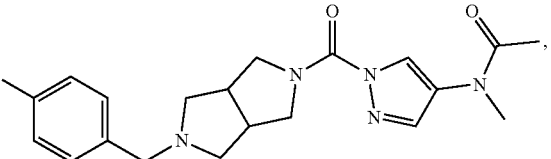
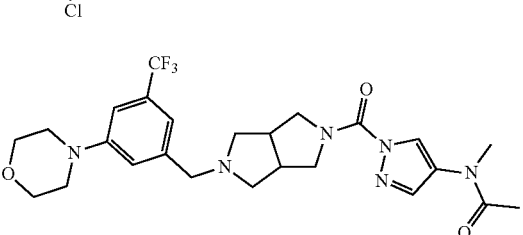
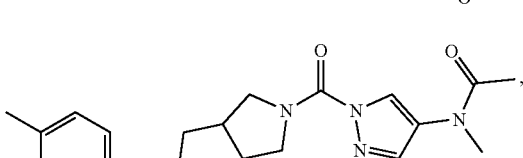
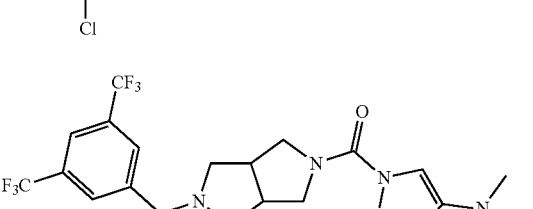
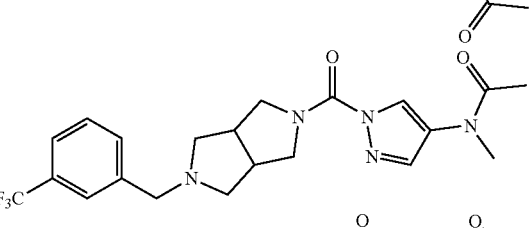
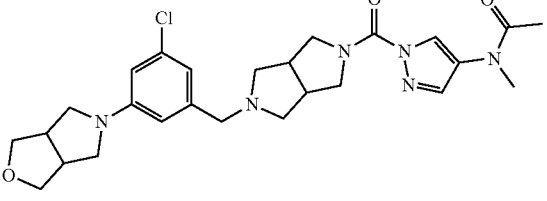

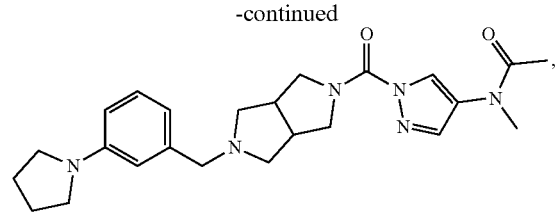
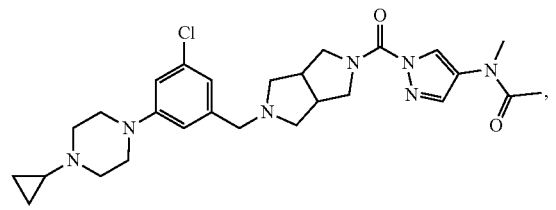
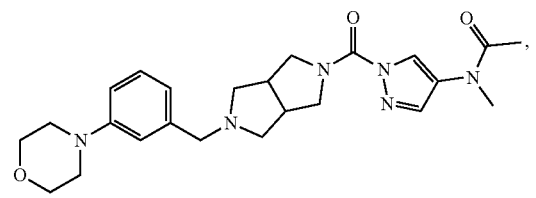
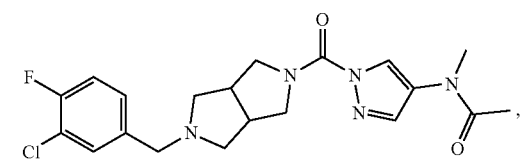
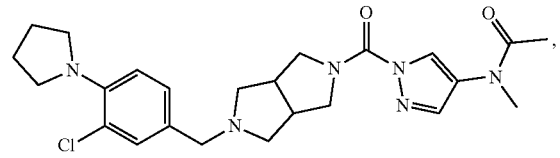
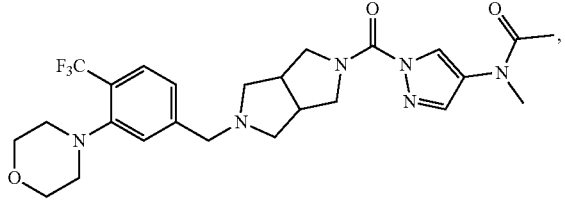
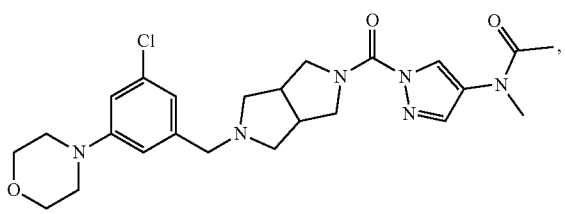
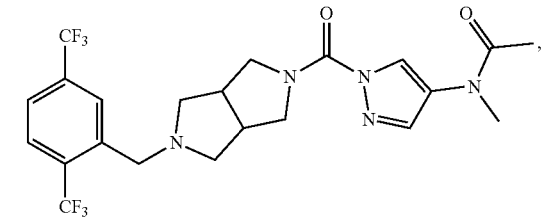
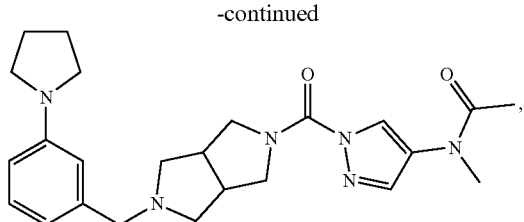
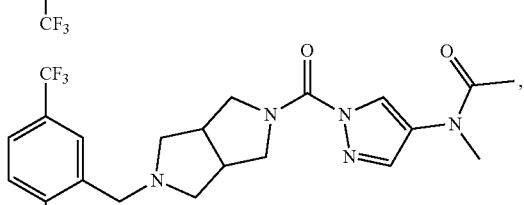
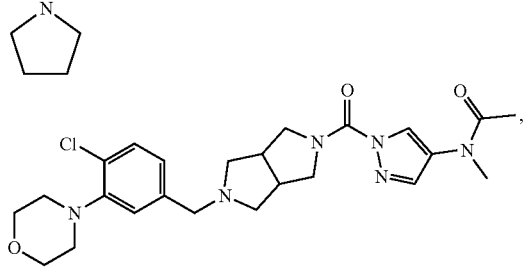
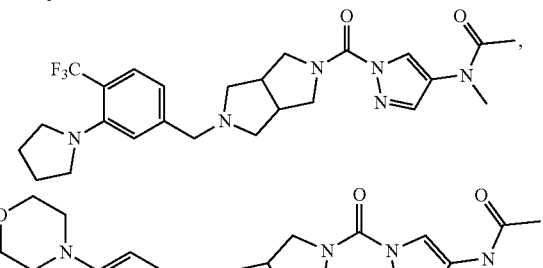
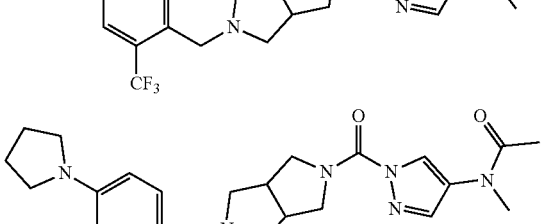
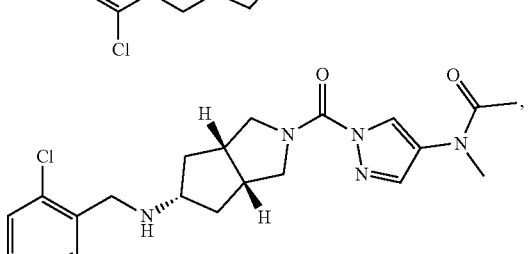
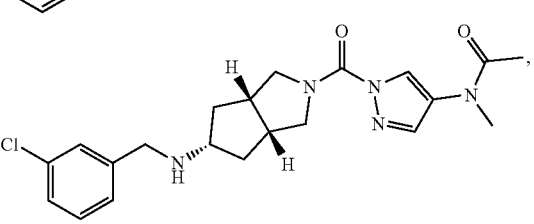

357
-continued
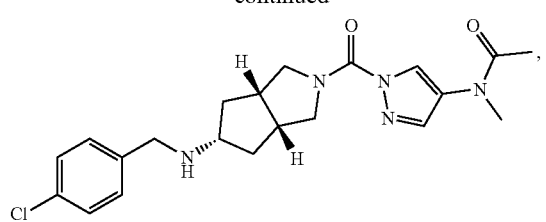
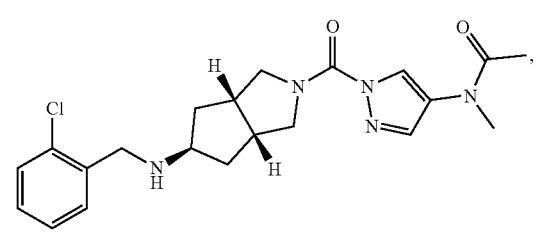
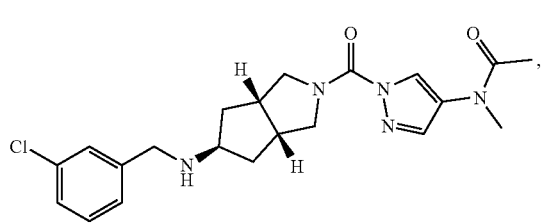
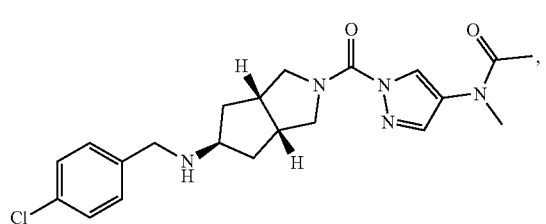
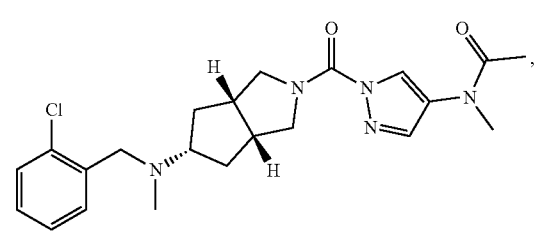
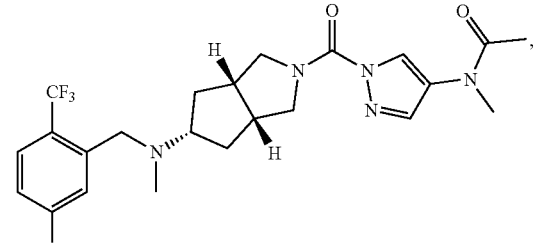
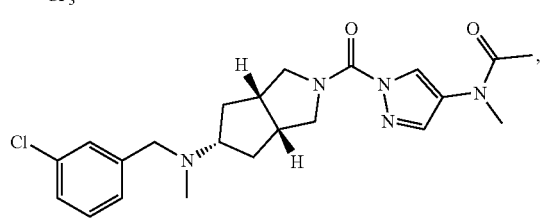
358
-continued
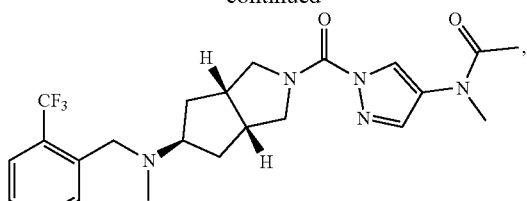
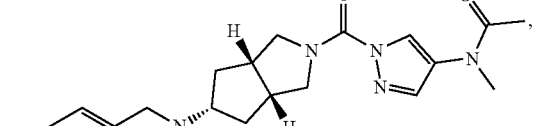
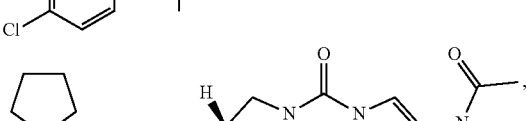
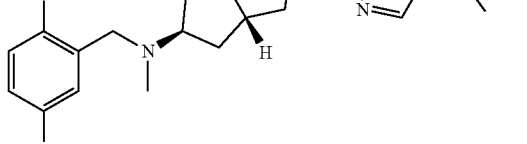
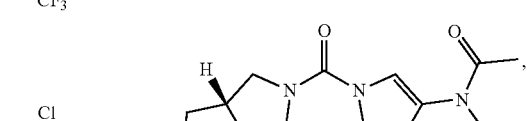
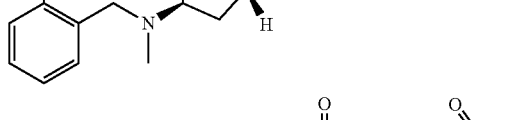

359
-continued
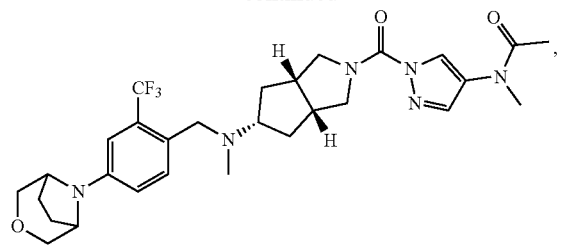
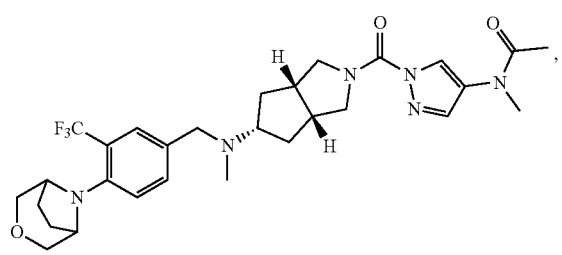
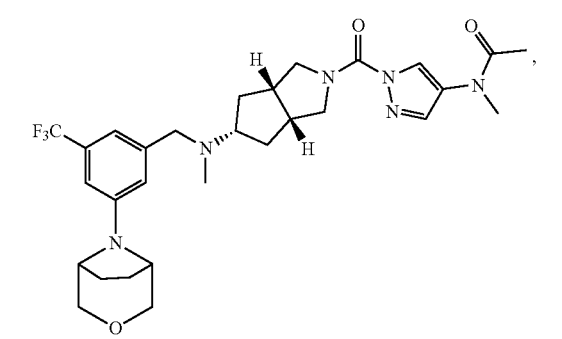
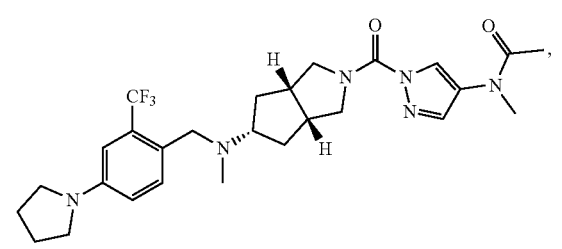
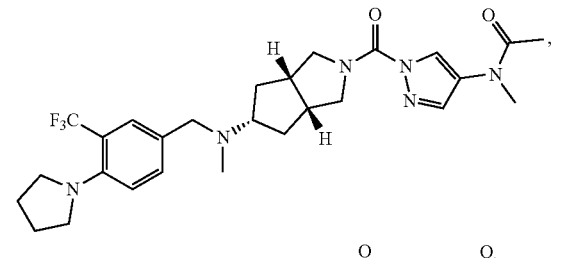
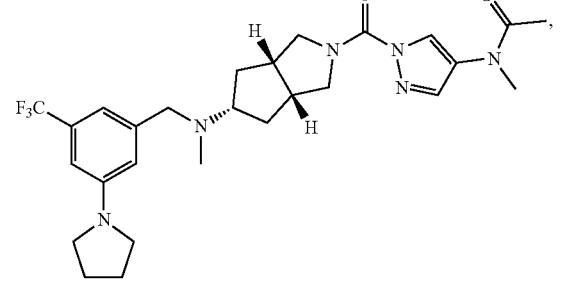
360
-continued
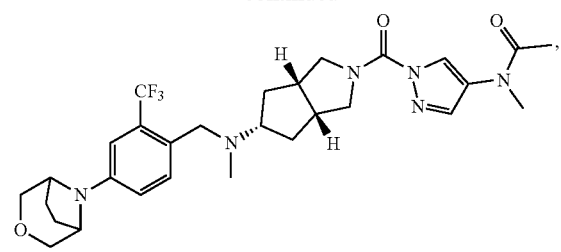
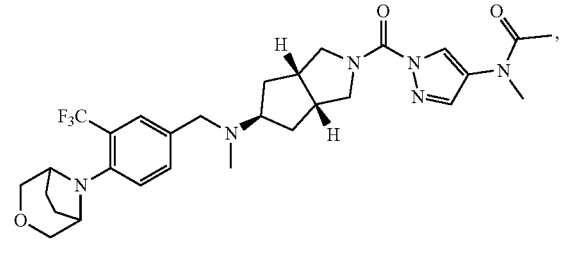
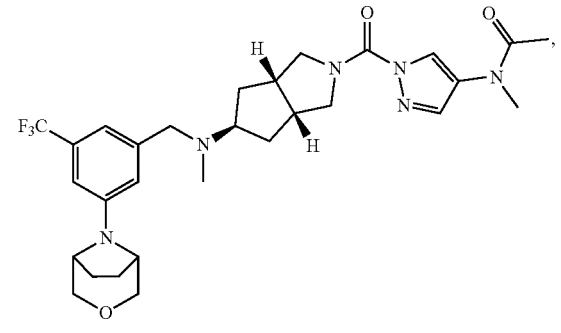
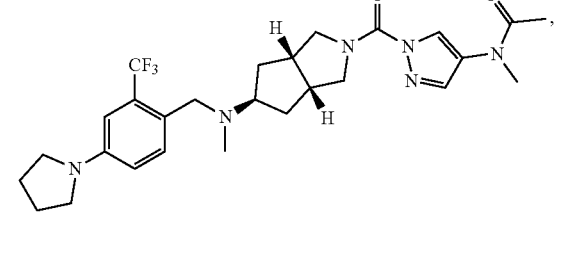
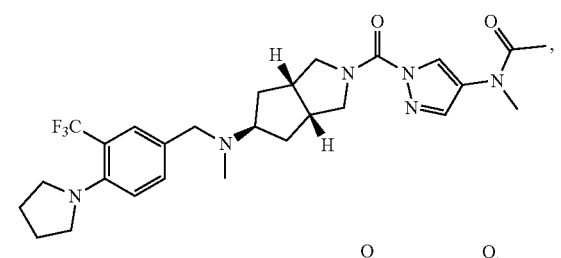
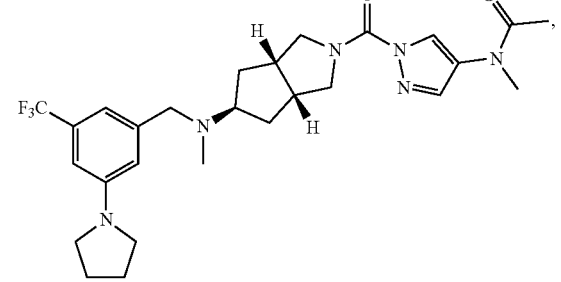

361
-continued
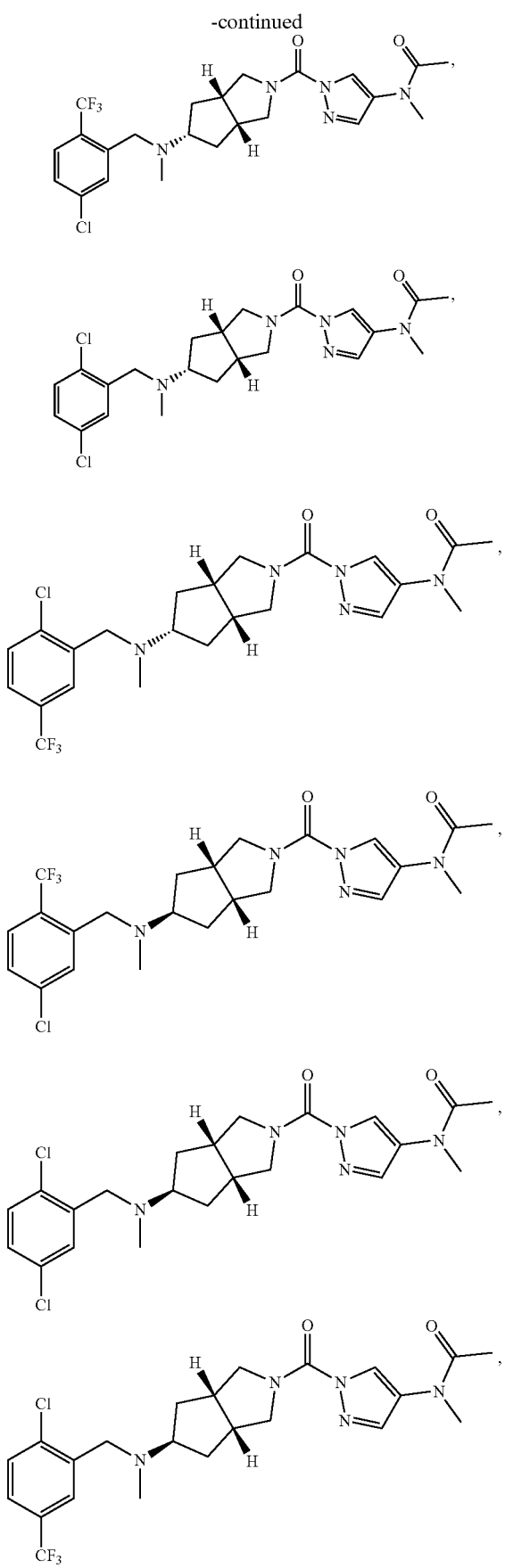
362
-continued
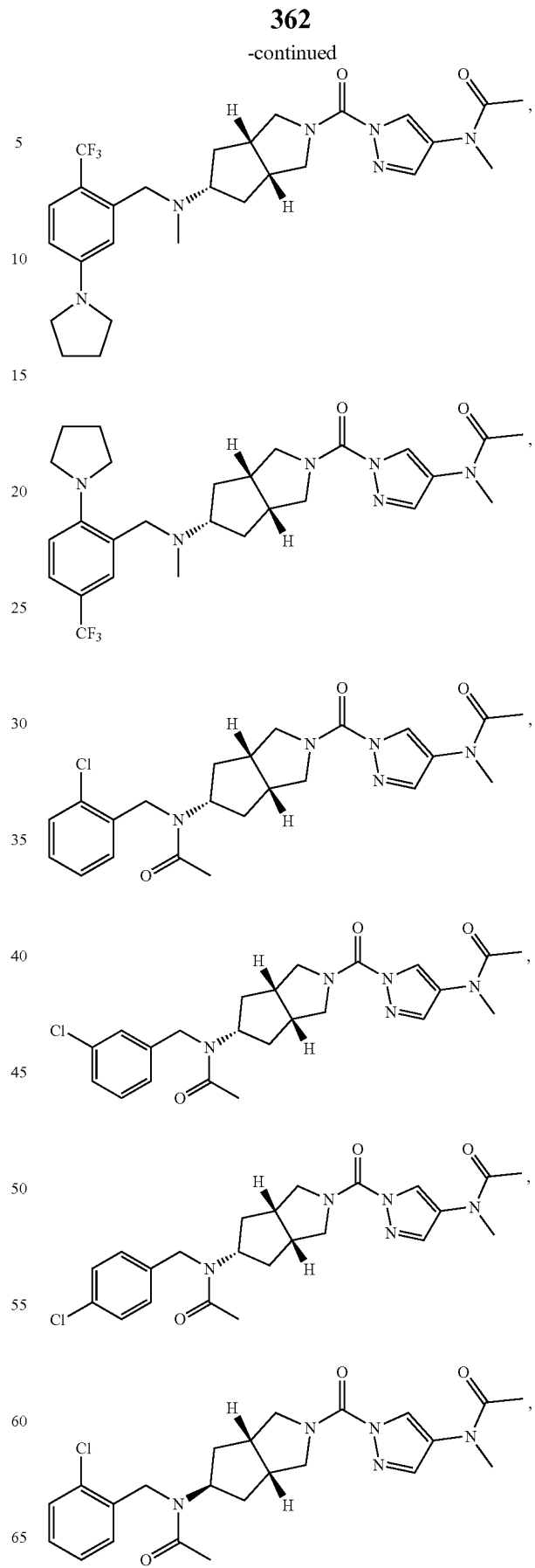

363
-continued
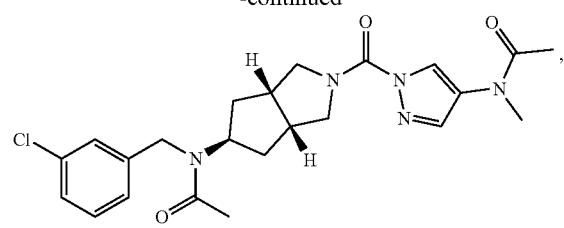
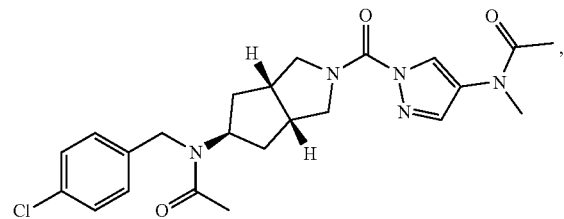
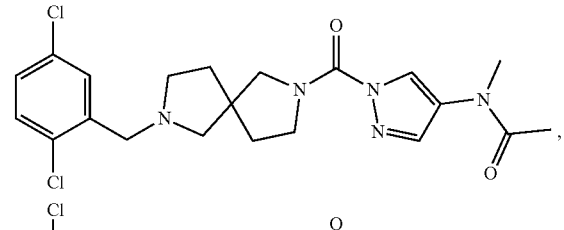
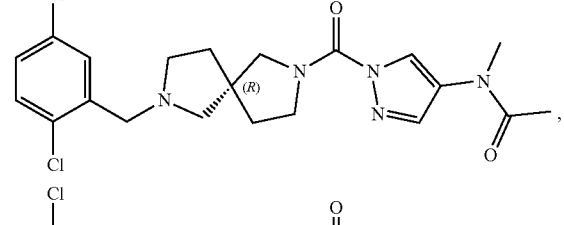
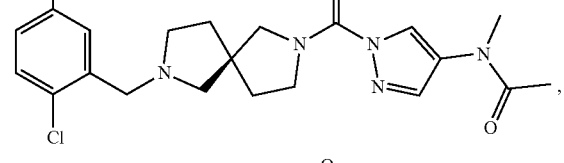
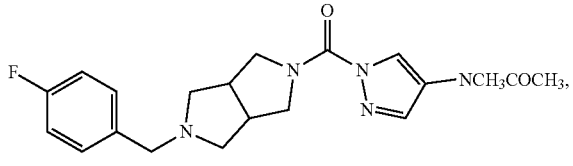
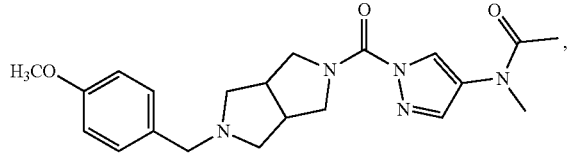
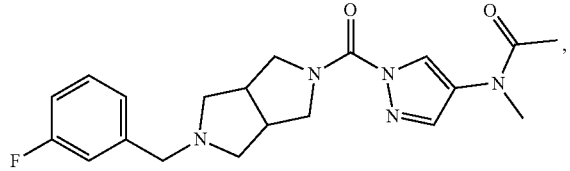
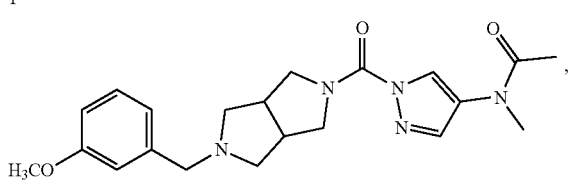
364
-continued
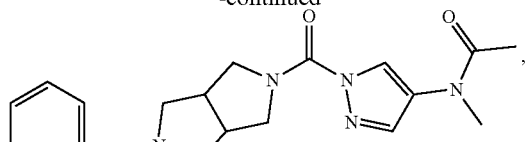
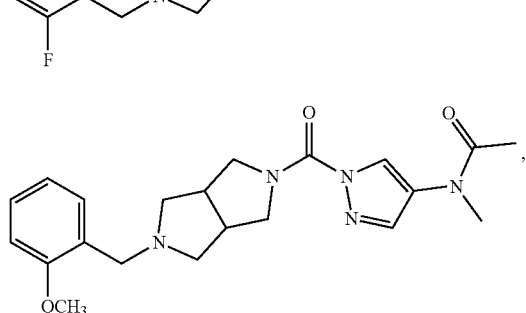
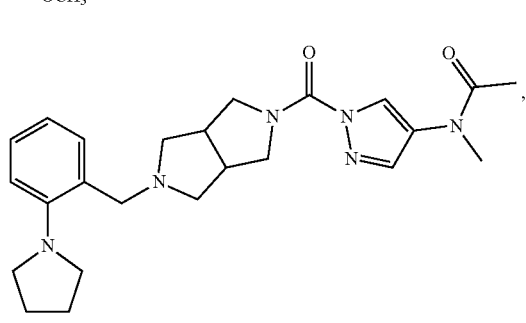
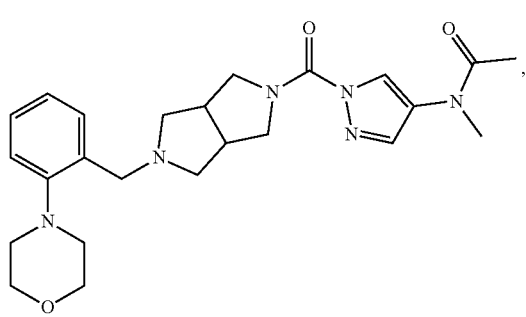
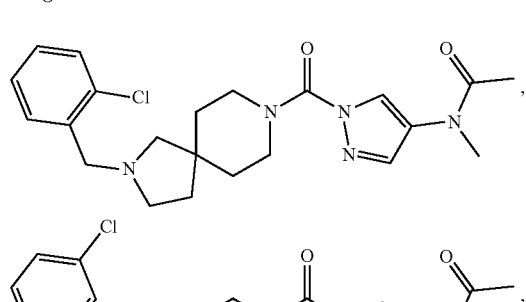
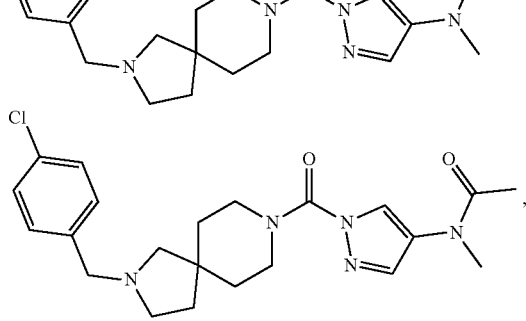

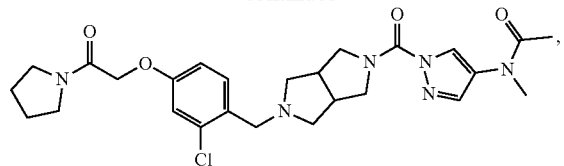
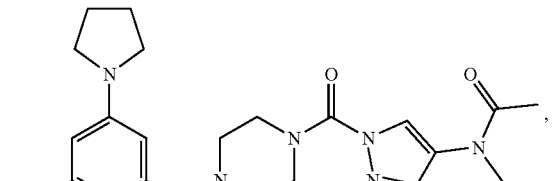
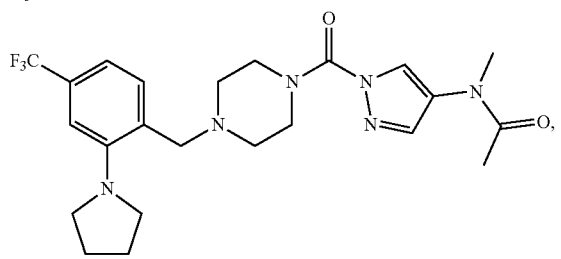
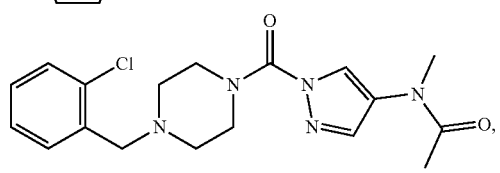
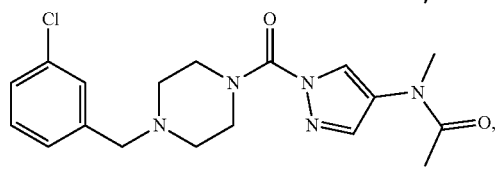
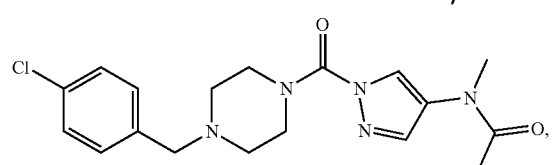
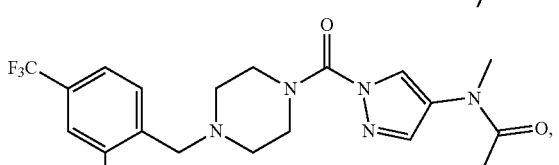
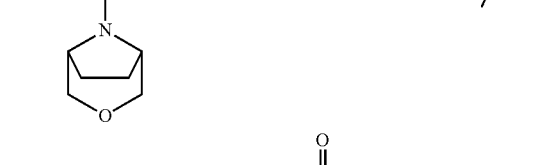
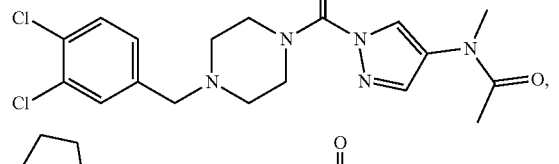
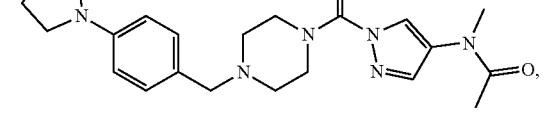
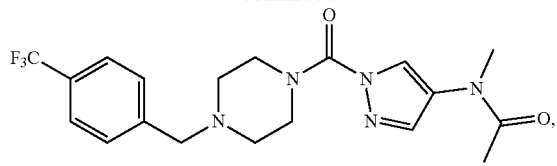
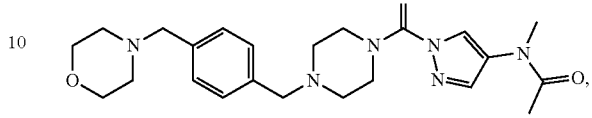
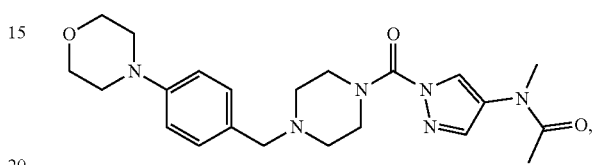
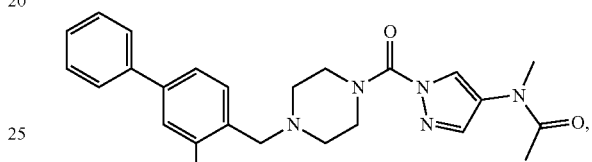
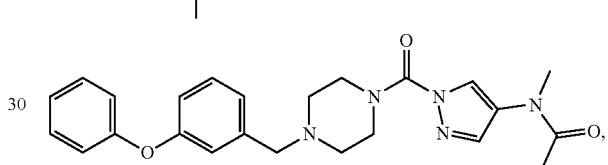
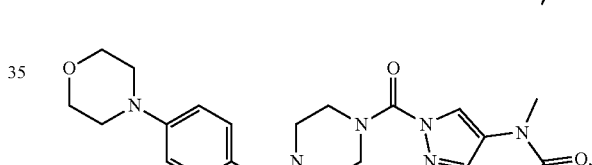
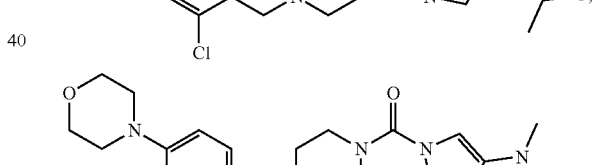
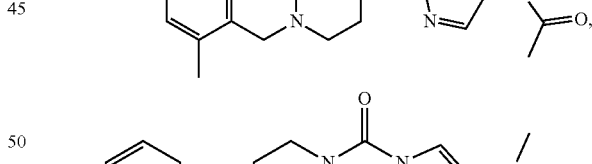
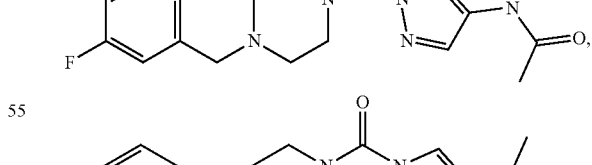
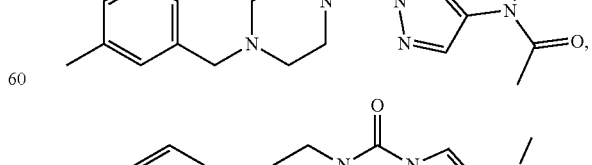
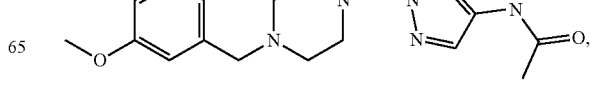

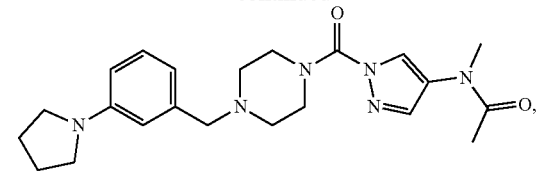
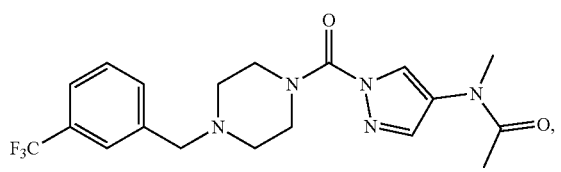
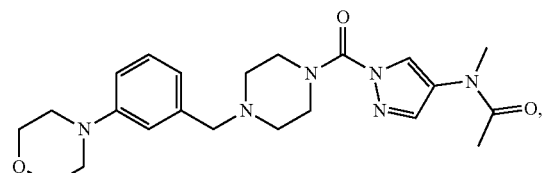
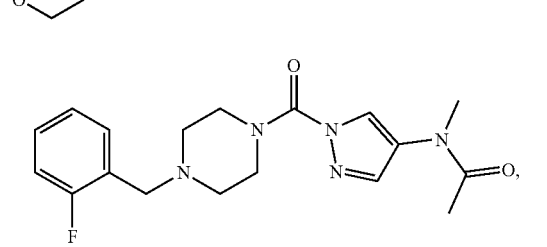
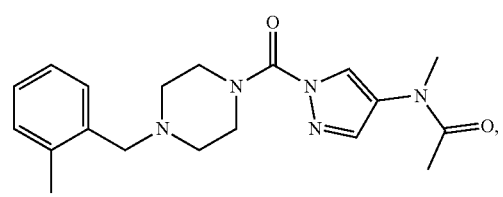
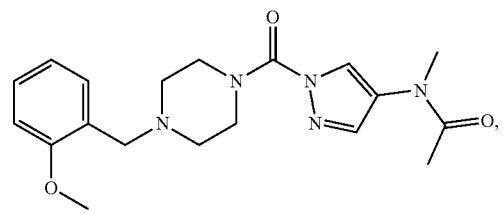
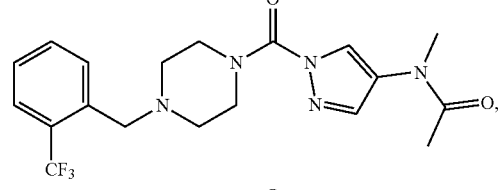
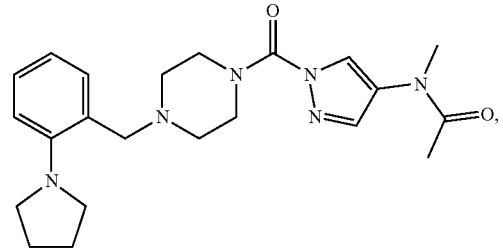
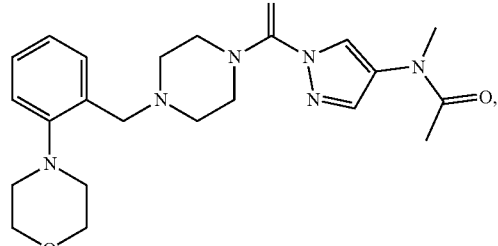
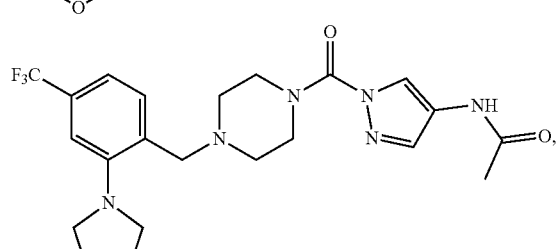
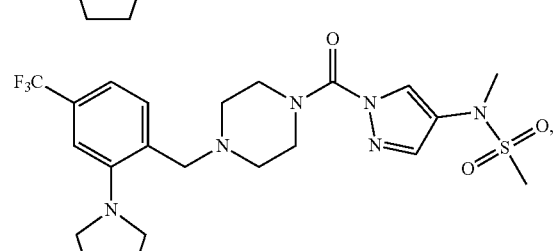
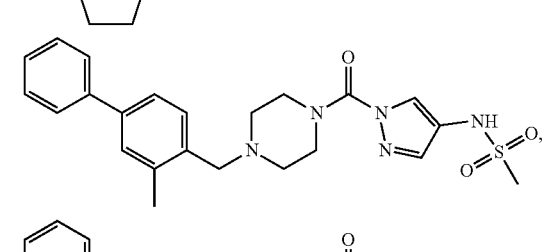
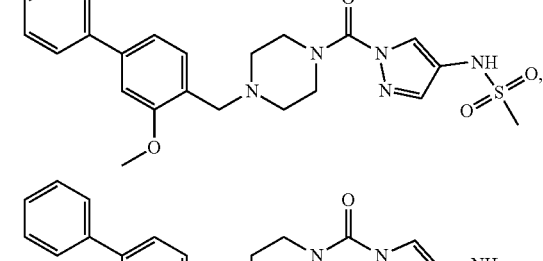
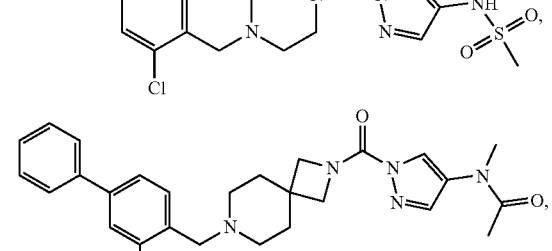
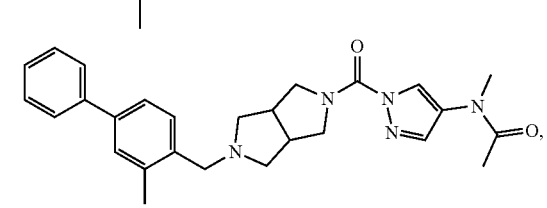

369
-continued
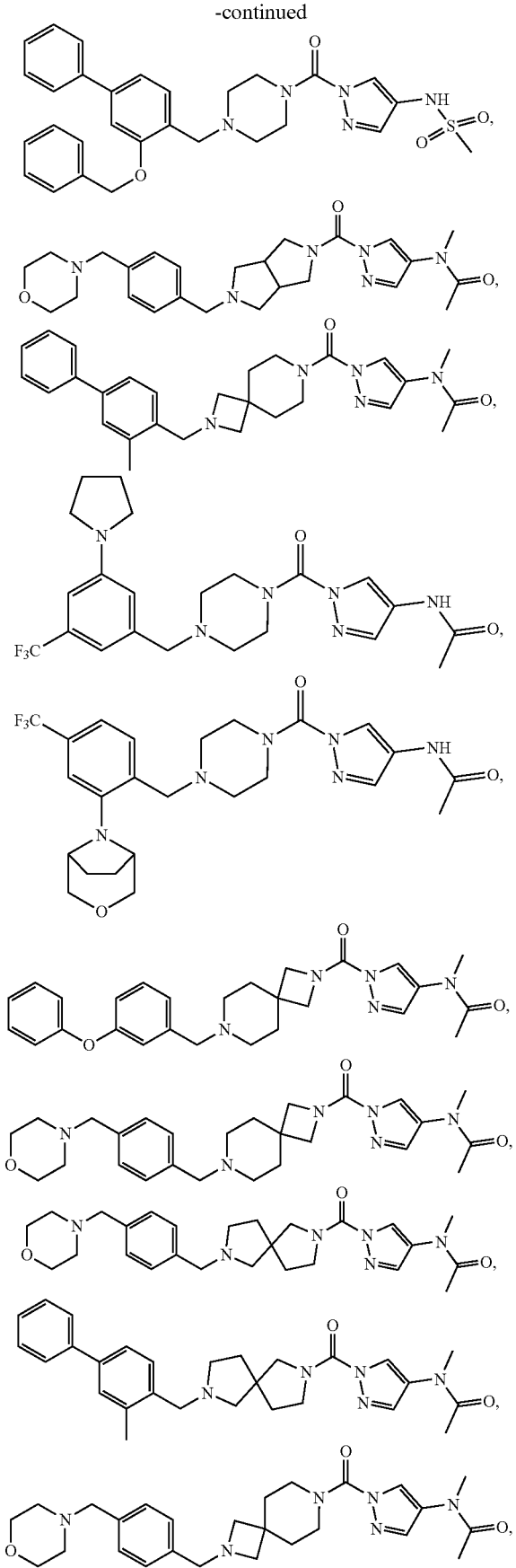
370
-continued
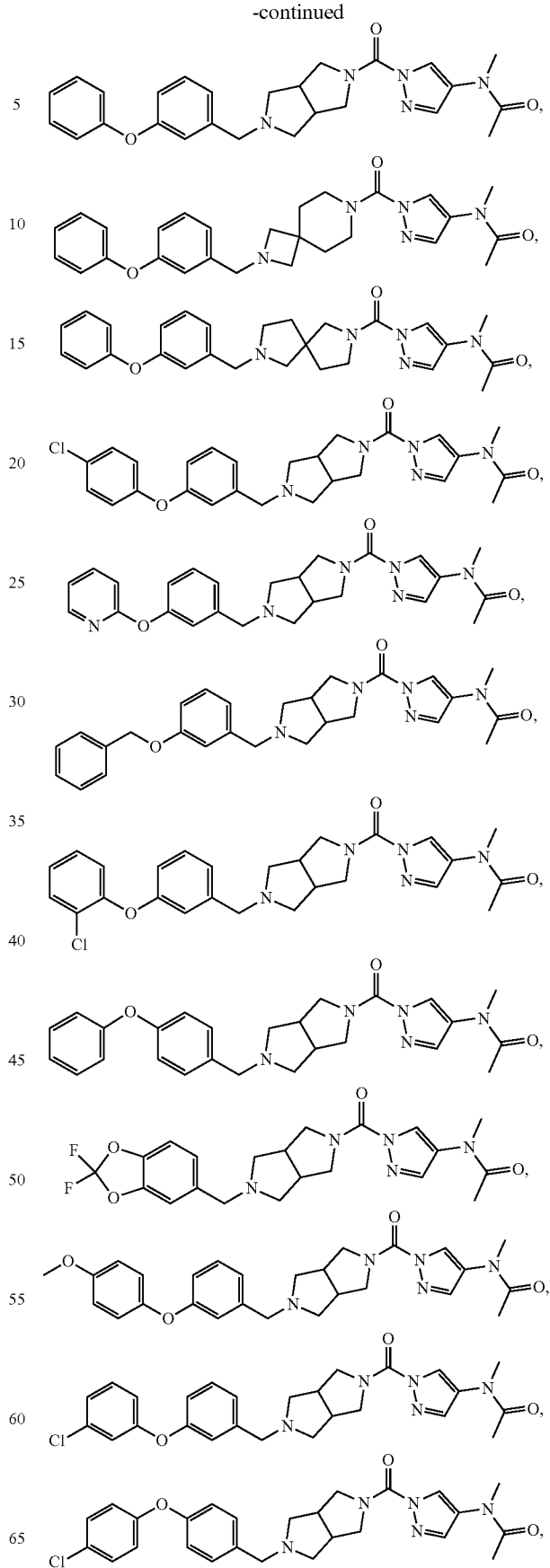

371
-continued

372
-continued

373
-continued
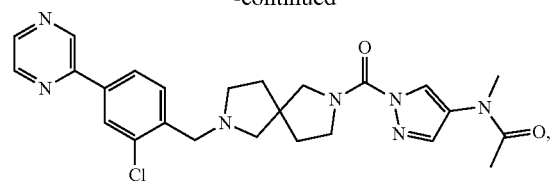
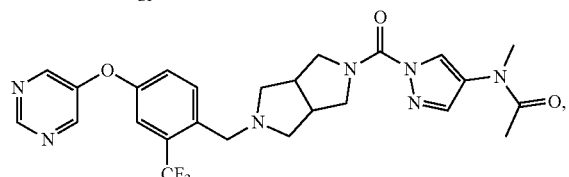
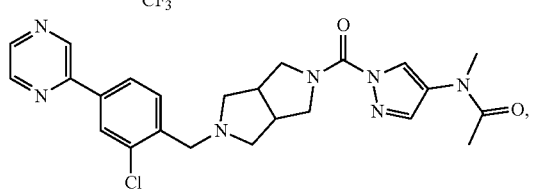
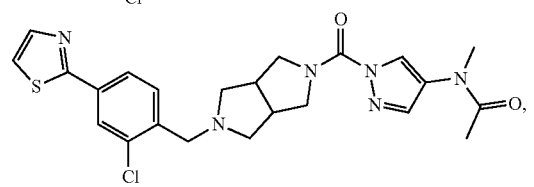
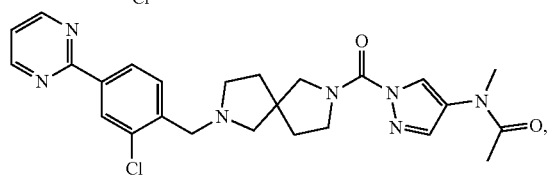
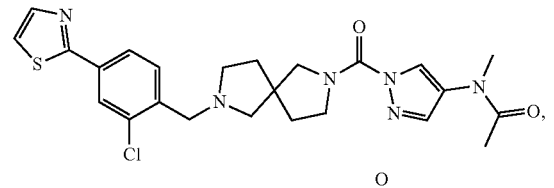
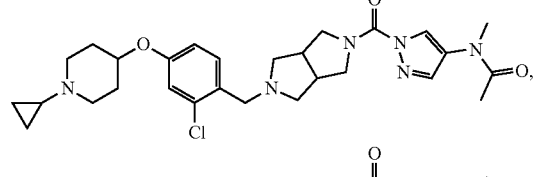
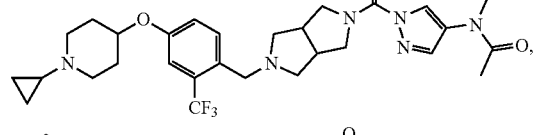
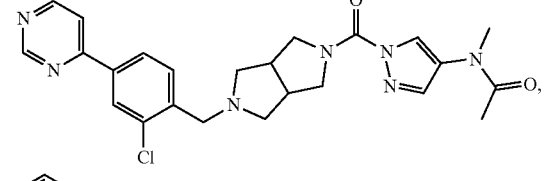
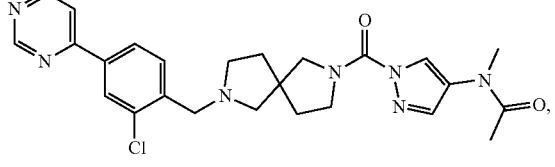
374
-continued
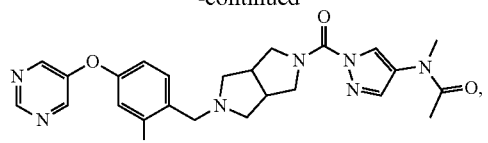
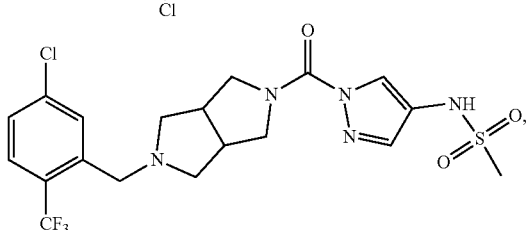
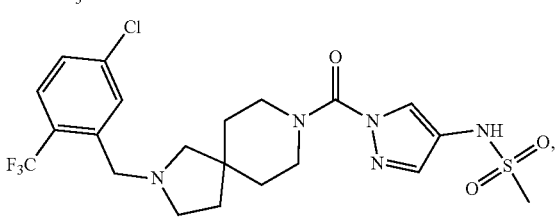
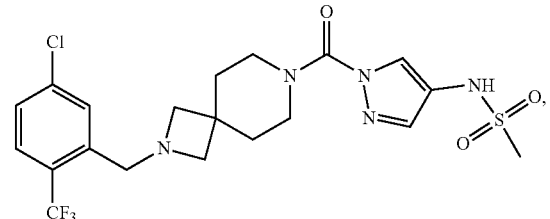
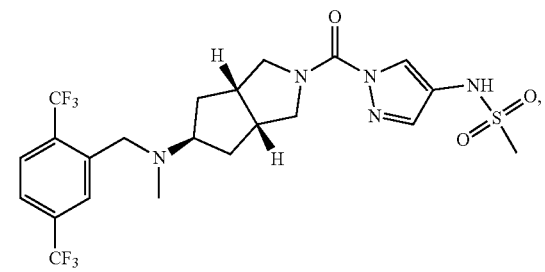
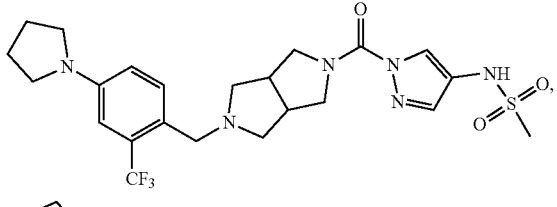
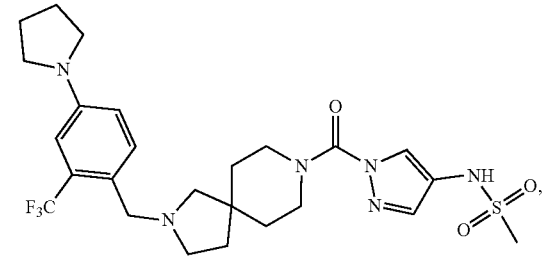
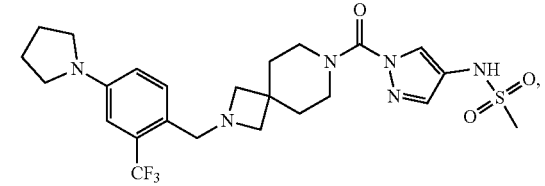

375
-continued
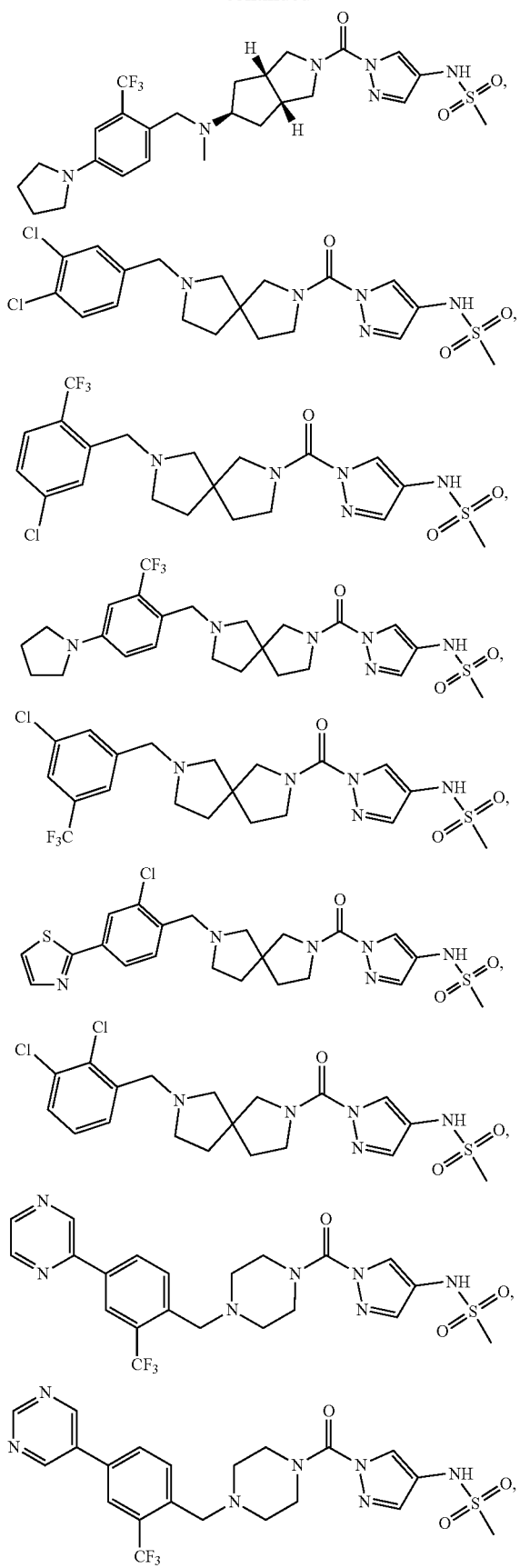
376
-continued
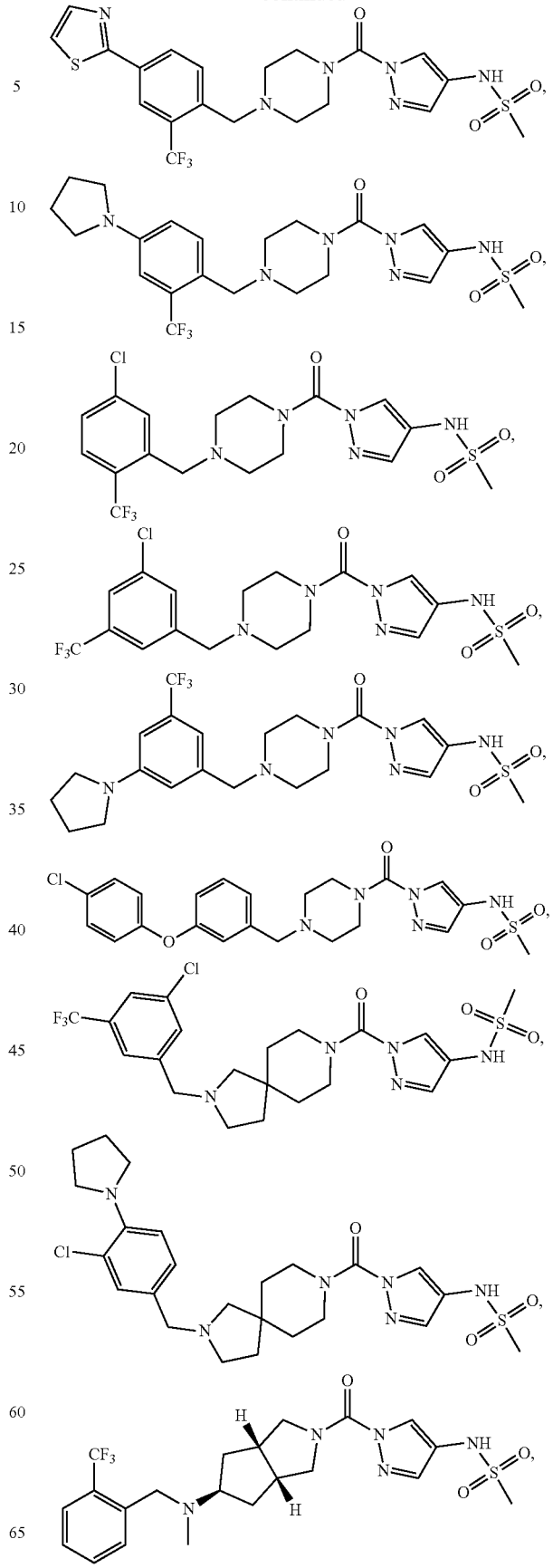

-continued

-continued

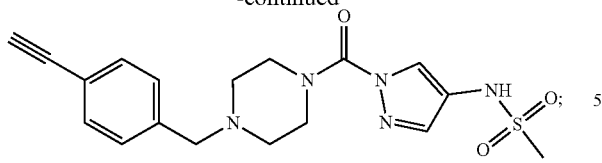

or a solvate, hydrate, tautomer, N-oxide, or pharmaceutically acceptable salt thereof.

19. A pharmaceutical composition comprising a compound of claim 1, or a solvate, hydrate, tautomer, N-oxide, or a pharmaceutically acceptable salt thereof, and at least one pharmaceutically acceptable excipient.

20. A method of treating a disease or disorder in a patient comprising administering to the patient in need thereof a therapeutically effective amount of a compound of claim 1, or a pharmaceutically acceptable salt or solvate thereof, wherein the disease or disorder is selected from epilepsy/seizure disorder, neuromyelitis optica (NMO), Tourette syndrome, persistent motor tic disorder, persistent vocal tic disorder, abdominal pain associated with irritable bowel syndrome, multiple sclerosis, Alzheimer's disease, and inflammatory bowel disease.

* * * * *